US011807872B2

(12) United States Patent
Kawaoka et al.

(10) Patent No.: US 11,807,872 B2
(45) Date of Patent: Nov. 7, 2023

(54) RECOMBINANT INFLUENZA VIRUSES WITH STABILIZED HA FOR REPLICATION IN EGGS

(71) Applicants: Wisconsin Alumni Research Foundation (WARF), Madison, WI (US); The University of Tokyo, Tokyo (JP)

(72) Inventors: Yoshihiro Kawaoka, Middleton, WI (US); Shinya Yamada, Bunkyo-ku (JP); Shiho Chiba, Madison, WI (US)

(73) Assignees: Wisconsin Alumni Research Foundation (WARF), Madison, WI (US); The University of Tokyo, Tokyo (JP)

( * ) Notice: Subject to any disclaimer, the term of this patent is extended or adjusted under 35 U.S.C. 154(b) by 0 days.

(21) Appl. No.: 17/004,583

(22) Filed: Aug. 27, 2020

(65) Prior Publication Data

US 2021/0102178 A1 Apr. 8, 2021

Related U.S. Application Data

(60) Provisional application No. 62/892,241, filed on Aug. 27, 2019.

(51) Int. Cl.
*C12N 7/00* (2006.01)
*A61K 39/00* (2006.01)

(52) U.S. Cl.
CPC ................ *C12N 7/00* (2013.01); *A61K 39/00* (2013.01); *C12N 2760/16021* (2013.01); *C12N 2760/16022* (2013.01); *C12N 2760/16034* (2013.01); *C12N 2760/16051* (2013.01)

(58) Field of Classification Search
CPC ........... C12N 2760/16121; C12N 2760/16134; C12N 2760/16111; C12N 2760/16143; C12N 2760/16021; C12N 7/00; C12N 2760/16034; A61K 39/145; A61K 39/12; A61K 39/00; A61P 31/16
See application file for complete search history.

(56) References Cited

U.S. PATENT DOCUMENTS

| | | | |
|---|---|---|---|
| 4,071,618 | A | 1/1978 | Konobe et al. |
| 4,659,569 | A | 4/1987 | Mitsuhashi et al. |
| 5,166,057 | A | 11/1992 | Palese et al. |
| 5,578,473 | A | 11/1996 | Palese et al. |
| 5,716,821 | A | 2/1998 | Wertz et al. |
| 5,750,394 | A | 5/1998 | Palese et al. |
| 5,786,199 | A | 7/1998 | Palese |
| 5,789,229 | A | 8/1998 | Wertz et al. |
| 5,820,871 | A | 10/1998 | Palese et al. |
| 5,840,520 | A | 11/1998 | Clarke et al. |
| 5,854,037 | A | 12/1998 | Palese et al. |
| 5,948,410 | A | 9/1999 | Van Scharrenburg et al. |
| 5,994,526 | A | 11/1999 | Meulewaeter et al. |
| 6,001,634 | A | 12/1999 | Palese et al. |
| 6,033,886 | A | 3/2000 | Conzelmann |
| 6,037,348 | A | 3/2000 | Colacino et al. |
| 6,146,642 | A | 11/2000 | Garcia-Sastre et al. |
| 6,169,175 | B1 | 1/2001 | Frace et al. |
| 6,194,546 | B1 | 2/2001 | Newton et al. |
| 6,270,958 | B1 | 8/2001 | Olivo et al. |
| 6,271,011 | B1 | 8/2001 | Lee et al. |
| 6,358,733 | B1 | 3/2002 | Motwani et al. |
| 6,455,298 | B1 | 9/2002 | Groner et al. |
| 6,544,785 | B1 | 4/2003 | Palese et al. |
| 6,656,720 | B2 | 12/2003 | Groner et al. |
| 6,825,036 | B2 | 11/2004 | Makizumi et al. |
| 6,843,996 | B1 | 1/2005 | Parkin et al. |
| 6,872,395 | B2 | 3/2005 | Kawaoka |
| 6,890,710 | B1 | 5/2005 | Palese et al. |
| 6,951,752 | B2 | 10/2005 | Reiter et al. |
| 6,951,754 | B2 | 10/2005 | Hoffmann |
| 6,974,695 | B2 | 12/2005 | Vogels et al. |
| 7,037,707 | B2 | 5/2006 | Webster et al. |
| 7,176,021 | B2 | 2/2007 | Kawaoka |
| 7,211,378 | B2 | 5/2007 | Kawaoka et al. |
| 7,226,774 | B2 | 6/2007 | Kawaoka |
| 7,312,064 | B2 | 12/2007 | Hoffmann |
| 7,335,356 | B2 | 2/2008 | Hart et al. |
| 7,507,411 | B2 | 3/2009 | Zhou et al. |
| 7,566,458 | B2 | 7/2009 | Yang et al. |
| 7,585,657 | B2 | 9/2009 | Kawaoka |
| 7,588,769 | B2 | 9/2009 | Kawaoka |

(Continued)

FOREIGN PATENT DOCUMENTS

| | | |
|---|---|---|
| AU | 2012204138 B2 | 5/2014 |
| AU | 2014202470 | 11/2016 |

(Continued)

OTHER PUBLICATIONS

"International Application Serial No. PCT/US2020/048130, Invitation to Pay Additional Fees mailed Jan. 13, 2021", 7 pgs.
Harding, Alfred T, et al., "Rationally Designed Influenza Virus Vaccines That Are Antigenically Stable during Growth in Egg", *MBIO*, vol. 8, No. 3, e00669-17, (2017), 1-16.
Kuwahara, Tomoko, et al., "Isolation of an Egg-Adapted Influenza A(H3N2) Virus without Amino Acid Substitutions at the Antigenic Sites of Its Hemagglutinin", *Japanese Journal of Infectious Diseases*, 71(3), (2018), 234-238.
Ramanunninair, Manojkumar, et al., "Molecular Signature of High Yield (Growth) Influenza A Virus Reassortants Prepared as Candidate Vaccine Seeds", *PLoS ONE*, 8(6): e65955, (2013), 1-16.

(Continued)

*Primary Examiner* — Bao Q Li
(74) *Attorney, Agent, or Firm* — Schwegman Lundberg & Woessner, P.A.

(57) ABSTRACT

Modified influenza virus neuraminidases are described herein that improve viral replication, thus improving the yield of vaccine viruses. Expression of such modified neuraminidases by influenza virus may also stabilize co-expressed hemagglutinins so that the hemagglutinins do not undergo mutation or decrease the need for HA binding to cells.

17 Claims, 102 Drawing Sheets

Specification includes a Sequence Listing.

(56) References Cited

U.S. PATENT DOCUMENTS 7,601,356 B2 10/2009 Jin et al.
7,670,837 B2 3/2010 Schwartz
7,682,618 B2 3/2010 Bavari et al.
7,723,094 B2 5/2010 Kawaoka et al.
7,833,788 B2 11/2010 Pau et al.
7,883,844 B2 2/2011 Nouchi et al.
7,955,833 B2 6/2011 Reiter et al.
7,959,930 B2 6/2011 De Wit et al.
7,968,101 B2 6/2011 Kawaoka et al.
7,972,843 B2 7/2011 Hoffmann
7,993,924 B2 8/2011 Billeter et al.
8,012,736 B2 9/2011 Hoffman et al.
8,043,856 B2 10/2011 Kawaoka et al.
8,048,430 B2 11/2011 Yang et al.
8,057,806 B2 11/2011 Kawaoka et al.
8,093,033 B2 1/2012 Kemble et al.
8,114,415 B2 2/2012 Hoffmann et al.
8,119,337 B2 2/2012 Gregersen
8,119,388 B2 2/2012 Schwartz et al.
8,298,805 B2 10/2012 Kawaoka
8,309,099 B2 11/2012 Hoffmann
8,354,114 B2 1/2013 Lu et al.
8,357,376 B2 1/2013 Liu et al.
8,409,843 B2 4/2013 Kemble et al.
8,460,914 B2 6/2013 Gregersen
8,465,960 B2 6/2013 Kawaoka et al.
8,475,806 B2 7/2013 Kawaoka
8,507,247 B2 8/2013 Kawaoka et al.
8,524,497 B2 9/2013 Reiter et al.
8,546,123 B2 10/2013 Lewis
8,574,591 B2 11/2013 Hoffmann et al.
8,574,593 B2 11/2013 Yang et al.
8,580,277 B2 11/2013 Yang et al.
8,591,914 B2 11/2013 Yang et al.
8,597,661 B2 12/2013 Kawaoka et al.
8,679,819 B2 3/2014 Kawaoka
8,877,209 B2 11/2014 Kawaoka et al.
8,900,595 B2 12/2014 Kawaoka et al.
9,101,653 B2 8/2015 Kawaoka et al.
9,109,013 B2 8/2015 Kawaoka et al.
9,222,118 B2 12/2015 Kawaoka et al.
9,254,318 B2 2/2016 Kawaoka et al.
9,284,533 B2 3/2016 Bilsel et al.
9,474,798 B2 10/2016 Watanabe et al.
9,757,446 B2 9/2017 LeFebvre et al.
9,890,363 B2 2/2018 Kawaoka
9,926,535 B2 3/2018 Kawaoka et al.
9,950,057 B2 4/2018 Kawaoka et al.
10,053,671 B2 8/2018 Kawaoka et al.
10,059,925 B2 8/2018 Kawaoka et al.
10,119,124 B2 11/2018 Watanabe et al.
10,130,697 B2 11/2018 Watanabe
10,172,934 B2 1/2019 Kawaoka et al.
10,246,686 B2 4/2019 Kawaoka et al.
10,358,630 B2 7/2019 Kawaoka et al.
10,494,613 B2 12/2019 Kawaoka et al.
10,513,692 B2 12/2019 Kawaoka et al.
10,633,422 B2 4/2020 Kawaoka et al.
10,808,229 B2 10/2020 Kawaoka et al.
11,007,262 B2 5/2021 Watanabe et al.
11,046,934 B2 6/2021 Kawaoka et al.
11,180,737 B2 11/2021 Kawaoka et al.
11,197,925 B2 12/2021 Kawaoka et al.
11,197,926 B2 * 12/2021 Kawaoka ............. C07K 14/005
11,241,492 B2 2/2022 Kawaoka et al.
11,384,339 B2 7/2022 Kawaoka et al.
11,389,523 B2 7/2022 Kawaoka et al.
11,390,649 B2 7/2022 Kawaoka et al.
2002/0010143 A1 1/2002 Barbosa et al.
2002/0164770 A1 11/2002 Hoffmann
2002/0197705 A1 12/2002 Kawaoka
2003/0035814 A1 2/2003 Kawaoka et al.
2003/0044962 A1 3/2003 Makizumi et al.
2003/0073223 A1 4/2003 Groner et al.
2003/0119183 A1 6/2003 Groner
2003/0194694 A1 10/2003 Kawaoka
2003/0215794 A1 11/2003 Kawaoka et al.
2004/0002061 A1 1/2004 Kawaoka
2004/0029251 A1 2/2004 Hoffman et al.
2004/0057967 A1 3/2004 Bavari et al.
2004/0063141 A1 4/2004 Lok
2004/0077086 A1 4/2004 Reiter et al.
2004/0132164 A1 7/2004 Doyle et al.
2004/0142322 A1 7/2004 Malcolm et al.
2004/0219170 A1 11/2004 Kawaoka
2004/0241139 A1 12/2004 Hobom et al.
2004/0242518 A1 12/2004 Chen et al.
2005/0003349 A1 1/2005 Kawaoka
2005/0037487 A1 2/2005 Kawaoka et al.
2005/0095583 A1 5/2005 Pekosz et al.
2005/0118140 A1 6/2005 Vorlop et al.
2005/0158342 A1 7/2005 Kemble et al.
2005/0186563 A1 8/2005 Hoffmann
2005/0202553 A1 9/2005 Groner et al.
2005/0232950 A1 10/2005 Kawaoka
2005/0266023 A1 12/2005 Bavari et al.
2005/0266026 A1 12/2005 Hoffmann et al.
2006/0057116 A1 3/2006 Kawaoka et al.
2006/0088909 A1 4/2006 Compans
2006/0099609 A1 5/2006 Bavari et al.
2006/0134138 A1 6/2006 Kawaoka et al.
2006/0166321 A1 7/2006 Kawaoka et al.
2006/0188977 A1 8/2006 Schwartz et al.
2006/0216702 A1 9/2006 Compans et al.
2006/0240515 A1 10/2006 Dimitrov et al.
2006/0246092 A1 11/2006 Neirynck et al.
2007/0141699 A1 6/2007 Kawaoka
2007/0231348 A1 10/2007 Kawaoka et al.
2008/0009031 A1 1/2008 Kawaoka
2008/0187557 A1 8/2008 Sambhara
2008/0233560 A1 9/2008 Hoffmann
2008/0254067 A1 10/2008 Trepanier et al.
2008/0274141 A1 11/2008 Groner et al.
2008/0292658 A1 11/2008 De Wit et al.
2008/0293040 A1 11/2008 Kawaoka et al.
2008/0311148 A1 12/2008 Hoffmann
2008/0311149 A1 12/2008 Hoffmann
2009/0017444 A1 1/2009 Kawaoka et al.
2009/0047728 A1 2/2009 Kawaoka et al.
2009/0074812 A1 3/2009 Watanabe et al.
2009/0081252 A1 3/2009 Gregersen
2009/0181446 A1 7/2009 Nouchi et al.
2009/0311669 A1 12/2009 Kawaoka
2009/0324640 A1 12/2009 Kawaoka et al.
2010/0080825 A1 4/2010 Kawaoka et al.
2010/0112000 A1 5/2010 Schwartz
2010/0183671 A1 7/2010 Gregersen et al.
2010/0247572 A1 9/2010 Kawaoka
2010/0267116 A1 10/2010 Kawaoka et al.
2011/0020374 A1 1/2011 Frazer
2011/0027314 A1 2/2011 Broeker
2011/0045022 A1 2/2011 Tsai
2011/0081373 A1 4/2011 Kawaoka et al.
2011/0110978 A1 5/2011 Kawaoka et al.
2011/0159031 A1 6/2011 Falkner et al.
2011/0236417 A1 9/2011 Watanabe et al.
2011/0263554 A1 10/2011 Kawaoka et al.
2011/0300604 A1 12/2011 Kawaoka et al.
2012/0020997 A1 1/2012 Hoffman et al.
2012/0034600 A1 2/2012 Gregersen
2012/0058124 A1 3/2012 Kurosawa et al.
2012/0115206 A1 5/2012 Schwartz et al.
2012/0156241 A1 6/2012 De Wit et al.
2012/0207785 A1 8/2012 Fabry et al.
2013/0095135 A1 4/2013 Collignon et al.
2013/0183741 A1 7/2013 Park et al.
2013/0230552 A1 9/2013 Kawaoka et al.
2013/0243744 A1 9/2013 Betenbaugh
2013/0316434 A1 11/2013 Reiter et al.
2014/0227310 A1 8/2014 Li et al.
2015/0017205 A1 1/2015 Kawaoka et al.
2015/0166967 A1 6/2015 Kawaoka et al.
2015/0307851 A1 10/2015 Kawaoka et al.
2015/0368621 A1 12/2015 Kawaoka et al.

(56) References Cited

U.S. PATENT DOCUMENTS

| | | | |
|---|---|---|---|
| 2016/0024193 | A1 | 1/2016 | Ayalon et al. |
| 2016/0024479 | A1 | 1/2016 | Kawaoka et al. |
| 2016/0115518 | A1 | 4/2016 | Kawaoka et al. |
| 2016/0208223 | A1 | 7/2016 | Kawaoka et al. |
| 2016/0215040 | A1 | 7/2016 | Kyratsous et al. |
| 2016/0355790 | A1 | 12/2016 | Kawaoka et al. |
| 2017/0058265 | A1 | 3/2017 | Kawaoka et al. |
| 2017/0067029 | A1 | 3/2017 | Kawaoka et al. |
| 2017/0096645 | A1 | 4/2017 | Watanabe et al. |
| 2017/0097334 | A1 | 4/2017 | Kawaoka et al. |
| 2017/0121391 | A1 | 5/2017 | Kawaoka et al. |
| 2017/0258888 | A1 | 9/2017 | Kawaoka |
| 2017/0298120 | A1 | 10/2017 | Sasisekharan |
| 2017/0354730 | A1 | 12/2017 | Kawaoka et al. |
| 2018/0245054 | A1 | 8/2018 | Kawaoka et al. |
| 2018/0273588 | A1 | 9/2018 | Kawaoka et al. |
| 2018/0340152 | A1 | 11/2018 | Kawaoka et al. |
| 2019/0032023 | A1 | 1/2019 | Kawaoka et al. |
| 2019/0048324 | A1 | 2/2019 | Kawaoka et al. |
| 2019/0117759 | A1 | 4/2019 | Wantanabe et al. |
| 2019/0167781 | A1 | 6/2019 | Kawaoka et al. |
| 2020/0188506 | A1 | 6/2020 | Kawaoka et al. |
| 2020/0237899 | A1 | 7/2020 | Kawaoka et al. |
| 2020/0263142 | A1 | 8/2020 | Kawaoka et al. |
| 2020/0263143 | A1 | 8/2020 | Kawaoka et al. |
| 2020/0291384 | A1 | 9/2020 | Kawaoka et al. |
| 2021/0061862 | A1 | 3/2021 | Kawaoka et al. |
| 2021/0121545 | A1 | 4/2021 | Knoll et al. |
| 2021/0228708 | A1 | 7/2021 | Smith et al. |
| 2021/0246432 | A1 | 8/2021 | Kawaoka et al. |
| 2021/0252130 | A1 | 8/2021 | Watanabe et al. |
| 2021/0290754 | A1 | 9/2021 | Kawaoka et al. |
| 2021/0299249 | A1 | 9/2021 | Kawaoka et al. |
| 2022/0025339 | A1 | 1/2022 | Kawaoka et al. |
| 2022/0202926 | A1 | 6/2022 | Kawaoka et al. |
| 2022/0241396 | A1 | 8/2022 | Kawaoka et al. |

FOREIGN PATENT DOCUMENTS

| | | | |
|---|---|---|---|
| AU | 2014290203 | B2 | 12/2020 |
| AU | 2017221444 | B2 | 11/2021 |
| BR | PI0410702 | B1 | 4/2022 |
| CA | 2379012 | A1 | 1/2001 |
| CA | 2816242 | C | 1/2019 |
| CN | 1826407 | A | 8/2006 |
| CN | 101472941 | A | 7/2009 |
| CN | 1826407 | B | 9/2013 |
| CN | 105296356 | A | 2/2016 |
| CN | 103540614 | B | 2/2018 |
| CN | 109477074 | A | 3/2019 |
| CN | 113874496 | A | 12/2021 |
| CN | 114929269 | A | 8/2022 |
| CN | 109477074 | B | 1/2023 |
| EP | 0687471 | A1 | 12/1995 |
| EP | 0700991 | A1 | 3/1996 |
| EP | 0702085 | A1 | 3/1996 |
| EP | 0704533 | A1 | 4/1996 |
| EP | 1201760 | A1 | 5/2002 |
| EP | 2010557 | B1 | 2/2014 |
| EP | 1572910 | B1 | 12/2015 |
| EP | 1631663 | B1 | 8/2016 |
| EP | 2747778 | B1 | 12/2017 |
| EP | 3009507 | B1 | 6/2020 |
| EP | 2493912 | B1 | 7/2020 |
| EP | 3022296 | B1 | 12/2022 |
| IL | 171831 | A | 5/2015 |
| JP | 07-203958 | | 8/1995 |
| JP | H08510749 | A | 11/1996 |
| JP | H10500113 | A | 1/1998 |
| JP | 2002536992 | A | 11/2002 |
| JP | 2003528570 | A | 9/2003 |
| JP | 2004500842 | A | 1/2004 |
| JP | 2004531232 | A | 10/2004 |
| JP | 2005523698 | A | 8/2005 |
| JP | 2005245302 | A | 9/2005 |
| JP | 2005535288 | A | 11/2005 |
| JP | 2006525815 | A | 11/2006 |
| JP | 2007518395 | A | 7/2007 |
| JP | 2007525175 | A | 9/2007 |
| JP | 2007529997 | A | 11/2007 |
| JP | 2008520248 | A | 6/2008 |
| JP | 2009511084 | A | 3/2009 |
| JP | 2009514850 | A | 4/2009 |
| JP | 2009523252 | A | 6/2009 |
| JP | 2009532352 | A | 9/2009 |
| JP | 2009539965 | A | 11/2009 |
| JP | 2010530248 | A | 9/2010 |
| JP | 2011530295 | A | 12/2011 |
| JP | 4927290 | | 5/2012 |
| JP | 4927290 | B2 | 5/2012 |
| JP | 2013507990 | A | 3/2013 |
| JP | 2013511280 | A | 4/2013 |
| JP | 2014131516 | A | 4/2013 |
| JP | 2014039551 | A | 3/2014 |
| JP | 2016144463 | A | 7/2014 |
| JP | 2016521553 | A | 1/2016 |
| JP | 2016524915 | A | 7/2016 |
| JP | 2016169225 | A | 8/2016 |
| JP | 2017197555 | A | 8/2016 |
| JP | 2016500007 | A | 9/2016 |
| JP | 2018064493 | A | 9/2017 |
| JP | 2017527557 | A | 11/2017 |
| JP | 2019510481 | A | 4/2018 |
| JP | 6352974 | B2 | 6/2018 |
| JP | 6375329 | B2 | 7/2018 |
| JP | 2020010711 | A | 4/2019 |
| JP | 2020114250 | A | 1/2020 |
| JP | 2021036878 | A | 7/2020 |
| JP | 2021533157 | A | 1/2021 |
| JP | 2021184761 | A | 3/2021 |
| JP | 2021500891 | A | 12/2021 |
| JP | 2021536228 | A | 12/2021 |
| JP | 2022066209 | A | 12/2021 |
| JP | 2022172369 | A | 4/2022 |
| JP | 2022522112 | A | 4/2022 |
| JP | 2022527235 | A | 6/2022 |
| JP | 2022551805 | A | 12/2022 |
| JP | 2023011603 | A | 1/2023 |
| JP | 7244455 | B2 | 3/2023 |
| JP | 2023511444 | A | 3/2023 |
| KR | 101113432 | B1 | 2/2012 |
| MX | 285206 | | 3/2011 |
| NO | 341506 | | 11/2017 |
| WO | WO-9610631 | A1 | 4/1996 |
| WO | WO-9610632 | A1 | 4/1996 |
| WO | WO-9640955 | A1 | 12/1996 |
| WO | WO-9737000 | A1 | 10/1997 |
| WO | WO-9802530 | A1 | 1/1998 |
| WO | WO-9848834 | A1 | 11/1998 |
| WO | WO-9853078 | A1 | 11/1998 |
| WO | WO-9928445 | A1 | 6/1999 |
| WO | WO-0053786 | A1 | 9/2000 |
| WO | WO-0060050 | A2 | 10/2000 |
| WO | WO-2000060050 | A2 | 10/2000 |
| WO | WO-0060050 | A3 | 1/2001 |
| WO | WO-2001004333 | A1 | 1/2001 |
| WO | WO-2001025462 | A1 | 4/2001 |
| WO | WO-0179273 | A2 | 10/2001 |
| WO | WO-2001079273 | A2 | 10/2001 |
| WO | WO-0183794 | A2 | 11/2001 |
| WO | WO-2001083794 | A2 | 11/2001 |
| WO | WO-03068923 | A2 | 1/2002 |
| WO | WO-02064757 | A2 | 8/2002 |
| WO | WO-0210143 | A1 | 9/2002 |
| WO | WO-02074795 | A2 | 9/2002 |
| WO | WO-03076462 | A1 | 8/2003 |
| WO | WO-2003068923 | A2 | 8/2003 |
| WO | WO-2003080846 | A1 | 10/2003 |
| WO | WO-03091401 | A2 | 11/2003 |
| WO | WO-2003091401 | A2 | 11/2003 |
| WO | WO-2004094466 | A2 | 11/2004 |
| WO | WO-04112831 | A2 | 12/2004 |
| WO | WO-2004112831 | A2 | 12/2004 |
| WO | WO-2004112831 | A3 | 12/2004 |

(56) References Cited

FOREIGN PATENT DOCUMENTS

| | | | |
|---|---|---|---|
| WO | WO-05028658 | A2 | 3/2005 |
| WO | WO-05028658 | A3 | 3/2005 |
| WO | WO-2005028658 | A2 | 3/2005 |
| WO | WO-2005062820 | A2 | 7/2005 |
| WO | WO-2006051069 | A2 | 5/2006 |
| WO | WO-2007044024 | A2 | 4/2007 |
| WO | WO-2007044024 | A3 | 4/2007 |
| WO | WO-2007126810 | A2 | 11/2007 |
| WO | WO-2007126810 | A3 | 11/2007 |
| WO | WO-2007146057 | A2 | 12/2007 |
| WO | WO-2007146057 | A3 | 12/2007 |
| WO | WO-08156681 | A3 | 12/2008 |
| WO | WO-2008147496 | A2 | 12/2008 |
| WO | WO-2008147496 | A3 | 12/2008 |
| WO | WO-2008156681 | A2 | 12/2008 |
| WO | WO-2008156778 | A2 | 12/2008 |
| WO | WO-2008156778 | A3 | 12/2008 |
| WO | WO-2008157583 | A1 | 12/2008 |
| WO | WO-09008921 | A3 | 1/2009 |
| WO | WO-09008921 | A9 | 1/2009 |
| WO | WO-2009007244 | A2 | 1/2009 |
| WO | WO-2009008921 | A2 | 1/2009 |
| WO | WO-2009014919 | A2 | 1/2009 |
| WO | WO-2008156778 | A9 | 2/2009 |
| WO | WO-09128867 | A2 | 10/2009 |
| WO | WO-2009152181 | A1 | 12/2009 |
| WO | WO-2009128867 | A3 | 3/2010 |
| WO | WO-2010053573 | A2 | 5/2010 |
| WO | WO-2010053573 | A3 | 7/2010 |
| WO | WO-2011014645 | A1 | 2/2011 |
| WO | WO-2011056591 | A1 | 5/2011 |
| WO | WO-2011087839 | A1 | 7/2011 |
| WO | WO-2011126370 | A1 | 10/2011 |
| WO | WO-2011130627 | A2 | 10/2011 |
| WO | WO-2012045882 | A2 | 4/2012 |
| WO | WO-2012177924 | A2 | 12/2012 |
| WO | WO-2013032942 | A1 | 3/2013 |
| WO | WO-2013032942 | A9 | 3/2013 |
| WO | WO-2013034069 | A1 | 3/2013 |
| WO | WO-2013087945 | A2 | 6/2013 |
| WO | WO-2013148302 | A1 | 10/2013 |
| WO | WO-2014195920 | A2 | 12/2014 |
| WO | WO-2015009743 | A1 | 1/2015 |
| WO | WO-2015134488 | A1 | 9/2015 |
| WO | WO-2015142671 | A2 | 9/2015 |
| WO | WO-2015196150 | A2 | 12/2015 |
| WO | WO-2015196150 | A3 | 12/2015 |
| WO | WO-2016144933 | A1 | 9/2016 |
| WO | WO-2016207853 | A2 | 12/2016 |
| WO | WO-2017007839 | A1 | 1/2017 |
| WO | WO-2017040203 | A1 | 3/2017 |
| WO | WO-2017136575 | A1 | 8/2017 |
| WO | WO-2017143236 | A1 | 8/2017 |
| WO | WO-2019//084310 | A1 | 5/2019 |
| WO | WO-2019241579 | A1 | 12/2019 |
| WO | WO-2020033527 | A2 | 2/2020 |
| WO | WO-2020041311 | A1 | 2/2020 |
| WO | WO-2020/033527 | A3 | 3/2020 |
| WO | WO-2020163804 | A1 | 8/2020 |
| WO | WO-2020167432 | A2 | 8/2020 |
| WO | WO-2020223699 | A1 | 11/2020 |
| WO | WO-2020167432 | A3 | 12/2020 |
| WO | WO-2020264141 | A1 | 12/2020 |
| WO | WO-2021/041624 | A2 | 3/2021 |
| WO | 2021041624 | | 5/2021 |
| WO | WO-2021150874 | A1 | 7/2021 |
| WO | WO-2021195410 | A1 | 9/2021 |
| WO | WO-2021242597 | A1 | 12/2021 |

OTHER PUBLICATIONS

Wang, Weijia, et al., "Identification of Critical Residues in the Hemagglutinin and Neuraminidase of Influenza Virus H1N1pdm for Vaccine Virus Replication in Embryonated Chicken Eggs", Journal of Virology, 87(8), (2013), 4642-4649.

Wei, Kai, et al., "Influenza A Virus Acquires Enhanced Pathogenicity and Transmissibi1ity after Serial Passages in Swine", *Journal of Virology*, 88(20), (Oct. 2014), 11981-11994.

"International Application Serial No. PCT/US2020/048130, International Search Report dated Apr. 20, 2021", 9 pgs.

"International Application Serial No. PCT/US2020/048130, Written Opinion dated Apr. 20, 2021", 9 pgs.

"International Application Serial No. PCT/US2020/048130, International Preliminary Report on Patentability dated Mar. 10, 2022", 11 pgs.

"European Application Serial No. 20768781.5, Response to Communication pursuant to Rules 161 and 162 filed Oct. 17, 2022", 17 pgs.

Result 1, NCBI Blast nucleotide search of SEQ ID NO:3, database "nr"; Result 4, NCBI Blast nucleotide search of SEQ ID NO:4, database "nr", (Jul. 22, 2006), 1 pgs.

Result 2, NCBI Blast nucleotide search of SEQ ID NO:5, database "nr"; Result 4, NCBI Blast nucleotide search of SEQ ID NO:6, database "nr", (Jul. 22, 2006), 6 pgs.

Results 1, NCBI Blast nucleotide search of SEQ ID NO:7, database "nr"; Result 1, NCBI Blast nucleotide search of SEQ ID NO:8, database "nr", (Jul. 23, 2006), 8 pgs.

Result 17, NCBI Blast nucleotide search of SEQ ID No:2, database "nr", (Jul. 18, 2006), 3 pgs.

Result 7, NCBI Blast nucleotide search of SEQ ID: 1, database "nr", (Jul. 18, 2006), 3 pgs.

FLUMISTTM Package Insert Templte, [Online]. Retrieved from the Internet: http://www.fda.gov/downloads/BiologicsBloodVaccinesIVaccines/ApprovedProducts/UCM294307.pdf, (Mar. 1, 2012), 26 pgs.

"1.A.32 The Type B Influenza Virus NB Channel (NB-C) Family", Transport Protein Database, (University of California, San Diego, The Sailer Laboratory Bioinformatics Group) [online}. http://www.web.archive.org/web/200301311055254/http://tcdb.ucsd.edu/tcdb/tcfamilybrowse.php?tcname=1.A.32, (Archived Jan. 31, 2003), 1 pg.

"U.S. Appl. No. 10/855,975 Response filed Aug. 28, 2007 to Final Office Action dated Jun. 28, 2007", 16 pgs.

"2018-19 ACIP Background—Immunogenicity, Efficacy, and Effectiveness of Influenza Vaccines", [online]. [archived on Dec. 3, 2018]. Retrieved from the Internet: <URL: https://web.archive.org/web/20181203190316/https://www.cdc.gov/flu/professionals/acip/2018-2019/background/immunogenicity.htm>, (updated Aug. 23, 2018), 5 pgs.

"Final O.A dated Jun. 28, 2007", 5 pgs.

"Application Serial No. 04809419.7, Office Action dated Sep. 9, 2009", 3 pgs.

"U.S. Appl. No. 09/834,095, Advisory Action dated Jan. 8, 2004", 3 pgs.

"U.S. Appl. No. 09/834,095, Final Office Action dated Aug. 26, 2003", 12 pgs.

"U.S. Appl. No. 09/534,095, Non-Final Office Action dated Nov. 4, 2002", 12 pgs.

"U.S. Appl. No. 09/834,095, Notice of Allowance dated Sep. 27, 2004", 13 pgs.

"U.S. Appl. No. 09/834,095, Office Action dated Apr. 20, 2004", 11 pgs.

"U.S. Appl. No. 09/834,095, Response filed Feb. 4, 2003 to Office Action dated Nov. 4, 2002", 14 pgs.

"U.S. Appl. No. 09/834,095, Response filed Jun. 12, 2003 to Restriction Requirement dated Apr. 22, 2003", 2 pgs.

"U.S. Appl. No. 09/834,095, Response filed Jun. 18, 2004 to Office Action dated Apr. 20, 2004", 11 pgs.

"U.S. Appl. No. 09/834,095, Response filed Aug. 1, 2002 to Restriction Requirement dated Jul. 1, 2002", 3 pgs.

"U.S. Appl. No. 09/834,095, Response filed Nov. 26, 2003 to Final Office Action dated Aug. 26, 2003", 10 pgs.

"U.S. Appl. No. 09/834,095, Restriction Requirement dated Apr. 22, 2003", 5 pgs.

"U.S. Appl. No. 09/834,095, Restriction Requirement dated Jul. 1, 2002", 9 pgs.

"U.S. Appl. No. 09/834,095, Supplemental Amendment filed Aug. 4, 2004", 7 pgs.

(56) References Cited

OTHER PUBLICATIONS

"U.S. Appl. No. 10/081,170, Advisory Action dated Sep. 27, 2004", 3 pgs.
"U.S. Appl. No. 10/081,170, Final Office Action dated Apr. 12, 2006", 7 pgs.
"U.S. Appl. No. 10/081,170, Final Office Action dated Jul. 13, 2004", 8 pgs.
"U.S. Appl. No. 10/081,170, Non Final Office Action dated Jan. 15, 2004", 9 pgs.
"U.S. Appl. No. 10/081,170, Non Final Office Action dated Feb. 8, 2005", 9 pgs.
"U.S. Appl. No. 10/081,170, Non Final Office Action dated Aug. 24, 2005", 9 pgs.
"U.S. Appl. No. 10/081,170, Notice of Allowance dated Sep. 18, 2006", 8 pgs.
"U.S. Appl. No. 10/081,170, Preliminary Amendment filed May 20, 2003", 2 pgs.
"U.S. Appl. No. 10/081,170, Preliminary Amendment filed Jun. 6, 2002", 1 pg.
"U.S. Appl. No. 10/081,170, Response filed Jan. 24, 2006 to Non Final Office Action dated Aug. 24, 2005", 11 pgs.
"U.S. Appl. No. 10/081,170, Response filed Apr. 12, 2004 to Non Final Office Action dated Jan. 15, 2004", 12 pgs.
"U.S. Appl. No. 10/081,170, Response filed Jun. 8, 2005 to Non Final Office Action dated Feb. 8, 2005", 11 pgs.
"U.S. Appl. No. 10/081,170, Response filed Aug. 17, 2006 to Final Office Action dated Apr. 12, 2006", 9 pgs.
"U.S. Appl. No. 10/081,170, Response filed Sep. 13, 2004 to Final Office Action dated Jul. 13, 2004", 10 pgs.
"U.S. Appl. No. 10/081,170, Response filed Oct. 10, 2003 to Restriction Requirement dated Sep. 10, 2003", 3 pgs.
"U.S. Appl. No. 10/081,170, Restriction Requirement dated Sep. 10, 2003", 4 pgs.
"U.S. Appl. No. 10/353,856, Final Office Action dated Jun. 1, 2006", 10 pgs.
"U.S. Appl. No. 10/353,856, Non-Final Office Action dated Sep. 30, 2005", 9 pgs.
"U.S. Appl. No. 10/353,856, Non-Final Office Action dated Dec. 16, 2004", 11 pgs.
"U.S. Appl. No. 10/353,856, Notice of Allowance dated Oct. 18, 2006", 9 pgs.
"U.S. Appl. No. 10/353,856, Preliminary Amendment filed May 20, 2003", 2 pgs.
"U.S. Appl. No. 10/353,856, PTO Response to 312 Amendment dated Mar. 8, 2007", 2 pgs.
"U.S. Appl. No. 10/353.856, Response filed Feb. 28, 2006 to Non-Final Office Action dated Sep. 30, 2005", 10 pgs.
"U.S. Appl. No. 10/353,856, Response filed Apr. 7, 2005 to Non-Final Office Action dated Dec. 16, 2004", 10 pgs.
"U.S. Appl. No. 10/353,856, Response filed Aug. 17, 2006 to Final Office Action dated Jun. 1, 2006", 11 pgs.
"U.S. Appl. No. 10/353,856, Response filed Oct. 8, 2004 to Restriction Requirement dated Sep. 10, 2004", 2 pgs.
"U.S. Appl. No. 10/353,856, Restriction Requirement dated Sep. 10, 2004", 5 pgs.
"U.S. Appl. No. 10/353,856, Supplemental Amendment filed Jan. 9, 2007", 4 pgs.
"U.S. Appl. No. 10/353,856, Supplemental Preliminary Amendment filed Jun. 23, 2003", 4 pgs.
"U.S. Appl. No. 10/827,995, Final Office Action dated Nov. 15, 2006", 10 pgs.
"U.S. Appl. No. 10/827,995, Non-Final Office Action dated Jun. 2, 2006", 15 pgs.
"U.S. Appl. No. 10/827,995, Non-Final Office Action dated Oct. 25, 2007", 7 pgs.
"U.S. Appl. No. 10/827,995, Notice of Allowance dated Feb. 17, 2009", 9 pgs.
"U.S. Appl. No. 10/827,995, Notice of Allowance dated Jul. 2, 2008", 9 pgs.
"U.S. Appl. No. 10/827,995, Notice of Allowance dated Oct. 17, 2008", 7 pgs.
"U.S. Appl. No. 10/827,995, Notice of Non-Compliant Amendment dated Jul. 25, 2007", 4 pgs.
"U.S. Appl. No. 10/827,995, Proposed Examiner's Amendment dated Jun. 5, 2008", 6 pgs.
"U.S. Appl. No. 10/827,995, Response filed Mar. 3, 2008 to Office Action dated Oct. 25, 2007", 10 pgs.
"U.S. Appl. No. 10/827,995, Response filed May 14, 2007 Final Office Action dated Nov. 15, 2006", 16 pgs.
"U.S. Appl. No. 10/827,995, Response filed Aug. 13, 2007 to Notice of Non-Compliant Amendment dated Jul. 25, 2007", 16 pgs.
"U.S. Appl. No. 10/827,995, Response filed Aug. 17, 2006 Non-Final Office Action dated Jun. 2, 2006", 15 pgs.
"U.S. Appl. No. 10/855,875 , Response filed May 17, 2012 to Non Final Office Action dated Mar. 15, 2012", 15 pgs.
"U.S. Appl. No. 10/855,875, Final Office Action dated Mar. 11, 2008", FOAR, 20 Pgs.
"U.S. Appl. No. 10/855,875, Final Office Action dated Aug. 2, 2006", 34 pgs.
"U.S. Appl. No. 10/855,875, Final Office Action dated Dec. 10, 2010", 15 pgs.
"U.S. Appl. No. 10/855,875, Non Final Office Action dated Mar. 15, 2012", 15 pgs.
"U.S. Appl. No. 10/855,875, Non-Final Office Action dated Feb. 19, 2010", 7 pgs.
"U.S. Appl. No. 10/855,875, Non-Final Office Action dated May 3, 2007", 13 pgs.
"U.S. Appl. No. 10/855,875, Non-Final Office Action dated Aug. 7, 2009", 32 pgs.
"U.S. Appl. No. 10/855,875, Non-Final Office Action dated Nov. 6, 2008", 12 pgs.
"U.S. Appl. No. 10/855,875, Non-Final Office Action dated Nov. 30, 2005", 13 pgs.
"U.S. Appl. No. 10/855,875, Notice of Allowance dated Mar. 4, 2013", 8 pgs.
"U.S. Appl. No. 10/855,875, Preliminary Amendment filed Feb. 2, 2007", 14 pgs.
"U.S. Appl. No. 10/855,875, Response filed Jan. 29, 2007 to Final Office Action dated Aug. 2, 2007", 14 pgs.
"U.S. Appl. No. 10/855,875, Response filed Mar. 18, 2011 to Final Office Action dated Dec. 10, 2010", 15 pgs.
"U.S. Appl. No. 10/855,875, Response filed Aug. 17, 2010 to Non Final Office Action dated Feb. 19, 2010", 20 pgs.
"U.S. Appl. No. 10/855,875, Response filed Dec. 7, 2009 to Non Final Office Action dated Aug. 7, 2009", 15 pgs.
"U.S. Appl. No. 10/855,875, Response filed Mar. 31, 2009 to Non Final Office Action dated Nov. 6, 2008", 14 pgs.
"U.S. Appl. No. 10/855,875, Response filed May 1, 2006 Non-Final Office Action dated Nov. 30, 2005", 13 pgs.
"U.S. Appl. No. 10/855,875, Response filed Aug. 18, 2008 to final Office Action dated Mar. 11, 2008", 15 pgs.
"U.S. Appl. No. 10/855,875, Response filed Sep. 20, 2005 to Restriction Requirement dated Jul. 26, 2005", 4 pgs.
"U.S. Appl. No. 10/855,875, Restriction Requirement dated Dec. 23, 2011", 9 pgs.
"U.S. Appl. No. 10/855,875, Restriction Requirement dated Jul. 26, 2005", 9 pgs.
"U.S. Appl. No. 10/855,975, Advisory Action dated Sep. 6, 2006", 3 pgs.
"U.S. Appl. No. 10/855,975, Advisory Action dated Sep. 13, 2007", 3 pgs.
"U.S. Appl. No. 10/855,975, Advisory Action dated Dec. 24, 2008", 4 pgs.
"U.S. Appl. No. 10/855,975, Final Office Action dated May 17, 2006", 7 pgs.
"U.S. Appl. No. 10/855,975, Final Office Action dated Jun. 28, 2007", 7 pgs.
"U.S. Appl. No. 10/855,975, Final Office Action dated Aug. 7, 2008", 5 pgs.
"U.S. Appl. No. 10/855,975, Non-Final Office Action dated Jan. 4, 2008", 10 pgs.

(56) References Cited

OTHER PUBLICATIONS

"U.S. Appl. No. 10/855,975, Non-Final Office Action dated Jan. 19, 2007", 7 pgs.
"U.S. Appl. No. 10/855,975, Non-Final Office Action dated May 29, 2009", 5 pgs.
"U.S. Appl. No. 10/855,975, Non-Final Office Action dated Nov. 30, 2005", 11 pgs.
"U.S. Appl. No. 10/855,975, Notice of Allowance dated Dec. 16, 2009", 19 pgs.
"U.S. Appl. No. 10/855,975, Response filed Jan. 29, 2009 to Advisory Action dated Dec. 24, 2008", 15 pgs.
"U.S. Appl. No. 10/855,975, Response filed Feb. 28, 2006 to Non-Final Office Action dated Nov. 30, 2005", 15 pgs.
"U.S. Appl. No. 10/855,975, Response filed Apr. 3, 2008 to Non Final Office Action dated Jan. 4, 2008", 16 pgs.
"U.S. Appl. No. 10/855,975, Response filed Apr. 19, 2007 to Non-Final Office Action dated Jan. 19, 2007", 16 pgs.
"U.S. Appl. No. 10/855,975, Response filed Aug. 13, 2009 to Non Final Office Action dated May 29, 2009", 19 pgs.
"U.S. Appl. No. 10/855,975, Response filed Aug. 17, 2006 to Final Office Action dated May 17, 2006", 13 pgs.
"U.S. Appl. No. 10/855,975, Response filed Aug. 28, 2007 to Final Office Action dated Jun. 28, 2007", 15 pgs.
"U.S. Appl. No. 10/855,975, Response filed Sep. 28, 2005 to Restriction Requirement dated Jul. 12, 2005", 3 pgs.
"U.S. Appl. No. 10/855,975, Response filed Dec. 11, 2008 to Final Office Action dated Aug. 7, 2008", 14 pgs.
"U.S. Appl. No. 10/855,975, Restriction Requirement dated Jul. 12, 2005", 8 pgs.
"U.S. Appl. No. 10/855,875, Response filed Nov. 2, 2007 to Office Action dated May 3, 2007", 16 pgs.
"U.S. Appl. No. 11/043,768 Non-Final Office Action dated Sep. 27, 2010", 8 pgs.
"U.S. Appl. No. 11/043,768, Final Office Action dated Jun. 27, 2008", 8 pgs.
"U.S. Appl. No. 11/043,768, Non-Final Office Action dated Feb. 23, 2010", 6 pgs.
"U.S. Appl. No. 11/043,768, Non-Final Office Action dated Feb. 23, 2009", 7 pgs.
"U.S. Appl. No. 11/043,768, Non-Final Office Action dated Nov. 28, 2007", 9 pgs.
"U.S. Appl. No. 11/043,768, Notice of Allowance dated Jun. 29, 2011", 12 pgs.
"U.S. Appl. No. 11/043,768, Response filed May 2, 2011 to Final Office Action dated Feb. 3, 2011", 11 pgs.
"U.S. Appl. No. 11/043,768, Response filed Jun. 15, 2010 to Non Final Office Action dated Feb. 23, 2010", 9 pgs.
"U.S. Appl. No. 11/043,768, Response filed Jun. 23, 2009 to Non-Final Office Action dated Feb. 23, 2009", 9 pgs.
"U.S. Appl. No. 11/043,768, Response filed Sep. 13, 2007 to Restriction Requirement dated Mar. 13, 2007", 10 pgs.
"U.S. Appl. No. 11/043,768, Response filed Oct. 26, 2010 to Non Final Office Action dated Sep. 27, 2010", 11 pgs.
"U.S. Appl. No. 11/043,768, Response filed Dec. 12, 2008 to Final Office Action dated Jun. 27, 2008", 9 pgs.
"U.S. Appl. No. 11/043,768, Response filed Mar. 10, 2008 to Office Action dated Nov. 28, 2007", 12 pgs.
"U.S. Appl. No. 11/043,768, Restriction Requirement dated Mar. 13, 2007", 9 pgs.
"U.S. Appl. No. 11/043,786, Final Office Action dated Feb. 3, 2011", 10 pgs.
"U.S. Appl. No. 11/283,498, Non Final Office Action dated Sep. 3, 2009", 5 pgs.
"U.S. Appl. No. 11/283,498, Non Final Office Action dated Jul. 9, 2007", 7 pgs.
"U.S. Appl. No. 11/283,498, Non-Final Office Action dated Jan. 23, 2008", 20 pgs.
"U.S. Appl. No. 11/283,498, Non-Final Office Action dated Apr. 29, 2010", 10 pgs.
"U.S. Appl. No. 11/283,498, Notice of Allowance dated Feb. 23, 2011", 9 pgs.
"U.S. Appl. No. 11/283,498, Response filed Jan. 4, 2010 to Non Final Office Action dated Sep. 3, 2009", 12 pgs.
"U.S. Appl. No. 11/283,498, Response filed Oct. 28, 2010 to Non Final Office Action dated Apr. 29, 2010", 13 pgs.
"U.S. Appl. No. 11/283,498, Response filed Nov. 7, 2007 to Office Action dated Jul. 9, 2007", 17 pgs.
"U.S. Appl. No. 11/283,498, Response filed Apr. 16, 2007 to Restriction Requirement dated Oct. 16, 2006", 17 pgs.
"U.S. Appl. No. 11/283,498, Response filed Jul. 22, 2008 to Non Final Office Action dated Jan. 23, 2008", 12 pgs.
"U.S. Appl. No. 11/283,498, Restriction Requirement dated Oct. 16, 2006", 6 pgs.
"U.S. Appl. No. 11/283,498, Supplemental Amendment Response to Non Final Office Action dated Oct. 28, 2010", 11 pgs.
"U.S. Appl. No. 11/509,249, Final Office Action dated Jun. 12, 2008", 5 pgs.
"U.S. Appl. No. 11/509,249, Non Final Office Action with Restriction Requirement dated Aug. 24, 2007", 8 pgs.
"U.S. Appl. No. 11/509,249, Notice of Allowance dated Apr. 9, 2009", 7 pgs.
"U.S. Appl. No. 11/509,249, Notice of Allowance dated Nov. 17, 2008", 4 pgs.
"U.S. Appl. No. 11/509,249, Response filed Feb. 20, 2008 to Non Final Office Action dated Aug. 24, 2007", 11 pgs.
"U.S. Appl. No. 11/509,249, Response filed Oct. 6, 2008 to Office Action dated Jun. 12, 2008", 11 pgs.
"U.S. Appl. No. 11/644,179 , Response filed Oct. 21, 2013 to Final Office Action dated May 21, 2013", 8 pgs.
"U.S. Appl. No. 11/644,179, Final Office Action dated May 21, 2013", 11 pgs.
"U.S. Appl. No. 11/644,179, Final Office Action dated Jul. 2, 2010", 8 pgs.
"U.S. Appl. No. 11/644,179, Non Final Office Action dated Nov. 29, 2012", 19 pgs.
"U.S. Appl. No. 11/644,179, Non Final Office Action dated Dec. 8, 2009", 7 pgs.
"U.S. Appl. No. 11/644,179, Notice of Allowance dated Nov. 1, 2013", 11 pgs.
"U.S. Appl. No. 11/644.179, Preliminary Amendment filed Dec. 22, 2006", 5 pgs.
"U.S. Appl. No. 11/644.179, Response filed Jan. 30, 2008 to Restriction Requirement dated Oct. 30, 2007", 5 pgs.
"U.S. Appl. No. 11/644,179, Response filed Apr. 8, 2010 to Non Final Office Action dated Dec. 8, 2009", 8 pgs.
"U.S. Appl. No. 11/644,179, Response filed Aug. 17, 2010 to Final Office Action dated Jul. 2, 2010", 8 pgs.
"U.S. Appl. No. 11/644,179, Restriction Requirement dated Oct. 30, 2007", 7 pgs.
"U.S. Appl. No. 11/644,179, Supplemental Preliminary Amendment filed Feb. 6, 2008", 6 pgs.
"U.S. Appl. No. 11/644,179. Response filed Feb. 20, 2013 to Non Final Office Action dated Nov. 29, 2012", 10 pgs.
"U.S. Appl. No. 11/654,863 Final Office Action dated Jul. 17, 2017", 11 pgs.
"U.S. Appl. No. 11/654,863 Restriction Requirement dated Sep. 3, 2010", 5 pgs.
"U.S. Appl. No. 11/654,863, Appeal Brief filed Apr. 30, 2014", 22 pgs.
"U.S. Appl. No. 11/654,863, Appeal Decision dated Aug. 3, 2016", 11 pgs.
"U.S. Appl. No. 11/654,863, Decision on Pre-Appeal Brief Request dated Dec. 5, 2013", 2 pgs.
"U.S. Appl. No. 11/654,863, Declaration of Dr. Heinz Feldmann dated Jan. 9, 2018", 2 pgs.
"U.S. Appl. No. 11/654,863, Declaration of Yoshihiro Kawaoka dated Apr. 18, 2012", 2 pgs.
"U.S. Appl. No. 11/654,863, Examiner's Answer to Appeal Brief dated Jun. 18, 2014", 10 pgs.
"U.S. Appl. No. 11/654,863, Final Office Action dated Jul. 11, 2013", 9 pgs.

(56) References Cited

OTHER PUBLICATIONS

"U.S. Appl. No. 11/654,863, Final Office Action dated Sep. 12, 2018", 12 pgs.
"U.S. Appl. No. 11/654,863, Final Office Action dated Oct. 25, 2011", 9 pgs.
"U.S. Appl. No. 11/654,863, Non Final Office Action dated Feb. 11, 2013", 10 pgs.
"U.S. Appl. No. 11/654,863, Non Final Office Action dated Mar. 29, 2018", 12 pgs.
"U.S. Appl. No. 11/654,863, Non Final Office Action dated Jun. 27, 2011", 9 pgs.
"U.S. Appl. No. 11/654,863, Non Final Office Action dated Dec. 2, 2010", 8 pgs.
"U.S. Appl. No. 11/654,863, Non Final Office Action dated Dec. 21, 2016", 14 pgs.
"U.S. Appl. No. 11/654,863, Pre-Appeal Brief Request filed Nov. 11, 2013", 5 pgs.
"U.S. Appl. No. 11/654,863, Preliminary Amendment filed May 7, 2007", 15 pgs.
"U.S. Appl. No. 11/654,863, Reply Brief filed Aug. 18, 2014", 6 pgs.
"U.S. Appl. No. 11/654,863, Response filed Jan. 17, 2018 to Final Office Action dated Jul. 17, 2017", 9 pgs.
"U.S. Appl. No. 11/654,863, Response filed Apr. 18, 2012 to Final Office Action dated Oct. 25, 2011", 8 pgs.
"U.S. Appl. No. 11/654,863, Response filed Jun. 2, 2011 to Non Final Office Action dated Dec. 2, 2010", 6 pgs.
"U.S. Appl. No. 11/654,863, Response filed Jun. 7, 2013 to Non Final Office Action dated Feb. 11, 2013", 10 pgs.
"U.S. Appl. No. 11/654,863, Response filed Jun. 21, 2017 to Non Final Office Action dated Dec. 21, 2016", 11 pgs.
"U.S. Appl. No. 11/654,863, Response filed Jul. 9, 2018 to Non Final Office Action dated Mar. 29, 2018", 10 pgs.
"U.S. Appl. No. 11/654,863, Response filed Sep. 28, 2010 to Restriction Requirement dated Sep. 3, 2010", 6 pgs.
"U.S. Appl. No. 11/654,863, Response filed Oct. 6, 2011 to Non Final Office Action dated Jun. 27, 2011", 9 pgs.
"U.S. Appl. No. 11/729,557, Advisory Action dated May 9, 2011", 3 pgs.
"U.S. Appl. No. 11/729,557, Advisory Action dated Dec. 24, 2014", 3 pgs.
"U.S. Appl. No. 11/729,557, Final Office Action dated Feb. 2, 2011", 14 pgs.
"U.S. Appl. No. 11/729,557, Final Office Action dated Aug. 20, 2009", 13 pgs.
"U.S. Appl. No. 11/729,557, Final Office Action dated Sep. 12, 2014", 14 pgs.
"U.S. Appl. No. 11/729,557, Non Final Office Action dated Feb. 18, 2015", 13 pgs.
"U.S. Appl. No. 11/729,557, Non Final Office Action dated Feb. 26, 2014", 16 pgs.
"U.S. Appl. No. 11/729,557, Non-Final Office Action dated Jan. 30, 2009", 20 pgs.
"U.S. Appl. No. 11/729,557, Non-Final Office Action dated Feb. 22, 2010", 16 pgs.
"U.S. Appl. No. 11/729,557, Non-Final Office Action dated Aug. 23, 2010", 15 pgs.
"U.S. Appl. No. 11/729,557, Notice of Allowance dated Sep. 30, 2015", 11 pgs.
"U.S. Appl. No. 11/729,557, Respons filed Jun. 22, 2010 to Non Final Office Action dated Feb. 22, 2010", 33 pgs.
"U.S. Appl. No. 11/729,557, Response filed Apr. 27, 2011 to Final Office Action dated Feb. 2, 2011", 14 pgs.
"U.S. Appl. No. 11/729,557, Response filed Apr. 30, 2009 to Non Final Office Action dated Jan. 30, 2009", 18 pgs.
"U.S. Appl. No. 11/729,557, Response filed May 22, 2014 to Non Final Office Action dated Feb. 26, 2014", 13 pgs.
"U.S. Appl. No. 11/729,557, Response filed May 28, 2008 to Restriction Requirement dated Nov. 28, 2007", 13 pgs.
"U.S. Appl. No. 11/729,557, Response filed Jun. 22, 2010 to Non Final Office Action dated Feb. 22, 2010", 16 pgs.
"U.S. Appl. No. 11/729,557, Response filed Jun. 22, 2015 to non Final Office Action dated Feb. 18, 2015", 13 pgs.
"U.S. Appl. No. 11/729,557, Response filed Oct. 28, 2010 to Non Final Office Action dated Aug. 23, 2010", 13 pgs.
"U.S. Appl. No. 11/729,557, Response filed Dec. 1, 2009 to Final Office Action dated Aug. 26, 2009", 16 pgs.
"U.S. Appl. No. 11/729,557, Response filed Dec. 11, 2014 to Final Office Action dated Sep. 12, 2014", 15 pgs.
"U.S. Appl. No. 11/729,557, Restriction Requirement dated Nov. 28, 2007", 9 pgs.
"U.S. Appl. No. 11/810,956, Final Office Action dated Mar. 22, 2010", 8 pgs.
"U.S. Appl. No. 11/810,956, Non-Final Office Action dated Aug. 11, 2009", 9 pgs.
"U.S. Appl. No. 11/810,956, Response filed Jan. 11, 2010 to Non Final Office Action dated Aug. 11, 2009", 8 pgs.
"U.S. Appl. No. 11/810,956, Response filed Apr. 23, 2009 to Restriction Requirement dated Mar. 23, 2009", 6 pgs.
"U.S. Appl. No. 11/810,956, Restriction Requirement dated Mar. 23, 2009", 6 pgs.
"U.S. Appl. No. 12/058,389, Advisory Action dated Jan. 2, 2013", 2 pgs.
"U.S. Appl. No. 12/058,389, Final Office Action dated Jan. 22, 2010", 8 pgs.
"U.S. Appl. No. 12/058,389, Final Office Action dated Nov. 14, 2012", 7 pgs.
"U.S. Appl. No. 12/058,389, Non Final Office Action dated Aug. 10, 2012", 5 pgs.
"U.S. Appl. No. 12/058,389, Non Final Office Action dated Dec. 8, 2011", 8 pgs.
"U.S. Appl. No. 12/058,389, Non-Final Office Action dated Apr. 13, 2009", 12 pgs.
"U.S. Appl. No. 12/058,389, Notice of Allowability dated Mar. 22, 2013", 8 pgs.
"U.S. Appl. No. 12/058,389, Notice of Allowance dated Feb. 20, 2013", 9 pgs.
"U.S. Appl. No. 12/058,389, Preliminary Amendment filed Jun. 23, 2008", 7 pgs.
"U.S. Appl. No. 12/058,389, Respnse filed Nov. 6, 2012 to Non Final Office Action dated Aug. 10, 2012", 7 pgs.
"U.S. Appl. No. 12/058,389, Response filed Feb. 6, 2009 to Restriction Requirement dated Dec. 3, 2008", 7 pgs.
"U.S. Appl. No. 12/058,389, Response filed Apr. 10, 2012 to Non Final Office Action dated Dec. 8, 2011", 7 pgs.
"U.S. Appl. No. 12/058,389, Response filed Jun. 16, 2010 to Final Office Action dated Jan. 22, 2010", 6 pgs.
"U.S. Appl. No. 12/058,389, Response filed Oct. 13, 2009 to Non Final Office Action dated Apr. 13, 2009", 9 pgs.
"U.S. Appl. No. 12/058,389, Response filed Dec. 18, 2012 to Non Final Office Action dated Nov. 14, 2012", 7 pgs.
"U.S. Appl. No. 12/058,389, Restriction Requirement dated Dec. 3, 2008", 7 pgs.
"U.S. Appl. No. 12/113,690, Final Office Action dated Apr. 15, 2011", 10 pgs.
"U.S. Appl. No. 12/113,690, Non-Final Office Action dated Nov. 10, 2010", 11 pgs.
"U.S. Appl. No. 12/113,690, Notice of Allowability dated Aug. 19, 2013", 9 pgs.
"U.S. Appl. No. 12/113,690, Notice of Allowance dated Jul. 18, 2013", 14 pgs.
"U.S. Appl. No. 12/113,690, Preliminary Amendment filed Jul. 31, 2008", 14 pgs.
"U.S. Appl. No. 12/113,690, Response filed Jun. 23, 2011 to Final Office Action dated Apr. 15, 2011", 17 pgs.
"U.S. Appl. No. 12/113,690, Response filed Aug. 5, 2010 to Restriction Requirement dated Apr. 6, 2010", 14 pgs.
"U.S. Appl. No. 12/113,690, Response filed Dec. 22, 2010 to Non Final Office Action dated Nov. 10, 2010", 19 pgs.
"U.S. Appl. No. 12/113,690, Restriction Requirement dated Apr. 6, 2010", 10 pgs.

(56) References Cited

OTHER PUBLICATIONS

"U.S. Appl. No. 12/139,183, Non Final Office Action dated Jan. 6, 2011", 12 pgs.
"U.S. Appl. No. 12/139,183, Non-Final Office Action dated Jan. 4, 2010", 6 pgs.
"U.S. Appl. No. 12/139,183, Non-Final Office Action dated Jul. 13, 2010", 15 pgs.
"U.S. Appl. No. 12/139,183, Notice of Allowance dated Jun. 27, 2011", 11 pgs.
"U.S. Appl. No. 12/139,183, Preliminary Amendment filed Sep. 11, 2008", 17 pgs.
"U.S. Appl. No. 12/139,183, Response filed Mar. 22, 2011 to Non Final Office Action dated Jan. 6, 2011", 21 pgs.
"U.S. Appl. No. 12/139,183, Response filed Apr. 12, 2010 to Non Final Office Action dated Jan. 4, 2010", 17 pgs.
"U.S. Appl. No. 12/139,183, Response filed Aug. 18, 2009 to Restriction Requirement dated Jul. 24, 2009", 16 pgs.
"U.S. Appl. No. 12/139,183, Response filed Sep. 21, 2010 to Non Final Office Action dated Jul. 12, 2010", 21 pgs.
"U.S. Appl. No. 12/139,183, Restriction Requirement dated Jul. 24, 2009", 12 pgs.
"U.S. Appl. No. 12/214,414, Advisory Action dated Feb. 2, 2016", 5 pgs.
"U.S. Appl. No. 12/214,414, Advisory Action dated Apr. 14, 2015", 6 pgs.
"U.S. Appl. No. 12/214,414, Advisory Action dated Oct. 21, 2011", 5 pgs.
"U.S. Appl. No. 12/214,414, Examiner Interview Summary dated Dec. 11, 2015", 3 pgs.
"U.S. Appl. No. 12/214,414, Final Office Action dated Jan. 20, 2015", 28 pgs.
"U.S. Appl. No. 12/214,414, Final Office Action dated Aug. 2, 2011", 7 pgs.
"U.S. Appl. No. 12/214,414, Final Office Action dated Nov. 18, 2015", 17 pgs.
"U.S. Appl. No. 12/214,414, Non Final Office Action dated Jun. 12, 2014", 28 pgs.
"U.S. Appl. No. 12/214,414, Non Final Office Action dated Dec. 10, 2010", 6 pgs.
"U.S. Appl. No. 12/214,414, Non-Final Office Action dated Mar. 2, 2010", 9 pgs.
"U.S. Appl. No. 12/214,414, Notice of Allowance dated Jun. 7, 2016", 18 pgs.
"U.S. Appl. No. 12/214,414, Response filed Jan. 19, 2016 to Final Office Action dated Nov. 18, 2015", 14 pgs.
"U.S. Appl. No. 12/214,414, Response filed Feb. 18, 2016 to Final Office Action dated Nov. 18, 2015", 14 pgs.
"U.S. Appl. No. 12/214,414, Response filed Mar. 26, 2015 to Final Office Action dated Jan. 20, 2015", 13 pgs.
"U.S. Appl. No. 12/214,414, Response filed May 3, 2011 to Non Final Office Action dated Dec. 10, 2010", 12 pgs.
"U.S. Appl. No. 12/214,414, Response filed Jul. 20, 2015 to Advisory Action dated Apr. 15, 2015", 14 pgs.
"U.S. Appl. No. 12/214,414, Response filed Aug. 31, 2010 to Non Final Office Action dated Mar. 2, 2010", 11 pgs.
"U.S. Appl. No. 12/214,414, Response filed Oct. 3, 2011 to Non Final Office Action dated Aug. 2, 2011", 9 pgs.
"U.S. Appl. No. 12/214,414, Response filed Oct. 14, 2014 to Non Final Office Action dated Jun. 12, 2014", 16 pgs.
"U.S. Appl. No. 12/214,414, Response filed Dec. 21, 2011 to Advisory Action dated Oct. 21, 2011", 10 pgs.
"U.S. Appl. No. 12/245,296, Final Office Action dated Jul. 11, 2013", 15 pgs.
"U.S. Appl. No. 12/245,296, Final Office Action dated Dec. 17, 2010", 16 pgs.
"U.S. Appl. No. 12/245,296, Non Final Office Action dated Mar. 25, 2013", 14 pgs.
"U.S. Appl. No. 12/245,296, Non-Final Office Action dated Jun. 1, 2010", 13 pgs.
"U.S. Appl. No. 12/245,296, Notice of Allowance dated Aug. 1, 2014", 10 pgs.
"U.S. Appl. No. 12/245,296, Preliminary Amendment dated Jan. 28, 2009", 14 pgs.
"U.S. Appl. No. 12/245,296, Response filed Jan. 8, 2013 to Final Office Action dated Jul. 11, 2013", 10 pgs.
"U.S. Appl. No. 12/245,296, Response filed Apr. 8, 2010 to Restriction Requirement dated Mar. 9, 2010", 6 pgs.
"U.S. Appl. No. 12/245,296, Response filed May 17, 2011 to Final Office Action dated Dec. 17, 2010", 10 pgs.
"U.S. Appl. No. 12/245,296, Response filed Jun. 7, 2013 to Non Final Office Action dated Mar. 25, 2013", 9 pgs.
"U.S. Appl. No. 12/245,296, Response filed Oct. 1, 2010 to Non Final Office Action dated Jun. 1, 2010", 12 pgs.
"U.S. Appl. No. 12/245,296, Restriction Requirement dated Mar. 9, 2010", 6 pgs
"U.S. Appl. No. 12/467,492, Restriction Requirement dated Nov. 22, 2010", 6 pgs
"U.S. Appl. No. 12/470.287, Response filed Jan. 23, 2012 to Non Final Office Action dated Jul. 7, 2011", 13 pgs.
"U.S. Appl. No. 12/470,287 , Response filed May 31, 2012, to Final Office Action dated Apr. 3, 2012", 14 pgs.
"U.S. Appl. No. 12/470,287, Corrected Notice of Allowability dated Sep. 11, 2012", 2 pgs.
"U.S. Appl. No. 12/470,287, Final Office Action dated Apr. 3, 2012", 7 pgs.
"U.S. Appl. No. 12/470,287, Non Final Office Action dated Jul. 22, 2011", 9 pgs.
"U.S. Appl. No. 12/470,287, Notice of Allowance dated Jun. 19, 2012", 5 pgs.
"U.S. Appl. No. 12/470,287, Response filed Apr. 28, 2011 to Restriction Requirement dated Dec. 29, 2010", 8 pgs.
"U.S. Appl. No. 12/470,287, Restriction Requirement dated Dec. 29, 2010", 6 pgs.
"U.S. Appl. No. 12/854,578 , Response filed Oct. 1, 2012 to Non Final Office Action dated Jun. 29, 2012", 10 pgs.
"U.S. Appl. No. 12/854,578, Final Office Action dated Nov. 29, 2012", 8 pgs.
"U.S. Appl. No. 12/854,578, Non Final Office Action dated Jun. 29, 2012", 8 pgs.
"U.S. Appl. No. 12/854,578, Notice of Allowance dated Apr. 10, 2013", 6 pgs.
"U.S. Appl. No. 12/854,578, PTO Response to 312 Amendment dated Jul. 18, 2013", 2 pgs.
"U.S. Appl. No. 12/854,578. Response filed Feb. 28, 2013 to Final Office Action dated Nov. 29, 2012", 8 pgs.
"U.S. Appl. No. 12/854,578, Restriction Requirement dated Apr. 6, 2012", 6 pgs.
"U.S. Appl. No. 12/912,411, Advisory Action dated Feb. 5, 2014", 3 pgs.
"U.S. Appl. No. 12/912,411, Examiner Interview Summary dated Feb. 11, 2014", 2 pgs.
"U.S. Appl. No. 12/912,411, Final Office Action dated Jan. 14, 2015", 10 pgs.
"U.S. Appl. No. 12/912,411, Final Office Action dated Oct. 25, 2013", 11 pgs.
"U.S. Appl. No. 12/912,411, Non Final Office Action dated Jun. 7, 2013", 8 pgs.
"U.S. Appl. No. 12/912,411, Non Final Office Action dated Sep. 24, 2014", 11 pgs.
"Application U.S. Appl. No. 12/912,411, Notice of Allowability dated May 20, 2015", 7 pgs.
"U.S. Appl. No. 12/912,411, Notice of Allowance dated Apr. 8, 2015", 11 pgs.
"U.S. Appl. No. 12/912,411, Response filed Jan. 27, 2014 to Final Office Action dated Oct. 25, 2013", 11 pgs.
"U.S. Appl. No. 12/912,411, Response filed Feb. 18, 2013 to Restriction Requirement dated Oct. 17, 2012", 9 pgs.
"U.S. Appl. No. 12/912,411, Response filed Feb. 25, 2014 to Final Office Action dated Oct. 25, 2013", 11 pgs.
"U.S. Appl. No. 12/912,411, Response filed Mar. 16, 2015 to Final Office Action dated Jan. 14, 2015", 9 pgs.

(56) References Cited

OTHER PUBLICATIONS

"U.S. Appl. No. 12/912,411, Response filed Dec. 31, 2014 to Non Final Office Action dated Sep. 24, 2014", 12 pgs.
"U.S. Appl. No. 12/912,411, Restriction Requirement dated Oct. 17, 2012", 9 pgs.
"U.S. Appl. No. 13/070,110 Response filed Feb. 14, 2017 to Final Office Action dated Sep. 14, 2016", 8 pgs.
"U.S. Appl. No. 13/070,110, Advisory Action dated Mar. 3, 2017", 5 pgs.
"U.S. Appl. No. 13/070,110, Examiner Interview Summary dated Jan. 16, 2018", 3 pgs.
"U.S. Appl. No. 13/070,110, Final Office Action dated Apr. 3, 2015", 18 pgs.
"U.S. Appl. No. 13/070,110, Final Office Action dated Jun. 12, 2013", 7 pgs.
"U.S. Appl. No. 13/070,110, Final Office Action dated Sep. 14, 2016", 12 pgs.
"U.S. Appl. No. 13/070.110, Non Final Office Action dated Jul. 21, 2017", 14 pgs.
"U.S. Appl. No. 13/070.110, Non Final Office Action dated Oct. 2, 2014", 24 pgs.
"U.S. Appl. No. 13/070.110, Non Final Office Action dated Dec. 11, 2015", 19 pgs.
"U.S. Appl. No. 13/070.110, Non Final Office Action dated Dec. 21, 2012", 7 pgs.
"U.S. Appl. No. 13/070,110, Notice of Allowance dated Mar. 26, 2018", 6 pgs.
"U.S. Appl. No. 13/070,110, Notice of Allowance dated Jul. 20, 2018", 7 pgs.
"U.S. Appl. No. 13/070,110, Preliminary Amendment filed Jun. 6, 2011", 4 pgs.
"U.S. Appl. No. 13/070,110, PTO Response to Rule 312 Communication dated Aug. 15, 2018", 2 pgs.
"U.S. Appl. No. 13/070,110, Response filed Jan. 22, 2018 to Non Final Office Action dated Jul. 21, 2017", 10 pgs.
"U.S. Appl. No. 13/070,110, Response filed Mar. 22, 2013 to Non Final Office Action dated Dec. 21, 2012", 8 pgs.
"U.S. Appl. No. 13/070,110, Response filed May 27, 2016 to Non Final Office Action dated Dec. 11, 2015", 13 pgs.
"U.S. Appl. No. 13/070,110, Response filed Jun. 20, 2017 to Advisory Action dated Mar. 3, 2017", 13 pgs.
"U.S. Appl. No. 13/070,110, Response filed Sep. 3, 2014 to Restriction Requirement dated Jul. 8, 2014", 7 pgs.
"U.S. Appl. No. 13/070,110, Response filed Oct. 2, 2015 to Final Office Action dated Apr. 3, 2015", 11 pgs.
"U.S. Appl. No. 13/070,110, Response filed Nov. 12, 2013 to Final Office Action dated Jun. 12, 2013", 9 pgs.
"Application U.S. Appl. No. 13/070,110, Response filed Dec. 30, 2014 to Non Final Office Action dated Oct. 2, 2014", 13 pgs.
"U.S. Appl. No. 13/070,110, Restriction Requirement dated Jul. 8, 2014", 7 pgs.
"U.S. Appl. No. 13/113,244, Final Office Action dated Feb. 27, 2014", 8 pgs.
"U.S. Appl. No. 13/113,244, Non Final Office Action dated Jul. 5, 2013", 6 pgs.
"U.S. Appl. No. 13/113,244, Non Final Office Action dated Oct. 1, 2012", 7 pgs.
"U.S. Appl. No. 13/113,244, Notice of Allowance dated Jun. 30, 2014", 9 pgs.
"U.S. Appl. No. 13/113,244, Preliminary Amendment filed Aug. 11, 2011", 4 pgs.
"U.S. Appl. No. 13/113,244, Response filed Jan. 30, 2012 to Restriction Requirement dated Oct. 31, 2011", 10 pgs.
"U.S. Appl. No. 13/113,244, Response filed Feb. 20, 2013 to Non Final Office Action dated Oct. 1, 2012", 12 pgs.
"U.S. Appl. No. 13/113,244, Response filed Jun. 13, 2014 to Final Office Action dated Feb. 27, 2014", 6 pgs.
"U.S. Appl. No. 13/113,244, Response filed Oct. 31, 2013 to Non Final Office Action dated Jul. 5, 2013", 12 pgs.
"U.S. Appl. No. 13/113.244, Restriction Requirement dated Oct. 31, 2011", 8 pgs.
"U.S. Appl. No. 13/127.951, Advisory Action dated Jul. 16, 2014", 3 pgs.
"U.S. Appl. No. 13/127,951, Final Office Action dated Apr. 9, 2014", 23 pgs.
"U.S. Appl. No. 13/127.951, Non Final Office Action dated Sep. 26, 2013", 18 pgs.
"U.S. Appl. No. 13/127,951, Notice of Allowance dated Jul. 20, 2015", 7 pgs.
"U.S. Appl. No. 13/127,951, Preliminary Amendment filed May 5, 2011", 7 pgs.
"U.S. Appl. No. 13/127,951, PTO Response to Rule 312 Communication dated Oct. 23, 2015", 2 pgs.
"U.S. Appl. No. 13/127,951, Response filed Mar. 18, 2014 to Non Final Office Action dated Sep. 26, 2013", 14 pgs.
"U.S. Appl. No. 13/127,951, Response filed Jul. 7, 2014 to Final Office dated Apr. 9, 2014", 10 pgs.
"Application U.S. Appl. No. 13/127.951, Response filed Aug. 30, 2013 to Restriction Requirement dated Apr. 30, 2013", Aug. 30, 2013.
"U.S. Appl. No. 13/127,951, Response filed Oct. 9, 2014 to Advisory Action dated Jul. 16, 2014", 10 pgs.
"U.S. Appl. No. 13/127,951, Restriction Requirement dated Apr. 30, 2013", 15 pgs.
"U.S. Appl. No. 13/594,611, Final Office Action dated Aug. 15, 2014", 7 pgs.
"U.S. Appl. No. 13/594,611, Non Final Office Action dated Apr. 24, 2014", 9 pgs.
"U.S. Appl. No. 13/594,611, Notice of Allowance dated Jan. 13, 2015", 7 pgs.
"U.S. Appl. No. 13/594,611, PTO Response to Rule 312 Communication dated Apr. 16, 2015", 2 pgs.
"U.S. Appl. No. 13/594,611, Response filed Feb. 25, 2014 to Restriction Requirement dated Jan. 27, 2014", 8 pgs.
"U.S. Appl. No. 13/594,611, Response filed Jul. 7, 2014 to Non Final Office Action dated Apr. 24, 2014", 9 pgs.
"U.S. Appl. No. 13/594,611, Response filed Dec. 15, 2014 to Final Office Action dated Aug. 15, 2014", 10 pgs
"U.S. Appl. No. 13/594,611, Restriction Requirement dated Jan. 27, 2014", 8 pgs.
"U.S. Appl. No. 14/332,121, Non Final Office Action dated May 16, 2016", 9 pgs.
"U.S. Appl. No. 14/332,121, Notice of Allowance dated Feb. 15, 2017", 10 pgs.
"U.S. Appl. No. 14/332.121, Notice of Allowance dated Jun. 15, 2017", 8 pgs.
"U.S. Appl. No. 14/332,121, Notice of Allowance dated Oct. 11, 2017", 8 pgs.
"U.S. Appl. No. 14/332,121, Preliminary Amendment filed Sep. 30, 2014", 5 pgs.
"U.S. Appl. No. 14/332,121, Response filed Jan. 29, 2016 to Restriction Requirement dated Jul. 30, 2015", 9 pgs.
"U.S. Appl. No. 14/332,121, Response filed Sep. 7, 2017 to Notice of Allowability dated Jun. 15, 2017", 8 pgs.
"U.S. Appl. No. 14/332,121, Response filed Oct. 11, 2016 to Non Final Office Action dated May 16, 2016", 9 pgs.
"U.S. Appl. No. 14/332,121, Restriction Requirement dated Jul. 30, 2015", 9 pgs.
"U.S. Appl. No. 14/332.121, Supplemental Amendment filed Jan. 23, 2017", 10 pgs.
"U.S. Appl. No. 14/528.997, Advisory Action dated Aug. 9, 2017", 3 pgs.
"U.S. Appl. No. 14/528.997, Final Office Action dated Feb. 10, 2017", 9 pgs.
"Application U.S. Appl. No. 14/528,997, Non Final Office Action dated Jun. 16, 2016", 12 pgs.
"U.S. Appl. No. 14/528,997, Non Final Office Action dated Jun. 29, 2018", 7 pgs.
"U.S. Appl. No. 14/528,997, Notice of Allowance dated Mar. 8, 2019", 7 pgs.
"U.S. Appl. No. 14/528,997, PTO Response to Rule 312 Communication dated Jun. 19, 2019", 2 pgs.

(56) References Cited

OTHER PUBLICATIONS

"U.S. Appl. No. 14/528,997, Response filed Mar. 16, 2016 to Restriction Requirement dated Sep. 16, 2015", 11 pgs.
"U.S. Appl. No. 14/528,997, Response filed Jul. 27, 2017 to Final Office Action dated Feb. 10, 2017", 11 pgs.
"U.S. Appl. No. 14/528,997, Response filed Oct. 10, 2016 to Non Final Office Action dated Jun. 16, 2016", 12 pgs.
"U.S. Appl. No. 14/528,997, Response filed Nov. 16, 2018 to Non Final Office Action dated Jun. 29, 2018", 11 pgs.
"U.S. Appl. No. 14/528,997, Restriction Requirement dated Sep. 16, 2015", 8 pgs.
"U.S. Appl. No. 14/699,213, Advisory Action dated Mar. 7, 2018", 3 pgs.
"U.S. Appl. No. 14/699,213, Final Office Action dated Dec. 1, 2017", 11 pgs.
"U.S. Appl. No. 14/699,213, Non Final Office Action dated Jun. 2, 2017", 12 pgs.
"U.S. Appl. No. 14/699,213, Non-Final Office Action dated Jan. 11, 2019", 10 pgs.
"U.S. Appl. No. 14/699,213, Notice of Allowance dated Jul. 30, 2019", 8 pgs.
"U.S. Appl. No. 14/699,213, Preliminary Amendment filed Apr. 30, 2015", 8 pgs.
"U.S. Appl. No. 14/699,213, PTO Response to Rule 312 Communication dated Nov. 19, 2019", 2 pgs.
"U.S. Appl. No. 14/699,213, Response filed Feb 15 2017 to Restriction Requirement dated Aug. 15, 2016", 9 pgs.
"U.S. Appl. No. 14/699,213, Response filed Feb. 27, 2018 to Final Office Action dated Dec. 1, 2017", 34 pgs.
"U.S. Appl. No. 14/699,213, Response filed Aug. 22, 2017 to Non Final Office Action dated Jun. 2, 2017", 12 pgs.
"U.S. Appl. No. 14/699.213, Response filed Apr. 11, 2019 to Non-Final Office Action dated Jan. 11, 2019", 13 pgs.
"U.S. Appl. No. 14/699,213, Restriction Requirement dated Aug. 15, 2016", 10 pgs.
"U.S. Appl. No. 14/745,236, Advisory Action dated Nov. 15, 2017", 2 pgs.
"U.S. Appl. No. 14/745,236, Final Office Action dated Aug. 25, 2017", 16 pgs.
"U.S. Appl. No. 14/745,236, Non Final Office Action dated Feb. 2, 2017", 14 pgs.
"U.S. Appl. No. 14/745,236, Notice of Allowability dated Jul. 5, 2018", 4 pgs.
"U.S. Appl. No. 14/745,236, Notice of Allowance dated Feb. 5, 2018"9 pgs.
"U.S. Appl. No. 14/745,236, PTO Response to Rule 312 Communication dated Jul. 10, 2018", 2 pgs.
"U.S. Appl. No. 14/745,236, Response filed May 2, 2017 to Non Final Office Action dated Feb. 2, 2017", 10 pgs.
"U.S. Appl. No. 14/745,236, Response filed Nov. 6, 2017 to Final Office Action dated Aug. 25, 2017", 12 pgs.
"U.S. Appl. No. 14/745,236, Response filed Dec. 14, 2017 to Final Office Action dated Aug. 25, 2017", 12 pgs.
"U.S. Appl. No. 14/745,236, Response filed Dec. 23, 2016 to Restriction Requirement dated Sep. 23, 2016", 8 pgs.
"U.S. Appl. No. 14/745,236, Restriction Requirement dated Sep. 23, 2016", 8 pgs.
"U.S. Appl. No. 14/816.807, Non Final Office Action dated Oct. 3, 2017", 7 pgs.
"U.S. Appl. No. 14/816.807, Notice of Allowance dated Apr. 20, 2018", 8 pgs.
"U.S. Appl. No. 14/816.807, Preliminary Amendment filed Aug. 11, 2015", 8 pgs.
"U.S. Appl. No. 14/816,807, PTO Response to Rule 312 Communication dated Jul. 6, 2018", 2 pgs.
"U.S. Appl. No. 14/816,807, Response filed Jan. 3, 2018 to Non Final Office Action dated Oct. 3, 2017", 8 pgs.
"U.S. Appl. No. 14/816,807, Response filed May 1, 2017 to Restriction Requirement dated Nov. 1, 2016", 9 pgs.
"U.S. Appl. No. 14/816.807, Restriction Requirement dated Nov. 1, 2016", 8 pgs.
"U.S. Appl. No. 14/919.431, Preliminary Amendment filed Jan. 4, 2016", 8 pgs.
"U.S. Appl. No. 15/000,851, Non Final Office Action dated Jan. 26, 2017"15 pgs.
"U.S. Appl. No. 15/000,851, Notice of Allowance dated Nov. 8, 2017", 9 pgs.
"U.S. Appl. No. 15/000,851, Preliminary Amendment filed Feb. 3, 2016", 3 pgs.
"U.S. Appl. No. 15/000,851, Response filed Jul. 26, 2017 to Non Final Office Action dated Jan. 26, 2017", 16 pgs.
"U.S. Appl. No. 15/000,851, Response filed Oct. 12, 2016 to Restriction Requirement dated May 12, 2016", 11 pgs.
"U.S. Appl. No. 15/000,851, Restriction Requirement dated May 12, 2016", 6 pgs.
"U.S. Appl. No. 15/000,851, Supplemental Amendment filed Apr. 4, 2016", 10 pgs.
"U.S. Appl. No. 15/170,556, Final Office Action dated Jul. 30, 2019", 6 pgs.
"U.S. Appl. No. 15/170,556, Non Final Office Action dated Feb. 8, 2019", 11 pgs.
"U.S. Appl. No. 15/170,556, Non Final Office Action dated Jul. 27, 2018", 10 pgs.
"U.S. Appl. No. 15/170,556, Notice of Allowability dated Jan. 29, 2020", 4 pgs.
"U.S. Appl. No. 15/170, 556, Notice of Allowance dated Nob. 27, 2019", 8 pgs.
"U.S. Appl. No. 15/170,556, Preliminary Amendment filed Aug. 22, 2016", 9 pgs.
"U.S. Appl. No. 15/170.556, Response filed Apr. 5, 2018 to Restriction Requirement dated Feb. 16, 2018", 8 pgs.
"U.S. Appl. No. 15/170,556, Response filed Oct. 29, 2018 to Non Final Office Action dated Jul. 27, 2018", 9 pgs.
"U.S. Appl. No. 15/170,556, Response filed Nov. 18, 2019 to Final Office Action dated Jul. 30, 2019", 8 pgs.
"U.S. Appl. No. 15/170,556, Response filed Apr. 15, 2019 to Non Final Office Action dated Feb. 8, 2019", 9 pgs.
"U.S. Appl. No. 15/170,556, Restriction Requirement dated Feb. 16, 2018", 7 pgs.
"U.S. Appl. No. 15/170,556. PTO Response to Rule 312 Communication dated Apr. 3, 2020", 2 pgs.
"U.S. Appl. No. 15/203,581, Examiners Interview Summary dated Sep. 11, 2017", 1 pg.
"U.S. Appl. No. 15/203,581, Notice of Allowance dated Sep. 11, 2017", 12 pgs.
"U.S. Appl. No. 15/203,581, Preliminary Amendment filed Sep. 22, 2016", 4 pgs.
"U.S. Appl. No. 15/203,581, PTO Response to Rule 312 Communication dated Dec. 27, 2017", 2 pgs.
"U.S. Appl. No. 15/203,581, Response filed Aug. 15, 2017 to Restriction Requirement dated Jun. 16, 2017", 8 pgs.
"U.S. Appl. No. 15/203,581, Restriction Requirement dated Jun. 16, 2017", 8 pgs.
"U.S. Appl. No. 15/204,381, Advisory Action dated Feb. 7, 2019", 3 pgs.
"U.S. Appl. No. 15/204,381, Advisory Action dated Aug. 25, 2020", 3 pgs.
"U.S. Appl. No. 15/204,381, Final Office Action dated Feb. 27, 2020", 21 pgs.
"U.S. Appl. No. 15/204,381, Final Office Action dated Jul. 9, 2021", 14 pgs.
"U.S. Appl. No. 15/204,381, Final Office Action dated Sep. 21, 2018", 10 pgs.
"U.S. Appl. No. 15/204,381, Non Final Office Action dated Feb. 23, 2018", 10 pgs.
"U.S. Appl. No. 15/204,381, Non Final Office Action dated Jun. 13, 2019", 23 pgs.
"U.S. Appl. No. 15/204,381, Non Final Office Action Oct. 6, 2020", 15 pgs.
"U.S. Appl. No. 15/204,381, Preliminary Amendment filed Oct. 25, 2016", 74 pgs.

(56) References Cited

OTHER PUBLICATIONS

"U.S. Appl. No. 15/204,381, Response filed Jan. 2, 2019 to Final Office Action dated Sep. 21, 2018", 6 pgs.
"U.S. Appl. No. 15/204,381, Response filed Jan. 19, 2018 to Restriction Requirement dated Oct. 13, 2017", 6 pgs.
"U.S. Appl. No. 15/204,381, Response filed Apr. 6, 2021 to Non Final Office Action dated Oct. 6, 2020", 12 pgs.
"U.S. Appl. No. 15/204,381, Response filed May 30, 2018 to Non Final Office Action dated Feb. 23, 2018", 9 pgs.
"U.S. Appl. No. 15/204,381, Response filed Jul. 27, 2020 to Final Office Action dated Feb. 27, 2020", 11 pgs.
"U.S. Appl. No. 15/204,381, Response filed Aug. 27, 2020 to Advisory Action dated Aug. 25, 2020", 2 pgs.
"U.S. Appl. No. 15/204,381, Response filed Nov. 14, 2019 to Non Final Office Action dated Jun. 13, 2019", 9 pgs.
"U.S. Appl. No. 15/204,381, Response filed Mar. 21, 2019 to Advisory Action dated Feb. 7, 2019"7 pgs.
"U.S. Appl. No. 15/204,381, Restriction Requirement dated Oct. 13, 2017", 10 pgs.
"U.S. Appl. No. 15/227,147, Preliminary Amendment filed Oct. 10, 2016", 7 pgs.
"U.S. Appl. No. 15/227,147, Restriction Requirement dated Jan. 19, 2017", 14 pgs.
"U.S. Appl. No. 15/247,006 Response filed Jun. 4, 2018 to Final Office Action dated Feb. 4, 2019", 7 pgs.
"U.S. Appl. No. 15/247,006, Examiner Interview Summary dated Nov. 27, 2017", 4 pgs.
"U.S. Appl. No. 15/247,006, Final Office Action dated Feb. 4, 2019", 8 pgs.
"U.S. Appl. No. 15/247,006, Non Final Office Action dated Apr. 20, 2018", 7 pgs.
"U.S. Appl. No. 15/247,006, Non Final Office Action dated Sep. 8, 2017", 8 pgs.
"U.S. Appl. No. 15/247,006, Notice of Allowance dated Jun. 24, 2019", 7 pgs.
"U.S. Appl. No. 15/247,006, Notice of Allowance dated Oct. 8, 2019", 7 pgs.
"U.S. Appl. No. 15/247,006, Preliminary Amendment filed Nov. 22, 2016", 3 pgs.
"U.S. Appl. No. 15/247,006, Response filed May 3, 2017 to Restriction Requirement dated Mar. 17, 2017", 12 pgs.
"U.S. Appl. No. 15/247,006, Response filed Oct. 22, 2018 to Non Final Office Action dated Apr. 20, 2018", 14 pgs.
"U.S. Appl. No. 15/247,006, Response filed Dec. 7, 2017 to Non Final Office Action dated Sep. 8, 2017", 13 pgs.
"U.S. Appl. No. 15/247,006, Restriction Requirement dated Mar. 17, 2017", 9 pgs.
"U.S. Appl. No. 15/292,595, Non Final Office Action dated Sep. 25, 2017", 13 pgs.
"U.S. Appl. No. 15/292,595, Notice of Allowance dated Feb. 28, 2018", 9 pgs.
"U.S. Appl. No. 15/292,595, Notice of Allowance dated Jun. 20, 2018", 9 pgs.
"U.S. Appl. No. 15/292,595, Preliminary Amendment filed Dec. 27, 2016", 5 pgs.
"U.S. Appl. No. 15/292,595, Response filed Dec. 22, 2017 to Non Final Office Action dated Sep. 25, 2017", 9 pgs.
"U.S. Appl. No. 15/436,245, Corrected Notice of Allowability dated Nov. 10, 2021", 2 pgs.
"U.S. Appl. No. 15/436,245, Final Office Action dated Mar. 24, 2021", 9 pgs.
"U.S. Appl. No. 15/436,245, Final Office Action dated Nov. 18, 2019", 9 pgs.
"U.S. Appl. No. 15/436,245, Non Final Office Action dated Apr. 19, 2019", 9 pgs.
"U.S. Appl. No. 15/436,245, Non Final Office Action dated Sep. 4, 2020", 9 pgs.
"U.S. Appl. No. 15/436,245, Notice of Allowance dated Aug. 3, 2021", 9 pgs.
"U.S. Appl. No. 15/436,245, Preliminary Amendment filed May 5, 2017", 3 pgs.
"U.S. Appl. No. 15/436,245, PTO Response to Rule 312 Communication dated Oct. 27, 2021", 2 pgs.
"U.S. Appl. No. 15/436,245, Response filed Apr. 27, 2020 to Final Office Action dated Nov. 18, 2019", 10 pgs.
"U.S. Appl. No. 15/436,245, Response filed Jun. 24, 2021 to Final Office Action dated Mar. 24, 2021", 11 pgs.
"U.S. Appl. No. 15/436,245, Response filed Dec. 4, 2020 to Non Final Office Action dated Sep. 4, 2020", 12 pgs.
"U.S. Appl. No. 15/436,245, Response filed Jul. 29, 2019 to Non-Final Office Action dated Apr. 19, 2019", 11 pgs
"U.S. Appl. No. 15/436,245, Restriction Requirement dated Oct. 11, 2018", 9 pgs.
"U.S. Appl. No. 15/436,245, Supplemental Amendment filed Jul. 19, 2021", 10 pgs.
"U.S. Appl. No. 15/593,039, Non Final Office Action dated Feb. 6, 2018", 8 pgs.
"U.S. Appl. No. 15/593,039, Notice of Allowance dated Jul. 11, 2018", 5 pgs.
"U.S. Appl. No. 15/593,039, Preliminary Amendment filed Jul. 25, 2017", 7 pgs.
"U.S. Appl. No. 15/593,039, PTO Response to Rule 312 Communication dated Oct. 9, 2018", 2 pgs.
"U.S. Appl. No. 15/593,039, Response filed Apr. 30, 2018 to Non Final Office Action dated Feb. 4, 2018", 8 pgs.
"U.S. Appl. No. 15/593,039, Response filed Dec. 18, 2017 to Restriction Requirement dated Oct. 18, 2017", 8 pgs.
"U.S. Appl. No. 15/593,039, Restriction Requirement dated Oct. 18, 2017", 6 pgs.
"U.S. Appl. No. 15/593,039, Supplemental Preliminary Amendment filed Jul. 26, 2017", 4 pgs.
"U.S. Appl. No. 15/865,364, Notice of Allowance dated Nov. 15, 2018", 7 pgs.
"U.S. Appl. No. 15/865,364, Preliminary Amendment filed Apr. 10, 2018", 10 pgs.
"U.S. Appl. No. 15/905,454, Preliminary Amendment filed Nov. 2, 2018", 5 pgs.
"U.S. Appl. No. 15/905,454, Restriction Requirement dated Jan. 3, 2019", 6 pgs.
"U.S. Appl. No. 15/915,486 Supplemental Preliminary Amendment filed Mar. 12, 2019", 5 pgs.
"U.S. Appl. No. 15/915,486, Advisory Action dated Jun. 28, 2021", 7 pgs.
"U.S. Appl. No. 15/915,486, Advisory Action dated Jul. 13, 2020", 3 pgs.
"U.S. Appl. No. 15/915,486, Final Office Action dated Jan. 11, 2022", 9 pgs.
"U.S. Appl. No. 15/915,486, Final Office Action dated Jan. 27, 2020", 8 pgs.
"U.S. Appl. No. 15/915,486, Final Office Action dated Feb. 1, 2021", 8 pgs.
"U.S. Appl. No. 15/915,486, Non Final Office Action dated Sep. 2, 2021", 8 pgs.
"U.S. Appl. No. 15/915,486, Non Final Office Action dated Sep. 15, 2020", 10 pgs.
"U.S. Appl. No. 15/915,486, Non Final Office Action dated Oct. 24, 2019", 10 pgs.
"U.S. Appl. No. 15/915,486, Response filed Jan. 3, 2020 to Non Final Office Action dated Oct. 24, 2019", 8 pgs.
"U.S. Appl. No. 15/915, Response filed Jun. 1, 2021 to Final Office Action dated Feb. 1, 2021", 10 pgs.
"U.S. Appl. No. 15/915,486, Response filed Jun. 23, 2020 to Final Office Action dated Jan. 27, 2020", 7 pgs.
"U.S. Appl. No. 15/915,486, Response filed Jul. 27, 2021 to Advisory Action dated Jun. 28, 2021", 10 pgs.
"U.S. Appl. No. 15/915,486, Response filed Nov. 30, 2021 to Non Final Office Action dated Sep. 2, 2021", 6 pgs.
"U.S. Appl. No. 15/915,486, Response filed Dec. 21, 2020 to Non Final Office Action dated Sep. 15, 2020", 7 pgs.
"U.S. Appl. No. 15/915,486, Restriction Requirement dated Aug. 5, 2019", 9 pgs.

(56) References Cited

OTHER PUBLICATIONS

"U.S. Appl. No. 15/966,092, Interview Summary dated Mar. 2, 2021", 2 pgs.
"U.S. Appl. No. 15/966,092, Non Final Office Action dated Jun. 26, 2020", 22 pgs.
"U.S. Appl. No. 15/966,092, Notice of Allowance dated Feb. 11, 2021", 5 pgs.
"U.S. Appl. No. 15/966,092, Response filed Oct. 26, 2020 to Non Final Office Action dated Jun. 26, 2020", 9 pgs.
"U.S. Appl. No. 16/046,250, Non Final Office Action dated Mar. 6, 2020", 10 pgs.
"U.S. Appl. No. 16/046,250, Notice of Allowance dated Jun. 15, 2020", 9 pgs.
"U.S. Appl. No. 16/046,250, Response filed Jun. 3, 2020 to Non Final Office Action dated Mar. 6, 2020", 10 pgs.
"Application U.S. Appl. No. 16/046,250, Response filed Oct. 25, 2019 to Restriction Requirement dated Jul. 25, 2019", 9 pgs.
"U.S. Appl. No. 16/046,250, Restriction Requirement dated Jul. 25, 2019", 7 pgs.
"U.S. Appl. No. 16/170,321, Advisory Action dated Feb. 23, 2021", 3 pgs.
"U.S. Appl. No. 16/170,321, Corrected Notice of Allowability dated Sep. 29, 2021", 2 pgs.
"U.S. Appl. No. 16/170,321, Final Office Action dated Dec. 14, 2020", 13 pgs.
"U.S. Appl. No. 16/170,321, Non Final Office Action dated Apr. 13, 2020", 13 pgs.
"U.S. Appl. No. 16/170,321, Notice of Allowance dated Aug. 4, 2021", 10 pgs.
"U.S. Appl. No. 16/170,321, PTO Response to Rule 312 Communication dated Sep. 21, 2021", 2 pgs.
"U.S. Appl. No. 16/170,321, Response filed Jan. 24, 2020 to Restriction Requirement dated Nov. 27, 2019", 9 pgs.
"U.S. Appl. No. 16/170,321, Response filed Jan. 26, 2021 to Final Office Action dated Dec. 14, 2020", 9 pgs.
"U.S. Appl. No. 16/170,321, Response filed Mar. 9, 2021 to Advisory Action dated Feb. 23, 2021", 9 pgs.
"U.S. Appl. No. 16/170,321, Response filed Sep. 11, 2020 to Non Final Office Action dated Apr. 13, 2020", 9 pgs.
"U.S. Appl. No. 16/170,321, Restriction Requirement dated Nov. 27, 2019", 10 pgs.
"U.S. Appl. No. 16/173,605 Preliminary Amendment filed Nov. 18, 2019", 5 pgs.
"U.S. Appl. No. 16/173,605, Final Office Action dated Jul. 27, 2020", 7 pgs.
"U.S. Appl. No. 16/173,605, Non Final Office Action dated Mar. 13, 2020", 10 pgs.
"U.S. Appl. No. 16/173,605, Notice of Allowance dated Jan. 13, 2021", 6 pgs.
"U.S. Appl. No. 16/173,605, Response filed Jul. 13, 2020 to Non Final Office Action dated Mar. 13, 2020", 13 pgs.
"U.S. Appl. No. 16/173,605, Response filed Dec. 21, 2020 to Final Office Action dated Jul. 27, 2020", 7 pgs.
"U.S. Appl. No. 16/545,761, Final Office Action dated Oct. 20, 2021", 10 pgs.
"U.S. Appl. No. 16/545.761, Non Final Office Action dated Feb. 11, 2021", 12 pgs.
"U.S. Appl. No. 16/545.761, Notice of Allowance dated Mar. 9, 2022", 6 pgs.
"U.S. Appl. No. 16/545.761, Preliminary Amendment filed Feb. 7, 2020", 9 pgs.
"U.S. Appl. No. 16/545.761, PTO Response to Rule 312 Communication dated May 13, 2022", 2 pgs.
"U.S. Appl. No. 16/545,761, Response filed Feb. 16, 2022 to Final Office Action dated Oct. 20, 2021", 10 pgs.
"U.S. Appl. No. 16/545,761, Response filed Jun. 30, 2021 to Non Final Office Action Feb. 11, 2021", 13 pgs.
"U.S. Appl. No. 16/547,262, Non Final Office Action dated Mar. 31, 2021", 13 pgs.
"U.S. Appl. No. 16/547.262, Notice of Allowance dated Jul. 22, 2021", 7 pgs.
"U.S. Appl. No. 16/547,262, Response filed Jun. 30, 2021 to Non Final Office Action dated Mar. 31, 2021", 12 pgs.
"U.S. Appl. No. 16/547,262, Response filed Dec. 17, 2020 to Restriction Requirement dated Jul. 17, 2020", 12 pgs.
"U.S. Appl. No. 16/547,262, Restriction Requirement dated Jul. 17, 2020", 6 pgs.
"U.S. Appl. No. 16/694,748, Non Final Office Action dated Nov. 9, 2021", 6 pgs.
"U.S. Appl. No. 16/694,748, Notice of Allowance dated Mar. 3, 2022", 9 pgs.
"U.S. Appl. No. 16/694,748, Preliminary Amendment filed May 8, 2020", 7 pgs.
"U.S. Appl. No. 16/694,748, Response filed Feb. 9, 2022 to Non Final Office Action dated Nov. 9, 2021", 7 pgs.
"U.S. Appl. No. 16/694,748, Response filed Jul. 27, 2021 to Restriction Requirement dated Jan. 27, 2021", 8 pgs.
"U.S. Appl. No. 16/694.748, Restriction Requirement dated Jan. 27, 2021", 9 pgs.
"U.S. Appl. No. 16/749.910, Notice of Allowance dated Sep. 22, 2021", 10 pgs.
"U.S. Appl. No. 16/749,910, Response filed Jun. 17, 2021 to Restriction Requirement dated Apr. 19, 2021", 11 pgs.
"U.S. Appl. No. 16/749,910, Restriction Requirement dated Apr. 19, 2021", 9 pgs.
"U.S. Appl. No. 16/785,449, Final Office Action dated Mar. 18, 2022", 12 pgs.
"U.S. Appl. No. 16/785,449, Non Final Office Action dated Jul. 21, 2021", 9 pgs.
"U.S. Appl. No. 16/785,449, Non Final Office Action dated Sep. 22, 2022", 13 pgs.
"U.S. Appl. No. 16/785,449, Response filed Jan. 20, 2023 to Non Final Office Action dated Sep. 22, 2022", 8 pgs.
"U.S. Appl. No. 16/785,449, Response filed Jun. 27, 2022 to Final Office Action dated Mar. 18, 2022", 7 pgs.
"U.S. Appl. No. 16/785,449, Response filed Jul. 2, 2021 to Restriction Requirement dated Jun. 21, 2021", 6 pgs.
"U.S. Appl. No. 16/785,449, Response filed Dec. 17, 2021 to Non Final Office Action Jul. 21, 2021", 8 pgs.
"U.S. Appl. No. 16/785,449, Restriction Requirement dated Jun. 21, 2021", 8 pgs.
"U.S. Appl. No. 16/785,449, Final Office Action dated Mar. 22, 2023", 16 pgs.
"U.S. Appl. No. 16/865,194, Notice of Allowance dated Mar. 3, 2022", 9 pgs.
"U.S. Appl. No. 16/865,194, Response filed Dec. 20, 2021 to Restriction Requirement dated Oct. 20, 2021", 11 pgs.
"U.S. Appl. No. 16/865.194, Restriction Requirement dated Oct. 20, 2021", 7 pgs.
"U.S. Appl. No. 17/155,625, Advisory Action dated Jan. 20, 2023", 3 pgs.
"U.S. Appl. No. 17/155,625, Final Office Action dated Sep. 28, 2022", 18 pgs.
"U.S. Appl. No. 17/155,625, Non Final Office Action dated May 26, 2022", 10 pgs.
"U.S. Appl. No. 17/155,625, Notice of Allowance dated Apr. 12, 2023", 11 pgs.
"U.S. Appl. No. 17/155,625, Response filed Feb. 28, 2023 to Advisory Action dated Jan. 20, 2023", 8 pgs.
"U.S. Appl. No. 17/155,625, Response filed Aug. 29, 2022 to Non Final Office Action dated May 26, 2022", 8 pgs.
"U.S. Appl. No. 17/155,625, Response filed Dec. 28, 2022 to Final Office Action dated Sep. 28, 2022", 8 pgs.
"U.S. Appl. No. 17/155,625, Restriction Requirement dated Mar. 3, 2022", 9 pgs.
"U.S. Appl. No. 17/212,836, Non Final Office Action dated Feb. 16, 2023", 12 pgs.
"U.S. Appl. No. 17/212,836, Response filed Oct. 19, 2022 to Restriction Requirement dated Aug. 19, 2022", 6 pgs.
"U.S. Appl. No. 17/212,836, Restriction Requirement dated Aug. 19, 2022", 7 pgs.

(56) References Cited

OTHER PUBLICATIONS

"U.S. Appl. No. 17/229,001, Preliminary Amendment filed Apr. 26, 2021", 7 pgs.
"U.S. Appl. No. 17/266,049, Non Final Office Action dated Mar. 14, 2023", 12 pgs.
"U.S. Appl. No. 17/352,845, Non Final Office Action dated Dec. 16, 2022", 15 pgs.
"U.S. Appl. No. 17/578,939, Non Final Office Action dated Apr. 21, 2023", 5 pgs.
"U.S. Appl. No. 17/578,939, Preliminary Amendment filed Apr. 14, 2022", 9 pgs.
"U.S. Appl. No. 17/813,178, Preliminary Amendment filed Jan. 18, 2023", 7 pgs.
"U.S. Appl. No. 17/813,200, Preliminary Amendment filed Mar. 7, 2023", 10 pgs.
"U.S. Appl. No. 14/528,997, Preliminary Amendment filed Dec. 8, 2014", 3 pgs.
"U.S. Appl. No. 14/919,431, Restriction Requirement dated Feb. 3, 2016", 18 pgs.
"Australian Application Serial No. 2001255336, Examiners First Report dated Feb. 16, 2005", 2 pgs.
"Australian Application Serial No. 2001255336, Response filed Aug. 23, 2005 to Examiner's First Report dated Feb. 16, 2005", 10 pgs.
"Australian Application Serial No. 2003219745, Examiner's First Report dated Feb. 14, 2007", 2 pgs.
"Australian Application Serial No. 2003219745, Response filed Mar. 14, 2008 to Examiner's First Report dated Feb. 14, 2007", 24 pgs.
"Australian Application Serial No. 2004249133, First Examiner's Report dated May 5, 2008", 4 pgs.
"Australian Application Serial No. 2004249133, Response filed Mar. 30, 2009 to First Examiner's Report dated May 5, 2008", 30 pgs.
"Australian Application Serial No. 2004274860, Office Action dated May 21, 2008", 2 pgs.
"Australian Application Serial No. 2007245192, Office Action dated Aug. 25, 2011", 2 pgs.
"Australian Application Serial No. 2007245192, Response filed Feb. 28, 2012 to Office Action dated Aug. 25, 2011", 22 pgs.
"Australian Application Serial No. 2008203186, First Examiner Report dated Jan. 28, 2011", 2 pgs.
"Australian Application Serial No. 2008203186, Office Action dated Sep. 16, 2010", 1 page.
"Australian Application Serial No. 2008203186, Response filed Mar. 28, 2011 to First Examiner Report dated Jan. 28, 2011", 53 pgs.
"Australian Application Serial No. 2008203186, Response filed Aug. 29, 2011 to Official Action dated Apr. 13, 2011", 20 pgs.
"Australian Application Serial No. 2012204138, First Examiner Report dated Jul. 16, 2013", 4 pgs.
"Australian Application Serial No. 2012204138, Response filed Dec. 24, 2013 to First Examiner Report dated Jul. 16, 2013", 21 pgs.
"Australian Application Serial No. 2014202470, First Examiner Report dated Jul. 20, 2015", 2 pgs.
"Australian Application Serial No. 2014202470, Response filed Jul. 4, 2016 to Subsequent Examiners Report dated Feb. 1, 2016", 3 pgs.
"Australian Application Serial No. 2014202470, Response filed Jul. 20, 2016 to Subsequent Examiners Report dated Jul. 19, 2016", 15 pgs.
"Australian Application Serial No. 2014202470, Response filed Dec. 1, 2015 to First Examiner Report dated Jul. 20, 2015", 22 pgs.
"Australian Application Serial No. 2014202470, Subsequent Examiners Report dated Feb. 1, 2016", 2 pgs.
"Australian Application Serial No. 2014202470, Subsequent Examiners Report dated Jul. 19, 2016", 3 pgs.
"Australian Applicatino Serial No. 2014290302, First Examination Report dated Oct. 10, 2019", 4 pgs.
"Australian Application Serial No. 2014290203, Response filed Mar. 13, 2020 to First Examination Report dated Oct. 10, 2019", 16 pgs.
"Australian Application Serial No. 2014290203, Response filed Jun. 24, 2020 to Subsequent Examiners Report dated Mar. 23, 2020", 16 pgs.
"Australian Application Serial No. 2014290203, Response filed Sep. 29, 2020 to Subsequent Examiners Report dated Jul. 21, 2020", 25 pgs.
"Australian Application Serial No. 2014290203, Response filed Dec. 9, 2020 to Subsequent Examiners Report dated Oct. 6, 2020", 14 pgs.
"Australian Application Serial No. 2014290203, Subsequent Examiners Report dated Mar. 23, 2020", 6 pgs.
"Australian Application Serial No. 2014290203, Subsequent Examiners Report dated Jul. 21, 2020", 5 pgs.
"Australian Application Serial No. 2014290203, Subsequent Examiners Report dated Oct. 6, 2020", 4 pgs.
"Australian Application Serial No. 2017221444, First Examination Report dated Jul. 8, 2020", 6 pgs.
"Australian Application Serial No. 2017221444, fourth Examiners Report dated Jun. 29, 2021", 3 pgs.
"Australian Application Serial No. 2017221444, Response filed Jan. 25, 2021 to Subsequent Examiners Report dated Nov. 27, 2020", 18 pgs.
"Australian Application Serial No. 2017221444, Response filed Jun. 2, 2021 to Subsequent Examiners Report dated Feb. 24, 2021", 20 pgs.
"Australian Application Serial No. 2017221444, Response filed Jul. 6, 2021 to Fourth Examiners Report dated Jun. 29, 2021", 7 pgs.
"Australian Application Serial No. 2017221444, Response filed Nov. 13, 2020 to First Examination Report dated Jul. 8, 2020", 13 pgs.
"Australian Application Serial No. 2017221444, Subsequent Examiners Report dated Feb. 24, 2021", 4 pgs.
"Australian Application Serial No. 2017221444, Subsequent Examiners Report dated Nov. 27, 2020", 4 pgs.
"Australian Application Serial No. 2021201844, First Examination Report filed Sep. 29, 2022", 3 pgs.
"Australian Application Serial No. 2021201844, Response filed Feb. 3, 2023 to First Examination Report filed Sep. 29, 2022", Claims not amended in Response filed, 4 pgs.
"Australian Application Serial No. 2021201844, Voluntary Amendment filed Dec. 6, 2021", 17 pgs.
"Australian Application Serial No. 2021204721, First Examination Report dated Mar. 16, 2023", 6 pgs.
"Australian Application Serial No. 2008203186, Subsequent Examiner Report dated Apr. 13, 2011", 2 pgs.
"Avian Inluenza", Queensland Government—Department of Primary Industries, (Observed Feb. 22, 2003), 2 pgs.
"Avian Inluenza", http://www.iah.bbsrc.ac.uk/reports/1997/ainf.html, (Observed Feb. 22, 2003), 2 pgs.
"Brazil Application Serial No. PI 0410702-0, Office Action dated Oct. 6, 2020", (w/ English Translation), 9 pgs.
"Brazil Application Serial No. PI 0410702-0, Response filed Dec. 14, 2020 to Office Action dated Oct. 6, 2020", (w/ English Translation of Claims), 42 pgs.
"Brazil Application Serial No. PI0307679-2, Office Action dated May 16, 2017", 2 pgs.
"Brazil Application Serial No. PI0307679-2, Response filed Jul. 13, 2017 to Office Action dated May 16, 2017", 9 pgs.
"Brazilian Application Serial No. PI 0307679-2, Office Action published in Patent Gazette No. 1871 of Nov. 14, 2006", 2 pgs.
"Brazilian Application Serial No. PI 0307679-2, Petition filed Jan. 10, 2007 in response to publication dated Nov. 14, 2006", 6 pgs.
"Brazilian Application Serial No. PI 0410702-0, Office Action dated Nov. 1, 2019", (w/ English Translation), 6 pgs.
"Brazilian Application Serial No. PI 0410702-0, Response filed Feb. 6, 2020 to Office Action dated Nov. 1, 2019", (w/ English Translation of Claims), 92 pgs.
"Brazilian Application Serial No. PI0307679-2, Final Office Action dated Jul. 6, 2020", w/o English Translation, 6 pgs.
"Brazilian Application Serial No. PI0307679-2, Office Action dated May 13, 2019", (w/ English Translation), 17 pgs.
"Brazilian Application Serial No. PI0307679-2, Office Action dated Oct. 3, 2019", (w/ English Translation), 6 pgs.

(56) References Cited

OTHER PUBLICATIONS

"Brazilian Application Serial No. PI0307679-2, Office Action dated Dec. 20, 2016", 2 pgs.
"Brazilian Application Serial No. PI0307679-2, Response filed Feb. 1, 2017 to Office Action dated Dec. 20, 2016", 6 pgs.
"Brazilian Application Serial No. PI0307679-2, Response filed Aug. 16, 2019 to Office Action dated May 13, 2019", (w/ English Translation of Claims), 29 pgs.
"Brazilian Application Serial No. PI0307679-2, Response filed Dec. 11, 2019 to Office Action dated Oct. 3, 2019", w/ English Claims, 59 pgs.
"Brazilian Application Serial No. PI10410702-0, Office Action dated Feb. 23, 2012", w/ English Translation, 4 pgs.
"Brazilian Application Serial No. PI10410702-0, Office Action dated Apr. 1, 2020", (w/ English Summary), 6 pgs.
"Brazilian Application Serial No. PI10410702-0, Response filed May 7, 2012 to Office Action dated Feb. 23, 2012", w/ English Claims, 11 pgs.
"Brazilian Application Serial No. PI10410702-0, Response filed Aug. 28, 2020 to office Action dated Apr. 1, 2020", (w/ English Translation of Claims), 86 pgs.
"Canadian Application Serial No. 11/509,249, Response filed May 16, 2011 to Office Action dated Nov. 18, 2010", 15 pgs.
"Candian Application Serial No. 2,406,180, Office Action dated Sep. 9, 2008", 5 pgs.
"Canadian Application Serial No. 2,406,180, Office Action dated Nov. 10, 2011", 3 pgs.
"Canadian Application Serial No. 2,406,180, Office Action dated Nov. 23, 2009", 3 pgs.
"Canadian Application Serial No. 2,406,180, Office Action dated Dec. 10, 2010", 2 Pgs.
"Canadian Application Serial No. 2,406,180, Response filed Jan. 26, 2009 to Official Action dated Sep. 9, 2008", 22 pgs.
"Canadian Application Serial No. 2,406,180, Response filed May 7, 2012 to Office Action dated Nov. 10, 2011", 11 pgs.
"Canadian Application Serial No. 2,406,180, Response filed May 21, 2010 to Office action dated Nov. 23, 2009", 13 pgs.
"Canadian Application Serial No. 2,406,180, Response filed Jun. 14, 2011 to Office Action dated Dec. 10, 2010", 10 pgs.
"Canadian Application Serial No. 2,406,180, Response dated Jun. 10, 2011 to Office Action dated Dec. 10, 2010", 10 pgs.
"Canadian Application Serial No. 2,492,097, Office Action dated Jan. 10, 2012", 4 pgs.
"Candian Application Serial No. 2,492,097, Office Action dated Apr. 24, 2008", 3 pgs.
"Canadian Application Serial No. 2,492,097, Office Action dated Jul. 31, 2009", 3 pgs.
"Canadian Application Serial No. 2,492,097, Response filed Jan. 29, 2010 to Office Action dated Jul. 31, 2009", 13 pgs.
"Canadian Application Serial No. 492,097, Response filed May 2, 2012 to Office Action dated Jan. 10, 2012", 12 pgs.
"Canadian Application Serial No. 2,492,097, Response filed Oct. 23, 2008 to Office Action dated Apr. 24, 2008", 14 pgs.
"Canadian Application Serial No. 2,522,081, Amendment After Allowance filed Aug. 10, 2012", 3 pgs.
"Canadian Application Serial No. 2,522,081, Office Action filed Nov. 18, 2011", 11 pgs.
"Canadian Application Serial No. 2,522,081, Office Action dated Jun. 8, 2011", 2 pgs.
"Canadian Application Serial No. 2,522,081, Office Action dated Aug. 30, 2010", 2 pgs.
"Canadian Application Serial No. 2,522,081, Office Action dated Oct. 8, 2009", 6 pgs.
"Canadian Application Serial No. 2,522,081, Response filed Feb. 28, 2011 to Office Action dated Aug. 30, 2010", 10 pgs.
"Canadian Application Serial No. 2,522,081, Response filed Apr. 8, 2010 to Office Action dated Oct. 8, 2009", 30 pgs.
"Canadian Application Serial No. 2,522 081, Response filed Nov. 18, 2011 to Office Action dated Jun. 6, 2011", 11 pgs.
"Canadian Application Serial No, 2,525,953, Amendment and Response filed Feb. 1, 2017 to Office Action dated Aug. 1, 2016", 28 pgs.
"Canadian Application Serial No. 2,525,953, Non Final Office Action dated Mar. 30, 2022", 4 pgs.
"Canadian Application Serial No. 2,525,953, Office Action dated Jan. 21, 2016", 6 pgs.
"Canadian Application Serial No. 2,525,953, Office Action dated Jan. 29, 2020", 4 pgs.
"Canadian Application Serial No. 2,525,953, Office Action dated Apr. 28, 2021", 7 pgs.
"Canadian Application Serial No. 2,525,953, Office Action dated Jul. 31, 2012", 4 pgs.
"Canadian Application Serial No. 2,525,953, Office Action dated Aug. 1, 2016", 6 pgs.
"Canadian Application Serial No. 2,525,953, Office Action dated Aug. 16, 2013", 3 pgs.
"Canadian Application Serial No. 2,525,953, Office Action dated Oct. 3, 2017", 4 pgs.
"Canadian Application Serial No. 2,525,953, Office Action dated Nov. 2, 2018", 6 pgs.
"Canadian Application Serial No. 2,525,953, Office Action dated Nov. 6, 2014", 3 pgs.
"Canadian Application Serial No. 2,525,953, Office Action dated Jun. 22, 2011", 4 pgs.
"Canadian Application Serial No. 2,525,953, Office Action received Jun. 22, 2011", 4 pgs.
"Canadian Application Serial No. 2,525,953, Response filed Jan. 31, 2013 to Office Action dated Jul. 31, 2012", 11 pgs.
"Canadian Application Serial No. 2,525,953, Response filed Feb. 1, 2017 to Office Action dated Aug. 1, 2016", 28 pgs.
"Canadian Application Serial No. 2,525,953, Response filed Feb. 14, 2014 to Office Action dated Aug. 16, 2013", 16 pgs.
"Canadian Application Serial No. 2,525,953, Response filed Apr. 3, 2018 to Office Action dated Oct. 3, 2017", 46 pgs.
"Canadian Application Serial No. 2,525,953, Response filed May 1, 2015 to Office Action dated Nov. 6, 2014", 23 pgs.
"Canadian Application Serial No. 2,525,953, Response filed May 2, 2019 to Office Action dated Nov. 2, 2018", 31 pgs.
"Canadian Application Serial No. 2,525 953 Response filed May 25, 2020 to Office Action dated Jan. 29, 2020", 35 pgs.
"Canadian Application Serial No. 2,525,953, Response filed Jul. 11, 2016 to Office Action dated Jan. 21, 2016", 21 pgs.
"Canadian Application Serial No. 2,525,953, Response filed Aug. 26, 2021 to Office Action dated Apr. 28, 2021", 16 pgs.
"Canadian Application Serial No. 2,525,953, Response filed Dec. 22, 2011 to Office Action dated Jun. 22, 2011", 17 pgs.
"Canadian Application Serial No. 2,647,985, Response filed Sep. 30, 2013 to Office Action dated May 15, 2013", 20 pgs.
"Canadian Application Serial No. 2,647,985, Office Action dated may 15, 2013", 3 pgs.
"Canadian Application Serial No. 2,816,242, Office Action dated Jun. 16, 2014", 3 pgs.
"Canadian Application Serial No. 2,816,242, Office Action dated Jul. 12, 2017", 4 pgs.
"Canadian Application Serial No. 2,816,242, Office Action dated Sep. 16, 2016", 4 pgs.
"Canadian Application Serial No. 2,816,242, Office Action dated Oct. 5, 2015", 6 pgs.
"Canadian Application Serial No. 2,816,242, Response filed Jan. 3, 2018 to Office Action dated Jul. 12, 2017", 13 pgs.
"Canadian Application Serial No. 2,816,242, Response filed Mar. 10, 2017 to Office Action dated Sep. 16, 2016", 18 pgs.
"Canadian Application Serial No. 2,816,242, Response filed Apr. 5, 2016 to Office Action dated Oct. 5, 2015", 13 pgs.
"Canadian Application Serial No. 2,816,242, Response filed Dec. 16, 2014 to Office Action dated Jun. 16, 2014", 9 pgs.
"Canadian Application Serial No. 2492097, Office Action dated Nov. 18, 2010", 4 pgs.
"Canadian Application Serial No. 3,014,435, Office Action dated Oct. 26, 2021", 4 pgs.
"Canadian Application Serial No. 3,014,435, Office Action dated Nov. 6, 2020", 5 pgs.

(56) References Cited

OTHER PUBLICATIONS

"Canadian Application Serial No. 3,014,435, Office Action dated Nov. 13, 2019", 4 pgs.
"Canadian Application Serial No. 3,014,435, Response filed Feb. 25, 2022 to Office Action dated Oct. 26, 2021", 15 pgs.
"Canadian Application Serial No. 3,014,435, Response filed Mar. 5, 2021 to Office Action dated Nov. 6, 2020", 20 pgs.
"Canadian Application Serial No. 3,014 435 Response filed Mar. 13, 2020 to Office Action dated Nov. 13, 2019", 18 pgs.
"Chinese Application Serial No. 202080048487.4, Voluntary Amendment filed Dec. 5, 2022", w/ English Claims, 33 pgs.
"Chinese Application Serial No. 03808356.6, Office Action dated Sep. 5, 2008", (English Translation), 6 pgs.
"Chinese Application Serial No. 03808356.6, Office Action received Jul. 1, 2011", (w/ English Translation of Office Action), 8 pgs.
"Chinese Application Serial No. 03808356.6, Reexamination Notice dated Nov. 26, 2012", (w/ English Translation), 9 pgs.
"Chinese Application Serial No. 03808356.6, Response filed Mar. 11, 2013 to Office Action dated Nov. 26, 2012", (w/ English Translation of Amended Claims), 9 pgs.
"Chinese Application Serial No. 03808356.6, Response filed Mar. 16, 2009 to Office Action dated Sep. 5, 2008", (w/ English Translation of Claims 8 pgs.
"Chinese Application Serial No. 03808356.6, Response filed Oct. 14, 2011 to Office Action dated Jul. 1, 2011", (w/ English Translation of Amended Claims), 25 pgs.
"Chinese Application Serial No. 200480017037, First Office Action dated 05-25-07", (w/ English Translation), 10 pgs.
"Chinese Application Serial No. 200480017037, Response filed Oct. 30, 2007 to First Office Action dated May 25, 2007", (w/ English Translation of Claims), 26 pgs.
"Chinese Application Serial No. 200480017037.X, Response filed May 14, 2010 to Third Office Action dated Mar. 1, 2010", (w/ English Translation of Claims), 16 pgs.
"Chinese Application Serial No. 200480017037.X, Response filed Aug. 4, 2009 to Second Office Action dated Mar. 20, 2009", (w/ English Translation of Amended Claims), 15 pgs.
"Chinese Application Serial No. 200480017037.X, Second Office Action dated Mar. 20, 2009", (English Translation), 7 pgs.
"Chinese Application Serial No. 200480017037.X, Third Office Action dated Mar. 1, 2010", (w/ English Translation), 9 pgs.
"Chinese Application Serial No. 200480021259.9 Office Action dated Sep. 11, 2009", (English Translation), 7 pgs.
"Chinese Application Serial No. 200480021259.9 Response filed Aug. 20, 2010 to Office Action dated May 6, 2010", (w/ English Translation of Claims), 26 pgs.
"Chinese Application Serial No. 200480021259.9, First Office Action dated Aug. 24, 2007", (w/ English Translation), 9 pgs.
"Chinese Application Serial No. 200480021259.9, Notice of Reexamination dated Jul. 3, 2012", (w/ English Translation), 10 pgs.
"Chinese Application Serial No. 200480021259.9, Office Action dated Jan. 11, 2011", (w/ English Translation), 15 pgs.
"Chinese Application Serial No. 200480021259.9, Office Action dated May 6, 2010", (w/ English Translation), 12 pgs.
"Chinese Application Serial No. 200480021259.9, Office Action dated Jul. 3, 2012", w/ English Translation), 10 pgs.
"Chinese Application Serial No. 200480021259.9, Reexamination Decision dated Mar. 25, 2013", (w/ English Translation), 17 pgs.
"Chinese Application Serial No. 200480021259.9, Request for Reexamination filed Apr. 26, 2011", (w/ English Translation of Amended Claims), 23 pgs.
"Chinese Application Serial No. 200480021259.9, Response filed Mar. 7, 2008 to Office Action dated Aug. 24, 2007", (w/ English Translation of Claims), 13 pgs.
"Chinese Applications Serial No. 200480021259.9, Response filed Oct. 16, 2012 to Office Action dated Jul. 3, 2012", (w/ English Translation of Claims), 13 pgs.
"Chinese Application Serial No. 200480022014, First Office Action dated Aug. 24, 2007", w/English Translation, 6 pgs.
"Chinese Application Serial 200580046922.5, Office Action dated Jul. 24, 2009", 12 pgs.
"Chinese Application Serial No. 2200780020095.1, Decision on Rejection dated Jul. 22, 2013", (w/ English Translation), 11 pgs.
"Chinese Application Serial No. 200780020095.1, First Office Action dated Jun. 24, 2011", (w/ English Translation), 13 pgs.
"Chinese Application Serial No. 200780020095.1, Office Action dated Jan. 29, 2013", (w/ English Translation), 10 pgs.
"Chinese Application Serial No. 200780020095.1, Office Action Mar. 5, 2015", (w/ English Translation), 12 pgs.
"Chinese Application Serial No. 200780020095.1, Office Action dated Apr. 26, 2016", (w/ English Summary), 4 pgs.
"Chinese Application Serial No. 200780020095.1, Office Action dated May 3, 2012", (w/ English Translation), 10 pgs.
"Chinese Application Serial No. 200780020095.1, Office Action dated Nov. 2, 2016", (w/ English Translation), 11 pgs.
"Chinese Application Serial No. 200780020095.1, Response filed Jan. 6, 2017 to Office Action dated Nov. 2, 2016", (w/ English Translation of Claims), 15 pgs.
"Chinese Application Serial No. 200780020095.1, Response filed Jun. 9, 2013 to Office Action dated Jan. 29, 2013", (w/ English Translation of Claims), 10 pgs.
"Chinese Application Serial No. 200780020095.1, Response filed Jun. 23, 2015 to Office Action dated Mar. 5, 2015", (w/ English Translation of Claims), 16 pgs.
"Chinese Application Serial No. 200780020095.1, Response filed Jun. 30, 2016 to Office Action dated Apr. 26, 2016", (w/ English Translation of Claims), 22 pgs.
"Chinese Application Serial No. 200780020095.1, Response filed Sep. 16, 2012 to Office Action dated May 3, 2012", (w/ English Translation of Claims), 17 pgs.
"Chinese Application Serial No. 200780020095.1, Response filed Nov. 5, 2013 to to Decision on Rejection dated Jul. 22, 2013", (w/ English Translation of Claims), 12 pgs.
"Chinese Application Serial No. 200780020095.1, Response filed Nov. 8, 2011 to Office Action dated Jun. 24, 2011", (w/ English Translation of Amended Claims), 20 pgs.
"Chinese Application Serial No. 201310400039.8, Notice of Reexamination dated Aug. 26, 2016", (w/ English Translation), 7 pgs.
"Chinese Application Serial No. 201310400039.8, Office Action dated Feb. 12, 2015", (w/ English Translation), 10 pgs.
"Chinese Application Serial No. 201310400039.8, Office Action dated Feb. 15, 2016", (w/ English Translation), 12 pgs.
"Chinese Application Serial No. 201310400039.8, Office Action dated Apr. 1, 2017", (English Translation), 10 pgs.
"Chinese Application Serial No. 201310400039.8, Office Action dated Aug. 7, 2015", (w/ English Translation), 10 pgs.
"Chinese Application Serial No. 201310400039.8, Office Action dated Aug. 21, 2014", (w/ English Translation), 13 pgs.
"Chinese Application Serial No. 201310400039.8, Office Action Response dated Jun.1 6, 2017", W / English Claims, 8 pgs.
"Chinese Application Serial No. 201310400039.8, Response filed Jan. 4, 2015 to Office Action dated Aug. 21, 2014", (w/ English Translation of Claims), 10 pgs.
"Chinese Application Serial No. 201310400039.8, Response filed Apr. 27, 2015 to Office Action dated Feb. 12, 2015", (w/ English Translation of Claims), 16 pgs.
"Chinese Application Serial No. 201310400039.8, Response filed Jun. 1, 2016 to Office Action dated Feb. 15, 2016", (w/ English Translation of Claims), 9 pgs.
"Chinese Application Serial No. 201310400039.8, Response filed Oct. 10, 2016 to Notice of Reexamination dated Aug. 26, 2016", (w/ English Translation of Claims), 12 pgs.
"Chinese Application Serial No. 201310400039.8, Response filed Oct. 20, 2015 to Office Action dated Aug. 7, 2015", (w/ English Translation of Claims), 11 pgs.
"Chinese Application Serial No. 20131040039.8, Response filed Aug. 14, 2017 to Office Action Response dated Jun. 16, 2017", W/ English Claims, 11 pgs.
"Chinese Application Serial No. 20131040039.8, Response filed Aug. 7, 2017 to Office Action Response dated Jun. 16, 2017", W/ English Claims, 10 pgs.

(56) References Cited

OTHER PUBLICATIONS

"Chinese Application Serial No. 201780024821.0, Office Action dated Jun. 15, 2022", (w/ English Translation), 6 pgs.
"Chinese Application Serial No. 201780024821.0, Office Action dated Nov. 30, 2021", (w/ English Translation), 21 pgs.
"Chinese Application Serial No. 201780024821.0, Response filed Apr. 12, 2022 to Office Action dated Nov. 30, 2021", (w/ English Translation of Claims), 17 pgs.
"Chinese Application Serial No. 201780024821.0, Response filed Aug. 30, 2022 to Office Action dated Jun. 15, 2022", w/ English Claims, 18 pgs.
"Chinese Application Serial No. 20178004821.0, Response to Examiner Telephone Interview filed Sep. 26, 2022", w/ English Claims, 10 pgs.
"Chinese Application Serial No. 202080048487.4, Notification to Make Rectification dated Jan. 18, 2022", w/o English Translation, 1 pg.
"Chinese Application Serial No. 202080048487.4, Notification to Make Rectification dated May 26, 2022"w/o English translation, 1 pg.
"Chinese Application Serial No. 200480021259.9, Office Action dated May 8, 2009", (w/ English Translation), 6 pgs.
"Confirmed Cases of Avian Influenza A(HSN1)", World Health Organization, (Jan. 28, 2004), 1 pg.
"Declaration of Anne Koch Ballard dated Oct. 6, 2011", 1 pg.
"Eruasian Application No. 200501890, Notice of Allowance dated Jun. 23, 2009", 1 pg.
"Eurasian Application Serial No. 200501890, Office Action dated Mar. 23, 2007", (w English Translation), 2 pgs.
"Eurasian Application Serial No. 200501890, Office Action dated Sep. 4, 2008", (English Translation), 1 pg.
"Eurasian Application Serial No. 200501890, Office Action dated Dec. 17, 2007", (w/ English Translation), 6 pgs.
"Eurasian Application Serial No. 200501890, Response filed Mar. 26, 2008 to Office Action dated Dec. 17, 2007", (w/ English Translation of Claims), 15 pgs.
"Eurasian Application Serial No. 20050189, Response filed Jun. 14, 2007 to Office Action dated Mar. 23, 2007", (w/ English Translation of Claims), 11 pgs.
"Eurasian Application Serial No. 200501890, Response filed Dec. 17, 2008 to Office Action dated Sep. 4, 2008", (w/ English Translation of Claims), 14 pgs.
"Eurasian Application Serial No. 200701097,Office Action dated Sep. 4, 2008", OAR-MISC, 2 pgs.
"Eurasion Application Serial No. 200701097, Office Action dated Jun. 16, 2009", 3 pgs
"European Application 0475033.9, Communication dated Oct. 12, 2006", 6 pgs.
"European Application 0475033.9, Communications dated Dec. 8, 2006", 4 pgs.
"European Application 04750333.9, Communication dated Apr. 11, 2008", 6 pgs.
"European Application 04750333.9, Response filed Oct. 4, 2007 to Communication dated Dec. 8, 2006", 42 pgs.
"European Application 04750333.9, Response filed Nov. 21, 2006 to Communication Oct. 12, 2006", 4 pgs.
"European Application Serial 17709236.8, Response filed Apr. 26, 2019 to Communication Pursuant to Rules 161(1) and 162 EPC dated Oct. 19, 2018", 9 pgs.
"European Application Serial No. 21705801.5, Response to Communication pursuant to Rules 161 and 162 filed Mar. 28, 2023", 13 pgs.
"European Application Serial No. 03716017.3, Office Action dated Aug. 23, 2012", 4 pgs.
"European Application Serial No. 01928486.8 Office Action dated Oct. 1, 2009", 2 pgs.
"European Application Serial No. 01928486.8, Communication dated Aug. 10, 2007", 3 pgs.
"European Application Serial No. 01928486.8, Communication dated Sep. 20, 2005", 4 pgs.
"European Application Serial No. 10928486.8, Office Action dated Feb. 19, 2009", 3 pgs.
"European Application Serial No. 01928486.8, Response filed Jan. 30, 2006 to Communication dated Sep. 20, 2005", 9 pgs.
"European Application Serial No. 01928486.8, Response filed Aug. 28, 2009 to Communication dated Feb. 19, 2009", 5 pgs.
"European Application Serial No. 01928486.8, Response filed Jan. 21, 2008 to Communication dated Aug. 10, 2007", 11 pgs.
"European Application Serial No. 01928486.8, Response filed Dec. 9, 2009 to Office Action dated Oct. 1, 2009", 11 pgs.
"European Application Serial No. 02724994.5, Office Action dated Mar. 27, 2009", 2 pgs.
"European Application Serial No. 03716017.3, Communication and Supplementary European Search Report dated Jan. 2, 2008", 8 pgs.
"European Application Serial No. 03716017.3, Communication dated May 23, 2006", 3 pgs.
"European Application Serial No. 03716017.3, Communication dated Jul. 26, 2006", 2 pgs.
"European Application Serial No. 03716017.3, Communication dated Oct. 20, 2008", 7 pgs.
"European Application Serial No. 03716017.3, Further Written Submissions filed Mar. 19, 2015", 45 pgs.
"European Application Serial No. 03716017.3, Office Action dated Jul. 27, 2010", 4 pgs.
"European Application Serial No. 03716017.3, Response filed Feb. 4, 2011 to Office Action dated Jul. 27, 2010", 12 pgs.
"European Application Serial No. 03716017.3, Response filed Feb. 27, 2015 to Summons dated Nov. 3, 2014", 29 pgs.
"European Application Serial No. 03716017.3, Response filed Mar. 4, 2013 to Examination Notification Art. 94(3) dated Aug. 23, 2012", 19 pgs.
"European Application Serial No. 03716017.3, Response filed Mar. 24, 2015 to Office Action dated Nov. 3, 2014", 38 pgs.
"European Application Serial No. 03716017.3, Response filed Jul. 28, 2006 to Communication dated May 23, 2006", 5 pgs.
"European Application Serial No. 03716017.3, Response filed Aug. 19, 2009 to Communication dated Oct. 20, 2008", 17 pgs.
"European Application Serial No. 03716017.3, Response filed Sep. 28, 2015", 13 pgs.
"European Application Serial No. 03716017.3, Result of Consultation dated Mar. 17, 2015", 5 pgs.
"European Application Serial No. 03716017.3, Summons to Attend Oral proceedings dated Nov. 3, 2014", 5 pgs.
"European Application Serial No. 04750333.9, Office Action Jan. 22, 2009", 5 pgs.
"European Application Serial No. 04750333.9, Response filed Oct. 21, 2008 to Communication dated Apr. 11, 2008", 15 pgs.
"European Application Serial No. 04750333.9, Response filed Nov. 17, 2009 to Communication dated Jan. 22, 2009", 17 pgs.
"European Application Serial No. 04750333.9, Summons To Attend Oral Proceedings dated Aug. 3, 2011", 13 pgs.
"European Application Serial No. 04776133.3, Communication dated Mar. 30, 2006", 3 pgs.
"European Application Serial No. 04776133.3, Examination Notification Art. 94(3) dated Jul. 28, 2015", 4 pgs.
"European Application Serial No. 04776133.3, Examination Notification Art. 94(3) dated Nov. 25, 2013", 5 pgs.
"European Application Serial No. 04776133.3, Office Action dated Jan. 5, 2010", 4 pgs.
"European Application Serial No. 04776133.3, Response filed Jan. 25, 2007 to Communication dated Mar. 30, 2006", 20 pgs.
"European Application Serial No. 04776133.3, Response filed Apr. 30, 2014 to Examination Notification Art. 94(3) dated Nov. 25, 2013", 12 pgs.
"European Application Serial No. 04776133.3, Response filed Jul. 15, 2010 to Office Action dated Jan. 5, 2010", 9 pgs.
"European Application Serial No. 04776133.3, Response filed Sep. 18, 2015 to Examination Notification Art. 94(3) dated Jul. 28, 2015", 47 pgs.
"European Application Serial No. 04709419.7, Communication dated Apr. 3, 2007", 3 pgs.
"European Application Serial No. 04809419.7, Response filed Oct. 19, 2007 to Communication dated Apr. 3, 2007", 20 pgs.

(56) References Cited

OTHER PUBLICATIONS

"European Application Serial No. 07754132.4, Office Action dated Apr. 28, 2009", 4 pgs.
"European Application Serial No. 07754132.4, Office Action dated Sep. 5, 2011", 5 pgs.
"European Application Serial No. 07754132.4, Office Action dated Nov. 2, 2012", 4 pgs.
"European Application Serial No. 07754132.4, Response filed Feb. 5, 2010 to Office Action dated Apr. 28, 2009", 15 pgs.
"European Application Serial No. 07754132.4, Response filed Mar. 15, 2012 to Office Action dated Sep. 5, 2011", 21 pgs.
"European Application Serial No. 07754132.4, Response filed May 10, 2013 to Office Action dated Nov. 2, 2012", 14 pgs.
"European Application Serial No. 07754132.4, Response filed Jun. 26, 2013", 8 pgs.
"European Application Serial No. 10777154.5, Communication PurSuant to Article 94(3) EPC dated Apr. 4, 2018", 7 pgs.
"European Application Serial No. 10777154.5, Communication Pursuant to Article 94(3) EPC dated Jun. 11, 2019", 3 pgs.
"European Application Serial No. 10777154.5, Communication Pursuant to Article 94(3) EPC dated Oct. 12, 2017", 7 pgs.
"European Application Serial No. 10777154.5, Examination Notification Art. 94(3) dated Oct. 6, 2014", 7 pgs.
"European Application Serial No. 10777154.5, Office Action dated May 2, 2016", 6 pgs.
"European Application Serial No. 10777154.5, Office Action dated Jul. 4, 2012", 2 pgs.
"European Application Serial No. 10777154.5, Response filed May 13 2019 to Summons to Attend Oral Proceedings dated Jan. 7, 2019", 35 pgs.
"European Application Serial No. 10777154.5, Response filed Jun. 4, 2019 to Summons to Attend Oral Proceedings dated Jan. 7, 2019", 9 pgs.
"European Application Serial No. 10777154.5, Response filed Jan. 14, 2013 to Office Action dated Jul. 4, 2012", 12 pgs.
"European Application Serial No. 10777154.5, Response filed Feb. 21, 2018 to Communication Pursuant to Article 94(3) EPC dated Oct. 12, 2017", 12 pgs.
"European Applicatino Serial No. 10777154.5, Response filed Jul. 29, 2019 to Communication Pursuant to Article 94(3) EPC dated Jun. 11, 2019", 57 pgs.
"European Application Serial No. 10777154.5, Response filed Sep. 7, 2018 to Communication Pursuant to Article 94(3) EPC dated Apr. 4, 2018", 18 pgs.
"European Application Serial No. 10777154.5, Response filed Sep. 8, 2016 to Office Action dated May 2, 2016", 69 pgs.
"European Application Serial No. 10777154.5, Summons to Attend Oral Proceeding dated Jan. 7, 2019", 5 pgs.
"European Application Serial No. 12761841.1, Communication pursuant to Article 94(3) EPC dated Dec. 23, 2016", 6 pgs.
"European Application Serial No. 12761841.1, Response filed Feb. 23, 2017 to Communication pursuant to Article 94(3) EPC dated Dec. 23, 2016", 9 pgs.
"European Application Serial No. 12761841.1, Voluntary Amendment filed Dec. 1, 2014", 5 pgs.
"European Application Serial No. 14745060.5, Communication Pursuant to Article 94(3) EPC dated Feb. 6, 2018", 5 pgs.
"European Application Serial No. 14745060.5, Communication Pursuant to Article 94(3) EPC dated Mar. 12, 2020", 4 pgs.
"European Application Serial No. 14745060.5, Communication Pursuant to Article 94(3) EPC dated Jul. 18, 2019", 5 pgs.
"European Application Serial No. 14745060.5, Communication Pursuant to Article 94(3) EPC dated Sep. 15, 2021", 4 pgs.
"European Application Serial No. 14745060.5, Communication Pursuant to Article 94(3) EPC dated Sep. 18, 2018", 4 pgs.
"European Application Serial No. 14745060.5, Communication Pursuant to Article 94(3) EPC dated Nov. 9, 2020", 4 pgs.
"European Application Serial No. 14745060.5, Office Action dated Feb. 23, 2016", 2 pgs.
"European Application Serial No. 14745060.5, Response filed Jan. 5, 2022 to Communication Pursuant to Article 94(3) EPC dated Sep. 15, 2021", 79 pgs.
"European Application Serial No. 14745060.5, Response filed Jan. 28, 2020 to Communication Pursuant to Article 94(3) EPC dated Jul. 18, 2019", 9 pgs.
"European Application Serial No. 14745060.5, Response filed Mar. 27, 2019 to Communication Pursuant to Article 94(3) EPC dated Sep. 18, 2018", 13 pgs.
"European Application Serial No. 14745060.5, Response filed May 12, 2021 to Communication Pursuant to Article 94(3) EPC dated Nov. 29, 2020", 12 pgs.
"European Application Serial No. 14745060.5, Response filed Jun. 15, 2018 to Communication Pursuant to Article 94(3) EPC dated Feb. 6, 2018", 14 pgs.
"European Application Serial No. 14745060.5, Response filed Jul. 17, 2020 to Communication Pursuant to Article 94(3) EPC dated Mar. 12, 2020", 52 pgs.
"European Application Serial No. 14745060.5, Response filed Dec. 22, 2016 to Communication pursuant to Rules 161(1) and 162 EPC dated Feb. 23, 2016", 6 pgs.
"European Application Serial No. 15197386.4, Communication Pursuant to Article 94(3) EPC dated Feb. 21, 2018", 5 pgs.
"European Application Serial No. 15197386.4, Communication Pursuant to Article 94(3) EPC dated Apr. 21, 2017", 5 pgs.
"European Application Serial No. 15197386.4, Communication Pursuant to Article 94(3) EPC dated Jun. 19, 2019", 4 pgs.
"European Application Serial No. 15197386.4, extended European Search Report dated Feb. 26, 2016", 11 pgs.
"European Application Serial No. 15197386.4, Response filed Jul. 3, 2018 to Communication Pursuant to Article 94(3) EPC dated Feb. 21, 2018", 7 pgs.
"European Application Serial No. 15197386.4, Response filed Aug. 27, 2019 to Communication Pursuant to Article 94(3) EPC dated Jun. 19, 2019", 61 pgs.
"European Application Serial No. 15197386.4, Response filed Oct. 20, 2016 to Extended European Search Report dated Feb. 26, 2016", 4 pgs.
"European Application Serial No. 15197386.4, Response filed Oct. 31, 2017 to Communication Pursuant to Article 94(3) EPC dated Apr. 21, 2017", 5 pgs.
"European Application Serial No. 16778485.9, Communication Pursuant to Article 94(3) EPC dated Feb. 18, 2022", 4 pgs.
"European Application Serial No. 16778485.9, Communication Pursuant to Article 94(3) EPC dated May 25, 2020", 5 pgs.
"European Application Serial No. 16778485.9, Communication Pursuant to Article 94(3) EPC dated Aug. 22, 2019", 5 pgs.
"European Application Serial No. 16778485.9, Office Action dated Apr. 30, 2018", 3 pgs.
"European Application Serial No. 16778485.9, Response filed Aug. 9, 2022 to Communication Pursant to Article 94(3) EPC dated Feb. 18, 2022", 14 pgs.
"European Application Serial No. 16778485.9, Response filed Oct. 5, 2020 to Communication Pursuant to Article 94(3) EPC dated May 25, 2020", 14 pgs.
"European Application Serial No. 16778485.9, Response filed Nov. 8, 2018 to Office Action dated Apr. 30, 2018", 18 pgs.
"European Application Serial No. 16778485.9, Response filed Dec. 19, 2019 to Communication Pursuant to Article 94(3) EPC dated Aug. 22, 2019", 20 pgs.
"European Application Serial No. 17709236.8, Communication Pursuant to Article 94(3) EPC dated Jun. 8, 2022", 6 pgs.
"European Application Serial No. 17709236.8, Communication Pursuant to Article 94(3) EPC dated Jul. 6, 2021", 10 pgs.
"European Application Serial No. 17709236.8, Response filed Jan. 17, 2022 to Communication Pursuant to Article 94(3) EPC dated Jul. 6, 2021", 13 pgs.
"European Application Serial No. 17709236.8, Response filed Oct. 11, 2022 to Communication Pursuant to Article 94(3) EPC dated Jun. 8, 2022", 65 pgs.
"European Application Serial No. 18800815.5, Response to Communication pursuant to Rules 161(1) and 162 EPC filed Dec. 15, 2020", 14 pgs.

(56) References Cited

OTHER PUBLICATIONS

"European Application Serial No. 19778696.5, Response to Communication persuant to Rules 161 and 162 filed Oct. 15, 2021", 39 pgs.
"European Application Serial No. 20714015.3, Response filed to Communication persuant to Rules 161 and 162 filed Apr. 7, 2022", 10 pgs.
"European Application Serial No. 20731609.2, Response to Communication persuant to Rules 161 and 162 filed Mar. 16, 2022", 17 pgs.
"Evaluation of Medicines for human Use", EMEA/CPMP/BWP/2289/01, London The European Agency for the Evaluation of Medicinal Products, Committee for Proprietary Medicinal Products (CPMP), (Feb. 20, 2003), 14.
"Fluzone Influenza Virus Vaccine", Sanofi Aventis Pasteur, Swiftwater, (Jul. 2005), 12 pgs.
"Gen Bank Acession AFP82914", matrix protein 1 [Influenza A virus (A/reassortant/IVR-148(Brisbane/59/2007 x Texas/1/1997) (H1N1))], (2012), 2 PGS.
"Gen Bank Accession JX414012", Influenza A virus (A/reassortant/IVR-148(Brisbane/59/2007 x Texas/1/1997)(H1 N1)) segment 7 matrix protein 2 (M2) and matrix protein 1 (M1) genes, complete cds, (2012), 2 pgs.
"Gen Bank Acessions QHU7913", surface glycoprotein [Severe acute respiratory syndrome coronavris 2], (Mar. 17, 2020), 3 pgs.
"Genbank", CY002484.1, (2005), 2 pgs.
"Genbank Acession # AAA43733, Neuraminidase Protein of Influenza B/Beijing/1/87/virus,", (1993) 4 pg.
"Genbank Acession # AAU94753, Neuraminidase Protein of Influenza B/Aichi/5/88 virs,", (2004), 7 pgs.
"Genbank Accession # ABA02233, Neuraminidase Protein of Influenza B/Perth/211/2001 virus", (2006), 3 pgs.
"Genbank Accession #, ", neuraminidase influenza virus B/memphis/20/96,, (1999), 3 pgs.
"GFP antibody (ab6556) datasheet", (r) abcam. [online]. [retrieved on Dec. 5, 2004]. Retrieved from the Internet: <URL: http://www.abcam.com/index.html?datasheet=6556>, (2004), 5 pgs.
"hemagglutinin [Influenza A virus (A/swine/France/WVL13/1995(H1N1))]", GenBank Accession# AC025026, (May 22, 2009), 1 pg.
"hemagglutinin [Influenza B virus (B/Hong Kong/330/2001)]", GenBank ABL77178.1, (2006), 1 pg.
"https://www.abcam.corn/gfp-antibody-ab6556", [online]. [accessed on Dec. 5, 2004]. Retrieved from the Internet: http://www.abcam.comlindex.html?datasheet=6556, (Dec. 5, 2004), 5 pgs.
"Identification by siRNA of host proteins involved in Ebolavirus replication" Index of GLRCE: documents from 2007 Great Lakes Regional Center of Excellence Index, Retrieved from the Internet: URL:http://www.rcebiodefense.org/glrce/docs/2007/Kawaokja.pdf [retrieved on Jan. 14, 2010], (2007), 8 pgs.
"Indian Application Serial No. 02082/KOLNP/2005, Examination Report dated Mar. 17, 2008", 1 pg.
"Indian Application Serial No. 02082/KOLNP/2005, Examination Report dated Dec. 28, 2007", 1 pg.
"Indian Application Serial No. 02082/KOLNP/2005, First Examination Report dated Jan. 25, 2007", 9 pgs.
"Indian Application Serial No. 02082/KOLNP12005, Response filed Jan. 22, 2008 to Examination Report dated Dec. 28, 2007", 13 pgs.
"Indian Application Serial No. 02082/KOLNP/2005, Response filed Jun. 10, 2008 to Examination Report dated Mar. 17, 2008", 3 pgs.
"Indian Application Serial No. 02082/KOLNP/2005, Response filed Nov. 19, 2007 to First Examination Report dated Jan. 25, 2007", 26 pgs.
"Indian Application Serial No. 1026/KOLNP/2009, First Examiner Report dated Mar. 13, 2014", 2 pgs.
"Indian Application Serial No. 2272/KOLNP/2005, First Examination Report dated Mar. 17 2008", 10 pgs.
"Indian Application Serial No. 2272/KOLNP/2005, Response filed Oct. 11, 2008 to First Examination Report dated Mar. 17, 2008", 27 pgs.
"Indian Application Serial No. 2272/KOLNP/2005, Response filed Mar. 16, 2009 to Subsequent Examination Report dated Mar. 6, 2009", 12 pgs
"Indian Application Serial No. 2272/KOLNP/2005, Subsequent Examination Report dated Mar. 6, 2009", 1 pg.
"Indian Application Serial No. 2388/KOLNP/2005, First Examination Report dated Mar. 28, 2007", 10 pgs.
"Influenza B/Ann Arbor/1/66 (cold-adapted) nonstructural protein (seg 8) RNA, complete cds", GenBank Accession M20224, (Aug. 2, 1993), 2 pgs
"Influenza B/lee/40, neuraminidase & nb (seg 6) ma", Database EM_VI E.B.I. Hinxton U.K., (Jun., 13, 1985), 10 pgs.
"Influenza virus A/CHR/ 157/83 genomic RNA for haemagglutinin", (2012), 2 pgs.
"International Application No, PCT/US2004/016680, International Search Report", (dated Feb. 2. 2005), 7 pgs.
"International Application Serial No. PCT/US2021/033365, International Search Report dated Sep. 24, 2021", 6 pgs.
"International Application Serial No. PCT/US201/033365, Written Opinion dated Sep. 24, 2021", 6 pgs.
"International Application Serial No. PCT/US01/11963, Amendment filed Sep. 9, 2002 to Written Opinion dated Aug. 7, 2002", 12 pgs.
"International Application Serial No. PCT/US01/11963, International Preliminary Examination Report dated Oct. 15, 2002", 13 pgs.
"International Application Serial No. PCT/US01/11963, International Search Report dated May 7, 2002", 5 pgs.
"International Application Serial No. PCT/US01/11963, Written Opinion dated Jun. 14, 2002", 2 pgs.
"International Application Serial No. PCT/US01/11963, Written Opinion dated Aug. 7, 2002", 6 pgs.
"International Application Serial No. PCT/US02/05455, International Preliminary Examination Report dated Aug. 17, 2004", 4 pgs.
"International Application Serial No. PCT/US02/05455, International Search Report dated Mar. 25, 2003", 3 pgs.
"International Application Serial No. PCT/US03/04233, International Search Report dated Dec. 16, 2005", 7 pgs.
"International Application Serial No. PCT/US2004/012050, International Search Report dated Feb. 2, 2005", 8 pgs.
"International Application Serial No. PCT/US2004/012050, Written Opinion dated Feb. 2, 2005", 12 pgs.
"International Application Serial No. PCT/US2004/016649, International Preliminary Report on Patentability dated Dec. 15, 2005", 7 pgs.
"International Application Serial No. PCT/US2004/016649, International Search Report dated Apr. 18, 2005", 6 pgs.
"International Application Serial No. PCT/US2004/016680, International Preliminary Report on Patentability dated Dec. 15 2005", 11 pgs.
"International Application Serial No. PCT/US2005/041991, International Search Report dated Jun. 4, 2007", 5 pgs.
"International Application Serial No. PCT/US2005/041991, Written Opinion dated Jun. 4, 2007", 6 pgs.
"International Application Serial No. PCT/US2007/007562, International Preliminary Report on Patentability dated Oct. 9, 2008", 5 pgs.
"International Application Serial No. PCT/US2007/007562, International Search Report dated Jan. 14, 2008", 8 pgs.
"International Application Serial No. PCT/US2007/007562, Written Opinion dated Jan. 14, 2008", 9 pgs.
"International Application Serial No. PCT/US2007/013407, International Search Report dated Oct. 24, 2008", 10 pgs.
"International Application Serial No. PCT/US2007/013407, Written Opinion dated Oct. 24, 2008", 14 pgs.
"International Application Serial No. PCT/US2008/004125, International Search Report dated Feb. 20, 2009", 6 pgs.
"International Application Serial No. PCT/US2008/004125, Written Opinion dated Feb. 20, 2009", 8 pgs.

(56) References Cited

OTHER PUBLICATIONS

"International Application Serial No. PCT/US2008/005641, International Preliminary Report on Patentability dated Nov. 10, 2009", 9 pgs.
"International Application Serial No. PCT/US2008/005641, International Search Report dated Feb. 4, 2009", 6 pgs.
"International Application Serial No. PCT/US2008/005641, Written Opinion dated Feb. 4, 2009", 8 pgs.
"International Application Serial No. PCT/US2008/007417, International Search Report dated Jan. 30, 2009", 20 pgs.
"International Application Serial No. PCT/US2008/007417, Written Opinion dated Jan. 30, 2009", 10 pgs.
"International Application Serial No. PCT/US2008/007582, International Preliminary Report on Patentability dated Jan. 7, 2010", 9 pgs.
"International Application Serial No. PCT/US2008/007582, International Search Report and Written Opinion dated Feb. 18, 2009", 16 pgs.
"International Application Serial No. PCT/US2009/00058, International Search Report dated Feb. 9, 2010", 3 pgs.
"International Application Serial No. PCT/US2009/00056, Written Opinion dated Feb. 9, 2010", 5 pgs.
"International Application Serial No. PCT/US2009/006019, International Preliminary Report on Patentability dated May 19, 2011", 8 pgs.
"International Application Serial No. PCT/US2009/006019, Invitation to Pay Additional Fee dated Apr. 6, 2010", 8 pgs.
"International Application Serial No. PCT/US2009/006019, Search Report dated Jun. 10, 2010", 7 pgs.
"international Application Serial No. PCT/US2009/006019, Written Opinion dated Jun. 10, 2010", 6 pgs.
"International Application Serial No. PCT/US2009/054128, Preliminary Report on Patentability dated May 10, 2012", 10 pgs.
"International Application Serial No. PCT/US2010/054128, Search Report dated Feb. 23, 2011", 6 pgs.
"International Application Serial No. PCT/US2010/054129, Written Opinion dated Feb. 23, 2011", 8 pgs.
"International Application Serial No. PCT/US2012/052368, International Preliminary Report on Patentability dated Mar. 13, 2014", 8 pgs.
"International Application Serial No. PCT/US2012/052368. International Search Report dated Dec. 3, 2012", 4 pgs.
"International Application Serial No. PCT/US2012/052368, Written Opinion dated Dec. 3, 2012", 6 pgs.
"International Application Serial No. PCT/US2014/046731, International Preliminary Report on Patentability dated Jan. 28, 2016", 12 pgs.
"International Application Serial No. PCT/US2014/046731, International Search Report dated Nov. 25, 2014", 9 pgs.
"International Application Serial No. PCT/US2014/046731, Written Opinion dated Nov. 25, 2014", 10 pgs.
"International Application Serial No. PCT/US2015/036803, International Preliminary Report on Patentability dated Dec. 29, 2016", 10 pgs.
"International Application Serial No. PCT/US2015/036803, International Search Report dated Dec. 11, 2015", 8 pgs.
"International Application Serial No. PCT/US2015/036803, Invitation to Pay Add'l Fees and Partial Search Rpt dated Oct. 2, 2015", 8 pgs.
"International Application Serial No. PCT/US2015/036803, Written Opinion dated Dec. 12, 2015", 8 pgs.
"International Application Serial No. PCT/US2016/041172, International Preliminary Report on patentability dated Jan. 18, 2018", 10 pgs.
"International Application Serial No. PCT/US2016/041172, International Search Report dated Oct. 27, 2016", 6 pgs.
"International Application Serial No. PCT/US2016/041172, Written Opinion dated Oct. 27, 2016", 8 pgs.
"International Application Serial No. PCT/US2016/048691, International Preliminary Report on Patentability dated Mar. 15, 2018", 7 pgs.
"International Application Serial No. PCT/US2016/048691, International Search Report dated Nov. 22, 2016", 7 pgs.
"International Application Serial No. PCT/US2016/048691, Written Opinion dated Nov. 22, 2016", 6 pgs.
"International Application Serial No. PCT/US2017/018443, International Preliminary Report on Patentability dated Aug. 30, 2018", 11 pgs.
"International Application Serial No. PCT/US2017/018443, International Search Report dated May 22, 2017", 9 pgs.
"International Application Serial No. PCT/US2017/018443, Written Opinion dated May 22, 2017", 9 pgs.
"International Application Serial No. PCT/US2018/057576, International Preliminary Report on Patentability dated May 7, 2020", 12 pgs.
"International Application Serial No. PCT/US2018/057576, International Search Report dated Mar. 25, 2019", 7 pgs.
"International Application Serial No. PCT/US2018/057576, Invitation to Pay Additional Fees and Partial Search Report dated Jan. 31, 2019", 16 pgs.
"International Application Serial No. PCT/US2018/057576, Written Opinion dated Mar. 25, 2019", 10 pgs.
"International Application Serial No. PCT/US2019/037084, International Preliminary Report on Patentability dated Dec. 24, 2020", 12 pgs.
"International Applicaation Serial No. PCT/US2019/037084, International Search Report dated Nov. 14, 2019", 10 pgs.
"International Application Serial No. PCT/US2019/037084, Invitation to Pay Add'l Fees and Partial Search Report dated Sep. 24, 2019", 10 pgs.
"International Application Serial No. PCT/US2019/037084, Written Opinion dated Nov. 14, 2019", 10 pgs.
"International Application Serial No. PCT/US2019/045476, International Preliminary Report on Patentability dated Feb. 18, 2021", 13 pgs.
"International Application Serial No. PCT/US2019/045476, International Search Report dated Feb. 11, 2020", 8 pgs.
"International Application Serial No. PCT/US2019/045476, Invitation to Pay Additional Fees dated Dec. 17, 2019", 14 pgs.
"International Application Serial No. PCT/US2019/045476, Written Opinion dated Feb. 11, 2020", 13 pgs.
"International Application Serial No. PCT/US2019/046263, International Preliminary Report on Patentability dated Mar. 4, 2021", 8 pgs.
"International Application Serial No. PCT/US2019/047263, International Search Report dated Dec. 20, 2019", 5 pgs.
"International Application Serial No. PCT/US2019/047263, Written Opinion dated Dec. 20, 2019", 6 pgs.
"International Application Serial No. PCT/US2020/014659, International Preliminary Report on Patentability dated Aug. 5, 2021", 12 pgs.
"International Application Serial No. PCT/US2020/014659, International Search Report dated Nov. 6, 2020", 7 pgs.
"International Application Serial No. PCT/US2020/014659, Invitation to Pay Addition Fees dated Sep. 16, 2020", 11 pgs.
"International Application Serial No. PCT/US2020/014659, Written Opinion dated Nov. 6, 2020", 10 pgs.
"International Application Serial No. PCT/US2020/017342, International Preliminary Report on Patentability dated Aug. 19, 2021", 8 pgs.
"International Application Serial No. PCT/US2020/017342, International Search Report dated Jun. 26, 2020", 6 pgs.
"International Application Serial No. PCT/US2020/017342, Written Opinion dated Jun. 26, 2020", 6 pgs.
"International Application Serial No. PCT/US2020/031176, International Preliminary Report on Patentability dated Nov. 11, 2021", 9 pgs.
"International Application Serial No. PCT/US2020/031176, International Search Report dated Jul. 22, 2020", 6 pgs.
"International Application Serial No. PCT/US2020/031176, Written Opinion dated Jul. 22, 2020", 7 pgs.

(56) References Cited

OTHER PUBLICATIONS

"International Application Serial No. PCT/US2021/014586, International Preliminary Report on Patentability dated Aug. 4, 2022", 10 pgs.
"International Application Serial No. PCT/US2021/014586, International Search Report dated May 20, 2021", 7 pgs.
"International Application Serial No. PCT/US2021/014586, Written Opinion dated May 20, 2021", 8 pgs.
"International Application Serial No. PCT/US2021/024200, International Preliminary Report on Patentability dated Oct. 6, 2022", 8 pgs.
"International Application Serial No. PCT/US2021/024200, Internatinal Search Report dated Jul. 16, 2021", 6 pgs.
"International Application Serial No. PCT/US2021/024200, Written Opinion dated Jul. 16, 2021", 6 pgs.
"International Application Serial No. PCT/US2021/033365, International Preliminary Report on Patentability dated Dec. 8, 2022", 8 pgs.
"Israel Application Serial No. 163,546, Office Action dated Nov. 12, 2009", w/English Translation, 1 pg.
"Israel Application Serial No. 163,546, Office Action dated Dec. 26, 2007", w/English Translation, 1 pg.
"Israel Application Serial No. 163,546, Response filed May 9, 2008 to Office Action dated Dec. 26, 2007", w/English Translation, 2 pgs.
"Israel Application Serial No. 163,546, Response filed Jun. 8, 2010 to Office Action dated Nov. 12, 2009", w/English Claims, 3 pgs.
"Israel Application Serial No. 163,546, Response filed Aug. 16, 2009 to Substantive Examination Report dated Feb. 23, 2009", w/English Claims, 4 pgs.
"Israel Application Serial No. 163,546, Response filed Oct. 20, 2010 to Office Action dated Jun. 8, 2010", w/English Claims, 8 pgs.
"Israel Application Serial No. 163,546, Response filed Nov. 27, 2008 to First Examination Report dated Jul. 28, 2008", w/English Claims, 13 pgs.
"Israel Application Serial No. 163546, Office Action dated Jun. 8, 2010", w/English Translation, 2 pgs.
"Israel Application Serial No. 183026, Office Action dated Feb. 9, 2009", w/English Translation, 2 pgs.
"Israel Application Serial No. 238584, Office Action dated Jul. 24, 2017", w/English Translation, 2 pgs.
"Israel Application Serial No. 238584, Response filed Nov. 21, 2017 to Office Action dated Jul. 24, 2017", W/English Translation, 2 pgs.
"Israel Application Serial No. 171831, Notification of Defects dated Nov. 10, 2008", w/English Translation, 10 pgs.
"Israeli Application Serial No. 163,546, First Examination Report dated Jul. 28, 2008", (English Translation), 2 pgs.
"Israeli Application Serial No. 163,546, Substantive Examination Report dated Feb. 23, 2009", w/English Translation, 3 pgs.
"Israeli Application Serial No. 171372, Office Action dated Feb. 21, 2010", w/English Translation, 2 pgs.
"Israeli Application Serial No. 171372, Office Action dated Nov. 6, 2008", (Translation), 12 pgs.
"Israeli Application Serial No. 171372, Response filed Nov. 18, 2010 to Office Action dated Feb. 21, 2010", w/English Translation, 19 pgs.
"Israeli Application Serial No. 171831, Office Action dated Feb. 21, 2010", w/ English Translation, 2 pgs.
"Israeli Application Serial No. 171831, Office Action dated Apr. 18, 2012", (English Translation), 2 pgs.
"Israeli Application Serial No. 171831, Response filed Jan. 20, 2011 to Office Action dated Feb. 21, 2010", w/English Translation, 18 pgs.
"Israeli Application Serial No. 171831, Response filed Jun. 24, 2009 to Notification of Defects dated Nov. 10, 2008", w/English Claims, 10 pgs.
"Israeli Application Serial No, 171831, Response filed Nov. 6, 2012 to Office Action dated Apr. 18, 2012", w/English Claims, 54 pgs.
"Israeli Application Serial No. 211324, Office Action dated Sep. 18, 2014", w/English Translation, 5 pgs.
"Israeli Application Serial No. 211324, Office Action dated Oct. 18, 2015", w/English Translation, 4 pgs.
"Israeli Application Serial No. 211324, Response filed Feb. 16, 2016 to Office Action dated Oct. 18, 2015", w/English Claims, 4 pgs.
"Israeli Application Serial No. 211324, Response filed Mar. 31, 2015 to Office Action dated Sep. 8, 2014", w/English Translation, 21 pgs.
"Israeli Application Serial No. 238584, Notification of Defects in Patent Application dated Jul. 21, 2019", (w/ English Translation), 5 pgs.
"Israeli Application Serial No. 238584, Office Action dated Apr. 14, 2016", (English Translation), 3 pgs.
"Israeli Application Serial No. 238584, Office Action dated Aug. 23, 2018", (w/ English Translation), 6 pgs.
"Israeli Application Serial No. 238584, Response filed Aug. 3, 2016 to Office Action dated Apr. 14, 2016", (English Translation of Claims), 19 pgs.
"Israeli Application Serial No. 238584, Response filed Nov. 21, 2017 to Office Action dated Jul. 24, 2017", (Translation), 2 pgs.
"Israeli Application Serial No. 238584, Response filed Nov. 21, 2019 to Notification of Defects in Patent Application dated Jul. 21, 2019", (w/ English Translation of Claims). 6 pgs.
"Israeli Application Serial No. 238584, Response filed Dec. 10, 2018 to Office Action dated Aug. 23, 2018", (w/ English Translation of Claims), 10 pgs.
"Israeli Application Serial No. 171372, Office Action dated Feb. 20, 2011", (Translation), 2 pgs.
"Japanese Application No. 2001-576868, Office Action dated May 31, 2011", (w/ English Translation), 5 pgs.
"Japanese Application No. 2011-576868, Response filed Apr. 26, 2011 to Office Action dated Nov. 2, 2010", (w/ Translation of Amended Claims), 14 pgs.
"Japanese Application Serial No. 2022-144559, Voluntary Amendment filed Nov. 9, 2022", w/ English Claims, 14 pgs.
"Japanese Application Serial No. 2022-544779, Voluntary Amendment filed Sep. 9, 2022", w/ English Claims, 8 pgs.
"Japanese Application Serial No. 2001-576868, Office Action dated Nov. 2, 2010", w/ English Translation), 10 pgs.
"Japanese Application Serial No. 2001-576868, Response filed Dec. 1, 2011 to Office Action dated May 3, 2011", (w/ English Translation of Amended Claims), 37 pgs.
"Japanese Application Serial No. 2003-315106, Amended Claims filed Oct. 15, 2009 in Response to Office Action dated Jun. 24, 2009", (English Translation), 6 pgs.
"Japanese Application Serial No. 2003-315106, Notice of Allowance dated Jan. 5, 2010", (w/ English Translation), 5 pgs.
"Japanese Application Serial No. 2003-315106, Office Action dated Jun. 24, 2009", w/ English Translation), 10 pgs.
"Japanese Application Serial No. 2003-568038, Amendment filed Aug. 19, 2005", (English Translation), 8 pgs.
"Japanese Application Serial No. 2003-568038, Notice of Allowance dated Nov. 30, 2009", w/out English Translation, 3 pgs.
"Japanese Application Serial No. 2003-568038, Office Action dated May 15, 2009", (w/ English Translation), 7 pgs.
"Japanese Application Serial No. 2003-568038, Office Action dated Jul. 10, 2008", (w/ English Translation), 11 pgs.
"Japanese Application Serial No. 2003-568038, Office Action dated Jul. 21, 2005", w/out English Translation, 3 pgs.
"Japanese Application Serial No. 2003-568038, Request for Examination filed Aug. 19, 2005 in Response to Official Action dated Jul. 21, 2005", (w/ Partial English Translation of Specification), 8 pgs.
"Japanese Application Serial No. 2003-568038, Response filed Sep. 14, 2009 to Office Action dated May 15, 2009", (w/ English Translation of Amended Claims), 10 pgs.
"Japanese Application Serial No. 2003-568038, Response filed Dec. 10, 2008 to Office Action dated Jul. 10, 2008", (w/ English Translation of Amended Claims), 15 pgs.
"Japanse Application Serial No. 2006-513125, Office Action dated Mar. 9, 2010", (English Translation), 11 pgs.
"Japanese Application Serial No. 2006-513125, Response filed Aug. 30, 2010 to Office Action dated Mar. 9, 2010", (w/ English Translation of Amended Claims), 60 pgs.

(56) References Cited

OTHER PUBLICATIONS

"Japanese Application Serial No. 2006-533439, Decision of Final Rejection dated Aug. 14, 2012", (w/ English Translation), 5 pgs.
"Japanese Application Serial No. 2006-533439, Office Action dated Mar. 9, 2010", (w/ English Translation), 20 pgs.
"Japanese Application Serial No. 2006-533439, Office Action dated Mar. 27, 2012", w/ English Translation, 8 pgs.
"Japanese Applications Serial No. 2006-533439, Response filed May 21, 2012 to Office Action dated Mar. 27, 2012", (w/ English Translation of Amended Claims), 19 pgs.
"Japanese Application Serial No. 2006-533439, Response filed Aug. 3, 2011 to Office Action dated Feb. 15, 2011", (w/ English Translation of Amended Claims), 18 pgs.
"Japanese Application Serial No. 2006-533439, Office Action dated Feb. 15, 2011", (w/ English Translation), 13 pgs.
"Japanese Application Serial No. 2006-533439; Office Action Response filed Jul. 9, 2010", (w/ English Translation of Claims), 25 pgs.
"Japanese Application Serial No. 2008-315106, Office Action dated Jun. 24, 2009", (w/ English Translation), 10 pgs.
"Japanese Application Serial No. 2008-315106, Response filed Oct. 15, 2009 to Office Action dated Jun. 24, 2009", w/English Translation, 103 pgs.
"Japanese Application Serial No. 2008-315108, Response filed Oct. 15, 2009 to Office Action dated Jun. 24, 2009", (w/ English Translation of Amended Claims), 103 pgs.
"Japanese Application Serial No. 2008-315106, Response filed Dec. 3, 2009 to Office Action dated Jun. 24, 2009", (w/ English Translation of Claims), 9 pgs.
"Japanese Application Serial No. 2009-238781, Office Action dated Oct. 11, 2011", (w/ English Translation), 3 pgs.
"Japanese Application Serial No. 2009-502945, Examiners Decision of Final Refusal dated Nov. 12, 2013", (w/ English Translation), 8 pgs.
"Japanese Application Serial No. 2009-502945, Office Action dated Oct. 23, 2012", (w/ English Translation), 16 pgs.
"Japanese Application Serial No. 2009-502945, Response filed Mar. 10, 2013 to Office Action dated Oct. 23, 2012", (w/ English Translation of Claims), 18 pgs.
"Japanese Application Serial No. 2011-111048, Office Action dated Jun. 25, 2013", (w/ English Translation), 7 pgs.
"Japanese Application Serial No. 2011-111048, Office Action dated Sep. 18, 2012", (w/ English Translation), 10 pga.
"Japanese Application Serial No. 2011-111048, Response filed Sep. 25, 2012 to Office Action dated Jun. 25, 2013", (w/ English Translation of Amended Claims), 18 pgs.
"Japanese Application Serial No. 2011-111048, Response filed Mar. 15, 2013", (w/ Translation of Amended Claims), 14 pgs.
"Japanese Application Serial No. 2012-273898, Office Action dated Jun. 10, 2014", (w/ English Translation), 7 pgs.
"Japanese Application Serial No. 2012-273898, Response filed Sep. 4, 2014 to Office Action dated Jun. 10, 2014", W/ English Claims, 9 pgs.
"Japanese Application Serial No. 2012-536963, Amendment and Argument filed Jun. 26, 2015 to Office Action dated Jan. 6, 2015", (w/ English Translation of Amended Claims), 12 pgs.
"Japanese Application Serial No. 2012-536963, Examiners Decision of Final Refusal dated Nov. 17, 2015", (w/ English Translation), 8 pgs.
"Japanese Application Serial No. 2012-536963, Office Action dated Jan. 6, 2015", (w/ English Translation), 14 pgs.
"Japanese Application Serial No. 2012-536963, Voluntary Amendment filed Jun. 27, 2012", (w/ English Translation of Amended Claims), 17 pgs.
"Japanese Application Serial No. 2013-198377, Office Action dated Jan. 6, 2015", (w/ English Translation), 9 pgs.
"Japanese Application Serial No. 2014-049025 Response filed Sep. 4, 2015 to Office Action dated Jun. 16, 2015", (w/ Amended Claims), 12 pgs.
"Japanese Application Serial No. 2014-049025, Examiners Decision of Final Refusal dated Feb. 2, 2016", W/ English Translation, 5 pgs.
"Japanese Application Serial No. 2014-049025, Office Action dated Jun. 16, 2015", (w/ English Translation), 6 pgs.
"Japanese Application Serial No. 2014-527339, Examiners Decision of Final Refusal dated Feb. 7, 2017", (w/ English Translation), 5 pgs.
"Japanese Application Serial No. 2014-527339, Office Action dated May 31, 2016", (w/ English Translation), 10 pgs.
"Japanese Application Serial No. 2014-527339, Response filed Sep. 16, 2016 to Office Action dated May 31, 2016", (w/ English Translation of Amended Claims), 33 pgs.
"Japanese Application Serial No. 2016-053990, Office Action dated Jun. 6, 2017", (w/ English Translation), 4 pgs.
"Japanese Application Serial No. 2016-053990, Response filed Dec. 6, 2017 to Office Action dated Jun. 6, 2017", (w/ English Translation of Amended Claims), 14 pgs.
"Japanese Application Serial No. 2016-110879, Office Action dated May 30, 2017", (w/ English Translation), 7 pgs.
"Japanese Application Serial No. 2016-110879, Response filed Nov. 30, 2017 to Office Action dated May 30, 2017", (w/ English Translation of Claims), 25 pgs.
"Japanese Application Serial No. 2016-527046, Examiners Decision of Final Refusal dated May 21, 2019", (w/ English Translation), 20 pgs.
"Japanese Application Serial No. 2016-527046, Reasons For Rejection dated Aug. 14, 2018", (w/ English Translation), 14 pgs.
"Japanese Application Serial No. 2016-527046, Response filed Dec. 4, 2018 to Reasons For Rejection dated Aug. 14, 2018", (w/ English Translation of Amended Claims), 18 pgs.
"Japanese Application Serial No. 2017-111526, Office Action dated May 14, 2019", (w/ English Translation), 6 pgs.
"Japanese Application Serial No. 2017-111526, Office Action dated Jun. 26, 2018"(w/ English Translation), 5 pgs.
"Japanese Application Serial No. 2017-111526, Response filed Dec. 21, 2018 to Office Action dated Jun. 26, 2018", (w/ English Translation of Amended Claims), 7 pgs.
"Japanese Application Serial No. 2018-510751, Examiners Decisison of Final Refusal dated Dec. 17, 2019", w/ English Translation, 10 pgs.
"Japanese Application Serial No. 2018-510751, Notification of Reasons for Refusal dated Mar. 13, 2019", (w/ English Translation), 14 pgs.
"Japanese Application Serial No. 2018-510751, Response filed Apr. 17, 2020 to Examiners Decision of Final Refusal dated Dec. 17, 2019", w/ English Claims, 7 pgs.
"Japanese Application Serial No. 2018-510751, Response filed Aug. 9, 2019 to Notification of Reasons for Refusal dated Mar. 13, 2019", (w/ English Translation of Claims), 24 pgs.
"Japanese Application Serial No. 2018-543688, Notification of Reasons for Rejection dated Oct. 29, 2019", w/ English Translation, 14 pgs.
"Japanese Application Serial No. 2018-5436788, Office Action dated Jun. 30, 2020", w/ English translation, 11 pgs.
"Japanese Application Serial No. 2018-543688, Response filed Apr. 28, 2020 to Notification of Reasons for Rejection dated Oct. 29, 2019", w/ English Claims, 12 pgs.
"Japanese Application Serial No. 2019-171818, Examiners Decision of Final Refusal dated Oct. 5, 2021", (w/ English Translation), 15 pgs.
"Japanese Application Serial No. 2019-171818, Notification of Reasons for Rejection dated Nov. 10, 2020", (w/ English Translation), 11 pgs.
"Japanese Application Serial No. 2019-171818, Preliminary Examination Report dated May 10, 2022", (w/ English Translation), 2 pgs.
"Japanese Application Serial No. 2019-171818, Response filed Feb. 4, 2022 to Examiners Decision of Final Refusal dated Oct. 5, 2021", (w/ English Translation of Claims), 21 pgs.
"Japanese Application Serial No. 2019-171818, Response filed May 10, 2021 to Notification of Reasons for Rejection dated Nov. 10, 2020", (w/ English Translation of Claims), 12 pgs.

(56) References Cited

OTHER PUBLICATIONS

"Japanese Application Serial No. 2019-171818, Response filed Dec. 2, 2022 to Preliminary Examination Report dated May 10, 2022", w/ English Claims, 44 pgs.
"Japanese Application Serial No. 2019-171818, Trial Brief filed Mar. 30, 2022", (w/ English Translation), 14 pgs.
"Japanese Application Serial No. 2020-073952, Examiners Decisions of Final Refusal dated Aug. 4, 2022", w/ English translation, 3 pgs.
"Japanese Applications Serial No. 2020-073952, Final Notification of Reasons for Refusal dated Jan. 25, 2022", w/ English Translation, 11 pgs.
"Japanese Application Serial No. 2020-073952, Notification of Reasons for Refusal dated May 20, 2021", w/o English Translation, 2 pgs.
"Japanese Application Serial No. 2020-073952, Response filed Apr. 20, 2022 to Final Notification of Reasons for Refusal dated Jan. 25, 2022", w/ English Claims, 40 pgs.
"Japanese Application Serial No. 2020-073952, Response filed Sep. 9, 2021 to Notification of Reasons for Refusal dated May 20, 2021", w/ English Claims, 27 pgs.
"Japanese Application Serial No. 2020-073952, Response filed Dec. 2, 2022 to Examiners Decision of Final Refusal dated Aug. 4, 2022", w/ English Claims, 36 pgs.
"Japanese Application Serial No. 2020-182540, Examiners Decision of Final Refusal dated Jun. 7, 2022", (w/ English Translation), 11 pgs.
"Japanese Application Serial No. 2020-182549, Notification of Reasons for Refusal dated Nov. 30, 2021", (w/ English Translation),, 10 pgs.
"Japanese Application Serial No. 2020-182549, Preliminary Examination Report dated Jan. 17, 2023", w/ English Translation, 3 pgs.
"Japanese Application Serial No. 2020-182549, Response filed Feb. 28, 2022 to Notification of Reasons for Refusal dated Nov. 30, 21", (w/ English Translation of Claims), 52 pgs.
"Japanese Application Serial No. 2020-182549, Response filed Oct. 6, 2022 to Examiners Decision of Final Refusal dated Jun. 27, 2022", w/ English Claims, 21 pgs.
"Japanese Application Serial No. 2020-523276, Examiners Decision of Final Refusal dated May 10, 2022", w/ English Translation, 13 pgs.
"Japanese Application Serial No. 2020-523276, Notification of Reasons for Refusal dated Jul. 27, 2021", w/ English Translation, 12 pgs.
"Japanese Application Serial No. 2020-523276, Response filed Jan. 12, 2022 to Notification of Reasons for Refusal dated Jul. 27, 2021", wl English Claims, 27 pgs.
"Japanese Application Serial No. 2021-146743, Notification of Reasons for Rejection dated Aug. 17, 2022", w/ English Translation, 3 pgs
"Japanese Application Serial No. 2021-146743, Response filed Feb. 17, 2023 to Notification of Reasons for Rejection dated Aug. 17, 2022 ", w/ English Claims, 34 pgs.
"Japanese Application Serial No. 2021-506434, Examiners Decision of Final Refusal dated Jan. 10, 2023", w/ English Translation, 10 pgs.
"Japanese Application Serial No. 2021-506434, Notification of Reasons for Refusal dated May 10, 2022", w/ English translation, 10 pgs.
"Japanese Application Serial No. 2021-506434, Response filed Feb. 18, 2022 to Office Action dated Dec. 21, 2021", 135 pgs.
"Japanese Application Serial No. 2021-506434, Response filed Nov. 7, 2022 to Notification of Reasons for Refusal dated May 10, 2022", w/ English Claims, 13 pgs.
"Japanese Application Serial No. 2021-509824, Voluntary Amendment filed Aug. 18, 2022", w/ English Claims, 39 pgs.
"Japanese Application Serial No. 2021-542525, Notification of Reasons for Refusal dated Dec. 13, 2022", w/ English Translation, 14 pgs.
"Japanese Application Serial No. 2006-513125, Final Office Action dated Jan. 18, 2011", (English Translation), 4 pgs.
"Korean Application Serial No. 10-2005-7020077, Response filed Apr. 28, 2008 to Examination Report dated Dec. 28, 2007", (w/ English Translation of Revised Claims), 41 pgs.
"Korean Application Serial No. 10-2004-7012647, Office Action dated Feb. 26, 2010", (w/ English Translation), 7 pgs.
"Korean Application Serial No. 10-2004-7012647, Response filed Jun. 10, 2010 to Office Action dated Feb. 26, 2010", (W/ English Translation of Claims), 17 pgs
"Korean Application Serial No. 10-2005-7020077, Examination Report dated Dec. 28, 2007", (w/ English Translation), 8 pgs.
"Korean Application Serial No. 10-2005-7020077, Notice of Preliminary Rejection dated Jun. 28, 2007", (w/ English Translation), 9 pgs.
"Korean Application Serial No. 10-2005-7020077, Response filed Aug. 28, 2007 to Notice of Preliminary Rejection dated Jun. 28, 2007", (w/ English Translation), 40 pgs.
"Korean Application Serial No. 10-2005-7022564, Notice of Preliminary Rejection dated Jul. 25, 2007", W/ English Translation, 5 pgs.
"Korean Application Serial No. 10-2005-7022564, Office Action dated Aug. 6, 2008", W/ English Translation, 4 pgs.
"Korean Application Serial No. 10-2005-7022564, Response and Amendment filed Dec. 29, 2008 to Office Action dated Aug. 6, 2008", W/ English Translation, 16 pgs.
"Korean Application Serial No. 10-2005-7022564, Response filed Mar. 25, 2008 to Notice of Preliminary Rejection dated Jul. 25, 2007", (w/ English Translation of Claims), 35 pgs.
"Korean Application Serial No. 10-2005-7022564, Response filed Dec. 29, 2008 to Office Action dated Aug. 6, 2008", (w/ English Translation of Claims), 16 pgs.
"Korean Application Serial No. 10-2010-7011520, Office Action dated Jul. 20, 2010", (w/ English Translation), 6 pgs.
"Korean Applicaation Serial No. 10-2010-7011520, Response filed Oct. 20, 2010 to Office Action dated Jul. 20, 2010", (w/ English Translation of Amended Claims), 30 pgs.
"Korean Application Serial No. 10-2010-7011520, Amended Claims filed May 24, 2011 in Response to Office Action dated Feb. 24, 2011", (English Translation of Amended Claims), 22 pgs.
"Korean Application Serial No. 10-2010-7011520, office Action dated Feb. 24, 2011", (w/ English Translation), 5 pgs.
"Mexican Application No. PA/a/2005/012712 Office Action dated Jul. 21, 2009", (w/ English Translation), 9 pgs.
"Mexican Application Serial No. MX/a/2009/006341, Office Action dated Mar. 29, 2012", (English Translation), 1 pg.
"Mexican Application Serial No. MX/a/2009/006341, Response filed Jun. 4, 2012 to Mar. 29, 2012", (w/ English Translation of Amended Claims), 16 pgs.
"Mexican Application Serial No. MX/a/2012/009249 Response filed Sep. 10, 2015 to Office Action dated May 19, 2015", (w/ English Translation of Claims), 21 pgs.
"Mexican Application Serial No. MX/a/2012/009249, Office Action dated Feb. 5, 2016", W/ English Claims, 2 pgs.
"Mexican Application Serial No. MX/a/2012/009249, Office Action dated May 19, 2015", (English Translation), 1 pg.
"Mexican Application Serial No. MX/a/2012/009249, Response filed Mar. 29, 2016 to Office Action dated Feb. 5, 2016", (English Translation of Claims), 18 pgs.
"Mexican Application Serial No. PA/a/2004/007914, Office Action dated Feb. 14, 2008", (w/ English Translation), 3 pgs.
"Mexican Application Serial No. PA/a/2004/007914, Office Action dated Feb. 22, 2008", (English Translation), 3 pgs.
"Mexican Application Serial No. PA/a/2004/007914, Response filed Jun. 11, 2008 to Office Action dated Feb. 22, 2008", (w/ English Translation of Claims), 68 pgs.
"Mexican Application Serial No. PA/a/2005/011250, Office Action dated Aug. 23, 2010", W/ English Translation, 4 pgs.
"Mexican Application Serial No. PA/a/2005/011250, Response filed Dec. 20, 2010 to Office Action dated Aug. 23, 2010", (w/ English Translation of Claims), 14 pgs.
"Mexican Application Serial No. PA/a/2005/012712, Office Action dated Aug. 11, 2009", (English Translation), 5 pgs.

(56) References Cited

OTHER PUBLICATIONS

"Mexican Application Serial No. PA/a/2005/012712, Response filed Sep. 28, 2009 to Office Action dated Jul. 21, 2009", (w/ English Translation of Claims), 24 pgs.
"Mexican Application Serial No. PA/a/2005/012712, Office Action dated May 12, 2010", (w/ English Translation), 19 pgs.
"Mexican Application Serial No. PA/a/2005/012712, Office Action dated Jun. 9, 2010", (w/ English Translation), 11 pgs.
"Mexican Application Serial No. PA/a/2005/012712, Office Action dated Nov. 30, 2009", (w/ English Translation), 14 pgs.
"Mexican Application Serial No. PA/a/2005/012712, Official Action dated Mar. 5, 2009", (English Translation), 2 pgs.
"Mexicann Application Serial No. PA/a/2005/012712, Response filed Feb. 3, 2010 to Office Action dated Nov. 30, 2009", (w/ English Translation of Amended Claims), 22 pgs.
"Mexicans Application Serial No. PA/a/2005/012712, Response filed Sep. 27, 2010 to Office Action dated May 12, 2010", (w/ English Translation of Claims), 19 pgs.
"Mexico Application Serial No. PA/a/2005/012712, Response filed Jun. 12, 20009, to Official Action dated Mar. 5, 2009", (w/ English Translation of Claims), 11 pgs.
"neuraminidase [Influenza A virus (A/Aichi/2/1968 (H3N2))]", GenBank: BAD15542.1, NCBI, [online], Retrieved from the Internet: <URL: http://www.ncbi.nlm.nih.gov/protein/46401580>, (2008) 3 pgs.
"neuraminidase [Influenza B virus]", GenBank: CAB71147.1, NCBI, [online], Retrieved from the Internet: <URL: http://www.ncbi.nlm.nih.gov/protein/5861026>, (2005), 3 pgs.
"Neuraminidase, partial [Influenza A virus (A/swine/France/WVL13/1995(H1N1))]", GenBank Acession# AC025028, (May 22, 2009), 2 pgs.
"New Zealand Application Serial No. 542935, Examination Report dated Feb. 25, 2008", 2 pgs.
"New Zealand Application Serial No. 542935, Examination Report dated Jun. 14, 2006", 2 pgs.
"New Zealand Application Serial No. 542935, Response filed Jun. 30, 2008 to Examination Report dated Feb. 25, 2008", 32 pgs.
"New Zealand Application Serial No. 542935, Response filed Aug. 7, 2007 to Examination Report dated Jun. 14, 2006", 18 pgs.
"New Zealand Application Serial No. 542935, Voluntary Amendments filed Sep. 12, 2007", 10 pgs.
"New Zealand Application Serial No. 543446, Examination Report dated Feb. 29, 2008", 2 pgs.
"New Zealand Application No. 543446, Examination Report dated May 12, 2008", 1 pg.
"New Zealand Application Serial No. 543446,, Response dated Mar. 20, 2008 to Examination Report dated Feb. 29, 2008", 2 pgs.
"New Zealand Application Serial No. 543587, Examination Report dated Mar. 1, 2007", 1 pg.
"New Zealand Application Serial No. 54387, Examination Report dated Jul. 7, 2006", 2 pgs.
"New Zeland Application Serial No. 54387, Response filed Aug. 7, 2007 to Examination Reports dated Jul. 7, 2006 and Mar. 1, 2007", 24 pgs.
"New Zealand Application Serial No. 54587, Second Examination Report dated Feb. 25, 2008", 2 pgs.
"New Zealand Application Serial No. 555245, First Examination Report dated Aug. 26, 2008", 2 pgs.
"New Zealand Application Serial No. 555245, Subsequent Examiner Report dated Jul. 3, 2009", 1 pg.
"nonstructural protein 1 [influenza B virus (B/Hong Kong/330/2001)]", GenBank AAT69443.1, (2006), 1 pg.
"Norway Application Serial No. 20056074, Office Action dated Jan. 17, 2017", (English Translation), 5 pgs.
"Norway Application Serial No. 20056074, Office Action dated Apr. 25, 2017", (w English Translation), 3 pgs.
"Norway Application Serial No. 20056074, Office Action Response dated Apr. 18, 2017", W/ English Claims, 27 Pgs.
"Norway Application No. 20056074, Response filed Jul. 25, 2017 to Office Action dated Apr. 25, 2017", (w/ English Translation of Amended Claims), 111 pgs.
"Nucleotide sequences of influenza virus segments 1 and 3 reveal mosaic structure of a small viral RNA segment", Database Uniprot, (Nov. 14, 2001), 2 pgs.
"Nucleotides Sequences of Influenza Virus Segments 1 and 3 Reveal Mosaic Structrure of Small Viral RNA Segment", Database UniProt EBI / Accession No. NC_002023, (Jul. 10, 2008), 15 pgs.
"PCT Application Serial No, PCT/US2005/041991, International Preliminary Report on Patentability / Written Opinion dated Jul. 19, 2007", 8 pgs.
"polymerase acidic [influenza a virus (A/swine/Shizuoka/120/97(H3N2))]", GenBank AA015329.1, (2003), 1 pg.
"polymerase PA [Influenza a virus (A/swine/Yangzhou/1/2008(H9N2))]", GenBank: ADK98493.1, [Online], Retrieved from the Internet: <URL: https://www.ncbi.nim.nih.gov/protein/ADK98493.1/>, 2 pgs.
"polymerase PA [Influenza B virus (B/Hong Kong/330/2001)]", GenBank ABL7718 6 .1, (2006), 1 pg.
"polymerase PB1 [Influenza B virus (B/Hong Kong1330/2001)]", GenBank ABL77187, (2006), 1 pg.
"Polymerase PB2 [Influenza B virus (B/Hong Kong/330/2001)] GenBank ABL77188.1", (2006), 1 pg.
"RecName: Full=Non-structural protein 1; Short=NS1; AltNarne: Full=NS1 B", GenPept Accesion P08013, NS1 of Influenza B strain B/Yamagatall /73, (Dec. 9, 2015), 2 pgs.
"RNA World", http://faculty.uca.edul~benw/bio14415/lecturel0a/ts1d003.htm, (Observed Feb. 25, 2003), 1 pg.
"Russian Federation Application No, 2005136233, Office Action mailed 12-25-07", 2 pgs.
"Russian Federation Application No. 2005136233, Response filed May 29 2008 to Office Action dated Dec. 25, 2007", (w/ Partial English Translation), 7 pgs.
"Russian Federation Application Serial No. 2005136233, First Office Action dated Feb. 27, 2007", (w/ English Translation), 5 pgs.
"Russian Federation Application Serial No. 2005136233, Response filed Jun. 14, 2007 to First Office Action dated Feb. 27, 2007", (English Translation of Claims), 6 pgs.
"Russian Federation Application Serial No. 2005136233, Response filed Nov. 20, 2007 to Office Action", (w/ English Translation of Amended Claims.), 18 pgs
"Singapore Application Serial No. 200507467-9, Invitation to Respond to Written Opinion dated Jun. 19, 2007", 5 pgs.
"Singapore Application Serial No. 200506858-0, Examination Report dated Feb. 9, 2007", 4 pgs.
"Singapore Application Serial No. 200506858-0, Response filed Dec. 22, 2006 to Written Opinion dated Jul. 26, 2006", 18 pgs.
"Singaporean Application Serial No. 200506858-0, Written Opinion dated Jul. 26, 2006", 8 pgs.
"Singaporean Application Serial No. 200507468-7, Examination Report dated Mar. 19, 2008", 5 pgs.
"Singaporean Application Serial No. 20057468-7, Invitation to Respond to Written Opinion dated Jun. 12, 2007", 6 pgs.
"Singapore Application Serial No. 200507468-7, Response filed Nov. 7, 2007 to Invitation to Respond to Written Opinion dated Jun. 12, 2007", 9 pgs.
"ST3GAL6 Gene ID: 478535", ncbi, nlm, [Online]. Retrieved from the Internet: <URL: https://www.ncbi.nlm.nig.gov/gene/47853>Sep. 14, 2022, (Aug. 17, 2022), 14 pgs.
"The Influenza Virus: Structure and Replication", Rapid Reference to Influenza. Elsevier Ltd. [Online], Retrieved from the Internet: http://www. rapidreferenceinfluenza.com/chapter/B978-0-7234-3433-7.50009-8/aim/influenza-virus-structure, (2006), 6 pgs.
"The Integral Membrane Proteins of Influenza A, B, and C Viruses", The Influenza Sequence Database, http://www.flu.lani.gov/review/fluc.review2.htlm, (Obseerved Feb. 26, 2003), 1 pg.
"Ukrainese Application Serial No. 200512619, Response filed Jan. 21, 2010 to Office Action dated Jun. 17, 2009", W/ English Claims, 14 pgs.
"Ukrainian Application Serial No. 200512619, Office Action dated Feb. 27, 2009", (w/ English Translation), 21 pg.

(56) References Cited

OTHER PUBLICATIONS

"Ukrainian Application Serial No. 200512619, Office Action dated Jun. 17, 2009", (w/ English Translation), 4 pg.
"Ukrainian Application Serial No. 200512619, Response filed Apr. 8, 2009 to Office Action dated Feb. 27, 2009", (w/ English Translation of Claims), 9 pgs.
Abram, M. E, et al., "Nature, position, and frequency of mutations made in a single cycle of HIV-1replication", J. Virol., 84(19), (Oct. 2010), 9864-78.
Air, Gillian M., et al., "Antigenic, Sequence, and Crystal Variation in Influenza B Neuraminidase", Virology, 177(2), (1990), 578-587.
Air, Gillian M., et al., "Antigenic, Sequence, and Crystal Variation in Influenza B Neuraminidase", Virology vol. 177, (1990), 578-587.
Akarsu, H., et al., "Crystal structure of the M1 protein-binding domain of the influenza A virus nuclear export protein (NEP/NS2).", EMBO J., 22(18), (Sep. 15, 2003), 4646-55.
Albo, C., et al., "The 5'Ends of thogoto Virus (Orthomyxoviridae) mRNAS Are Homogenenous in both Length and Sequence", Journal of Virology, 70(12), (1996), 9013-9017.
Alonso-Caplen, et al., "Efficient Transcription, Not Translation, Is Dependent on Adenovirus Tripartite Leader Sequences at Late Times of Infection", Journal of Virology, vol. 62, No. 5, 1606-1616, (1988), 11 pgs.
Author Unknown, "New Approaches to Influenza Vaccine", Medscape—Infections in Medicine, http://www.medscape.comiviewarticle1417404_3, (Observed Feb. 26. 2003), 4 pgs.
Avetisyan, G, et al., "Cell-mediated immune responses to influenza vaccination in healthy volunteers and allogeneic stem cell transplant recipients", Bone Marrow Transplant 411-415, (2005), 5 pgs.
Avilov, Sergiy V., et al., "Influenza a virus progeny vRNP trafficking in live infected cells studied with the virus-encoded fluorescently tagged PB2 protein", Vaccine, 30, (2012), 7411- 7417.
Avilov, Sergiy V., et al., "Replication-Competent Influenza a Virus That Encodes a Split-Green Fluorescent Protein-Tagged PB2 Polymerase Subunit Allows", Journal of Virology, 86, (2012), 1433-1448.
Baez, M., et al., "Complete nucleotide sequence of the influenza a/PRI8/34 virus NS gene and comparison with the NS genes of the A/Udorn/72 and A/fFPV/Rostocig34 strains", Nucleic Acids Research, 23(8), (1980), 5845-5858.
Bai, B., et al., "Virus-Like Particles of SARS-Like Coronavirus Formed by Membrane Proteins from Different Origins Demonstrate Stimulating Activity in Human Dendritic Cells", PloS One, 3(7): e2685, (2008). 1-12.
Bancroft, C. T, et al., "Evidence for segment-nonspecific packaging of the influenza a virus genome", J Viral., 76(14), (Jul. 2002), 7133-9.
Banerjee, A. K., et al., "Gene Expression of Vesicular Stomatitis Virus Genorne RNA.", Virology, 188(2), (1992), 417-428.
Baron, M. D., et al., "Rescue of Rinderpest Virus From Cloned cDNA", Journal of Virology, 71(2), (1997), 1265-1271.
Basler, C. F, et al., "Mutation of Neuraminidase Cysteine Residues Yields Temprature-Sensitive Influenza Viruses", Journal of Virology, 73(10), (Jun. 30, 1999), 8095-8103.
Bears, A. S., "Trials in Man With Live Recombinants Made From A/PR/8/34 (H0 N1) and Wild H3 N2 Influenza Viruses", the Lancet, 2(7938), (1975), 729-732.
Bedford, M. T, et al., "FBP WW domains and the Abl SH3 domain bind to a specific class of proline-rich ligands", EMBO J., 16(9), (May 1, 1997), 2376-83.
Betakova, T., et al,, "The NB protein is an integral component of the membrane of influenza B virus.", J Gen Viral., 77 ( Pt 11), (Nov. 1996), 2689-94.
Biere, Barbara, et al., "Differentiation of Influenza B Virus Lineages Yarnagata and Victoria by Real-Time PCR", Journal of Clinical Microbiology, vol. 48, No. 4 1425-1427, (2010), 3 pgs
Bilsel, P., et al., "Mutations in the Cytoplasmic Tail of Influenza a Virus Neuraminidase Affect Incorporation into Virions", Journal of Virology, 67(11), (Nov. 30, 1993), 6762-6767.
Blount, K. F., et al., "The Hammerhead Ribozyme", Biochemical Society Transactions, 30(6), (2002), 1119-1122.
Bourmakina, S. V, et al., "Reverse genetics studies on the Filamentous morphology of influenza .A Virus", Journal of General Virology (2003) 84 (2003), 517-527.
Bowie, et al., "Deciphering the Message in Protein Sequences: Tolerance to Amino Acid Substitutions", Science, 247, (Mar. 1990), 1306-1310.
Bowie, J. U., et al., "Deciphering the Message in Protein Sequences: Tolerance to Amino Acid Substitutions", Science, 247(0948) 1306-1310, (1990), 5 pgs.
Boyer, J. C., et al., "Infectious transcripts and cDNA clones of RNA viruses", Virology, 198(2), (Feb. 1994), 415-426.
Bradfute, S. B. "The Early Clinical Development of Ebola Virus Treatments", Exp. Opin. Invest, Drugs 26(1):, (2017), 5 pgs.
Bradsher, K., "Cases of New Bird Flue in Hong Kong Prompt Worldwide Alerts", the New York Times web site, (Observed Feb. 22, 2003), 3 pgs.
Bradsher, K., "Man's Death of 'Bird Flu' in Hong Kong Raises Fears", the New York Times web site, (Observed Feb. 22, 200), 3 pgs.
Brandli, A. W, et al., "A Polarized Epithelial Cell Mutant Deficient in Translocation of UDP-galactose into the Golgi Complex", Journal of Biological Chemistry, 263(31), (Nov. 5, 1988), 16283-16290.
Brands, R., et al., "Influvac: A Safe Madin Darby Canine Kidney (MDCK) Cell Culture-Based Influenza Vaccine", Dev, Biol. Stand 98, (1999), 93-100.
Brassard, D.L., et al.. "Influenza B virus NB glycoprotein is a component of the virion", Vi101., 220(2), No Document, (1996), 350-360.
Bridgen, A., et al., "Rescue of a Segmented Negative-Strand RNA Virus Entirely From Cloned Complementary DNAs", Proc, Natl. Acad. Sci, USA, 93, (1996), 15400-15404.
Broecker, Felix, et al., "A mosaic hemagglutinin-based influenza virus vaccine candidate protects mice from challenge with divergent H3N2 strains", npj Vaccines (2019) 31, www.nature.com/npjvaccines Published in partnership with the Sealy Center for Vaccine Development, (Jul. 19, 2019), 9 pages.
Broecker, Felix, et al., "Extending the Stalk Enhances Inmunogenicity of the Influenza Virus Neuraminidase", Journal of Virology, 93(18), e00840-19, (Sep. 1, 2019), 1-12.
Broecker, Felix, et al,, "Irnmunodominance of Antigenic Site B in the Hemagglutinin of the Current H3N2 in?tienza Virus in Humans and Mice", Journal of Virology, 92(20): e01100-18, (Oct. 2018), 1-13.
Brooke, C B, "Biological activities of 'noninfectious' influenza a virus particles", Future Viral 9(1) 41-51, (Jan. 2014), 16 pgs.
Brown, E. G., et al., "Genetic analysis of mouse-adapted influenza A virus identifies roles for the NA, PB1, and PB2 genes in virulence", Virus Research, 61(1), (May 1999), 63-76.
Brown, TA, "Studying Dna", Genomes—NCBI Bookshelf, Brown TA. Genomes. 2nd edition, Oxford: Wiley-Liss: 2002, (2002), 26 pgs.
Bruhl, P., et al., "Humoral and Cell-Mediated Immunity to Vero Cell-Derived Influenza Vaccine", Vaccine, 19, (2001), 1149-1158.
Buchholz, U. J., et al., "Generation of Bovine Respiratory Syncytial Virus (Brsv) From cDNA: BRSV NS2 is Not Essentiial for Virus Replication in Tissue Culture, and the Human RSV Leader Region Acts as a Functional BRSV Genome Promoter", Journal of Virology, 73(1), (1999), 251-259.
Bukreyev, A., et al., "Chimeric human parainfluenza virus bearing the Ebola virus glycoprotein as the sole surface protein is immunogenic and highly protective against Ebola virus challenge", Virology, 383(2), (Abstract Only), (2009). 1 pg.
Bukreyev, A., et al,, "Recovery of infectious respiratory syncytial virus expressing an additional, foreign gene", Journal of Virology, 70(10), (Oct. 1996), 6634-6641.
Bullido, R., et al., "Influenza a Virus NEP (NS2 protein) Downregulates RNA Synthesis of Model Template RNAs", Journal of Virology, 75(10), (May 2001), 4912-4917.
Bullido, R., et al., "Influenza A virus NEP (NS2 protein) downregulates RNA synthesis of model templates RNAs", Journal of Virology, vol. 75 4912-4917, (May 2001), 6 pgs.

(56) References Cited

OTHER PUBLICATIONS

Burmeister, W. P., et al., "The 2.2 A resolution crystal structure of influenza B neuraminidase and its complex with sialic acid", the EMBO Journal, 11(1), (1992), 49-56.
Cannon, Joseph G., "Chapter Nineteen—Analog Design", In: Burger's Medicinal Chemistry and Drug Discovery, Fifth Edition, vol. I: Principles and Practice, Wiley-Interscience, (1995), 783-802.
Cao, S., et al,, "Characterization of the Nucleocytoplasmic Shuttle of the Matrix Protein of Influenza B Virus", Journal of Virology., 88(13), (Jul. 2014), 7464-7473.
Cardona, C. J., "Avian Influenza", http://www.vetmeducdavis.eduivetex/Inf-Po_AvianinfluenzaFS.html, ((Observed Feb. 22, 2003), 3 pgs.
Castrucci, M. R, et al., "Attenuation of Influenza a Virus by Insertion of a Foreign Epitope into the Neuraminidase", Journal of Virology, 66(8), (1992), 4647-4653.
Castrucci, M. R., et al., "Biologic Importance of Neuraminidase Stalk Length in Influenza a Virus", Journal of Virology, 67(2), (1993), 759-764.
Castrucci, M. R, et al., "Protection against Lethal Lymphocytic Choriomeningitis Virus (LCMV) Infection by Immunization of Mice with an Influenza Virus Containing an LCMV Epitope Recognized by Cytotoxic T Lymphocytes", Journal of Virology, 68(6), (1994), 3486-3490.
Castrucci, Maria R., et al., "Reverse genetics system for generation of an influenza A virus mutant containing a deletion of the carboxyl-terminal residue of M2 protein.", J Virol., 69(5), (May, 1995), 2725-8.
Catchpole, A. P, et al,, "Alternative base pairs attenuate influenza A virus when introduced into the duplex region of the conserved viral Rna promoter of either the NS Or the PA gene", Journal of General Virology, 84, (2003), 507-515.
Chan, Winnie, et al., "The cold adapted and temperature sensitive influenza A/Ann Arbor/6/60 virus, the master donor virus for live attenuated influenza vaccines, has multiple defects in replication at the restrictive temperature", Virology, 380(2), (2008), 304-311.
Chang, M. W. et al. "Analysis of Hiv Wild-Type and Mutant Structures via in Silico Docking against Diverse Ligand Libraries", J. Chem. Inf. Model., 47(3), (2007), 1258-1262.
Chen, H. et al., "Generation and evaluation of a high-growth reassortant H9N2 influenza A virus as a pandemic vaccine candidate", Vaccine, 21(17-18), (May 16, 2003), 1974-9.
Chen, Z., et al., "Influenza a Virus NS1 Protein Targets Poly(A)-Binding Protein H of the Cellular 3'-End Processing Machinery", The EMBO Journal, 18(8), (1999), 2273-2283.
Chevalie, Christophe, et al., "PB1-F2 Influenza a Virus Protein Adopts a B-Sheet Conformation and Forms Amyloid Fibers in Membrane Environments", The of Biological Chemistry, 285(17), (2010), 13233-13243.
Chiba, Shiho, et al., "Multivalent nanoparticle-based vaccines protect hamsters against SARS-CoV-2 after a single immunization", Communications Biology, 4: 597, (2021), 1-9.
Cho, Alice, et al., "Implications of Broadly Neutralizing Antibodies in the Development of a Universal Influenza Vaccine", Current Opinion in Virology, vol. 17 110-115, (1 Apr. 2016), 6 pgs.
Chothia, Cyrus, et al., "Canonical Structures for the Hypervariable Regions of Immunoglobulins.", J Mol Biol., 196(4), (1987), 901-917.
Chowrira, B M., et al., "In Vitro and in Vivo Comparision of Hammerhead, Hairpin, and Hepatitis Delta Virus Self-Processing Ribozyme Cassettes", The Journal of Biological Chemistry, 269(41). (1994), 25856-25864.
Chung, C, et al., "Glycoengineering of Chinese Hamster Ovary Cells for Improving Biotherapeutics Efficacies", A dissertation submitted to Johns Hopkins University in conformity with the requirements for the degree of Doctor of Philosophy, Retrieved from the Internet: <https://jscholarship.library.jhu.edu/handle/177>, (2016), 137 pgs.
Claas, E C. J., et al., "Human Influenza a H5N1 Virus Related to a Highly Pathogenic Avian Influenza Virus", The Lancet, 351, (1998), 472-477.
Clarke, D. K., et al., "Rescue of Mumps Virus from cDNA", Journal of Virology, 74(10), (2000), 4831-4838.
Cohen, Alexander A., et al,, "Mosaic nanopart cies elicit cross-reactive immune responses to zoonotic coronaviruses in mice", Science, 371(6530), and Supplementary Materials, (2021), 735-741 (30 pgs).
Coleman, P. M., et al., "Sequence and Structure Alignment of Paramyxovirus Hemagglutinin-Neuraminidase with Influenza Virus Neuraminidase", Journal of Virology, 67(6), (1993), 2972-2980.
Collins, P. L., et al., "Chapter 41 - Parainfluenza Viruses", in: Fields Virology, edited by Fields, B. N., et al. (3rd Edition, 1996, Lippincott - Raven Publishers, Philadelphia, PA, 1205-1241.
Collins, P. L., et al., "Production of Infectious Human Respiratory Syncytial Virus From Cloned cDNA Confirms an Essential Role for the Transcription Elongation Factor From the 5' Proximal Open Reading Frame of the M2 mRNA in Gene Expression and Provides a Capability for Vaccine D", Proc. Natl. Acad. Sci, USA, 92, (1995), 11563-11567
Collins, P. L., "Rescue of Synthetic Analogs of Respiratory Syncytial Virus Genomic RNA and Effect of Truncations and Mutations on the Expression of a Foreign Reporter Gene", Proc. Natl. Acad. Sci. USA, 88, (1991), 9663-9667.
Conzelmann, K.-K., "Genetic Engineering of Animal Rna Viruses", Trends in Microbiology, 4(10), (1996), 386-393.
Conzelmann, K.-K., "Genetic manipulation of non-segmented negative-strand Rna viruses", Journal of General Virology, 77(Pt. 3), (Mar., 1996), 381-389.
Conzelmann, K.-K., "Nonsegmented Negative-Strand RNA Viruses: Genetics and Manipulation of Viral Genomes", Annu. Rev. Genet., 32, (1998), 123-162.
Conzelmann, K.-K., "Rescue of Synthetic Genomic RNA Analogs of Rabies Virus by Plasmid-Encoded Proteins", Journal of Virology, 68(2), (1994), 713-719.
Craven, R. C., et al., "Late Domain Function Identified in the Vesicular Stomatitis Virus M Protein by Use of Rhabdovirus-Retrovirus Chimeras", Journal of Virology, 73(4), (1999), 3359-3365.
Crescenzo-Chaigne, B., et al., "Comparative Analysis of the Ability of the Polymerase Complexes of Influenza Viruses Type a, B and C to Assemble into Functional RNPs that Allow Expression and Replication of Heterotypic Model Rna Templates in Vivo", Virology, 265(2), (1999), 342-353.
Cunningham, Brian C, et al., "High-Resolution Epitope Mapping of hGH-Receptor Interactions by Alanine-Scanning Mutagenesis", Science 244:4908, (1989), 6 pgs.
Da Silva, Diogo V, et al., "Assembly of Subtype 1 Influenza Neuraminidase Is Driven by Both the Transmembrane and Head Domains", Journal of Biological Chemistry, 288(1), (Jan. 1, 2013), 644-653.
Daddario-Dicaprio, K. M, et al., "Cross-protection against Marburg virus strains by using a live, attenuated recombinant vaccine", J Virol., 80(19), (Oct. 2006), 9659-66.
De, B. P., et al., "Requirements and Functions of Vesicular Stomatitis Virus L and NS Proteins in the Transcription Process in Vitro", Biochemical and Biophysical Research Communications, 126(11(1985), 40-49.
De, B. P., et al., "Rescue of synthetic analogs of genome RNA of human parainfluenza virus type 3", Virology, 196(1), (Sep. 1993), 344-348.
De, B. P., et al., "Reverse Genetics of Negative Strand Rna Viruses", Indian Journal of Biochemistry & Biophysics, 31, (1994), 367-375.
De Filette, Marina, et al., "An influenza a vaccine based on tetrameric ectodomain of matrix protein 2", J Biol Chem. 2008 ; 283 (17):, (Feb. 5, 2008), 11382-7.
De La Luna, S., et al., "Influenza virus naked RNA can be expressed upon transfection into cells co-expressing the three subunits of the polymerase and the nucleoprotein from simian virus 40 recombinant viruses", Journal of General Virology, 74(pt. 3), (Mar., 1993). 535-539.

(56) References Cited

OTHER PUBLICATIONS

De La Luna, S., et al., "Influenza Virus NS1 Protein Enhances the Rate of Translation Initiation of Viral mRNAs", Journal of Virology, 69(4), (1995), 2427-2435.
Del Guidice, G., et al., 'What are the limits of adjuvanticity?, (Abstract), Vaccine, 20(Suppl 1), S38-S41, (2001), 1 pg.
Desheva, J, a, et al., "Characterization of an influenza a H5N2 reassortant as a candidate for live-attenuated and inactivated vaccines against highly pathogenic H5N1 viruses with pandemic potential", Vaccine, 24, (2006), 6859-6866.
Desselberger, Ulrich, et al., "The 3' and 5'-terminal sequences of influenza a, B and C virus RNA segments are highly conserved and show partial inverted complementarity", Gene, 8 (3), (Feb. 1980), 315-328.
Dimmock, Nigel J, et al., "In vivo antiviral activity: defective interfering virus protects better against virulent Influenza A virus than avirulent virus", Journal of General Virology 87, (Jan. 8, 2006), 1259-1265.
Dimock, K., et al,, "Rescue of Synthetic Analogs of Genomic RNA and Replicative-Intermediate RNA of Human Parainfluenza Virus Type 3", Journal of Virology, 67(5), (1993), 2772-2778.
Dollenmaier, G., el. al., "Membrane-Associated Respiratory Syncytial Virus F Protein Expressed From a Human Rhinovirus Type 14 Vector Is Immunogenic", Virology, 281(2), (Mar. 15, 2001), 216-230.
Dos Santos Afonso, Emmanuel, et al,, "The generation of recombinant influenza a viruses expressing a PB2 fusion protein requires the conservation of a packaging signal overlapping the coding and noncoding regions at the 5V end of the PB2 segment", Virology, 341, (2005), 34-46.
Dreher, T. W., et al., "Mutational Analysis of the Sequence and Structural Requirements in Brorne Mosaic Virus RNA for Minus Strand Promoter Activity", Journal of Molecular Biology, 201 (1), (1988), 31-40.
Du, Q., "Ribozyrne Enzymology", http://academic.brooklyn.cuny.edu/chemizhuang/QD/toppage1.htm, (Observed Feb. 25, 2003), 8 pgs.
Duff, K. C., et al., "The secondary structure of influenza a M2 transmembrane domain", FEBS Letters, 311 (3), (Oct. 1992), pp. 256-258.
Duff, K. C., et al., "The Transrnembrane Domain of Influenza a M2 Protein Forms Amantadine-Sensitive Proton Channels in Planar Lipid Bilayers", Vilology, 190(1), (Sep. 1992), pp. 485-489.
Duhaut, S., et al., "Approximately 150 Nucleotides from the 5' End of an Influenza a segment 1 Defective Virion RNA Are needed for Genome Stability during passage of Defective Virus in Infected Cells", Virology, 275(2) 278-285 Academic Press, Orlando, US, (Sep. 30, 2000), 8 pgs.
Duhaut, S. D, et al., "Defective segment 1 RNAs that interfere with production of infectious influenza A virus require at least 150 nucleotides of 5' sequence: evidence from a plasmid-driven system", Journal of General Virology 83, (2002), 403-411.
Duhaut, S. D, et al., "Heterologous Protection of Misce from a lethal human Hini Influenza a Virus Infection by H3NB Equine Defective Interfering Virus: Comparison of Defective RNA Sequences Isolated from the Di Inoculum and Mouse Lung", Virology, 248(2), Academic Press, Orlando, US, (Sep. 1, 1998), 241-253.
Duhaut, Susan, et al., "Approximately 150 Nucleotides from the 5' End of an Influenza A Segment 1 defective virion RNA are Needed for Genome Stability During Passage of Defective Virus in Infected Cells.", Virology, 275(2), (2000), 278-285.
Dumoulin, Mireille, et al., "Single-domain antibody fragments with high conformational stability", Protein Science, 11, (2002), 500-515.
Dunham, Eleca J,, et al., "Different Evolutionary Trajectories of European Avian-Like and Classical Swine H1N1 Influenza A Viruses", Journal of Virology, 83(11), (Jun. 2009), 5485-5494.
Dunn, E. F., et al., "Transcription of a recombinant bunyavirus RNA template by transiently expressed bunyavirus proteins", Virology, 211(1), (1995), 133-143.
Durbin, A. P, et al., "Human Parainfluenza Virus Type 3 (PIV3) Expressing the Hemagglutinin Protein of Measles Virus Provides a Potential Method for Immunization Against Measles Virus and PIV3 in Early Infancy", Journal of Virology, 74(15), (Aug. 2000), 6821-6831.
Durbin, A. P., et al., "Recovery of infectious human parainfluenza virus type 3 from cDNA", Virology. 235(2), (Sep. 1. 1997), 323-332.
Dyall, J., et al., ""Identification of inhibitors of Ebola virus with a subgenornic replication system "", Antiviral Research,70(1), 19th International Conference on Antiviral Research, San Juan, PR (May 7-11, 20006), (May 2006), p. A39.
Elhefnawi, M, et al., "Identification of novel conserved functional motifs across most Influenza A viral strains", Virology Journal, 8:44, (2011), 10 pages.
Elliott, R. M., "Emerging Viruses: the Bunyaviridae", Molecular Medicine, 3(9), (1997), 572-577.
Elliott, R. M., et al., "Rescue of Infectious Bunyavirus Entirely From Cloned cDNA", 10th International Conference on Negative Strand Virus, (Abstract No. 96), (1997), 1 pg.
Elliott, R. M., et al., "Some Highlights of Virus Research in 1990", Journal of General Virology, 72(Part 8), (1991), 1761-1779.
Emerson, S. U., et al., "Both NS And L Proteins Are Required for in Vitro Rna Synthesis by Vesicular Stomatitis Virus", Journal of Virology, 15(6), (1975), 1348-1356.
Enami, K., et al., "Influenza virus NS1 protein stimulates translation of the M1 protein", Journal of Virology, 68 1432-1437, (1994), 6 pgs.
Enami, M., "An Influenza Virus Containing Nine Different RNA Segments", Virology, 185(1), (1991), 291-298.
Enami, M., et al., "High-Efficiency Formation of Influenza Virus Transfectants", Journal of Virology, 65(5), (1991), 2711-2713.
Enami, M., et al., "Introduction of Site-Specific Mutations Into the Genome of Influenza Wits", Proc. Natl. Acad. Sci. USA, 87, (1990), 3802-3805.
Enterlein, S., et al., "Antiviral Strategies Against : Exploring Gene Silencing Mechanisms to Identify Potential Antiviral Targets", Antiviral Research, 70(1), (Abstract 33), 19th International Conference on Antiviral Research, San Juan, PR (May 7-11, 2006), (May 2006), p. A38.
Enterlein, S., et al., "Untersuchungen zur Replikation and Transkription von Marburgund Ebolavirus", [Online]. 2005, Philipps-Universitat Marburg , XP002563470, Retrieved from the Internet: <URL:httplideposit.ddb,delcgi-binidokserv?id n=9770056078,dok_var=d18,dok_ext=pdf&filen arne=977005607 .pdf> [retrieved on Jan. 15, 2010], (2005), p. 70-p. 84.
Essere, Boris, et al., "Critical role of segment-specific packaging signals in genetic reassortment of influenza A viruses", Proc. Natl. Acad. Sci. USA, 110(40), (2013), E3840-E3848.
Fahey, J. L., et al., "Status of Immune-Based Therapies in HIV Infection and Aids", Clinincal and Experimental Immunology, 88(1), (1992), 1-5.
Fan. J, et al., "Preclinical study of influenza virs A M2 preptide conjugate vaccines in mice ferrets, and rhesus monkeys", Vaccine, 22, (2004), 2993-3003.
Feng, L., et al., "The mouse Pol l terminator is more efficient than the hepatitis delta virus ribozyme in generating influenza-virus-like RNAs with precise 3'ends in a plasmid-only-based virus rescue system", Arch Virol., 154(7), (2009), 1151-6.
Fields, S., et al., "Nucleotides Sequences of Influenza Virus Segments 1 and 3 Reveal Mosaic Structure of Small Virla RNA Segment", Cell 28, (1982), 303-313.
Fischer, W. B, et al., "Viral ion channels: structure and function.", Biochim Biophys Acta., 1561(1), (Mar. 19, 2002), 27-45.
Flandorfer, A., et al., "Chimeric Influenza A Viruses with a Functional Influenza B Virus Neuraminidase or Hemagglutinin", Journal of Virology, 77(17), (2003), 9116-9123.
Fleming, D. M, et al., "Comparison of the efficacy and safety of live attenuated cold-adapted influenza vaccine, trivalent, with trivalent inactivated influenza virus vaccine in children and adolescents with asthma", Pediatr Infect Dis J., 25(1), (2006), 860-869.

(56) References Cited

OTHER PUBLICATIONS

Fodor, E., et al., "Rescue of Influenza A virus from Recombinant DNA", Journal of Virology, 73(11), XP002151487; ISSN:0022-538X, (Nov. 1999), 9679-9682.
Forbes, Nicole E, et al., "Multifunctional Adaptive NS1 Mutations Are Selected upon Human Influenza Virus Evolution in the Mouse", Plos One, vol. 7, No. 2, (Feb. 21, 2012), 20 pgs.
Forbes, P., et al., "Influenza Virus NS1 Protein Inhibits Pre-mRNA Splicing and Blocks mRNA Nucleocytoplasmic Transport", The EMBO Journal, 13(3), (1994), 704-12.
Fouchier R. A. M., et al., "Avian Influenze A Virus (H7N7) Associated With Human Conjuctivitis and a Fatal Case of Acute Respiratory Distress Syndrome", Proc. Natl. Acad. Sci. USA, 101(5) 1356-1361, (2004), 6 pgs.
Friers, et al., "Soluble recombinant influenza vaccines", Phil. Trans. R. Soc. Lond. B (2001). vol. 356 1961-1963, (2001), 4 pgs.
Fuji, Y., et al., "Selective incorporation of influenza virus RNA segments into virions", Proc. Natl. Acad. Sci. USA, 100(4) 2002-2007, (2003), 6 pgs.
Fujii, Ken, et al., "Importance of both the Coding and the Segment-Speci?c Noncoding Regions of the In?uenza A Virus NS Segment for its Ef?cient", Journal of Virology, 79(6), (Mar. 2005), 3766-3774.
Fujii, Y, et al., "The packaging of influenza viral genome", Virus, 52 (1), Uirusu (Japanese Journa, Name) (Jun. 2002), 203-206.
Gao, Qinshan, et al., "A Nine-Segment In?uenza A Virus Carrying Subtype H1 and H3 He,agglutinins", Journal of Virology, 84(16), (Aug. 2010), 8062-8071.
Gao, Qinshan, et al., "A Seven-Segmented Influenza A Virus Expressing the Influenza C Virus Glycoprotein HEF", Journal of Virology, 82(13), (Jul. 2008), 6419-6426.
Gao, Qinshan, et al., "The In?uenza A Virus PB2, PA, NP and M Segments Play a Pivotal Role during Genome Packaging", Journal of Virology, 86(13), Chou, (Jul. 2011), 043-7051.
Garay, R. P, et al., "Cancer relapse under chemotherapy: why TLR2/4 receptor agonists can help", Eur J Pharmacol., 563(1-3), (Jun. 1, 2007), 1-17.
Garcia-Sastre, A., et al., "Genetic Manipulation of Negative-Strand RNA Virus Genomes", Annu. Rev. Microbiol., 47, (1993), 765-790.
Garcia-Sastre, A., et al., "Introduction of Foreign Sequences into the Genome of Influenza a Virus", Dev. Biol. Stand. vol. 82, (1994), 237-246.
Garcia-Sastre, A., et al., "introduction of Foreign Sequences into the Genome of Influenza A Virus", in: Recombinant Vectors in Vaccine Development. Dev. Biol. Stand., 82, Fred Brown. Editor, (1994), 237-246.
Garcia-Sastre, A., et al., "Introduction of foreign sequences into the genome of influenza A virus,", Dev Biol Stand., 82, (1994), 237-246.
Garcia-Sastre, A., et al., "The cytoplasmic tail of the neuraminidase protein of influenza a virus does not play an important role in the packaging of this protein into viral envelopes", Virus Research, 37(1), (1995), 37-47.
Garcia-Sastre, A., et al., "Use of a Mammalian internal ribosomal entry site element for expression of a foreign protein by transfectant influenza virus.", Journal of Virolog, 68(10), (1994), 6254-6261.
Garcia-Sastre, Adolfo, et al., "Use of a Mammalian Internal Ribosomal Entry Site Element for Expression of a Foreign Protein by a Transfectant Influenza Virus", Journal of Virology, 68(10) 6254-6261, (Jun. 30, 1994), 8 pgs.
Garcin, D., et al., "A Highly Recombinogenic System for the Recovery of Infectious Sendai Paramyxovirus From cDNA: Generation of a Novel Copy-Back Nondefective Interfering Virus", The EMBO Journal, 14(24), (1995), 6087-6094.
Garrett, L., "Deadly Ebola, Avian Influenza Re-Emerging", Newsday.com, (Feb. 20, 2003), 3 pgs.
Genbank, "", ABD36884.1, (2007), 2 pgs
Gerdil, C., "The Annual Production Cycle for Influenza Vaccine", Vaccine, 21 1776-1779, (2003), 4 pgs.
Ghate, Anita A, et al., "Influenza Type B Neura inidase Can Replace the Function of Type a Neuraminidase", Virology, 264 (2), (Nov. 1999). 265-277.
Giddings, A M, et al., "The matrix protein of HIV-1 is not sufficient for assembly and release of virus-like particles", Virology, 248(1), (1998), 108-16.
Giles, Brendan Michael, "Development of Broadly Reactive Vaccine for Highly Pathogenic H5N1 Influenza", Retrieved from the Internet: URL<httpl/search.proquest,com/docview/928138363>, (Jan. 1, 2011), 283 pgs.
Gilleland, H. E, et al., "Chimeric Influenza Virus Incorporating Epitopes of Outer Membrane Protein F as a Vaccine Against Pulmonary Infection with Pseudomonas Aeruginosa", Behring Inst. Mitt. 98, (Feb. 28, 1997), 291-301.
Gomez-Puertas, P., et al., "Influenza Virus Matrix Protein Is the Major Driving Force in Virus Budding", Journal of Virology, 74 11538-11547, (Dec. 1, 2000), 10 pgs.
Gorman, O T, et al., "Evolution of influenza a virus PB2 genes: implications for evolution of the ribonucleoprotein complex and origin of human influenza A virus", J. Viral., 64(10), (Oct 1990), 4893-4902.
Gotea, V, et al., "The functional relevance of somatic synonymous mutations in melanoma and other cancers", Pigment Cell & Melanoma Research, 28 issue 6, (Nov. 1, 2015), 673-686.
Goto, H., "Mutations Affecting the Sensitivity of the Influenza Virus Neuraminidase to 4-Guanidino-2, 4-dideoxy 2, 3-dehydro-N-acetylneuraminic Acid", Virology, 238, (1997), 265-272.
Goto, Hideo, et al "The Genome-Packaging Signal of the Influenza a Virus Genome Comprises a Genome Incorporation Signal and a Genome-Bundling Signal", Journal of Virology: vol. 87 No. 21, (Nov. 2013), 11316-11322.
Govorkova, E A, et al,, "Replication of Influenza A Viruses in a Green Monkey Kidney Continuous Cell Line (Vero)", J. Infect. Dis. 172(1), (1995), 250-253.
Grambas, S., et al., "Influence of amantadine resistance mutations on the pH regulatory Junction of the M2 protein of influenza A viruses", Virology, 191(2), (Dec. 1992), 541-549.
Green, R. F., et al., "Glycosylation Does Not Determine Segregation of Viral Envelope Proteins in the Plasma Membrane of Epithelial Cells", J. Cell Biool., 89(2), (1981), 230-239.
Groseth, A., "13. Generation of Recombinant Ebola Viruses Using Reverse Genetics", in: Hoenen T., et al. (eds), Ebolaviruses: Methods and Protocols, Methods in Molecular Biology, vol. 182, (2017), 177-187.
Groseth, A., et al., "RNA Polymerase I-Driven Minigenorne System for Ebola Viruses", Journal of Virology, 79(7), (2005), 4425-4433.
Grosfeld, H., et al., "RNA Replication by Respiratory Syncytial Virus (RSV) Is Directed by the N, P, and L Proteins; Transcription Also Occurs Under These Conditions but Requires RSV Superinfection for Efficient Synthesis of Full-Length mRNA", Journal of Virology, 69(9), (1995), 5677-5686.
Gubareva, "Molecular mechanisms of influenza virus resistance of neuraminidase inhibitors", Virus Research, vol. 103, (2004), pp. 199-203.
Gunther, S, et al., "Application of real-time Pcr for testing antiviral compounds against Lassa virus, Sars coronavirus and Ebola virus in vitro", Antiviral Research, Elsevier by, NL, vol. 63, No. 3, XP004580000 ISSN: 0166-3542, (Sep. 1, 2004), 209-215.
Hagen, M., et al,, "Recombinant Influenza Virus Polymerase: Requirement of both 5' and 3' Viral Ends for Endonuclease Activity", Journal of Virology, 68(3), (1994), 1509-1515.
Hai, Rong, et al., "Influenza B Virus NS1-Truncated Mutants: Live-Attenuated Vaccine Approach", Journal of Virology, 820112008), 10580-10590.
Halfmann, P., et al., "Generation of biologically contained Ebola viruses", Proceedings of the National Academy of Sciences of the United States of America 1129-1133, vol. 105, No. 4, XP002563467 ISSN: 1091-6490 the whole document, (Jan. 29, 2008), 6 pgs.
Halfmann, P., et al., "Replication-Deficient Ebolavirus as a Vaccine Candidate", Journal of Virology, vol. 83, No. 8 3810-3815, XP002563468; ISSN: 1098-5514; the whole document, (Apr. 2009), 6 pgs.

(56) References Cited

OTHER PUBLICATIONS

Halfmann, Peter J., et al., "Potent neutralization of SARS-CoV-2 including variants of concern by vaccines presenting the receptor-binding domain multivalently from nanoscaffolds", Bioengineering & Translational Medicine, 6(3): e10253, (2021), 8 pgs.
Halperin, S. A., et al., "Safety and Immunogenicity of a Trivalent, Inactivated, Mammalian Cell Culture-Derived Influenza Vaccine in Healthy Adults, Seniors, and Children", Vaccine, 20 1240-1247, (2002), 8 pgs.
Halstead, Scott B,, et al., "Dengue Antibody-Dependent Enhancement: Knowns and Unknowns", Microbiology Spectrum, 2(6), (2014), 1-18.
Harmsen, M. M., et al., "Properties, production, and applications of camelid single-domain antibody fragments", Appl Microbiol Biotechnol,77, (2007), 13-22.
Harty, R. N, et al., "A PPxY Motif within the VP40 Protein of Ebola Virus Interacts Physically and Functionally with a Ubiquitin Ligase: Implications for Filovirus Budding", Proc. Natl. Acad. Sci, 97 (25), (Dec. 5, 2000), 13871-1 3876.
Harty, Ronald N, "A Proline-Rich Motif within the Matrix Protein of Vesicular Stomatitis Virus and Rabies Virus Interacts with WW Domains of Cellular Proteins: Implications for Viral Budding", Journal of Virology, 73 (4), (1999), 2921-2929.
Harvey, K. F, et al., "All three WW domains of murine Nedd4 are involved in the regulation of epithelial sodium channels by intracellular Nat.", J Biol Chem., 274(18), (Apr. 30, 1999), 12525-30.
Hatada, E., et al., "Binding of Influenza a Virus NS1 Protein to dsRNA in vitro". Journal of General Virology, 73, (1992), 3325-3329.
Hatakeyama, S., et al., "Dissection and identification of regions required to form pseudoparticles by the interaction between the nucleocapsid (N) and membrane (M) proteins of Sars coronavirus", Virology, 380(1), (2008), 99-108.
Hatakeyama, S., et al., "Emergence of Influenza B Viruses With Reduced Sensitivity to Neuraminidase Inhibitors", Journal of the American Medical Association, 297(13) 1435-1442, (Apr. 4, 2007), 8 pgs.
Hatakeyama, S., et al., "Enhanced Expression of an a2,6-Linked Sialic Acid on MDCK Cells Improves Isolation of Human Influenza Viruses and Evaluation of Their Sensitivity to a Neuraminidase Inhibitor", J Olin Microbiol, 43(8), (2005), 4139-4146.
Hatakeyma, S., et al., "The molecular basis of resistance to anti-influenza drugs", Japanese Journal of Clinical Medicine—Nippon Rinsho, 64(10) 1845-1852, (Oct. 1, 2006), 8 pgs.
Hatta, M., et al., "The NB protein of influenza B virus is not necessary for virus replication in vitro", Journal of Virology, 77(10),(May, 2003), 6050-6054.
Hay, A. J., et al., "The role of the M2 protein in influenza a virus infection", Proceedings of the International Conference on Options for the Control of Influenza, Courchevel, (1992), 281-288.
He, B., et al., "Recovery of infectious SV5 from cloned DNA and expression of a foreign gene", Virology, 237(2), (1997), 249-260.
He, X., et al., "Generation of SARS-CoV-2 reporter replicon for high-throughput antiviral screening and testing", Proc. Natl. Acad. Sci. USA, 118(15): e2025866118, (2021), 8 pgs.
Helenius, A., "Unpacking the Incoming Influenza Virus", Cell, 69, (May 1992), pp. 577-578.
Hevey, Michael, et al., "Marburg virus vaccines based upon alphavirus replicons protect guinea pigs and nonhuman primates", Virology, 251(1) (Nov. 10, 1998.), 28-37.
Hickman, Danielle, et al., "An avian live attenuated master backbone for potential use in epidemic and pandemic influenza vaccines", Journal of General Virology, 89(Part 11), (2008), 2682-2690.
Hiromoto, Y., et al., "Phylogenetic Analysis of the Three Polymerase Genes (PB1, PB2 and PA) of Influenza B Virus", Journal of General Virology, 81, (Apr. 2000), 929-937.
Hiti, A. L., et al., "P03470—Neuraminidase", Entrez Protein Database, http://www.ncbi.nlm.nih.gov/entrez/viewer.fcgi?db=protein &val=84028231, (1982), 730-734.
Hiti, A. L., et al., "P©347©- Neuraminidase", Entrez Protein Database, [online]. [retrieved on Aug. 30, 2006], Retrieved from the Internet: <URL: http://www,ncbi.nlm.nih.govientrez/viewer.fcgi?db=protein&val=84028231>, (1982), 730-734 (8 pgs.).
Ho, Y., et al., "Assembly of human severe acute respiratory syndrome coronavirus-like particles", Biochem Biophys Res Common, 318(4), (2004), 833-838.
Hoenen, T., et al., "11. Reverse Genetics Systems for Filoviruses", In: Perez, Daniel (Ed.). Reverse Genetics of RNA Viruses: Methods and Protocols, Methods in Molecular Biology, vol. 1602, (2017), 159-170.
Hoenen, Thomas, et al., "Minigenomes, Transcription and Replication Competent Virus-Like Particles and Beyong: Reverse Genetics Systgems for Filoviruses and other Negative Stranded Hemorrhagic Fever Viruses", Antiviral Res., 91:195, (2011), 30.
Hoffman, E., et al., "Ambisense Approach for the Generation of Influenza a Virus: vRNA and mRNA Synthesis from One Template", Virology 267(2) 310-317, (Feb. 15, 2006), 8 pgs.
Hoffman, Lucas R, et al., "Structure-Based Identification of an Inducer of the Low-pH Conformational Change in the Influenza Virus Hernagglutinin: Irreversible Inhibition of Infectivity", Journal of Virology , vol. 71, No. 11, (Nov. 1997), 8808-8820.
Hoffman, M. A., et al., "An Infectious Clone of Human Parainfluenza Virus Type 3", Journal of Virology, 71(6), (1997), 4272-4277.
Hoffmann, E,, et al., "A DNA transfection system for generation of influenza A virus from eight plasmids", Proc Natl Acad Sci U S A., 97(11), (May 23, 2000), 6108-13.
Hoffmann, E., et al., "Ambisense Approach for the Generation of Influenza A Virus: vRNA and mRNA Synthesis from One Template", Virology, 267, (2004 310-317.
Hoffmann, E., et al., "Eight-plasmid System for Rapid Generation of Influenza Virus Vaccines", Vaccine, Butterworth Scientific Guildford, 20(25-56), (Aug. 19, 2002), 3165-3170.
Hoffmann, E., et al., "Rescue of Influenza B Virus from Eight Plasmids", Proceedings of the National Academy of Sciences of USA, National Academy of Science, 99(17), (Aug. 20, 2002), 11411-11416.
Hoffmann, Erich, et al,, "A DNA transfection system for generation of influenza a virus from eight plasmids", Proceedings of the National Academy of Sciences, vol. 97, No. 11, (2000), 6108- 6113.
Holmes, E. C, et al., "Whole-Genome Analysis of Human Influenza A Virus Reveals Multiple Persistent Lineages and Reassortment Among Recent H3N2 Viruses", PLoS Biology, 3(9) 1579-1589, (2005), 11 pgs.
Holsinger, L. J., et al., "Influenza a Virus M2 Ion Channel Protein: a Structure-Function Analysis", Journal of Virology, 68 (3), (1994), pp. 1551-1563.
Honda, A., et al., "RNA Polymerase of Influenza Virus: Role of NP in RNA Chain Elongation", The Journal of Biochemistry, 104(6), (1988), 1021-1026.
Honda, Ayae, et al,, "Differential Roles of Viral RNA and cRNA in Functional Modulation of the Influenza Virus RNA Polymerase", The Journal of Biological Chemistry, 276(33), (2001), 31179-31185.
Horimoto, "Designing Vaccines for Pandemic Influenza", Current Topics Microbiol irrirnunol 333, (2009), 165-176.
Horimoto, T., et al., "Enhanced growth of seed viruses for H5N1 influenza vaccines", Virology, 366(1), (Sep. 15, 2007), 23-27.
Horimoto, T., et al., "Generation of Influenza A Viruses with Chimeric (TypeA/B) Hemagglutinins", Journal of Virology, 77(4) 8031-8038, (2003), 11 pgs.
Horimoto, T., et al "Reverse Genetics Provides Direct Evidence for a Correction of Hemagglutinin Cleavability and Virulence of an Avian Influenza A Virus", Journal of Virology, 68(5), (1994), 3120-3128.
Horimoto, T., et al., "The Development and Characterization of H5 Influenza Virus Vaccines Derived from a 2003 Human Isolate", Vaccine, 24(17) 3669-3676, (2006), 8 pgs.
Hossain, M. J., et al., "Establishment and Characterization of a Madin-Darby Canine Kidney Reporter Cell Line for Influenza a Virus Assays", J Clin Microbiol, 48(7), (2010), 2515-2523.

(56) References Cited

OTHER PUBLICATIONS

Hsieh, P.-K., et al., "Assembly of Severe Acute Respiratory Syndrome Coronavirus RNA Packaging Signal into Virus-Like Particles Is Nucleocapsid Dependent", J Viral., 79(22), (2005), 13848-13855.
Huang, T. S, et al., "Determinaton of Influenza Virus Proteins Required for Genome Replication", Jounal of Virology, Vol. 64 5669-5673, (1990), 5 pgs.
Huang, T,-S., et al., "Determination of Influenza Virus Proteins Required for Genome Replication", Journal of Virology, 64(11), (1990), 5669-5673.
Huang, Y., et al,, "Generation of Synthetic Severe Acute Respiratory Syndrome Coronavirus Pseudoparticles: Implications for Assembly and Vaccine Production", J. Viral 78(22), (Nov. 2004.), 12557-12565.
Huddleston, J. A., et al., "The Sequence of the Nucleoprotein Gene of Human Influenza A Virus, Strain A/NT/60/68", Nucleic Acids Research, 10(3), (1982), 1029-1038.
Huggins, J., et al., "Antiviral drug therapy of filovirus infections: S-adenosylhomocysteine hydrolase inhibitors inhibit Ebola virus in vitro and in a lethal mouse model.", Journal of Infectious Diseases, Vol , 179. Nr .(Suppl 1), XP002574255 ISSN: 0022-1899 'abstract, (Feb. 1999), 240-247.
Hughes, M. T., et al., "Adaptation of Influenza a Viruses to Cells Expressing Low Levels of Sialic Acid Leads to Loss of Neuraminidase Activity", Journal of Virology, 75(8), (2001), 3766-3770.
Hughes, M. T., et al., "Influenza a Viruses Lacking Sialidase Activity Can Undergo Multiple Cycles of Replication in Cell Culture, Eggs, or Mice", Journal of Virology, 74 (11), (2000), 5206-5212.
Hughes, M. T, et al., "Influenza a Viruses Lacking Sialidase Activity Can Undergo Multiple Cycles of Replication in Cell Culture, Eggs, or Mice", Journal of Virology, 74(11) 5206-212, (2000), 7 pgs.
Huisman, W., et al., "Vaccine-induced enhancement of viral infections", Vaccine, 27(4), (2009), 505-512.
Hunt, R., "Virology—Chapter Eight—Vaccines: Past Successes and Future Prospects", Microbiology and Immunology On-Line, http://www.med.sc.edu:85/lectureivaccines.htm, (Observed Feb. 26, 2003), 15 pgs.
Hurt, A. C, et al., "Identification of a human influenza type B strain with reduced sensitivity to neuraminidase inhibitor drugs", Virus Research, vol. (10412004), 205-211.
Hutchinson, Edward C., et al., "Genome packaging in influenza A virus", Journal of General Virology, 91(Pt 2), (2010), 313-328.
Hwang, Jung-Shan, et al., "Expression of Functional Influenza Virus RNA Polymerase in the Methylotrophic Yeast Pichia pastoris", Journal of Virology, 74(9), (2000), 4074-4084.
Isakova-Sivak, Irina, et al., "Characterization of Reverse Genetics-Derived Cold-Adapted Master Donor Virus a/Leningrad/134/17/57 (H2N2) and Reassortants with H5N1 Surface Genes in a Mouse Model", Clinical and Vaccine Immunology, 21(5), (May 2014), 722-731.
Ito, T, et al., "Differences in Sialic Acid-Galactose Linkages in the Chicken Egg Amnion and Allantois Influence Human Influenza Virus Receptor Specificity and Variant Selection", Journal of Virology, 71 (4) (Apr. 1997), 3357-3362.
Ives, J. A., et al., "The H274Y mutation in the influenza A/H1N1 neuraminidase active site following oseltamivir phosphate treatment leave virus severely compromised both in vitro and in vivo.", Antiviral Research, 55(2), (2002), 307-317.
Iwatsuki-Horimoto, K., et al., "The cytoplasmic tail of the influenza A virus M2 protein plays a role in viral assembly.", J Viral., 80(11), (Jun. 2006), 5233-40.
Jackson, et al., "Characterization of recombinant influenza B viruses with key neurarninidase inhibitor resistance mutations,", Journal of Antimicrobial Chemotherapy, vol. (55), (2005), 162-169.
Jackson, D., et al., "A reverse genetics approach for recovery of recombinant influenza B viruses entirely from cDNA.", J Viral., 76(22), (Nov., 2002.), 11744-7.
Jahrling, P. B., et al., "Ebola Hemorrhagic Fever: Evaluation of Passive Immunotherapy in Nonhuman Primates", J. Infect. Dis. 196, (2007), 4 pgs.
Jang, S.-W., et al., "Deoxygedunin, a Natural Product with Potent Neurotrophic Activity in Mice", PLoS One 5(7): e11528, (2010), 1-15.
Jasenosky, Luke D, et al., "Ebola Virus VP40-Induced Particle Formation and Association with the Lipid Bilayer", Journal of Virology, 75 (110, (Jun. 2001), 5205-5214.
Jennings, Philip a., et al., "Does the Higher Order Structure of the Influenza Virus Ribonucleoprotein Guide Sequence Rearrangements in Influenza Viral RNA?", Cell, 34, (Sep. 1983), 619-627.
Jiang, H, et al., "Influenza virus genome C4 promoter/origin attenuates its transcription and replication activity by the low polymerase recognition activity", Virology, 408(2), (2010), 190196.
Jiang, Y., et al., "Genome wide analysis of protein protein interactions and involvement of viral proteins in SARS CoV 2 replication", Cell Biosci, 11:140, 2021, 16 pgs., (2021), 16 pgs.
Jin, H., et al., "Imparting temperature sensitivity and attenuation in ferrets to A/Puerto Rico/8/34 influenza virus by transferring the genetic signature for temperature sensitivity from cold-adapted A/Ann Arbor/6/60", Journal of Virology, 78(2), (2004), 995-998.
Jin, H., et al., "influenza virus hemagglutinin and neuraminidase cytoplasmic tails control particle shape", The EMBO Journal, 16(6), (1997), 1236-1247.
Jin, H., et al., "The influenza virus hemagglutinin cytoplasmic tail is not essential for virus assembly or infectivity", The EMBOL Journal, 13(22), (1994), 5504-5515.
Johnson, David A, et al., "TLR Agonists as Vaccine Adjuvants", Vaccine Adjuvants and Delivery Systems, (2007), 131-156.
Johnson, R. F., et al., "Ebola Virus VP35-VP40 Interaction Is Sufficient for Packaging 3E-5E Minigenome RNA into Virus-Like Particles", Journal of Virology, 80(11), (Jun. 2006), 5135-5144.
Ju, X., et al., "A novel cell culture system modeling the SARS-CoV-2 life cycle", PloS Pathogens, 17(3): e1009439, (2021), 23 pgs.
Justice, P. A., et al., "Membrane Vesiculation Function and Exocytosis of Wild-Type and Mutant Matrix Proteins of Vesicular Stomatitis Virus", Journal of Virology, 69(5), (1995), 3156-3160.
Kang, Byoung-Hoon, et al., "Ultrafast and Real-Time Nanoplasmonic On-Chip Polymerase Chain Reaction for Rapid and Quantitative Molecular Diagnostics", ACS Nano, 15(6), (2021), 10194-10202.
Kaplan, G., et al., "In vitro Synthesis of Infectious Poliovirus RNA", Proc. Natl. Acad. Sci. USA, 82, (1985), 8824-8428.
Katinger, D., et al., "Attenuated Influenza Viruses as a Vector for Mucosal immunization Against HIV-1", Vaccines, 97, Cold Spring Harbor, (1997), 315-319.
Kato, A., et al., "Initiation of Sendai Virus Multiplication From Transfected cDNA or RNA With Negative or Positive Sense", Genes to Cells, 1, (1996), 569-579.
Kawaka, Y, et al., "Sequence requirements for cleavage activation of influenza virus hemagglutinin expressed in mammalian cells", Proc Natl Acad Sci., 85(2), (1988), 324-328.
Kawaoka, Y., "Identification by siRNA of host proteins involved in Ebolavirus replication", Great Lakes Regional Center of Excellence for Biodefense and Emerging Infectious Disease Research, [Online]; Retrieved from the Internet: s/2007/Kawaoka.pdf> [retrieved on Jan. 13, 2010]p. 10, under item C, -& Anonymous: "Index of GLRCE: documents from 2007" Great Lakes Regional Center of Excellence Index, [Online] 2007, XP002563469 Retrieved from the Internet: URL:http://www.rcebiodefense.org/glrce/docs/2007>[retrieved on Jan. 14, 2010] -&Kawaoka Y.;, (2007), pp. 1-19.
Kawaoka, Y., "Mutant Cells with Altered Sialic Acid", U.S. Appl. No. 11/644,179 filed Dec. 22, 2006, 51 pgs.
Kawaoka, Y., "Prevention and Control of Ebola Virus Infection (Ongoing Research)", Great Lakes Regional Center of Excellence (GLRCE) Annual Meeting Schedule, (Abstract), [online] [retrived on Jan. 14, 2010]. Retrieved from the Internet: <URL:http://www.rcebiodefense.org/glrce/annualmeeting/2007Agenda.pdf>, (Nov. 29, 2007), 4 pgs.
Keitel, W. A., et al., "Chapter 28—Live Cold Adapted, Reassortant Influenza Vaccines (USA)", In: Textbook of Influenza, Nicholson, K. G., et al., Editors, Blackwell Science Ltd., (1998), 373-390.

(56) References Cited

OTHER PUBLICATIONS

Kijima, H., et al., "Therapeutic Application of Ribozymes", Pharmac. Ther., 68(2), (1995), 247-267.
Kilbourne, E. D, et al., "Related studies of a recombinant influenza-virus vaccine. I. Derivation and characterization of virus and vaccine", J Infect Dis., 124(5), (Nov. 1971), 449-62.
Kim, H. et al., "Cold adaptation generates mutations associated with the growth of influenza B vaccine viruses", Vaccine, 33(43), (2015), 5786-5793.
Kim, Min-Chul, et al., "Supplementation of Influenza Split Vaccines with Conserved M2 Ectodomains Overcomes Strain Specificity and Provides Long-term Cross Protection", Molecular Therapy, 22(7), (2014), 1364-1374.
Kimura, N., et al., "An In Vivo Study of the Replication Origin in the Influenza Virus Complementary RNA", The Journal of Biochemistry, 113(1), (1993), 88-92.
Kimura. N., et al., "Transcription of a Recombinant Influenza Virus RNA in Cells That Can Expresss the Inflenza Virus RNA Polymerase and Nucleoprotein Genes", Journal of General Virology, 73, (1992), 1321-1328.
Kiseleva, I., "Role of individual genes of the A-Leningrad/134/17/57 (H2N2) cold-adapted donor strain in manifestation of the temperature-senesitive phenotype of reassortant influenza A viruses", International Congress Series, vol. 1263, (2004), 547-550.
Kiseleva, Irina V, et al., "PB2 and Pa genes control the expression of the temperature-sensitive phenotype of cold-adapted B/USSR/60/69 influenza master donor virus", Journal of General Virology, 91(4), (2010), 931-937.
Kistner, O., et al., "A Novel Mammalian Cell (Vero) Derived Influenza Virus Vaccine: Development, Characterization and Industrial Scale Production", Wiener Klinische Wochenschrift, 111/5, (1999). 207-214.
Kistner, O., et al,, "Development of a mammalian cell (Vero) derived candidate influenza virus vaccine", Vaccine, 16(9-10), (May-Jun. 1998), 960-8.
Kistner, O., et al., "Development of a Vero Cell-Derived Influenza Whole Virus Vaccine", Dev. Biol. Stand., 98, (1999), 101-110.
Kistner, Otfried, et al., "Cell culture (vero) derived whole cirus (H5N1) vaccine based on wild-type virus strain induces-cross protective immune response", Vaccine, 25(32), (2007), 6028-6036.
Kittel, Christian, et al., "Generation of an Influenza a Virus Vector Expressing Biologically Active Human Interleukin-2 from the NS Gene Segment", Journal of Virology, 79(16), (Aug. 2005), 10672-10677.
Kobayashi, H., et al., "A replication-incompetent influenza virus bearing the HN glycoprotein of human parainfluenza virus as a bivalent vaccine", Vaccine, 31(52), (2013), 6239-6246.
Kobayashi, M., et al., "Reconstitution of Influenza Virus RNA Polymerase From Three Subunits Expressed Using Recombinant Baculovirus System", Virus Research, 22, (1992), 235-245.
Kochendoerfer, G. G, et al., "Total Chemical Synthesis of the Integral Membrane Protein Influenza a Virus M2: Role of its C-Terminal Domain in Tetramer Assembly", Biochemistry 38, (1999), 11905-11913.
Kon, Theone C, et al., "Influenza Vaccine Manufacturing: Effect of Inactivation, Splitting and Site of Manufacturing, Comparison of Influenza Vaccine Production Processes", PLoS One, 11(3), e0150700, (2016-03-09), 19 pgs.
Konarska, M. M., et al., "Structure of RNAs Replicated by the DNA-Dependent T7 RNA Polymerase", Cell, 63(2), (1990), 609-618.
Konduru, K., et al., "Ebola virus glycoprotein Fc fusion protein confers protection against lethal challenge in vaccinated mice", Vaccine, 29(16), (Apr. 5, 2011), 2968-77.
Koopmans, M., et al., "Transmission of H7N7 Avian Influenza Virus to Human Beings During a Large Outbreak in Commercial Poultry Farms in the Netherlands", The Lancet, 363 587-593, (2004), 7 pgs.
Kopecky, S. A, et al., "Matrix protein and another viral component contribute to induction of apoptosis in cells infected with vesicular stornatitis virus", J Virol., 75(24), (Dec. 2001), Abstract Only.
Kovacova, A., et al., "Sequence similarities and evolutionary relationships of influenza virus a hemagglutinins,", Virus Genes, 24(1), (2002), 57-63.
Kovacova, Andrea, et al., "Sequence Similarities and Evolutionary Relationships of Influenza Vrus a Hernagglutinins", Virus Genes, 24(1), (2002), 57-63.
Kovesdi, et al., Adenoviral vectors for gene transfer, Current Opinion in Biotechnology, vol. 8, (1997), 583-589.
Kovesdi, I., et al., "Adenoviral Vectors for Gene Transfer", Current Opinion in Biotechnology, 8(5). (Oct. 1997), 583-589.
Krystal, M., et al., "Expression of the Three Influenza Virus Polymerase Proteins in a Single Cell Allows Growth Complementation of Viral Mutants", Proc. Nati. Acad, Sci. USA, 83, (1986), 2709-2713.
Krystal, M., "Influenza B/Lee/40, hemagglutinin (seg 4), complete segment.", Database ,EM_VI E.B.I. Hinxton U.K., (Apr. 25, 1990), 9 pgs.
Kugelman, J. R., et al., "Emergence of Ebola Virus Escape Variants in Infected Nonhuman Primates Treated with the MB-003 Antibody Cocktail", Cell Reports 12, (Sep. 2015), 2111-2120.
Kumar, P. K. R., et al., "Artificial Evolution and Natural Ribozymes", The FASEB Journal, 9, (1995), 1183-1195.
Kunik, Vered, et al., "Paratorne: an online tool for systematic identification of antigen-binding regions in antibodies based on sequence or structure", Nucleic Acids Research, vol. 40, Issue W1, (2012), W521-W524.
Kunkel, T. A., "Rapid and Efficient Site-Specific Mutagenesis Without Phenotypic Selection", Proc, Natl. Acad, Sci, USA, 82, (1985), 488-492
Kuwahara, Tomoko, et al., "Characterization of cell-derived and egg-passaged influenza A/Saitama/103/2014 (H3N2) strain", the 65th Annual Meeting of the Japanese Society of Virology, (2017), 1 pg.
Lamb, Robert A., et al., "Chapter 20—Paramyxoviridae: The Viruses and Their Replication", In: Fundamental Virology, Fields, B. N., et al editors, Lippincott-Raven (2nd Edition), (1996), 577-647.
Latham, T, et al., "Formation of Wild-Type and Chimeric Influenza Virus-Like Particles following Simultaneous Expression of Only Four Structural Proteins", Journal of Virology 75 (13), (2001), 6154-6165.
Lawson, N. D., "Recombinant Vesicular Stomatitis Viruses From DNA", Proc, Natl. Acad. ,Sci, USA, 92(10), (1995), 4477-4481.
Laxman, B., "Noninvasive Real-Time Imaging of Apoptosis", PNAS, 99(26), (2002), 16551-16555.
Lazarovits, Janette, et al., "Endocytosis of Chimeric Influenza Virus Hernaggulutinin Proteins That Lack a Cytoplasmic Recognition Feature for Coated Pits", the Journal of Cell Biology, vol. 134, No. 2, (1996), 339-348.
Le, T., "CaSpeR5, a family of Drosophila transgenesis and shuttle vectors with improved multiple cloning sites", Biotechniques, 42(2), (Feb. 2007), 164-166.
Leahy, M. B., et al., "An Endonuclease Switching Mechanism in the Virion RNA and cRNA Promoters of Thogoto Orthomyxovirus", Journal of Virology, 72(3), (1998), 2305-2309.
Leahy, M. B., et al., "In Vitro Polymerase Activity of Thogoto Virus: Evidence for a Unique Cap-Snatching Mechanism in a Tick-Borne Orthomyxovirus", Journal of Virology, 71(11), (1997), 8347-8351.
Leahy, M. B., et al., "Striking Conformational Similarities between the Transcription Promoters of Thogoto and Influenza A Viruses: Evidence for Intrastrand Base Pairing in the 5' Promoter Arm", Journal of Virology, 71(11), (1997), 8352-8356.
Leal, et al., "New challenges in therapeutic vaccines against HIV infection", Expert Review of Vaccines. vol. 16, No. 6, (2017), 587-600.
Lee, C. W. et al., "Generation of reassortant influenza vaccines by reverse genetics that allows utilization of a DIVA (Differentiating Infected from Vaccinated Animals) strategy for the control of avian influenza", Vaccine, vol. 22, (2004), 3175-3181.
Lee, D.-H., et al., "H9N2 avian influenza virus-like particle vaccine provides protective immunity and a strategy for the differentiation of infected from vaccinated animals", Vaccine, vol. 29, (2011), 4003-4007.

(56) References Cited

OTHER PUBLICATIONS

Lee, Dong-Hun, et al., "Progress and hurdles in development of influenza virus-like particle vaccines for veterinary use", Korean Vaccine Society, (2014), 133-139.
Lee, Jeffrey E., et al., "Complex of a Protective Antibody with Its Ebola Virus Gp Peptide Epitope: Unusual Features of a V?x Light Chain", J. Mol. Biol., 375, (2007), 202-216.
Lee, Jong-Soo, et al., "The Highly Conserved HA2 Protein of the Influenza a Virus Induces a Cross Protective Immune Response", Journal of Virological Methods, 194(1-2), (2013), 280-288.
Lee, M. S, et al., "Genetic and pathogenic characterization of H6Nl avian influenza viruses isolated in Taiwan between 1972 and 2005", Avian Diseases, 50(4), (Dec. 2006), 561-571.
LeFranc, Marie-Paule, et al., "IMGT unique numbering for immunoglobulin and T cell receptor variable domains and Ig superfamily V-like domains", Developmental & Comparative Immunology, 27, (2003), 55-77.
Lembo, A, et al,, "Administration of a synthetic TLR4 agonist protects mice from pneumonic tularemia,", J Immunol., 180(11), 7574-81.
Levis, R., et al., "Deletion Mapping of Sindbis Virus Di RNAs Derived From cDNAs Defines the Sequences Essential for Replication and Packaging", Cell, 44, (1986), 137-145.
Li, et al., "Selection of antigenically advanced variants of seasonal influenza viruses", Nature Microbiology, 1 (6), (2016), 1-10.
Li, Feng, et al., "Generation of Replication-Competent Recombinant Influenza a Viruses Carrying a Reporter Gene Harbored in the Neuraminidase Segment", Journal of Virology, 84(22), (Nov. 2010), 12075-12081.
Li, Junvvei, et al., "Engineering Influenza Viral Vectors", Bioengineered, vol. 4, No. 1, (Jan. 1, 2013), 9-14.
Li, K. S., et al,, "Genesis of a highly pathogenic and potentially pandemic H5N1 influenza virus in eastern Asia", Nature, vol. 430, (2004), 209-213 pgs.
Li, K. S, et al., "Genesis of a highly pathogenic and potentially pandemic H5NI influenza virus in eastern Asia", Nature, 430(6996), (8 Jul. 2004), 209-213.
Li, Qi, et al., "Screening of the high yield influenza B virus on MDCK cell and cloning of its whole genome", (English Abstract), Chinese Journal of Virology, 3, (Sep. 30, 2004), 1 pg.
Li, Qi, et al., "Screening of the high yield influenza B virus on MDCK cell and cloning of its whole genome", International Congress Series 1263, (2004), 610-614.
Li, S., et al., "Electroporation of Influenza Virus Ribonucleoprotein Complexes for Rescue of the Nucleoprotein and Matrix Genes", Virus Research, 37(2), (1995), 153-161.
Li, S., et al., "Influenza a Virus Transfectants with Chimeric Hernagglutinins Containing Epitopes from Different Subtypes", Journal of Virology, 66(1), (1992), 399-404.
Li, S., et al,, "Recombinant Influenza A Virus Vaccines for the Pathogenic Human a/HongKong/97 (H5N1) Viruses", J Infect Ibis., 179(5), (1999), 1132-1138.
Li, Shengqiang, et al., "Influenza A Virus Transfectants with Chimeric Hemagglutinins containing Epitopes from different subtypes", Journal of Virology 399-404, (1992) 6 pgs.
Li, Y, et al., "The I binding specificity of human VH4-34 (VH4-21) encoded antibodies is determined by both VH framework region 1 and complemntarity determining region 3", J. Mol. Biol. 256 577-589, (1996), 13 pgs.
Li. Y, et al., "Viral liposomes released from insect cells infected with recombinant baculovirus expressing the matrix protein of vesicular stomatitis virus". Journal of Virology. 67 (7), (1993), 4415-4420.
Lin, Y P, et al., "Adaptation of egg-grown and transfectant influenza viruses for growth in mammalian cells: selection of hemagglutinin mutants with elevated pH of membrane fusion", Virology, 233(2), (1997), 402-410.
Lin, Yi Pu, et al., "Adaptation of Egg-Grown and Transfectant Influenza Viruses for Growth in Mammalian Cells: Selection of Hernagglutinin Mutants with Elevated pH of Membrane Fusion", Virology, vol. 233, Issue 2, (1997), 402-410.
Liu, Bo, et al., "Comparison of three methods in construction fusion gene of influenza A virus Nucleoprotein", (English Abstract), Zhonghua Shi Yan He Lin Chuang Bing Du Xue Za Zhi, 26(1), 70-74, (Feb. 2012), 1 pg.
Liu, C., et al., "Influenza type A virus neuraminidase does not play a role in viral entry, replication, assembly, or budding.", Journal of Virology, 69(2), (1995), 1099-1106.
Liu, C., et al., "Selection and Characterization of a Neuraminidase-Minus Mutant of influenza Virus and its Rescue by Cloned Neuraminidase Genes", Virology, 194(1), (1993), 403-407.
Liu, Y., et al., "A live-attenuated Sars-CoV-2 vaccine candidate with accessory protein deletions", bioRxiv [online]. [retrieved 2022-06-10]. Retrieved from the Internet: <URL: https://www.biorxiv.org/content/10.1101/2022.02.14.480460v1.full.pdf>, (2022), 44 pgs.
Liu, Z, et al., "Fine mapping of the antigen-antibody interaction of scFv215 a recombinant antibody inhibiting RNA polymerase II from Drosophila melanogaster", J. Mol. Recog. 12:103-111, (1999), 9 pgs.
Lobo, Ingrid A., "Predicting Vaccine Effectiveness Using Systems Biology", Nature Education, 8(3):9, [online]. Retrieved from the Internet: <URL: https://www,nature.com/scitable/nated/topicpage/predicting-vaccine-effectiveness-using-systems-biology-132628443>, (2015), 4 pgs.
Longnecker, R., et al., "Ww- and SH3-domain interactions with Epstein-Barr virus LIVIP2A", Exp Cell Res., 257(2), (Jun. 15, 2000), Abstract Only.
Lott, W. B., et al., "A Two-Metal Ion Mechanism Operates in the Hammerhead Ribozyme-Mediated Cleavage of an Rna Substrate", Proc. Natl. Acad. Sci. USA, 95, (1998), 542-547.
Lu, Xiuhua, et al., "Cross-protective immunity in mice induced by live-attenuated or inactivated vaccines against highly pathogenic influenza a (H5N1) viruses", Vaccine, 24(4446), (2006), 6588-6593.
Lugovtsev, V. Y., et al., "Genetic Composition and Mutational Pattern of Influenza B Viruses Adapted to Replication in Embryonated Eggs", GenBank: AAT69446,1, (2005), 1 pg.
Luo, M., "Inhibitors of Influenza Virus Neurarninidase", Abstract No. W0296, from a paper presented at the Annual Meeting of the American Crystallographic Association, httpliwww.hwi.buffalo.edu/ACNACA98/abstractsitext/W0296.html, (Observed Feb. 27, 2003), 1 pg.
Luytjes, W., "Amplification, Expression, and Packaging of a Foreign Gene by Influenza Virus", Cell, 59(6), (1989), 1107-1113.
Ma, Y.-J., et al., "Cellular micro RNA let-7c inhibits M1 protein expression of the H1N1 influenza a virus in infected human lung epithelial cells", J. Cell. Mol. Med., 16(10), (2012), 2539-2546.
Manicassamy, Balaji, et al., "Analysis of in vivo dynamics of influenza virus infection in mice using a GFP reporter virus", Proc Nail Acad Sci. USA, 107(25), (2010), 11531-11536.
Mansky, L. M, "Retrovirus mutation rates and their role in genetic variation", J Gen Viral., 79 (Pt 6), (Jun. 1998), 1337-45.
Manz, Benjamin, et al,, "Disruption of the Viral Polymerase Complex Assembly as a Novel Approach to Attenuate Influenza A Virus", the Journal of Biological Chemistry, 286(10), (2011), 8414-8424.
Mark, A, et al., "Effect of Mutations and Deletions in a Bicistronic mRNA on the Synthesis of Influenza B Virus NB and NA Glycoproteins", Journal of Virology, vol. 77, No. 10, (May 2003), 6050-6054.
Marsh, Glenn A., et al., "Specific Residues of the Influenza A Virus Hemagglutinin Viral RNA Are Important for Efficient Packaging into Budding Virions", Journal of Virology. 81(18), (Sep. 2007), 9727-9736.
Martin, J., et al., "Studies of the Binding Properties of Influenza Hemagglutinin Receptor-Site Mutants", Virology, 241(1), (Feb. 1, 1998), 101-111.
Martinez-Sobrido, L., et al,, "Hemagglutinin-Pseudotyped Green Fluorescent Protein-Expressing Influenza Viruses for the Detection of Influenza Virus Neutralizing Antibodies", J Viral., 84(4)A2010), 2157-2163.
Martorelli Di, Genova B., et al., "Intestinal delta-6-desaturase activity determines host range for Toxoplasma sexual reproduction", PLOS Biology, vol. 17, No. 8, E3000364, (Aug. 20, 2019), XP055619380, (Aug. 20 2019), 1-19.

(56) References Cited

OTHER PUBLICATIONS

Marzi, et al., "An Ebola whole-virus vaccine is protective in nonhuman primates", Science 348(6233) 439-442, (Apr. 2015), 4 pgs.
Masuda, H., et al., "Substitution of Amino Acid Residue in Influenza A Virus Hemagglutinin Affects Recognition of Sialyl-Oligosaccharides Containing N-Glycolylneuraminic Acid", FEBS Letters, 464, (1999), 71-74.
Matrosovich, M, et al., "Overexpression of the [alpha]-2,6-sialyltransferase in MDCK cells increases influenza virus sensitivity to neuraminidase inhibitors", Journal of Virology, the American Society for Microbiology, US, vol. 77, No. 15, (1 Aug. 2003), 8418-8425.
Matsuoka, et al., "Neuraminidase Stalk Length and Additional Glycosylation of the Hemagglutinin Influence the Virulence of Influenza H5N1 Viruses for Mice", Journal of Virology, vol. 83, No. 9 (2009), pp. 4704-4708.
Matsuzaki, Y., et al,, "Epitope Mapping of the Hemagglutinin Molecule of A/(H1N1)pdrn09 Influenza Virus by Using Monoclonal Antibody Escape Mutants", Journal of Virology, 88(21) 12364-12373, (2014), 10 pgs.
Matta, M, et al., "Cell-surface sialoglycoconjugate structures in wild-type and mutant Crithidia fasciculata", Parasitol. Res., 85(4), (1999), 293-299.
McCown, M F, et al., "The influenza a virus M2 cytoplasmic tail is required for infectious virus production and efficient genome packaging.", J Virol., 79(6), (Mar. 2005), 3595-605.
McCown, M. F, et al., "Distinct domains of the influenza a virus M2 protein cytoplasmic tail mediate binding to the M1 protein and facilitate infectious virus production.", J Virol., 80(16), (Aug. 2006), 8178-89.
McCullers, et al "Multiple Genotypes of Influenza B Virus Circulated between 1979 and 2003,", Journal of Virology, vol. (78), No. (23) 12817-12828, (2004). 13 pgs.
McCullers, Jonathan A., et al., "A single amino acid change in the C-terminal domain of the matrix protein M1 of influenza B virus confers mouse adaption and virulence", Virology, 336(2) 318-326, (Jun. 5, 2005), 9 pgs.
McKee, Dwight L, et al., "Candidate drugs against SARS-CoV-2 and Covid-19", Pharmacological Research, Academic Press, London, GB, vol. 157, (Apr. 29, 2020.), 9 pgs.
McKimm, J. L., et al., "Mutations in a Conserved Residue in the Influenza Virus Neuraminidase Active Site Decreases Sensitivity to Neu5Ac2en-Derived Inhibitors", Journal of Virology, 72(3), (1998), 2456-2462.
McSharry, J. J, et al., "Phenotypic Drug Susceptibility Assay for Influenza Virus Neuraminidase Inhibitors", Cinical and Diagnostic Laboratory Immunology vol. (11), No.(2) (2004), 10 pgs.
Mebatsion, Teshome, et al., "Budding of Rabies Virus Particles in the Absence of the Spike Glycoprotein", Cell, 84(6), (1996), 941-951.
Mebatsion, Teshome, et al., "Matrix Protein of Rabies Virus Is Responsible for the Assembly and Budding of Bullet-Shaped Particles and Interacts with the Transmembrane Spike Glycoprotein G", Journal of Virology, 73 (1), (Jan. 1999.), 242/250.
Mena, I., "Rescue of a Synthetic Choramphenicol Acetyltransferase RNA into influenza Virus-Like Particles obtained from recombinant plasmids", Journal of Virology, 70(8), (1996), 5016-5024.
Mena, I., et al., "Synthesis of biologically active influenza virus core proteins using a vaccinia virus-T7 RNA polymerase expression system", Journal of General Virology, 75 2109-2114, (1994), 6 pgs.
Mena, I., et al., "Synthesis of Biologically Active Influenza Virus Core Proteins Using a Vaccinia Virus-T7 RNA Polymerase Expression System", Journal of General Virology, 75, (1994), 2109-2114.
Mishin, V. P, et al., "Protection afforded by intranasal immunization with the neuraminidase-lacking mutant of influenza A virus in a ferret model", Vaccine, 23(22), (Apr. 22, 2005), 2922-.
Mitnaul, et al., "The Cytoplasmic Tail of Influenza A Virus Neuraminidase (NA) Affects NA Incorporation into Virons, Viron Morphology, and Virulence in Mice but is not essential for Virus Replication", Journal of Virology, 70 (2), (1996), 873-879.
Mitnaul, L. J., et al,, "Balanced Hernagglutinin and Neuraminidase Activities are Critical for Efficient Replication of Influenza A Virus", Journal of Virology, 74 (13), (2000), 6015-6020.
Mittler, E., et al,, "Role of the transmernbrane domain of marburg virus surface protein GP in assembly of the viral envelope.", J Virol, 81(8), (Apr. 2007), 3942-8.
Miyoshi, H., et al., "Development of Self-Inactivating Lentivirus Vector", Journal of Virology, 72(10), (1998), 8150-8157.
Monto, A. S, et al, "Detection of influenza viruses resistant to neuraminidase inhibitors in global surveillance during the first 3 years of their use", Antirnicrobal Agents and Chemotherapy, 50(7) 2395-2402, (2006), 8 pgs.
Monto, Arnold S, et al., "Comparative efficacy of inactivated and live attenuated influenza vaccines.", N Engl J Med., 361(13) 1260-7, (Sep. 24, 2009), 8 pgs.
Morita, S., et al., "Plat-E: an efficient and stable system for trsansient packaging of retroviruses", Gene Therapy, 7(12), (2000), 1063-1066.
Moss, B., et al., "New Mammalian Expression Vectors", Nature, 348, (1990), 91-92.
Moyer, S. A., et al., "Assembly and Transcription of Synthetic Vesicular Stomatitis Virus Nucleocapsids", Journal of Virology, 65(5), (1991), 2170-2178.
Muhlberger, E., et al., "Comparision orf the Transcription and Replication Strategies of Marburg Virus and Ebola Virus by Using Artificial Replication Systems", Journal of Virology, 73(3) 2333-2342, (1999), 10 pgs.
Muhlberger, E., et al,, "Three of the four nucleocapsid proteins of Marburg virus,NP, VP35, and L, are sufficient to mediate replication and transcription of Marburg virus-specific monocistronic minigenomes", Journal of Virology, 72(11) 8756-8764, (1998), 11 pgs.
Muhlberger, Elke, "Filovirus replication and transcription", Future Virol,, 2:205, (2007), 16 pgs.
Murakami, Shin, et al., "Enhanced Growth of Influenza Vaccine Seed Viruses in Vero Cells Mediated by Broadening the Optimal pH Range for Virus Membrane Fusion", J Virol 86(3), (2014), 1405-1410
Murakami, Shin, et al., "Growth Determinants for H5N1 Influenza Vaccine Seed Viruses in Merck Cells", Journal of Virology, vol. 82, No. 21, (Nov. 2008), 10502-10509.
Muramoto, Y., et al., "Hierarchy among Viral Rna (vRNA) Segments in Their Role in vRNA Incorporation into Influenza a Virions", J. Virol., 80(5), (2006), 2318-2325.
Muramoto, Yukiko, "Hierarchy among Viral RNA (vRNA) Segments in Their Role in vRNA Incorporation into Influenza a Virions", Journal of Virology, 80(5), (2006), 2318-2325.
Murphy, B. R, et al., "An influenza a live attenuated reassortant virus possessing three temperature-sensitive mutations in the PB2 polymerase gene rapidly loses temperature sensitivity following replication in hamsters", Vaccine:15(12-13) 1372-8, (1997), 7 pgs.
Murphy, Brian R, et al, "Virulence of Avian Influenza a Viruses for Squirrel Monkeys", Infection and Immunity 37 (3), (Sep. 1982), 1119-1126.
Muster, T., et al., "An Influenza A Virus Containing Influenza B Virus 5' and 3' Noncoding Regions on the Neuraminidase Gene is Attenuated in Mice", Proc. Natl. Acad. Sci. USA, 88, (1991), 5177-5181.
Muyldermans, S, "Nanobodies: Natural single-domain antibodies", Ann. Rev, Biochem. 82, (2013), 1 pg.
Naim, H. Y., et al., "Basis for Selective Incorporation of Glycoproteins into the Influenza Virus Envelope", Journal of Virology, 67(8), (1993), 4831-4841.
Naito, S., et al., "Function and Structure of RNA Polymerase From Vesicular Stomatitis Virus", the Journal of Biological Chemistry, 251(14), (1976), 4307-4314.
Nara, et al., "How Can Vaccines Against Influenza and Other Viral Diseases Be Made More Effective?", PLoS Biology, 8 (12), (2010), e1000571.

(56) References Cited

OTHER PUBLICATIONS

Nara, P, L., et al,, "Simple, Rapid. Quantitative, Syncytium-Forming Microassay for the Detection of Human Immunodeficiency Virus Neutralizing Antibody", Aids Research and Human Retroviruses, 3(3), (1987), 283-302.
Neirynck, S., "A universal influenza a vaccine based on the extracellular domain of the M2 protein", Nature Medicine, 5 (10), (Oct. 1999), pp, 1157-1163.
Nemeroff, M. E., et al., "Influenza Virus NS1 Protein Interacts With the Cellular 30 kDa Subunit of CPSF and Inhibits 3' End Formation of Cellular Pre-mRNAs", Molecular Cell, 1(7), (1998), 991-1000.
Neumann, G., et al., "A Decade After the Generation of a Negative-Sense Rna Virus From Cloned cDNA-What Have We Learned?", Journal of General Virology, 83(11), (Nov. 2002), 2635-2662.
Neumann, G., el. al, "An improved Reverse Genetics System for Influenza A Virus Generation and its Implications for Vaccine Production", Proc. Nail, Acad. Sci. USA, 102(46) 16825-16829, (2005), 5 pgs.
Neumann, G., et al., "An improved reverse genetics system for influenza A virus generation and its implications for vaccine production", Proc. Natl. Acad. Sci, USA. 102(46), (2005), 16825-16829.
Neumann, G., et al., "Emergence and pandemic potential of swine-origin HIN1 influenza virus", Nature (London), 459(7249), (Jun. 2009.), 931-939.
Neumann, G., et al., "Generation of influenza a virus from cloned cDNAs—historical perspective and outlook for the new millenium. ", Rev Med Viral., 12(1), XP002314285, (Jan.-Feb. 2002), 13-30.
Neumann, G., et al., "Generation of influenza A viruses entirely from cloned cDNAs", Proc. Nati. Acad. Sci. USA., 96(16), (1999), 9345-9350.
Neumann, G., et al., "Genetic Engineering of Influenza and Other Negative-Strand RNA Viruses Containing Segmented Genornes", Advances in Virus Research, 53, (1999), 265300.
Neumann, G., et al., "Influenza a virus NS2 protein mediates vRNP nuclear export through Nes-independent interaction with hCRM1", The EMBO Journal, 19 (24), (2000), 6751-6758.
Neumann, G., et al., "Mutational analysis of influenza virus promoter elements in vivo", Journal of General Virology, 76 1709-1717, (1995), 9 pgs.
Neumann, G., et al., "Nuclear Import and Export of Influenza Virus Nucleoprotein", Journal of Virology, 71(12), (1997), 9690-9700.
Neumann, G., et al., "Plasmid-driven formation of influenza virus-like particles", J Virol., 74(1), [Online] Retrieved From Internet: <http://www.ncbi.n1m.nih.govipmc/articles/PMC111569/>, (Jan. 2000), 547-551.
Neumann, G., et al., "Reverse genetics of influenza virus.", Virology, 287(2). (Sep. 1, 2001), 243-50.
Neumann, G., et al., "Reverse Genetics of Influenza Viruses—Applications in Research and Vaccine Design", Monographs in Virology, 27, (2008), 118-133.
Neumann, G., et al., "Rna Polymerase I-Mediated Expression of Influenza Viral RNA Molecules", Virology, 202(1), (1994), 477-479.
Neumann, G., et al., "Synthesis of Influenza Virus: New impetus from an old enzyme, RNA polymerase I", Virus Research 82(1-2). (Jan. 30, 2002), 153-158.
Neumann, Gabriele, "MiniReview Reverse Genetics of Influenza Virus", Virology, vol. 287, (2001), 243-250.
Neumann, Gabriele, et al., "Reverse Genetics Demonstrates that Proteolytic Processing of the Ebola Virus Glycoprotein Is Not Essential for Replication in Cell Culture", Journal of Virology, 76 (1), (Jan. 2002), 406-410.
Nicolson, C., et al., "Generation of Influenza Vaccine Viruses on Vero Cells by Reverse Genetics: an H5N1 Candidate Vaccine Strain Produced Under a Quality System", Vaccine, 23 2943-2952, (2005), 10 pgs.
Niwa, H. et al "Efficient Selection for High-Expression Transfectants With a Novel Eukaryotic Factor", Gene, 108(2), (1991), 193-199.
Noda, Takeshi, et al., "Three-dimensional analysis of ribonucleoprotein complexes in influenza a virus", Nature Communications, 3, (2012), 1-6.
Odagiri, T., et al., "Nucleotide Sequence of the Pa Gene of Influenza AiWSN/33 (H1N1)", Nucleic Acids Research, 18 (3), Department of Virology, (Jan. 9, 1990), 1 pg.
Odagiri, Takato, et al., "Segment-Specific Noncoding Sequences of the in?uenza Virus Genome RNA Are Involved in the Speci?c Competition between Defective Interfering RNA and Its Progenitor RNA Segment at the Virion Assembly Step", Journal of Virology, 71(3), (1997), 2138-2145.
Olivo, P. D, et al., "Detection and quantitation of human respiratory syncytial virus (RSV) using minigenome cDNA and a Sindbis virus replicon: a prototype assay for negative-strand RNA viruses,", Virology, 251(1), (Nov. 10, 1998), 198-205.
Onishi M., et al,, "Applications of retrovirus-mediated expression cloning", Experimental Hematology, 24(2), (1996), 324-329.
Orkin, S. H, et al., "Report and Recommendations of the Panel to Assess the NIH Investment in Research on Gene Therapy", http://www.nih.govinews/panelrep.html, (Dec. 7, 1995), 37 pgs.
Ozaki, "Generation of High-Yielding Influenza a Viruses in African Green Monkey Kidney (Vero) Cells by Reverse Genetics", J Virol 78(4), (2004), 1851-1857.
Ozaki, H., et al., "Generation of High-Yielding Influenza a Viruses in African Green Money Kidney (Vero) Cells by Reverse Genetiics", Journal of Virology, 78(4) 1851-1857, (2004), 6 pgs.
Ozawa, M., et al., "An adenovirus vector-mediated reverse genetics system for influenza A virus generation". Journal of Virology. The American society for Microbiology, US vol. 81 (17), XP002471230, ISSN: 0022-538X, (Jun. 27,2007), 9556-9559.
Ozavva, M., et al., "Replication-incompetent influenza a viruses that stably express a foreign gene", Journal of General Virology, 92(Part 12)., (2011), 2879-2888.
Palache, a. M., et al., "Safety, Reactogenicity and Immunogenicity of Madin Darby Canine Kidney Cell-Derived Inactivated Influenza Subunit Vaccine. A Meta-Analysis of Clinical Studies", Dev. Biol. Stand., 98 133-134 abstract, 0999), 1 pg.
Palese, P., et al., "47. Orthomyxoviridae: the Viruses and Their Replication", In: Fields Virology (5th Edition), (2007), 90 pgs.
Palese, P., "Negative-Strand RNA Viruses: Genetic Engineering and Applications", Proc, Natl. Acad. Sci. USA, 93(21), (1996), 11354-11358.
Park, Eun K., et al., "The M2 Ectodomain is important for its incorporation into influenza A virions", J. of Virology, vol. 72, No. 3, XP002196797, (Mar. 1998), 2449-2455.
Park, K. H., et al., "Rescue of a Foreign Gene by Sendai Virus", Proc. Natl. Acad. Sci, USA, 88, (1991), 5537-5541.
Pattnaik, A. K., et al, "Cells That Express All Five Proteins of Vesicular Stomatitis Virus From Cloned cDNAs Support Replication, Assembly, and Budding of Defective Interfering Particles", Proc, Natl. Acad, Sci. USA, 88(4), (1991), 1379-1383.
Pattnaik, A. K., et al,, "The Termini of Vsv Di Particle RNAs are Sufficient to Signal Rna Encapsidation, Replication, and Budding to Generate infectious Particles", Virology, 206, (1995), 760-764.
Peeters, B. P. H., et al,, "Rescue of Newcastle Disease Virus From Cloned cDNA: Evidence That Cleavability of the Fusion Protein Is a Major Determinant for Virulence", Journal of Virology, 73(6), (1999), 5001-5009.
Peiris, J. S. M., et al., "Re-Emergence of Fatal Human Influenza a Subtype H5N1 Disease", the Lancet, 363 617-619, (2004), 3 pgs.
Pekosz, A., "Commentary—Reverse Genetics of Negative-Strand Rna Viruses: Closing the Circle", Proc. Natl. Acad. Sci. USA, 96, (1999), 8804-8806.
Pekosz, A., et al., "Influenza C virus CM2 integral membrane glycoprotein is produced from a polypeptide precursor by cleavage of an internal signal sequence", PNAS, vol. 95, XP002196653, (Oct. 1998), 13233-13238.
Pelet, T., et al., "High throughput screening assay for negative single stranded RNA virus polymerase inhibitors", Journal of Virological Methods, 128 29-36, (2005), 8 pgs.
Percy, N., et al., "Expression of a Foreign Protein by Influenza A Virus", Journal of Virology, 68(7), (1994), 4486-4492.

(56) References Cited

OTHER PUBLICATIONS

Perdue, M., et al; "Virulence and the Avian Influenza Virus Hemagglutinin Gene", United States Department of Agriculture—Agriculture Research Service, http://wwwilps.ars.usda.gov/publications/publicationslitm?SEQ_NO_155=106036, (Observed Feb. 22, 2003), 1 pg.
Perez, D. R., et al., "The Matrix 1 Protein of Influenza A Virus Inhibits the Transcriptase Activity of a Model Influenza Reporter Genome in Vivo". Virology, 249(1), (1998), 52-61.
Perez, Jasmine T., et al., "Unit 15G.4—Insertion of a GFP Reporter Gene in Influenza Virus", Curr Protoc Microbiol., (2013), 20 pgs.
Peterson, B. C., et al., "Homologous sequences other than insertion elements can serve as recombination sites in plasmid drug resistance gene amplification", Journal of Bacteriology, Oct. 1983 156(1) 177-185, (1983), 5 pgs.
Piatti, G., "Identification of immunodominant epitopes in the filamentous Hemagglutinin of Bordetella pertusis", FEMS Immunology and Medical Microbiology, 23(3), (1999), 235-241.
Piller, S C., et al., "Vpr protein of human immunodeficiency virus type 1 forms cation-selective channels in planar lipid bilayers", PNAS, 93, (1996), 111-1115.
Ping, J., et al,, "Development of high-yield influenza B virus vaccine viruses", Proc. Natl. Acad. Sci. USA, 113(51), (Dec. 5, 2016), E8296-E8305.
Ping, Jihui, et al., "Development of high-yield influenza a virus vaccine viruses", Nature Communications, [online]. Retrieved from the Internet: <http://www.nature.eorniarticle-assets/n pgincomms/2015/150902Incomms9148/extref/nc omms9148-sl.pdf>, (Sep. 2, 2015), 50 pgs.
Pinto, L. H., et al., "Influenza Virus M2 Protein Has Ion Channel Activity", Cell, 69, (May 1992), pp. 517-528.
Pittman, Kelly J., et al., "Z-DNA Binding Protein Mediates Host Control of Toxoplasma gondii Infection", Infection and Immunity, 84(10), (Oct. 2016), 3063-3070.
Plant, E P, et al,, "Mutations to A/PuertoRico/8/34 PB1 gene improves seasonal reassortant influenza A virus growth kinetics", Vaccine, 31(1), (Dec. 1, 2012), 207-212.
Pleschka, S., et al,, "A Plasmid-Based Reverse Genetics System for Influenza A Virus", Journal of Virology, 70(61(1996), 4188-4192.
Pley, H. W., et al., "Three-Dimensional Structure of a Hammerhead Ribozyme", Nature, 372, (1994), 68-74.
Popova, Lyubov, et al., "Immunodominance of Antigenic Site 8 over Site of Hemagglutinin of Recent H3N2 Influenza Viruses", Plos One, vol. 7 No. 7, (Jul. 25, 2012), e41895.
Portela, a., et al., "Replication of orthornyxoviruses", Advances in Virus Research, 54, (1999), 319-348.
Potter, C, W., "Chapter 1 - Chronicle of Influenza Pandemics", in: Textbook of Influenza, Nicoholson, K. G., et al., Editors, (Blackwell Scientific Publication), (1998), 3-18.
Powell, Robin H., et al., "Wrn conditioned media is sufficient for in vitro propagation of intestinal organoids from large farm and small companion animals", Biology Open, vol. 6, No. 5, (Mar. 27, 2017), XP055620505, (Mar. 27, 2017), 698-705.
Preston, Andrew, "Choosing a Cloning Vector", Methods in Molecular Biology, vol. 235, E. coli Plasmid Vectors 19-27, Edited by: N. Casali and A. Preston, (2003), 9 pgs.
Pushko, P et al., "Replicon-Helper Systems from Attenuated Venezuelan Equine Encephalitis Virus: Expression of Heterologous Genes in Vitro and Immunization against Heterologous Pathogens in Vivo", Virology, 239(2), (Abstract Only), (1997), 1 page.
Puzelli, S., et al., "Changes in the Hernagglutinins and Neuraminidase of Human Influenza B Viruses Isolated in Italy During the 2001-02, 2002-03, and 2003-04 Seasons", Journal of Medical Virology, 74(4) 629-640, (2004), 12 pgs.
Qiu, Y., et al., "The Influenza Virus NS1 Protein Binds to a Specific Region in Human U6 snRNA and Inhibits U6-U2 and U6-U4 snRNA Interactions During Splicing", RNA, 1, (1995), 304-316.
Qiu, Y., et al., "The Influenza Virus NS1 Protein Is a Poly(a)-Binding Protein That Inhibits Nuclear Export of mRNAs Containing Poly(a)", Journal of Virology, 68(4), (1994), 2425-2432.
Racaniello, V. R., et al., "Cloned Poliovirus Complimentary DNA Is Infectious in Mammalian Cells", Science, 214, (1981), 4 pgs.
Radecke, F., et al,, "Rescue of Measles Viruses From Cloned DNA", The EMBO Journal, 14(23), (1995), 5773-5784.
Radecke, F., et al., "Reverse Genetics Meets the Nonsegmented Negative-Strand RNA Viruses", Reviews in Medical Virology, 7, (.1997), 49-63.
Ray, M. K., et al., "A Novel Glycosylation Phenotype Expressed by Lec 23, a Chinese Hamster Ovary Mutant Deficient in alpha-Glucosidase I", Journal of Biological Chemistry, 266(34), (1991), 22818-22825.
Rayner, J., et al "Alphavirus vectors and vaccination", Reviews in Medical Virology, 12, (2002), 279-296.
Reed, M. L, et al., "Amino Acid Residues in the Fusion peptide Pocket Regulate the pH of Activation of the H5N1 Influenza Virus Hemagglutinin Protein", . J. Viral., 83(8), (2009), 3568-3580.
Restifo, N. P., et al., "Transfectant Influenza A Viruses are Effective Recombinant Immunogens in the Treatment of Experimental Cancer", Virology, 249(1998), 89-97.
Ricardo-Lax, I., et al., "Replication and single-cycle delivery of SARS-CoV-2 replicons", Science, 374(6571), (2021), 1099-1106 (9 pgs).
Rimmelzwaan, G. F., et al., "Use of GFP-expressing influenza viruses for the detection of influenza virus A/H5N1 neutralizing antibodies", Vaccine, 29(18), (2011), 3424-3430.
Roberts, A., et al., "MiniReview—Recovery of Negative-Strand RNA Viruses From Plasmid DNAs: a Positive Approach Revitalizes a Negative Field", Virology, 247(1), (1998), 1-6.
Robison, C. S, et al., "The Membrane-Proximal Stem Region of Vesicular Stomatitis Virus G Protein Confers Efficient Virus Assembly", Journal of Virology, 74 (5), (Mar, 2000), 2239- 2246.
Rodrigues, M., et al., "Influenza and Vaccinia Viruses Expressing Malaria CD8+ T and B Cell Epitopes. Comparison of Their Immunogenicity and Capacity to Induce Protective Immunity", J. Immunol,, 153(10), (1994), 4636-4648.
Roivianova, J., et al., "Live cold-adapted influenza A vaccine produced in Vero cell line", Virus Research, 103, (2004), 187-193.
Rose, J. K., "Positive Strands to the Resue Again: A Segmented Negative-Strand RNA Virus derived from cloned cDNAS", Proc. Natl. Acad. Sci. USA, 94, (1996), 14998-15000.
Ruigrok, R W, et al,, "Characterization of three highly purified influenza virus strains by electron microscopy", J Gen Virol 65 (Pt 4) 799-802, (Apr. 1984), 4 pgs.
Ruigrok, R W, et al., "Structural Characterization and Membrane Binding Properties of the Matrix Protein VP40 of Ebola Virus", Journal of Molecular Biology, 300(1), (2000), 103-112.
Ruiz-Arguello, M. B, et al., "Phosphatidylinositol-Dependent Membrane Fusion Induced by a Putative Fusogenic Sequence of Ebola Virus", Journal of Virology, 72(3), (Mar. 1998), 1775-1781.
Sansom, M. S., et al., "Influenza virus m2 Protein: a molecular modeling study of the ion channel", Protein Engineering, 6 (1), (1993), pp. 65-74.
Saphire, E. O., et al., "Feverish Quest for Ebola Immunotherapy: Straight or Cocktail", Trends Microbial, 24(9), (Sep. 2016), 684-686.
Satterlee, B., "Production of HSN1 avian influenza virus vaccine by plasmid-based reverse genetics technology", Basic Biotechnology eJournal, vol. 4, pp. 93-98, (2008), 93-98 Pgs.
Saunders, Kevin O., et al., "Neutralizing antibody vaccine for pandemic and pre-emergent coronaviruses", Nature, 594, (2021), 553-559 (27 pgs).
Schares, G., et al., "Oocysts of Neospora caninum, Hammondia heydorni, Toxoplasma gondii and Hammondia hammondi in faeces collected from dogs in Germany", International Journal of Parsitology, vol. 35, No. 14 (Dec. 1, 2005), XP027737007, (Dec. 1, 2005), 1525-1537.
Schickli, J. H, et al., "Plasmid-only Resule of Inflenza A Virus Vaccine Canadidates", Philohophical Transaction of the Royal Society of London. Series B, Biological Sciences, 356(1416), (Dec. 29, 2001), 1965-1973.
Schlesinger, S., "RNA Viruses as Vectors for the Expression of Heterologous Proteins", Molecular Biotechnology, 3(2), (1995), 155-165.

(56) References Cited

OTHER PUBLICATIONS

Schmidt, Kristina Maria, et al., "Marburg Virus Reverse Genetics Systems", Viruses 2016, 8, 178; doi: 10.3390 / v806178, www.mdpi.com/journal.viruses, (2016), 17 pgs.
Schnell, M. J., "Infectious Rabies Viruses From Cloned cDNA", The EMBO Journal, 13(18), (1994), 4195-4203.
Schnell, Matthias J. et al., "Requirement for non-specific glycoprotein cytoplasmic domain sequence to drive efficient budding of vesicular stomatitis virus", EMB Journal, 17 (5), (1998), 1289-1296.
Schotsaert, M, et al., "Universal M2 ectodomain-based influenza A vaccines: prelcinical and clinical developments", Expert Rev V accines. Apr. 2009;8(4):, 499-508.
Schultz-Cherry, S., et al., "Influenza Virus NS1 Protein Induces Apoptosis in Cultured Cells", Journal of Virology, 75(17), (2001), 7875-7881.
Seong, B. L., et al., "A New Method for Reconstituting Influenza Polymerase and RNA in Vitro: A Study of Promoter Elements for cRNA and vRNA Synthesis in Vitro and Viral Resue in Vivo", Virology, 186(1), (1992), 247-260.
Sherdian, Cormac, et al., "Innovators target vaccines for variants and shortages in global South", Nature Biotechnology, 39(4), (Apr. 2021), 393-396.
Shi, Pei-Yong, "Infectious cDNA Clone of the Epidemic West Nile Virus from New York City", Journal of Virology 5847-5856, (Jun. 2002), 10 pgs.
Shimojima, M., et al,, "Tyro3 family-mediated cell entry of Ebola and Marburg viruses", J Virol., 80(20). (Oct. 2006), 10109-16.
Shinya, Kyoko, et al., "Characterization of a Neurarninidase-Deficient Influenza A Virus as a Potential Gene Delivery Vector and a Live Vaccine", Journal of Virology, 78(6), (2004), 3083-3088.
Shortridge, K. F., et al., "Characterization of Avian H5N1 Influenza Viruses From Poultry in Hong Kong", Virology, 252 331-342, (1998), 12 pgs.
Sidhu, M. S. et al., "Rescue of Synthetic Measles Virus Minireplicons: Measles Genomic Termini Direct Efficient Expression and Propagation of a Reporter Gene", Virology, 208, (1995), 800-807.
Silvas, J. A., et al., "Contribution of SARS-CoV-2 Accessory Proteins to Viral Pathogenicity in K18 Human ACE2 Transgenic Mice", J Virol, 95(17): e00402-21, (Sep. 2021), 1-14.
Siu, Y. L., et al., "The M, E, and N Structural Proteins of the Severe Acute Respiratory Syndrome Coronavirus Are Required for Efficient Assembly, Trafficking, and Release of Virus-Like Particles", J Virol., 82(22), (2008), 11318-11330.
Skehel, J. J., et al., "On the Mechanism of Inhibition of Influenza Virus Replication by Amantadine Hydrochloride", the Journal of General Virology, 38 (1), (1977), pp. 97-110.
Smatti, Maria K., et al., "Viral-Induced Enhanced Disease Illness", Front Microbiol, vol. 9: Article 2991, (Dec. 2018), 1-19.
Smeenk, et al., "Mutations in the Hemagglutinin and Matrix Genes of a Virulent Influenza Virus Variant, A/FM/1/47-Ma, Control Different Stages in Pathogenesis", Virus Research 44, (1996), 79-95.
Smura, T, "Surface glycoprotein [Severe acute respiratory syndrome coronavirus 2]", Gen Barth Accessions QH062107. (Feb. 11, 2020), 2 pgs.
Stray, S. J., et al., "Influenza virus infection of desialylated cells", Glycobiology, 10(7), 42000), 649-658.
Strobel, I., et al., "Efficient Expression of the Tumor-Associated Antigen Mage-3 in Human Dendritic Cells, Using an Avian Influenza Virus Vector", Human Gene Therapy, 11(16), (2000), 2207-2218.
Stroud, Chad K., et al., "Disruption of FADS2 gene in mice impairs male reproduction and causes dermal and intestinal ulceration", Journal of Lipid Research, vol. 50, (2009), 1870-1880.
Subbarao, E. K., et al., "Rescue of an InfluenzaA Virus Wild-Type PB2 Gene and a Mutant Derivative Bearing a Site-Specific Temperature-Sensitive and Attenuating Mutation", Journal of Virology, 67(12), (1993), 7223-7228.
Subbarao, E. K., et al., "Sequential Addition of Temperature-Sensitive Missense Mutations into the PB2 Gene of Influenza a Transfectant Viruses Can Effect an Increase in Temperature Sensitivity and Attenuation and Permits the Rational Design of a Genetically Engineered Live Influen", Journal of Virology, 69(10),11995), 5969-5977.
Subbarao, K., et al., "Characterization of an Avian Influenza a (H5N1) Virus Isolated From a Child With a Fatal Respiratory Illness", Science, 279, (1998), 393-396.
Subbarao, K., et al., "Evaluation of a Genetically Modified Reassortant H5N1 Influenza a Virus Vaccine Candidate Generated by Plasmid-based Reverse Genetics"; Virology, vol. 305(1), (Jan. 5, 2003), 192-200.
Sugawara, K., et al., "Development of Vero Cell-Derived Inactivated Japanese Encephalities Vaccine", Biologicals, 30 303-314, (2002), 12 pgs.
Sugrue, R. J., et al., "Specific structural alteration of the influenza haemagglutinin by amantadine", The EMBO Journal, 9 (11), (1990), pp. 3469-3476.
Sugrue, R. J., et al., "Structural Characteristics of the M2 Protein of Influenza a Viruses: Evidence That It Forms a Tetrameric Channel", Virology, 180, (1991), pp. 617-624.
Suguitan, A. L, et al., "Live, Attenuated Influenza a H5N1 Candidate Vaccines Provide Broad Cross-Protection in Mice and Ferrets", PLoS Med., 3(9), (2006), 1541-1555.
Sun, Weina, et al., "Development of Influenza B Universal Vaccine Candidates Usingthe "Mosaic" Hemagglutinin Approach", American Society for Microbiology, Journal of Virology, Vaccines and Antiviral Agents, vol. 93, Issue 12, (Jun. 2019), 17 pgs.
Sunstrom, N. A., et al., "Ion Channels formed by NB, an influenza B virus Protein", J. of Membrane Biology, vol. 150, XP002196654, (Dec. 1996), 127-132.
Sweet, T. M., et al., "Creation of amantadine resistant clones of influenza type a virus using a new transfection procedure.", J Virol Methods., 69(1-2), (Dec. 1997), 103-11.
Szewczyk, B., "Purification, Thioredoxin Renaturation; and Reconstituted Activity of the Three Subunits of the Influenza a Virus RNA Polymerase", Proc. Natl. Acad. Sci. USA, 85, (1988), 7907-7911.
Taira, K., et al., "Construction of a novel RNA-transcript-trimming plasmid which can be used both in vitro in place of run-off and (G)-free transcriptions and in vivo as multisequences transcription vectors", Nucleic Acids Research, 19(19), (1991), 5125-5130.
Takada, A., et al., "DolAinregulation of betal integrins by Ebola virus glycoprotein: implication for virus entry", Virology, 278(1), (Dec. 2000), Abstract Only.
Takada, Ayato, et al., "A system for functional analysis of Ebola? virus?glycoprotein", Proc. Natl. Acad. Sci. USA, 94(26), (1997), 14764-14769.
Takada, Ayato, et al., "Antibody-dependent enhancement of viral infection: molecular mechanisms and in vivo implications", Rev Med Virol, 13(6), (2003), 387-398.
Takada, Ayato, et al., "Epitopes Required for Antibody-Dependent Enhancement of Ebola Virus Infection", J Infect Dis, 196 (Suppl 2), (2007), S347-S356.
Takada, Ayato, et al., "identification of Protective Epitopes on Ebola Virus Glycoprotein at the Single Amino Acid Level by Using Recombinant Vesicular Stomatitis Viruses", Journal of Virology, 77(2), (2003), 1069-1074.
Takada, Ayato, et al., "Infectivity-Enhancing Antibodies to Ebola Virus Glycoprotein", Journal of Virology, 75(5), (2001), 2324-2330.
Takada, Ayato, et al., "Protective efficacy of neutralizing antibodies against Ebola virus infection", Vaccine; 25(6), (2007), 993-999.
Takada. Ayato, et al., "The pathogenesis of Ebola hemorrhagic fever", Trends in Microbiology, 9(10), (2001), 506-511.
Takada, Kosuke, et al., "A Humanized Mdck Cell Line for the Efficient Isolation and Propagation of Human Influenza Viruses", Nature Microbiology, Nature Publishing Group UK; London, vol. 4; No. 8, (Apr. 29, 2019), 1268-1273.
Takeda. M., et al., "Influenza a virus M2 ion channel activity is essential for efficient replication in tissue culture,", J Virol., 76(3), (Feb. 2002). 1391-9.
Takeda, T., et al., "Expression of Podocalyxin Inhibits Cell-Cell Adhesion and Modifies Junctional Properties in Madin-Darby Canine Kidney Cells", Molecular Biology of the Cell, 11, (2000), 3219-3232.

(56) References Cited

OTHER PUBLICATIONS

Takeuchi, K., et al., "Influenza Virus M2 Protein Ion Channel Activity Stabilizes the Native Form of Fowl Plague Virus Hemagglutinin during Intracellular Transport", Journal of Virology, 68 (2); (Feb. 1994), pp. 911-919
Tan, Tiong Kit, et al., "A Covid-19 vaccine candidate using SpyCatcher multimerization of the SARS-CoV-2 spike protein receptor-binding domain induces potent neutralising antibody responses", Nature Communications, 12: 542, (2021), 1-16.
Tang, et al., "Recombinant adenovirus encoding the Ha gene from swine H3N2 influenza virus partially protects mice from challenge with heterologous virus: AIHKI1/68 (H3N2)", Archives of Virology, vol. 147 2125-2141. (2002), 17 pgs.
Tannock, G. A, et al., "Relative immunogenicity of the cold-adapted influenza virus A/Ann Arbor/6/60 (A/AA/6/60-ca), recombinants of A/Aa/6/60-ca, and parental strains with similar surface antigens.", infect Irnmun., 43(2), (Feb. 1984), 457-62.
Taylor, J., et al., "Newcastle Disease Virus Fusion Protein Expressed in a Fowlpox Virus Recombinant Confers Protection in Chickens", Journal of Virology, 64(41), (1990), 1441-1450.
Terry, G., et al., "The Contruction of Defective Interfering Rubella Virus Particles", Archives of Virology, 145(3), (2000), 625-633.
Tetsutani, K., et al., "Adjuvants in Influenza Vaccines", Vaccine 2012, vol. 30, (2012), 4 pgs.
Thao, Tran Thi Nhu, et al., "Rapid reconstruction of SARS-CoV-2 using a synthetic genomics platform", Nature, vol. 582 561-565, (2020), 24 pgs.
Theriault, S., "The role of reverse genetics systems in determining filovirus pathogenicity", Archives of Virology, Supplementurn. 157-177, (2005), 22 pgs.
Thompson, Christine M, et al., "Critical assessment of influenza VLP production in Sf9 and HEK293 expression systems", BMC Biotechnology; 15(1), (May 16, 2015), 12 pgs.
Thompson, W. W., et al "Mortality Associated With Influenza and Respiratory Syncytial Virus in the United States", JAMA, 289(2) 179-186, (2003), 8 pgs.
Tobler, K, et al., "Effect of cytoplasmic tail truncations on the activity of the M(2) ion channel of influenza A virus", J Virol., 73(12), (Dec. 1999), 9695-9701.
Towner; J 5, et al., "Generation of eGFP express ing recombinant Zaire ebolavirus for analysis of early pathogenesis events and high-throughput antiviral drug screening", Virology, Academic Press ;Orlando, U.S., vol. 332, No. 1 20-27, XP004715289 ISSN: 0042-6822 the whole document, (Feb. 5, 2005), 8 pgs.
Treanor, J. J, et al, "The B allele of the ns. gene of avian influenza viruses, but not the a allele, attenuates a human influenza A virus for squirrel monkeys", Virology, 171(1), (1989), 1-9.
Uraki, R., et al., "A Bivalent Vacine Based on a PB2-Knockout Influenza Virus Protects Mice From Secondary Pneumoccal Pneumonia", the Journal of Infectious Diseases, 212(12), (2015), 1939-1948.
Uraki, R., et al., "A Novel Bivalent Vaccine Based on a PB2-Knockout Influenza Virus Protects Mice from Pandemic H1N1 and Highly Pathogenic H5N1 Virus Challenges", Journal of Virology, 87(14), (2013), 7874-7881.
Vaishnava, Shipra, et al., "The Antibacterial Lectin Regilly Promotes the Spatial Segregation of Microbiota and Host in the Intestine", Science, 334 255-258, (2011), 4 pgs.
Vanessa, Monteil, et al., "Inhibition of SARS-CoV-2 Infections in Engineered Human Tissues Using Clinical-Grade Soluble Human ACE2", Cell, vol. 181 905-913, Retrieved from the Internet: <URL:https://www.ncbi.n1.nih.gov/pmc/articles/PMC7181998/pdfh-nain4Af>, (Apr. 24, 2020), 17 pgs.
Varner, Chad, "Developing Synthetic Multivalent Cellular Effectors", Thesis, School of Chemical and Biomolecular Engineering, Georgia Institute of Technology, (Aug. 2017), 88 pgs.
Verma, I. M, et al., "Gene Therapy—Promises, Problems and Prospects", Nature, 389, (1997), 239-242.
Via, L. E, et al., "Isolation of restriction fragments from large plasmids recovered from bacteria with multiple plasmids", Biotechniques, 11(4), (Oct. 1991), Abstract Only.
Victor, Sylvia T., et al., "A Replication-Incompetent PB2-Knockout Influenza a Virus Vaccine Vector", Journal of Virology, 2012, 86(8):4123; DOL: 10.1128/Jvi.06232-11. Journals.Asm.org;, Downloaded from http://jvi.asmorg/ on Aug. 20, 2012 by Univ. Of Wisonsin—Mad, (Feb. 1, 2012),
Victor, Sylvia, et al., "A Replication-Incompetent PB2-Knockout Influenza a Virus Vaccine Vector", Journal of Virology, vol. 86, No. 8, (Apr. 2012), 4123-4128.
Vincke, C, et al., "Introduction to heavy chain antibodies and derived nanobodies", Meth. Mol. Biol. 911, (2012), 13 pgs.
Voeten, J. T, et al., "Characterization of high-growth reassortant influenza a viruses generated in MDCK cells cultured in serum-free medium", Vaccine, Vol, 17, (1999), 1942-1950.
Volchkov, Viktor E, et al,, "Recovery of Infectious Ebola Virus from Complementary DNA: RNA Editing of the GP Gene and Viral Cytotoxicity", Science Magazine, 291, (Mar. 2001), 1965-1969.
Von Wielink, R., et al., "Mutations in the M-Gene Segment can Substantially Increase Replication Efficiency of NS1 Deletion Influenza A Virus in MCK Cells", Journal of Virology. vol. 86, (2012), 12341-12350.
Waap, Helga, et al., "In vitro isolation and seroprevalence ofin stray cats and pigeons in Lisbon, Portugal", Veterinary Parasitology, vol. 187, No. 3 XP028492469 542-547, (Jan. 17, 2012), 6 pgs.
Wagner, R., et al., "Interdependence of hemagglutinin glycosylation and neuraminidase as regulators of influenza virus growth: a study by reverse genetics", Journal of Virology, 74 (14), (Jul. 2000), 6316-6323.
Walker, W. S, et al., "HEL-Flu: an influenza virus containing the hen egg lysozyme epitope recognized by CD4-T cells from mice transgenic for an alphabeta TCR", J. Immunol., 159(6), (Sep. 1997), 2563-2566.
Wan, Yushun, et al., "Molecular mechanism for Antibody-Dependent Enhancement of Coronavirus EntrM". Journal of Virology, 94(5): e02015-19, (2019), 1-15.
Wang, et al., "Glycoengineering of Cho Cells to Improve Product Quality", Methods in Molecular Biology book series (MIMB, vol. 1603) 25-44, (May 11, 2017), 256 pgs.
Wang, B., et al., "Construction of Non-infectious SARS-CoV-2 Replicons and Their Application in Drug Evaluation", Virologica Sinica, 36, (2021), 890-900.
Wang, C., et al., "Ion Channel Activity of Influenza A Virus M2 Protein: Characterization of the Amantadine Block", Journal of Virology, 67 (9), (Sep. 1993), pp. 5585-5594.
Wang, Sheng-Fan, et al., "Antibody-dependent Sars coronavirus infection is mediated by antibodies against spike proteins", Biochem Biophys Res Commun, 451 208-214, (2014), 8 pgs.
Wang, Wenlig, et al., "Robust Immunity and Heterologous Protection against Influenza in Mice Elicited by a Novel Recombinant NP-M2e Fusion Protein Expressed in E. coli", PLoS One 7(12): e52488, (Dec. 2012), 1-13.
Wanitchang, Asavvin, et al., "Characterization of influenza A virus pseudotyped with the spike protein of porcine epidemic diarrhea virus", Archives of Virology, 163(12), (2018), 3255-3264.
Ward, C. D., et al,, "Direct Measurement of the Poliovirus RNA Polymerase Error Frequency in Vitro", Journal of Virology, 62(2), (1988), 558-562.
Wareing, M. D, et al., "Immunogenic and isotype-specific responses to Russian and US cold-adapted influenza a vaccine donor strains NLeningrad/134117/57, A/Leningrad/134/47/57, and A/Ann Arbor/6168 (H2N2) in mice.", J Med Virol., 65(1), (Sep. 2001), 171-7.
Warfield, et al., "", PNAS, Vol, 100(26), (2003), pp. 5889-15894.
Watanabe, S., et al., "Ebola virus (EBOV) VP24 inhibits transcription and replication of the EBOV genome", J Infect Dis., 196(Suppl 2), (Nov. 15, 2007), S284-90.
Watanabe, S., et al., "Influenza a Virus Lacking M2 Protein as a Live Attenuated Vaccine", Journal of Virology, 83(11), (2009), 5947-59511.

(56) References Cited

OTHER PUBLICATIONS

Watanabe, S., et al., "Production of Novel Ebola Virus-Like Particles from cDNAs: an Alternative to Ebola Virus Generation by Reverse Genetics", Journal of Virology. 78(2). (Jan. 2004), 999-1005.
Watanabe, T,, et al., "Influenza A virus can undergo multiple cycles of replication without M2 ion channel activity", J Vivol., 75(12), (Jun. 2001), 5656-62.
Watanabe, T., et al., "Influenza A Virus with Defective M2 Ion Channel Activity as a Live Vaccine", Virology, 299(2), (Aug. 1, 2002), 266-270.
Watanabe, T., et al., "Novel Approach to the Development of Effective H5N1 In?uenza A Virus Vaccines: Use of M2 Cytoplasmic Tail Mutants", Journal of Virology, 82(5), (2008), 2486-2492.
Watanabe, Tokiko, et al., "Exploitation of Nucleic Acid Packaging Signals to Generate a Novel In?uenza Virus-Based Vector Stably Expressing Two Foreign Genes", Journal of Virology, 77(19), (Oct. 2003), 10575-10583.
Watanabe, Tokiko, et al., "Exploitation of Nucleic Acid Packaging Signals to Generate a Novel Influenza Virus-Based Vector Stably Expressing Two Foreign Genes", Journal of Virology, 77(19), (Oct. 2003), 10575-10583.
Watanabe, Tokiko, et al., "Influenza A Virus Can Undergo Multiple Cycles of Replication without M2 Ion Channel Activity", Journal of Virology 75(12), (2001), 5656-5662.
Weber, F., et al., "Conserved vRNA end sequences of thogot-orthomyxovirus suggest a new panhandle structure", Archives of Virology, 142(5), (1997), 1029-1033.
Weber, F., et al., "Nucleoprotein Viral RNA and mRNA of thogot Virus: a Novel "Cap-Stealing" Mechanism in Tick-Borne Othomyxoviruses?", Journal of VIROLOGY, 70(12), (1996), 8361-8367.
Webster, R G, et al., "Evolution and moelcular epidermiology of H9N2 influenza A viruses from quail in southern China", XP002744257, retrieved from EBI accession No. UNIPR0T:A3R6C9 Database accession No. A3R6C9 the whole document, (Apr. 3, 2007), 1 pg.
Wei, Hung-Ju, et al., "Fabrication of influenza virus-like particles using M2 fusion proteins for imaging single viruses and designing vaccines", Vaccine, 29, (2011), 7163-7172.
Wentworth, D E, et al., "The NIAID Influenza Genome Sequencing Project", XP002744258, retrieved from EBI accession No. UNIPROT:U3S198 Database accession No. U3S198 the whole document, (Dec. 11, 2013), 1 pg.
Whelan, S. P. J., wt al., "Efficient Recovery of Infectious VESICULAR Stomatitis Virus Entirely from cDNA Clones", Proc. Natl. Acad. Sci. USA, 92, (1995), 8388-8392.
Wiedmer, T., et al., "Identification of three new members of the phospholipid scramblase gene family", Biochim Biophys Acta, 1467(1), (Jul. 31, 2000), Abstract Only.
Williams, Mark A., et al., "Effect of Mutations and Deletions in a Bicistronic mRNA on the Synthesis of Influenza B Virus NB and NA Glycoproteins", Journal of Virology, 63(1), (1989), 28-35.
Wills, J. W., et al., "An Assembly Domain of the Rous Sarcoma Virus Gag Protein Required Late in Budding", Journal fo Virology, 68(10), (1994), 6605-6618.
Wilson et al., "Vaccine Potential of Ebola Virus VP24, VP30, VP35 and VP40 Proteins", Virology 286, (2001), 384-90.
Wilson, Julie A, et al., "Epitopes Involved in Antibody-Medidated Protection from Ebola Virus", Science , 287(5458), (Mar. 2000), 1664-1666.
Winkler, K, et al., "Changing the antigen binding specificity by single point mutations of an anti-p24 (HIV-1) antibody", J. Immunol. 165 4505-4514, (2000), 11 pgs.
Winter, G., et al., "The use of synthetic oligodeoxynucleotide primers in cloning and sequencing segment 8 of influenza virus (A/PR/8/34)", Nucleic Acids Res., 9(2), (1981), 237-245.
Wolff, et al., "Downstream porcessing of cell culture-derived virus particles", Expert Rev. Vaccines 10(10) 1451-1475, (2011), 25 pgs.
Wood, J. M., et al., "From Lethal Virus to Life-Saving Vaccine: Developing Inactivated Vaccines for Pandemic Influenza", Nature Reviews Microbiology, 2(10), (2004), 842-847.
Wu, Rui, et al., "A live bivalent influenza vaccine based on a H9N2 virus strain", Vaccine, 28, (2010), 673-680.
Wu, Tai Te, et al., "An Analysis of the Sequences of the Variable Regions of Bence Jones Proteins and Myeloma Light Chains and Their Implications for Anti-body complementarity", J. Exp. Med., 132(2), (1970), 211-250.
Xiang, J, et al., "Modification in framework region 1 results in a decreased affinity of chimeric anti-Tag72 antibody", Mol. Immunol. 28(1/2), (1991), 141-148.
Xu, Jiayu, et al., "The Cold-Adapted, Temperature-Sensitive SARS-Co V-2 Strain TS11 Is Attenuated in Syrian Hamsters and a Candidate Attenuated Vaccine", Viruses 2023, 15, 95. https://doi.org/10,3390/v15010095, (2023), 23.
Xu, Ruodan, et al,, "Construction of SARS-CoV-2 Virus-Like Particles by Mammalian Expression System", Frontiers in Bioengineering and Technology, 8:862, (2020), 1-6.
Xu, X., et al., "Reassortment and evolution of current human influenza A and B viruses", Virus Research, 103, (2004), 55-60.
Yagi, Y., et al., "In silico panning for a non-competitive peptide inhibitor", BMC Bioinformatics, 8(11), (2007), 11 pgs.
Yamamoto, K., et al., "Orientation Dependence in Homologous Recombination", Genetics 1996 May: 143(1): 27-36, (1996), 27-36.
Yamanaka, K., et al., "In vivo Analysis of the Promoter Structure of the Influenza Virus RNA Genome Using a Transfection System With an Engineered RNA", Proc. Natl. Acad. Sci. USA, 88, (1991), 5369-5373.
Yang, P., et al,, "Hemagglutinin Specificity and Neuraminidase Coding Capacity of Meuraminidase-Deficient Influenza Viruses", Virology, 229(1), (1997), 155-165.
Yang, Z. Y, et al., "Identification of the Ebola virus glycoprotein as the main viral determinant of vascular cell cytotoxicity and injury", Nat Med., 6(8), (Aug., 2000), Abstract Only.
Yannarell, Dean A., et al., "Factors affecting the yield of cold-adapted influenza virus vaccine", Journal of Virological Methods, vol. 64, 161-169, (1997), 1 pg.
Yasuda, J., "Growth Control of Influenza a Virus by M1 Protein: Analysis of Transfectant Viruses Carrying the Chimeric M Gene", Journal of Virology, 68(12), (1994), 8141-8146.
Yen, H L, et al. "Neuraminidase Inhibitor-Resistant Recombinant a/Vietnam/1203/04 (KSN1) Influenza Viruses Retain Their Replication Efficiency and Pathogenicity in Vitro and in Vivo", Journal of Virology., vol. 81, No. 22, (Nov. 15, 2007), 12418-1 2426.
Yi, Pu Lin, et al, "Adaptation of Egg-Grown and Transfectant Influenza Viruses for Growth in Mammalian Cells: Selection of Hemagglutinin Mutants with Elevated pH of Membrane Fusion", Virology, 233(2), (Jul. 7, 1997), 402-410
Yip, Ming S., et al., "Antibody-dependent infection of human macrophages by severe acute respiratory syndrome coronavirus", Virology Journal, 11: 82, (2014), 11 pgs.
Yonezawa, A., et al "Studies of Eboa Virus Glycoprotein-Mediated Entry and Fusion by Using Pseudotyped Human Immunodeficiency Virus Type 1 Virions: Involvement of Cytoskeletal Proteins and Enhancement by Tumor Necrosis Factor Alpha", Journal of Virology, 79(2), (2005), 918-926.
Yu, Q., et al "Functional cDNA Clones of the Human Respiratory Syncytial (RS) Virus N, P, and L Proteins Support Replication of RS Virus Genomic RNA Analogs and Define Minimal trans-Acting Requirements for Rna Replication", Journal of Virology, 69(4), (1995), 2412-2419.
Yusoff, K., et al., "Nucleotide Sequence Analysis of the L Gene of Newcastle Disease Virus: Homologies With Sendai and Vesicular Stomatitis Viruses", Nucleic Acids Research, 15(10), (1987), 3961-3976.
Zaghouani, H, et al., "Induction of Antibodies to the Envelope Protein of the Human Immunodeficiency Virus by Immunization With Monoclonal Anti-Idiotypes", Proc. Natl. Acad. Sci. USA, 88, (1991), 5645-5649.
Zaghouani, H., et al., "Cells Expressing an H Chain 1g Gene Carrying a Viral T Cell Epitope are Lysed by Specific Cytolytic T Cells", the Journal of Immunology, 148(11), (1992), 3604-3609.

(56) References Cited

OTHER PUBLICATIONS

Zanin, M., et al., "An Amino Acid in the Stalk Domain of N1 Neuraminidase is Critical for Enzymatic Activity", Journal of Virology, 2017, Vo. 91, No. 2, (Jan. 2017), 12 pgs.
Zebedee, S. L, et al., "Characterization of the Influenza Virus M2 Integral Membrane Protein and Expression at the Infected-Cell Surface from Cloned cDNA", Journal of Virology, 56(2), (Nov. 1985), 502-511.
Zeitlin, L., et al., "Antibody Therapeutics for Ebola Virus Disease", Curr Opin. Viral. 17:, (2016), 11 pgs.
Zhang, Baoshan, et al., "A platform incorporating trimeric antigens into self-assembling nanoparticles reveals SARS-CoV-2-spike nanoparticles to elicit substantially higher neutralizing responses than spike alone", Scientific Reports 10, Article Number: 18149, ,(2020), 13 pgs.
Zhang, H., et al., "Expression of Functional Influenza Virus a Polymerase Proteins and Template From Cloned cDNAs in Recombinant Vaccinia Virus Infected Cells", Biochemical and Biophysical Research Communications, 200(1), (1994), 95-101.
Zhang, Q.-Y., et al., "SARS-CoV-2 replicon for high-throughput antiviral screening", J Gen Viral., 102(5), (2021), 1-4.
Zhang, V. Q, et al., "Easy two-step method for randomizing and cloning gene fragments", *Methods Mol Biol., 634, (2010), Abstract Only.
Zhang, Xuming, et al., "Expression of Interferon-y by a Coronavirus Defective-Interfering RNA Vector and its Effect on Viral Replication, Spread, and Pathogenicity", Medical Institute, University of Southern California School of Medicine, (May 1997), 327-338
Zhang, Y., et al., "A bacterial artificial chromosome (BAC)-vectored noninfectious replicon of SARS-CoV-2", Antiviral Research, vol. 185, 104974, (Jan. 2021), 1-9.
Zhao, Lili, et al., "New Insights into the Nonconserved Noncoding Region of the Subtype-Determinant Hemagglutinin and Neuraminidase Segments of Influenza A Viruses", Journal of Virology, 88(19) 11493-11503, (Oct. 2014), 11 pgs.
Zhou, Yan, "Membrane-Anchored Incorporation of a Foreign Protein in Recombinant Influenza Virions", Virology 246(1), (1998), 83-94.
Zobel, A et al., "RNA Polymerase I Catalysed Transcription of Insert Viral cDNA", Nucleic Acids Research, 21(16), (1993), 3607-3614.
"Japanese Application Serial No. 2022-513269, Notification of Reasons for Refusal dated Jun. 6, 2023", w English Translation, 15 pgs.

* cited by examiner

A/Yokohama/2017/03 PB2

AGCAAAAGCAGGTCAATTATATTCAGTATGGAAAGAATAAAAGAACTACGGAACCTGATGTCGCAGTCTCGCACT
CGCGA
GATACTGACAAAAACCACAGTGGACCATATGGCCATAATTAAGAAGTACACATCGGGGAGACAGGAAAAGAACC
CGTCAC
TTAGGATGAAATGGATGATGGCAATGAAATACCCAATCACTGCTGACAAAAGGATAACAGAAATGGTTCCGGAGA
GAAAT
GAACAAGGACAAACTCTATGGAGTAAAATGAGTGATGCTGGATCAGATCGAGTGATGGTATCACCTTTGGCTGTG
ACATG
GTGGAATAGAAATGGACCCGTGACAAGTACGGTCCATTACCCAAAAGTATACAAGACTTATTTTGACAAAGTCGA
AAGGT
TAAAACATGGAACCTTTGGCCCTGTTCATTTTAGAAATCAAGTCAAGATACGCCGAAGAGTAGACACAAACCCTGG
TCAT
GCGGACCTCAGTGCCAAGGAGGCACAAGATGTAATTATGGAAGTTGTTTTTCCCAATGAAGTGGGAGCCAGGATA
CTAAC
ATCAGAATCGCAATTAACAATAACTAAAGAGAAAAAAGAAGAACTCCGAGATTGCAAAATTTCTCCCTTGATGGTT
GCAT
ACATGTTAGAGAGAGAACTTGTCCGAAAAACAAGATTTCTCCCAGTTGCTGGCGGAACAAGCAGTATATACATTG
AAGTT
TTACATTTGACTCAAGGGACGTGTTGGGAACAAATGTACACTCCAGGTGGAGAAGTGAGGAATGACGATGTTGAC
CAAAG
CCTAATTATTGCAGCCAGGAACATAGTAAGAAGAGCCGCAGTATCAGCAGATCCACTAGCATCTTTATTGGAGATG
TGCC
ACAGCACACAAATTGGCGGGACAAGGATGGTGGACATTCTTAGACAGAACCCGACTGAAGAACAAGCTGTGGAT
ATATGC
AAGGCTGCAATGGGATTGAGAATCAGCTCATCCTTCAGCTTTGGTGGGTTTACATTTAAAAGAACAAGCGGGTCAT
CAGT
CAAAAAAGAGGAAGAAGTGCTTACAGGCAATCTCCAAACATTGAAGATAAGAGTACATGAGGGGTATGAGGAGT
TCACAA
TGGTGGGGAAAAGAGCAACAGCTATACTCAGAAAAGCAACCAGAAGATTGGTTCAGCTCATAGTGAGTGGAAGA
GACGAA

FIG. 1A

CAGTCAATAGCCGAAGCAATAATTGTGGCCATGGTGTTTTCACAAGAGGATTGCATGATAAAAGCAGTTAGAGGT
GACCT

GAATTTCGTCAACAGAGCAAATCAGCGGTTGAACCCCATGCATCAGCTTTTAAGGCATTTTCAGAAAGATGCGAAA
GTGC

TTTTTCAGAATTGGGGAATTGAACACATCGACAGTGTAATGGGAATGGTTGGAGTATTACCAGATATGACTCCAA
GCACA

GAGATGTCAATGAGAGGAATAAGAGTCAGCAAAATGGGTGTGGATGAATACTCCAGTACAGAGAGGGTGGTGGT
TAGCAT

TGATCGGTTTTTGAGAGTTCGAGACCAACGCGGGAATGTATTATTATCTCCTGAAGAGGTTAGTGAAACACAGGG
AACTG

AGAGACTGACAATAACTTATTCATCGTCGATGATGTGGGAGATTAACGGTCCTGAGTCGGTTTTGGTCAATACTTA
TCAA

TGGATCATCAGAAATTGGGAAGCTGTCAAAATTCAATGGTCTCAGAATCCTGCAATGTTGTACAACAAAATGGAAT
TTGA

ACCATTTCAATCTTTAGTCCCCAAGGCCATTAGAAGCCAATACAGTGGGTTTGTCAGAACTCTATTCCAACAAATGA
GAG

ACGTACTTGGGACATTTGACACCACCCAGATAATAAAGCTTCTCCCTTTTGCAGCCGCTCCACCAAAGCAAAGCAG
AATG

CAGTTCTCTTCACTGACTGTAAATGTGAGGGGATCAGGGATGAGAATACTTGTAAGGGGCAATTCTCCTGTATTCA
ACTA

CAACAAGACCACTAAAAGACTAACAATTCTCGGAAAAGATGCCGGCACTTTAATTGAAGACCCAGATGAAAGCAC
ATCCG

GAGTGGAGTCCGCTGTATTGAGAGGGTTTCTCATTATAGGTAAGGAAGACAGAAGATACGGGCCAGCATTAAGC
ATCAAT

GAACTGAGTAACCTTGCAAAAGGGGAAAAGGCTAATGTGCTAATCGGGCAAGGAGACGTGGTGTTGGTAATGAA
ACGAAA

ACGGGACTCTAGCATACTTACTGACAGCCAGACAGCGACCAAAAGAATTCGGATGGCCATCAATTAATGTTGAAT
AGTTT

AAAAACGACCTTGTTTCTACT (SEQ ID NO:4)

<u>A/Yokohama/2017/03 PB1</u>

AGCAAAAGCAGGCAAACCATTTGAATGGATGTCAATCCGACTCTACTGTTCCTAAAGGTTCCAGCGCAAAATGCCA
TAAG

FIG. 1B

CACCACATTCCCTTATACTGGAGATCCTCCATACAGCCATGGAACAGGAACAGGGTACACCATGGACACAGTCAAC
AGAA
CACACCAATATTCAGATAAGGGGAAGTGGACGACAAATACAGAAACTGGGGCACCCCAACTCAACCCAATTGATG
GACCA
CTACCTGAGGATAATGAGCCAAGTGGATATGCACAAACAGACTGTGTCCTGGAGGCTATGGCCTTCCTTGAAGAA
TCCCA
CCCAGGTATCTTTGAGAACTCATGCCTTGAAACAATGGAAGTCGTTCAACAAACAAGGGTGGACAAACTAACCCA
AGGTC
GCCAGACTTATGATTGGACATTAAACAGAAATCAACCGGCAGCAACTGCATTAGCCAACACCATAGAAGTTTTTAG
ATCG
AATGGACTAACAGCTAATGAATCAGGAAGGCTAATAGATTTCCTCAAGGATGTGATGGAATCAATGGATAAAGAG
GAAAT
GGAGATAACAACACACTTTCAAAGAAAAAGGAGAGTAAGAGACAACATGACCAAGAAAATGGTCACACAAAGAA
CAATAG
GGAAGAAAAAACAAAGAGTGAATAAGAGAGGCTATCTAATAAGAGCTTTGACATTGAACACGATGACCAAAGAT
GCAGAG
AGAGGTAAATTAAAAA GAAGGGCTATTGCAACACCCGGGATGCAAATTAGAGGGTTCGTGTACTTCGTTGAAACT
TTAGC
TAGAAGCATTTGCGAAAAGCTTGAACAGTCTGGACTTCCGGTTGGGGGTAATGAAAAGAAGGCCAAACTGGCAA
ATGTTG
TGAGAAAAATGATGACTAATTCACAAGACACAGAGCTTTCTTTCACAATCACTGGGGACAACACTAAGTGGAATG
AAAAT
CAAAACCCTCGAATGTTTTTGGCGATGATTACATATATCACAAAAAATCAACCTGAGTGGTTCAGAAACATCCTGA
GCAT
CGCACCAATAATGTTCTCAAACAAAATGGCAAGACTGGGAAAAGGATACATGTTCGAGAGTAAGAGAATGAAACT
CCGAA
CACAAATACCCGCAGAAATGCTAGCAAACATTGACCTGAAGTATTTCAATGAATCAACAAGGAAGAAAATTGAGA
AAATA
AGGCCTCTTCTAATAGATGGCACAGCATCATTGAGCCCTGGGATGATGATGGGCATGTTCAACATGCTAAGTACG
GTTTT
AGGAGTCTCGATACTGAATCTTGGGCAAAAGAAATACACCAAGACAACATACTGGTGGGATGGGCTCCAATCCTC
CGACG
ATTTTGCCCTCATAGTGAATGCACCAAATCATGAGGGAATACAAGCAGGAGTGGATAGATTTTACAGGACCTGCA
AGTTA

FIG. 1C

GTGGGAATCAACATGAGCAAAAAGAAGTCCTATATAAATAAAACAGGGACATTTGAATTCACAAGCTTTTTTTATC
GATA

TGGATTTGTGGCTAATTTTAGCATGGAGCTGCCCAGTTTTGGAGTGTCTGGAATAAACGAGTCAGCTGATATGAGC
ATTG

GAGTAACAGTGATAAAGAACAACATGATAAACAATGACCTTGGACCAGCAACAGCCCAGATGGCTCTCCAATTGT
TCATC

AAAGACTACAGATATACATATAGGTGCCATAGAGGAGACACACAAATTCAGACGAGAAGATCATTCGAGCTAAAG
AAGCT

GTGGGATCAAACCCAATCAAGGGCAGGACTATTGGTATCAGATGGGGGACCAAACTTATACAATATCCGGAATCT
TCACA

TCCCTGAAGTCTGCTTAAAGTGGGAGCTAATGGATGAGAATTATCGGGGAAGACTTTGTAATCCCCTGAATCCCTT
TGTC

AGCCATAAAGAAATTGAGTCTGTAAACAATGCTGTAGTGATGCCAGCCCATGGTCCGGCCAAAAGTATGGAATAT
GATGC

CGTTGCAACTACACACTCCTGGATTCCCAAGAGGAACCGCTCTATTCTCAACACAAGCCAAAGGGGAATTCTTGAG
GATG

AACAGATGTACCAGAAGTGCTGCAACTTGTTCGAGAAATTTTTCCCTAGTAGTTCATATAGGAGACCGATTGGAAT
TTCT

AGCATGGTGGAGGCCATGGTGTCTAGGGCCCGGATTGATGCCAGAATTGACTTCGAGTCTGGACGGATTAAGAA
GGAAGA

GTTCTCTGAGATCATGAAGATCTGTTCCACCATTGAAGAACTCAGACGGCAAAAATAATGAATTTAGCTTGTCCTTC
ATG

AAAAAATGCCTTGTTTCTACT (SEQ ID NO:5)

<u>A/Yokohama/2017/03 PA</u>

AGCAAAAGCAGGTACTGATTCGAAATGGAAGATTTTGTGCGACAATGCTTCAACCCGATGATTGTCGAACTTGCA
GAAAA

AGCAATGAAAGAGTATGGGGAGGATCTGAAAATTGAAACAAACAAATTTGCAGCAATATGCACTCACTTGGAGGT
ATGTT

TCATGTATTCAGATTTTCATTTCATCAATGAACAAGGCGAATCAATAGTGGTAGAACTTGATGATCCAAATGCACTG
TTA

AAGCACAGATTTGAAATAATCGAGGGGAGAGACAGAACAATGGCCTGGACAGTAGTAAACAGTATCTGCAACAC
TACTGG

FIG. 1D

AGCTGAAAAACCGAAGTTTCTACCAGATTTGTATGATTACAAGGAGAACAGATTCATCGAAATTGGAGTGACAAG
GAGAG
AAGTCCACATATATTACCTTGAAAAGGCCAATAAGATTAAATCTGAGAACACACACATTCACATTTTCTCATTCACT
GGG
GAGGAAATGGCCACAAAGGCAGACTACACTCTCGACGAGGAAAGCAGGGCTAGGATTAAGACCAGGCTATTTAC
CATAAG
ACAAGAAATGGCCAACAGAGGCCTCTGGGATTCCTTTCGTCAGTCCGAAAGAGGCGAAGAAACAATTGAAGAAA
AATTTG
AAATCTCAGGAACTATGCGTAGGCTTGCCGACCAAAGTCTCCCACCGAACTTCTCCTGCCTTGAGAATTTTAGAGC
CTAT
GTGGATGGATTCGAACCGAACGGCTGCATTGAGGGCAAGCTTTCTCAAATGTCCAAAGAAGTGAATGCCCAAATT
GAACC
TTTTCTGAAGACAACACCAAGACCAATCAAACTTCCGAATGGACCTCCTTGTTATCAGCGGTCCAAGTTCCTCCTGA
TGG
ATGCTTTAAAATTGAGCATTGAAGACCCAAGTCACGAAGGAGAAGGGATCCCATTATATGATGCGATCAAGTGCA
TAAAA
ACATTCTTTGGATGGAAAGAACCTTATATAGTCAAACCACACGAAAAGGGAATAAATTCAAATTACCTGCTGTCAT
GGAA
GCAAGTATTGTCAGAATTGCAGGACATTGAAAATGAGGAGAAGATTCCAAGGACTAAAAACATGAAGAAAACGA
GTCAAC
TAAAGTGGGCTCTTGGTGAGAACATGGCACCAGAGAAAGTAGACTTTGAAAACTGCAGAGACATAAGCGATTTGA
AGCAA
TATGATAGTGACGAACCTGAATTAAGGTCACTTTCAAGCTGGATACAGAATGAGTTCAACAAGGCCTGCGAGCTA
ACTGA
TTCAATCTGGATAGAGCTCGATGAAATTGGAGAGGACGTAGCCCCAATTGAATACATTGCAAGCATGAGGAGGAA
TTATT
TCACAGCAGAGGTGTCCCATTGTAGAGCCACTGAGTACATAATGAAGGGGGTATACATTAATACTGCCCTGCTCAA
TGCA
TCCTGTGCAGCAATGGACGATTTTCAACTAATTCCCATGATAAGCAAGTGCAGAACTAAAGAGGGAAGGCGAAAA
ACCAA
TTTATATGGATTCATCATAAAGGGAAGATCTCATTTAAGGAATGACACAGATGTGGTAAACTTTGTGAGCATGGAG
TTTT
CTCTCACTGACCCGAGACTTGAGCCACATAAATGGGAGAAATACTGTGTCCTTGAGATAGGAGATATGTTACTAAG
AAGT

FIG. 1E

GCCATAGGCCAAATTTCAAGGCCTATGTTCTTGTATGTGAGGACAAACGGAACATCAAAGGTCAAAATGAAATGG
GGAAT

GGAGATGAGACGTTGCCTCCTTCAGTCACTCCAGCAGATCGAGAGCATGATTGAAGCCGAGTCCTCGGTTAAAGA
GAAAG

ACATGACCAAAGAGTTTTTTGAGAATAAATCAGAAGCATGGCCCATTGGGGAGTCCCCCAAGGGAGTGGAAGAA
GGTTCC

ATTGGGAAAGTCTGTAGGACTCTATTGGCTAAGTCAGTGTTCAATAGCCTGTATGCATCACCACAATTGGAAGGAT
TTTC

AGCGGAGTCAAGAAAACTGCTCCTTGTTGTTCAGGCTCTTAGGGACAACCTCGAACCTGGGACCTTTGATCTTGGG
GGGC

TATATGAAGCAATTGAGGAGTGCCTGATTAATGATCCCTGGGTTTTGCTCAATGCGTCTTGGTTCAACTCCTTCCTG
ACA

CATGCATTAAAATAGTTATGGCAGTGCTACTATTTGTTATCCGTACTGTCCAAAAAAGTACCTTGTTTCTACT(SEQ
ID NO:6)

A/Yokohama/2017/03 HA

AGCAAAAGCAGGGGATAATTCTATTAACCATGAAGACTATCATTGCTTTGAGCTACATTCTATGTCTGGTTTTCGCT
CAA

AAGCTTCCCGGAAATGACAACAGCACGGCAACGCTGTGCCTTGGGCACCATGCAGTACCAAACGGAACGATAGTG
AAAAC

AATCACGAATGACCAAATTGAAGTTACTAATGCTACTGAGCTGGTTCAGAGTTCCTCAACAGGTGGAATATGCGAC
AGTC

CTCATCAGATCCTTGATGGAGAAAACTGCACACTAATAGATGCTCTATTGGGAGACCCTCAGTGTGATGGCTTCCA
AAAT

AAGAAATGGGACCTTTTTGTTGAACGCAGCAAAGCCTACAGCAACTGTTACCCTTATGATGTGCCGGATTATGCCT
CCCT

TAGGTCACTAGTTGCCTCATCCGGCACACTGGAGTTTAACAATGAAAGCTTCAATTGGACTGGAGTCACTCAGAAT
GGAA

CAAGCTCTGCTTGCAAAAGGAGATCTAATAAAAGTTTCTTTAGTAGATTGAATTGGTTGACCCACTTAAAATACAA
ATAC

CCAGCATTGAACGTGACTATGCCAAACAATGAAAAATTTGACAAATTGTACATTTGGGGGGTTCACCACCCGGGTA
CGGA

FIG. 1F

CAGTGATCAAATCAGCCTATATGCTCAAGCATCAGGAAGAATCACAGTCTCTACCAAAAGAAGCCAACAAACTGTA
ATCC
CGAATATCGGATCTAGACCCAGGGTAAGGGATGTCTCCAGCAGAATAAGCATCTATTGGACAATAGTAAAACCGG
GAGAC
ATACTTTTGATTAACAGCACAGGGAATCTAATTGCTCCTCGGGGTTACTTCAAAATACGAAGTGGGAAAAGCTCAA
TAAT
GAGATCAGATGCACCCATTGGCAAATGCAATTCTGAATGCATCACTCCAAATGGAAGCATTCCCAATGACAAACCA
TTTC
AAAATGTAAACAGGATCACATATGGGGCCTGTCCCAGATATGTTAAGCAAAACACTCTGAAATTGGCAACAGGGA
TGCGA
AATGTACCAGAGAAACAAACTAGAGGCATATTTGGCGCAATCGCGGGTTTCATAGAAAATGGTTGGGAGGGAAT
GGTGGA
CGGTTGGTACGGTTTCAGGCATCAAAATTCTGAGGGCACAGGACAAGCAGCAGATCTCAAAAGCACTCAAGCAGC
AATCA
ACCAAATCAATGGGAAACTGAATAGGTTAATCGGGAAAACAAACGAGAAATTCCATCAGATTGAAAAAGAATTCT
CAGAA
GTAGAAGGGAGAATTCAGGACCTCGAGAAATATGTTGAGGACACTAAAATAGATCTCTGGTCATACAACGCGGA
GCTTCT
TGTTGCCCTGGAGAACCAACATACAATTGATCTAACTGACTCAGAAATGAACAAACTGTTTGAAAGAACAAAGAA
GCAAC
TGAGGGAAAATGCTGAGGATATGGGCAATGGTTGTTTCAAAATATACCACAAATGTGACAATGCCTGCATAGAGT
CAATC
AGAAATGGAACTTATGACCATGATGTATACAGAGATGAAGCATTAAACAACCGGTTCCAGATCAAAGGTGTTGAG
CTGAA
GTCAGGATACAAAGATTGGATCCTATGGATTTCCTTTGCCATATCATGTTTTTTGCTCTGTGTTGCTTTGTTGGGGTT
CA
TCATGTGGGCCTGCCAAAAAGGCAACATTAGGTGCAACATTTGCATTTGAGTGCATTAATTAAAAACACCCTTGTT
TCTACT (SEQ ID NO:7)

A/Yokohama/2017/03 NP

AGCAAAAGCAGGGTTAATAATCACTCACTGAGTGACATCAAAATCATGGCGTCCCAAGGCACCAAACGGTCTTAT
GAACA

FIG. 1G

GATGGAAACTGATGGGGATCGCCAGAATGCAACTGAGATTAGGGCATCCGTCGGGAAGATGATTGATGGAATTG
GGAGAT

TCTACATCCAAATGTGCACTGAACTTAAACTCAGTGATTATGAAGGGCGGTTGATCCAGAACAGCTTGACAATAGA
GAAA

ATGGTGCTCTCTGCTTTTGATGAAAGAAGGAATAAATATCTGGAAGAACACCCCAGCGCGGGGAAAGATCCTAAG
AAAAC

TGGGGGGCCCATATACAGGAGAGTAGATGGAAAATGGATGAGGGAACTCGTCCTTTATGACAAAGAAGAAATAA
GGCGAA

TCTGGCGCCAAGCCAACAATGGTGAGGATGCGACAGCTGGTCTAACTCACATAATGATCTGGCATTCCAATTTGAA
TGAT

GCAACATACCAGAGGACAAGAGCTCTTGTTCGAACCGGAATGGATCCCAGAATGTGCTCTCTGATGCAGGGCTCG
ACTCT

CCCTAGAAGGTCCGGAGCTGCAGGTGCTGCAGTCAAAGGAATCGGGACAATGGTGATGGAGCTGATCAGAATGG
TCAAAC

GGGGGATCAACGATCGAAATTTCTGGAGAGGTGAGAATGGGCGGAAAACAAGAAGTGCTTATGAGAGAATGTG
CAACATT

CTTAAAGGAAAATTTCAAACAGCTGCACAAAGAGCAATGGTGGATCAAGTGAGAGAAAGTCGGAACCCAGGAAA
TGCTGA

GATCGAAGATCTCATATTTTTGGCAAGATCTGCATTGATATTGAGAGGATCAGTTGCTCACAAATCTTGCCTACCTG
CCT

GTGTGTATGGACCTGCAGTATCCAGTGGGTACGACTTCGAAAAAGAGGGATATTCCTTGGTGGGAATAGACCCTT
TCAAA

CTACTTCAAAATAGCCAAGTATACAGCCTAATCAGACCTAACGAGAATCCAGCACACAAGAGTCAGCTGGTATGG
ATGGC

ATGCCATTCTGCTGCATTTGAAGATTTAAGATTGTTAAGCTTCATCAGAGGGACAAAAGTATCTCCACGAGGGAAA
CTTT

CAACTAGAGGAGTACAAATTGCTTCAAATGAGAACATGGATAATATGGGATCGAGCACTCTTGAACTGAGAAGCG
GGTAC

TGGGCCATAAGGACCAGGAGTGGAGGAAACACTAATCAACAGAGGGCCTCCGCAGGCCAAACCAGTGTGCAACC
TACGTT

TTCTGTACAAAGAAACCTCCCATTTGAAAAGTCAACCATCATGGCAGCATTCACTGGAAATACGGAGGGAAGAACT
TCAG

ACATGAGGGCAGAAATCATAAGAATGATGGAAGGTGCAAAACCAGAAGAAGTGTCGTTCCGGGGGAGGGGAGT
TTTCGAG

FIG. 1H

CTCTCAGACGAGAAGGCAACGAACCCGATCGTGCCCTCTTTTGATATGAGTAATGAAGGATCTTATTTCTTCGGAG
ACAA
TGCAGAAGAGTACGACAATTAAGGAAAAATACCCTTGTTTCTACT (SEQ ID NO:8)

A/Yokohama/2017/03 NA

AGCAAAAGCAGGAGTAAAGATGAATCCAAATCAAAAGATAATAACGATTGGCTCTGTTTCCCTCACCATTTCCACA
ATAT
GCTTCTTCATGCAAATTGCCATCCTGATAACTACTGTAACATTGCATTTCAAGCAATATGAATTCAACTCCCCCCCAA
AC
AACCAAGTGATGCTGTGTGAACCAACAATAATAGAAAGAAACATAACAGAGATAGTGTATCTGACCAACACCACC
ATAGA
GAAGGAAATATGCCCCAAACTAGCAGAATACAGAAATTGGTCAAAGCCGCAATGTAACATTACAGGATTTGCACC
TTTTT
CTAAGGACAATTCGATTCGGCTTTCCGCTGGTGGGGACATCTGGGTGACAAGAGAACCTTATGTGTCATGCGATCC
TGAC
AAGTGTTATCAATTTGCCCTTGGACAGGGAACAACACTAAACAACGTGCATTCAAATGACATAGTACATGATAGGA
CCCC
TTATCGGACCCTATTGATGAATGAGTTGGGTGTTCCATTTCATCTGGGGACCAAGCAAGTGTGCATAGCATGGTCC
AGCT
CAAGTTGTCACGATGGAAAAGCATGGCTGCATGTTTGTGTAACGGGGGATGATGAAAATGCAACTGCTAGCTTCA
TTTAC
AATGGGAGGCTTGCAGATAGTATTGTTTCATGGTCCAAAAAAATCCTCAGGACCCAGGAGTCAGAATGCGTTTGT
ATCAA
TGGAACTTGTACAGTAGTAATGACTGATGGGAGTGCTTCAGGAAAAGCTGATACTAAAATACTATTCATTGAGGA
GGGGA
AAATTGTTCATACTAGCACATTATCAGGAAGTGCTCAGCATGTCGAGGAGTGCTCCTGTTATCCTCGATATCCTGGT
GTC
AGATGTGTCTGCAGAGACAACTGGAAAGGCTCCAATAGGCCCATCGTAGATATAAACATAAAGGATTATAGCATT
GTTTC
CAGTTATGTGTGCTCAGGACTTGTTGGAGACACACCCAGAAAAAACGACAGCTCCAGCAGTAGCCATTGCTTGGA
TCCAA
ACAATGAGGAAGGTGGTCATGGAGTGAAAGGCTGGGCCTTTGATGATGGAAATGACGTGTGGATGGGAAGAAC
GATCAGC

FIG. 1I

GAGAAGTTACGCTCAGGATATGAAACCTTCAAAGTCATTGAAGGCTGGTCCAACCCTAACTCCAAATTGCAGATAA
ATAG

GCAAGTCATAGTTGACAGAGGTAACAGGTCCGGTTATTCTGGTATTTTCTCTGTTGAAGGCAAAAGCTGCATCAAT
CGGT

GCTTTTATGTGGAGTTGATAAGGGGAAGAAAACAGGAAACTGAAGTCTTGTGGACCTCAAACAGTATTGTTGTGT
TTTGT

GGCACCTCAGGTACATATGGAACAGGCTCATGGCCTGATGGGGCGGACATCAATCTCATGCCTATATAAGCTTTCG
CAAT

TTTAGAAAAAAACTCCTTGTTTCTACT (SEQ ID NO:9)

Which encodes M N P N Q K I I T I G S V S L T I S T I C F F M Q I A I L I T T V T L H F K Q Y E
F N S P P N N Q V M L C E P T I I E R N I T E I V Y L T N T T I E K E I C P K L A E Y R N W S
K P Q C N I T G F A P F S K D N S I R L S A G G D I W V T R E P Y V S C D P D K C Y Q F A L
G Q G T T L N N V H S N D I V H D R T P Y R T L L M N E L G V P F H L G T K Q V C I A W
S S S S C H D G K A W L H V C V T G D D E N A T A S F I Y N G R L A D S I V S W S K K I L
R T Q E S E C V C I N G T C T V V M T D G S A S G K A D T K I L F I E E G K I V H T S T L S
G S A Q H V E E C S C Y P R Y P G V R C V C R D N W K G S N R P I V D I N I K D Y S I V S S
Y V C S G L V G D T P R K N D S S S S S H C L D P N N E E G G H G V K G W A F D D G N D
V W M G R T I S E K L R S G Y E T F K V I E G W S N P N S K L Q I N R Q V I V D R G N R S
G Y S G I F S V E G K S C I N R C F Y V E L I R G R K Q E T E V L W T S N S I V V F C G T S G
T Y G T G S W P D G A D I N L M P I (SEQ ID NO:3)

A/Yokohama/2017/03 M

AGCAAAAGCAGGTAGATATTGAAAGATGAGCCTTCTAACCGAGGTCGAAACGTATGTTCTCTCTATCGTTCCATCA
GGCC

CCCTCAAAGCCGAGATCGCGCAGAGACTTGAAGATGTCTTTGCTGGGAAAAACACAGATCTTGAGGCTCTCATGG
AATGG

CTAAAGACAAGACCAATTCTGTCACCTCTGACTAAGGGGATTCTGGGGTTTGTGTTCACGCTCACCGTGCCCAGTG
AGCG

AGGACTGCAGCGTAGACGCTTTGTCCAAAATGCCCTCAATGGGAATGGAGATCCAAATAACATGGACAAAGCAGT
TAAAC

TGTATAGGAAACTTAAGAGGGAGATAACGTTCCATGGGGCCAAAGAAATAGCTCTCAGTTATTCTGCTGGTGCAC
TTGCC

FIG. 1J

AGTTGCATGGGCCTCATATACAATAGGATGGGGGCTGTAACCACTGAAGTGGCATTTGGCCTGGTATGTGCAACA
TGTGA
GCAGATTGCTGACTCCCAGCACAGGTCTCATAGGCAAATGGTGGCAACAACCAATCCATTAATAAGGCATGAGAA
CAGAA
TGGTTTTGGCCAGCACTACAGCTAAGGCTATGGAGCAAATGGCTGGATCAAGTGAGCAGGCAGCGGAGGCCATG
GAGATT
GCTAGTCAGGCCAGGCAAATGGTGCAGGCAATGAGAGCCATTGGGACTCATCCTAGCTCCAGTACTGGTCTAAGA
GATGA
TCTTCTTGAAAATTTGCAGACCTATCAGAAACGAATGGGGGTGCAGATGCAACGATTCAAGTGACCCACTTGTTGT
TGCC
GCGAGTATCATTGGGATCTTGCACTTGATATTGTGGATTCTTGATCGTCTTTTTTTCAAATGCGTCTATCGACTCTTC
AA
ACACGGCCTTAAAAGAGGCCCTTCTACGGAAGGAGTACCTGAGTCTATGAGGGAAGAGTATCGAAAGGAACAGC
AGAATG (SEQ ID NO:10)

CTGTGGATGCTGACGACAGTCATTTTGTCAGCATAGAGTTGGAGTAAAAAACTACCTTGTTTCTACT

A/Yokohama/2017/03 NS

AGCAAAAGCAGGGTGACAAAGACATAATGGATTCCAACACTGTGTCAAGTTTCCAGGTAGATTGCTTTCTTTGGCA
TATC
CGGAAACAAGTTGTAGACCAAGAACTGAGTGATGCCCCATTCCTTGATCGGCTTCGCCGAGATCAGAGGTCCCTA
AGGGG
AAGAGGCAATACTCTCGGTCTAGACATCAAAGCAGCCACCCATGTTGGAAAGCAAATTGTAGAAAAGATTCTGAA
AGAAG
AATCTGATGAGGCACTTAAAATGACCATGGTCTCCACACCTGCTTCGCGATACATAACTGACATGACTATTGAGGA
ATTG
TCAAGAAACTGGTTCATGCTAATGCCCAAGCAGAAAGTGGAAGGACCTCTTTGCATCAGAATGGACCAGGCAATC
ATGGA
GAAAAACATCATGTTGAAAGCGAATTTCAGTGTGATTTTTGACCGACTAGAGACCATAGTATTACTAAGGGCTTTC
ACCG
AAGAGGGAGCAATTGTTGGCGAAATCTCACCATTGCCTTCTTTTCCAGGACATACTATTGAGGATGTCAAAAATGC
AATT

FIG. 1K

GGGGTCCTCATCGGAGGACTTGAATGGAATGATAACACAGTTCGAGTCTCTAAAAATCTACAGAGATTCGCTTGG
AGAAG
CAGTAATGAGAATGGGGGACCTCCACTTACTCCAAAACAGAAACGGAAAATGGCGAGAACAGCTAGGTCAAAAG
TTTGAA
GAGATAAGATGGCTGATTGAAGAAGTGAGACACAGACTAAAAACAACTGAAAATAGCTTTGAACAAATAACATTC
ATGCA
AGCATTACAACTGCTGTTTGAAGTGGAACAGGAGATAAGAACTTTCTCATTTCAGCTTATTTAATGATAAAAAACA
CCCT
TGTTTCTACT (SEQ ID NO:11)

FIG. 1L

MNPNQKIITIGSVSLTISTICFFMQIAILITTVTLHFKQYEFNSPPNNQVMLCEPTIIERNVTEIVYLTNTTIEKEI
CPKPAEYRNWSKPQCGITGFAPFSKDNSIRLSAGGDIWVTREPYVSCDPDKCYQFALGQGTTLNNVHSNNTVRDRTP
YRTLLMNELGVPFHLGTKQVCIAWSSSSCHDGKAWLHVCITGDDKNATASFIYNGRLVDSVVSWSKDILRTQESECV
CINGTCTVVMTDGSASGKADTKILFIEEGKIVHTSKLSGSAQHVEECSCYPRYPGVRCVCRDNWKGSNRPIVDINIK
DHSIVSSYVCSGLVGDTPRKNDSSSSSHCLDPNNEEGGHGVKGWAFDDGNDVWMGRTINETSRLGYETFKVVEGWSN
PKSKLQINRQVIVDRGDRSGYSGIFSVEGKSCINRCFYVELIRGRKEETEVLWTSNSIVVFCGTSGTYGTGSWPDGA
DLNLMPI (SEQ ID NO:2)

FIG. 2

>Y2017M3L4-NA(32A, 147N, 329D, 347Q, del46-50aa)
ATGAATCCAAATCAAAAGATAATAACGATTGGCTCTGTTTCCCTCACCATTTCCACAATA
TGCTTCTTCATGCAAATTGCCATCCTGATAACTGCTGTAACATTGCATTTCAAGCAATAT
GAATTCAACTCCCCCATGCTGTGTGAACCAACAATAATAGAAAGAAACATAACAGAGATA
GTGTATCTGACCAACACCACCATAGAGAAGGAAATATGCCCCAAACTAGCAGAATACAGA
AATTGGTCAAAGCCGCAATGTAACATTACAGGATTTGCACCTTTTTCTAAGGACAATTCG
ATTCGGCTTTCCGCTGGTGGGGACATCTGGGTGACAAGAGAACCTTATGTGTCATGCGAT
CCTGACAAGTGTTATCAATTTGCCCTTGGACAGGGAACAACACTAAACAACGTGCATTCA
AATAACATAGTACATGATAGGACCCCTTATCGGACCCTATTGATGAATGAGTTGGGTGTT
CCATTTCATCTGGGGACCAAGCAAGTGTGCATAGCATGGTCCAGCTCAAGTTGTCACGAT
GGAAAAGCATGGCTGCATGTTTGTGTAACGGGGGATGATGAAAATGCAACTGCTAGCTTC
ATTTACAATGGGAGGCTTGCAGATAGTATTGTTTCATGGTCCAAAAAAATCCTCAGGACC
CAGGAGTCAGAATGCGTTTGTATCAATGGAACTTGTACAGTAGTAATGACTGATGGGAGT
GCTTCAGGAAAAGCTGATACTAAAATACTATTCATTGAGGAGGGAAAATTGTTCATACT
AGCACATTATCAGGAAGTGCTCAGCATGTCGAGGAGTGCTCCTGTTATCCTCGATATCCT
GGTGTCAGATGTGTCTGCAGAGACAACTGGAAAGGCTCCAATAGGCCCATCGTAGATATA
AACATAAAGGATTATAGCATTGTTTCCAGTTATGTGTGCTCAGGACTTGTTGGAGACACA
CCCAGAAAAGACGACAGCTCCAGCAGTAGCCATTGCTTGGATCCAAACAATGAGGAAGGT
GGTCAAGGAGTGAAAGGCTGGGCCTTTGATGATGGAAATGACGTGTGGATGGGAAGAACG
ATCAGCGAGAAGTTACGCTCAGGATATGAAACCTTCAAAGTCATTGAAGGCTGGTCCAAC
CCTAACTCCAAATTGCAGATAAATAGGCAAGTCATAGTTGACAGAGGTAACAGGTCCGGT
TATTCTGGTATTTTCTCTGTTGAAGGCAAAAGCTGCATCAATCGGTGCTTTTATGTGGAG
TTGATAAGGGGAAGAAAACAGGAAACTGAAGTCTTGTGGACCTCAAACAGTATTGTTGTG
TTTTGTGGCACCTCAGGTACATATGGAACAGGCTCATGGCCTGATGGGGCGGACATCAAT
CTCATGCCTATATAAGCTTTCGCAATTTTAGAAAAAAACTCCTTGTTTCTACT (SEQ ID NO:12)

M N P N Q K I I T I G S V S L T I S T I C F F M Q I A I L I T A V T L H F K Q
Y E F N S P M L C E P T I I E R N I T E I V Y L T N T T I E K E I C P K L A E
Y R N W S K P Q C N I T G F A P F S K D N S I R L S A G G D I W V T R E P
Y V S C D P D K C Y Q F A L G Q G T T L N N V H S N N I V H D R T P Y R
T L L M N E L G V P F H L G T K Q V C I A W S S S S C H D G K A W L H V
C V T G D D E N A T A S F I Y N G R L A D S I V S W S K K I L R T Q E S E
C V C I N G T C T V V M T D G S A S G K A D T K I L F I E E G K I V H T S
T L S G S A Q H V E E C S C Y P R Y P G V R C V C R D N W K G S N R P I
V D I N I K D Y S I V S S Y V C S G L V G D T P R K D D S S S S S H C L D
P N N E E G G Q G V K G W A F D D G N D V W M G R T I S E K L R S G Y
E T F K V I E G W S N P N S K L Q I N R Q V I V D R G N R S G Y S G I F S
V E G K S C I N R C F Y V E L I R G R K Q E T E V L W T S N S I V V F C G
T S G T Y G T G S W P D G A D I N L M P I (SEQ ID NO:1)

>Y2017M3L4HA
ATGAAGACTATCATTGCTTTGAGCTACATTCTATGTCTGGTTTTCGCTCAAAAGCTTCCC
GGAAATGACAACAGCACGGCAACGCTGTGCCTTGGGCACCATGCAGTACCAAACGGAACG
ATAGTGAAAACAATCACGAATGACCAAATTGAAGTTACTAATGCTACTGAGCTGGTTCAG
AGTTCCTCAACAGGTGGAATATGCGACAGTCCTCATCAGATCCTTGATGGAGAAAACTGC
ACACTAATAGATGCTCTATTGGGAGACCCTCAGTGTGATGGCTTCCAAAATAAGAAATGG

FIG. 3A

GACCTTTTTGTTGAACGCAGCAAAGCCTACAGCAACTGTTACCCTTATGATGTGCCGGAT
TATGCCTCCCTTAGGTCACTAGTTGCCTCATCCGGCACACTGGAGTTTAACAATGAAAGC
TTCAATTGGACTGGAGTCACTCAGAATGGAACAAGCTCTGCTTGCAAAAGGAGATCTAAT
AAAAGTTTCTTTAGTAGATTGAATTGGTTGACCCACTTAAAATACAAATACCCAGCATTG
AACGTGACTATGCCAAACAATGAAAAATTTGACAAATTGTACATTTGGGGGGTTCACCAC
CCGGGTACGGACAGTGATCAAATCAGCCTATATGCTCAAGCATCAGGAAGAATCACAGTC
TCTACCAAAAGAAGCCAACAAACTGTAATCCCGAATATCGGATCTAGACCCAGGGTAAGG
GATGTCTCCAGCAGAATAAGCATCTATTGGACAATAGTAAAACCGGGAGACATACTTTTG
ATTAACAGCACAGGGAATCTAATTGCTCCTCGGGGTTACTTCAAAATACGAAGTGGGAAA
AGCTCAATAATGAGATCAGATGCACCCATTGGCAAATGCAATTCTGAATGCATCACTCCA
AATGGAAGCATTCCCAATGACAAACCATTTCAAAATGTAAACAGGATCACATATGGGGCC
TGTCCCAGATATGTTAAGCAAAACACTCTGAAATTGGCAACAGGGATGCGAAATGTACCA
GAGAAACAAACTAGAGGCATATTTGGCGCAATCGCGGGTTTCATAGAAAATGGTTGGGAG
GGAATGGTGGACGGTTGGTACGGTTTCAGGCATCAAAATTCTGAGGGCACAGGACAAGCA
GCAGATCTCAAAAGCACTCAAGCAGCAATCAACCAAATCAATGGGAAACTGAATAGGTTA
ATCGGGAAAACAAACGAGAAATTCCATCAGATTGAAAAAGAATTCTCAGAAGTAGAAGGG
AGAATTCAGGACCTCGAGAAATATGTTGAGGACACTAAAATAGATCTCTGGTCATACAAC
GCGGAGCTTCTTGTTGCCCTGGAGAACCAACATACAATTGATCTAACTGACTCAGAAATG
AACAAACTGTTTGAAAGAACAAAGAAGCAACTGAGGGAAAATGCTGAGGATATGGGCAAT
GGTTGTTTCAAAATATACCACAAATGTGACAATGCCTGCATAGAGTCAATCAGAAATGGA
ACTTATGACCATGATGTATACAGAGATGAAGCATTAAACAACCGGTTCCAGATCAAAGGT
GTTGAGCTGAAGTCAGGATACAAAGATTGGATCCTATGGATTTCCTTTGCCATATCATGT
TTTTTGCTCTGTGTTGCTTTGTTGGGGTTCATCATGTGGGCCTGCCAAAAAGGCAACATT
AGGTGCAACATTTGCATTTGAGTGCATTAATTAAAAACACCCTTGTTTCTACT (SEQ ID NO:13)

>Y2017M3L4-M(M1-23Q)
ATGAGCCTTCTAACCGAGGTCGAAACGTATGTTCTCTCTATCGTTCCATCAGGCCCCCTC
AAAGCCCAGATCGCGCAGAGACTTGAAGATGTCTTTGCTGGGAAAAACACAGATCTTGAG
GCTCTCATGGAATGGCTAAAGACAAGACCAATTCTGTCACCTCTGACTAAGGGGATTCTG
GGGTTTGTGTTCACGCTCACCGTGCCCAGTGAGCGAGGACTGCAGCGTAGACGCTTTGTC
CAAAATGCCCTCAATGGGAATGGAGATCCAAATAACATGGACAAAGCAGTTAAACTGTAT
AGGAAACTTAAGAGGGAGATAACGTTCCATGGGGCCAAAGAAATAGCTCTCAGTTATTCT
GCTGGTGCACTTGCCAGTTGCATGGGCCTCATATACAATAGGATGGGGGCTGTAACCACT
GAAGTGGCATTTGGCCTGGTATGTGCAACATGTGAGCAGATTGCTGACTCCCAGCACAGG
TCTCATAGGCAAATGGTGGCAACAACCAATCCATTAATAAGGCATGAGAACAGAATGGTT
TTGGCCAGCACTACAGCTAAGGCTATGGAGCAAATGGCTGGATCAAGTGAGCAGGCAGCG
GAGGCCATGGAGATTGCTAGTCAGGCCAGGCAAATGGTGCAGGCAATGAGAGCCATTGGG
ACTCATCCTAGCTCCAGTACTGGTCTAAGAGATGATCTTCTTGAAAATTTGCAGACCTAT
CAGAAACGAATGGGGGTGCAGATGCAACGATTCAAGTGACCCACTTGTTGTTGCCGCGAG
TATCATTGGGATCTTGCACTTGATATTGTGGATTCTTGATCGTCTTTTTTTCAAATGCGT
CTATCGACTCTTCAAACACGGCCTTAAAAGAGGCCCTTCTACGGAAGGAGTACCTGAGTC
TATGAGGGAAGAGTATCGAAAGGAACAGCAGAATGCTGTGGATGCTGACGACAGTCATTT
TGTCAGCATAGAGTTGGAGTAAAAAACTACCTTGTTTCTACT (SEQ ID NO:14)

>Y2017M3L4-NP(101N)
ATGGCGTCCCAAGGCACCAAACGGTCTTATGAACAGATGGAAACTGATGGGGATCGCCAG
AATGCAACTGAGATTAGGGCATCCGTCGGGAAGATGATTGATGGAATTGGGAGATTCTAC
ATCCAAATGTGCACTGAACTTAAACTCAGTGATTATGAAGGGCGGTTGATCCAGAACAGC
TTGACAATAGAGAAAATGGTGCTCTCTGCTTTTGATGAAAGAAGGAATAAATATCTGGAA
GAACACCCCAGCGCGGGGAAAGATCCTAAGAAAACTGGGGGGCCCATATACAGGAGAGTA
AATGGAAAATGGATGAGGGAACTCGTCCTTTATGACAAAGAAGAAATAAGGCGAATCTGG
CGCCAAGCCAACAATGGTGAGGATGCGACAGCTGGTCTAACTCACATAATGATCTGGCAT

FIG. 3B

TCCAATTTGAATGATGCAACATACCAGAGGACAAGAGCTCTTGTTCGAACCGGAATGGAT
CCCAGAATGTGCTCTCTGATGCAGGGCTCGACTCTCCCTAGAAGGTCCGGAGCTGCAGGT
GCTGCAGTCAAAGGAATCGGGACAATGGTGATGGAGCTGATCAGAATGGTCAAACGGGGG
ATCAACGATCGAAATTTCTGGAGAGGTGAGAATGGGCGGAAAACAAGAAGTGCTTATGAG
AGAATGTGCAACATTCTTAAAGGAAAATTTCAAACAGCTGCACAAAGAGCAATGGTGGAT
CAAGTGAGAGAAAGTCGGAACCCAGGAAATGCTGAGATCGAAGATCTCATATTTTTGGCA
AGATCTGCATTGATATTGAGAGGATCAGTTGCTCACAAATCTTGCCTACCTGCCTGTGTG
TATGGACCTGCAGTATCCAGTGGGTACGACTTCGAAAAAGAGGGATATTCCTTGGTGGGA
ATAGACCCTTTCAAACTACTTCAAAATAGCCAAGTATACAGCCTAATCAGACCTAACGAG
AATCCAGCACACAAGAGTCAGCTGGTATGGATGGCATGCCATTCTGCTGCATTTGAAGAT
TTAAGATTGTTAAGCTTCATCAGAGGGACAAAAGTATCTCCACGAGGGAAACTTTCAACT
AGAGGAGTACAAATTGCTTCAAATGAGAACATGGATAATATGGGATCGAGCACTCTTGAA
CTGAGAAGCGGGTACTGGGCCATAAGGACCAGGAGTGGAGGAAACACTAATCAACAGAGG
GCCTCCGCAGGCCAAACCAGTGTGCAACCTACGTTTTCTGTACAAAGAAACCTCCCATTT
GAAAAGTCAACCATCATGGCAGCATTCACTGGAAATACGGAGGGAAGAACTTCAGACATG
AGGGCAGAAATCATAAGAATGATGGAAGGTGCAAAACCAGAAGAAGTGTCGTTCCGGGGG
AGGGGAGTTTTCGAGCTCTCAGACGAGAAGGCAACGAACCCGATCGTGCCCTCTTTTGAT
ATGAGTAATGAAGGATCTTATTTCTTCGGAGACAATGCAGAAGAGTACGACAATTAAGGA
AAAATACCCTTGTTTCTACT (SEQ ID NO:15)

>Y2017M3L4-NS
ATGGATTCCAACACTGTGTCAAGTTTCCAGGTAGATTGCTTTCTTTGGCATATCCGGAAA
CAAGTTGTAGACCAAGAACTGAGTGATGCCCCATTCCTTGATCGGCTTCGCCGAGATCAG
AGGTCCCTAAGGGGAAGAGGCAATACTCTCGGTCTAGACATCAAAGCAGCCACCCATGTT
GGAAAGCAAATTGTAGAAAAGATTCTGAAAGAAGAATCTGATGAGGCACTTAAAATGACC
ATGGTCTCCACACCTGCTTCGCGATACATAACTGACATGACTATTGAGGAATTGTCAAGA
AACTGGTTCATGCTAATGCCCAAGCAGAAAGTGGAAGGACCTCTTTGCATCAGAATGGAC
CAGGCAATCATGGAGAAAAACATCATGTTGAAAGCGAATTTCAGTGTGATTTTTGACCGA
CTAGAGACCATAGTATTACTAAGGGCTTTCACCGAAGAGGGAGCAATTGTTGGCGAAATC
TCACCATTGCCTTCTTTTCCAGGACATACTATTGAGGATGTCAAAAATGCAATTGGGGTC
CTCATCGGAGGACTTGAATGGAATGATAACACAGTTCGAGTCTCTAAAAATCTACAGAGA
TTCGCTTGGAGAAGCAGTAATGAGAATGGGGGACCTCCACTTACTCCAAAACAGAAACGG
AAAATGGCGAGAACAGCTAGGTCAAAAGTTTGAAGAGATAAGATGGCTGATTGAAGAAGT
GAGACACAGACTAAAAACAACTGAAAATAGCTTTGAACAAATAACATTCATGCAAGCATT
ACAACTGCTGTTTGAAGTGGAACAGGAGATAAGAACTTTCTCATTTCAGCTTATTTAATG
ATAAAAAACACCCTTGTTTCTACT (SEQ ID NO:16)

>Y2017M3L4-PB1
ATGGATGTCAATCCGACTCTACTGTTCCTAAAGGTTCCAGCGCAAAATGCCATAAGCACC
ACATTCCCTTATACTGGAGATCCTCCATACAGCCATGGAACAGGAACAGGGTACACCATG
GACACAGTCAACAGAACACACCAATATTCAGATAAGGGGAAGTGGACGACAAATACAGAA
ACTGGGGCACCCCAACTCAACCCAATTGATGGACCACTACCTGAGGATAATGAGCCAAGT
GGATATGCACAAACAGACTGTGTCCTGGAGGCTATGGCCTTCCTTGAAGAATCCCACCCA
GGTATCTTTGAGAACTCATGCCTTGAAACAATGGAAGTCGTTCAACAAACAAGGGTGGAC
AAACTAACCCAAGGTCGCCAGACTTATGATTGGACATTAAACAGAAATCAACCGGCAGCA
ACTGCATTAGCCAACACCATAGAAGTTTTTAGATCGAATGGACTAACAGCTAATGAATCA
GGAAGGCTAATAGATTTCCTCAAGGATGTGATGGAATCAATGGATAAAGAGGAAATGGAG
ATAACAACACACTTTCAAAGAAAAAGGAGAGTAAGAGACAACATGACCAAGAAAATGGTC
ACACAAAGAACAATAGGGAAGAAAAAACAAAGAGTAAATAAGAGAGGCTATCTAATAAGA
GCTTTGACATTGAACACGATGACCAAAGATGCAGAGAGAGGTAAATTAAAAAGAAGGGCT
ATTGCAACACCCGGGATGCAAATTAGAGGGTTCGTGTACTTCGTTGAAACTTTAGCTAGA
AGCATTTGCGAAAAGCTTGAACAGTCTGGACTTCCGGTTGGGGGTAATGAAAAGAAGGCC

FIG. 3C

AAACTGGCAAATGTTGTGAGAAAAATGATGACTAATTCACAAGACACAGAGCTTTCTTTC
ACAATCACTGGGGACAACACTAAGTGGAATGAAAATCAAAACCCTCGAATGTTTTTGGCG
ATGATTACATATATCACAAAAAATCAACCTGAGTGGTTCAGAAACATCCTGAGCATCGCA
CCAATAATGTTCTCAAACAAAATGGCAAGACTGGGAAAAGGATACATGTTCGAGAGTAAG
AGAATGAAACTCCGAACACAAATACCCGCAGAAATGCTAGCAAACATTGACCTGAAGTAT
TTCAATGAATCAACAAGGAAGAAAATTGAGAAAATAAGGCCTCTTCTAATAGATGGCACA
GCATCATTGAGCCCTGGGATGATGATGGGCATGTTCAACATGCTAAGTACGGTTTTAGGA
GTCTCGATACTGAATCTTGGGCAAAAGAAATACACCAAGACAACATACTGGTGGGATGGG
CTCCAATCCTCCGACGATTTTGCCCTCATAGTGAATGCACCAAATCATGAGGGAATACAA
GCAGGAGTGGATAGATTTTACAGGACCTGCAAGTTAGTGGGAATCAACATGAGCAAAAAG
AAGTCCTATATAAATAAAACAGGGACATTTGAATTCACAAGCTTTTTTTATCGATATGGA
TTTGTGGCTAATTTTAGCATGGAGCTGCCCAGTTTTGGAGTGTCTGGAATAAACGAGTCA
GCTGATATGAGCATTGGAGTAACAGTGATAAAGAACAACATGATAAACAATGACCTTGGA
CCAGCAACAGCCCAGATGGCTCTCCAATTGTTCATCAAAGACTACAGATATACATATAGG
TGCCATAGAGGAGACACACAAATTCAGACGAGAAGATCATTCGAGCTAAAGAAGCTGTGG
GATCAAACCCAATCAAGGGCAGGACTATTGGTATCAGATGGGGGACCAAACTTATACAAT
ATCCGGAATCTTCACATCCCTGAAGTCTGCTTAAAGTGGGAGCTAATGGATGAGAATTAT
CGGGGAAGACTTTGTAATCCCCTGAATCCCTTTGTCAGCCATAAAGAAATTGAGTCTGTA
AACAATGCTGTAGTGATGCCAGCCCATGGTCCGGCCAAAAGTATGGAATATGATGCCGTT
GCAACTACACACTCCTGGATTCCCAAGAGGAACCGCTCTATTCTCAACACAAGCCAAAGG
GGAATTCTTGAGGATGAACAGATGTACCAGAAGTGCTGCAACTTGTTCGAGAAATTTTTC
CCTAGTAGTTCATATAGGAGACCGATTGGAATTTCTAGCATGGTGGAGGCCATGGTGTCT
AGGGCCCGGATTGATGCCAGAATTGACTTCGAGTCTGGACGGATTAAGAAGGAAGAGTTC
TCTGAGATCATGAAGATCTGTTCCACCATTGAAGAACTCAGACGGCAAAAATAATGAATT
TAGCTTGTCCTTCATGAAAAAATGCCTTGTTTCTACT (SEQ ID NO:17)

>Y2017M3L4-PA
ATGGAAGATTTTGTGCGACAATGCTTCAACCCGATGATTGTCGAACTTGCAGAAAAAGCA
ATGAAAGAGTATGGGGAGGATCTGAAAATTGAAACAAACAAATTTGCAGCAATATGCACT
CACTTGGAGGTATGTTTCATGTATTCAGATTTTCATTTCATCAATGAACAAGGCGAATCA
ATAGTGGTAGAACTTGATGATCCAAATGCACTGTTAAAGCACAGATTTGAAATAATCGAG
GGGAGAGACAGAACAATGGCCTGGACAGTAGTAAACAGTATCTGCAACACTACTGGAGCT
GAAAAACCGAAGTTTCTACCAGATTTGTATGATTACAAGGAGAACAGATTCATCGAAATT
GGAGTGACAAGGAGAGAAGTCCACATATATTACCTTGAAAAGGCCAATAAGATTAAATCT
GAGAACACACACATTCACATTTTCTCATTCACTGGGGAGGAAATGGCCACAAAGGCAGAC
TACACTCTCGACGAGGAAAGCAGGGCTAGGATTAAGACCAGGCTATTTACCATAAGACAA
GAAATGGCCAACAGAGGCCTCTGGGATTCCTTTCGTCAGTCCGAAAGAGGCGAAGAAACA
ATTGAAGAAAAATTTGAAATCTCAGGAACTATGCGTAGGCTTGCCGACCAAAGTCTCCCA
CCGAACTTCTCCTGCCTTGAGAATTTTAGAGCCTATGTGGATGGATTCGAACCGAACGGC
TGCATTGAGGGCAAGCTTTCTCAAATGTCCAAAGAAGTGAATGCCCAAATTGAACCTTTT
CTGAAGACAACACCAAGACCAATCAAACTTCCGAATGGACCTCCTTGTTATCAGCGGTCC
AAGTTCCTCCTGATGGATGCTTTAAAATTGAGCATTGAAGACCCAAGTCACGAAGGAGAA
GGGATCCCATTATATGATGCGATCAAGTGCATAAAAACATTCTTTGGATGGAAAGAACCT
TATATAGTCAAACCACACGAAAAGGGAATAAATTCAAATTACCTGCTGTCATGGAAGCAA
GTATTGTCAGAATTGCAGGACATTGAAAATGAGGAGAAGATTCCAAGGACTAAAAACATG
AAGAAAACGAGTCAACTAAAGTGGGCTCTTGGTGAGAACATGGCACCAGAGAAAGTAGAC
TTTGAAAACTGCAGAGACATAAGCGATTTGAAGCAATATGATAGTGACGAACCTGAATTA
AGGTCACTTTCAAGCTGGATACAGAATGAGTTCAACAAGGCCTGCGAGCTAACTGATTCA
ATCTGGATAGAGCTCGATGAAATTGGAGAGGACGTAGCCCCAATTGAATACATTGCAAGC
ATGAGGAGGAATTATTTCACAGCAGAGGTGTCCCATTGTAGAGCCACTGAGTACATAATG
AAGGGGGTATACATTAATACTGCCCTGCTCAATGCATCCTGTGCAGCAATGGACGATTTT
CAACTAATTCCCATGATAAGCAAGTGCAGAACTAAAGAGGGAAGGCGAAAAACCAATTTA
TATGGATTCATCATAAAGGGAAGATCTCATTTAAGGAATGACACAGATGTGGTAAACTTT

FIG. 3D

GTGAGCATGGAGTTTTCTCTCACTGACCCGAGACTTGAGCCACATAAATGGGAGAAATAC
TGTGTCCTTGAGATAGGAGATATGTTACTAAGAAGTGCCATAGGCCAAATTTCAAGGCCT
ATGTTCTTGTATGTGAGGACAAACGGAACATCAAAGGTCAAAATGAAATGGGGAATGGAG
ATGAGACGTTGCCTCCTTCAGTCACTCCAGCAGATCGAGAGCATGATTGAAGCCGAGTCC
TCGGTTAAAGAGAAAGACATGACCAAAGAGTTTTTGAGAATAAATCAGAAGCATGGCCC
ATTGGGGAGTCCCCCAAGGGAGTGGAAGAAGGTTCCATTGGGAAAGTCTGTAGGACTCTA
TTGGCTAAGTCAGTGTTCAATAGCCTGTATGCATCACCACAATTGGAAGGATTTTCAGCG
GAGTCAAGAAAACTGCTCCTTGTTGTTCAGGCTCTTAGGGACAACCTCGAACCTGGGACC
TTTGATCTTGGGGGGCTATATGAAGCAATTGAGGAGTGCCTGATTAATGATCCCTGGGTT
TTGCTCAATGCGTCTTGGTTCAACTCCTTCCTGACACATGCATTAAAATAGTTATGGCAG
TGCTACTATTTGTTATCCGTACTGTCCAAAAAAGTACCTTGTTTCTACT (SEQ ID NO:18)

>M3L4-PB2(147I)
ATGGAAAGAATAAAAGAACTACGGAACCTGATGTCGCAGTCTCGCACTCGCGAGATACTG
ACAAAAACCACAGTGGACCATATGGCCATAATTAAGAAGTACACATCGGGGAGACAGGAA
AAGAACCCGTCACTTAGGATGAAATGGATGATGGCAATGAAATACCCAATCACTGCTGAC
AAAAGGATAACAGAAATGGTTCCGGAGAGAAATGAACAAGGACAAACTCTATGGAGTAAA
ATGAGTGATGCTGGATCAGATCGAGTGATGGTATCACCTTTGGCTGTGACATGGTGGAAT
AGAAATGGACCCGTGACAAGTACGGTCCATTACCCAAAAGTATACAAGACTTATTTTGAC
AAAGTCGAAAGGTTAAAACATGGAACCTTTGGCCCTGTTCATTTTAGAAATCAAGTCAAG
ATACGCCGAAGAGTAGACATAAACCCTGGTCATGCGGACCTCAGTGCCAAGGAGGCACAA
GATGTAATTATGGAAGTTGTTTTTCCCAATGAAGTGGGAGCCAGGATACTAACATCAGAA
TCGCAATTAACAATAACTAAAGAGAAAAAAGAAGAACTCCGAGATTGCAAAATTTCTCCC
TTGATGGTTGCATACATGTTAGAGAGAGAACTTGTCCGAAAAACAAGATTTCTCCCAGTT
GCTGGCGGAACAAGCAGTATATACATTGAAGTTTTACATTTGACTCAAGGGACGTGTTGG
GAACAAATGTACACTCCAGGTGGAGAAGTGAGGAATGACGATGTTGACCAAAGCCTAATT
ATTGCAGCCAGGAACATAGTAAGAAGAGCCGCAGTATCAGCAGATCCACTAGCATCTTTA
TTGGAGATGTGCCACAGCACACAAATTGGCGGGACAAGGATGGTGGACATTCTTAGACAG
AACCCGACTGAAGAACAAGCTGTGGATATATGCAAGGCTGCAATGGGATTGAGAATCAGC
TCATCCTTCAGCTTTGGTGGGTTTACATTTAAAAGAACAAGCGGGTCATCAGTCAAAAAA
GAGGAAGAAGTGCTTACAGGCAATCTCCAAACATTGAAGATAAGAGTACATGAGGGGTAT
GAGGAGTTCACAATGGTGGGGAAAAGAGCAACAGCTATACTCAGAAAAGCAACCAGAAGA
TTGGTTCAGCTCATAGTGAGTGGAAGAGACGAACAGTCAATAGCCGAAGCAATAATTGTG
GCCATGGTGTTTTCACAAGAGGATTGCATGATAAAAGCAGTTAGAGGTGACCTGAATTTC
GTCAACAGAGCAAATCAGCGGTTGAACCCCATGCATCAGCTTTTAAGGCATTTTCAGAAA
GATGCGAAAGTGCTTTTTCAGAATTGGGGAATTGAGCACATCGACAGTGTAATGGGAATG
GTTGGAGTATTACCAGATATGACTCCAAGCACAGAGATGTCAATGAGAGGAATAAGAGTC
AGCAAAATGGGTGTGGATGAATACTCCAGTACAGAGAGGGTGGTGGTTAGCATTGATCGG
TTTTTGAGAGTTCGAGACCAACGCGGGAATGTATTATTATCTCCTGAAGAGGTTAGTGAA
ACACAGGGAACTGAGAGACTGACAATAACTTATTCATCGTCGATGATGTGGGAGATTAAC
GGTCCTGAGTCGGTTTTGGTCAATACTTATCAATGGATCATCAGAAATTGGGAAGCTGTC
AAAATTCAATGGTCTCAGAATCCTGCAATGTTGTACAACAAAATGGAATTTGAACCATTT
CAATCTTTAGTCCCCAAGGCCATTAGAAGCCAATACAGTGGGTTTGTCAGAACTCTATTC
CAACAAATGAGAGACGTACTTGGGACATTTGACACCACCCAGATAATAAAGCTTCTCCCT
TTTGCAGCCGCTCCACCAAAGCAAAGCAGAATGCAGTTCTCTTCACTGACTGTAAATGTG
AGGGGATCAGGGATGAGAATACTTGTAAGGGGCAATTCTCCTGTATTCAACTACAACAAG
ACCACTAAAAGACTAACAATTCTCGGAAAAGATGCCGGCACTTTAATTGAAGACCCAGAT
GAAAGCACATCCGGAGTGGAGTCCGCTGTATTGAGAGGGTTTCTCATTATAGGTAAGGAA
GACAGAAGATACGGGCCAGCATTAAGCATCAATGAACTGAGTAACCTTGCAAAAGGGGAA
AAGGCTAATGTGCTAATCGGGCAAGGAGACGTGGTGTTGGTAATGAAACGAAAACGGGAC
TCTAGCATACTTACTGACAGCCAGACAGCGACCAAAAGAATTCGGATGGCCATCAATTAA
TGTTGAATAGTTTAAAAACGACCTTGTTTCTACT (SEQ ID NO:19)

FIG. 3E

>M3L4-PB2(147I,344L)
ATGGAAAGAATAAAAGAACTACGGAACCTGATGTCGCAGTCTCGCACTCGCGAGATACTG
ACAAAAACCACAGTGGACCATATGGCCATAATTAAGAAGTACACATCGGGGAGACAGGAA
AAGAACCCGTCACTTAGGATGAAATGGATGATGGCAATGAAATACCCAATCACTGCTGAC
AAAAGGATAACAGAAATGGTTCCGGAGAGAAATGAACAAGGACAAACTCTATGGAGTAAA
ATGAGTGATGCTGGATCAGATCGAGTGATGGTATCACCTTTGGCTGTGACATGGTGGAAT
AGAAATGGACCCGTGACAAGTACGGTCCATTACCCAAAAGTATACAAGACTTATTTTGAC
AAAGTCGAAAGGTTAAAACATGGAACCTTTGGCCCTGTTCATTTTAGAAATCAAGTCAAG
ATACGCCGAAGAGTAGACATAAACCCTGGTCATGCGGACCTCAGTGCCAAGGAGGCACAA
GATGTAATTATGGAAGTTGTTTTCCCAATGAAGTGGGAGCCAGGATACTAACATCAGAA
TCGCAATTAACAATAACTAAAGAGAAAAAAGAAGAACTCCGAGATTGCAAAATTTCTCCC
TTGATGGTTGCATACATGTTAGAGAGAGAACTTGTCCGAAAAACAAGATTCCTCCCAGTT
GCTGGCGGAACAAGCAGTATATACATTGAAGTTTTACATTTGACTCAAGGGACGTGTTGG
GAACAAATGTACACTCCAGGTGGAGAAGTGAGGAATGACGATGTTGACCAAAGCCTAATT
ATTGCAGCCAGGAACATAGTAAGAAGAGCCGCAGTATCAGCAGATCCACTAGCATTTTTA
TTGGAGATGTGCCACAGCACACAAATTGGCGGGACAAGGATGGTGGACATTCTTAGACAG
AACCCGACTGAAGAACAAGCTGTGGATATATGCAAGGCTGCAATGGGATTGAGAATCAGC
TCATCCTTCAGCTTTGGTGGGTTTACATTTAAAAGAACAAGCGGGTCATCAGTCAAAAAA
GAGGAAGAACTGCTTACAGGCAATCTCCAAACATTGAAGATAAGAGTACATGAGGGGTAT
GAGGAGTTCACAATGGTGGGGAAAAGAGCAACAGCTATACTCAGAAAAGCAACCAGAAGA
TTGGTTCAGCTCATAGTGAGTGGAAGAGACGAACAGTCAATAGCCGAAGCAATAATTGTG
GCCATGGTGTTTTCACAAGAGGATTGCATGATAAAAGCAGTTAGAGGTGACCTGAATTTC
GTCAACAGAGCAAATCAGCGGTTGAACCCCATGCATCAGCTTTTAAGGCATTTTCAGAAA
GATGCGAAAGTGCTTTTTCAGAATTGGGGAATTGAGCACATCGACAGTGTAATGGGAATG
GTTGGAGTATTACCAGATATGACTCCAAGCACAGAGATGTCAATGAGAGGAATAAGAGTC
AGCAAAATGGGTGTGGATGAATACTCCAGTACAGAGAGGGTGGTGGTTAGCATTGATCGG
TTTTTGAGAGTTCGAGACCAACGCGGGAATGTATTATTATCTCCTGAAGAGGTTAGTGAA
ACACAGGGAACTGAGAGACTGACAATAACTTATTCATCGTCGATGATGTGGGAGATTAAC
GGTCCTGAGTCGGTTTTGGTCAATACTTATCAATGGATCATCAGAAATTGGGAAGCTGTC
AAAATTCAATGGTCTCAGAATCCTGCAATGTTGTACAACAAAATGGAATTTGAACCATTT
CAATCTTTAGTCCCCAAGGCCATTAGAAGCCAATACAGTGGGTTTGTCAGAACTCTATTC
CAACAAATGAGAGACGTACTTGGGACATTTGACACCACCCAGATAATAAAGCTTCTCCCT
TTTGCAGCCGCTCCACCAAAGCAAAGCAGAATGCAGTTCTCTTCACTGACTGTAAATGTG
AGGGGATCAGGGATGAGAATACTTGTAAGGGGCAATTCTCCTGTATTCAACTACAACAAG
ACCACTAAAAGACTAACAATTCTCGGAAAAGATGCCGGCACTTTAATTGAAGACCCAGAT
GAAAGCACATCCGGAGTGGAGTCCGCTGTATTGAGAGGGTTTCTCATTATAGGTAAGGAA
GACAGAAGATACGGGCCAGCATTAAGCATCAATGAACTGAGTAACCTTGCAAAAGGGGAA
AAGGCTAATGTGCTAATCGGGCAAGGAGACGTGGTGTTGGTAATGAAACGAAAACGGGAC
TCTAGCATACTTACTGACAGCCAGACAGCGACCAAAAGAATTCGGATGGCCATCAATTAA
TGTTGAATAGTTTAAAAACGACCTTGTTTCTACT (SEQ ID NO:20)

>M3L4-PB2(147I,344L,358K)
ATGGAAAGAATAAAAGAACTACGGAACCTGATGTCGCAGTCTCGCACTCGCGAGATACTG
ACAAAAACCACAGTGGACCATATGGCCATAATTAAGAAGTACACATCGGGGAGACAGGAA
AAGAACCCGTCACTTAGGATGAAATGGATGATGGCAATGAAATACCCAATCACTGCTGAC
AAAAGGATAACAGAAATGGTTCCGGAGAGAAATGAACAAGGACAAACTCTATGGAGTAAA
ATGAGTGATGCTGGATCAGATCGAGTGATGGTATCACCTTTGGCTGTGACATGGTGGAAT
AGAAATGGACCCGTGACAAGTACGGTCCATTACCCAAAAGTATACAAGACTTATTTTGAC
AAAGTCGAAAGGTTAAAACATGGAACCTTTGGCCCTGTTCATTTTAGAAATCAAGTCAAG
ATACGCCGAAGAGTAGACATAAACCCTGGTCATGCGGACCTCAGTGCCAAGGAGGCACAA
GATGTAATTATGGAAGTTGTTTTCCCAATGAAGTGGGAGCCAGGATACTAACATCAGAA
TCGCAATTAACAATAACTAAAGAGAAAAAAGAAGAACTCCGAGATTGCAAAATTTCTCCC
TTGATGGTTGCATACATGTTAGAGAGAGAACTTGTCCGAAAAACAAGATTCCTCCCAGTT

FIG. 3F

```
GCTGGCGGAACAAGCAGTATATACATTGAAGTTTTACATTTGACTCAAGGGACGTGTTGG
GAACAAATGTACACTCCAGGTGGAGAAGTGAGGAATGACGATGTTGACCAAAGCCTAATT
ATTGCAGCCAGGAACATAGTAAGAAGAGCCGCAGTATCAGCAGATCCACTAGCATCTTTA
TTGGAGATGTGCCACAGCACACAAATTGGCGGGACAAGGATGGTGGACATTCTTAGACAG
AACCCGACTGAAGAACAAGCTGTGGATATATGCAAGGCTGCAATGGGATTGAGAATCAGC
TCATCCTTCAGCTTTGGTGGGTTTACATTTAAAAGAACAAGCGGGTCATCAGTCAAAAAA
GAGGAAGAACTGCTTACAGGCAATCTCCAAACATTGAAGATAAGAGTACATAAGGGGTAT
GAGGAGTTCACAATGGTGGGGAAAAGAGCAACAGCTATACTCAGAAAAGCAACCAGAAGA
TTGGTTCAGCTCATAGTGAGTGGAAGAGACGAACAGTCAATAGCCGAAGCAATAATTGTG
GCCATGGTGTTTTCACAAGAGGATTGCATGATAAAAGCAGTTAGAGGTGACCTGAATTTC
GTCAACAGAGCAAATCAGCGGTTGAACCCCATGCATCAGCTTTTAAGGCATTTTCAGAAA
GATGCGAAAGTGCTTTTTCAGAATTGGGGAATTGAGCACATCGACAGTGTAATGGGAATG
GTTGGAGTATTACCAGATATGACTCCAAGCACAGAGATGTCAATGAGAGGAATAAGAGTC
AGCAAAATGGGTGTGGATGAATACTCCAGTACAGAGAGGGTGGTGGTTAGCATTGATCGG
TTTTTGAGAGTTCGAGACCAACGCGGGAATGTATTATTATCTCCTGAAGAGGTTAGTGAA
ACACAGGGAACTGAGAGACTGACAATAACTTATTCATCGTCGATGATGTGGGAGATTAAC
GGTCCTGAGTCGGTTTTGGTCAATACTTATCAATGGATCATCAGAAATTGGGAAGCTGTC
AAAATTCAATGGTCTCAGAATCCTGCAATGTTGTACAACAAAATGGAATTTGAACCATTT
CAATCTTTAGTCCCCAAGGCCATTAGAAGCCAATACAGTGGGTTTGTCAGAACTCTATTC
CAACAAATGAGAGACGTACTTGGGACATTTGACACCACCCAGATAATAAAGCTTCTCCCT
TTTGCAGCCGCTCCACCAAAGCAAAGCAGAATGCAGTTCTCTTCACTGACTGTAAATGTG
AGGGGATCAGGGATGAGAATACTTGTAAGGGGCAATTCTCCTGTATTCAACTACAACAAG
ACCACTAAAAGACTAACAATTCTCGGAAAAGATGCCGGCACTTTAATTGAAGACCCAGAT
GAAAGCACATCCGGAGTGGAGTCCGCTGTATTGAGAGGGTTTCTCATTATAGGTAAGGAA
GACAGAAGATACGGGCCAGCATTAAGCATCAATGAACTGAGTAACCTTGCAAAAGGGGAA
AAGGCTAATGTGCTAATCGGGCAAGGAGACGTGGTGTTGGTAATGAAACGAAAACGGGAC
TCTAGCATACTTACTGACAGCCAGACAGCGACCAAAAGAATTCGGATGGCCATCAATTAA
TGTTGAATAGTTTAAAAACGACCTTGTTTCTACT (SEQ ID NO:21)
```

FIG. 3G

| | | | | | | | | |
|---|---|---|---|---|---|---|---|---|
| T32A | wt | wt | mutation | mutation | mutation | mutation | wt | mutation |
| D147N | wt | mutation | wt | mutation | mutation | mutation | wt | mutation |
| N329D | wt | mutation | mutation | wt | mutation | mutation | wt | mutation |
| H347Q | wt | mutation | mutation | mutation | wt | mutation | wt | mutation |
| Δ 46-50aa | wt | wt | wt | wt | wt | wt | mutation | mutation |

N.A: not analyzed

| HA | HK4801 | HK4801 | HK4801 | HK4801 |
|---|---|---|---|---|
| NA | HK4801 | Y2017-M3L4 | HK4801 | Y2017-M3L4 |
| Backbone | Y2017 | Y2017 | HY-PR8 | HY-PR8 |

Yokohama/2017/2003 NA

Upper: wild-type
Lower: Y2017-M3L4

```
    1 MNPNQKIITIGSVSLTISTICFFMQIAILITTVTLHFKQYEFNSPPNNQVMLCEPTIIER  60
                                     A             -----
                                   T32A       del 46-50aa
   61 NITEIVYLTNTTIEKEICPKLAEYRNWSKPQCNITGFAPFSKDNSIRLSAGGDIWVTREP 120

121 YVSCDPDKCYQFALGQGTTLNNVHSNDIVHDRTPYRTLLMNELGVPFHLGTKQVCIAWSS 180
                                N
                              D147N
  181 SSCHDGKAWLHVCVTGDDENATASFIYNGRLADSIVSWSKKILRTQESECVCINGTCTVV 240

241 MTDGSASGKADTKILFIEEGKIVHTSTLSGSAQHVEECSCYPRYPGVRCVCRDNWKGSNR 300

301 PIVDINIKDYSIVSSYVCSGLVGDTPRKNDSSSSSHCLDPNNEEGGHGVKGWAFDDGNDV 360
                                  D                 Q
                                N329D             H347Q
  361 WMGRTISEKLRSGYETFKVIEGWSNPNSKLQINRQVIVDRGNRSGYSGIFSVEGKSCINR 420

421 CFYVELIRGRKQETEVLWTSNSIVVFCGTSGTYGTGSWPDGADINLMPI*           470
```

FIG. 8

N3 (Accession No. AAO62039.1)

```
  1 mnpnqkiiti gvvnttlsti alligvgnli fntvihekig dhqtvihptt ttpaipncsd
 61 tiitynntvi nnittiitea erlfkpplpl cpfrgffpfh kdnairlgen kdvivtrepy
121 vscdndncws falaqgallg tkhsngtikd rtpyrsliqf pigtapvlgn ykeiciawss
181 sscfdgkewm hvcmtgndnd asaqiiyagr mtdsikswkr dilrtqesec qcidgtcvva
241 vtdgpaansa dhrvywireg rivkyenvpk tkiqhleecs cyvdidvyci crdnwkgsnr
301 pwmrinneti letgyvcskf hsdtprpadp stvscdspsn vnggpgvkgf gfkvgndvwl
361 grtmstsgrs qfeiikvaeg winspnhaks vtqtlvsnnd wsgysgsfiv ktkacfqpcf
421 yvelirgrpn knddvswtsn sivtfcgldn epgsgnwpdg snigfmpk  (SEQ ID NO:30)
```

N4 (Accession No. AAO62043.1)

```
  1 mnpnqkiiti gsvsiiltti glllqitslc siwfshynqv tqtheqpcsn nttnyynetf
 61 vnvtnvqnny ttviepsapd vvhyssgrdl cpirgwapls kdngirigsr gevfvirepf
121 iscsisecrt ffltqgalln dkhsngtvkd rspfrtlmsc pigvapspsn srfesvawsa
181 tacsdgpgwl tlgitgpdat avavlkyngi itdtlkswkg nimrtqesec vcqdefcytl
241 itdgpsdaqa fykilkirkg kivsmkdvda tgfhfeecsc ypsgtdiecv crdnwrgsnr
301 pwirfnsdld yqigyvcsgi fgdnprpvdg tgscnspvnn gkgrygvkgf sfrygdgvwi
361 grtkslesrs gfemvwdang wvstdkdsng vqdiidndnw sgysgsfsir gettgrnctv
421 pcfwvemirg qpkektiwts gssiafcgvn sdttgwswpd gallpfdidk (SEQ ID NO:31)
```

N6 (Accession No. AAO62070.1)

```
  1 mnpnqkiici satgmtlsvv slligianlg lniglhykmg dtpdvnipnm netnstttii
 61 nnhtqnnftn itniivnkne egtflnltkp lcevnswhil skdnairige dahilvtrep
121 ylscdpqgcr mfalsqgttl rgrhangtih drspfralis wemgqapspy nvrvecigws
181 stschdgisr msicmsgann nasavvwygg rpvteipswa gnilrtqese cvchkgicpv
241 vmtdgpannr aatkiiyfke gkiqkieela gntqhieecs cygavgvikc icrdnwkgan
301 rpvitidpem mthtskylcs kiltdtsrpn dptngncdap itggspdpgv kgfafldren
361 swlgrtiskd srsgyemlkv pnaetdtqsg pishqvivnn qnwsgysgaf idywankecf
421 npcfyvelir grpkessvlw tsnsivalcg skerlgswsw hdgaeiiyfk (SEQ ID NO:32)
```

N7 (Accession No. AIK26357.1)

```
  1 mnpnqklfal sqvaialsil nlligisnvg lnvslhlkgs sdqdknwtct svtqnnttli
 61 entyvnnttv idketgtakp nylmlnkslc kvegwvvvak dnairfgese qiivtrepyv
121 scdplgckmy alhqgttirn khsngtihdr tafrglistp lgsppvvsns dflcvgwsst
181 schdgigrmt icvqgnndna tatvyydrrl tttiktwagn ilrtqesecv chngtcvvim
241 tdgsassqay tkvlyfhkgl vikeealkgs arhieecscy ghnskvtcvc rdnwqganrp
301 vieidmname htsqylctgv ltdtsrpsdk smgdcnnpit gspgapgvkg fgfldssntw
361 lgrtisprsr sgfemlkipn aetdpnskit ergeivdnnn wsgysgsfid ywdessecyn
421 pcfyvelirg rpeeakyvgw tsnslialcg spisvgsgsf pdgaqiqyfs (SEQ ID NO:33)
```

FIG. 9A

N8 (Accession No. AIK26315.1)

1 mnpnqkiitv gsvslglvvl nillhivsit vtvlvlpgng nnkncnetvi reynetvrie
61 kvtqwhntnv ieyiekpesg hfmnntealc dakgfapfsk dngirigsrg hvfvirepfv
121 scsptecrtf fltqgsllnd khsngtvkdr spyrtlmsve igqspnvyqa rfeavawsat
181 achdgkkwmt igvtgpdaka vavvhyggip tdvinswagd ilrtqessct ciqgecywvm
241 tdgpanrqaq yrafkakqgk ivgqteisfn gshieecscy pnegkvecvc rdnwtgtnrp
301 vlvispdlsy ragylcaglp sdtprgedsq ftgsctspvg nqgygvkgfg frqgndvwmg
361 rtisrtsrsg feilkvrngw vqnskeqikr qvvvdnlkws gysgsftlpv eltkrnclvp
421 cfwvemirgk peektiwtss ssivmcgvdh eiadwswhdg ailpfdidkm (SEQ ID NO:34)

N9 (Accession No. ALH21371)

1 mnpnqkilct sataiiigai avligianlg lniglhlkpg cncshsqpet tntsqtiinn
61 yynetnitni qmeertsrnf nnltkglcti nswhiygkdn avrigessdv lvtrepyvsc
121 dpdecrfyal sqgttirgkh sngtihdrsq yraliswpls spptvynsrv ecigwsstsc
181 hdgksrmsic isgpnnnasa vvwynrrpvt eintwarnil rtqesecvch ngvcpvvftd
241 gsatgpadtr iyyfkegkil kwesltgtak hieecscyge rtgitctcrd nwqgsnrpvi
301 qidpvamtht sqyicspvlt dnprpndpni gkcndpypgn nnngvkgfsy ldgantwlgr
361 tistasrsgy emlkvpnalt ddrskpiqgq tivlnadwsg ysgsfmdywa egdcyracfy
421 velirgrpke dkvwwtsnsi vsmcsstefl gqwnwpdgak ieyfl (SEQ ID NO:35)

FIG. 9B agcgaaagca ggtcaattat attcaatatg gaaagaataa aagaactaag aaatctaatg
tcgcagtctc gcacccgcga gatactcaca aaaaccaccg tggaccatat ggccataatc
aagaagtaca catcaggaag acaggagaag aacccagcac ttaggatgaa atggatgatg
gcaatgaaat atccaattac agcagacaag aggataacgg aaatgattcc tgagagaaat
gagcaaggac aaactttatg gagtaaaatg aatgatgccg gatcagaccg agtgatggta
tcacctctgg ctgtgacatg gtggaatagg aatggaccaa tgacaaatac agttcattat
ccaaaaatct acaaaactta ttttgaaaga gtcgaaaggc taaagcatgg aacctttggc
cctgtccatt ttagaaacca agtcaaaata cgtcggagag ttgacataaa tcctggtcat
gcagatctca gtgccaagga ggcacaggat gtaatcatgg aagttgtttt ccctaacgaa
gtgggagcca ggatactaac atcggaatcg caactaacga taaccaaaga gaagaaagaa
gaactccagg attgcaaaat ttctcctttg atggttgcat acatgttgga gagagaactg
gtccgcaaaa cgagattcct cccagtggct ggtggaacaa gcagtgtgta cattgaagtg
ttgcatttga ctcaaggaac atgctgggaa cagatgtata ctccaggagg ggaagtgaag
aatgatgatg ttgatcaaag cttgattatt gctgctagga acatagtgag aagagctgca
gtatcagcag acccactagc atctttattg gagatgtgcc acagcacaca gattggtgga
attaggatgg tagacatcct taagcagaac ccaacagaag agcaagccgt ggatatatgc
aaggctgcaa tgggactgag aattagctca tccttcagtt ttggtggatt cacatttaag
agaacaagcg gatcatcagt caagagagag gaagaggtgc ttacgggcaa tcttcaaaca
ttgaagataa gagtgcatga gggatctgaa gagttcacaa tggttgggag aagagcaaca
gccatactca gaaaagcaac caggagattg attcagctga tagtgagtgg gagagacgaa
cagtcgattg ccgaagcaat aattgtggcc atggtatttt cacaagagga ttgtatgata
aaagcagtta gaggtgatct gaatttcgtc aatagggcga atcagcgact gaatcctatg
catcaacttt taagacattt tcagaaggat gcgaaagtgc tttttcaaaa ttggggagtt
gaacctatcg acaatgtgat gggaatgatt gggatattgc ccgacatgac tccaagcatc
gagatgtcaa tgagaggagt gagaatcagc aaaatgggtg tagatgagta ctccagcacg
gagagggtag tggtgagcat tgaccggttc ttgagagtca gggaccaacg aggaaatgta
ctactgtctc ccgaggaggt cagtgaaaca cagggaacag agaaactgac aataacttac
tcatcgtcaa tgatgtggga gattaatggt cctgaatcag tgttggtcaa tacctatcaa
tggatcatca gaaactggga aactgttaaa attcagtggt cccagaaccc tacaatgcta
tacaataaaa tggaatttga accatttcag tctttagtac ctaaggccat tagaggccaa
tacagtgggt ttgtaagaac tctgttccaa caaatgaggg atgtgcttgg gacatttgat
accgcacaga taataaaact tcttcccttc gcagccgctc caccaaagca aagtagaatg
cagttctcct catttactgt gaatgtgagg ggatcaggaa tgagaatact tgtaaggggc
aattctcctg tattcaacta caacaaggcc acgaagagac tcacagttct cggaaaggat
gctggcactt taaccgaaga cccagatgaa ggcacagctg gagtggagtc cgctgttctg
aggggattcc tcattctggg caaagaagac aggagatatg ggccagcatt aagcatcaat
gaactgagca accttgcgaa aggagagaag gctaatgtgc taattgggca aggagacgtg
gtgttggtaa tgaaacgaaa acgggactct agcatactta ctgacagcca gacagcgacc
aaaagaattc ggatggccat caattagtgt cgaatagttt aaaaacgacc ttgtttctac
t (SEQ ID NO:39)which encodes M E R I K E L R N L M S Q S R T R E I L T K T T V D H M A I I K K Y T S G R Q
E K N P A L R M K W M M A M K Y P I T A D K R I T E M I P E R N E Q G Q T
L W S K M N D A G S D R V M V S P L A V T W W N R N G P M T N T V H Y P
K I Y K T Y F E R V E R L K H G T F G P V H F R N Q V K I R R R V D I N P G
H A D L S A K E A Q D V I M E V V F P N E V G A R I L T S E S Q L T I T K E K
K E E L Q D C K I S P L M V A Y M L E R E L V R K T R F L P V A G G T S S V
Y I E V L H L T Q G T C W E Q M Y T P G G E V K N D D V D Q S L I I A A R N
I V R R A A V S A D P L A S L L E M C H S T Q I G G I R M V D I L K Q N P T E

FIG. 10A

E Q A V D I C K A A M G L R I S S S F S F G G F T F K R T S G S S V K R E E E
V L T G N L Q T L K I R V H E G S E E F T M V G R R A T A I L R K A T R R L I
Q L I V S G R D E Q S I A E A I I V A M V F S Q E D C M I K A V R G D L N F V
N R A N Q R L N P M H Q L L R H F Q K D A K V L F Q N W G V E P I D N V M
G M I G I L P D M T P S I E M S M R G V R I S K M G V D E Y S S T E R V V V
S I D R F L R V R D Q R G N V L L S P E E V S E T Q G T E K L T I T Y S S S M
M W E I N G P E S V L V N T Y Q W I I R N W E T V K I Q W S Q N P T M L Y
N K M E F E P F Q S L V P K A I R G Q Y S G F V R T L F Q Q M R D V L G T F
D T A Q I I K L L P F A A A P P K Q S R M Q F S S F T V N V R G S G M R I L V
R G N S P V F N Y N K A T K R L T V L G K D A G T L T E D P D E G T A G V
E S A V L R G F L I L G K E D R R Y G P A L S I N E L S N L A K G E K A N V L
I G Q G D V V L V M K R K R D S S I L T D S Q T A T K R I R M A I N agcgaaagca ggcaaaccat ttgaatggat gtcaatccga ccttactttt cttaaaagtg
ccagcacaaa atgctataag cacaactttc ccttataccg gagaccctcc ttacagccat
gggacaggaa caggatacac catggatact gtcaacagga cacatcagta ctcagaaaag
ggaagatgga caacaaacac cgaaactgga gcaccgcaac tcaacccgat tgatgggcca
ctgccagaag acaatgaacc aagtggttat gcccaaacag attgtgtatt ggaagcaatg
gctttccttg aggaatccca tcctggtatt tttgaaaact cgtgtattga aacgatggag
gttgttcagc aaacacgagt agacaagctg acacaaggcc gacagaccta tgactggact
ttaaatagaa accagcctgc tgcaacagca ttggccaaca caatagaagt gttcagatca
aatggcctca cggccaatga gtcaggaagg ctcatagact tccttaagga tgtaatggag
tcaatgaaaa aagaagaaat ggggatcaca actcattttc agagaaagag acgggtgaga
gacaatatga ctaagaaaat gataacacag agaacaatag gtaaaaggaa acagagattg
aacaaaaggg gttatctaat tagagcattg accctgaaca caatgaccaa agatgctgag
agagggaagc taaaacggag agcaattgca accccaggga tgcaaataag ggggtttgta
tactttgttg agacactggc aaggagtata tgtgagaaac ttgaacaatc agggttgcca
gttggaggca atgagaagaa agcaaagttg gcaaatgttg taaggaagat gatgaccaat
tctcaggaca ccgaactttc tttcaccatc actggagata acaccaaatg gaacgaaaat
cagaatcctc ggatgttttt ggccatgatc acatatatga ccagaaatca gcccgaatgg
ttcagaaatg ttctaagtat tgctccaata atgttctcaa acaaaatggc gagactggga
aaagggtata tgtttgagag caagagtatg aaacttagaa ctcaaatacc tgcagaaatg
ctagcaagca ttgatttgaa atatttcaat gattcaacaa gaaagaagat tgaaaaaatc
cgaccgctct taatagaggg gactgcatca ttgagccctg gaatgatgat gggcatgttc
aatatgttaa gcactgtatt aggcgtctcc atcctgaatc ttggacaaaa gagatacacc
aagactactt actggtggga tggtcttcaa tcctctgacg atttgctctt gattgtgaat
gcacccaatc atgaagggat tcaagccgga gtcgacaggt ttatcgaac ctgtaagcta
cttggaatca atatgagcaa gaaaaagtct tacataaaca gaacaggtac atttgaattc
acaagttttt tctatcgtta tgggtttgtt gccaatttca gcatggagct tcccagtttt
ggggtgtctg ggatcaacga gtcagcggac atgagtattg gagttactgt catcaaaaac
aatatgataa acaatgatct tggtccagca acagctcaaa tggcccttca gttgttcatc
aaagattaca ggtacacgta ccgatgccat agaggtgaca cacaaataca aacccgaaga
tcatttgaaa taaagaaact gtgggagcaa acccgttcca aagctggact gctggtctcc
gacggaggcc caaatttata caacattaga aatctccaca ttcctgaagt ctgcctaaaa
tgggaattga tggatgagga ttaccagggg cgtttatgca acccactgaa cccatttgtc
agccataaag aaattgaatc aatgaacaat gcagtgatga tgccagcaca tggtccagcc
aaaaacatgg agtatgatgc tgttgcaaca acacactcct ggatccccaa aagaaatcga
tccatcttga atacaagtca aagaggagta cttgaagatg aacaaatgta ccaaaggtgc
tgcaatttat ttgaaaaatt cttccccagc agttcataca gaagaccagt cgggatatcc
agtatggtgg aggctatggt ttccagagcc cgaattgatg cacggattga tttcgaatct

FIG. 10B ggaaggataa agaaagaaga gttcactgag atcatgaaga tctgttccac cattgaagag
ctcagacggc aaaaatagtg aatttagctt gtccttcatg aaaaaatgcc ttgtttctac t(SEQ ID NO:40) which encodes
M D V N P T L L F L K V P A Q N A I S T T F P Y T G D P P Y S H G T G T G Y
T M D T V N R T H Q Y S E K G R W T T N T E T G A P Q L N P I D G P L P E D
N E P S G Y A Q T D C V L E A M A F L E E S H P G I F E N S C I E T M E V V
Q Q T R V D K L T Q G R Q T Y D W T L N R N Q P A A T A L A N T I E V F R
S N G L T A N E S G R L I D F L K D V M E S M K K E E M G I T T H F Q R K R
R V R D N M T K K M I T Q R T I G K R K Q R L N K R G Y L I R A L T L N T M
T K D A E R G K L K R R A I A T P G M Q I R G F V Y F V E T L A R S I C E K
L E Q S G L P V G G N E K K A K L A N V V R K M M T N S Q D T E L S F T I T
G D N T K W N E N Q N P R M F L A M I T Y M T R N Q P E W F R N V L S I A
P I M F S N K M A R L G K G Y M F E S K S M K L R T Q I P A E M L A S I D L
K Y F N D S T R K K I E K I R P L L I E G T A S L S P G M M M G M F N M L S
T V L G V S I L N L G Q K R Y T K T T Y W W D G L Q S S D D F A L I V N A P
N H E G I Q A G V D R F Y R T C K L L G I N M S K K K S Y I N R T G T F E F
T S F F Y R Y G F V A N F S M E L P S F G V S G I N E S A D M S I G V T V I K
N N M I N N D L G P A T A Q M A L Q L F I K D Y R Y T Y R C H R G D T Q I Q
T R R S F E I K K L W E Q T R S K A G L L V S D G G P N L Y N I R N L H I P E
V C L K W E L M D E D Y Q G R L C N P L N P F V S H K E I E S M N N A V M
M P A H G P A K N M E Y D A V A T T H S W I P K R N R S I L N T S Q R G V L
E D E Q M Y Q R C C N L F E K F F P S S S Y R R P V G I S S M V E A M V S R
A R I D A R I D F E S G R I K K E E F T E I M K I C S T I E E L R R Q K
agcgaaagca ggtactgatt caaaatggaa gattttgtgc gacaatgctt caatccgatg
attgtcgagc ttgcggaaaa aacaatgaaa gagtatgggg aggacctgaa aatcgaaaca
aacaaatttg cagcaatatg cactcacttg gaagtatgct tcatgtattc agatttccac
ttcatcaatg agcaaggcga gtcaataatc gtagaacttg gtgatcctaa tgcacttttg
aagcacagat ttgaaataat cgagggaaga gatcgcacaa tggcctggac agtagtaaac
agtatttgca acactacagg ggctgagaaa ccaaagtttc taccagattt gtatgattac
aaggaaaata gattcatcga aattggagta acaaggagag aagttcacat atactatctg
gaaaaggcca ataaaattaa atctgagaaa acacacatcc acattttctc gttcactggg
gaagaaatgg ccacaagggc cgactacact ctcgatgaag aaagcagggc taggatcaaa
accaggctat tcaccataag acaagaaatg gccagcagag gcctctggga ttcctttcgt
cagtccgaga gaggagaaga gacaattgaa gaaaggtttg aaatcacagg aacaatgcgc
aagcttgccg accaaagtct cccgccgaac ttctccagcc ttgaaaattt tagagcctat
gtggatggat tcgaaccgaa cggctacatt gagggcaagc tgtctcaaat gtccaaagaa
gtaaatgcta gaattgaacc tttttgaaa acaacaccac gaccacttag acttccgaat
gggcctccct gttctcagcg gtccaaattc ctgctgatgg atgccttaaa attaagcatt
gaggacccaa gtcatgaagg agagggaata ccgctatatg atgcaatcaa atgcatgaga
acattctttg gatggaagga acccaatgtt gttaaaccac acgaaaaggg aataaatcca
aattatcttc tgtcatggaa gcaagtactg gcagaactgc aggacattga gaatgaggag
aaaattccaa agactaaaaa tatgaaaaaa acaagtcagc taaagtgggc acttggtgag
aacatggcac cagaaaaggt agactttgac gactgtaaag atgtaggtga tttgaagcaa
tatgatagtg atgaaccaga attgaggtcg cttgcaagtt ggattcagaa tgagttcaac

FIG. 10C aaggcatgcg aactgacaga ttcaagctgg atagagcttg atgagattgg agaagatgtg
gctccaattg aacacattgc aagcatgaga aggaattatt tcacatcaga ggtgtctcac
tgcagagcca cagaatacat aatgaagggg gtgtacatca atactgcctt acttaatgca
tcttgtgcag caatggatga tttccaatta attccaatga taagcaagtg tagaactaag
gagggaaggc gaaagaccaa cttgtatggt ttcatcataa aaggaagatc ccacttaagg
aatgacaccg acgtggtaaa ctttgtgagc atggagtttt ctctcactga cccaagactt
gaaccacaca aatgggagaa gtactgtgtt cttgagatag gagatatgct tctaagaagt
gccataggcc aggtttcaag gcccatgttc ttgtatgtga ggacaaatgg aacctcaaaa
attaaaatga aatggggaat ggagatgagg cgttgtctcc tccagtcact tcaacaaatt
gagagtatga ttgaagctga gtcctctgtc aaagagaaag acatgaccaa agagttcttt
gagaacaaat cagaaacatg gcccattgga gagtctccca aaggagtgga ggaaagttcc
attgggaagg tctgcaggac tttattagca aagtcggtat ttaacagctt gtatgcatct
ccacaactag aaggattttc agctgaatca agaaaactgc ttcttatcgt tcaggctctt
agggacaatc tggaacctgg gacctttgat cttggggggc tatatgaagc aattgaggag
tgcctaatta atgatccctg ggttttgctt aatgcttctt ggttcaactc cttccttaca
catgcattga gttagttgtg gcagtgctac tatttgctat ccatactgtc caaaaaagta
ccttgtttct act (SEQ ID NO:41) which encodes M E D F V R Q C F N P M I V E L A E K T M K E Y G E D L K I E T N K F A A I
C T H L E V C F M Y S D F H F I N E Q G E S I I V E L G D P N A L L K H R F E
I I E G R D R T M A W T V V N S I C N T T G A E K P K F L P D L Y D Y K E N
R F I E I G V T R R E V H I Y Y L E K A N K I K S E K T H I H I F S F T G E E M
A T R A D Y T L D E E S R A R I K T R L F T I R Q E M A S R G L W D S F R Q
S E R G E E T I E E R F E I T G T M R K L A D Q S L P P N F S S L E N F R A Y
V D G F E P N G Y I E G K L S Q M S K E V N A R I E P F L K T T P R P L R L P
N G P P C S Q R S K F L L M D A L K L S I E D P S H E G E G I P L Y D A I K C
M R T F F G W K E P N V V K P H E K G I N P N Y L L S W K Q V L A E L Q D
I E N E E K I P K T K N M K K T S Q L K W A L G E N M A P E K V D F D D C
K D V G D L K Q Y D S D E P E L R S L A S W I Q N E F N K A C E L T D S S W
I E L D E I G E D V A P I E H I A S M R R N Y F T S E V S H C R A T E Y I M K
G V Y I N T A L L N A S C A A M D D F Q L I P M I S K C R T K E G R R K T N
L Y G F I I K G R S H L R N D T D V V N F V S M E F S L T D P R L E P H K W
E K Y C V L E I G D M L L R S A I G Q V S R P M F L Y V R T N G T S K I K M
K W G M E M R R C L L Q S L Q Q I E S M I E A E S S V K E K D M T K E F F E
N K S E T W P I G E S P K G V E E S S I G K V C R T L L A K S V F N S L Y A S
P Q L E G F S A E S R K L L L I V Q A L R D N L E P G T F D L G G L Y E A I E
E C L I N D P W V L L N A S W F N S F L T H A L S agcaaaagca gggtagataa tcactcactg agtgacatca aaatcatggc gtcccaaggc
accaaacggt cttacgaaca gatggagact gatggagaac gccagaatgc cactgaaatc
agagcatccg tcggaaaaat gattggtgga attggacgat tctacatcca aatgtgcaca
gaacttaaac tcagtgatta tgagggacgg ttgatccaaa acagcttaac aatagagaga
atggtgctct ctgcttttga cgaaaggaga aataaatacc tggaagaaca tcccagtgcg
gggaaagatc ctaagaaaac tggaggacct atatacagaa gagtaaacgg aaagtggatg
agagaactca tcctttatga caaagaagaa ataaggcgaa tctggcgcca agctaataat
ggtgacgatg caacggctgg tctgactcac atgatgatct ggcattccaa tttgaatgat
gcaacttatc agaggacaag ggctcttgtt cgcaccggaa tggatcccag gatgtgctct

FIG. 10D ctgatgcaag gttcaactct ccctaggagg tctggagccg caggtgctgc agtcaaagga
gttggaacaa tggtgatgga attggtcagg atgatcaaac gtgggatcaa tgatcggaac
ttctggaggg gtgagaatgg acgaaaaaca agaattgctt atgaaagaat gtgcaacatt
ctcaaaggga aatttcaaac tgctgcacaa aaagcaatga tggatcaagt gagagagagc
cggaacccag ggaatgctga gttcgaagat ctcacttttc tagcacggtc tgcactcata
ttgagagggt cggttgctca caagtcctgc ctgcctgcct gtgtgtatgg acctgccgta
gccagtgggt acgactttga aagagaggga tactctctag tcggaataga ccctttcaga
ctgcttcaaa acagccaagt gtacagccta atcagaccaa atgagaatcc agcacacaag
agtcaactgg tgtggatggc atgccattct gccgcatttg aagatctaag agtattgagc
ttcatcaaag ggacgaaggt ggtcccaaga gggaagcttt ccactagagg agttcaaatt
gcttccaatg aaaatatgga gactatggaa tcaagtacac ttgaactgag aagcaggtac
tgggccataa ggaccagaag tggaggaaac accaatcaac agagggcatc tgcgggccaa
atcagcatac aacctacgtt ctcagtacag agaaatctcc cttttgacag aacaaccgtt
atggcagcat tcactgggaa tacagagggg agaacatctg acatgaggac cgaaatcata
aggatgatgg aaagtgcaag accagaagat gtgtctttcc aggggcgggg agtcttcgag
ctctcggacg aaaaggcagc gagcccgatc gtgccttcct ttgacatgag taatgaagga
tcttatttct tcggagacaa tgcagaggag tacgacaatt aaagaaaaat accettgttt
ctact (SEQ ID NO:42) which encodes M A S Q G T K R S Y E Q M E T D G E R Q N A T E I R A S V G K M I G G I G R
F Y I Q M C T E L K L S D Y E G R L I Q N S L T I E R M V L S A F D E R R N K
Y L E E H P S A G K D P K K T G G P I Y R R V N G K W M R E L I L Y D K E E
I R R I W R Q A N N G D D A T A G L T H M M I W H S N L N D A T Y Q R T R
A L V R T G M D P R M C S L M Q G S T L P R R S G A A G A A V K G V G T M
V M E L V R M I K R G I N D R N F W R G E N G R K T R I A Y E R M C N I L K
G K F Q T A A Q K A M M D Q V R E S R N P G N A E F E D L T F L A R S A L I
L R G S V A H K S C L P A C V Y G P A V A S G Y D F E R E G Y S L V G I D P
F R L L Q N S Q V Y S L I R P N E N P A H K S Q L V W M A C H S A A F E D L
R V L S F I K G T K V V P R G K L S T R G V Q I A S N E N M E T M E S S T L
E L R S R Y W A I R T R S G G N T N Q Q R A S A G Q I S I Q P T F S V Q R N L
P F D R T T V M A A F T G N T E G R T S D M R T E I I R M M E S A R P E D V
S F Q G R G V F E L S D E K A A S P I V P S F D M S N E G S Y F F G D N A E E
Y D N agcaaaagca ggtagatatt gaaagatgag tcttctaacc gaggtcgaaa cgtacgttct
ctctatcatc ccgtcaggcc ccctcaaagc cgagatcgca cagagacttg aagatgtctt
tgcagggaag aacaccgatc ttgaggttct catggaatgg ctaaagacaa gaccaatcct
gtcacctctg actaagggga ttttaggatt tgtgttcacg ctcaccgtgc ccagtgagcg
aggactgcag cgtagacgct ttgtccaaaa tgcccttaat gggaacgggg atccaaataa
catggacaaa gcagttaaac tgtataggaa gctcaagagg gagataacat tccatggggc
caaagaaatc tcactcagtt attctgctgg tgcacttgcc agttgtatgg gcctcatata
caacaggatg gggctgtga ccactgaagt ggcatttggc ctggtatgtg caacctgtga
acagattgct gactcccagc atcggtctca taggcaaatg gtgacaacaa ccaacccact
aatcagacat gagaacagaa tggttttagc cagcactaca gctaaggcta tggagcaaat
ggctggatcg agtgagcaag cagcagaggc catggaggtt gctagtcagg ctaggcaaat
ggtgcaagcg atgagaacca ttgggactca tcctagctcc agtgctggtc tgaaaaatga
tcttcttgaa aatttgcagg cctatcagaa acgaatgggg gtgcagatgc aacggttcaa
gtgatcctct cgctattgcc gcaaatatca ttgggatctt gcacttgata ttgtggattc
ttgatcgtct tttttcaaa tgcatttacc gtcgctttaa atacggactg aaaggagggc

FIG. 10E cttctacgga aggagtgcca aagtctatga gggaagaata tcgaaaggaa cagcagagtg
ctgtggatgc tgacgatggt catttgtca gcatagagct ggagtaaaaa actaccttgt
ttctact (SEQ ID NO:43) which encodes MS L L T E V E T Y V L S I I P S G P L K A E I A Q R L E D V F A G K N T D L
E V L M E W L K T R P I L S P L T K G I L G F V F T L T V P S E R G L Q R R R
F V Q N A L N G N G D P N N M D K A V K L Y R K L K R E I T F H G A K E I S
L S Y S A G A L A S C M G L I Y N R M G A V T T E V A F G L V C A T C E Q I
A D S Q H R S H R Q M V T T T N P L I R H E N R M V L A S T T A K A M E Q
M A G S S E Q A A E A M E V A S Q A R Q M V Q A M R T I G T H P S S S A G
L K N D L L E N L Q A Y Q K R M G V Q M Q R F K agcaaaagca gggtgacaaa gacataatgg atccaaacac tgtgtcaagc tttcaggtag 60
attgctttct ttggcatgtc cgcaaacgag ttgcagacca agaactaggt gatgccccat 120
tccttgatcg gcttcgccga gatcagaaat ccctaagagg aaggggcagc actcttggtc 180
tggacatcga gacagccaca cgtgctggaa agcagatagt ggagcggatt ctgaaagaag 240
aatccgatga ggcacttaaa atgaccatgg cctctgtacc tgcgtcgcgt tacctaaccg 300
acatgactct tgaggaaatg tcaagggaat ggtccatgct catacccaag cagaaagtgg 360
caggccctct ttgtatcaga atggaccagg cgatcatgga taaaaacatc atactgaaag 420
cgaacttcag tgtgattttt gaccggctgg agactctaat attgctaagg gctttcaccg 480
aagagggagc aattgttggc gaaatttcac cattgccttc tcttccagga catactgctg 540
aggatgtcaa aaatgcagtt ggagtcctca tcggaggact tgaatggaat gataacacag 600
ttcgagtctc tgaaactcta cagagattcg cttggagaag cagtaatgag aatgggagac 660
ctccactcac tccaaaacag aaacgagaaa tggcgggaac aattaggtca gaagtttgaa 720
gaaataagat ggttgattga agaagtgaga cacaaactga aggtaacaga gaatagtttt 780
gagcaaataa catttatgca agccttacat ctattgcttg aagtggagca agagataaga 840
actttctcat ttcagcttat
ttaataataa aaaacaccct
tgtttctact
(SEQ ID NO:44)

1 mnpnqkiiti gsvcmtigma nlilqignii siwishsiql gnqnqietcn qsvityennt
61 wvnqtyvnis ntnfaagqsv vsvklagnss lcpvsgwaiy skdnsvrigs kgdvfvirep
121 fiscsplecr tffltqgall ndkhsngtik drspyrtlms cpigevpspy nsrfesvaws
181 asachdginw ltigisgpdn gavavlkyng iitdtikswr nnilrtqese cacvngscft
241 vmtdgpsngq asykifriek gkivksvemn apnyhyeecs cypdsseitc vcrdnwhgsn
301 rpwvsfnqnl eyqigyicsg ifgdnprpnd ktgscgpvss ngangvkgfs fkygngvwig
361 rtksisssrng femiwdpngw tgtdnnfsik qdivginews gysgsfvqhp eltgldcirp
421 cfwvelirgr pkentiwtsg ssisfcgvns dtvgwswpdg aelpftidk

N7

1 mnpnqklfal sgvaialsil nlligisnvg lnvslhlkgs sdqdknwtct svtqnnttli
61 entyvnnttv idketgtakp nylmlnkslc kvegwvvvak dnairfgese qiivtrepyv
121 scdplgckmy alhqgttirn khsngtihdr tafrglistp lgsppvvsns dflcvgwsst
181 schdgigrmt icvqgnndna tatvyydrrl tttiktwagn ilrtqesecv chngtcvvim
241 tdgsassqay tkvlyfhkgl vikeealkgs arhieecscy ghnskvtcvc rdnwqganrp
301 vieidmname htsqylctgv ltdtsrpsdk smgdcnnpit gspgapgvkg fgfldssntw
361 lgrtisprsr sgfemlkipn aetdpnskit erqeivdnnn wsgysgsfid ywdessecyn
421 pcfyvelirg rpeeakyvgw tsnslialcg spisvgsgsf pdgaqiqyfs

N9 mnpnqkilct sataiiigai avligianlg lniglhlkpg cncshsqpet tntsqtiinn
61 yynetnitni qmeertsrnf nnltkglcti nswhiygkdn avrigessdv lvtrepyvsc
121 dpdecrfyal sqgttirgkh sngtihdrsq yraliswpls spptvynsrv ecigwsstsc
181 hdgksrmsic isgpnnnasa vvwynrrpva eintwarnil rtqesecvch ngvcpvvftd
241 gsatgpadtr iyyfkegkil kwesltgtak hieecscyge rtgitctcrd nwqgsnrpvi
301 qidpvamtht sqyicspvlt dnprpndpni gkcndpypgn nnngvkgfsy ldgantwlgr
361 tistasrsgy emlkvpnalt ddrskpiqgq tivlnadwsg ysgsfmdywa egdcyracfy
421 velirgrpke dkvwwtsnsi vsmcsstefl gqwnwpdgak ieyfl

N2

1 mnpnqkiiti gsvsltisti cffmqiaili ttvtlhfkqy efnsppnnqv mlceptiier
61 niteivyltn ttiekeicpk laeyrnwskp qcnitgfapf skdnsirlsa ggdiwvtrep
121 yvscdpdkcy qfalgqgttl nnvhsndivh drtpyrtllm nelgvpfhlg tkqvciawss
181 sschdgkawl hvcvtgdden atasfiyngr ladsivswsk kilrtqesec vcingtctvv
241 mtdgsasgka dtkilfieeg kivhtstlsg saqhveecsc yprypgvrcv crdnwkgsnr

FIG. 11A 301 pivdinikdy sivssyvcsg lvgdtprknd sssssheldp nneegghgvk gwafddgndv
361 wmgrtisekl rsgyetfkvi egwsnpnskl qinrqvivdr gnrsgysgif svegkscinr
421 cfyvelirgr kqetevlwts nsivvfcgts gtygtgswpd gadinlmpi

FIG. 11B

| | | | | | | | | | | | |
|---|---|---|---|---|---|---|---|---|---|---|---|
| T32A | wt | mutant | mutant | mutant | wt | mutant | mutant | mutant | wt | mutant | mutant |
| D147N | wt | mutant | mutant | wt | mutant | mutant | mutant | wt | mutant | mutant | mutant |
| N329D | wt | mutant | wt | mutant | mutant | mutant | wt | mutant | mutant | mutant | mutant |
| H347Q | wt | wt | mutant | mutant | mutant | wt | mutant | mutant | mutant | mutant | mutant |
| Δ46-50aa | wt | mutant | mutant | mutant | mutant | wt | wt | wt | wt | wt | mutant |

| Passage 1 | | | Passage 2 | | | Passage 3 | | |
|---|---|---|---|---|---|---|---|---|
| Egg | Virus Titer (pfu/ml) | HA Mutation | Egg | Virus Titer (pfu/ml) | HA Mutation | Egg | Virus Titer (pfu/ml) | HA Mutation |
| A | $2.6x10^6$ | none | A1 | $6.6x10^6$ | none | A1a | $5.3x10^7$ | none |
| | | | | | | A1b | $1.2x10^8$ | none |
| | | | | | | A1c | $3.7x10^7$ | none |
| | | | A2 | $3.5x10^7$ | none | A2a | $5.8x10^7$ | none |
| | | | | | | A2b | $1.0x10^8$ | none |
| | | | A3 | $2.8x10^7$ | none | A3a | $3.0x10^7$ | none |
| | | | | | | A3b | $5.5x10^7$ | none |
| B | $3.7x10^7$ | none | B1 | $1.15x10^8$ | none | B1a | $4.3x10^6$ | none |
| | | | | | | B1b | $1.6x10^8$ | none |
| | | | B2 | $4.85x10^7$ | none | B2a | $2.1x10^7$ | none |
| | | | | | | B2b | $4.3x10^7$ | none |
| C | $9.0x10^5$ | none | C1 | $2.65x10^7$ | none | C1a | $5.3x10^7$ | none |
| | | | | | | C1b | $9.3x10^6$ | none |
| | | | C2 | $6.45x10^7$ | none | C2a | $3.8x10^7$ | none |
| | | | C3 | $1.6x10^6$ | none | C3a | $3.4x10^8$ | none |
| | | | | | | C3b | $3.9x10^8$ | none |

FIG. 13

| AM: amniotic cavity | AM1 | | | AM1AL1 | | | AM1AL2 | | | | AM1AL3 | | | | AM1AL4 | | | | AM1AL5 | | | |
|---|---|---|---|---|---|---|---|---|---|---|---|---|---|---|---|---|---|---|---|---|---|---|
| AL: allantoic cavity | Titer pfu/ml | Mutation HA | Mutation NA | Titer pfu/ml | Mutation HA | Mutation NA | Egg | Titer pfu/ml | Mutation HA | Mutation NA | Egg | Titer pfu/ml | Mutation HA | Mutation NA | Egg | Titer pfu/ml | Mutation HA | Mutation NA | Egg | Titer pfu/ml | Mutation HA | Mutation NA |
| | $1.1x10^{8}$ | nd | nd | $9.4x10^{6}$ | none | T148K, D151E, H347G | a | $1.2x10^{6}$ | none | T148K, D151E, H347G | a | $1.5x10^{7}$ | none | 4M* | | | | | a | $1.1x10^{7}$ | none | 4M |
| | | | | | | | | | | | | | | | a | $1.1x10^{8}$ | none | 4M | b | $2.6x10^{7}$ | none | 4M |
| | | | | | | | | | | | | | | | | | | | c | $3.2x10^{7}$ | none | 4M |
| Virus generated by reverse genetics | | | | | | | | | | | | | | | | | | | d | $1.1x10^{7}$ | none | 4M |
| | | | | | | | | | | | | | | | b | $1.1x10^{8}$ | none | 4M | a | $7.5x10^{6}$ | none | 4M |
| HA: A/HK/4801/2014 | | | | | | | b | $1.1x10^{7}$ | none | T148K, D151E, H347G | a | $2.3x10^{7}$ | none | 4M | a | $1.2x10^{8}$ | none | 4M | a | $1.6x10^{7}$ | none | 4M |
| NA: A/HK/4801/2014NA(T148K, N329X, 347X | | | | | | | | | | | | | | | | | | | b | $1.6x10^{7}$ | none | 4M |
| backbone: High Yield-PR8 | | | | | | | | | | | | | | | | | | | c | $7.3x10^{6}$ | none | 4M |
| | | | | | | | | | | | | | | | | | | | d | $1.9x10^{7}$ | none | 4M |
| titer: $4x10^{4}$ (pfu/ml) | | | | | | | | | | | | | | | | | | | e | $2.5x10^{7}$ | none | 4M |
| | | | | | | | | | | | | | | | b | $6.6x10^{8}$ | none | 4M | a | $1.3x10^{7}$ | none | 4M |
| | | | | | | | | | | | | | | | | | | | b | $1.3x10^{7}$ | none | 4M |
| | | | | | | | | | | | | | | | | | | | c | $1.0x10^{7}$ | none | 4M |
| | | | | | | | | | | | | | | | | | | | d | $3.2x10^{7}$ | none | 4M |
| | | | | | | | | | | | b | $3.1x10^{7}$ | none | 4M | a | $3.3x10^{8}$ | none | 4M | a | $8.0x10^{6}$ | none | 4M |
| | | | | | | | | | | | | | | | | | | | b | $1.7x10^{7}$ | none | 4M |
| | | | | | | | | | | | | | | | | | | | c | $6.9x10^{7}$ | none | 4M |
| | | | | | | | | | | | | | | | b | $5.8x10^{8}$ | none | 4M | a | $2.7x10^{7}$ | none | 4M |

FIG. 14

| Passage 1 | | | Passage 2 | | | Passage 3 | | |
|---|---|---|---|---|---|---|---|---|
| Egg | Virus Titer (pfu/ml) | HA Mutation | Egg | Virus Titer (pfu/ml) | HA Mutation | Egg | Virus Titer (pfu/ml) | HA Mutation |
| A | $2.6x10^6$ | none | A1 | $6.6x10^6$ | none | A1a | $5.3x10^7$ | none |
| | | | | | | A1b | $1.2x10^8$ | none |
| | | | | | | A1c | $3.7x10^7$ | none |
| | | | A2 | $3.5x10^7$ | none | A2a | $5.8x10^7$ | none |
| | | | | | | A2b | $1.0x10^8$ | none |
| | | | A3 | $2.8x10^7$ | none | A3a | $3.0x10^7$ | none |
| | | | | | | A3b | $5.5x10^7$ | none |
| B | $3.7x10^7$ | none | B1 | $1.15x10^8$ | none | B1a | $4.3x10^6$ | none |
| | | | | | | B1b | $1.6x10^8$ | none |
| | | | B2 | $4.85x10^7$ | none | B2a | $2.1x10^7$ | none |
| | | | | | | B2b | $4.3x10^7$ | none |
| C | $9.0x10^5$ | none | C1 | $2.65x10^7$ | none | C1a | $5.3x10^7$ | none |
| | | | | | | C1b | $9.3x10^6$ | none |
| | | | C2 | $6.45x10^7$ | none | C2a | $3.8x10^7$ | none |
| | | | C3 | $1.6x10^6$ | none | C3a | $3.4x10^8$ | none |
| | | | | | | C3b | $3.9x10^8$ | none |

FIG. 19

| AM: amniotic cavity | AM1 | | | AM1AL1 | | | AM1AL2 | | | | AM1AL3 | | | | AM1AL4 | | | | AM1AL5 | | | |
|---|---|---|---|---|---|---|---|---|---|---|---|---|---|---|---|---|---|---|---|---|---|---|
| AL: allantoic cavity | Titer pfu/ml | Mutation HA | Mutation NA | Titer Pfu/ml | Mutation HA | Mutation NA | Egg | Titer pfu/ml | Mutation HA | Mutation NA | Egg | Titer pfu/ml | Mutation HA | Mutation NA | Egg | Titer pfu/ml | Mutation HA | Mutation NA | Egg | Titer pfu/ml | Mutation HA | Mutation NA |
| | $1.1x10^8$ | nd | nd | $9.4x10^6$ | none | T148K, D151E, H347G | a | $1.2x10^6$ | none | T148K, D151E, H347G | a | $1.5x10^7$ | none | 4M* | | | | | a | $1.1x10^7$ | none | 4M |
| | | | | | | | | | | | | | | | a | $1.1x10^8$ | none | 4M | b | $2.6x10^7$ | none | 4M |
| | | | | | | | | | | | | | | | | | | | c | $3.2x10^7$ | none | 4M |
| Virus generated by reverse genetics | | | | | | | | | | | | | | | | | | | d | $1.1x10^7$ | none | 4M |
| | | | | | | | | | | | | | | | b | $1.1x10^8$ | none | 4M | a | $7.5x10^6$ | none | 4M |
| HA: A/HK/4801/2014 | | | | | | | b | $1.1x10^7$ | none | T148K, D151E, H347G | a | $2.3x10^7$ | none | 4M | a | $1.2x10^8$ | none | 4M | a | $1.6x10^7$ | none | 4M |
| NA: A/HK/4801/2014NA(T148K, N329X, 347X) | | | | | | | | | | | | | | | | | | | b | $1.6x10^7$ | none | 4M |
| backbone: High Yield-PR8 | | | | | | | | | | | | | | | | | | | c | $7.3x10^6$ | none | 4M |
| | | | | | | | | | | | | | | | | | | | d | $1.9x10^7$ | none | 4M |
| titer: $4x10^4$ (pfu/ml) | | | | | | | | | | | | | | | | | | | e | $2.5x10^7$ | none | 4M |
| | | | | | | | | | | | | | | | b | $6.6x10^8$ | none | 4M | a | $1.3x10^7$ | none | 4M |
| | | | | | | | | | | | | | | | | | | | b | $1.3x10^7$ | none | 4M |
| | | | | | | | | | | | | | | | | | | | c | $1.0x10^7$ | none | 4M |
| | | | | | | | | | | | | | | | | | | | d | $3.2x10^7$ | none | 4M |
| | | | | | | | | | | | b | $3.1x10^7$ | none | 4M | a | $3.3x10^8$ | none | 4M | a | $8.0x10^6$ | none | 4M |
| | | | | | | | | | | | | | | | | | | | b | $1.7x10^7$ | none | 4M |
| | | | | | | | | | | | | | | | | | | | c | $6.9x10^7$ | none | 4M |
| | | | | | | | | | | | | | | | b | $5.8x10^8$ | none | 4M | a | $2.7x10^7$ | none | 4M |

| | | | | | | | | | | | | | |
|---|---|---|---|---|---|---|---|---|---|---|---|---|---|
| K189E-N158K-A212T | P4 | Inoculation | 6.0 | | | 5.0 | | | 4.0 | | | 3.0 | | |
| | | Harvested | 4.3 | 2.6 | 6.5 | 1.3 | N.D. | N.D. | N.D. | N.D. | N.D. | N.D. | N.D. | N.D. |
| | P5 | Inoculation | 6.0 | | | 5.0 | | | 4.0 | | | | | |
| | | Harvested | 6.3 | 2.6 | 7.3 | 4.9 | 5.9 | 6.3 | 4.2 | 4.1 | 1.8 | | | |
| | P6 | Inoculation | 6.1 | | | 5.1 | | | 4.1 | | | | | |
| | | Harvested | 5.5 | 7.7 | 6.6 | 6.0 | 6.1 | 6.9 | 8.0 | 4.7 | 9.0 | | | |
| | P7 | Inoculation | 4.5 | | | 3.5 | | | 2.5 | | | 1.5 | | |
| | | Harvested | 6.3 | 5.8 | 6.2 | 6.3 | 7.3 | 7.4 | 7.8 | 8.6 | 5.6 | 6.4 | 2.7 | 2.1 |
| | P8 | Inoculation | 3.4 | | | 2.4 | | | 1.4 | | | 0.4 | | |
| | | Harvested | 8.0 | 7.9 | 7.1 | 2.3 | 4.6 | 6.2 | 8.2 | 4.8 | 2.7 | N.D. | N.D. | N.D. |
| | P9 | Inoculation | 2.3 | | | 1.3 | | | 0.3 | | | | | |
| | | Harvested | 8.2 | 5.1 | 3.5 | 1.8 | 1.3 | 6.5 | N.D. | N.D. | 1.8 | | | |
| | P10 | Inoculation | 3.1 | | | 2.1 | | | 1.1 | | | | | |
| | | Harvested | 3.9 | 2.9 | 8.8 | 8.8 | 5.4 | 6.5 | 4.3 | 3.8 | 5.1 | | | |
| | P11 | Inoculation | 4.0 | | | 3.0 | | | 2.0 | | | | | |
| | | Harvested | 6.9 | 6.4 | 4.6 | 8.8 | 8.7 | 6.0 | 3.0 | 8.0 | 8.0 | | | |

| | | | |
|---|---|---|---|
| Inoculation | | | <-Titer (log10 PFU/egg) |
| Egg1 | Egg2 | Egg3 | <-Titer (log10 PFU/mL) |

FIG. 21

HA/NA Mutations (HA-K189E/N158K/A212T Mutant Virus)

| | | HA | | NA | | | |
|---|---|---|---|---|---|---|---|
| | | | | **148** | 151 | **245** | 346 |
| K189E/N158K/A212T | Passage | | | **T** | D | **N** | G |
| | E4 | No Mutation | | **K** | E | **S** | |
| | E6 | No Mutation | | **K** | E | **S** | V |
| | E7 | No Mutation | | **K** | E | **S** | V |
| | E10 | No Mutation | | **K** | E | **S** | V |

| | | WT | WT | NA Mutants | | |
|---|---|---|---|---|---|---|
| Alaska NA | 148 | T | T | K | T | K |
| | 151 | D | D | E | D | E |
| | 245 | N | N | S | N | S |
| | 346 | G | G | G | V | V |
| Alaska HA | | | WT | WT | WT | WT |

| | | WT | WT | NA Mutants | | |
|---|---|---|---|---|---|---|
| Alaska NA | 148 | T | T | K | T | K |
| | 151 | D | D | E | D | E |
| | 245 | N | N | S | N | S |
| | 346 | G | G | G | V | V |
| Alaska HA | | | WT | WT | WT | WT |

Locations of amino acid substitutions in the neuraminidase proteins of egg-adapted influenza A/Hong Kong/4801/2014(H3N2) and A/Alaska/232/2015(H3N2).

HK/4801/2014 Alaska/232/2015

Introduction of NA mutations (in Figure 1) into the NA of H3N2 viruses from the 2017-18 season enhanced HY-PR8-backbone virus growth without HA mutations

| | | | | | |
|---|---|---|---|---|---|
| HA | wt | wt | wt | wt | wt |
| NA | wt | T148K<br>D151E<br>-<br>-<br>H347G<br>T369K | T148K<br>D151E<br>N245S<br>-<br>H347G<br>T369K | T148K<br>D151E<br>N245S<br>G346V<br>-<br>T369K | T148K<br>D151E<br>N245S<br>G346V<br>H347G<br>T369K |

$2x10^4$ pfu/egg, 3 days, 37°C, Backbone: HY-PR8

Mutations observed in NA mutant viruses (HY-PR8 backbone) in Figure 2 during egg passages
A/Yokohama/147/2017
| HA | Mutant NA | | P1 | P6 | P8 | P10 |
|---|---|---|---|---|---|---|
| 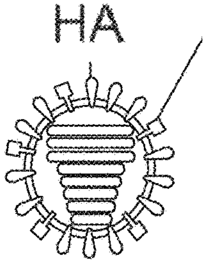 | T148K,D151E, H347G,T369K | HA | none | none | D225G | nd |
| | | NA | none | none | N147D N245S | nd |
| 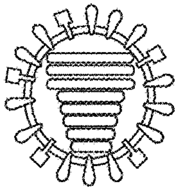 | T148K,D151E, N245S,H347G, T369K | HA | none | D225N | nd | nd |
| | | NA | none | none | nd | nd |
| 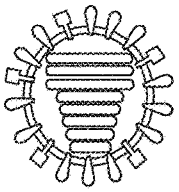 | T148K,D151E, N245S,G346V, T369K | HA | none | N158H | nd | nd |
| | | NA | none | none | nd | nd |
| 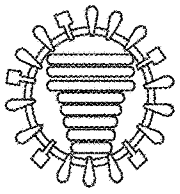 | T148K,D151E, N245S,G346V, H347G,T369K | HA | none | none | K27E | K27E D225G |
| | | NA | none | none | R150R/L | K431N/K |
nd: not determined
FIG. 27

Introduction of NA mutations (in Figure 1) into the NA of H3N2 viruses from the 2017-18 season enhanced HY-PR8-backbone virus growth without HA mutations Yokohama/48/2018 (subclade: 3C.2A/re)

| HA | wt | wt | wt | wt | wt |
|---|---|---|---|---|---|
| NA | wt | T148K<br>D151E<br>-<br>-<br>H347G<br>T369K | T148K<br>D151E<br>N245S<br>-<br>H347G<br>T369K | T148K<br>D151E<br>N245S<br>G346V<br>-<br>T369K | T148K<br>D151E<br>N245S<br>G346V<br>H347G<br>T369K |

$2x10^4$ pfu/egg, 3 days, 37°C, Backbone: HY-PR8

Mutations observed in NA mutant viruses (HY-PR8 backbone) in Figure 4 during egg passages
A/Yokohama/48/2018
| HA Mutant NA | | | P1 | P8 | P10 |
|---|---|---|---|---|---|
| 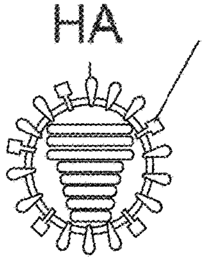 | T148K,D151E, H347G,T369K | HA | none | none | H156R D225G |
| | | NA | none | R150S N245S | R150S N245S |
| 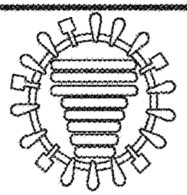 | T148K,D151E, N245S,H347G, T369K | HA | none | none | **none** |
| | | NA | none | K148I | K148I R150R/S |
| 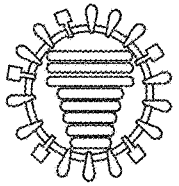 | T148K,D151E, N245S,G346V, T369K | HA | none | T160K L194P | nd |
| | | NA | none | R150S | nd |
| 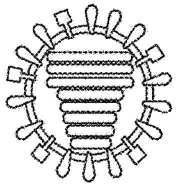 | T148K,D151E, N245S,G346V, H347G,T369K | HA | none | none | T160K L194P |
| | | NA | none | R150S | R150S |
nd: not determined
FIG. 29

HY-PR8-backbone virus possessing A/Yokohama/48/2018HA and A/Yokohama/48/2018NA (T148K, D151E, N245S, H347G, and T369K) acquired the same NA-K148I mutation, and no HA mutations were detected.

A/Yokohama/48/2018

| | P1 | P10 |
|---|---|---|
| HA | none | **none** |
| NA | none | K148I |

A HY-PR8 backbone virus possessing A/Yokohama/48/2018HA and A/Yokohama/48/2018NA(T148I, D151E, N245S, H347G, and T369K) only acquired the HA-435L mutation in the stem region.

A/Yokohama/48/2018

HA

Mutant NA

T148I,D151E,
N245S,H347Q,
T369K

| | P1 | P10 |
|---|---|---|
| HA | none | H435L |
| NA | none | none |

HA-H435L locates to the stem region of the HA trimer.
A previous study reported that HA-H435L did not affect antigenicity
Kuwahara et al. Jpn. J. Infect. Dis., 2018
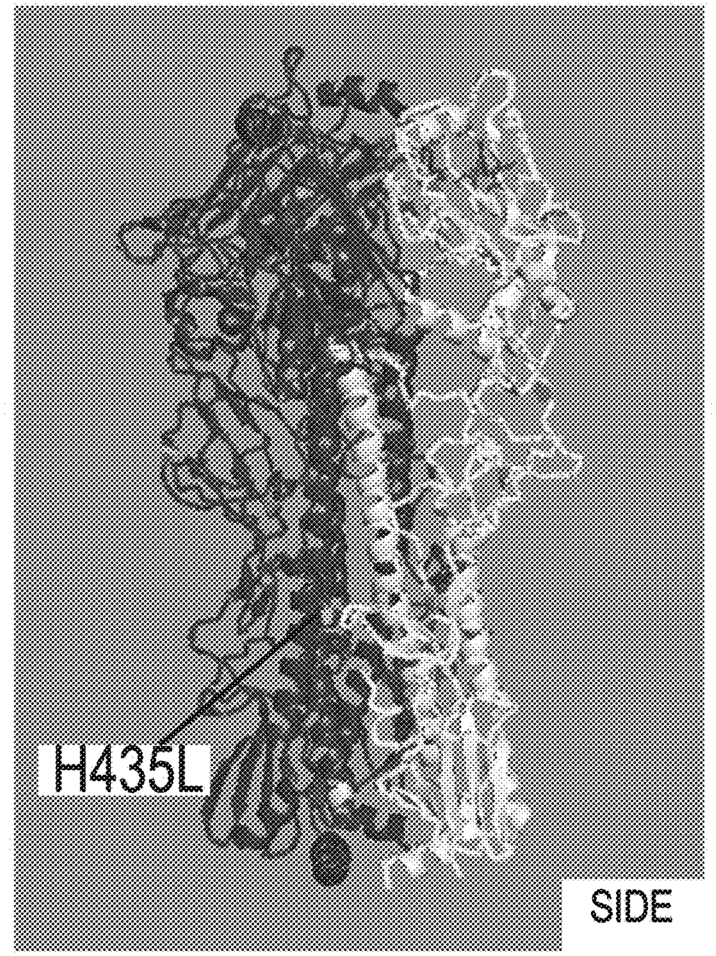
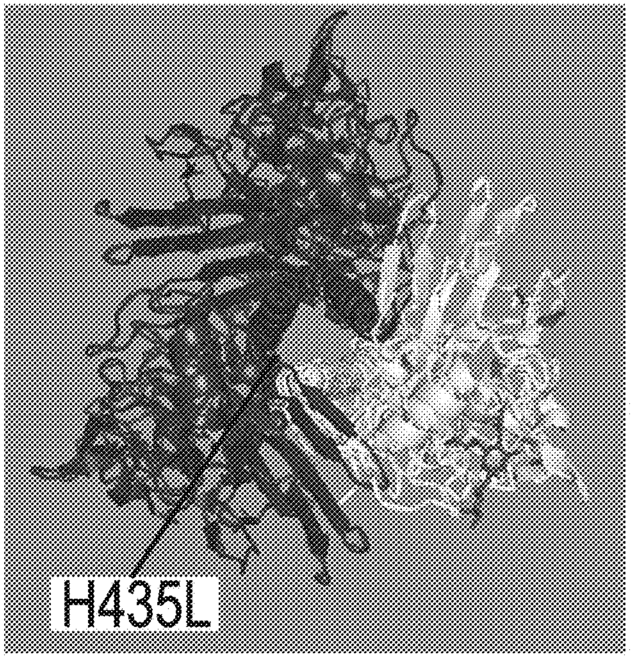
FIG. 32

Effect of introducing NA-T148I, D151E, N245S, H347G, and T369K into the NA of H3N2 viruses from the 2017-18 season

| HA | Yokohama/48/2018 | | Yokohama/147/2017 | |
|---|---|---|---|---|
| NA | Yokohama/48/2018 | | Yokohama/147/2017 | |
| | T148K<br>D151E<br>N245S<br>H347G<br>T369K | <u>T148I</u><br>D151E<br>N245S<br>H347G<br>T369K | T148K<br>D151E<br>N245S<br>H347G<br>T369K | <u>T148I</u><br>D151E<br>N245S<br>H347G<br>T369K |
| subclade | 3C.A2/re | | 3C.2A 1b/135K | |

$2x10^4$ pfu/egg, 3 days, 37℃, Backbone: HY-PR8

Effect of introducing NA-T148I, D151E, N245S, H347G, and T369K into the NA of H3N2 viruses from the 2018-19 season

| | | | | |
|---|---|---|---|---|
| HA | Delaware/33/2018 | | Tokyo/UT-GR85/2019 | |
| NA | Delaware/33/2018 | | Tokyo/UT-GR85/2019 | |
| | WT | T148K D151E N245S H347G T369K | T148I D151E N245S H347G T369K | WT | T148K D151E N245S H347G T369K | T148I D151E N245S H347G T369K |
| subclade | 3C.2A 1b/135K | | 3C.2A 1b/131K | |

2x$10^4$ pfu/egg, 3 days, 37° C., Backbone: HY-PR8

Yokohama48NA (T148I, D151E, N245S, H347G, and T369K) enhanced the growth of viruses possessing the HA of H3N2 viruses of the 2017-18 and 2018-19 seasons 2x10$^4$ pfu/egg, 3 days, 37°C, Backbone: HY-PR8

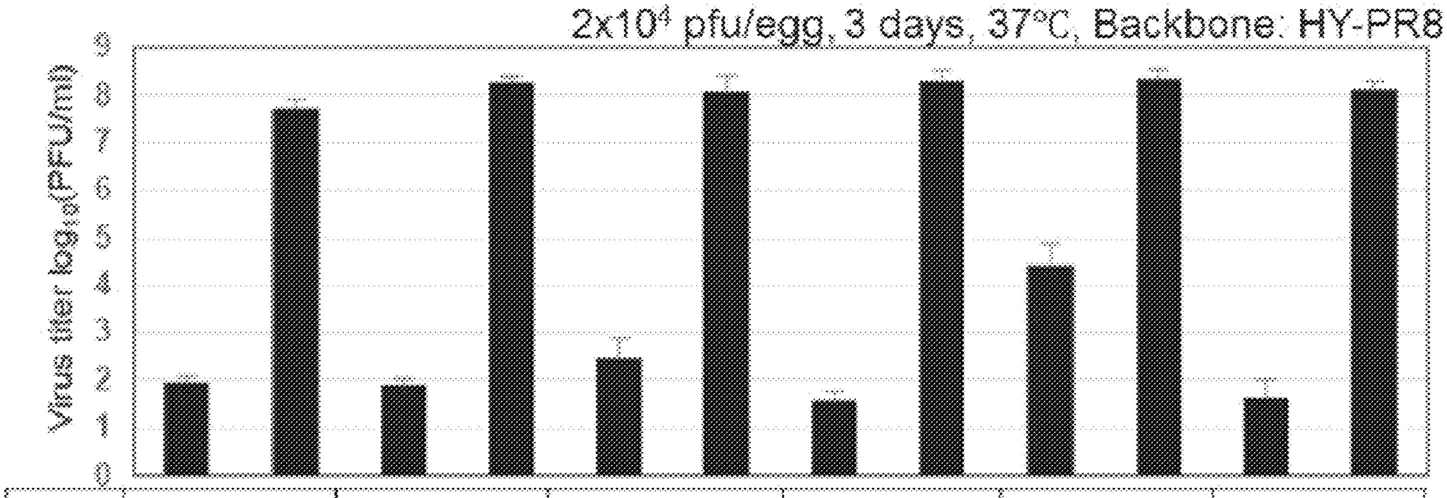

| HA | Yokohama48 | | Yokohama147 | | Delaware33 | | SPB324 | | GR85 | | IC1820 | |
|---|---|---|---|---|---|---|---|---|---|---|---|---|
| NA | Yokohama48 | Yokohama48NA (T148I D151E N245S H347G T369K) | Yokohama147 | Yokohama48NA (T148I D151E N245S H347G T369K) | Delaware 33 | Yokohama48NA (T148I D151E N245S H347G T369K) | SPB324 | Yokohama48NA (T148I D151E N245S H347G T369K) | GR85 | Yokohama48NA (T148I D151E N245S H347G T369K) | IC1820 | Yokohama48NA (T148I D151E N245S H347G T369K) |
| subclade | 3C.A2/re | | 3C.2A 1b/135K | | 3C.2A 1b/135K | | | | 3C.2A 1b/131K | | | |
| season | 2017/18 | | | | 2018/19 | | | | | | | |

Yokohama48: Yokohama/48/2018, Yokohama/147/2017: Yokohama147,
Delaware33: Delaware/33/2018, SPB324:Saint-Petersburg/RII-324S/2019
GR85: Tokyo/UT-GR85/2019, IC1820: A/Kanagawa/IC1820/2019

FIG. 35

The growth of Kansas/14/2017 (next vaccine strain) was enhanced by introducing the NA mutations T148I, D151E, N245S, H347G, and T369K or by possessing Yokohama48NA (T148I, D151E, N245S, H347G, and T369K)

| | | | |
|---|---|---|---|
| HA | Kansas14 | Kansas14 | Kansas14 |
| NA | Kansas14 | Kansas14NA (T148I, D151E, N245S, H347G, T369K) | Yokohama48NA (T148I, D151E, N245S, H347G, T369K) |

$2x10^4$ pfu/egg, 3 days, 37°C, Backbone: HY-PR8

Neutralization by human monoclonal IgG clone F045-092 against viruses possessing Aichi/2/68HA and wild-type or mutant NA from 2017-18 season H3N2 viruses

| NA segment | Microneutralization titer against H3N2 viruses (μg/ml) | |
|---|---|---|
| | F045-092 | Fab fragment of F045-092 |
| Aichi/2/68NA | 0.31 | 5 |
| Yokohama48NA | 0.031 | 5 |
| Yokohama48NA (T148K, D151E, N245S, H347G, and T369K) | 20 | >20 |
| Yokohama48NA (T148I, D151E, N245S, H347G, and T369K) | 20 | >20 |
| Yokohama48NA (T148K, D151E, N245S, G346V, H347G, and T369K) | >20 | >20 |
| Yokohama147NA | 0.08 | 5 |
| Yokohama147NA (T148K, D151E, N245S, H347G, and T369K) | >20 | >20 |
| Yokohama147NA (T148K, D151E, N245S, G346V, H347G, and T369K) | >20 | >20 |

HY-PR8 backbone, HA: Aichi/2/68

FIG. 38

>A/Hong Kong/4801/2014NA(T148K)

ATGAATCCAAATCAAAAGATAATAACGATTGGCTCTGTTTCTCTCACCATTTCCACAATATGCTTTTTCATGC
AAATTGCCATTTTGATAACTACTGTAACATTGCATTTCAAGCAATATGAATTCAACTCCCCCCAAACAACC
AAGTGATGCTGTGTGAACCAACAATAATAGAAAGAAACATAACAGAGATAGTGTATTTAACCAACACCACC
ATAGAGAAGGAAATATGCCCCAAACCAGCAGAATACAGAAATTGGTCAAAACCGCAATGTGGCATTACAG
GATTTGCACCTTTCTCTAAGGACAATTCGATCAGGCTTTCCGCTGGTGGGGACATCTGGGTGACAAGAGA
ACCTTATGTGTCATGCGATCCTGACAAGTGTTATCAATTTGCCCTTGGACAGGGAACAACACTAAACAACG
TGCATTCAAATAACAAAGTACGTGATAGGACCCCTTATCGGACTCTATTGATGAATGAGTTGGGTGTTCCTT
TCCATCTGGGGACCAAGCAAGTGTGCATAGCATGGTCCAGCTCAAGTTGTCACGATGGAAAAGCATGGCT
GCATGTTTGTATAACGGGGGATGATAAAAATGCAACTGCTAGCTTCATTTACAATGGGAGGCTTGTAGATA
GTGTTGTTTCATGGTCCAAAGATATTCTCAGGACCCAGGAGTCAGAATGCATTTGTATCAATGGAACTTGT
ACAGTAGTAATGACTGATGGAAGTGCTTCAGGAAAAGCTGATACTAAAATACTATTCATTGAGGAGGGGA
AAATCGTTCATACTAGCACATTGTCAGGAAGTGCTCAGCATGTCGAAGAGTGCTCTTGCTATCCTCGATATC
CTGGTGTCAGATGTGTCTGCAGAGACAACTGGAAGGGCTCCAATCGGCCCATCGTAGATATAAACATAAA
GGATCATAGCATTGTTTCCAGTTATGTGTGTTCAGGACTTGTTGGAGACACACCCAGAAAAAACGACAGC
TCCAGCAGTAGCCATTGTTTGGATCCTAACAATGAAGAAGGTGGTCATGGAGTGAAAGGCTGGGCCTTT
GATGATGGAAATGACGTGTGGATGGGAAGAACAATCAACGAGACGTCACGCTTAGGGTATGAAACCTTC
AAAGTCATTGAAGGCTGGTCCAACCCTAAGTCCAAATTGCAGACAAATAGGCAAGTCATAGTTGACAGAG

FIG. 40A

GTGATAGGTCCGGTTATTCTGGTATTTTCTCTGTTGAAGGCAAAAGCTGCATAAATCGGTGCTTTTATGTG

GAGTTGATTAGGGGAAGAAAAGAGGAAACTGAAGTCTTGTGGACCTCAAACAGTATTGTTGTGTTTTGT

GGCACCTCAGGTACATATGGAACAGGCTCATGGCCTGATGGGGCGGACCTCAATCTCATGCCTATATAAGC

TTTCGCAATTTTAGAAAAAACT (SEQ ID NO:51)

> A/Hong Kong/4801/2014NA(T148K, D151E, H347G, T369K)

ATGAATCCAAATCAAAAGATAATAACGATTGGCTCTGTTTCTCTCACCATTTCCACAATATGCTTTTTCATGC

AAATTGCCATTTTGATAACTACTGTAACATTGCATTTCAAGCAATATGAATTCAACTCCCCCCAAACAACC

AAGTGATGCTGTGTGAACCAACAATAATAGAAAGAAACATAACAGAGATAGTGTATTTAACCAACACCACC

ATAGAGAAGGAAATATGCCCCAAACCAGCAGAATACAGAAATTGGTCAAAACCGCAATGTGGCATTACAG

GATTTGCACCTTTCTCTAAGGACAATTCGATCAGGCTTTCCGCTGGTGGGGACATCTGGGTGACAAGAGA

ACCTTATGTGTCATGCGATCCTGACAAGTGTTATCAATTTGCCCTTGGACAGGGAACAACACTAAACAACG

TGCATTCAAATAACAAAGTACGTGAAAGGACCCCTTATCGGACTCTATTGATGAATGAGTTGGGTGTTCCT

TTCCATCTGGGGACCAAGCAAGTGTGCATAGCATGGTCCAGCTCAAGTTGTCACGATGGAAAAGCATGGC

TGCATGTTTGTATAACGGGGGATGATAAAAATGCAACTGCTAGCTTCATTTACAATGGGAGGCTTGTAGAT

AGTGTTGTTTCATGGTCCAAAGATATTCTCAGGACCCAGGAGTCAGAATGCATTTGTATCAATGGAACTTG

TACAGTAGTAATGACTGATGGAAGTGCTTCAGGAAAAGCTGATACTAAAATACTATTCATTGAGGAGGGG

AAAATCGTTCATACTAGCACATTGTCAGGAAGTGCTCAGCATGTCGAAGAGTGCTCTTGCTATCCTCGATAT

FIG. 40B

CCTGGTGTCAGATGTGTCTGCAGAGACAACTGGAAGGGCTCCAATCGGCCCATCGTAGATATAAACATAA
AGGATCATAGCATTGTTTCCAGTTATGTGTGTTCAGGACTTGTTGGAGACACACCCAGAAAAAACGACAG
CTCCAGCAGTAGCCATTGTTTGGATCCTAACAATGAAGAAGGTGGTGGCGGAGTGAAAGGCTGGGCCTT
TGATGATGGAAATGACGTGTGGATGGGAAGAACAATCAACGAGAAGTCACGCTTAGGGTATGAAACCTT
CAAAGTCATTGAAGGCTGGTCCAACCCTAAGTCCAAATTGCAGACAAATAGGCAAGTCATAGTTGACAGA
GGTGATAGGTCCGGTTATTCTGGTATTTTCTCTGTTGAAGGCAAAAGCTGCATAAATCGGTGCTTTTATGT
GGAGTTGATTAGGGGAAGAAAAGAGGAAACTGAAGTCTTGTGGACCTCAAACAGTATTGTTGTGTTTTG
TGGCACCTCAGGTACATATGGAACAGGCTCATGGCCTGATGGGGCGGACCTCAATCTCATGCCTATATAAG
CTTTCGCAATTTTAGAAAAAACT (SEQ ID NO:69)

> A/Alaska/232/2015NA
ATGAATCCAAATCAAAAGATAATAACGATTGGCTCTGTTTCTCTCACCATTTCCACAATATGCTTCTTCATGC
AAATTGCCATCCTGATAACTACTGTAACATTGCATTTCAAGCAATATGAATTCAACTCCCCCCCAAACAACC
AAGTGATGCTGTGTGAACCAACAATAATAGAAAGAAACATAACAGAGATAGTGTATTTGACCAACACCAC
CATAGAGAAGGAAATATGCCCCAAACCAGCAGAATACAGAAATTGGTCAAAACCGCAATGTGGCATTACA
GGATTTGCACCTTTCTCTAAGGACAATTCGATTAGGCTTTCCGCTGGTGGGGACATCTGGGTGACAAGAG
AACCTTATGTGTCATGCGATCCTGACAAGTGTTATCAATTTGCCCTTGGACAGGGAACAACACTAAACAAC
GTGCATTCAAATAACACAGTACGTGATAGGACCCCTTATCGGACTCTATTGATGAATGAGTTGGGTGTTCC

FIG. 40C

TTTCCATCTGGGGACCAAGCAAGTGTGCATAGCATGGTCCAGCTCAAGTTGTCACGATGGAAAAGCATGG
CTGCATGTTTGTATAACGGGGGATGATAAAAATGCAACTGCTAGCTTCATTTACAATGGGAGGCTTGTAGA
TAGTGTTGTTTCATGGTCCAAAGATATTCTCAGGACCCAGGAGTCAGAATGCGTTTGTATCAATGGAACTT
GTACAGTAGTAATGACTGATGGAAATGCTACAGGAAAAGCTGATACTAAAATACTATTCATTGAGGAGGG
GAAAATCGTTCATACTAGCAAATTGTCAGGAAGTGCTCAGCATGTCGAAGAGTGCTCTTGCTATCCTCGAT
ATCCTGGTGTCAGATGTGTCTGCAGAGACAACTGGAAAGGATCCAACCGGCCCATCGTAGATATAAACATA
AAGGATCATAGCATTGTTTCCAGTTATGTGTGTTCAGGACTTGTTGGAGACACACCCAGAAAAAACGACA
GCTCCAGCAGTAGCCATTGTTTGAATCCTAACAATGAAGAAGGTGGTCATGGAGTGAAAGGCTGGGCCT
TTGATGATGGAAATGACGTGTGGATGGGGAGAACAATCAACGAGACGTCACGCTTAGGGTATGAAACCT
TCAAAGTCGTTGAAGGCTGGTCCAACCCTAAGTCCAAATTGCAGATAAATAGGCAAGTCATAGTTGACAG
AGGTGATAGGTCCGGTTATTCTGGTATTTTCTCTGTTGAAGGCAAAAGCTGCATCAATCGGTGCTTTTATGT
GGAGTTGATTAGGGGAAGAAAAGAGGAAACTGAAGTCTTGTGGACCTCAAACAGTATTGTTGTGTTTTG
TGGCACCTCAGGTACATATGGAACAGGCTCATGGCCTGATGGGGCGGACCTCAATCTCATGCATATATAA
(SEQ ID NO:52)

>A/Alaska/232/2015NA(T148K, D151E, N245S, G346V, T369K)
ATGAATCCAAATCAAAAGATAATAACGATTGGCTCTGTTTCTCTCACCATTTCCACAATATGCTTCTTCATGC
AAATTGCCATCCTGATAACTACTGTAACATTGCATTTCAAGCAATATGAATTCAACTCCCCCCCAAACAACC

FIG. 40D

AAGTGATGCTGTGTGAACCAACAATAATAGAAAGAAACATAACAGAGATAGTGTATTTGACCAACACCAC
CATAGAGAAGGAAATATGCCCCAAACCAGCAGAATACAGAAATTGGTCAAAACCGCAATGTGGCATTACA
GGATTTGCACCTTTCTCTAAGGACAATTCGATTAGGCTTTCCGCTGGTGGGGACATCTGGGTGACAAGAG
AACCTTATGTGTCATGCGATCCTGACAAGTGTTATCAATTTGCCCTTGGACAGGGAACAACACTAAACAAC
GTGCATTCAAATAACAAAGTACGTGAGAGGACCCCTTATCGGACTCTATTGATGAATGAGTTGGGTGTTCC
TTTCCATCTGGGGACCAAGCAAGTGTGCATAGCATGGTCCAGCTCAAGTTGTCACGATGGAAAAGCATGG
CTGCATGTTTGTATAACGGGGGATGATAAAAATGCAACTGCTAGCTTCATTTACAATGGGAGGCTTGTAGA
TAGTGTTGTTTCATGGTCCAAAGATATTCTCAGGACCCAGGAGTCAGAATGCGTTTGTATCAATGGAACTT
GTACAGTAGTAATGACTGATGGAAGTGCTACAGGAAAAGCTGATACTAAAATACTATTCATTGAGGAGGG
GAAAATCGTTCATACTAGCAAATTGTCAGGAAGTGCTCAGCATGTCGAAGAGTGCTCTTGCTATCCTCGAT
ATCCTGGTGTCAGATGTGTCTGCAGAGACAACTGGAAAGGATCCAACCGGCCCATCGTAGATATAAACATA
AAGGATCATAGCATTGTTTCCAGTTATGTGTGTTCAGGACTTGTTGGAGACACACCCAGAAAAAACGACA
GCTCCAGCAGTAGCCATTGTTTGAATCCTAACAATGAAGAAGGTGTTCATGGAGTGAAAGGCTGGGCCTT
TGATGATGGAAATGACGTGTGGATGGGGAGAACAATCAACGAGAAGTCACGCTTAGGGTATGAAACCTT
CAAAGTCGTTGAAGGCTGGTCCAACCCTAAGTCCAAATTGCAGATAAATAGGCAAGTCATAGTTGACAGA
GGTGATAGGTCCGGTTATTCTGGTATTTTCTCTGTTGAAGGCAAAAGCTGCATCAATCGGTGCTTTTATGT
GGAGTTGATTAGGGGAAGAAAAGAGGAAACTGAAGTCTTGTGGACCTCAAACAGTATTGTTGTGTTTTG
TGGCACCTCAGGTACATATGGAACAGGCTCATGGCCTGATGGGGCGGACCTCAATCTCATGCATATATAA
(SEQ ID NO:70)

FIG. 40E

A/Yokohama/147/2017NA

ATGAATCCAAATCAAAAGATAATAACGATTGGCTCTGTTTCTCTCACAATTTCCACAATATGCTTCTTCATGC

AAATTGCCATCCTGATAACTACTGTAACATTGCATTTCAAGCAATATGAATTCAACTCCCCCCAAATAACCA

AGTGATGCTGTGTGAACCAACAATAATAGAAAGAAACATAACAGAGATAGTGTATTTGACCAACACCACC

ATAGAGAAGGAAATATGCCCCAAACCAGCAGAATACAGAAATTGGTCAAAACCGCAATGTGGCATTACAG

GATTTGCACCTTTCTCTAAAGACAATTCGATTAGGCTTTCCGCTGGTGGGGACATCTGGGTGACAAGAGA

ACCTTATGTGTCATGCGATCTTGACAAGTGTTATCAATTTGCCCTTGGACAGGGAACAACACTAAACAACG

TGCATTCAAATAACACAGTACGTGATAGGACCCCTTATCGGACTCTATTGATGAATGAGTTGGGTGTTCCTT

TCCATCTGGGGACCAAGCAAGTGTGCATAGCATGGTCCAGCTCAAGTTGTCACGATGGAAAAGCATGGCT

GCATGTTTGTATAACGGGGGATGATAAAAATGCAACTGCTAGCTTCATTTACAwATGGGAGGCTTGTAGAT

AGTGTTGTTTCATGGTCCAACGATATTCTCAGGACCCAGGAGTCAGAATGCGTTTGTATCAATGGAACTTG

TACAGTAGTAATGACTGATGGAAATGCTACAGGAAAAGCTGATACTAAAATACTATTCATTGAGGAGGGG

AAAATCGTTCATACTAGCAAATTGTCAGGAAGTGCTCAGCATGTCGAAGAGTGCTCTTGCTATCCTCGATAT

CCTGGTGTCAGATGTGTCTGCAGAGACAACTGGAAAGGATCCAACCGGCCCATCATAGATATAAACATAA

AGGATCATAGCATTGTTTCCAGTTATGTGTGTTCAGGACTTGTTGGAGACACACCCAGAAAAAGCGACAG

CTCCAGCAGTAGCCATTGTTTGAATCCTAACAATGAAGAAGGTGGTCATGGAGTGAAAGGCTGGGCCTTT

FIG. 40F

GATGATGGAAATGACGTGTGGATGGGGAGAACAATCAACGAGACGTCACGCTTAGGGTATGAAACCTTC
AAAGTCGTTGAAGGCTGGTCCAACCCTAAGTCCAAATTGCAGATAAATAGGCAAGTCATAGTTGACAGAG
GTGATAGGTCCGGTTATTCTGGTATTTTCTCTGTTGAAGGCAAAAGCTGCATCAATCGGTGCTTTTATGTG
GAGTTGATCAGGGGAAGAAAAGAGGAAACTGAAGTCTTGTGGACCTCAAACAGTATTGTTGTGTTTTGT
GGCACCTCAGGTACATATGGAACAGGCTCATGGCCTGATGGGGCGGACCTCAATCTCATGCATATATAA
(SEQ ID NO:53)

>A/Yokohama/48/2018NA
ATGAATCCAAATCAAAAGATAATAACGATTGGCTCTGTTTCTCTCACCATTTCCACAATATGCTTCTTCATGC
AAATTGCCATCCTGATAACTACTGTAACATTGCATTTCAAGCAATATGAATTCAACTCCCCCCAAATAACCA
AGTGATGCTGTGTGAACCAACAATAATAGAAAGAAACATAACAGAGATAGTGTATTTGACCAACACCACC
ATAGAGAAGGAAATATGCCCCAAACCAGCAGAATACAGAAATTGGTCAAAACCGCAATGTGGCATTACAG
GATTTGCACCTTTCTCTAAGGACAATTCGATTAGGCTTTCCGCTGGTGGGGACATCTGGGTGACAAGAGA
ACCTTATGTGTCATGCGATCCTGACAAGTGTTATCAATTTGCCCTTGGACAGGGAACAACACTAAACAACG
TGCATTCAAATAACACAGTACGTGATAGGACCCCTTATCGGACTCTATTGATGAATGAGTTGGGTGTTCCTT
TCCATCTGGGGACCAAGCAAGTGTGCATGGCATGGTCCAGCTCAAGTTGTCACGATGGAAAAGCATGGC
TGCATGTTTGTATAACTGGGGATGATAAAAATGCAACTGCTAGCTTCATTTACAATGGGAGGCTTGTAGAT
AGTGTTGTTTCATGGTCCAAAGATATTCTCAGGACCCAGGAGTCAGAATGCGTTTGCATCAATGGAACTTG

FIG. 40G

TACAGTAGTAATGACTGATGGAAATGCTACAGGAAAAGCTGATACTAAAATACTATTCATTGAGGAGGGG
AAAATCGTTCATACTAGCAAATTGTCAGGAAGTGCTCAGCATGTCGAAGAGTGCTCCTGCTATCCTCGATA
TCCTGGTGTCAGATGTGTCTGCAGAGACAACTGGAAAGGATCCAACCGGCCCATTGTAGATATAAACATA
AAGGATCATAGCATTGTTTCCAGTTATGTGTGTTCAGGACTTGTTGGAGACACACCCAGAAAAAGCGACA
GCTCCAGCAGTAGCCATTGTTTGAATCCTAACAATGAAGAAGGTGGTCATGGAGTGAAAGGCTGGGCCT
TTGATGATGGAAATGACGTGTGGATGGGGAGAACAATCAACGAGACGTCACGCTTAGGGTATGAAACCT
TCAAAGTCGTTGAAGGCTGGTCCAACTCTAAGTCCAAATTGCAGATAAATAGGCAAGTCATAGTTGACAG
AGGTGATAGGTCCGGTTATTCTGGTATTTTCTCTGTTGAAGGCAAAAGCTGCATCAATCGGTGCTTTTATGT
GGAGTTGATTAGGGGAAGAAAAGAGGAAACTGAAGTCTTGTGGACCTCAAACAGTATTGTTGTGTTTTG
TGGCACCTCAGGTACATATGGAACAGGCTCATGGCCTGATGGGGCGGACCTCAATCTCATGCATATATAA
(SEQ ID NO:54)

>A/Delaware/33/2018NA
ATGAATCCAAATCAAAAGATAATAACGATTGGCTCTGTTTCTCTCACAATTTCCACAATATGCTTCTTCATGC
AAATTGCCATCCTGATAACTACTGTAACATTGCATTTCAAGCAATATGAATTCAACTCCCCCCCAAATAACCA
AGTGATGCTGTGTGAACCAACAATAATAGAAAGAAACATAACAGAGATAGTGTATTTGACCAACACCACC
ATAGAGAAGGAAATATGCCCCAAACCAGCAGAATACAGAAATTGGTCAAAACCGCAATGTGGCATTACAG
GATTTGCACCTTTCTCTAAGGACAATTCGATTAGGCTTTCCGCTGGTGGGGACATCTGGGTGACAAGAGA

FIG. 40H

ACCTTATGTGTCATGCGATCTTGACAAGTGTTATCAATTTGCCCTTGGACAGGGAACAACACTAAACAACG
TGCATTCAAATAACACAGTACGTGATAGGACCCCTTATCGGACTCTATTGATGAATGAGTTGGGTGTTCCTT
TCCATCTGGGGACCAAGCAAGTGTGCATAGCATGGTCCAGCTCAAGTTGTCACGATGGAAAAGCATGGCT
GCATGTTTGTATAACGGGGGATGATAAAAATGCAACTGCTAGCTTCATTTACAATGGGAGGCTTGTAGATA
GTGTTGTCTCATGGTCCAATGATATTCTCAGGACCCAGGAATCAGAATGCGTTTGTATCAATGGAACTTGTA
CAGTAGTAATGACTGATGGAAATGCTACAGGAAAAGCTGATACTAAAATACTATTCATTGAGGAGGGGAA
AATCGTTCATACTAGCAAATTGTCAGGAAGTGCTCAGCATGTCGAAGAGTGCTCTTGCTATCCTCGATATCC
TGGTGTCAGATGTGTCTGCAGAGACAACTGGAAAGGATCCAACCGGCCCATCATAGATATAAACATAAAG
GATCATAGCATTGTTTCCAGTTATGTGTGTTCAGGACTTGTTGGAGACACACCCAGAAAAAGCGACAGCT
CCAGCAGTAGCCATTGTTTGAATCCTAACAATGAAGAAGGTGGTCATGGAGTGAAAGGCTGGGCCTTTG
ATGATGGAAATGACGTGTGGATGGGGAGAACAATCAACGAGACGTCACGCTTAGGGTATGAAACCTTCA
AAGTCGTTGAAGGCTGGTCCAACCCTAAGTCCAAATTGCAGATAAATAGGCAAGTCTTAGTTGACAGAGG
TGATAGGTCCGGTTATTCTGGTATTTTCTCTGTTGAAGGCAAAAGCTGCATCAATCGGTGCTTTTATGTGGA
GTTGATTAGGGGAAGAAAAGAGGAAACTGAAGTCTTGTGGACCTCAAACAGTATTGTTGTGTTTTGTGG
CACCTCAGGTACATATGGAACAGGCTCATGGCCTGATGGGGCGGACCTCAATCTCATGCATATATAAGCTT
TCGCAATTTTAGAAAAAACT (SEQ ID NO:55)

FIG. 40I

>A/Tokyo/UT-GR85/2019NA

ATGAATCCAAATCAAAAGATAATAACGATTGGCTCTGTTTCTCTCACAATTTCCACAATATGCTTCTTCATGC
AAATTGCCATCCTGATAACTACTGTAACATTGCATTTCAAGCAATATGAATTCAACTCCCCCCCAAATAACCA
AGTGATGCTGTGTGAACCAACAATAATAGAAAGAAACATAACAGAGATAGTGTATTTGACCAACACCACC
ATAGAGAAGGAAATATGCCCCAAACCAGCAGAATACAGAAATTGGTCAAAACCGCAATGTGGCATTACAG
GATTTGCACCTTTCTCTAAGGACAATTCGATTAGGCTTTCCGCTGGTGGGGACATCTGGGTGACAAGAGA
ACCTTATGTGTCATGCGATCTTGACAAGTGTTATCAATTTGCCCTTGGACAGGGAACAACACTAAACAACG
TGCATTCAAATAACACAGTACGTGATAGGACCCCTTATCGGACTCTATTGATGAATGAGTTGGGTGTTCCTT
TCCATCTGGGGACCAAGCAAGTGTGCATAGCATGGTCCAGCTCAAGTTGTCACGATGGAAAAGCATGGCT
GCATGTTTGTATAACGGGGGATGATAAAAATGCAACTGCTAGCTTCATTTACAATGGGAGGCTTGTAGATA
GTGTTGTTTCATGGTCCAACGATATTCTCAGGACCCAGGAGTCAGAATGCGTTTGTATCAATGGAACTTGT
ACAGTAGTAATGACTGATGGAAATGCTACAGGAAAGGCTGACACTAAAATACTATTCATTGAGGAGGGGA
AAATCGTACATACTAGCAAATTGTCAGGAAGTGCTCAGCATGTCGAAGAGTGCTCTTGCTATCCTCGATATC
CTGGTGTCAGATGTGTCTGCAGAGACAACTGGAAAGGATCCAACCGGCCCATCATAGATATAAACATAAA
GGATCATAGCATTGTTTCCAGGTATGTGTGTTCAGGACTTGTTGGAGACACACCCAGAAAAAGCGACAGC
TCCAGCAGTAGCCATTGTTTGAACCCTAACAATGAAAAAGGTGGTCATGGAGTGAAAGGCTGGGCCTTT
GATGATGGAAATGACGTGTGGATGGGGAGAACAATCAACGAGACGTCACGCTTAGGGTATGAAACCTTC
AAAGTCGTTGAAGGCTGGTCCAACCCTAAGTCCAAATTGCAGATAAATAGGCAAGTCATAGTTGACAGAG
GTGATAGGTCCGGTTATTCTGGTATTTTCTCTGTTGAAGGCAAAAGCTGCATCAATCGGTGCTTTTATGTRG

FIG. 40J

AGTTGATTAGGGGAAGAAAAGAGGAAACTGAAGTCTTGTGGACCTCAAACAGTATTGTTGTGTTTTGTG
GCACCTCAGGTACATATGGAACAGGCTCATGGCCTGATGGGGCGGACCTCAATCTCATGCATATATAAGCT
TTCGCAATTTTAGAAAAAACTCCTTGTTTCTACTG (SEQ ID NO:56)

>A/Saint-Petersburg/RII-324S/2019NA
ATGAATCCAAATCAAAAGATAATAACGATTGGCTCTGTTTCTCTCACAATTTCCACAATATGCTTCTTCATGC
AAATTGCCATCCTGATAACTACTGTAACATTGCATTTCAAGCAATATGAATTCAACTCCCCCCCAAATAACCA
AGTGATGCTGTGTGAACCAACAATAATAGAAAGAAACATAACAGAGATAGTGTATTTGACCAACACCACC
ATAGAGAAGGAAATATGCCCCAAACCAGCAGAATACAGAAATTGGTCAAAACCGCAATGTGGCATTACAG
GATTTGCACCTTTCTCTAAGGACAATTCGATTAGGCTTTCCGCTGGTGGGGACATCTGGGTGACAAGAGA
ACCTTATGTGTCATGCGATCTTGACAAGTGTTATCAATTTGCCCTTGGACAGGGGACAACACTAAACAACG
TGCATTCAAATAACACAGTACGTGATAGGACCCCTTACCGGACTCTATTGATGAATGAGTTGGGTGTTCCT
TTCCATCTGGGGACCAAGCAAGTGTGCATAGCATGGTCCAGCTCAAGTTGTCACGATGGAAAAGCATGGC
TGCATGTTTGTATAACGGGGGATGATAAAAATGCAACTGCTAGCTTCATTTACAATGGGAGGCTTGTAGAT
AGTGTTGTTTCATGGTCCAACGATATTCTCAGGACCCAGGAATCAGAATGCGTTTGTATCAATGGAACTTG
TACAGTAGTAATGACTGATGGAAATGCTACAGGAAAAGCTGATACTAAAATACTATTCATCGAGGAGGGG
AAAATCATTCATACTAGCAAATTGTCAGGAAGTGCTCAGCATGTCGAAGAGTGCTCTTGCTATCCTCGATAT
CCTGGTGTCAGATGTGTCTGCAGAGACAACTGGAAAGGATCCAACCGGCCCATCATAGATATAAACATAA

FIG. 40K

AGGATCATAGCATTGTTTCCAGTTATGTGTGTTCAGGACTTGTTGGAGACACACCCAGAAAAAGCGACAG
CTCCAGCAGTAGCCATTGTTTGAATCCTAACAATGAAGAAGGTGGTCATGGAGTGAAAGGCTGGGCCTTT
GATGATGGAAATGACGTGTGGATGGGGAGAACAATCAACGAGACGTCACGCTTAGGGTATGAAACCTTC
AAAGTCGTTGAAGGCTGGTCCAACCCTAAGTCCAAATTGCAGATAAATAGGCAAGTCATAGTTGACAGAG
GTGATAGGTCCGGTTATTCTGGTATTTTCTCTGTTGAAGGCAAAAGCTGCATCAATCGGTGCTTTTATGTG
GAGTTGATTAGGGGAAGAAAAGAGGAAACTGAAGTCTTGTGGACCTCAAACAGTATTGTTGTGTTTTGT
GGCACCTCAGGTACATATGGAACAGGCTCATGGCCTGATGGGGCGGACCTCAATCTCATGCATATATAAGC
TTTCGCAATTTTAGAAAAAAACTCCTTGTTTCTACT (SEQ ID NO:57)

>A/Kanagawa/IC1820/2019NA
ATGAATCCAAATCAAAAGATAATAACGATTGGCTCTGTTTCTCTCACAATTTCCACAATATGCTTCTTCATGC
AAATTGCCATCCTGATAACTACTGTAACATTGCATTTCAAGCAATATGAATTCAACTCCCCCCCAAATAACCA
AGTGATGCTGTGTGAACCAACAATAATAGAAAGAAACATAACAGAGATAGTGTATTTGACCAACACCACC
ATAGAGAAGGAAATATGCCCCAAACCAGCAGAATACAGAAATTGGTCAAAACCGCAATGTGGCATTACAG
GATTTGCACCTTTCTCTAAGGACAATTCGATTAGGCTTTCCGCTGGTGGGGACATCTGGGTGACAAGAGA
ACCTTATGTGTCATGCGATCTTGACAAGTGTTATCAATTTGCCCTTGGACAGGGAACAACACTAAACAACG
TGCATTCAAATAACACAGTACGTGATAGAACCCCTTATCGGACTCTATTGATGAATGAGTTGGGTGTTCCTT
TCCATCTGGGGACCAAGCAAGTGTGCATAGCATGGTCCAGCTCAAGCTGTCACGATGGAAAAGCATGGC

FIG. 40L

TGCATGTTTGTATAACGGGGGATGATAAAAATGCAACTGCTAGCTTCATTTACAATGGGAGGCTTGTAGAT
AGTGTTGTTTCATGGTCCAACGATATTCTCAGGACCCAGGAGTCAGAATGCGTTTGTATCAATGGAACTTG
TACAGTAGTAATGACTGATGGAAATGCTACAGGAAAAGCTGATACTAAAATACTATTCATTGAGGAGGGG
AAAATCGTTCATACTAGCAAATTGTCAGGAAGTGCTCAGCATGTCGAAGAGTGCTCTTGCTATCCTCGATAT
CCTGGTGTCAGATGTGTCTGCAGAGACAACTGGAAAGGATCCAACCGGCCCATCATAGATATAAACATAA
AGGATCATAGCATTGTTTCCAGGTATGTGTGTTCAGGACTTGTTGGAGACACACCCAGAAAAAGCGACAG
CTCCAGCAGTAGCCATTGTTTGAACCCTAACAATGAAAAAGGTGATCATGGAGTGAAAGGCTGGGCCTTT
GATGATGGAAATGACGTGTGGATGGGGAGAACAATCAACGAGACGTCGCGCTTAGGGTATGAAACCTTC
AAAGTCGTTGAAGGCTGGTCCAACCCTAAGTCCAAATTGCAGATAAATAGGCAAGTCATAGTTGACAGAG
GTGATAGGTCCGGTTATTCTGGTATTTTCTCTGTTGAAGGCAAAAGCTGCATCAATCGGTGCTTTTATGTG
GAGTTGATTAGGGGAAGAAAAGAGGAAACTGAAGTCTTGTGGACCTCAAACAGTATTGTTGTGTTTTGT
GGCACCTCAGGTACATATGGAACAGGCTCATGGCCTGATGGGGCGGACCTCAATCTCATGCATATATAA
(SEQ ID NO:58)

FIG. 40M

>A/Kansas/14/2017NA

ATGAATCCAAATCAAAAGATAATAACGATTGGCTCTGTTTCTCTCACCATTTCCACAATATGCTTCTTCATGC
AAATTGCCATCCTGATAACTACTGTAACATTGCATTTCAAGCAATATGAATTCAACTCCCCCCCAAACAACC
AAGTGATGCTGTGTGAACCAACAATAATAGAAAGAAACATAACAGAGATAGTGTATTTGACCAACACCAC
CATAGAGAGGGAAATATGCCCCAAACCAGCAGAATACAGAAATTGGTCAAAACCGCAATGTGGCATTACA
GGATTTGCACCTTTCTCTAAGGACAATTCGATTAGGCTTTCCGCTGGTGGGGACATCTGGGTGACAAGAG
AACCTTATGTGTCATGCGATCCTGACAAGTGTTATCAATTTGCCCTTGGACAGGGAACAACAATAAACAAC
GTGCATTCAAATAACACAGCACGTGATAGGACCCCTCATCGGACTCTATTGATGAATGAGTTGGGTGTTCC
TTTCCATCTGGGGACCAAGCAAGTGTGCATAGCATGGTCCAGCTCAAGTTGTCACGATGGAAAAGCATGG
CTGCATGTTTGTATAACGGGGGATGATAAAAATGCAACTGCTAGTTTCATTTACAATGGGAGGCTTGTAGA
TAGTGTTGTTTCATGGTCCAAAGATATTCTCAGGACCCAGGAGTCAGAATGCGTTTGTATCAATGGAACTT
GTACAGTAGTAATGACTGATGGAAATGCTACAGGAAAAGCTGATACTAAAATATTATTCATTGAGGAGGGG
AAAATCGTTCATACTAGCAAATTGTCAGGAAGTGCTCAGCATGTCGAAGAGTGCTCTTGCTATCCTCGATA
CCCTGGTGTCAGATGTGTCTGCAGAGACAACTGGAAAGGATCCAACCGGCCCATCGTAGATATAAACATA
AAGGATCATAGCATTGTTTCCAGTTATGTGTGTTCAGGACTTGTTGGAGACACACCCAGAAAAACCGACA
GCTCCAGCAGCAGCCATTGCTTGAATCCTAACAATGAAAAAGGTGGTCATGGAGTGAAAGGCTGGGCCT
TTGATGATGGAAATGACGTGTGGATGGGGAGAACAATCAACGAGACGTCACGCTTAGGGTATGAAACCT
TCAAAGTCGTTGAAGGCTGGTCCAACCCTAAGTCCAAATTGCAGATAAATAGGCAAGTCATAGTTGACAG
AGGTGATAGGTCCGGTTATTCTGGTATTTTCTCTGTTGAAGGCAAAAGCTGCATCAATCGGTGCTTTTATGT
GGAGTTGATTAGGGGAAGAAAAGAGGAAACTGAAGTCTTGTGGACCTCAAACAGTATTGTTGTGTTTTG
TGGCACCTCAGGTACATATGGAACAGGCTCATGGCCTGATGGGGCGGACCTCAATCTCATGCATATATAAG
CTTTCGCAATTTTAGAAAAAACT (SEQ ID NO:59)

FIG. 40N

>A/Hong Kong/4801/2014HA

ATGAAGACTATCATTGCTTTGGGCTACATTCTATGTCTGGTTTTCGCTCAAAAAATTCCTGGAAATGACAAT
AGCACGGCAACGCTGTGCCTTGGGCACCATGCAGTACCAAACGGAACGATAGTGAAAACAATCACAAAT
GACCGAATTGAAGTTACTAATGCTACTGAGCTGGTTCAGAATTCCTCAATAGGTGAAATATGCGACAGTCC
TCATCAGATCCTTGATGGAGAAAACTGCACACTAATAGATGCTCTATTGGGAGACCCTCAGTGTGATGGCT
TTCAAAATAAGAAATGGGACCTTTTTGTTGAACGAAGCAAAGCCTACAGCAACTGTTACCCTTATGATGTG
CCGGATTATGCCTCCCTTAGGTCACTAGTTGCCTCATCCGGCACACTGGAGTTTAACAATGAAAGCTTCAA
TTGGACTGGAGTCACTCAAAACGGAACAAGTTCTGCTTGCATAAGGAGATCTAGTAGTAGTTTCTTTAGTA
GATTAAATTGGTTGACCCACTTAAACTACACATACCCAGCATTGAACGTGACTATGCCAAACAATGAACAA
TTTGACAAATTGTACATTTGGGGGGTTCACCACCCGGGTACGGACAAGGACCAAATCTTCCTGTATGCTC
AATCATCAGGAAGAATCACAGTATCTACCAAAAGAAGCCAACAAGCTGTAATCCCAAATATCGGATCTAGA
CCTAGAATAAGGGATATCCCTAGCAGAATAAGCATCTATTGGACAATAGTAAAACCGGGAGACATACTTTT
GATTAACAGCACAGGGAATCTAATTGCTCCTAGGGGTTACTTCAAAATACGAAGTGGGAAAAGCTCAATA
ATGAGATCAGATGCACCCATTGGCAAATGCAAGTCTGAATGCATCACTCCAAATGGAAGCATTCCCAATGA
CAAACCATTCCAAAATGTAAACAGGATCACATACGGGGCCTGTCCCAGATATGTTAAGCATAGCACTCTGA
AATTGGCAACAGGAATGCGAAATGTACCAGAGAAACAAACTAGAGGCATATTTGGCGCAATAGCGGGTT
TCATAGAAAATGGTTGGGAGGGAATGGTGGATGGTTGGTACGGTTTCAGGCATCAAAATTCTGAGGGAA
GAGGACAAGCAGCAGATCTCAAAAGCACTCAAGCAGCAATCGATCAAATCAATGGGAAGCTGAATCGAT

FIG. 41A

TGATCGGGAAAACCAACGAGAAATTCCATCAGATTGAAAAAGAATTCTCAGAAGTAGAAGGAAGAATTC
AGGACCTTGAGAAATATGTTGAGGACACTAAAATAGATCTCTGGTCATACAACGCGGAGCTTCTTGTTGCC
CTGGAGAACCAACATACAATTGATCTAACTGACTCAGAAATGAACAAACTGTTTGAAAAAACAAAGAAGC
AACTGAGGGAAAATGCTGAGGATATGGGAAATGGTTGTTTCAAAATATACCACAAATGTGACAATGCCTG
CATAGGATCAATAAGAAATGGAACTTATGACCACAATGTGTACAGGGATGAAGCATTAAACAACCGGTTCC
AGATCAAGGGAGTTGAGCTGAAGTCAGGGTACAAAGATTGGATCCTATGGATTTCCTTTGCCATATCATGT
TTTTTGCTTTGTGTTGCCTTGTTGGGGTTCATCATGTGGGCCTGCCAAAAGGGCAACATTAGGTGCAACAT
TTGCATTTGAGTGCATTAATTAAAAACAC (SEQ ID NO:60)

> A/Alaska/232/2015HA

ATGAAGACTATCATTGCTTTGAGCTACATTCTATGTCTGGTTTTCGCTCAAAAAATTCCTGGAAATGACAAT
AGCACGGCAACGCTGTGCCTTGGGCACCATGCAGTACCAAACGGAACGATAGTGAAAACAATCACAAAT
GACCGAATTGAAGTTACTAATGCTACTGAGTTGGTTCAGAATTCCTCAATAGGTGAAATATGCGACAGTCC
TCATCAGATCCTTGATGGAGAGAACTGCACACTAATAGATGCTCTATTGGGAGACCCTCAGTGTGATGGCT
TTCAAAATAAGAAATGGGACCTTTTTGTTGAACGAAGCAAAGCCTACAGCAACTGTTACCCTTATGATGTG
CCGGATTATGCCTCCCTTAGGTCACTAGTTGCCTCATCCGGCACACTGGAGTTTAACAATGAAAGCTTCAA
TTGGACTGGAGTCACTCAAAACGGAACAAGTTCTGCTTGCATAAGGAGATCTAGTAGTAGTTTCTTTAGTA
GATTAAATTGGTTGACCCACTTAAACTACACATATCCAGCATTGAACGTGACTATGCCAAACAAGGAACAA

FIG. 41B

TTTGACAAATTGTACATTTGGGGGGTTCACCACCCGGGTACGGACAAGGACCAAATCTTCCTGTATGCTC
AATCATCAGGAAGAATCACAGTATCTACCAAAAGAAGCCAACAAGCTGTAATCCCAAATATCGGATCTAGA
CCCAGAATAAGGGATATCCCTAGCAGAATAAGCATCTATTGGACAATAGTAAAACCGGGAGACATACTTTT
GATTAACAGCACAGGGAATCTAATTGCTCCTAGGGGTTACTTCAAAATACGAAGTGGGAAAAGCTCAATA
ATGAGATCAGATGCACCCATTGGCAAATGCAAGTCTGAATGCATCACTCCAAATGGAAGCATTCCCAATGA
CAAACCATTCCAAAATGTAAACAGGATCACATACGGGGCCTGTCCCAGATATGTTAAGCATAGCACTCTGA
AATTGGCAACAGGAATGCGAAATGTACCAGAGAAACAAACTAGAGGCATATTTGGCGCAATAGCGGGTT
TCATAGAAAATGGTTGGGAGGGAATGGTGGATGGTTGGTACGGTTTCAGGCATCAAAATTCTGAGGGAA
GAGGACAAGCAGCAGATCTCAAAAGCACTCAAGCAGCAATCGATCAAATCAATGGGAAGCTGAATCGGT
TGATCGGGAAAACCAACGAGAAATTCCATCAGATTGAAAAAGAATTCTCAGAAGTAGAAGGAAGAGTTC
AAGACCTTGAGAAATATGTTGAGGACACTAAAATAGATCTCTGGTCATACAACGCGGAGCTTCTTGTTGCC
CTGGAGAACCAACATACAATTGATCTAACTGACTCAGAAATGAACAAACTGTTTGAAAAAACAAAGAAGC
AACTGAGGGAAAATGCTGAGGATATGGGAAATGGTTGTTTCAAAATATACCACAAATGTGACAATGCCTG
CATAGGATCAATAAGAAATGAAACTTATGACCACAATGTGTACAGGGATGAAGCATTAAACAACCGGTTCC
AGATCAAGGGAGTTGAGCTGAAGTCAGGGTACAAAGATTGGATCCTATGGATTTCCTTTGCCATATCATGT
TTTTTGCTTTGTGTTGCTTTGTTGGGGTTCATCATGTGGGCCTGCCAAAAGGGCAACATTAGATGCAACAT
TTGCATTTGA (SEQ ID NO:61)

FIG. 41C

A/Yokohama/147/2017HA

ATGAAGACTATCATTGCTTTGAGCTACATTCTATGTCTGGTTTTCGCTCAAAAAATTCCTGGAAATGACAAT

AGCACGGCAACGCTGTGCCTTGGGCACCATGCAGTACCAAACGGAACGATAGTGAAAACAATCACAAAT

GACCGAATTGAAGTTACTAATGCTACTGAGTTGGTTCAGAATTCCTCAATAGGTGAAATATGCGACAGTCC

TCATCAGATCCTTGATGGAGGGAACTGCACACTAATAGATGCTCTATTGGGGGACCCTCAGTGTGACGGC

TTTCAAAATAAGAAATGGGACCTTTTTGTTGAACGAAGCAGAGCCTACAGCAACTGTTACCCTTATGATGT

GCCGGATTATGCCTCCCTTAGGTCACTAGTTGCCTCATCCGGCACACTGGAGTTTAAAAATGAAAGCTTTA

ATTGGACTGGAGTCACTCAAAACGGAAAAAGTTCTGCTTGCATAAGGGGATCTAGTAGTAGTTTCTTTAG

TAGATTAAATTGGTTGACCCACTTAAACTACACATATCCAGCACTGAACGTGACTATGCCAAACAAGGAAC

AATTTGACAAATTGTACATTTGGGGGGTTCACCACCCGGGTACGGACAAGGACCAAATCTTCCTGTATGC

TCAATCATCAGGAAGAATCACAGTATCTACCAAAAGAAGCCAACAAGCTGTAATCCCAAATATTGGATCTA

GACCCAGAATAAGGGATATCCCTAGCAGAATAAGCATCTATTGGACAATAGTAAAACCGGGAGACATACTT

TTGATTAACAGCACAGGGAATCTAATTGCTCCTAGGGGTTACTTCAAAATACGAAGTGGGAAAAGCTCAA

TAATGAGATCAGATGCACCCATTGGCAAATGCAAGTCTGAATGCATCACTCCAAATGGAAGCATTCCCAAT

GACAAACCATTCCAAAATGTAAACAGGATCACATACGGGGCCTGTCCCAGATATGTTAAGCAAAGCACTC

TGAAATTGGCAACAGGAATGCGAAATGTACCAGAGAAACAAACTAGAGGCATATTTGGCGCAATAGCGG

GTTTCATAGAAAATGGTTGGGAGGGAATGGTGGATGGTTGGTACGGTTTCAGGCATCAAAATTCTGAGG

GAAGAGGACAAGCAGCAGATCTCAAAAGCACTCAAGCAGCAATCGATCAAATCAATGGGAAGCTGAATC

FIG. 41D

GATTGATCGGAAAAACCAACGAGAAATTCCATCAGATTGAAAAAGAATTCTCAGAAGTAGAAGGAAGAG
TTCAAGACCTTGAGAAATATGTTGAGGACACTAAAATAGATCTCTGGTCATACAACGCGGAGCTTCTTGTT
GCCCTGGAGAACCAACATACAATTGATCTAACTGACTCAGAAATGAACAAACTGTTTGAAAAAACAAAAA
AGCAACTGAGGGAAAATGCTGAGGATATGGGAAATGGTTGTTTCAAAATATACCACAAATGTGACAATGC
CTGCATAGGATCAATAAGAAATGAAACTTATGACCACAATGTGTACAGGGATGAAGCATTAAACAACCGG
TTCCAGATCAAGGGAGTTGAGCTGAAGTCAGGGTACAAAGATTGGATCCTATGGATTTCCTTTGCCATATC
ATGTTTTTGCTTTGTGTTGCTTTGTTGGGGTTCATCATGTGGGCCTGCCAAAAGGGCAACATTAGATGCA
ACATTTGCATTTGAGTGCATTAATTAAAAACACCCTTGTTTCTACT (SEQ ID NO:62)

>A/Yokohama/48/2018HA
ATGAAGACTATCATTGCTTTGAGCTACATTCTATGTCTGGTTTTCGCTCAAAAAATTCCTGGAAATGACAAT
AGCACGGCAACGCTGTGCCTTGGGCACCATGCAGTACCAAACGGAACGATAGTGAAAACAATCACAAAT
GACCGAATTGAAGTTACTAATGCTACTGAGTTGGTTCAGAATTCCTCAATAGGTGAAATATGCGACAGTCC
TCATCAGATCCTTGATGGAGAAAACTGCACACTAATAGATGCTCTATTGGGAGACCCTCAGTGTGATGGCT
TTCAAAATAAGAAATGGGACCTTTTTGTTGAAAGAAGCAAAGCCTACAGCAACTGTTACCCTTACGATGT
GCCGGATTATGCCTCCCTTAGGTCACTAGTTGCCTCATCCGGCACACTGGAGTTTAACAATGAAAGCTTCA
ATTGGACTGGAGTCAAACAAAACGGAACAAGTTCTGCTTGTATAAGGAAATCTAGTAGTAGTTTCTTTAGT
AGATTAAATTGGTTGACCCACTTAAACTACACATATCCAGCATTGAACGTGACTATGCCAAACAATGAACA

FIG. 41E

ATTTGACAAATTGTACATTTGGGGGGTTCACCACCCGGGTACGGACAAGGACCAAATCTTCCTGTATGCTC

AATCATCAGGAAGGATCACAGTATCTACCAAAAGAAGCCAACAAACTGTAATCCCAAATATCGGATCCAGG

CCCAGAATAAGGGATATCCCTAGCAGAATAAGCATCTATTGGACAATAGTAAAACCGGGAGACATACTTTT

GATTAACAGCACAGGGAATCTAATTGCTCCTAGGGGTTACTTCAAAATACAAAGTGGGAAAAGCTCAATA

ATGAGATCAGATGCACCCATTGGCAAATGCAAGTCTGAATGCATCACTCCAAATGGAAGCATTCCCAATGA

CAAACCATTCCAAAATGTAAACAGGATCACATACGGGGCCTGTCCCAGATATGTTAAGCATAGCACTCTGA

AATTGGCAACAGGAATGCGAAATGTACCAGAGAAACAAACTAGGGGCATATTTGGCGCAATAGCGGGTT

TCATAGAAAATGGTTGGGAGGGAATGGTGGATGGTTGGTACGGTTTCAGGCATCAAAATTCTGAAGGAA

GAGGACAAGCAGCAGATCTCAAAAGCACTCAAGCAGCAATCGATCAAATCAATGGGAAGCTGAATCGAT

TGATCGGGAAAACCAACGAGAAATTCCATCAGATTGAAAAAGAATTCTCAGAAGTAGAAGGAAGAATTC

AGGACCTTGAGAAATATGTTGAGGACACTAAAATAGATCTCTGGTCATACAACGCGGAGCTTCTTGTTGCC

CTGGAGAACCAACATACAATTGATCTAACTGACTCAGAAATGAACAAACTGTTTGAAAAAACAAAGAAGC

AACTGAGGGAAAATGCTGAGGATATGGGAAATGGTTGTTTCAAAATATACCACAAATGTGACAATGCCTG

CATAGGTTCAATAAGAAATGGAACTTATGACCACAATGTGTACAGGGATGAAGCATTAAACAACCGGTTCC

AGATCAAGGGAGTTGAGCTGAAGTCAGGGTACAAAGATTGGATCCTATGGATTTCCTTTGCCATATCATGT

TTTTTGCTTTGTGTTGCTTTGTTGGGGTTCATCATGTGGGCCTGCCAAAAGGGCAACATTAGATGCAATAT

TTGCATTTGAGTGCATTAATTAAAAACACCCTTGTTTCT (SEQ ID NO:63)

FIG. 41F

>A/Delaware/33/2018HA

ATGAAGGCTATCATTGCTTTGAGCTACATTCTATGTCTGGTTTTCGCTCAAAAAATTCCTGGAAATGACAAT
AGCACGGCAACGCTGTGCCTTGGGCACCATGCAGTACCAAACGGAACGATAGTGAAAACAATCACAAAT
GACCGAATTGAAGTTACTAATGCTACTGAGTTGGTTCAGAATTCCTCAATAGGTGAAATATGCGACAGTCC
TCATCAGATCCTTGATGGAGGGAACTGCACACTAATAGATGCTCTATTGGGGGACCCTCAATGTGACGGCT
TTCAAAATAAGAAATGGGACCTTTTTGTTGAACGAAGCAGAGCCTACAGCAACTGTTACCCTTATGATGTG
CCGGATTATGCCTCCCTTAGGTCACTAGTTGCCTCATCCGGCACACTGGAGTTTAAAAATGAAAGCTTCAA
TTGGGCTGGAGTCACTCAAAACGGAAAAAGTTCTGCTTGCATAAGGGGATCTAGTAGTAGTTTCTTTAGT
AGATTAAATTGGTTGACCCACTTAAACTACACATATCCAGCACTGAACGTGACTATGCCAAACAAGGAACA
ATTTGACAAATTGTACATTTGGGGGGTTCACCACCCGGGTACGGACAAGGACCAAATCTTCCTGTATGCTC
AATCATCAGGAAGAATCACAGTATCTACCAAAAGAAGCCAACAAGCTGTAATCCCAAATATAGGATCTAGA
CCCAGAATAAGGGATATCCCTAGCAGAATAAGCATCTATTGGACAATAGTAAAACCGGGAGACATACTTTT
GATTAACAGCACAGGGAATCTAATTGCTCCTAGGGGTTACTTCAAAATACGRAGTGGGAAAAGCTCAATA
ATGAGATCAGATGCACCCATTGGCAAATGCAAGTCTGAATGCATCACTCCAAATGGAAGCATTCCCAATGA
CAAACCATTCCAAAATGTAAACAGGATCACATACGGGGCCTGTCCCAGATATGTTAAGCAAAGCACTCTGA
AATTGGCAACAGGAATGCGAAATGTACCAGAGAAACAAACTAGAGGCATATTTGGCGCAATAGCGGGTT
TCATAGAAAATGGTTGGGAGGGAATGGTGGATGGTTGGTACGGTTTCAGGCATCAAAATTCTGAGGGAA
GAGGACAAGCAGCAGATCTCAAAAGCACTCAAGCAGCAATCGATCAAATCAATGGGAAGCTGAATCGAT

FIG. 41G

TGATCGGAAAAACCAACGAGAAATTCCATCAGATTGAAAAAGAATTCTCAGAAGTAGAAGGAAGAGTTC
AAGACCTTGAGAAATATGTTGAGGACACTAAAATAGATCTCTGGTCATACAACGCGGAGCTTCTTGTTGCC
CTGGAGAACCAACATACAATTGATCTAACTGACTCAGAAATGAACAAACTGTTTGAAAAAACAAAGAAGC
AACTGAGGGAAAATGCTGAGGATATGGGAAATGGTTGTTTCAAAATATACCACAAATGTGACAATGCCTG
CATAGGATCAATAAGAAATGAAACTTATGACCACAATGTGTACAGGGATGAAGCATTAAACAACCGGTTCC
AGATCAAGGGAGTTGAGCTGAAGTCAGGGTACAAAGATTGGATCCTATGGATTTCCTTTGCCATATCATGT
TTTTTGCTTTGTGTTGCTTTGTTGGGGTTCATCATGTGGGCCTGCCAAAAGGGCAACATTAGATGCAACAT
TTGCATTTGAGTGCATTAATTAAAAACAC (SEQ ID NO:64)

>A/Tokyo/UT-GR85/2019HA
ATGAAGACTATCATTGCTTTGAGCTACATTCTATGTCTGGTTTTCGCTCAAAAAATTCCTGGAAATGACAAT
AGCACGGCAACGCTGTGCCTTGGGCACCATGCAGTACCAAACGGAACGATAGTGAAAACAATCACAAAT
GACCGAATTGAAGTTACTAATGCTACTGAGTTGGTTCAGAATTCCTCAATAGGTGAAATATGCGACAGTCC
TCATCAGATCCTTGATGGAGGGAACTGCACACTAATAGATGCTCTATTGGGGGACCCTCAGTGTGACGGC
TTTCAAAATAAGAAATGGGACCTTTTTGTTGAACGAAGCAGAGCCTACAGCAACTGTTACCCTTATGATGT
ACCGGATTATGCCTCCCTTAGGTCACTAGTTGCCTCATCCGGCACACTGGAGTTTAAAAATGAAAGCTTCA
ATTGGACTGGAGTCAAACAAAACGGAACAAGTTCTGCTTGCATAAGGGGATCTAGTAGTAGTTTCTTTAG
TAGATTAAATTGGTTGACCCACTTAAACTACACATATCCAGCACTGAACGTGACTATGCCAAACAAGGAAC

FIG. 41H

AATTTGACAAATTGTACATTTGGGGGGTTCACCACCCGGGTACGGACAAGGACCAAATCTTCCTGTATGC
TCAATCATCAGGAAGAATCACAGTATCTACCAAAAGAAGCCAACAAGCTGTAATCCCAAATATCGGATTTA
GACCCAGAATAAGGGATATCCCTAGCAGAATAAGCATCTATTGGACAATAGTAAAACCGGGAGACATACTT
TTGATTAACAGCACAGGGAATCTAATTGCTCCTAGGGGTTACTTCAAAATACGAAGTGGGAAAAGCTCAA
TAATGAGATCAGATGCACCCATTGGCAAATGCAAGTCTGAATGCATCACTCCAAATGGAAGCATTCCCAAT
GACAAACCATTCCAAAATGTAAACAGGATCACATACGGGGCCTGTCCCAGATATGTTAAGCAGAGCACTC
TGAAATTGGCAACAGGAATGCGAAATGTACCAGAGAAACAAACTAGAGGCATATTTGGCGCAATAGCGG
GTTTCATAGAAAATGGTTGGGAGGGAATGATGGATGGTTGGTACGGTTTCAGGCATCAAAATTCTGAGG
GAAGAGGACAAGCAGCAGATCTCAAAAGCACTCAAGCAGCAATCGATCAAATCAATGGGAAGCTGAATC
GATTGATCGGAAAAACCAACGAGAAATTCCATCAGATTGAAAAAGAATTCTCAGAAGTAGAAGGAAGAG
TTCAAGACCTTGAGAAATATGTTGAGGACACTAAAATAGATCTCTGGTCATACAACGCGGAGCTTCTTGTT
GCCCTGGAGAACCAACATACAATTGACCTAACTGACTCAGAAATGAACAAACTGTTTGAAAAAACAAAG
AAGCAACTGAGGGAAAATGCTGAGGATATGGGAAATGGTTGTTTCAAAATATACCACAAATGTGACAATG
CCTGCATAGGATCAATAAGAAATGAAACTTATGACCACAATGTGTACAGGGATGAAGCATTAAACAACCG
GTTCCAGATCAAGGGAGTTGAGCTGAAGTCAGGGTACAAAGATTGGATCCTATGGATTTCCTTTGCCATAT
CATGTTTTTTGCTTTGTATTGCTTTGTTGGGGTTCATCATGTGGGCCTGCCAAAAGGGCAACATTAGATGC
AACATTTGCATTTGAGTGCATTAATTAAAAACACCCTTGTTTC (SEQ ID NO:65)

FIG. 41I

>A/Saint-Petersburg/RII-324S/2019HA

ATGAAGACTATCATTGCTTTGAGCTACATTCTATGTCTGGTTTTCGCTCAAAAAATTCCTGGAAATGACAAT
AGCACGGCAACGCTGTGCCTTGGGCACCATGCAGTACCAAACGGAACGATAGTGAAAACAATCACAAAT
GACCGAATTGAAGTTACTAATGCTACTGAGTTGGTTCAGAATTCCTCAATAGGTGAAATATGCAACAGTCC
TCATCAGATCCTTGATGGAGGGAACTGCACACTAATAGATGCTCTATTGGGGGACCCTCAGTGTGACGGC
TTTCAAAATAAGAAATGGGACCTTTTTGTTGAACGAAGCAGAGCCTACAGCAACTGTTACCCTTATGATGT
GCCGGATTATGCCTCCCTTAGGTCACTAGTTGCCTCATCCGGCACACTGGAGTTTAAAAATGAAAGCTTCA
ATTGGGCTGGAGTCACTCAAAACGGAAAAAGTTCTGCTTGCATAAGGGGTTCTAGTAGTAGTTTCTTTAG
TAGATTAAATTGGTTGACCCACTTAAACTACACATATCCAGCACTGAACGTGACTATGCCAAACAAGGAAC
AATTTGACAAATTGTACATTTGGGGGGTTCACCACCCGGGTACGGACAAGGACCAAATCTTCCTGTATGC
TCAACCATCAGGAAGAATCACAGTATCTACCAAAAGAAGCCAACAAGCTGTAATCCCAAATATCGGATCTA
GACCCAGAATAAGGGATATCCCTAGCAGAATAAGCATCTATTGGACAATAGTAAAACCGGGAGACATACTT
TTGATTAACAGCACAGGGAATCTAATTGCTCCTAGGGGTTACTTCAAAATACGAAGTGGGAAAAGCTCAA
TAATGAGATCAGATGCACCCATTGGCAAATGCAAGTCTGAATGCATCACTCCAAATGGAAGCATTCCCAAT
GACAAACCATTCCAAAATGTAAACAGAATCACATACGGGGCCTGTCCCAGATATGTTAAGCAAAGCACTCT
GAAATTGGCAACAGGAATGCGAAATGTACCAGAGAAACAAACTAGAGGCATATTTGGCGCAATAGCGGG
TTTCATAGAAAATGGTTGGGAGGGAATGGTGGATGGTTGGTACGGTTTCAGGCATCAAAATTCTGAGGG
AAGAGGACAAGCAGCAGATCTCAAAAGCACTCAAGCAGCAATCGATCAAATCAATGGGAAGCTGAATCG

FIG. 41J

ATTGATCGGAAAAACCAACGAGAAATTCCATCAGATTGAAAAAGAATTCTCAGAAGTAGAAGGAAGGGT
TCAAGACCTTGAGAAATATGTTGAGGACACTAAAATAGATCTCTGGTCATACAACGCGGAGCTTCTTGTTG
CCCTGGAGAACCAACATACAATTGATCTAACTGACTCAGAAATGAACAAACTGTTTGAAAAAACAAAGAA
GCAACTGAGGGAAAATGCTGAGGATATGGGGAATGGTTGTTTCAAAATATACCACAAATGTGACAATGCC
TGCATAGGATCAATAAGAAATGAAACTTATGACCACAATGTGTACAGGGATGAAGCATTAAACAACCGGTT
CCAGATCAAGGGAGTTGAGCTGAAGTCAGGGTACAAAGATTGGATCCTATGGATTTCCTTTGCCATATCAT
GTTTTTTGCTTTGTGTTGCTTTGTTGGGGTTCATCATGTGGGCCTGCCAAAAGGGCAACATTAGATGCAAC
ATTTGCATTTGAGTGCATTAATTAAAAACACCCTTGTTTCTACT (SEQ ID NO:66)

>A/Kanagawa/IC1820/2019HA
ATGAAGACTATCATTGCTTTGAGCTACATTCTATGTCTTGTTTTCGCTCAAGAAATCCCTGGAAATGACAAT
AGCACGGCAACGCTGTGTCTTGGGCACCATGCAGTACCAAACGGAACGATAGTGAAAACAATCACAAAT
GACCGAATTGAAGTTACTAATGCTACTGAGTTGGTTCAGAATTCCTCAATAGGTGAAATATGCGACAGTCC
TCATCAGATCCTTGATGGAGGGAACTGCACACTAATAGATGCTCTATTGGGGGACCCTCAGTGTGACGGC
TTTCAAAATAAGAAATGGGACCTTTTTGTTGAACGAAGCAGAGCCTACAGCAACTGTTACCCTTATGATGT
GCCGGATTATGCCTCCCTTAGGTCACTAGTTGCCTCATCCGGCACACTGGAGTTTAAAAATGAAAGCTTCA
ATTGGACTGGAGTCAAACAAAACGGAACAAGTTCTGCGTGCATAAGGGGATCTAGTAGTAGTTTCTTCAG
TAGATTAAATTGGTTGACCCACTTAAACTACACATATCCAGCACTGAACGTGACTATGCCAAACAAGGAAC

FIG. 41K

AATTTGACAAATTGTACATTTGGGGGGTTCACCACCCGGGTACGGACAAGGACCAAATCTTCCTGTATGC
TCAATCATCAGGAAGAATCACAGTATCTACCAAAAGAAGCCAACAAGCTGTAATCCCAAATATTGGATCTA
GACCCAGAATAAGGGATATCCCTAGCAGAATAAGCATCTATTGGACAATAGTAAAACCGGGAGACATACTT
TTGATTAACAGCACAGGGAATCTAATTGCTCCTAGGGGTTACTTCAAAATACGAAGTGGGAAAAGCTCAA
TAATGAGATCAGATGCACCCATTGGCAAATGCAAGTCTGAATGCATCACTCCAAATGGAAGCATTCCCAAT
GACAAACCGTTCCAAAATGTAAACAGGATCACATACGGGGCCTGTCCCAGATATGTTAAGCAAAGCACTC
TGAAATTGGCAACAGGAATGCGAAATGTACCAGAGAAACAAACCAGAGGCATATTTGGCGCAATAGCGG
GTTTCATAGAAAATGGTTGGGAGGGAATGGTGGATGGTTGGTACGGTTTCAGGCATCAAAATTCTGAGG
GAAGAGGACAAGCAGCAGATCTCAAAAGCACTCAAGCAGCAATCGATCAAATCAATGGGAAGCTGAATC
GATTGATCGGAAAAACCAACGAGAAATTCCATCAGATTGAAAAAGAATTCTCAGAAGTAGAAGGAAGAG
TTCAAGACCTTGAGAAATATGTTGAGGACACTAAAATAGATCTCTGGTCATACAACGCGGAGCTTCTTGTT
GCCCTGGAGAACCAACATACAATTGACCTAACTGACTCAGAAATGAACAAACTGTTTGAAAAAACAAAG
AAGCAACTGAGGGAAAATGCTGAGGATATGGGAAATGGTTGTTTCAAAATATACCACAAATGTGACAATG
CCTGCATAGGATCAATAAGAAATGAAACTTATGACCACAATGTGTACAGGGATGAAGCATTAAACAACCG
GTTCCAGATCAAGGGAGTTGAGCTGAAGTCAGGGTACAAAGATTGGATCCTATGGATTTCCTTTGCCATAT
CATGTTTTTTGCTTTGTATTGCTTTGTTGGGGTTCATCATGTGGGCCTGCCAAAAGGGCAACATTAGATGC
AACATTTGCATTTGA (SEQ ID NO:67)

FIG. 41L

>A/Kansas/14/2017HA

ATGAAGACTATCATTGCTTTGAGCTGCATTCTATGTCTGGTTTTCGCTCAAAAAATTCCTGGAAATGACAAT
AGCACGGCAACGCTGTGCCTTGGGCACCATGCAGTACCAAACGGAACGATAGTGAAAACAATCACGAAT
GACCGAATTGAAGTTACTAATGCTACTGAGCTGGTTCAGAACTCCTCAATAGGTGAAATATGCGACAGTCC
TCATCAGATCCTTGATGGAGAAAACTGCACACTAATAGATGCTCTATTGGGAGACCCTCAGTGTGATGGCT
TTCAAAATAAGAAATGGGACCTTTTCGTTGAACGAAACAAAGCCTACAGCAACTGTTACCCTTATGATGTG
CCGGATTATGCATCCCTTAGATCACTAGTTGCCTCATCCGGCACACTGGAGTTTAACAATGAAAGCTTCAAT
TGGGCTGGAGTCACTCAAAACGGAACAAGTTCTTCTTGCATAAGGGGATCTAAAAGTAGTTTCTTTAGTA
GATTAAATTGGTTGACCCACTTAAACTCCAAATACCCAGCATTAAACGTGACTATGCCAAACAATGAACAA
TTTGACAAATTGTACATTTGGGGTGTTCACCACCCGGGTACGGACAAGGACCAAATCTCCCTGTATGCAC
AATCATCAGGAAGAATCACAGTATCTACCAAAAGAAGCCAACAAGCTGTAATCCCGAATATCGGATCTAGA
CCCAGAATAAGGGATATCCCTAGCAGAATAAGCATCTATTGGACAATAGTAAAACCAGGAGACATACTTTT
GATTAACAGCACAGGGAATCTAATTGCTCCTAGGGGTTACTTCAAAATACGAAGTGGGAAAAGCTCAATA

FIG. 41M

ATGAGATCAGATGCACCCATTGGCAAGTGCAAGTCTGAATGCATCACTCCAAATGGAAGCATTCCAAATG
ACAAACCATTCCAAAATGTAAACAGGATCACATACGGGGCATGTCCCAGATATGTTAAGCAAAGCACTCTG
AAATTGGCAACAGGAATGCGAAATGTACCAGAGAGACAAACTAGAGGCATATTTGGCGCAATAGCGGGT
TTCATAGAAAATGGTTGGGAGGGAATGGTGGATGGTTGGTACGGCTTCAGGCATCAAAATTCTGAGGGA
AGAGGACAAGCAGCAGATCTTAAAAGCACTCAAGCAGCAATCGATCAAATCAATGGGAAGCTGAATCGA
TTGATCGGGAAAACCAACGAGAAATTCCATCAGATTGAAAAAGAGTTCTCAGAAGTAGAAGGGAGAATT
CAGGACCTTGAGAAATATGTTGAGGACACAAAAATAGATCTCTGGTCATACAACGCGGAGCTTCTTGTTG
CCCTGGAGAACCAACATACAATTGATCTAACTGACTCAGAAATGAACAAACTGTTTGAAAAAACAAAGAA
GCAACTGAGGGAAAATGCTGAGGATATGGGCAATGGTTGTTTCAAAATATACCACAAATGTGACAATGCC
TGCATGGGGTCAATCAGAAATGGAACTTATGACCACAATGTATACAGGGATGAAGCATTAAACAACCGGT
TCCAGATCAAGGGAGTTGAGCTGAAGTCAGGGTACAAAGATTGGATCCTATGGATTTCCTTTGCCATATCA
TGTTTTTTGCTTTGTGTTGCTCTGTTGGGGTTCATCATGTGGGCCTGCCAAAAGGGCAACATTAGGTGCA
ACATTTGCATTTGAGTGCATTAATTAAAAACAC (SEQ ID NO:68)

FIG. 41N

Location of combined NA mutations "6M" found in egg-grown A/Hong Kong/4801/2014 and A/Alaska/232/2015 (in Figure 25)

Introduction of 6M into the NA of A/Tokyo/UT-GR85/2019, A/Kanagawa/IC1820/2019 did not enhance HY-PR8-backbone virus growth but possessing Yokohama/147/2017NA(6M) allowed the viruses to replicate efficiently in eggs.

| HA | GR85 | | | | IC1820 | | | |
|---|---|---|---|---|---|---|---|---|
| NA | GR85 | | Yokohama147 | | IC1820 | | Yokohama147 | |
| | WT | T148K D151E N245S G346V H347G T369K (6M) | WT | T148K D151E N245S G346V H347G T369K (6M) | WT | T148K D151E N245S G346V H347G T369K (6M) | WT | T148K D151E N245S G346V H347G T369K (6M) |

**$P < 0.01$
(one-way ANOVA
followed by
Dunnett's test)

Mutations observed in the HA and NA proteins of HY-PR8 backbone viruses possessing Yokohama147NA(6M) during 10 passages in eggs[a]

| Viruses | | | Mutations after passages in eggs | | | |
|---|---|---|---|---|---|---|
| | | | P6 | | P10 | |
| Season | Subclade | HA segment | HA | NA | HA | NA |
| 2017–18 | 3C.A2/re | A/Yokohama/48/2018 | none | K431N | K453N | K431N |
| | 3C.2A 1b/135K | A/Yokohama/147/2017 (2nd trial) | none | none | G479E R545K | K431N/K[b] |
| | | A/Yokohama/147/2017 (3rd trial) | none | none | none | R430S |
| 2018–19 | 3C.2A 1b/135K | A/Delaware/33/2018 | none | none | none | R150S/R[c] |
| | | A/Saint-Petersburg/RII-324S/2019 | D225G | none | D225G G479E | none |
| | 3C.2A 1b/131K | A/Tokyo/UT-GR85/2019 | E484G | none | D225G E484G | K148Q |
| | | A/Kanagawa/IC1820/2019 | none | none | D225G | none |

[a]Amino acid mutations that occurred in the HA and NA proteins of HY-PR8 backbone viruses possessing Yokohama147NA(6M) and A/Yokohama/48/2018HA, A/Yokohama/147/2017HA, A/Delaware/33/2018HA, A/Saint-Petersburg/RII-324S/2019HA, A/Tokyo/UT-GR85/2019HA, or A/Kanagawa/IC1820/2019HA were determined after 6 and 10 passages in eggs. [b]N/K is a mixture of asparagine and lysine at position 431. [c]S/R is a mixture of serine and arginine at position 150.

FIG. 45

Mutations observed in the HA proteins of viruses possessing Yokohama147NA(6M) during 10 passages in eggs (in Figure 43, 44 and 45)

Mutations observed in the NA proteins of viruses possessing Yokohama147NA(6M) during 10 passages in eggs (in Figure 43, 44 and 45)

A/Kansas/14/2017

Mutations observed during egg passages

| | P1 | P10 |
|---|---|---|
| HA | none | none |
| NA | none | none |

RECOMBINANT INFLUENZA VIRUSES WITH STABILIZED HA FOR REPLICATION IN EGGS

CROSS-REFERENCE TO RELATED APPLICATIONS

This application claims the benefit of the filing date of U.S. application No. 62/892,241, filed on Aug. 27, 2019, the disclosure of which is incorporated by reference herein.

STATEMENT OF GOVERNMENT FUNDING

This invention was made with government support under HHSN272201400008C awarded by the National Institutes of Health. The government has certain rights in the invention.

BACKGROUND

Influenza is a major respiratory disease in some mammals including horses and is responsible for substantial morbidity and economic losses each year. In addition, influenza virus infections can cause severe systemic disease in some avian species, leading to death. The segmented nature of the influenza virus genome allows for reassortment of segments during virus replication in cells infected with two or more influenza viruses. The reassortment of segments, combined with genetic mutation and drift, can give rise to a myriad of divergent strains of influenza virus over time. The new strains exhibit antigenic variation in their hemagglutinin (HA) and/or neuraminidase (NA) proteins, and in particular the gene coding for the HA protein has a high rate of variability. The predominant current practice for the prevention of flu is vaccination. Most commonly, inactivated virus vaccines are used. As the influenza HA protein is the major target antigen for the protective immune responses of a host to the virus and is highly variable, the isolation of influenza virus and the identification and characterization of the HA antigen in viruses associated with recent outbreaks is important for vaccine production. Based on prevalence and prediction, a vaccine is designed to stimulate a protective immune response against the predominant and expected influenza virus strains.

There are four general types of influenza viruses, Type A, Type B, Type C, and Type D, which are defined by the absence of serological cross reactivity between their internal proteins. Influenza Type A viruses are further classified into subtypes based on antigenic and genetic differences of their glycoproteins, the HA and NA proteins. All the known HA and NA subtypes (H1 to H18 and N1 to N11) have been isolated from aquatic birds, which are thought to act as a natural reservoir for influenza.

Most influenza vaccines are produced in embryonated chicken eggs. However, the WHO-recommended influenza vaccine strains often do not replicate efficiently in embryonated chicken eggs, requiring serial passages in eggs in order to allow for adaptation of the virus. During adaptation and amplification in eggs, the hemagglutinin (HA) protein of influenza viruses often acquires egg-adapting mutations. These egg-adapting mutations in HA often alter the antigenicity of the viruses, resulting in vaccine viruses that are no longer optimally matched to the circulating virus strains.

SUMMARY

As described herein, an influenza virus was passaged 7 times in eggs (in triplicate) to study the mutations that occurred in the 6 non-immunogenic viral segments during adaptation. Surprisingly, the virus acquired no HA mutations and instead had mutations in the NA, PB2, NP, and M1 proteins. The NA mutations were identical in all three experiments, and they included a deletion and 4 amino acid mutations. The NA mutations were tested alone and it was found that they, e.g., alone or in various combinations, were responsible for the effect, which permitted efficient growth in eggs without HA mutations.

The present disclosure thus relates to influenza mutations that prevent the acquisition of antigenicity-compromising mutations in the hemagglutinin (HA) segment of influenza virus during growth in eggs. The mutations in the neuraminidase (NA) protein of human influenza viruses were found to 'stabilize' the HA during egg-passages, e.g., in the presence of the mutations in NA, the HA protein did not acquire egg-adapting mutations. Those NA mutations may also increase the vaccine virus yield.

The disclosure provides isolated recombinant, e.g., reassortant, influenza viruses with selected amino acid residues or deletions at specified positions in NA.

In one embodiment, the NA is selected to not encode a threonine at residue 32. In one embodiment, the NA is selected to not encode an aspartic acid (D) at position 147. In one embodiment, the NA is selected to not encode an asparagine (N) at residue 329. In one embodiment, the NA is selected to not encode a threonine (T) at residue 148 or residue 329. In one embodiment, the NA is selected to not encode a lysine (K) at residue 148 or residue 344. In one embodiment, the NA is selected to not encode a glycine (G) at residue 346. In one embodiment, the NA is selected to not encode a histidine (H) at residue 347. In one embodiment, the NA is selected to not encode an arginine (R) or an asparagine at residue 347. In one embodiment, the NA is selected to not encode a threonine at residue 369. In one embodiment, the NA is selected to not encode a NA having a threonine or lysine at position 148. In one embodiment, the NA is selected to not encode a NA having an aspartic acid at position 151. In one embodiment, the NA is selected to not encode a NA having an asparagine at position 245. In one embodiment, the NA is selected to not encode a NA having a glycine at position 346. In one embodiment, the NA is selected to have a deletion of one or more of residues 46 to 50. The numbering for NA is based on N2. In one embodiment, the disclosure provides an isolated recombinant reassortant influenza virus having six "internal" viral segments from a vaccine influenza virus, e.g., PR8UW, a NA viral segment with one or more of the specified residues at particular positions or a deletion of specified residues, or any combination thereof, and a HA viral segment, e.g., any of H1-H18, e.g., from a circulating influenza virus. Also provided are compositions comprising the recombinant influenza virus, pharmaceutical compositions such as vaccines.

Thus, for vaccine viruses that are to be grown or passaged in cells, e.g., in eggs, replacement of the residue at position 32, 147, 329, 347, or a deletion of one or more of residues 46 to 50, or any combination thereof, in NA, e.g., by mutation, or selection of a NA viral segment for a NA to not encode a threonine at residue 32, to not encode an aspartic acid at position 147, to not encode an asparagine at residue 329, to not encode a histidine at residue 347, to not encode a threonine at residue 369, or to have a deletion of one or more of residues 46 to 50, or any combination thereof, wherein the numbering is based on N2, may result in stabilization of HA and/or higher viral titers. In one embodiment, for vaccine viruses that are to be grown or passaged in cells, e.g., in eggs, replacement of the residue at position 148, 151, 245, 346, or any combination thereof, in NA, e.g., by mutation, or selection of a NA viral segment for a NA to not encode a threonine or lysine at residue 148, to not encode an aspartic acid at position 151, to not encode an asparagine at residue 245, to not encode a glycine at residue 346, or any combination thereof, wherein the numbering is based on N2, may result in stabilization of HA and/or higher viral titers.

In one embodiment, the disclosure provides an isolated recombinant influenza virus comprising PA, PB1, PB2, NP, NS, M, and HA viral segments and a NA viral segment that encodes an NA selected to not encode a threonine at residue 32, to not encode an aspartic acid at position 147, to not encode an asparagine at residue 329, to not encode a histidine at residue 347, to not encode a threonine at residue 369, or to have a deletion of one or more of residues 46 to 50, or any combination thereof, wherein the numbering is based on N2, wherein the recombinant influenza virus has enhanced replication in avian eggs or has a reduction in HA mutations when grown in avian eggs relative to a corresponding influenza virus that has a NA that encodes a threonine at residue 32, does not have a deletion of residues 46 or 50, encodes an aspartic acid at position 147, encodes an asparagine at residue 329, encodes a histidine at residue 347, or any combination thereof. In one embodiment, the disclosure provides an isolated recombinant influenza virus comprising PA, PB1, PB2, NP, NS, M, and HA viral segments and a NA viral segment that encodes an NA selected to not encode a threonine or lysine at residue 148, to not encode an aspartic acid at position 151, to not encode an asparagine at residue 245, to not encode a glycine at residue 346, to not encode a threonine at residue 369, or any combination thereof, wherein the numbering is based on N2, wherein the recombinant influenza virus has enhanced replication in avian eggs or has a reduction in HA mutations when grown in avian eggs relative to a corresponding influenza virus that has a NA that encodes a threonine, or lysine at residue 148, encodes an aspartic acid at position 151, encodes an asparagine at residue 245, encodes a glycine at residue 346, any combination thereof. In one embodiment, the isolated recombinant influenza virus is a reassortant. In one embodiment, the NA viral segment encodes a NA that has at least 80%, 85%, 90%, 95%, or 99% amino acid sequence identity to any one of SEQ ID Nos. 1-3, 30-38, 48-50, or 54. In one embodiment, the NA viral segment encodes a NA that has less than 100% amino acid sequence identity to SEQ ID NO:2 or SEQ ID NO:3. In one embodiment, the NA viral segment encodes a N2, N3, N7, or N9 and the positions in N3, N7, or N9 with the specified residue(s) correspond to the specified positions in N2. In one embodiment, the NA viral segment encodes a N1, N4, N5, N6, N8, N10 or N11 and the positions in N1, N4, N5, N6, N8, N10 or N11 with the specified residue(s) correspond to the specified positions in N2. In one embodiment, the residue at position 32 is A, I, G, or L. In one embodiment, the deletion is a deletion of residues 46 to 50. In one embodiment, the residue at position 147 is N or Q. In one embodiment, the residue at position 148 is I or K. In one embodiment, the residue at position 151 is E, Q, H or K. In one embodiment, the residue at position 245 is S, T, A, I, G, or L. In one embodiment, the residue at position 329 is S, V, I, L, A, G, D or E. In one embodiment, the residue at position 344 is E, Q, N, H or D. In one embodiment, the residue at position 346 is V, I, A, S, T, L, or L. In one embodiment, the residue at position 347 is G, Q, N, S, T, Y, C or W. In one embodiment, the residue at position 369 is K, H, R, E, P, or D. In one embodiment, the HA is H1, H3, H7, or H9. In one embodiment, the virus is an influenza A virus. In one embodiment, the PA, PB1, PB2, NP, M, and NS viral segments have at least 85% nucleic acid sequence identity to SEQ ID Nos. 24 to 29 or encode a polypeptide having at least 80%, 85%, 90%, 95%, or 99 amino acid sequence identity to a polypeptide encoded by SEQ ID Nos. 24 to 29 or 39-44. In one embodiment, the PB2 has I, A, L, or G at residue 147. In one embodiment, the virus is an influenza B virus. In one embodiment, the selected NA viral segment does not have an aspartic acid at position 147, does not have an asparagine at residue 329, and does not have an arginine or a histidine at residue 347. In one embodiment, the selected NA viral segment does not a threonine or lysine at position 148, does not have an aspartic acid at position 151, and does not have an asparagine at position 245. In one embodiment, the selected NA viral segment has at least two of: N or Q at position 147, D or E at residue 329, or Q or G at residue 347. In one embodiment, the selected NA viral segment has at least two of: I, L, G or A at position 148, E or Q at position 151, or S, I, T, V or G at position 245. In one embodiment, the selected NA viral segment has at least two of: I or L at position 148, E or Q at position 151, or S, I, T, V or G at position 245. In one embodiment, the selected NA viral segment has N or Q at position 147, S, D or E at residue 329, and Q or G at residue 347. In one embodiment, the selected NA viral segment has N or Q at position 147, S, D or E at residue 329, and V, S, I or L at residue 346. In one embodiment, the residue at position 369 is K, H, R, E, P, or D. In one embodiment, the selected NA viral segment has I, L, G or A at position 148, E or Q at position 151, S, I, T, V or G at position 245 and K, H, R, E, P, or D at position 369. In one embodiment, the selected NA viral segment has I or L at position 148, E or Q at position 151, S, I, T, V or G at position 245 and K, H, R, E, P, or D at position 369. In one embodiment, the residue at position 369 is K, H, R, E, or D.

Further provided is an isolated recombinant nucleic acid, e.g., a vector such as a viral vector, comprising a nucleic acid sequence that encodes an influenza virus NA selected to not encode a threonine at residue 32, to have a deletion of one or more of residues 46-50, to not encode an aspartic acid at position 147, to not encode an asparagine at residue 329, or to not encode a histidine at residue 347, or any combination thereof, wherein the numbering is based on N2. In one embodiment, the isolated recombinant nucleic acid does not encode a threonine or lysine at residue 148, to not encode an aspartic acid at position 151, to not encode an asparagine at residue 245, to not encode a glycine at residue 346, to not encode a threonine at residue 369, or any combination thereof. In one embodiment, the NA has at least 95% amino acid sequence identity to SEQ ID NO:1, SEQ ID NO:3, SEQ ID NO:48, or SEQ ID NO:49. In one embodiment, the NA has less than 100% amino acid sequence identity to SEQ ID NO:2 or SEQ ID NO:3. In one embodiment, the NA is a N2, N3, N7, or N9. In one embodiment, the NA is a N1, N4, N5, N6, N8, N10 or N11. In one embodiment, the residue at position 32 is A, I, G, or L. In one embodiment, the deletion is a deletion of residues 46 to 50. In one embodiment, the residue at position 147 is N or Q. In one embodiment, the residue at position 329 is D or E. In one embodiment, the residue at position 347 is Q, N, S, T, Y, C or W. In one embodiment, the residue at position 148 is I, L, G or A. In one embodiment, the residue at position 148 is I or L. In one embodiment, the residue at position 151 is E, N or Q. In one embodiment, the residue at position 245 is S, T, I, L, A, N, or V. In one embodiment, the residue at position 369 is K, H, R, E, P, or D.

Also provided is a method to prepare influenza virus. The method includes contacting a cell with: a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS DNA linked to a transcription termination sequence, wherein the PB1, PB2, PA, NP, NS, and M DNAs in the vectors for vRNA production are from one or more influenza vaccine virus isolates, wherein the NA DNA in the vector for vRNA production encodes an NA selected to not encode a threonine at residue 32, to not encode an aspartic acid at position 147, to not encode an asparagine at residue 329, to not encode a histidine at residue 347, to not encode a threonine or lysine at residue 148, to not encode an aspartic acid at position 151, to not encode an asparagine at residue 245, to not encode a glycine at residue 346, to not encode a threonine at residue 369, or to have a deletion of one or more of residues 46 to 50, or any combination thereof, wherein the numbering for NA residues is that for N2; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally comprising one or more of: a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, a vector for mRNA production comprising a promoter operably linked to a DNA segment encoding influenza virus NS1, or a vector for mRNA production comprising a promoter operably linked to a DNA segment encoding influenza virus NS2; in an amount effective to yield infectious influenza virus. In one embodiment, the NA has at least 80%, 85%, 90%, 95%, or 99% amino acid sequence identity to, for example, SEQ ID NO:1 SEQ ID NO:2, SEQ ID NO:3, SEQ ID NO:48 or SEQ ID NO:49. In one embodiment, the NA has at least 80%, 85%, 90%, 95%, or 99% amino acid sequence identity to, for example, SEQ ID Nos. 51-59 or 69-70. In one embodiment, the NA has less than 100% amino acid sequence identity to SEQ ID NO:2 or SEQ ID NO:3. In one embodiment, the NA is N2, N3, N7, or N9. In one embodiment, the NA is N1, N4, N5, N6, N8, N10 or N11. In one embodiment, the residue at position 32 is A, I, G, or L. In one embodiment, the deletion is a deletion of residues 46 to 50. In one embodiment, the residue at position 147 is N or Q. In one embodiment, the residue at position 329 is S, D or E. In one embodiment, the residue at position 347 is Q, N, S, T, Y, C or W. In one embodiment, the residue at position 148 is I, L, G or A. In one embodiment, the residue at position 148 is I or L. In one embodiment, the residue at position 151 is E, N or Q. In one embodiment, the residue at position 245 is S, T, I, L, A, N, or V. In one embodiment, the residue at position 329 is S, I, L, A, N, or V. In one embodiment, the residue at position 344 is E, Q, N, H or D. In one embodiment, the residue at position 346 is V, S, T, I, L, A, or V. In one embodiment, the residue at position 347 is G, S, T, I, L, A, or V. In one embodiment, the residue at position 369 is K, H, R, E, P, or D.

In one embodiment, the HA is H1, H3, H5, H7, or H9. In one embodiment, the virus is an influenza A virus. In one embodiment, PA, PB1, PB2, NP, M, and NS viral segments have at least 85%, 85%, 90%, 95%, or 99% nucleic acid sequence identity to SEQ ID Nos. 24 to 29 or 39 to 44 or encode a polypeptide having at least 80%, 85%, 90%, 95%, or 99% amino acid sequence identity to a polypeptide encoded by SEQ ID Nos. 24 to 29 or 39 to 44. In one embodiment, PB2 has I, A, L, or G at residue 147. In one embodiment, HA is H2, H4, H5, H6, H8, or any of H10-H18. In one embodiment, the virus is an influenza B virus.

Further provided is a method of immunizing an avian or a mammal with a composition having an effective amount of the virus described herein. In one embodiment, the composition comprises at least one other different influenza virus. In one embodiment, the mammal is a human. In one embodiment, the composition is administered intranasally or via injection.

Thus, the invention provides a method to select for influenza viruses with enhanced replication in cell culture, e.g., enhanced replication in embryonated eggs. The method includes providing cells suitable for influenza vaccine production; serially culturing one or more influenza virus isolates in eggs; and isolating serially cultured virus with enhanced growth relative to the one or more isolates prior to serial culture. Also provided is a method to identify a NA that stabilizes HA and/or that confers altered growth of a recombinant influenza virus, e.g., in eggs. The method includes introducing one or more substitutions or deletions as described herein into a NA viral segment to yield a mutant NA viral segment; and optionally identifying whether the mutant NA viral segment, when present in a replication competent recombinant influenza virus, results in enhanced replication of the recombinant influenza virus in eggs and optionally inhibits HA mutations, relative to a corresponding replication competent influenza virus without the one or more substitutions and/or deletions in NA.

In one embodiment, the disclosure provides isolated influenza type A virus with a characteristic residue(s) and/or deletion, or a combination thereof, in NA described herein. In one embodiment, the isolated influenza type A virus with a characteristic residue(s) and/or deletion, or a combination thereof, has an NA amino acid sequence with at least 80%, e.g., 90%, 92%, 95%, 97% or 99%, including any integer between 80 and 99, contiguous amino acid sequence identity to a polypeptide encoded by one of SEQ ID NOs:1, 2, 3, or 30-38. In one embodiment, the isolated influenza type A virus of the invention with a characteristic residue(s) and/or deletion, or a combination thereof, has an HA from any one of subtypes 1-18 of HA. In one embodiment the characteristic residue is a conservative substitution, e.g., relative to SEQ ID NO:2 or SEQ ID NO:3. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: threonine-valine-leucine-isoleucine-alanine; phenylalanine-tyrosine; lysine-arginine; alanine-valine; glutamic-aspartic; and asparagine-glutamine.

In one embodiment, a mutation is introduced into a NA viral segment of an influenza virus isolate, e.g., via recombinant DNA techniques including site-specific mutagenesis, or replacing a portion of the NA coding sequence with a portion that includes the characteristic residue(s) or deletion. In one embodiment, a NA viral segment with a characteristic residue and/or deletion described herein is combined with a HA segment, and internal viral segments of an influenza vaccine virus.

The disclosure provides a plurality of influenza virus vectors of the invention, e.g., those useful to prepare reassortant viruses including 6:1:1 reassortants, 6:2 reassortants and 7:1 reassortants. A 6:1:1 reassortant is an influenza virus with 6 internal viral segments from a vaccine virus, a HA viral segment that is from a different (second) viral isolate than the vaccine virus, and a NA viral segment with a characteristic residue(s) and/or deletion, or a combination thereof, as described herein, which is from a different viral source than the HA segment and the vaccine virus; a 6:2 reassortant is an influenza virus with 6 internal viral segments from a vaccine virus, and a NA viral segment having a characteristic residue(s) and/or deletion, or a combination thereof, which segment is from the same source as the HA segment, and a HA viral segment from a different viral isolate than the vaccine virus; and a 7:1 reassortant, in one embodiment, is an influenza virus with 6 internal viral segments and a HA segment from a vaccine virus, and a NA segment that is modified to include the characteristic residue(s) and/or deletion, or a combination thereof, which NA segment is from a different viral source than the vaccine virus.

In one embodiment of the invention, the plurality includes vectors for vRNA production selected from a vector comprising a promoter operably linked to an influenza virus PA DNA linked to a transcription termination sequence, a vector comprising a promoter operably linked to an influenza virus PB1 DNA linked to a transcription termination sequence, a vector comprising a promoter operably linked to an influenza virus PB2 DNA linked to a transcription termination sequence, a vector comprising a promoter operably linked to an influenza virus HA DNA linked to a transcription termination sequence, a vector comprising a promoter operably linked to an influenza virus NP DNA linked to a transcription termination sequence, a vector comprising a promoter operably linked to an influenza virus NA DNA linked to a transcription termination sequence, a vector comprising a promoter operably linked to an influenza virus M DNA linked to a transcription termination sequence, and a vector comprising a operably linked to an influenza virus NS DNA linked to a transcription termination sequence. In one embodiment, the DNAs for vRNA production of PB1, PB2, PA, NP, M, and NS, have sequences from an influenza virus that replicates to high titers in cultured mammalian cells such as MDCK cells, Vero cells or PER.C6® cells or embryonated eggs, and/or from a vaccine virus, e.g., one that does not cause significant disease in humans. The DNA for vRNA production of NA may be from any NA, e.g., any of N1-N11, and the DNA for vRNA production of HA may be from any HA, e.g., H1-H18. In one embodiment, the DNAs for vRNA production may be for an influenza B or C virus. For example, the DNAs for vRNA production include influenza B virus PA, PB1, PB2, NP, NS, and M or influenza B virus PA, PB1, PB2, NP, NS, M, and NA, wherein the vRNA for NA has a NA with a characteristic residue and/or deletion as described herein. The DNAs for vRNA production of NA and HA may be from different strains or isolates (6:1:1 reassortants) or from the same strain or isolate (6:2 reassortants), or the NA or HA may be from the same strain or isolate as that for the internal genes (7:1 reassortant). The plurality also includes vectors for mRNA production selected from a vector encoding influenza virus PA, a vector encoding influenza virus PB1, a vector encoding influenza virus PB2, and a vector encoding influenza virus NP, and optionally one or more vectors encoding NP, NS, M, e.g., M1 and M2, HA or NA. The vectors encoding viral proteins may further include a transcription termination sequence.

Viruses that may provide the internal genes for reassortants within the scope of the invention include viruses that have high titers, e.g., titers of at least about $10^5$ PFU/mL, e.g., at least $10^6$ PFU/mL, $10^7$ PFU/mL or $10^8$ PFU/mL; high titers in embryonated eggs, e.g., titers of at least about $10^7$ $EID_{50}$/mL, e.g., at least $10^8$ $EID_{50}$/mL, $10^9$ $EID_{50}$/mL or $10^{10}$ $EID_{50}$/mL; high titers in MDCK cells, e.g., titers of at least about $10^7$PFU/mL, e.g., at least $10^8$ PFU/mL, or high titers in two of more of those host cells.

Other reassortants with internal genes from other PR8 isolates or vaccine viruses may be employed in recombinant reassortant viruses.

In one embodiment, the DNAs for the internal genes for PB1, PB2, PA, NP, M, and NS encode proteins with substantially the same activity as a corresponding polypeptide encoded by one of SEQ ID NOs:24-29 or 39 to 44. As used herein, "substantially the same activity" includes an activity that is about 0.1%, 1%, 10%, 30%, 50%, 90%, e.g., up to 100% or more, or detectable protein level that is about 80%, 90% or more, the activity or protein level, respectively, of the corresponding full-length polypeptide. In one embodiment, the nucleic acid a sequence encoding a polypeptide which is substantially the same as, e.g., having at least 80%, e.g., 90%, 92%, 95%, 97% or 99%, including any integer between 80 and 99, contiguous amino acid sequence identity to, a polypeptide encoded by one of SEQ ID NOs:24-29 or 39 to 44. In one embodiment, the isolated and/or purified nucleic acid molecule comprises a nucleotide sequence which is substantially the same as, e.g., having at least 50%, e.g., 60%, 70%, 80% or 90%, including any integer between 50 and 100, or more contiguous nucleic acid sequence identity to one of SEQ ID NOs:24-29 and, in one embodiment, also encodes a polypeptide having at least 80%, e.g., 90%, 92%, 95%, 97% or 99%, including any integer between 80 and 99, contiguous amino acid sequence identity to a polypeptide encoded by one of SEQ ID NOs:24-29 or 39 to 44. In one embodiment, the influenza virus polypeptide has one or more, for instance, 2, 5, 10, 15, 20 or more, conservative amino acids substitutions, e.g., conservative substitutions of up to 10% or 20% of the residues, relative to a polypeptide encoded by one of SEQ ID NOs:24-29 or 39 to 44. Conservative amino acid substitutions refer to the interchangeability of residues having similar side chains.

For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: valine-leucine-isoleucine; phenylalanine-tyrosine; lysine-arginine; alanine-valine; glutamic-aspartic; and asparagine-glutamine. In one embodiment, the influenza virus polypeptide has one or more, for instance, 2, 3 or 4, nonconservative amino acid substitutions, relative to a polypeptide encoded by one of SEQ ID NOs:24-29.

In one embodiment, the nucleic acid a sequence encoding a NA polypeptide which is substantially the same as, e.g., having at least 80%, e.g., 90%, 92%, 95%, 97% or 99%, including any integer between 80 and 99, contiguous amino acid sequence identity to, one of SEQ ID Nos. 1-3 or 48-49, or a polypeptide encoded by one of SEQ ID NOs:51-59, or one of Accession Nos. ACP41107.1 (N1) (SEQ ID NO:36) AIK26357.1 (N7) (SEQ ID NO:37), ALH21372.1 (N9) (SEQ ID NO:45), or BAK86313.1 (N2) (SEQ ID NO:50), the sequences of which are incorporated by reference herein. In one embodiment, the isolated and/or purified nucleic acid molecule encodes a polypeptide having at least 80%, e.g., 90%, 92%, 95%, 97% or 99%, including any integer between 80 and 99, contiguous amino acid sequence identity to an one of SEQ ID NOs:1, 3, 30-35, or 48-49, one of Accession Nos. ACP41107.1 (N1) AIK26357.1 (N7), ALH21372.1 (N9), or BAK86313.1 (N2), or to a NA encoded by one of SEQ ID Nos. 51-59, the sequences of which are incorporated by reference herein. In one embodiment, the influenza virus polypeptide has one or more, for instance, 2, 5, 10, 15, 20 or more, conservative amino acids substitutions, e.g., conservative substitutions of up to 10% or 20% of the residues, relative to SEQ ID NOs:1, 3, 30-35, 48-49, or one of Accession Nos. ACP41107.1 (N1) AIK26357.1 (N7), ALH21372.1 (N9), or BAK86313.1 (N2), or a NA encoded by one of SEQ ID Nos. 51-59, the sequences of which are incorporated by reference herein. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: valine-leucine-isoleucine; phenylalanine-tyrosine; lysine-arginine; alanine-valine; glutamic-aspartic; and asparagine-glutamine. In one embodiment, the influenza virus polypeptide has one or more, for instance, 2, 3 or 4, nonconservative amino acid substitutions, relative to a polypeptide having one of SEQ ID NOs:1, 3, 30-35, 48-49, or one of Accession Nos. ACP41107.1 (N1) AIK26357.1 (N7), ALH21372.1 (N9), or BAK86313.1 (N2), or a NA encoded by one of SEQ ID Nos. 51-59, the sequences of which are incorporated by reference herein.

The invention thus includes the use of isolated and purified vectors or plasmids, which express or encode influenza virus proteins, or express or encode influenza vRNA, both native and recombinant vRNA. The vectors comprise influenza cDNA, e.g., influenza A (e.g., any influenza A gene including any of the 18 HA or 11 NA subtypes), B or C DNA (see Fields Virology (Fields et al. (eds.), Lippincott, Williams and Wickens (2013), which is specifically incorporated by reference herein). Any suitable promoter or transcription termination sequence may be employed to express a protein or peptide, e.g., a viral protein or peptide, a protein or peptide of a nonviral pathogen, or a therapeutic protein or peptide.

A composition or plurality of vectors of the invention may also comprise a heterologous gene or open reading frame of interest, e.g., a foreign gene encoding an immunogenic peptide or protein useful as a vaccine or in gene replacement, for instance may encode an epitope useful in a cancer therapy or vaccine, or a peptide or polypeptide useful in gene therapy. When preparing virus, the vector or plasmid comprising the gene or cDNA of interest may substitute for a vector or plasmid for an influenza viral gene or may be in addition to vectors or plasmids for all influenza viral genes. Thus, another embodiment of the invention comprises a composition or plurality of vectors as described above in which one of the vectors is replaced with, or further comprises, 5' influenza virus sequences optionally including 5' influenza virus coding sequences or a portion thereof, linked to a desired nucleic acid sequence, e.g., a desired cDNA, linked to 3' influenza virus sequences optionally including 3' influenza virus coding sequences or a portion thereof. In one embodiment, the desired nucleic acid sequence such as a cDNA is in an antisense (antigenomic) orientation. The introduction of such a vector in conjunction with the other vectors described above to a host cell permissive for influenza virus replication results in recombinant virus comprising vRNA corresponding to the heterologous sequences of the vector.

The promoter in a vector for vRNA production may be a RNA polymerase I promoter, a RNA polymerase II promoter, a RNA polymerase III promoter, a T7 promoter, or a T3 promoter, and optionally the vector comprises a transcription termination sequence such as a RNA polymerase I transcription termination sequence, a RNA polymerase II transcription termination sequence, a RNA polymerase III transcription termination sequence, or a ribozyme. Ribozymes within the scope of the invention include, but are not limited to, tetrahymena ribozymes, RNase P, hammerhead ribozymes, hairpin ribozymes, hepatitis ribozyme, as well as synthetic ribozymes. In one embodiment, the RNA polymerase I promoter is a human RNA polymerase I promoter.

The promoter or transcription termination sequence in a vRNA or virus protein expression vector may be the same or different relative to the promoter or any other vector. In one embodiment, the vector or plasmid which expresses influenza vRNA comprises a promoter suitable for expression in at least one particular host cell, e.g., avian or mammalian host cells such as canine, feline, equine, bovine, ovine, or primate cells including human cells, or for expression in more than one host.

In one embodiment, at least one vector for vRNA comprises a RNA polymerase II promoter linked to a ribozyme sequence linked to viral coding sequences linked to another ribozyme sequences, optionally linked to a RNA polymerase II transcription termination sequence. In one embodiment, at least 2, e.g., 3, 4, 5, 6, 7 or 8, vectors for vRNA production comprise a RNA polymerase II promoter, a first ribozyme sequence, which is 5' to a sequence corresponding to viral sequences including viral coding sequences, which is 5' to a second ribozyme sequence, which is 5' to a transcription termination sequence. Each RNA polymerase II promoter in each vRNA vector may be the same or different as the RNA polymerase II promoter in any other vRNA vector. Similarly, each ribozyme sequence in each vRNA vector may be the same or different as the ribozyme sequences in any other vRNA vector. In one embodiment, the ribozyme sequences in a single vector are not the same.

In one embodiment, at least one vector comprises sequences corresponding to those encoding PB1, PB2, PA, NP, M, or NS, or a portion thereof, having substantially the same activity as a corresponding polypeptide encoded by one of SEQ ID NOs:24-29 or 39 to 44, e.g., a sequence encoding a polypeptide with at least 80%, e.g., 85%, 90%, 92%, 95%, 98%, 99% or 100%, including any integer between 80 and 100, amino acid identity to a polypeptide encoded by one of SEQ ID NOs:24-29. Optionally, two vectors may be employed in place of the vector comprising a promoter operably linked to an influenza virus M cDNA linked to a transcription termination sequence, e.g., a vector comprising a promoter operably linked to an influenza virus M1 cDNA linked to a transcription termination sequence and a vector comprising a promoter operably linked to an influenza virus M2 cDNA linked to a transcription termination sequence.

A plurality of the vectors of the invention may be physically linked or each vector may be present on an individual plasmid or other, e.g., linear, nucleic acid delivery vehicle. In one embodiment, each vRNA production vector is on a separate plasmid. In one embodiment, each mRNA production vector is on a separate plasmid.

The invention also provides a method to prepare influenza virus. The method comprises contacting a cell with a plurality of the vectors of the invention, e.g., sequentially or simultaneously, in an amount effective to yield infectious influenza virus. The invention also includes isolating virus from a cell contacted with the plurality of vectors. Thus, the invention further provides isolated virus, as well as a host cell contacted with the plurality of vectors or virus of the invention. In another embodiment, the invention includes contacting the cell with one or more vectors, either vRNA or protein production vectors, prior to other vectors, either vRNA or protein production vectors. In one embodiment, the promoter for vRNA vectors employed in the method is a RNA polymerase I promoter, a RNA polymerase II promoter, a RNA polymerase III promoter, a T3 promoter or a T7 promoter. In one embodiment, the RNA polymerase I promoter is a human RNA polymerase I promoter. In one embodiment, each vRNA vector employed in the method is on a separate plasmid. In one embodiment, the vRNA vectors employed in the method are on one plasmid or on two or three different plasmids. In one embodiment, each mRNA vector employed in the method is on a separate plasmid. In one embodiment, the mRNA vectors for PA, PB1, PB2 and NP employed in the method are on one plasmid or on two or three different plasmids.

The methods of producing virus described herein, which do not require helper virus infection, are useful in viral mutagenesis studies, and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, ornithine transcarbamylase deficiency and central nervous system tumors). Thus, a virus for use in medical therapy (e.g., for a vaccine or gene therapy) is provided.

The invention also provides isolated viral polypeptides, and methods of preparing and using recombinant virus of the invention. The methods include administering to a host organism, e.g., a mammal, an effective amount of the influenza virus of the invention, e.g., an inactivated virus preparation, optionally in combination with an adjuvant and/or a carrier, e.g., in an amount effective to prevent or ameliorate infection of an animal such as a mammal by that virus or an antigenically closely related virus. In one embodiment, the virus is administered intramuscularly while in another embodiment, the virus is administered intranasally. In some dosing protocols, all doses may be administered intramuscularly or intranasally, while in others a combination of intramuscular and intranasal administration is employed. The vaccine may further contain other isolates of influenza virus including recombinant influenza virus, other pathogen(s), additional biological agents or microbial components, e.g., to form a multivalent vaccine. In one embodiment, intranasal vaccination, for instance containing with inactivated influenza virus, and a mucosal adjuvant may induce virus-specific IgA and neutralizing antibody in the nasopharynx as well as serum IgG.

The influenza virus of the invention may employed with other anti-virals, e.g., amantadine, rimantadine, and/or neuraminidase inhibitors, e.g., may be administered separately in conjunction with those anti-virals, for instance, administered before, during and/or after.

Thus, the modified neuraminidase comprises at least one, or at least two, or at least three modifications, wherein the modification comprise one or more amino acids within positions 29-35, one or more amino acids within positions 44-52, one or more amino acids within positions 144-154, one or more amino acid positions within 240-250, one or more amino acids within positions 326-333, one or more amino acid positions within 344-350, one or more amino acid positions within 365-375, or combinations thereof, wherein the numbering is that for N2. In one embodiment, the NA comprises a deletion of at least one proline, asparagine, glutamine, valine, or a combination of a proline, one or more asparagine(s), a glutamine, and a valine within positions 44-52; a substitution (replacement) of a threonine within positions 29-35; a substitution (replacement) of an threonine or an aspartic acid within positions 145-155; a substitution (replacement) of an asparagine within positions 240 to 250 or 326-333; a substitution (replacement) of a histidine within positions 345-350; or a combination thereof.

BRIEF DESCRIPTION OF FIGURES

FIGS. 1A-1L. Nucleotide sequences for the viral segments of A/Yokohama/2017/2003 (SEQ ID Nos. 4-11), and amino acid sequence of the NA of A/Yokohama/2017/2003 (SEQ ID NO:3).

FIG. 2. Amino acid sequence for the NA of A/Saitama/103/2014 (SEQ ID NO:2)

FIGS. 3A-3G. Nucleotide sequence of NA viral segment (SEQ ID NO:12) and amino acid sequences for NA of mutant of A/Yokohama/2017/2003 (SEQ ID NO:1), and nucleotide sequence of other viral segments of the mutant (SEQ ID Nos.12-21)

FIG. 8. Amino acid sequence comparison of Yokohama/2017/2003 NA wild-type (SEQ ID NO:3) and Y2017-M3L4 (SEQ ID NO:1).

FIGS. 9A-9B. Exemplary NA sequences for N3, N4, N6, N7, N8, and N9 (SEQ ID Nos. 30-35).

FIGS. 10A-10F. Exemplary sequences for the internal viral segments for a master vaccine strain (SEQ ID Nos. 39-44).

FIGS. 11A-11B. Exemplary NA sequences (SEQ ID Nos. 71-74corresponding to a respective N1, N7, N9 and N2, respectively).

FIG. 13. Titers of HK4801HA, Y2017-M3L4NA and HY-PR8 (PB2 C4U, 1504V; PB1 C4U, M40L/G180W; PA C4U, R401K; NP-I116L; NS1-A30P/R118K) and analyses for HA mutations in infected eggs over time.

FIG. 14 shows data for viruses passaged in eggs that had certain NA mutants but did not result in substitutions in HA.

FIG. 19 summarizes virus titers (HK4801HA, Y2017-M3L4NA and HY-PR8 (PB2 C4U, 1504V; PB1 C4U, M40L/G180W; PA C4U, R401K; NP 1116L; NS A30P/R118K) and HA status over time.

FIG. 20 summarizes virus titers and HA status for viruses with different NAs.

FIG. 21 provides inoculation and harvested virus titers in allantoic passages (HA-K189E/N158K/A212T mutant virus).

FIG. 27. Mutations observed in NA mutant viruses (HY-PR8 backbone) in FIG. 26 during egg passages.

FIG. 29. Mutations observed in NA mutant viruses (HY-PR8 backbone) in FIG. 28 during egg passages.

FIG. 32. HA-H435L locates to the stem region of the HA trimer. previous study reported that HA-H435L did not affect antigenicity (Kuwahara et al., Jpn. J. Infect. Dis., 2018).

FIG. 35. Yokohama48NA (T148I, D151E, N245S, H347G, and T369K) enhanced the growth of viruses possessing the HA of H3N2 viruses of the 2017-18 and 2018-19 seasons (SEQ ID Nos. 57-58).

FIG. 38. Neutralization by human monoclonal IgG clone F045-092 against viruses possessing Aichi/2/68HA and wild-type or mutant NA from 2017-18 season H3N2 viruses.

FIGS. 40A-40N. Exemplary NA sequences (SEQ ID Nos. 55-59 and 71-74) for modification and modified NA sequences (SEQ ID Nos 69-70); A/Hong Kong/4801/2014NA (T148K, D151E, H347G, T369K and A/Alaska/232/2015NA (T148K, D151E, N245S, G346V, T369K, respectively).

FIGS. 41A-41N. Exemplary HA sequences (SEQ ID Nos. 60-68) from strains that were stabilized.

FIG. 45. Mutations observed in the HA and NA proteins of HY-PR8 backbone viruses possessing Yokohama147NA (6M) during 10 passages in eggs.

DETAILED DESCRIPTION

Definitions

Figure 4:
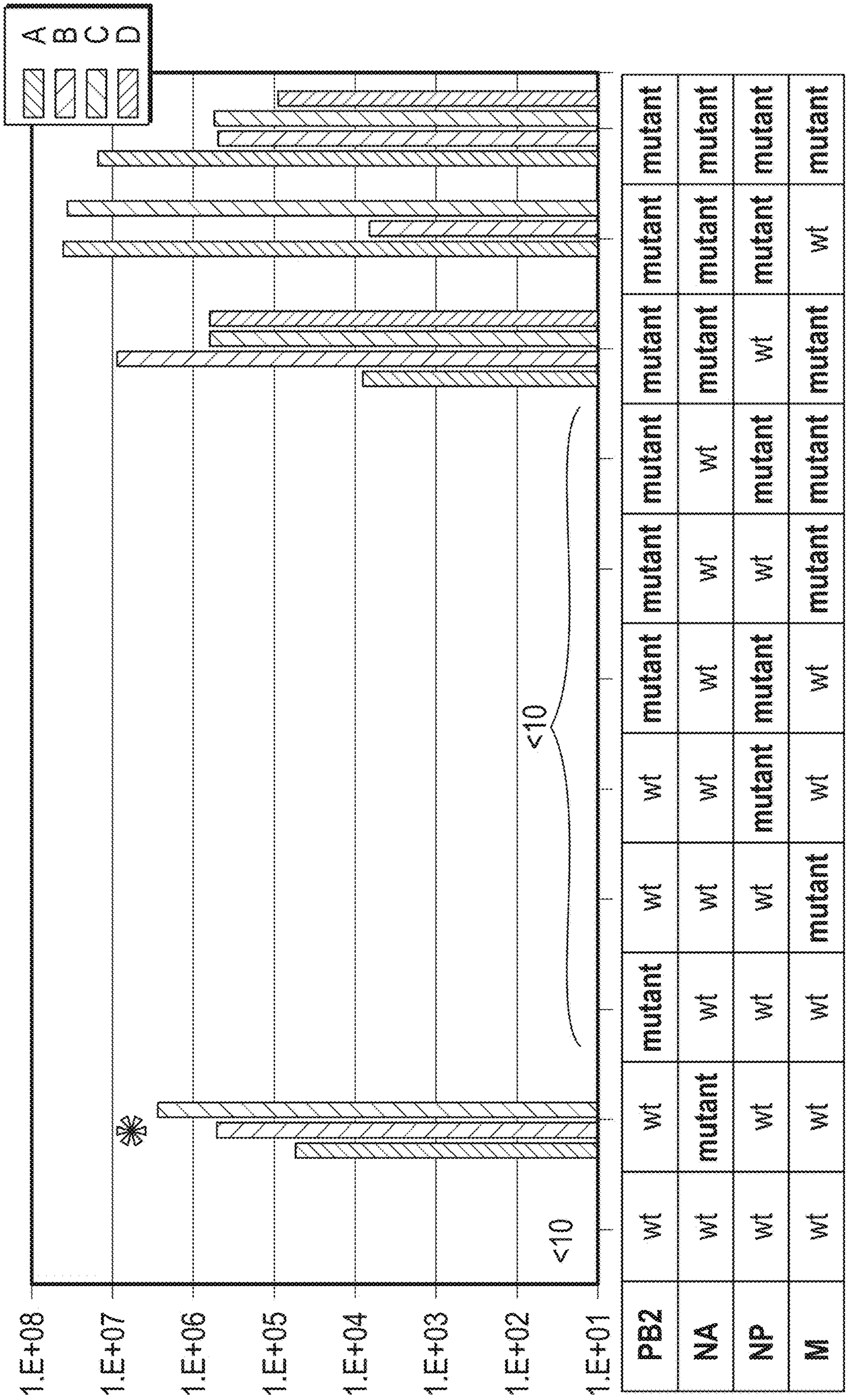
FIG. 4. Graph showing titers in eggs of various reassortants with the PB2, M, NA and NP segments of mutant and wild-type A/Yokohama/2017/2003. Virus inoculation: $2\times10^3$ pfu/egg into allantoic fluid, 72 h incubation at 37° C.

As used herein, the term "isolated" refers to in vitro preparation and/or isolation of a nucleic acid molecule, e.g., vector or plasmid, peptide or polypeptide (protein), or virus of the invention, so that it is not associated with in vivo substances, or is substantially purified from in vitro substances. An isolated virus preparation is generally obtained by in vitro culture and propagation, and/or via passage in eggs, and is substantially free from other infectious agents.

As used herein, "substantially purified" means the object species is the predominant species, e.g., on a molar basis it is more abundant than any other individual species in a composition, and preferably is at least about 80% of the species present, and optionally 90% or greater, e.g., 95%, 98%, 99% or more, of the species present in the composition.

As used herein, "substantially free" means below the level of detection for a particular infectious agent using standard detection methods for that agent.

A "recombinant" virus is one which has been manipulated in vitro, e.g., using recombinant DNA techniques, to introduce changes to the viral genome. Reassortant viruses can be prepared by recombinant or nonrecombinant techniques.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the disclosure, by the methodology of genetic engineering.

As used herein, a "heterologous" influenza virus gene or viral segment is from an influenza virus source that is different than a majority of the other influenza viral genes or viral segments in a recombinant, e.g., reassortant, influenza virus.

The terms "isolated polypeptide", "isolated peptide" or "isolated protein" include a polypeptide, peptide or protein encoded by cDNA or recombinant RNA including one of synthetic origin, or some combination thereof.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Alignments using these programs can be performed using the default parameters. Software for performing BLAST analyses is publicly available through the National Center for Biotechnology Information (http://www.ncbi.nlm.nih.gov/). The algorithm may involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm may also perform a statistical analysis of the similarity between two sequences. One measure of similarity provided by the BLAST algorithm may be the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

The BLASTN program (for nucleotide sequences) may use as defaults a wordlength (W) of 11, an expectation (E) of 10, a cutoff of 100, M=5, N=−4, and a comparison of both strands. For amino acid sequences, the BLASTP program may use as defaults a wordlength (W) of 3, an expectation (E) of 10, and the BLOSUM62 scoring matrix. See http://www.ncbi.nlm.nih.gov. Alignment may also be performed manually by inspection.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Influenza Virus Structure and Propagation

Influenza A viruses possess a genome of eight single-stranded negative-sense viral RNAs (vRNAs) that encode at least ten proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cRNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, influenza B virus does not have a M2 protein with ion channel activity but has BM2 and has a viral segment with both NA and NB sequences. Influenza C virus has only seven viral segments.

Cells that can be Used to Produce Virus

Any cell, e.g., any avian or mammalian cell, such as avian eggs, a human, e.g., 293T or PER.C6® cells, or canine, bovine, equine, feline, swine, ovine, rodent, for instance mink, e.g., MvLu1 cells, or hamster, e.g., CHO cells, or non-human primate, e.g., Vero cells, including mutant cells, which supports efficient replication of influenza virus can be employed to isolate and/or propagate influenza viruses. Isolated viruses can be used to prepare a reassortant virus. In one embodiment, host cells for vaccine production are continuous mammalian or avian cell lines or cell strains. A complete characterization of the cells to be used, may be conducted so that appropriate tests for purity of the final product can be included. Data that can be used for the characterization of a cell includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. In one embodiment, the passage level, or population doubling, of the host cell used is as low as possible.

In one embodiment, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity may be tested in cells that are at the same passage level as those used for vaccine production. The virus may be purified by a process that has been shown to give consistent results, before vaccine production (see, e.g., World Health Organization, 1982).

Virus produced by the host cell may be highly purified prior to vaccine or gene therapy formulation. Generally, the purification procedures result in extensive removal of cellular DNA and other cellular components, and adventitious agents. Procedures that extensively degrade or denature DNA may also be used.

Influenza Vaccines

A vaccine includes an isolated recombinant influenza virus of the invention, and optionally one or more other isolated viruses including other isolated influenza viruses, one or more immunogenic proteins or glycoproteins of one or more isolated influenza viruses or one or more other pathogens, e.g., an immunogenic protein from one or more bacteria, non-influenza viruses, yeast or fungi, or isolated nucleic acid encoding one or more viral proteins (e.g., DNA vaccines) including one or more immunogenic proteins of the isolated influenza virus of the invention. In one embodiment, the influenza viruses of the invention may be vaccine vectors for influenza virus or other pathogens.

A complete virion vaccine may be concentrated by ultrafiltration and then purified by zonal centrifugation or by chromatography. Viruses other than the virus of the invention, such as those included in a multivalent vaccine, may be inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976); or a nonionic detergent such as that commercialized under the name TRITON X100. The hemagglutinin may also be isolated after treatment of the virions with a protease such as bromelin, and then purified. The subunit vaccine may be combined with an attenuated virus of the invention in a multivalent vaccine.

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done. The split vaccine may be combined with an attenuated virus of the invention in a multivalent vaccine.

Inactivated Vaccines. Inactivated influenza virus vaccines are provided by inactivating replicated virus using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines.

Live Attenuated Virus Vaccines. Live, attenuated influenza virus vaccines, such as those including a recombinant virus of the invention can be used for preventing or treating influenza virus infection. Attenuation may be achieved in a single step by transfer of attenuated genes from an attenuated donor virus to a replicated isolate or reassorted virus according to known methods. Since resistance to influenza A virus is mediated primarily by the development of an immune response to the HA and/or NA glycoproteins, the genes coding for these surface antigens come from the reassorted viruses or clinical isolates. The attenuated genes are derived from an attenuated parent. In this approach, genes that confer attenuation generally do not code for the HA and NA glycoproteins.

Viruses (donor influenza viruses) are available that are capable of reproducibly attenuating influenza viruses, e.g., a cold adapted (ca) donor virus can be used for attenuated vaccine production. Live, attenuated reassortant virus vaccines can be generated by mating the ca donor virus with a virulent replicated virus. Reassortant progeny are then selected at 25° C. (restrictive for replication of virulent virus), in the presence of an appropriate antiserum, which inhibits replication of the viruses bearing the surface antigens of the attenuated ca donor virus. Useful reassortants are: (a) infectious, (b) attenuated for seronegative non-adult mammals and immunologically primed adult mammals, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible mammals both adults and non-adult.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene. Thus, new donor viruses can also be generated bearing attenuating mutations introduced by site-directed mutagenesis, and such new donor viruses can be used in the production of live attenuated reassortants vaccine candidates in a manner analogous to that described above for the ca donor virus. Similarly, other known and suitable attenuated donor strains can be reassorted with influenza virus to obtain attenuated vaccines suitable for use in the vaccination of mammals.

In one embodiment, such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking pathogenicity to the degree that the vaccine causes minimal chance of inducing a serious disease condition in the vaccinated mammal.

The viruses in a multivalent vaccine can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and nucleic acid screening (such as probe hybridization or PCR) to confirm that donor genes encoding the antigenic determinants (e.g., HA or NA genes) are not present in the attenuated viruses.

Pharmaceutical Compositions

Pharmaceutical compositions of the present invention, suitable for inoculation, e.g., nasal, parenteral or oral administration, comprise one or more influenza virus isolates, e.g., one or more attenuated or inactivated influenza viruses, a subunit thereof, isolated protein(s) thereof, and/or isolated nucleic acid encoding one or more proteins thereof, optionally further comprising sterile aqueous or non-aqueous solutions, suspensions, and emulsions. The compositions can further comprise auxiliary agents or excipients, as known in the art. The composition of the invention is generally presented in the form of individual doses (unit doses).

Conventional vaccines generally contain about 0.1 to 200 μg, e.g., 30 to 100 μg, 0.1 to 2 μg, 0.5 to 5 μg, 1 to 10 μg, 10 μg to 20 μg, 15 μg to 30 μg, or 10 to 30 μg, of HA from each of the strains entering into their composition. The vaccine forming the main constituent of the vaccine composition of the invention may comprise a single influenza virus, or a combination of influenza viruses, for example, at least two or three influenza viruses, including one or more reassortant(s).

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized.

Heterogeneity in a vaccine may be provided by mixing replicated influenza viruses for at least two influenza virus strains, such as 2-20 strains or any range or value therein. Vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-γ, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines are provided before any symptom or clinical sign of a pathogen infection becomes manifest. The prophylactic administration of the composition serves to prevent or attenuate any subsequent infection. When provided prophylactically, the gene therapy compositions of the invention, are provided before any symptom or clinical sign of a disease becomes manifest. The prophylactic administration of the composition serves to prevent or attenuate one or more symptoms or clinical signs associated with the disease.

When provided therapeutically, a viral vaccine is provided upon the detection of a symptom or clinical sign of actual infection. The therapeutic administration of the compound(s) serves to attenuate any actual infection. When provided therapeutically, a gene therapy composition is provided upon the detection of a symptom or clinical sign of the disease. The therapeutic administration of the compound(s) serves to attenuate a symptom or clinical sign of that disease.

Thus, a vaccine composition of the present invention may be provided either before the onset of infection (so as to prevent or attenuate an anticipated infection) or after the initiation of an actual infection. Similarly, for gene therapy, the composition may be provided before any symptom or clinical sign of a disorder or disease is manifested or after one or more symptoms are detected.

A composition is said to be "pharmacologically acceptable" if its administration can be tolerated by a recipient mammal. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of mammals. Protection may be limited to mitigating the severity or rapidity of onset of symptoms or clinical signs of the influenza virus infection.

Pharmaceutical Administration

A composition of the present invention may confer resistance to one or more pathogens, e.g., one or more influenza virus strains, by either passive immunization or active immunization. In active immunization, an attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a clinical sign or condition of the disease, or in the total or partial immunity of the individual to the disease. As used herein, a gene therapy composition is said to prevent or attenuate a disease if its administration results either in the total or partial attenuation (i.e., suppression) of a clinical sign or condition of the disease, or in the total or partial immunity of the individual to the disease.

A composition having at least one influenza virus of the present invention, including one which is attenuated and one or more other isolated viruses, one or more isolated viral proteins thereof, one or more isolated nucleic acid molecules encoding one or more viral proteins thereof, or a combination thereof, may be administered by any means that achieve the intended purposes.

For example, administration of such a composition may be by various parenteral routes such as subcutaneous, intravenous, intradermal, intramuscular, intraperitoneal, intranasal, oral or transdermal routes. Parenteral administration can be accomplished by bolus injection or by gradual perfusion over time.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

The dosage of a live, attenuated or killed virus vaccine for an animal such as a mammalian adult organism may be from about $10^2$-$10^{20}$, e.g., $10^3$-$10^{12}$, $10^2$-$10^{10}$, $10^5$-$10^{11}$$10^6$-$10^{15}$, $10^2$-$10^{10}$, or $10^{15}$-$10^{20}$ plaque forming units (PFU)/kg, or any range or value therein. The dose of one viral isolate vaccine, e.g., in an inactivated vaccine, may range from about 0.1 to 1000, e.g., 0.1 to 10 μg, 1 to 20 μg, 30 to 100 μg, 10 to 50 μg, 50 to 200 μg, or 150 to 300 μg, of HA protein. However, the dosage should be a safe and effective amount as determined by conventional methods, using existing vaccines as a starting point.

The dosage of immunoreactive HA in each dose of replicated virus vaccine may be standardized to contain a suitable amount, e.g., 0.1 μg to 1 μg, 0.5 μg to 5 μg, 1 μg to 10 μg, 10 μg to 20 μg, 15 μg to 30 μg, or 30 μg to 100 μg or any range or value therein, or the amount recommended by government agencies or recognized professional organizations. The quantity of NA can also be standardized, however, this glycoprotein may be labile during purification and storage.

The dosage of immunoreactive HA in each dose of replicated virus vaccine can be standardized to contain a suitable amount, e.g., 1-50 μg or any range or value therein, or the amount recommended by the U.S. Public Health Service (PHS), which is usually 15 μg, per component for older children >3 years of age, and 7.5 μg per component for children <3 years of age. The quantity of NA can also be standardized, however, this glycoprotein can be labile during the processor purification and storage (Kendal et al., 1980; Kerr et al., 1975). Each 0.5-ml dose of vaccine may contain approximately 0.1 to 0.5 billion viral particles, 0.5 to 2 billion viral particles, 1 to 50 billion virus particles, 1 to 10 billion viral particles, 20 to 40 billion viral particles, 1 to 5 billion viral particles, or 40 to 80 billion viral particles.

Exemplary Viruses

Useful modifications of influenza neuraminidase (NA) proteins are described herein that stabilize hemagglutinin (HA) protein during egg-passages of influenza viruses that express those modified neuraminidase proteins. Modified nucleic acids are also described that encode such modified neuraminidase proteins. The modifications can include deletions, substitutions and combinations thereof within the neuraminidase protein and nucleic acid sequences. Viruses that express such modified neuraminidase proteins exhibit significantly reduced acquisition of antigenicity-compromising mutations in hemagglutinin (HA) during growth of influenza in eggs.

For example, in some cases the modified neuraminidase can have at least one, or at least two, or at least three modifications. Amino acid positions within influenza neuraminidase proteins that can be modified include, for example, one or more amino acids within positions 29-35, one or more amino acids within positions 44-52, one or more amino acids within positions 144-154, one or more amino acid positions within 240-250, one or more amino acids within positions 326-333, one or more amino acid positions within 344-350, one or more amino acid positions within 365-375, and combinations thereof, based on N2 numbering. For example, the amino acid(s) can be any amino acid within these positions such as any of the amino acids listed in the table below.

| Original Residue | Exemplary Substitutions | Alternative Substitutions |
|---|---|---|
| Ala (A) | val; leu; ile | Val |
| Arg (R) | lys; gln; asn | Lys |
| Asn (N) | gln; his; lys; arg | Gln |
| Asp (D) | Glu, Asn | Glu, Asn |
| Cys (C) | Ser | Ser |
| Gln (Q) | Asn | Asn |
| Glu (E) | Asp | Asp |
| Gly (G) | Pro | Pro |
| His (H) | asn; gln; lys; arg; gln; | Arg; Gln |
| Ile (I) | leu; val; met; ala; phe norleucine | Leu |
| Leu (L) | norleucine; ile; val; met; ala; phe | Ile |
| Lys (K) | arg; gln; asn | Arg |
| Met (M) | leu; phe; Ile | Leu |
| Phe (F) | leu; val; ile; ala | Leu |
| Pro (P) | Gly | Gly |
| Ser (S) | Thr | Thr |
| Thr (T) | Ser, Ala | Ser, Als |
| Trp (W) | Tyr | Tyr |
| Tyr (Y) | trp; phe; thr; ser | Phe |
| Val (V) | ile; leu; met; phe; ala; norleucine | Leu |

In some cases, a selected amino acid within positions 29-35, positions 44-52, positions 144-154, positions 326-333, positions within 344-350, positions within 365-375, can have a conservative substitution. However, in other cases, the selected amino acid within positions 29-35, positions 44-52, positions 144-150, positions 326-333, positions within 344-350, positions within 365-375, can have a non-conservative substitution.

For example, a modified neuraminidase can have a deletion of at least one proline, asparagine, glutamine, valine, or a combination of a proline, one or more asparagine(s), a glutamine, and a valine within positions 44-52 of the modified neuraminidase. A modified neuraminidase can have a substitution (replacement) of a threonine within positions 29-35, where the replacement is any amino acid. A modified neuraminidase can have a substitution (replacement) of a threonine or an aspartic acid within positions 145-154 or 365 to 375, where the replacement is any amino acid. A modified neuraminidase can have a substitution (replacement) of an asparagine within positions 326-333, where the replacement is any amino acid. A modified neuraminidase can have a substitution (replacement) of a histidine within positions 345-350, where the replacement is any amino acid. Exemplary substitutions (replacements) for various types of amino acids are provided in the table above.

One example of an influenza A virus (A/Yokohama/2013/2003 (H3N2)) neuraminidase protein sequence is provided below (SEQ ID NO: 75)

```
1    MNPNQKIITI GSVSLTISTI CFFMQIAILI TTVTLHFKQY

41   EFNSPPNNQV MLCEPTIIER NITEIVYLTN TTIEKEICPK

81   LAEYRNWSKP QCNITGFAPF SKDNSIRLSA GGDIWVTREP

121  YVSCDPDKCY QFALGQGTTL NNVHSNDIVH DRTPYRTLLM
```

```
161    NELGVPFHLG TKQVCIAWSS SSCHDGKAWL HVCVTGDDEN
201    ATASFIYNGR LADSIVSWSK KILRTQESEC VCINGTCTVV
241    MTDGSASGKA DTKILFIEEG KIVHTSTLSG SAQHVEECSC
281    YPRYPGVRCV CRDNWKGSNR PIVDINIKDY SIVSSYVCSG
321    LVGDTPRKND SSSSSHCLDP NNEEGGHGVK GWAFDDGNDV
361    WMGRTISEKL RSGYETEKVI EGWSNPNSKL QINRQVIVDR
401    GNRSGYSGIF SVEGKSCINR CFYVELIRGR KQETEVLWTS
441    NSIVVFCGTS GTYGTGSWPD GADINLMPI
```

Amino acids that can be modified to improve the stability of co-expressed HA are highlighted in bold and with underlining within the sequence shown above. A nucleic acid that encodes such an influenza A virus (A/Yokohama/2013/2003 (H3N2)) neuraminidase protein sequence is shown below

```
                                          (SEQ ID NO: 76)
   1   AGCAAAAGCA GGAGTAAAGA TGAATCCAAA TCAAAAGATA
  41   ATAACGATTG GCTCTGTTTC CCTCACCATT TCCACAATAT
  81   GCTTCTTCAT GCAAATTGCC ATCCTGATAA CTACTGTAAC
 121   ATTGCATTTC AAGCAATATG AATTCAACTC CCCCCCAAAC
 161   AACCAAGTGA TGCTGTGTGA ACCAACAATA ATAGAAAGAA
 201   ACATAACAGA GATAGTGTAT CTGACCAACA CCACCATAGA
 241   GAAGGAAATA TGCCCCAAAC TAGCAGAATA CAGAAATTGG
 281   TCAAAGCCGC AATGTAACAT TACAGGATTT GCACCTTTTT
 321   CTAAGGACAA TTCGATTCGG CTTTCCGCTG GTGGGGACAT
 361   CTGGGTGACA AGAGAACCTT ATGTGTCATG CGATCCTGAC
 401   AAGTGTTATC AATTTGCCCT TGGACAGGGA ACAACACTAA
 441   ACAACGTGCA TTCAAATGAC ATAGTACATG ATAGGACCCC
 481   TTATCGGACC CTATTGATGA ATGAGTTGGG TGTTCCATTT
 521   CATCTGGGGA CCAAGCAAGT GTGCATAGCA TGGTCCAGCT
 561   CAAGTTGTCA CGATGGAAAA GCATGGCTGC ATGTTTGTGT
 601   AACGGGGGAT GATGAAAATG CAACTGCTAG CTTCATTTAC
 641   AATGGGAGGC TTGCAGATAG TATTGTTTCA TGGTCCAAAA
 681   AAATCCTCAG GACCCAGGAG TCAGAATGCG TTTGTATCAA
 721   TGGAACTTGT ACAGTAGTAA TGACTGATGG GAGTGCTTCA
 761   GGAAAAGCTG ATACTAAAAT ACTATTCATT GAGGAGGGGA
 801   AAATTGTTCA TACTAGCACA TTATCAGGAA GTGCTCAGCA
 841   TGTCGAGGAG TGCTCCTGTT ATCCTCGATA TCCTGGTGTC
 881   AGATGTGTCT GCAGAGACAA CTGGAAAGGC TCCAATAGGC
 921   CCATCGTAGA TATAAACATA AAGGATTATA GCATTGTTTC
 961   CAGTTATGTG TGCTCAGGAC TTGTTGGAGA CACACCCAGA
1001   AAAAACGACA GCTCCAGCAG TAGCCATTGC TTGGATCCAA
1041   ACAATGAGGA AGGTGGTCAT GGAGTGAAAG GCTGGGCCTT
1081   TGATGATGGA AATGACGTGT GGATGGGAAG AACGATCAGC
1121   GAGAAGTTAC GCTCAGGATA TGAAACCTTC AAAGTCATTG
1161   AAGGCTGGTC CAACCCTAAC TCCAAATTGC AGATAAATAG
1201   GCAAGTCATA GTTGACAGAG GTAACAGGTC CGGTTATTCT
1241   GGTATTTTCT CTGTTGAAGG CAAAAGCTGC ATCAATCGGT
1281   GCTTTTATGT GGAGTTGATA AGGGGAAGAA AACAGGAAAC
1321   TGAAGTCTTG TGGACCTCAA ACAGTATTGT TGTGTTTTGT
1361   GGCACCTCAG GTACATATGG AACAGGCTCA TGGCCTGATG
1401   GGGCGGACAT CAATCTCATG CCTATATAAG CTTTCGCAAT
1441   TTTAGAAAAA AACTCCTTGT TTCTACT
```

Modifications at the specified positions in neuraminidase can confer enhanced growth of the virus.

Another example of an influenza A virus (A/Yokohama/47/2002 (H1N2))) neuraminidase sequence 55 is shown below, with positions of modifications highlighted in bold and with underlining.

```
                                                (SEQ ID NO: 77)
          10         20         30         40
    MNPNQKIITI GSVSLTIATI CFLMQIAILV TTVTLHFKQY
          50         60         70         80
    ECNSPPNNQV MLCEPTIIER NITEIVYLTN TTIEKEICPK
          90        100        110        120
    LAEYRNWSKP QCNITGFAPF SKDNSIRLSA GGDIWVTREP
         130        140        150        160
    YVSCDPDKCY QFALGQGTTL NNVHSNDTVH DRTPYRTLLM
         170        180        190        200
    NELGVPFHLG TKQVCIAWSS SSCHDGKAWL HVCVTGDDGN
         210        220        230        240
    ATASFIYNGR LVDSIGSWSK KILRTQESEC VCINGTCTVV
         250        260        270        280
    MTDGSASGKA DTKILFIEEG KIVHTSLLSG SAQHVEECSC
         290        300        310        320
    YPRYPGVRCV CRDNWKGSNR PIVDINVKDY SIVSSYVCSG
         330        340        350        360
    LVGDTPRKND SSSSSHCLDP NNEEGGHGVK GWAFDDGNDV
         370        280        390        400
    WMGRTISEKL RSGYETFKVI EGWSKPNSKL QINRQVIVDR
         410        420        430        440
    GNRSGYSGIF SVEGKSCINR CFYVELIRGR NQETEVLWTS
         450        460
    NSIVVFCGTS GTYGTGSWPD GADINLMPI
```

Amino acids that can be modified to improve the stability of co-expressed HA are highlighted in bold and with underlining within the sequence shown above.

In some cases, in one or more modifications can also be introduced into HA, PA, PB1, PB2, NP, M1, M2, NS2, PB1-F2, PA-X, and/or NS1 proteins (and nucleic acids encoding such proteins).

Enhanced growth of the virus when passaged through embryonated chicken eggs or cultured cells is observed when the modified NA proteins are expressed and such expression can result in significantly higher viral titers. Thus, the invention provides a method for making influenza viruses with enhanced replication in cell culture or embryonated eggs. The method includes providing cells suitable for influenza vaccine production; modifying nucleic acids encoding the neuraminidase; and isolating virus strains with enhanced growth relative to the one or more unmodified viral isolates. In some cases, a method for making influenza viruses with enhanced replication in cell culture can involve, serially culturing one or more influenza virus isolates in embryonated chicken eggs; and isolating serially cultured virus with enhanced growth relative to the one or more isolates prior to serial culture. In some cases, the viruses can be grown or passaged within cells in culture, e.g., MDCK or Vero cells.

The modified neuraminidases can be expressed in a variety of influenza strains. For example, A/Puerto Rico/8/34 (H1N1), "PR8," virus often serves as the genetic backbone for generation of inactivated influenza vaccines. Some vaccine strains based on PR8 backbone can replicate to relatively low titers in eggs and cell culture, resulting in delayed vaccine production and vaccine shortage. However, expression of the modified neuraminidases described herein can improve replication of the PR8 (and other) influenza strains.

In one embodiment of the invention, vectors for vRNA production can include a vector comprising a promoter operably linked to a modified NA DNA linked to a transcription termination sequence, a vector comprising a promoter operably linked to an influenza virus PB1 DNA linked to a transcription termination sequence, a vector comprising a promoter operably linked to an influenza virus PB2 DNA linked to a transcription termination sequence, a vector comprising a promoter operably linked to an influenza virus HA DNA linked to a transcription termination sequence, a vector comprising a promoter operably linked to an influenza virus NP DNA linked to a transcription termination sequence, a vector comprising a promoter operably linked to an influenza virus NA DNA linked to a transcription termination sequence, a vector comprising a promoter operably linked to an influenza virus M DNA linked to a transcription termination sequence, and a vector comprising a operably linked to an influenza virus NS DNA linked to a transcription termination sequence. In one embodiment, the DNAs for vRNA production of PB1, PB2, PA, NP, M, and NS, have sequences from an influenza virus that replicates to high titers in cultured mammalian cells such as MDCK cells, Vero cells or PER.C6® cells or embryonated eggs, and/or from a vaccine virus, e.g., one that does not cause significant disease in humans. The DNA for vRNA production of NA may be from any NA, e.g., any of N1-N11, and the DNA for vRNA production of HA may be from any HA, e.g., H1-H18. In one embodiment, the DNAs for vRNA production may be for an influenza B or C virus. The DNAs for vRNA production of NA and HA may be from different strains or isolates (6:1:1 reassortants) or from the same strain or isolate (6:2 reassortants), or the NA may be from the same strain or isolate as that for the internal genes (7:1 reassortant). Vectors for mRNA production can include a vector encoding a modified NA, a vector encoding influenza virus PA, a vector encoding influenza virus PB1, a vector encoding influenza virus PB2, and a vector encoding influenza virus NP, and optionally one or more vectors encoding NP, NS, M, e.g., M1 and M2, HA or NA. The vectors encoding viral proteins may further include a transcription termination sequence.

Other reassortants with internal genes from other PR8 isolates or vaccine viruses may be employed in recombinant reassortant viruses of the invention. In particular, 5:1:2 reassortants having UW-PR8 PB1, PB2, PA, NP, and M ("5") and PR8 (Cam) NS ("1"); 6:1:1 reassortants having UW-PR8 (modified) NA, PB1, PB2, PA, NP, and M ("6") and PR8 (Cam) NS ("1"); and 7:1 reassortants having UW-PR8 PB1, PB2, PA, NP, M, (modified) NA, and NS ("7") may be employed.

The neuraminidases that can be modified can have sequences that vary from those described herein. However, in some cases, the modified neuraminidases can have substantially the same activity as a corresponding polypeptide described by sequence herein. As used herein, "substantially the same activity" includes an activity that is about 0.1%, 1%, 10%, 30%, 50%, 90%, e.g., up to 100% or more activity, or a detectable protein level that is about 80%, 90% or more protein level, of the corresponding protein described herein. In one embodiment, the nucleic acid encodes a polypeptide which is substantially the same as, e.g., having at least 80%, e.g., 90%, 92%, 95%, 97%, 98%, or 99%, including any integer between 80 and 99, contiguous amino acid sequence identity to a polypeptide encoded by one of sequences described herein. In one embodiment, the isolated and/or purified nucleic acid molecule comprises a nucleotide sequence which is substantially the same as, e.g., having at least 50%, e.g., 60%, 70%, 80% or 90%, including any integer between 50 and 100, or more contiguous nucleic acid sequence identity to one of the nucleic acid sequences described herein. In one embodiment, a nucleic acid also encodes a polypeptide having at least 80%, e.g., 90%, 92%, 95%, 97%, 98%, or 99%, including any integer between 80 and 99, contiguous amino acid sequence identity to a polypeptide described herein.

In one embodiment, a modified influenza virus neuraminidase polypeptide has one or more, for instance, 2, 5, 10, 15, 20 or more, conservative amino acids substitutions, e.g., conservative substitutions of up to 10% or 20% of 2, 5, 10, 15, 20 or more, of a combination of conservative and non-conservative amino acids substitutions, e.g., conservative substitutions of up to 10% or 20% of the residues, or relative to a polypeptide with one of the sequences disclosed herein.

The invention thus includes the use of isolated and purified vectors or plasmids, which express or encode influenza virus proteins, or express or encode influenza vRNA, both native and recombinant vRNA. The vectors comprise influenza cDNA, e.g., influenza A (e.g., any influenza A gene including any of the 18 HA or 11 NA subtypes), B or C DNA (see Fields Virology (Fields et al. (eds.), Lippincott, Williams and Wickens (2006), which is specifically incorporated by reference herein). Any suitable promoter or transcription termination sequence may be employed to express a protein or peptide, e.g., a viral protein or peptide, a protein or peptide of a nonviral pathogen, or a therapeutic protein or peptide.

A composition or plurality of vectors of the invention may also comprise a heterologous gene or open reading frame of interest, e.g., a foreign gene encoding an immunogenic peptide or protein useful as a vaccine or in gene replacement, for instance, may encode an epitope useful in a cancer therapy or vaccine, or a peptide or polypeptide useful in gene therapy. When preparing virus, the vector or plasmid comprising the gene or cDNA of interest may substitute for a vector or plasmid for an influenza viral gene or may be in addition to vectors or plasmids for all influenza viral genes. Thus, another embodiment of the invention comprises a composition or plurality of vectors as described above in which one of the vectors is replaced with, or further comprises, 5' influenza virus sequences optionally including 5' influenza virus coding sequences or a portion thereof, linked to a desired nucleic acid sequence, e.g., a desired cDNA, linked to 3' influenza virus sequences optionally including 3' influenza virus coding sequences or a portion thereof. In one embodiment, the desired nucleic acid sequence such as a cDNA is in an antisense (antigenomic) orientation. The introduction of such a vector in conjunction with the other vectors described above to a host cell permissive for influenza virus replication results in recombinant virus comprising vRNA corresponding to the heterologous sequences of the vector.

The promoter in a vector for vRNA production may be a RNA polymerase I promoter, a RNA polymerase II promoter, a RNA polymerase III promoter, a T7 promoter, or a T3 promoter, and optionally the vector comprises a transcription termination sequence such as a RNA polymerase I transcription termination sequence, a RNA polymerase II transcription termination sequence, a RNA polymerase III transcription termination sequence, or a ribozyme. Ribozymes within the scope of the invention include, but are not limited to, tetrahymena ribozymes, RNase P, hammerhead ribozymes, hairpin ribozymes, hepatitis ribozyme, as well as synthetic ribozymes. In one embodiment, the RNA polymerase I promoter is a human RNA polymerase I promoter.

The promoter or transcription termination sequence in a vRNA or virus protein expression vector may be the same or different relative to the promoter or any other vector. In one embodiment, the vector or plasmid which expresses influenza vRNA comprises a promoter suitable for expression in at least one particular host cell, e.g., avian or mammalian host cells such as canine, feline, equine, bovine, ovine, or primate cells including human cells, or for expression in more than one host.

In one embodiment, at least one vector for vRNA comprises a RNA polymerase II promoter linked to a ribozyme sequence linked to viral coding sequences linked to another ribozyme sequences, optionally linked to a RNA polymerase II transcription termination sequence. In one embodiment, at least 2, e.g., 3, 4, 5, 6, 7 or 8, vectors for vRNA production comprise a RNA polymerase II promoter, a first ribozyme sequence, which is 5' to a sequence corresponding to viral sequences including viral coding sequences, which is 5' to a second ribozyme sequence, which is 5' to a transcription termination sequence. Each RNA polymerase II promoter in each vRNA vector may be the same or different as the RNA polymerase II promoter in any other vRNA vector. Similarly, each ribozyme sequence in each vRNA vector may be the same or different as the ribozyme sequences in any other vRNA vector. In one embodiment, the ribozyme sequences in a single vector are not the same.

In one embodiment, the invention provides a plurality of influenza virus vectors for a reassortant, comprising a vector for vRNA production comprising a promoter operably linked to a modified influenza virus NA DNA linked to a transcription termination sequence, a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA linked to a transcription termination sequence, wherein the DNAs for the modified NA, PB1, PB2, PA, NP, NS, and M are from one or more influenza vaccine seed viruses and contain two or more of the characteristic residues at the specified position(s); and a vector for mRNA production comprising a promoter operably linked to a DNA segment encoding influenza virus NA, a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, a vector for mRNA production comprising a promoter operably linked to a DNA segment encoding influenza virus NS1, or a vector for mRNA production comprising a promoter operably linked to a DNA segment encoding influenza virus NS2. In one embodiment, at least one vector comprises sequences corresponding to those encoding PB1, PB2, PA, NP, M, or NS, or a portion thereof, having substantially the same activity as a corresponding polypeptide described herein or encoded by a nucleic acid described herein. Optionally, two vectors may be employed in place of the vector comprising a promoter operably linked to an influenza virus M cDNA linked to a transcription termination sequence, e.g., a vector comprising a promoter operably linked to an influenza virus M1 cDNA linked to a transcription termination sequence and a vector comprising a promoter operably linked to an influenza virus M2 cDNA linked to a transcription termination sequence.

A plurality of the vectors of the invention may be physically linked or each vector may be present on an individual plasmid or other, e.g., linear, nucleic acid delivery vehicle. In one embodiment, each vRNA production vector is on a separate plasmid. In one embodiment, each mRNA production vector is on a separate plasmid.

The invention also provides a method to prepare influenza virus. The method comprises contacting a cell with a plurality of the vectors of the invention, e.g., sequentially or simultaneously, in an amount effective to yield infectious influenza virus. The invention also includes isolating virus from a cell contacted with the plurality of vectors. Thus, the invention further provides isolated virus, as well as a host cell contacted with the plurality of vectors or virus of the invention. In another embodiment, the invention includes contacting the cell with one or more vectors, either vRNA or protein production vectors, prior to other vectors, either vRNA or protein production vectors. In one embodiment, the promoter for vRNA vectors employed in the method is a RNA polymerase I promoter, a RNA polymerase II promoter, a RNA polymerase III promoter, a T3 promoter or a T7 promoter. In one embodiment, the RNA polymerase I promoter is a human RNA polymerase I promoter. In one embodiment, each vRNA vector employed in the method is on a separate plasmid. In one embodiment, the vRNA vectors employed in the method are on one plasmid or on two or three different plasmids. In one embodiment, each mRNA vector employed in the method is on a separate plasmid. In one embodiment, the mRNA vectors for PA, PB1, PB2 and NP employed in the method are on one plasmid or on two or three different plasmids.

Exemplary viral sequences for a master vaccine strain (PR8UW)

HA (SEQ ID NO: 22)

AGCAAAAGCAGGGGAAAATAAAAACAACCAAAATGAAGGCAAACCTACTGGTCCTGTTATGTGCACT

TGCAGCTGCAGATGCAGACACAATATGTATAGGCTACCATGCGAACAATTCAACCGACACTGTTGAC

ACAGTACTCGAGAAGAATGTGACAGTGACACACTCTGTTAACCTGCTCGAAGACAGCCACAACGGAA

AACTATGTAGATTAAAAGGAATAGCCCCACTACAATTGGGGAAATGTAACATCGCCGGATGGCTCTT

GGGAAACCCAGAATGCGACCCACTGCTTCCAGTGAGATCATGGTCCTACATTGTAGAAACACCAAAC

TCTGAGAATGGAATATGTTATCCAGGAGATTTCATCGACTATGAGGAGCTGAGGGAGCAATTGAGCT

CAGTGTCATCATTCGAAAGATTCGAAATATTTCCCAAAGAAAGCTCATGGCCCAACCACAACACAAAC

GGAGTAACGGCAGCATGCTCCCATGAGGGGAAAAGCAGTTTTTACAGAAATTTGCTATGGCTGACGG

AGAAGGAGGGCTCATACCCAAAGCTGAAAAATTCTTATGTGAACAAAAAAGGGAAAGAAGTCCTTGT

ACTGTGGGGTATTCATCACCCGCCTAACAGTAAGGAACAACAGAATCTCTATCAGAATGAAAATGCTT

ATGTCTCTGTAGTGACTTCAAATTATAACAGGAGATTTACCCCGGAAATAGCAGAAAGACCCAAAGTA

AGAGATCAAGCTGGGAGGATGAACTATTACTGGACCTTGCTAAAACCCGGAGACACAATAATATTTG

AGGCAAATGGAAATCTAATAGCACCAATGTATGCTTTCGCACTGAGTAGAGGCTTTGGGTCCGGCAT

CATCACCTCAAACGCATCAATGCATGAGTGTAACACGAAGTGTCAAACACCCCTGGGAGCTATAAAC

AGCAGTCTCCCTTACCAGAATATACACCCAGTCACAATAGGAGAGTGCCCAAAATACGTCAGGAGTG

CCAAATTGAGGATGGTTACAGGACTAAGGAACATTCCGTCCATTCAATCCAGAGGTCTATTTGGAGC cATTGCCGGTTTTATTGAAGGGGGATGGACTGGAATGATAGATGGATGGTATGGTTATCATCATCAG

AATGAACAGGGATCAGGCTATGCAGCGGATCAAAAAAGCACACAAAATGCCATTAACGGGATTACAA

ACAAGGTGAACACTGTTATCGAGAAAATGAACATTCAATTCACAGCTGTGGGTAAAGAATTCAACAAA

TTAGAAAAAAGGATGGAAAATTTAAATAAAAAAGTTGATGATGGATTTCTGGACATTTGGACATATAAT

GCAGAATTGTTAGTTCTACTGGAAAATGAAAGGACTGTGGATTTCCATGACTCAAATGTGAAGAATCT

GTATGAGAAAGTAAAAAGCCAATTAAAGAATAATGCCAAAGAAATCGGAAATGGATGTTTTGAGTTCT

ACCACAAGTGTGACAATGAATGCATGGAAAGTGTAAGAAATGGGACTTATGATTATCCCAAATATTCA

GAAGAGTCAAAGTTGAACAGGGAAAAGGTAGATGGAGTGAAATTGGAATCAATGGGGATCTATCAGA

TTCTGGCGATCTACTCAACTGTCGCCAGTTCACTGGTGCTTTTGGTCTCCCTGGGGGCAATCAGTTT

CTGGATGTGTTCTAATGGATCTTTGCAGTGCAGAATATGCATCTGAGATTAGAATTTCAGAGATATGA

GGAAAAACACCCTTGTTTCTACT

NA (SEQ ID NO: 23)

AGCAAAAGCAGGGGTTTAAAATGAATCCAAATCAGAAAATAATAACCATTGGATCAATCTGTCTGGTA

GTCGGACTAATTAGCCTAATATTGCAAATAGGGAATATAATCTCAATATGGATTAGCCATTCAATTCAA

ACTGGAAGTCAAAACCATACTGGAATATGCAACCAAAACATCATTACCTATAAAAATAGCACCTGGGT

AAAGGACACAACTTCAGTGATATTAACCGGCAATTCATCTCTTTGTCCCATCCGTGGGTGGGCTATAT

ACAGCAAAGACAATAGCATAAGAATTGGTTCCAAAGGAGACGTTTTTGTCATAAGAGAGCCCTTTATT

TCATGTTCTCACTTGGAATGCAGGACCTTTTTTCTGACCCAAGGTGCCTTACTGAATGACAAGCATTC

AAGTGGGACTGTTAAGGACAGAAGCCCTTATAGGGCCTTAATGAGCTGCCCTGTCGGTGAAGCTCC

-continued

GTCCCCGTACAATTCAAGATTTGAATCGCTTGCTTGGTCAGCAAGTGCATGTCATGATGGCATGGGC

TGGCTAACAATCGGAATTTCAGGTCCAGATAATGGAGCAGTGGCTGTATTAAAATACAACGGCATAAT

AACTGAAACCATAAAAAGTTGGAGGAAGAAAATATTGAGGACACAAGAGTCTGAATGTGCCTGTGTAA

ATGGTTCATGTTTTACTATAATGACTGATGGCCCGAGTGATGGGCTGGCCTCGTACAAAATTTTCAAG

ATCGAAAAGGGGAAGGTTACTAAATCAATAGAGTTGAATGCACCTAATTCTCACTATGAGGAATGTTC

CTGTTACCCTGATACCGGCAAAGTGATGTGTGTGTGCAGAGACAATTGGCATGGTTCGAACCGGCCA

TGGGTGTCTTTCGATCAAAACCTGGATTATCAAATAGGATACATCTGCAGTGGGGTTTTCGGTGACAA

CCCGCGTCCCGAAGATGGAACAGGCAGCTGTGGTCCAGTGTATGTTGATGGAGCAAACGGAGTAAA

GGGATTTTCATATAGGTATGGTAATGGTGTTTGGATAGGAAGGACCAAAAGTCACAGTTCCAGACAT

GGGTTTGAGATGATTTGGGATCCTAATGGATGGACAGAGACTGATAGTAAGTTCTCTGTGAGGCAAG

ATGTTGTGGCAATGACTGATTGGTCAGGGTATAGCGGAAGTTTCGTTCAACATCCTGAGCTGACAGG

GCTAGACTGTATGAGGCCGTGCTTCTGGGTTGAATTAATCAGGGGACGACCTAAAGAAAAAACAATC

TGGACTAGTGCGAGCAGCATTTCTTTTTGTGGCGTGAATAGTGATACTGTAGATTGGTCTTGGCCAGA

CGGTGCTGAGTTGCCATTCAGCATTGACAAGTAGTGTGTTCAAAAAACTCCTTGTTTCTACT

PA (SEQ ID NO: 24)

AGCGAAAGCA GGTACTGATC CAAAATGGAA GATTTTGTGC GACAATGCTT CAATCCGATG

ATTGTCGAGC TTGCGGAAAA AACAATGAAA GAGTATGGGG AGGACCTGAA AATCGAAACA

AACAAATTTG CAGCAATATG CACTCACTTG GAAGTATGCT TCATGTATTC AGATTTTCAC

TTCATCAATG AGCAAGGCGA GTCAATAATC GTAGAACTTG GTGATCCAAA TGCACTTTTG

AAGCACAGAT TTGAAATAAT CGAGGGAAGA GATCGCACAA TGGCCTGGAC AGTAGTAAAC

AGTATTTGCA ACACTACAGG GGCTGAGAAA CCAAAGTTTC TACCAGATTT GTATGATTAC

AAGGAGAATA GATTCATCGA AATTGGAGTA ACAAGGAGAG AAGTTCACAT ATACTATCTG

GAAAAGGCCA ATAAAATTAA ATCTGAGAAA ACACACATCC ACATTTTCTC GTTCACTGGG

GAAGAAATGG CCACAAAGGC AGACTACACT CTCGATGAAG AAAGCAGGGC TAGGATCAAA

ACCAGACTAT TCACCATAAG ACAAGAAATG GCCAGGAGAG GCCTCTGGGA TTCCTTTCGT

CAGTCCGAGA GAGGAGAAGA GACAATTGAA GAAAGGTTTG AAATCACAGG AACAATGCGC

AAGCTTGCCG ACCAAAGTCT CCCGCCGAAC TTCTCCAGCC TTGAAAATTT TAGAGCCTAT

GTGGATGGAT TCGAACCGAA CGGCTACATT GAGGGCAAGC TGTCTCAAAT GTCCAAAGAA

GTAAATGCTA GAATTGAACC TTTTTTGAAA ACAACACCAC GACCACTTAG ACTTCCGAAT

GGGCCTCCCT GTTCTCAGCG GTCCAAATTC CTGCTGATGG ATGCCTTAAA ATTAAGCATT

GAGGACCCAA GTCATGAAGG AGAGGGAATA CCGCTATATG ATGCAATCAA ATGCATGAGA

ACATTCTTTG GATGGAAGGA ACCCAATGTT GTTAAACCAC ACGAAAAGGG AATAAATCCA

AATTATCTTC TGTCATGGAA GCAAGTACTG GCAGAACTGC AGGACATTGA GAATGAGGAG

AAAATTCCAA AGACTAAAAA TATGAAGAAA ACAAGTCAGC TAAAGTGGGC ACTTGGTGAG

AACATGGCAC CAGAAAAGGT AGACTTTGAC GACTGTAAAG ATGTAGGTGA TTTGAAGCAA

TATGATAGTG ATGAACCAGA ATTGAGGTCG CTTGCAAGTT GGATTCAGAA TGAGTTTAAC

AAGGCATGCG AACTGACAGA TTCAAGCTGG ATAGAGCTCG ATGAGATTGG AGAAGATGTG

GCTCCAATTG AACACATTGC AAGCATGAGA AGGAATTATT TCACATCAGA GGTGTCTCAC

TGCAGAGCCA CAGAATACAT AATGAAGGGA GTGTACATCA ATACTGCCTT GCTTAATGCA

TCTTGTGCAG CAATGGATGA TTTCCAATTA ATTCCAATGA TAAGCAAGTG TAGAACTAAG

-continued

GAGGGAAGGC GAAAGACCAA CTTGTATGGT TTCATCATAA AAGGAAGATC CCACTTAAGG

AATGACACCG ACGTGGTAAA CTTTGTGAGC ATGGAGTTTT CTCTCACTGA CCCAAGACTT

GAACCACATA AATGGGAGAA GTACTGTGTT CTTGAGATAG GAGATATGCT TATAAGAAGT

GCCATAGGCC AGGTTTCAAG GCCCATGTTC TTGTATGTGA GAACAAATGG AACCTCAAAA

ATTAAAATGA AATGGGGAAT GGAGATGAGG CGTTGCCTCC TCCAGTCACT TCAACAAATT

GAGAGTATGA TTGAAGCTGA GTCCTCTGTC AAAGAGAAAG ACATGACCAA AGAGTTCTTT

GAGAACAAAT CAGAAACATG GCCCATTGGA GAGTCCGCCA AAGGAGTGGA GGAAAGTTCC

ATTGGGAAGG TGTGCAGGAC TTTATTAGCA AAGTCGGTAT TCAACAGCTT GTATGCATCT

CCACAACTAG AAGGATTTTC AGCTGAATCA AGAAAACTGC TTCTTATCGT TCAGGCTCTT

AGGGACAACC TGGAACCTGG GACCTTTGAT CTTGGGGGGC TATATGAAGC AATTGAGGAG

TGCCTGATTA ATGATCCCTG GGTTTTGCTT AATGCTTGTT GGTTCAACTC GTTCGTTACA

CATGCATTGA GTTAGTTGTG GCAGTGCTAC TATTTGCTAT CCATACTGTC CAAAAAAGTA

CCTTGTTTCT ACT

PB1

(SEQ ID NO: 25)

AGCGAAAGCAGGCAAACCATTTGAATGGATGTCAATCCGACCTTACTTTTCTTAAAAGTGCCAGCACA

AAATGCTATAAGCACAACTTTCCCTTATACTGGAGACCCTCCTTACAGCCATGGGACAGGAACAGGA

TACACCATGGATACTGTCAACAGGACACATCAGTACTCAGAAAAGGGAAGATGGACAACAAACACCG

AAACTGGAGCACCGCAACTCAACCCGATTGATGGGCCACTGCCAGAAGACAATGAACCAAGTGGTTA

TGCCCAAACAGATTGTGTATTGGAGGCGATGGCTTTCCTTGAGGAATCCCATCCTGGTATTTTTGAAA

ACTCGTGTATTGAAACGATGGAGGTTGTTCAGCAAACACGAGTAGACAAGCTGACACAAGGCCGACA

GACCTATGACTGGACTCTAAATAGAAACCAACCTGCTGCAACAGCATTGGCCAACACAATAGAAGTG

TTCAGATCAAATGGCCTCACGGCCAATGAGTCTGGAAGGCTCATAGACTTCCTTAAGGATGTAATGG

AGTCAATGAACAAAGAAGAAATGGGGATCACAACTCATTTTCAGAGAAAGAGACGGGTGAGAGACAA

TATGACTAAGAAAATGATAACACAGAGAACAATGGGTAAAAAGAAGCAGAGATTGAACAAAAGGAGTT

ATCTAATTAGAGCATTGACCCTGAACACAATGACCAAAGATGCTGAGAGAGGGAAGCTAAAACGGAG

AGCAATTGCAACCCCAGGGATGCAAATAAGGGGGTTTGTATACTTTGTTGAGACACTGGCAAGGAGT

ATATGTGAGAAACTTGAACAATCAGGGTTGCCAGTTGGAGGCAATGAGAAGAAAGCAAAGTTGGCAA

ATGTTGTAAGGAAGATGATGACCAATTCTCAGGACACCGAACTTTCTTTCACCATCACTGGAGATAAC

ACCAAATGGAACGAAAATCAGAATCCTCGGATGTTTTTGGCCATGATCACATATATGACCAGAAATCA

GCCCGAATGGTTCAGAAATGTTCTAAGTATTGCTCCAATAATGTTCTCAAACAAAATGGCGAGACTGG

GAAAAGGGTATATGTTTGAGAGCAAGAGTATGAAACTTAGAACTCAAATACCTGCAGAAATGCTAGCA

AGCATCGATTTGAAATATTTCAATGATTCAACAAGAAAGAAGATTGAAAAAATCCGACCGCTCTTAATA

GAGGGGACTGCATCATTGAGCCCTGGAATGATGATGGGCATGTTCAATATGTTAAGCACTGTATTAG

GCGTCTCCATCCTGAATCTTGGACAAAAGAGATACACCAAGACTACTTACTGGTGGGATGGTCTTCA

ATCCTCTGACGATTTTGCTCTGATTGTGAATGCACCCAATCATGAAGGGATTCAAGCCGGAGTCGAC

AGGTTTTATCGAACCTGTAAGCTACTTGGAATCAATATGAGCAAGAAAAAGTCTTACATAAACAGAAC

AGGTACATTTGAATTCACAAGTTTTTTCTATCGTTATGGGTTTGTTGCCAATTTCAGCATGGAGCTTCC

CAGTTTTGGGGTGTCTGGGATCAACGAGTCAGCGGACATGAGTATTGGAGTTACTGTCATCAAAAAC

AATATGATAAACAATGATCTTGGTCCAGCAACAGCTCAAATGGCCCTTCAGTTGTTCATCAAAGATTA

CAGGTACACGTACCGATGCCATATAGGTGACACACAAATACAAACCCGAAGATCATTTGAAATAAAGA

AACTGTGGGAGCAAACCCGTTCCAAAGCTGGACTGCTGGTCTCCGACGGAGGCCCAAATTTATACAA

-continued

CATTAGAAATCTCCACATTCCTGAAGTCTGCCTAAAATGGGAATTGATGGATGAGGATTACCAGGGG

CGTTTATGCAACCCACTGAACCCATTTGTCAGCCATAAAGAAATTGAATCAATGAACAATGCAGTGAT

GATGCCAGCACATGGTCCAGCCAAAAACATGGAGTATGATGCTGTTGCAACAACACACTCCTGGATC

CCCAAAAGAAATCGATCCATCTTGAATACAAGTCAAAGAGGAGTACTTGAGGATGAACAAAAAATACCA

AAGGTGCTGCAATTTATTTGAAAAATTCTTCCCCAGCAGTTCATACAGAAGACCAGTCGGGATATCCA

GTATGGTGGAGGCTATGGTTTCCAGAGCCCGAATTGATGCACGGATTGATTTCGAATCTGGAAGGAT

AAAGAAAGAAGAGTTCACTGAGATCATGAAGATCTGTTCCACCATTGAAGAGCTCAGACGGCAAAAA

TAGTGAATTTAGCTTGTCCTTCATGAAAAAATGCCTTGTTTCTACT

PB2

(SEQ ID NO: 26)

AGCGAAAGCA GGTCAATTAT ATTCAATATG GAAAGAATAA AAGAACTACG AAATCTAATG

TCGCAGTCTC GCACCCGCGA GATACTCACA AAAACCACCG TGGACCATAT GGCCATAATC

AAGAAGTACA CATCAGGAAG ACAGGAGAAG AACCCAGCAC TTAGGATGAA ATGGATGATG

GCAATGAAAT ATCCAATTAC AGCAGACAAG AGGATAACGG AAATGATTCC TGAGAGAAAT

GAGCAAGGAC AAACTTTATG GAGTAAAATG AATGATGCCG GATCAGACCG AGTGATGGTA

TCACCTCTGG CTGTGACATG GTGGAATAGG AATGGACCAA TAACAAATAC AGTTCATTAT

CCAAAAATCT ACAAAACTTA TTTTGAAAGA GTCGAAAGGC TAAAGCATGG AACCTTTGGC

CCTGTCCATT TTAGAAACCA AGTCAAAATA CGTCGGAGAG TTGACATAAA TCCTGGTCAT

GCAGATCTCA GTGCCAAGGA GGCACAGGAT GTAATCATGG AAGTTGTTTT CCCTAACGAA

GTGGGAGCCA GGATAGTAAC ATCGGAATCG CAACTAACGA TAACCAAAGA GAAGAAAGAA

GAACTCCAGG ATTGCAAAAT TTCTCCTTTG ATGGTTGCAT ACATGTTGGA GAGAGAACTG

GTCCGCAAAA CGAGATTCCT CCCAGTGGCT GGTGGAACAA GCAGTGTGTA CATTGAAGTG

TTGCATTTGA CTCAAGGAAC ATGGTGGGAA CAGATGTATA CTCCAGGAGG GGAAGTGAGG

AATGATGATG TTGATCAAAG CTTGATTATT GCTGCTAGGA ACATAGTGAG AAGAGCTGCA

GTATCAGCAG ATCCACTAGC ATCTTTATTG GAGATGTGCC ACAGCACACA GATTGGTGGA

ATTAGGATGG TAGACATCCT TAGGCAGAAC CCAACAGAAG AGCAAGCCGT GGATATATGC

AAGGCTGCAA TGGGACTGAG AATTAGCTCA TCCTTCAGTT TTGGTGGATT CACATTTAAG

AGAACAAGCG GATCATCAGT CAAGAGAGAG GAAGAGGTGC TTACGGGCAA TCTTCAAACA

TTGAAGATAA GAGTGCATGA GGGATATGAA GAGTTCACAA TGGTTGGGAG AAGAGCAACA

GCCATACTCA GAAAAGCAAC CAGGAGATTG ATTCAGCTGA TAGTGAGTGG GAGAGACGAA

CAGTCGATTG CCGAAGCAAT AATTGTGGCC ATGGTATTTT CACAAGAGGA TTGTATGATA

AAAGCAGTCA GAGGTGATCT GAATTTCGTC AATAGGGCGA ATCAACGATT GAATCCTATG

CATCAACTTT TAAGACATTT TCAGAAGGAT GCGAAAGTGC TTTTTCAAAA TTGGGGAGTT

GAACCTATCG ACAATGTGAT GGGAATGATT GGGATATTGC CCGACATGAC TCCAAGCATC

GAGATGTCAA TGAGAGGAGT GAGAATCAGC AAAATGGGTG TAGATGAGTA CTCCAGCACG

GAGAGGGTAG TGGTGAGCAT TGACCGTTTT TTGAGAATCC GGGACCAACG AGGAAATGTA

CTACTGTCTC CCGAGGAGGT CAGTGAAACA CAGGGAACAG AGAAACTGAC AATAACTTAC

TCATCGTCAA TGATGTGGGA GATTAATGGT CCTGAATCAG TGTTGGTCAA TACCTATCAA

TGGATCATCA GAAACTGGGA AACTGTTAAA ATTCAGTGGT CCCAGAACCC TACAATGCTA

TACAATAAAA TGGAATTTGA ACCATTTCAG TCTTTAGTAC CTAAGGCCAT TAGAGGCCAA

TACAGTGGGT TTGTAAGAAC TCTGTTCCAA CAAATGAGGG ATGTGCTTGG GAGATTTGAT

-continued

ACCGCACAGA TAATAAAACT TCTTCCCTTC GCAGCCGCTC CACCAAAGCA AAGTAGAATG

CAGTTCTCCT CATTTACTGT GAATGTGAGG GGATCAGGAA TGAGAATACT TGTAAGGGGC

AATTCTCCTG TATTCAACTA TAACAAGGCC ACGAAGAGAC TCACAGTTCT CGGAAAGGAT

GCTGGCACTT TAACTGAAGA CCCAGATGAA GGCACAGCTG GAGTGGAGTC CGCTGTTCTG

AGGGGATTCC TCATTCTGGG CAAAGAAGAC AAGAGATATG GGCCAGCACT AAGCATCAAT

GAACTGAGCA ACCTTGCGAA AGGAGAGAAG GCTAATGTGC TAATTGGGCA AGGAGACGTG

GTGTTGGTAA TGAAACGGAA ACGGGACTCT AGCATACTTA CTGACAGCCA GACAGCGACC

AAAAGAATTC GGATGGCCAT CAATTAGTGT CGAATAGTTT AAAAACGACC TTGTTTCTAC T

NP (SEQ ID NO: 27)

AGCAAAAGCA GGGTAGATAA TCACTCACTG AGTGACATCA AAATCATGGC GTCTCAAGGC

ACCAAACGAT CTTACGAACA GATGGAGACT GATGGAGAAC GCCAGAATGC CACTGAAATC

AGAGCATCCG TCGGAAAAAT GATTGGTGGA ATTGGACGAT TCTACATCCA AATGTGCACC

GAACTCAAAC TCAGTGATTA TGAGGGACGG TTGATCCAAA ACAGCTTAAC AATAGAGAGA

ATGGTGCTCT CTGCTTTTGA CGAAAGGAGA AATAAATACC TTGAAGAACA TCCCAGTGCG

GGGAAAGATC CTAAGAAAAC TGGAGGACCT ATATACAGGA GAGTAAACGG AAAGTGGATG

AGAGAACTCA TCCTTTATGA CAAAGAAGAA ATAAGGCGAA TCTGGCGCCA AGCTAATAAT

GGTGACGATG CAACGGCTGG TCTGACTCAC ATGATGATCT GGCATTCCAA TTTGAATGAT

GCAACTTATC AGAGGACAAG AGCTCTTGTT CGCACCGGAA TGGATCCCAG GATGTGCTCT

CTGATGCAAG GTTCAACTCT CCCTAGGAGG TCTGGAGCCG CAGGTGCTGC AGTCAAAGGA

GTTGGAACAA TGGTGATGGA ATTGGTCAGA ATGATCAAAC GTGGGATCAA TGATCGGAAC

TTCTGGAGGG GTGAGAATGG ACGAAAAACA AGAATTGCTT ATGAAAGAAT GTGCAACATT

CTCAAAGGGA AATTTCAAAC TGCTGCACAA AAAGCAATGA TGGATCAAGT GAGAGAGAGC

CGGAACCCAG GGAATGCTGA GTTCGAAGAT CTCACTTTTC TAGCACGGTC TGCACTCATA

TTGAGAGGGT CGGTTGCTCA CAAGTCCTGC CTGCCTGCCT GTGTGTATGG ACCTGCCGTA

GCCAGTGGGT ACGACTTTGA AAGGGAGGGA TACTCTCTAG TCGGAATAGA CCCTTTCAGA

CTGCTTCAAA ACAGCCAAGT GTACAGCCTA ATCAGACCAA ATGAGAATCC AGCACACAAG

AGTCAACTGG TGTGGATGGC ATGCCATTCT GCCGCATTTG AAGATCTAAG AGTATTAAGC

TTCATCAAAG GGACGAAGGT GCTCCCAAGA GGGAAGCTTT CCACTAGAGG AGTTCAAATT

GCTTCCAATG AAAATATGGA GACTATGGAA TCAAGTACAC TTGAACTGAG AAGCAGGTAC

TGGGCCATAA GGACCAGAAG TGGAGGAAAC ACCAATCAAC AGAGGGCATC TGCGGGCCAA

ATCAGCATAC AACCTACGTT CTCAGTACAG AGAAATCTCC CTTTTGACAG AACAACCATT

ATGGCAGCAT TCAATGGGAA TACAGAGGGG AGAACATCTG ACATGAGGAC CGAAATCATA

AGGATGATGG AAAGTGCAAG ACCAGAAGAT GTGTCTTTCC AGGGGCGGGG AGTCTTCGAG

CTCTCGGACG AAAAGGCAGC GAGCCCGATC GTGCCTTCCT TTGACATGAG TAATGAAGGA

TCTTATTTCT TCGGAGACAA TGCAGAGGAG TACGACAATT AAAGAAAAAT ACCCTTGTTT CTACT

M (SEO ID NO: 28)

AGCAAAAGCA GGTAGATATT GAAAGATGAG TCTTCTAACC GAGGTCGAAA CGTACGTACT

CTCTATCATC CCGTCAGGCC CCCTCAAAGC CGAGATCGCA CAGAGACTTG AAGATGTCTT

TGCAGGGAAG AACACCGATC TTGAGGTTCT CATGGAATGG CTAAAGACAA GACCAATCCT

GTCACCTCTG ACTAAGGGGA TTTTAGGATT TGTGTTCACG CTCACCGTGC CCAGTGAGCG

AGGACTGCAG CGTAGACGCT TTGTCCAAAA TGCCCTTAAT GGGAACGGGG ATCCAAATAA

-continued

```
CATGGACAAA GCAGTTAAAC TGTATAGGAA GCTCAAGAGG GAGATAACAT TCCATGGGGC
CAAAGAAATC TCACTCAGTT ATTCTGCTGG TGCACTTGCC AGTTGTATGG GCCTCATATA
CAACAGGATG GGGGCTGTGA CCACTGAAGT GGCATTTGGC CTGGTATGTG CAACCTGTGA
ACAGATTGCT GACTCCCAGC ATCGGTCTCA TAGGCAAATG GTGACAACAA CCAATCCACT
AATCAGACAT GAGAACAGAA TGGTTTTAGC CAGCACTACA GCTAAGGCTA TGGAGCAAAT
GGCTGGATCG AGTGAGCAAG CAGCAGAGGC CATGGAGGTT GCTAGTCAGG CTAGACAAAT
GGTGCAAGCG ATGAGAACCA TTGGGACTCA TCCTAGCTCC AGTGCTGGTC TGAAAAATGA
TCTTCTTGAA AATTTGCAGG CCTATCAGAA ACGAATGGGG GTGCAGATGC AACGGTTCAA
GTGATCCTCT CACTATTGCC GCAAATATCA TTGGGATCTT GCACTTGACA TTGTGGATTC
TTGATCGTCT TTTTTTCAAA TGCATTTACC GTCGCTTTAA ATACGGACTG AAAGGAGGGC
CTTCTACGGA AGGAGTGCCA AAGTCTATGA GGGAAGAATA TCGAAAGGAA CAGCAGAGTG
CTGTGGATGC TGACGATGGT CATTTTGTCA GCATAGAGCT GGAGTAAAAA ACTACCTTGT
TTCTACT

NS
                                                   (SEQ ID NO: 29)
AGCAAAAGCA GGGTGACAAA AACATAATGG ATCCAAACAC TGTGTCAAGC TTTCAGGTAG
ATTGCTTTCT TTGGCATGTC CGCAAACGAG TTGCAGACCA AGAACTAGGC GATGCCCCAT
TCCTTGATCG GCTTCGCCGA GATCAGAAAT CCCTAAGAGG AAGGGGCAGT ACTCTCGGTC
TGGACATCAA GACAGCCACA CGTGCTGGAA AGCAGATAGT GGAGCGGATT CTGAAAGAAG
AATCCGATGA GGCACTTAAA ATGACCATGG CCTCTGTACC TGCGTCGCGT TACCTAACTG
ACATGACTCT TGAGGAAATG TCAAGGGACT GGTCCATGCT CATACCCAAG CAGAAAGTGG
CAGGCCCTCT TTGTATCAGA ATGGACCAGG CGATCATGGA TAAGAACATC ATACTGAAAG
CGAACTTCAG TGTGATTTTT GACCGGCTGG AGACTCTAAT ATTGCTAAGG GCTTTCACCG
AAGAGGGAGC AATTGTTGGC GAAATTTCAC CATTGCCTTC TCTTCCAGGA CATACTGCTG
AGGATGTCAA AAATGCAGTT GGAGTCCTCA TCGGAGGACT TGAATGGAAT GATAACACAG
TTCGAGTCTC TGAAACTCTA CAGAGATTCG CTTGGAGAAG CAGTAATGAG AATGGGAGAC
CTCCACTCAC TCCAAAACAG AAACGAGAAA TGGCGGGAAC AATTAGGTCA GAAGTTTGAA
GAAATAAGAT GGTTGATTGA AGAAGTGAGA CACAAAGTGA AGATAACAGA GAATAGTTTT
GAGCAAATAA CATTTATGCA AGCCTTACAT CTATTGGTTG AAGTGGAGCA AGAGATAAGA
ACTTTCTCGT TTCAGGTTAT TTAGTACTAA AAAACACCCT TGTTTCTACT
```

Exemplary Neuraminidase Modifications

Materials

Viruses: Y2017: A/Yokohama/2017/2003 (H3N2)

HK4801: A/Hong Kong/4801/2014 (H3N2)

Y2017-M3L4: Y2017 passaged 7 times in eggs

HY-PR8: high yield PR8 (H1N1)

Results

Y2017 virus was passaged 7 times in eggs (3 times in the amniotic cavity, followed by 4 times in the allantoic cavity). A progeny virus, Y2017-M3L4, grew efficiently in the allantoic cavity ($10^7$ to about $10^8$ PFU/mL), whereas the original Y2017 virus did not grow at all (<10 PFU/mL).

Mutations observed in Y2017-M3L4 virus were as follows:

TABLE 1

| | PB2 | NA | NP | M1 |
|---|---|---|---|---|
| eggA | T1471, V344L and T147I, V344L, E358K | del 46-50aa, T32A, Di 47N, N329D, H347Q | none | E23Q |
| eggB | T147I | del 46-50ea, T32A, D147N, N329D, H347Q | D101N | none |
| eggC | T147I | del 46-50ea, T32A, D147N, N329D, H347Q | D101N | none |

A comparison of the growth ability of mutant Y2017 viruses, generated by reverse genetics, in allantoic fluid revealed that NA mutations were responsible for the high growth of Y2017-M3L4 virus (FIG. 4). A plasmid with PB2-T147I was used for virus generation (PB2-T147I, V344L and PB2-T147I, V344L, E358K were not analyzed). Mutations were not observed in the HA gene of the virus possessing a mutated NA segment and its other genes from wild-type Y2017 after replication in allantoic fluid (FIG. 4).

Figure 5A:
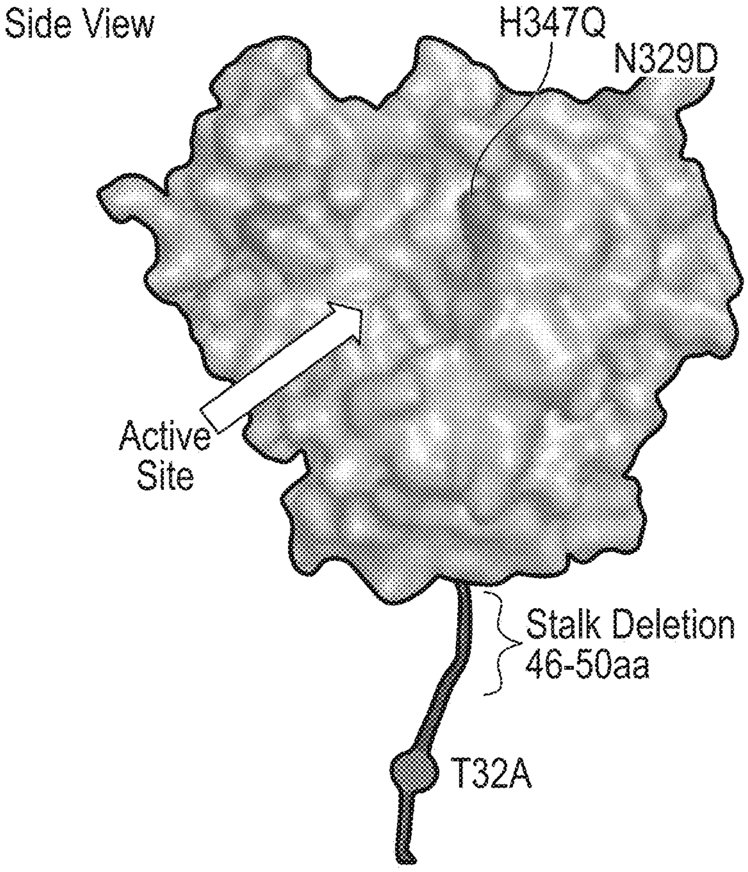
FIGS. 5A-5B. Locations of the NA mutations on the 3D structure of N2 NA.
Figure 5B:
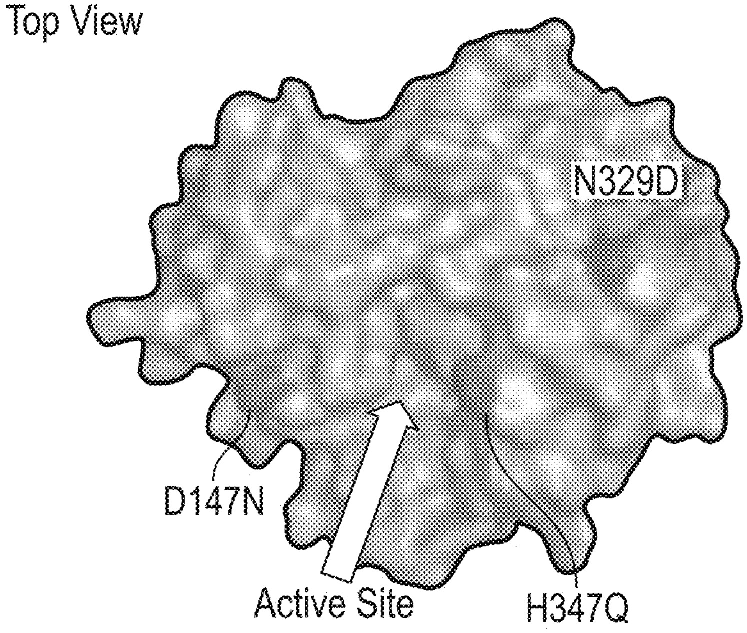

FIG. 5 shows the location of the NA mutations in Y2017-M3L4 in a 3D model.

Figure 6:
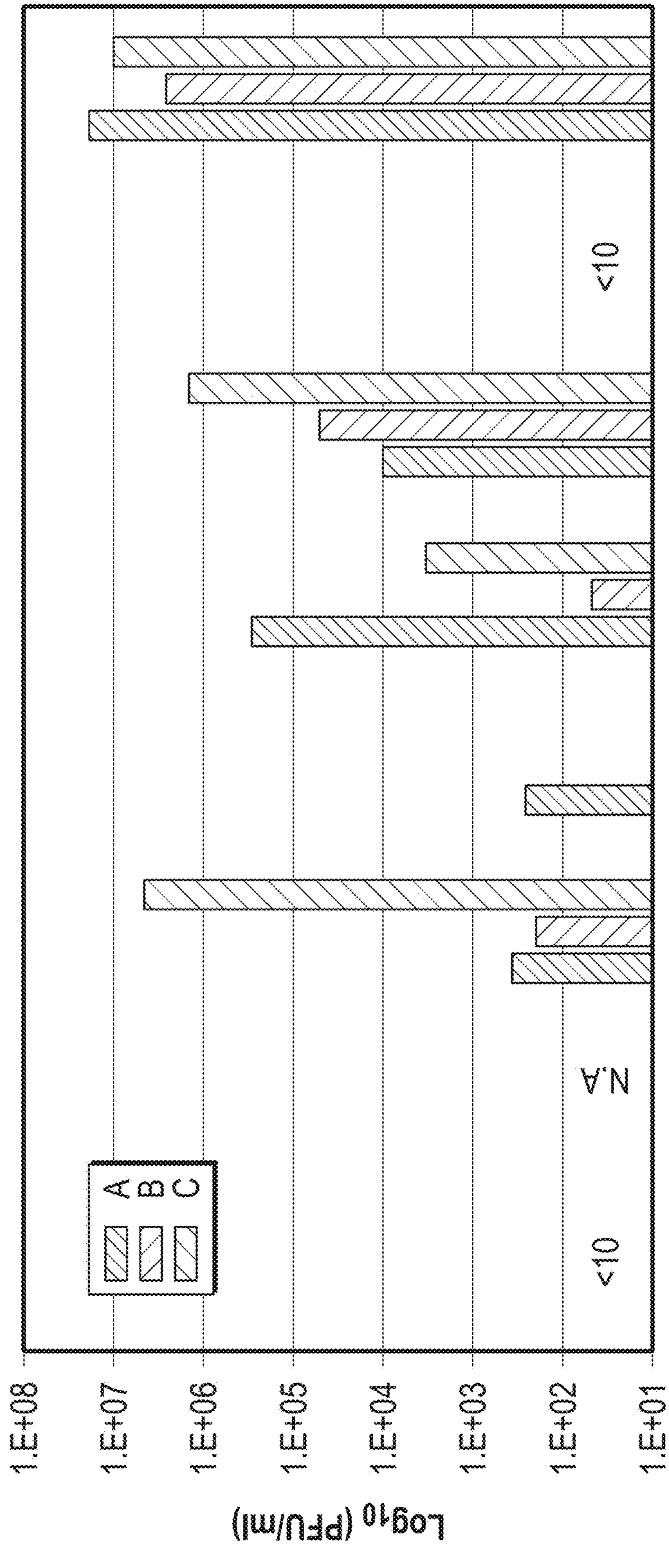
FIG. 6. Graph showing titers in eggs for recombinant viruses with specific mutations found in the mutant of A/Yokohama/2017/2003 ("Y2017-M3L4"). Virus inoculation: $2\times10^3$ pfu/egg into allantoic fluid, 72 h incubation at 37° C.

Comparison of the growth ability of Y2017 viruses with NA mutations revealed that NA-D147N, N329D, and H347Q generally contributed to the increased growth ability in allantoic fluid (FIG. 6).

Figure 7:
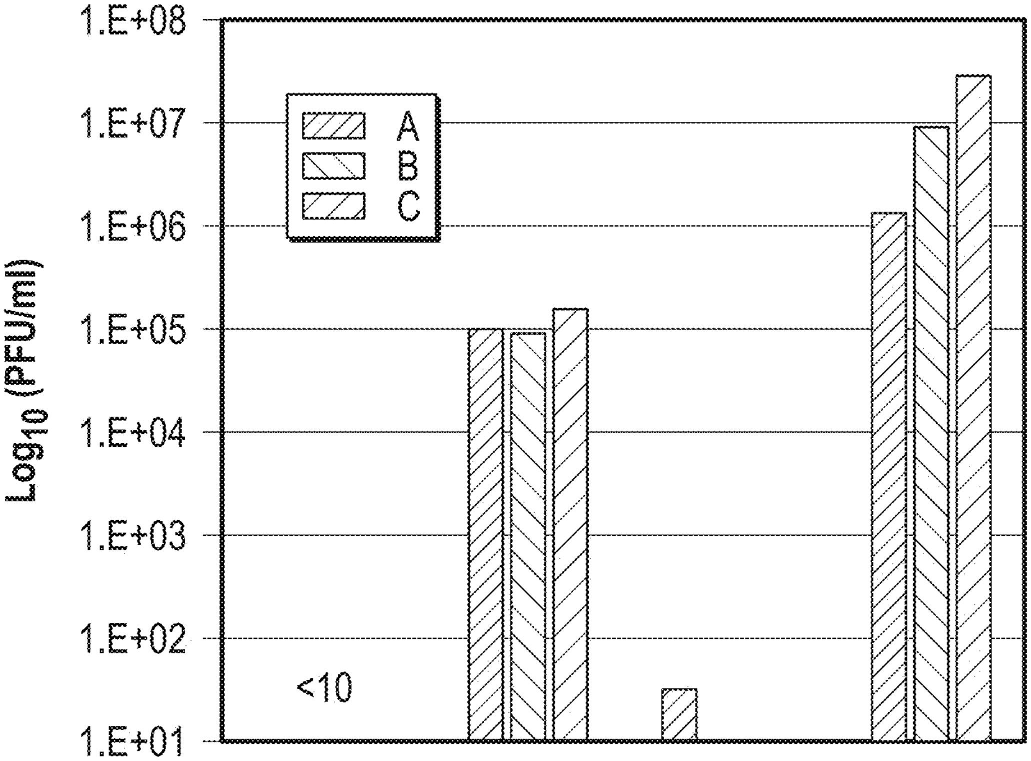
FIG. 7. Graph of virus titer in eggs for reassortants with two different backbones (PA, PB1, PB2, NP, NS and M) and two different HA and NA combinations (e.g., PB2-I504V, PB1-M40L/G180W, PA-R401K, NP-I116L, NS1-A30P/R118K; and NA of Y2017-M3L4 contains mutations; NA-T32A, D147N, N329D, H347Q and deletion of 46-50aa). Virus inoculation: $2\times10^3$ pfu/egg into allantoic fluid, 72 h incubation at 37° C.

The NA of Y2017-M3L4 allowed virus possessing HK4801HA to replicate efficiently in the allantoic cavity and the HY-PR8 backbone further enhanced the growth of this virus (FIG. 7).

In summary, described herein are influenza virus mutations that inhibit (e.g., prevent) the acquisition of antigenicity-compromising mutations in the hemagglutinin (HA) protein of influenza during growth in eggs and/or allow for enhanced replication. In one embodiment, the mutations are within the neuraminidase (NA) viral segment of human influenza viruses, and the mutant NA proteins stabilize the HA protein during egg-passages. Thus, in the presence of the mutant NA proteins, the HA protein does not acquire egg-adapting mutations. In some cases, the respective mutations in NA can also increase the yield of vaccine viruses.

Figure 12:
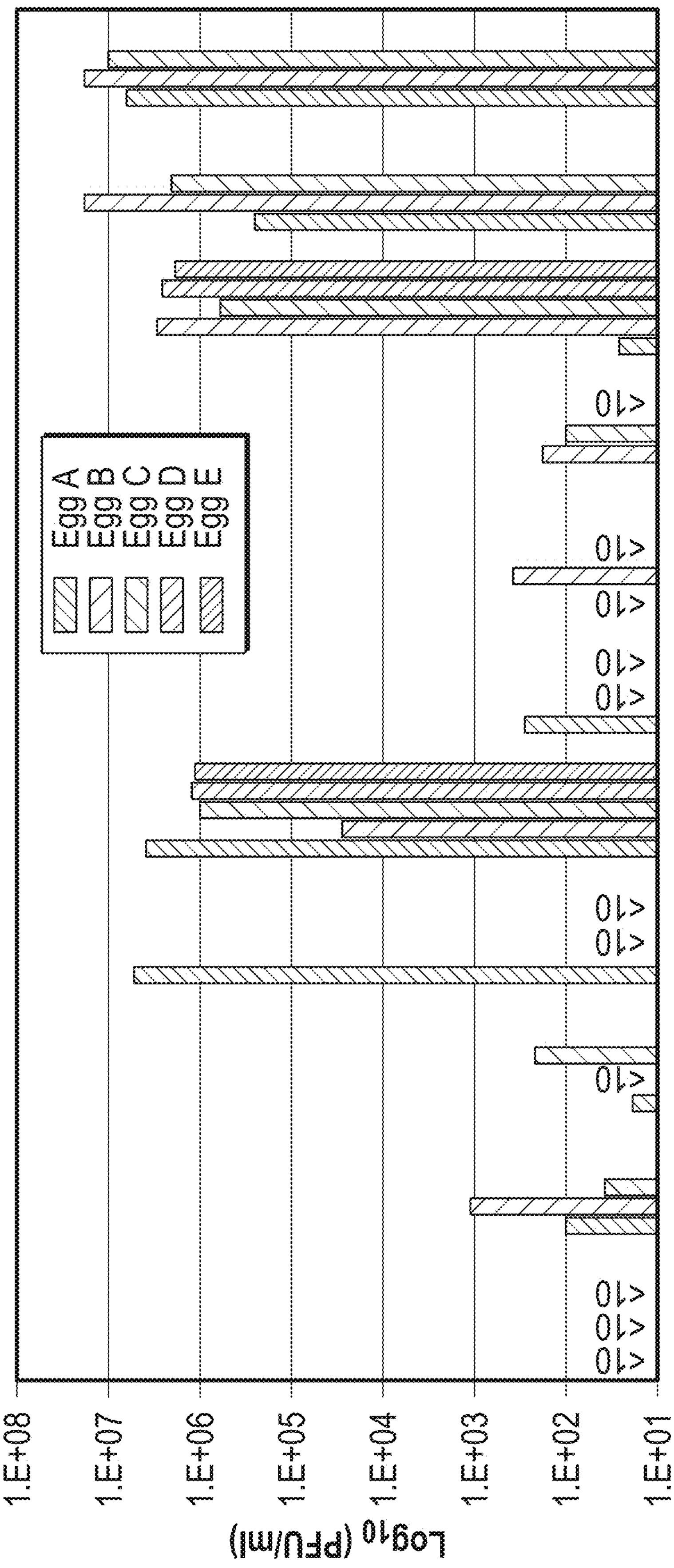
FIG. 12. Titers in eggs for various NA mutants.
Figure 15:
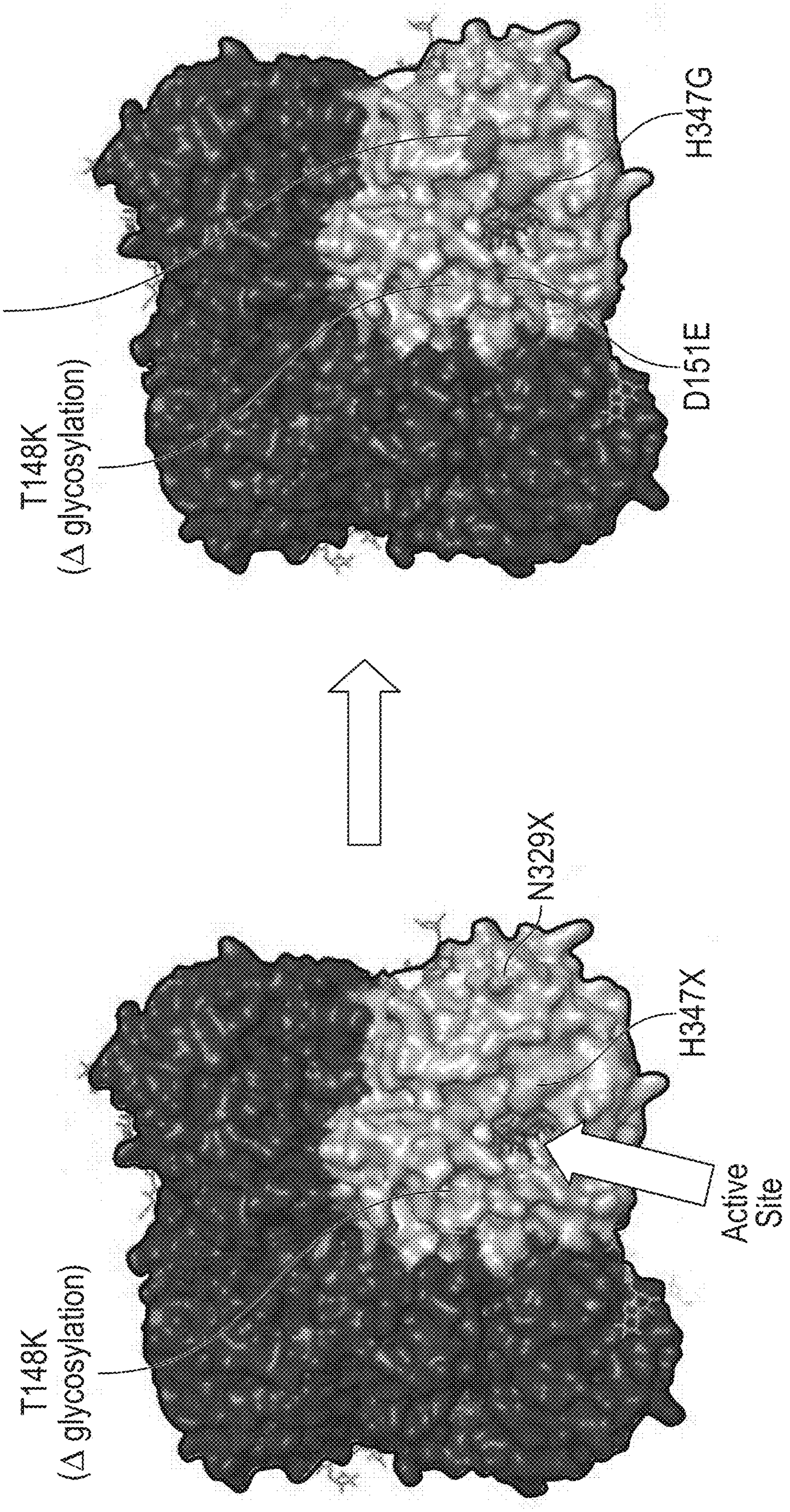
FIG. 15 is a schematic of the positions of certain NA residues.

Analysis of the growth capability of NA mutant viruses revealed that NA-D147N, N329D, and H347Q contribute to the increased growth capability of the viruses in allantoic fluid (FIG. 12). HA mutations were not observed in the virus possessing HK4801HA, Y2017-M3L4NA, and the HY-PR8 backbone (FIG. 13) after 3 passages in the allantoic cavity.

By passaging an HY-PR8 backbone virus possessing HK4801NA (T148K and the saturated mutations N329X and H347X) and HK4801HA in eggs, a virus possessing HK4801NA (T148K, D151E, H347G, and T369K) emerged that replicated efficiently in the allantoic cavity (FIG. 14; 4M=T148K, D151E, H347G, and T369K). HA mutations were not observed during passages in eggs (lx in the amniotic cavity then 5x in the allantoic cavity).

Figure 16:
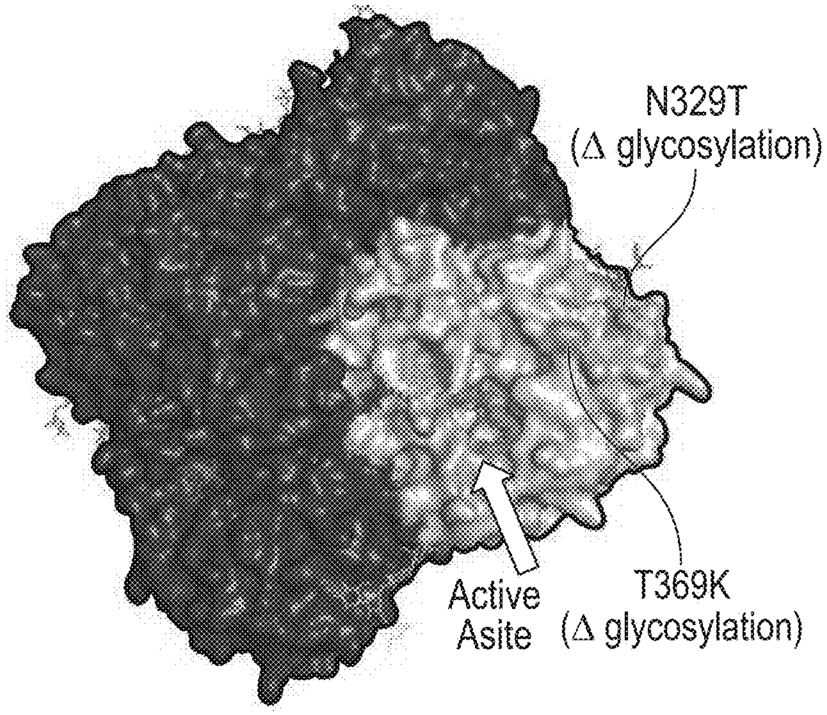
FIG. 16 is a schematic of the positions of certain NA residues.
Figure 17:
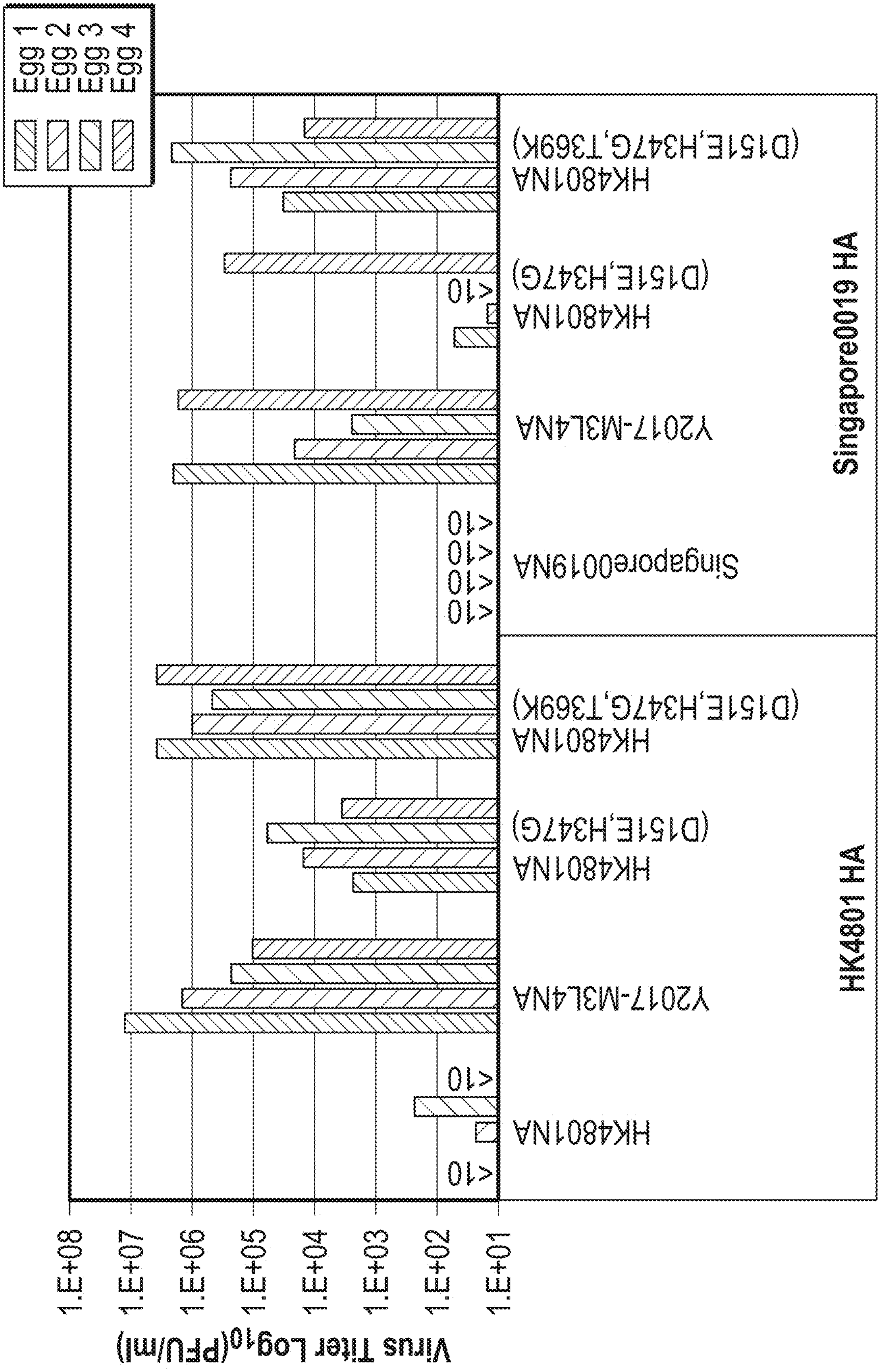
FIG. 17 shows virus titers for egg passaged isolates (HK4801NA (T148K, D151E, H347G, and T369K)) conferred efficient replication in the allantoic cavity to viruses possessing either HK4801HA or Singapore0019 HA (HY-PR8 backbone).

HK4801NA (T148K, D151E, H347G, and T369K) conferred efficient replication in the allantoic cavity to HY-PR8 backbone viruses possessing either HK4801HA or Singapore0019HA. Virus inoculation: $2\times10^3$ pfu/egg into allantoic fluid, 72 h incubation at 37° C. (FIG. 16).

The HA coding nucleic acid sequence and NA coding nucleic acid and amino acid sequences for Singapore0019 are as follows:

```
A/Singapore/INFINH-16-0019/2016(H3N2) HA
                                   (SEQ ID NO: 46)
atgaagactatcattggtttgagctacattctatgtctggttttcgctca

aaaaattcctggaaatgacaatagcacggcaacgctgtgccttgggcacc

atgcagtaccaaacggaacgatagtgaaaacaatcacaaatgaccgaatt

gaagttactaatgctactgagttggttcaaaattcctcaataggtaaaat

atgcgacagtcctcatcagatccttgatggagagaactgcacactaatag

atgctctattgggagaccctcagtgtgatggctttcaaaataagaaatgg

gacctttttgttgaacgaagcaaagcctacaggaactgttaccatatgat
```

-continued

```
gtgccggattatgcctcccttaggtcactagttgcctcatccggcacact

ggagtttaaaaatgaaagcttcaattggactggagtcactcaaaacggaa

caagttctgcttgcataaggggatctagtagtagtttctttagtagatta

aattggttgacccacttaaactacacatatccagcattgaacgtgactat

gccaaacaaggaacaatttgagaaattgtacatttgggggttcaccacc

cgggtagggacaaggaccaaatcttcctgtatgctcaatcatcaggaaga

atcacagtatctaccaaaagaagccaacaagctgtaatcccaaatatcgg

atctagaccgagaataagggatatcgctagcagaataagcatctattgga

caatagtaaaaccgggagacatacttttgattaacagcacagggaatcta

attgctcctaggggttacttcaaaatacgaagtgggaaaagctcaataat

gagatcagatgcacccattggcaaatgcaagtctgaatacatcactccaa

atggaagcattcccaatgacaaaccattccaaaatgtaaacaggatcaca

tacggggcctgtcccagatatgttaagcatagcactctgaaattggcaac

aggaatgcgaaatgtaccagagaaacaaactagaggcatatttggcgcaa

tagcgggtttcatagaaaatggttgggagggaatggtggatggttggtac

ggtttcaggcatcaaaattctgagggaagaggacaagcagcagatctcaa

aagcactcaagcagcaatcgatcaaatcaatgggaagctgaataggttga

tcggaaaaaccaacgagaaattccatcagattgaaaaagaattctcagaa

gtagaaggaagagttcaagaccttgagaaatatgttgaggacactaaaat

agatctctggtcatacaacgcggagcttcttgttgccctggagaaccaac

atacaattgatctaactgactcagaaatgaacaaactgtttgaaaaaaca

aagaagcaactgagggaaaatgctgaggatatgggaaatggttgtttcaa

aatataccacaaatgtgacaggcctgcatagaatcaataagaaatgaaac

ttatgaccacaatgtgtacagggatgaagcattgaacaaccggttccaga

tcaagggagttgagctgaagtcaggatacaaagattggatcctatggatt

tcctttgccatatcatgtttttttgctttgtgttgctttgttggggttcat

catgtgggcctgccaaaagggcaacattagatgcaacatttgcatttga

A/Singapore/INFINH-16-0019/2016(H3N2) NA
                                   (SEQ ID NO: 47)
atgaatccaaatcaaaagataataacgattggctctgtttctctcaccat

ttccacaatatgcttcttcatgcaaattgccatcctgataactactgtaa

cattgcatttcaagcaatatgaattcaactccccccaaacaaccaagtg

atgctgtgtgaaccaacaataatagaaagaaacataacagagatagtgta

tttgaccaacaccaccatagagaaggaaatatgccccaaaccagcagaat

acagaaattggtcaaaaccgcaatgtggcattacaggatttgcacctttc

tctaaggacaattcgattaggctttccgctggtggggacatctgggtgac

aagagaaccttatgtgtcatgcgatcctgacaagtgttatcaatttgccc

ttggacagggaacaacactaaacaacgtgcattcaaataacacagtacgt

gataggaccccttatcggactctattgatgaatgagttgggtgttccttt

ccatctggggaccaagcaagtgtgcatagcatggtccagctcaagttgtc

acgatggaaaagcatggctgcatgtttgtataacgggggatgataaaaat
```

-continued acaactgctagcttcatttacaatgggaggcttatagatagtgttgtttc atggtccaaagatattctcaggacccaggagtcagaatgcgtttgtatca atggaacttgtacagtagtaatgactgatggaaatgctacaggaaaagct gatactaaaatactattcattgaggaggggaaaatcgttcatactagcaa attgtcaggaagtgctcagcatgtcgaagagtgctcttgctatcctcgat atcctggtgtcagatgtgtctgcagagacaactggaaaggatccaaccgg cccatcgtagatataaacataaaggatcatagcattgtttccagttatgt gtgttcaggacttgttggagacacacccagaaaaaacgacagctccagca gtagccattgtttgaatcctaacaatgaagaaggtggtcatggagtgaaa ggctgggcctttgatgatggaaatgacgtgtggatggggagaacaatcaa cgagacgtcacgcttagggtatgaaaccttcaaagtcgttgaaggctggt ccaaccctaagtccaaattgcagataaataggcaagtcatagttgacaga ggtgataggtccggttattctggtatttttctctgttgaaggcaaaagctg catcaatcggtgcttttatgtggagttgattaggggaagaaaagaggaaa ctgaagtcttgtggacctcaaacagtattgttgtgtttgtggcacctca ggtacatatggaacaggctcatggcctgatggggcggacctcaatctcat gcatatataa which encodes (SEQ ID NO: 48)

M N P N Q K I I T I G S V S L T I S T I C F F M Q

I A I L I T T V T L H F K Q Y E F N S P P N N Q V

M L C E P T I I E R N I T E I V Y L T N T T I E K

E I C P K P A E Y R N W S K P Q C G I T G F A P F

S K D N S I R L S A G G D I W V T R E P Y V S C D

P D K C Y Q F A L G Q G T T L N N V H S N N T V R

D R T P Y R T L L M N E L G V P F H L G T K Q V C

I A W S S S S C H D G K A W L H V C I T G D D K N

A T A S F I Y N G R L I D S V V S W S K D I L R T

Q E S E C V C I N G T C T V V M T D G N A T G K A

D T K I L F I E E G K I V H T S K L S G S A Q H V

E E C S C Y P R Y P G V R C V C R D N W K G S N R

P I V D I N I K D H S I V S S Y V C S G L V G D T

P R K N D S S S S S H C L N P N N E E G G H G V K

G W A F D D G N D V W M G R T I N E T S R L G Y E

T F K V V E G W S N P K S K L Q I N R Q V I V D R

G D R S G Y S G I F S V E G K S C I N R C F Y V E

L I R G R K E E T E V L W T S N S I V V F C G T S

G T Y G T G S W P D G A D L N L M H I.

Figure 18:
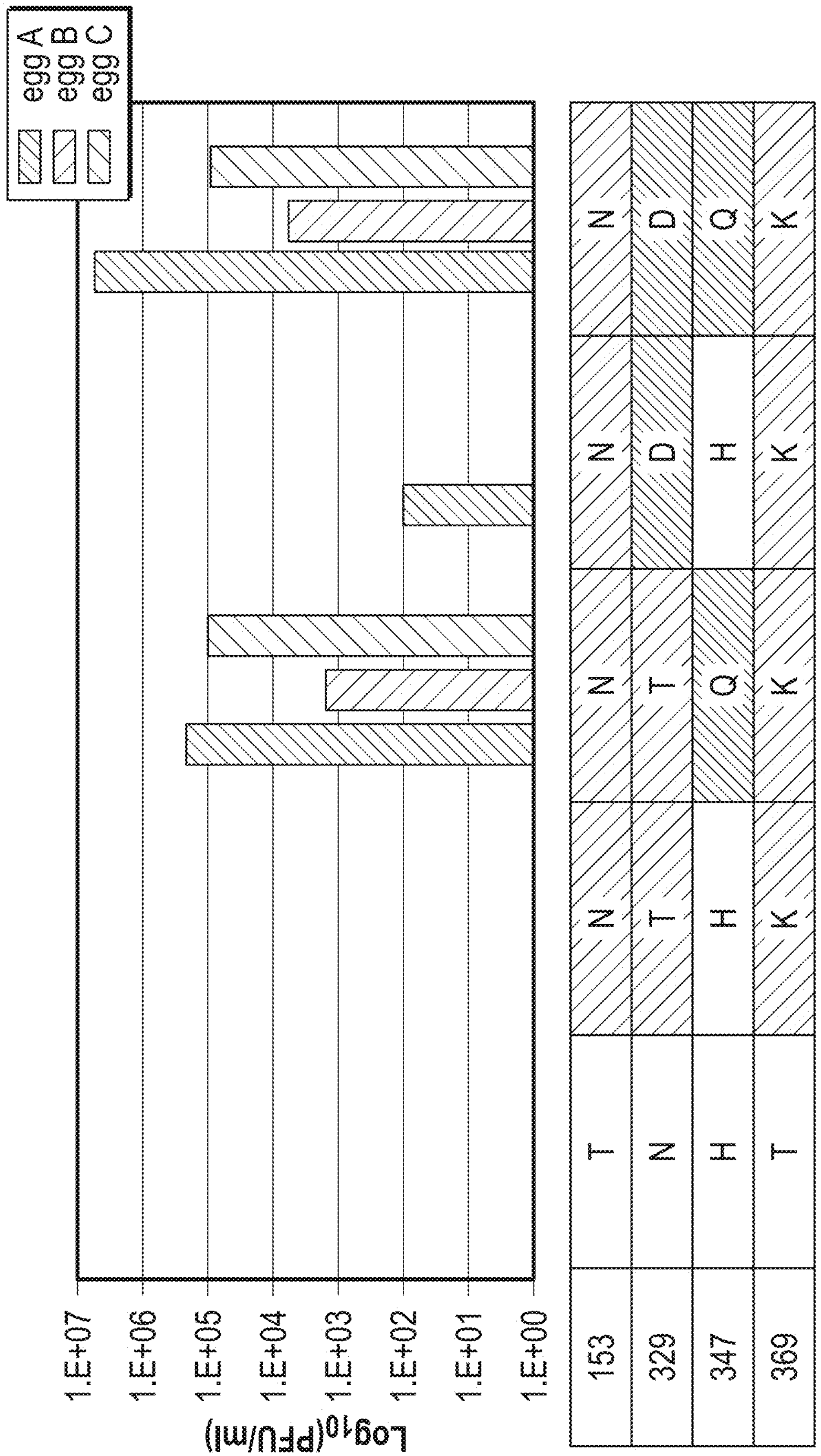
FIG. 18 shows egg titers for different combinations of selected residues at positions 153, 329, 347, and 369 in NA.

NA mutations T153N, N329T, and T369K allowed A/Saitama/102/2014 (H3N2) to replicate efficiently in the allantoic cavity (Kuwahara et al., 2018). Therefore, the effect of introducing NA-T153N, N329T (or D), T369K, and H347Q into HK4801NA (T148K) was examined. FIG. 18 reports on virus titers for different combinations of NA residues identified in screenings. FIGS. 19 and 20 report on virus titers for viruses with different combinations of selected NA residues.

Figures 22, 23A:
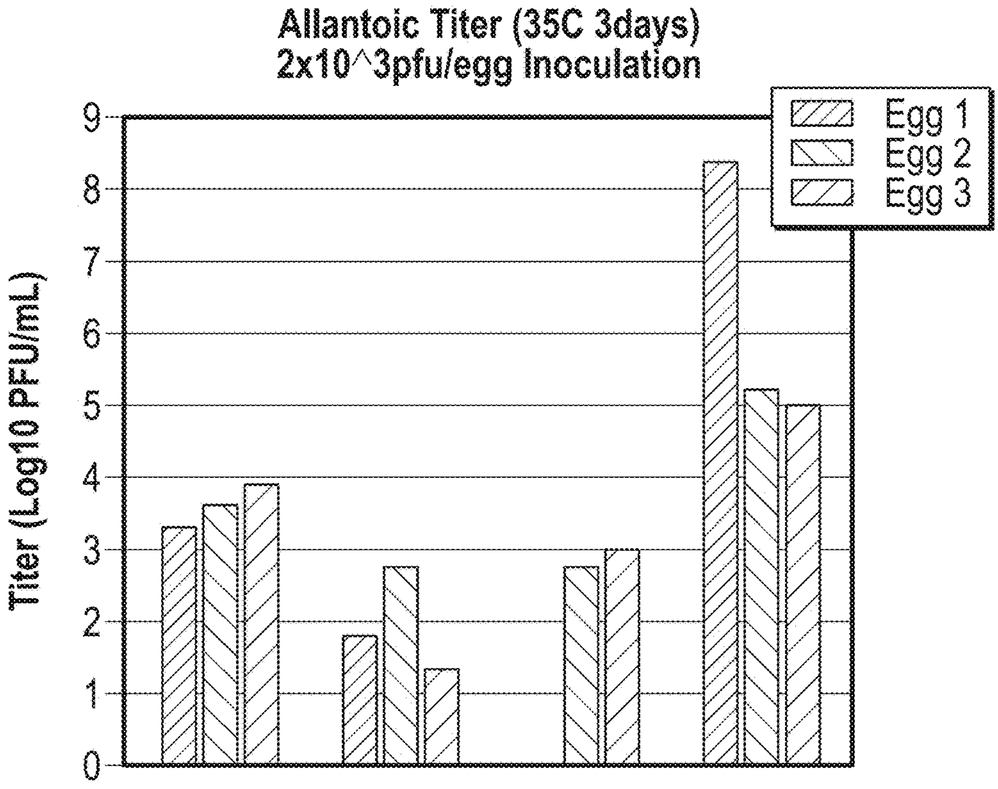
FIG. 22 shows detection of HA status after multiple passages.
FIGS. 23A-23B show egg titers for viruses with different NAs.

Alaska/232/2015_HY-PR8 (H3N2) WT/mutant virus were passaged in eggs and HA and NA segments sequenced. Alaska WT (a more recent H3N2 virus where WT has 245N, prior to 2015 H3N2 WT viruses had 245S), HA-R142S, -K189E viruses did not get mutations in HA, even after 3 amniotic and 10 allantoic passages. HA-K189E/N158K/A212T mutant did not get mutations in HA, but had some mutations in NA which exhibited improved growth in eggs since p6 (FIG. 21). The difference of NA mutations between p4 (normal growth) (NA-N245S mutation, virus grows more than 1000 fold better than with NA-245N) and p6 (better growth) was G346V (FIG. 22). Therefore, G346V may also contribute to 50 adaptation to eggs.

The NA for A/Alaska/232/2015 has the following sequence:

(SEQ ID NO: 49)

mnpnqkiiti gsvsltisti cffmqiaili ttvtlhfkqy efnsppnnqv mlceptiier niteivyltn ttiekeicpk paeyrnwskp qcgitgfapf skdnsirlsa ggdiwvtrep yvscdpdkcy gfalgqgttl nnvhsnntvr drtpyrtllm nelgvplhlg tkqvciawss sschdgkawl hvcitgddkn atasfiyngr lvdsvvswsk dilrtqesec vcingtctvv mtdgnatgka dtkilfieeg kivhtsklsg saqhveeesc yprypgvrcv crdnwkgsnr pivdinikdh sivssyvcsg lvgdtprknd ssssshclnp nneegghgvk gwafddgndv wmgrtinets rlgyetfkvv egwsnpkskl qinrqvivdr gdrsgysgif svegkscinr cfyvelirgr keetevlwts nsivvfcgts gtygtgswpd gadlnimhi.

Figure 23B:
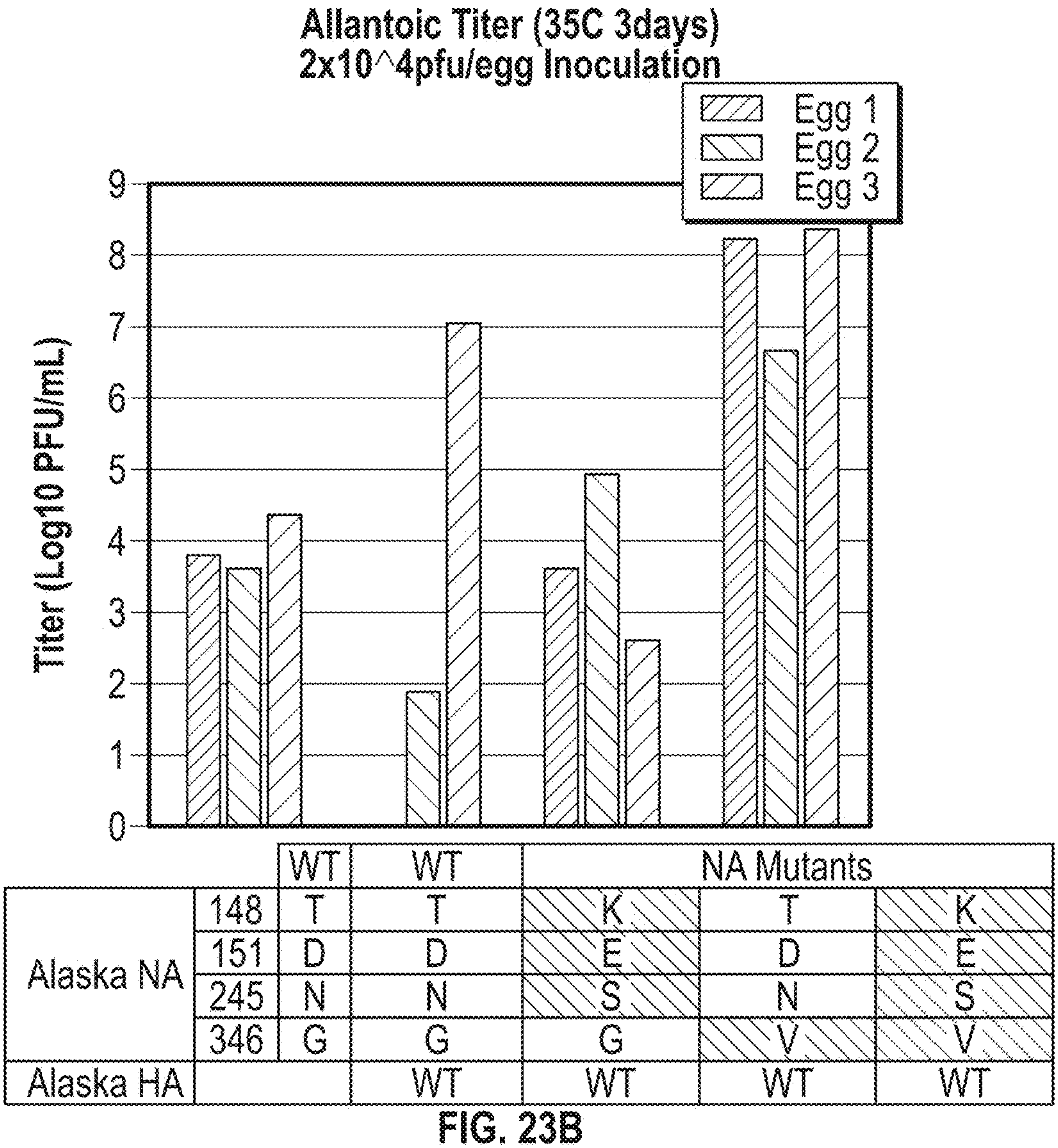
Figure 24:
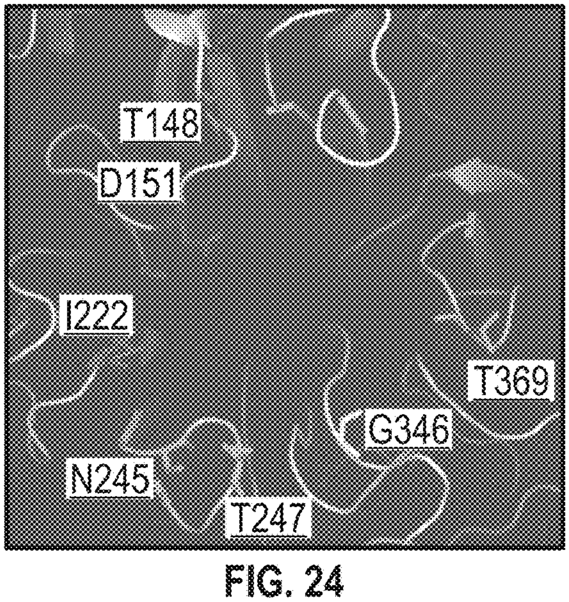
FIG. 24 is an enlarged view of the NA activity center. Most egg-adapted mutations are located in/around the NA active site.
Figure 25:
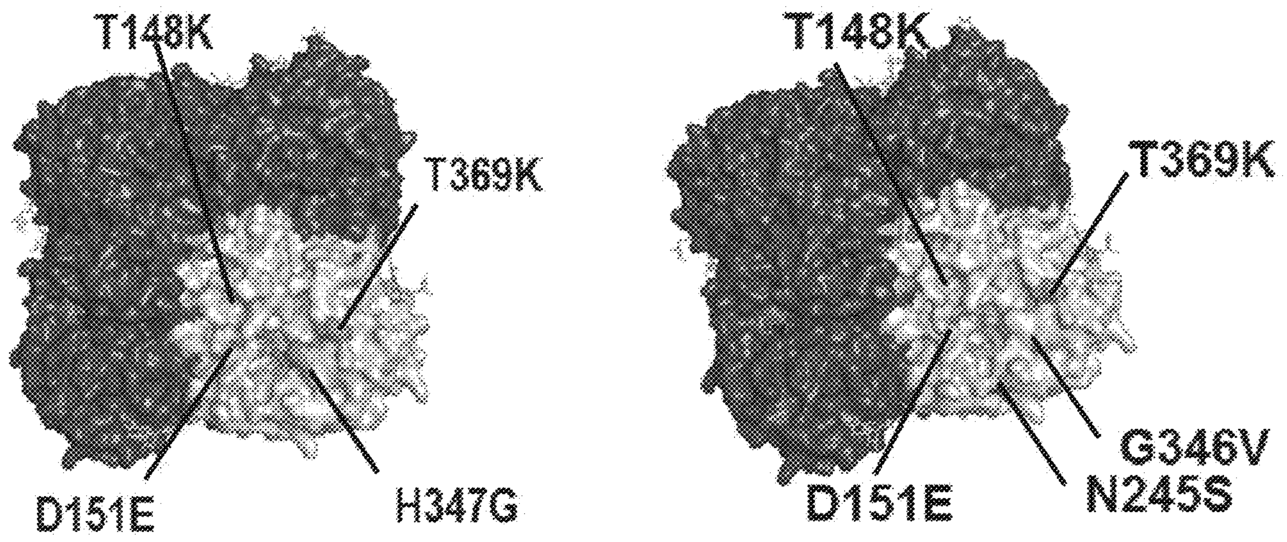
FIG. 25. Locations of amino acid substitutions in the neuraminidase proteins of egg-adapted influenza A/Hong Kong/4801/2014 (H3N2) and A/Alaska/232/2015 (H3N2) (SEQ ID Nos. 51-52).
Figure 26:
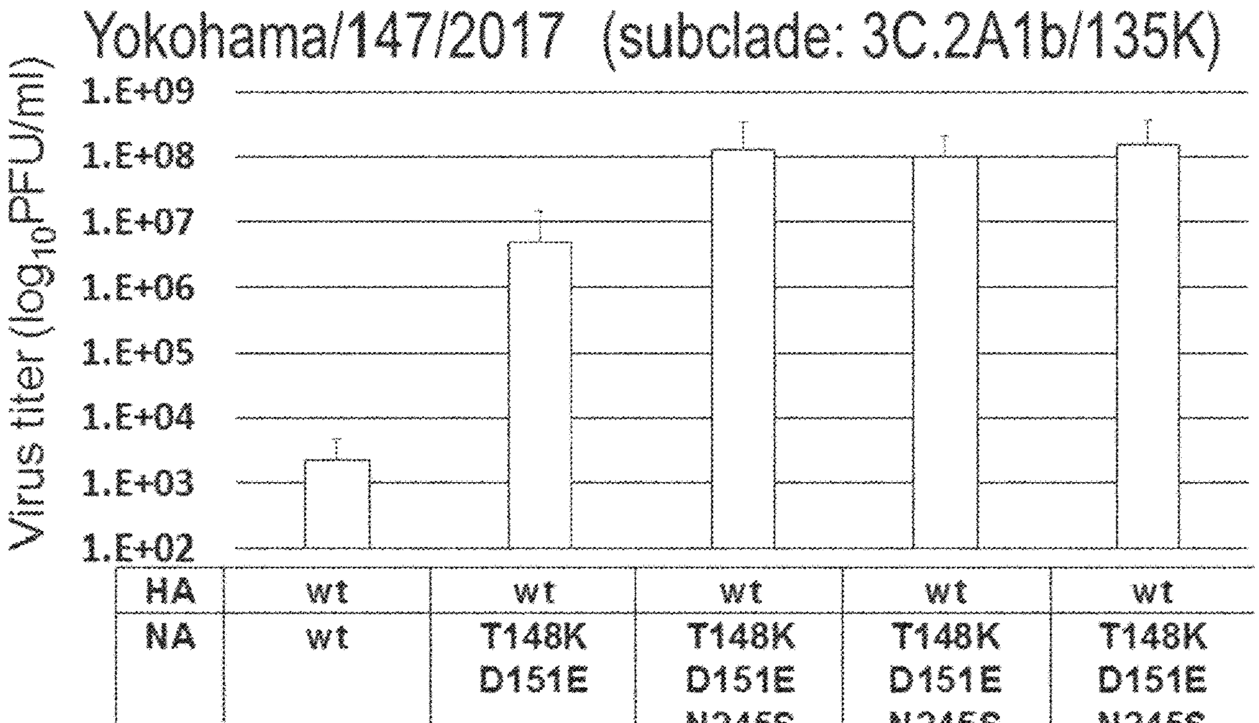
FIG. 26. Introduction of NA mutations (see FIG. 25) into the NA of H3N2 viruses from the 2017/18 season (SEQ ID NO:53) enhanced HY-PR8 backbone virus growth without HA mutations.
Figure 28:
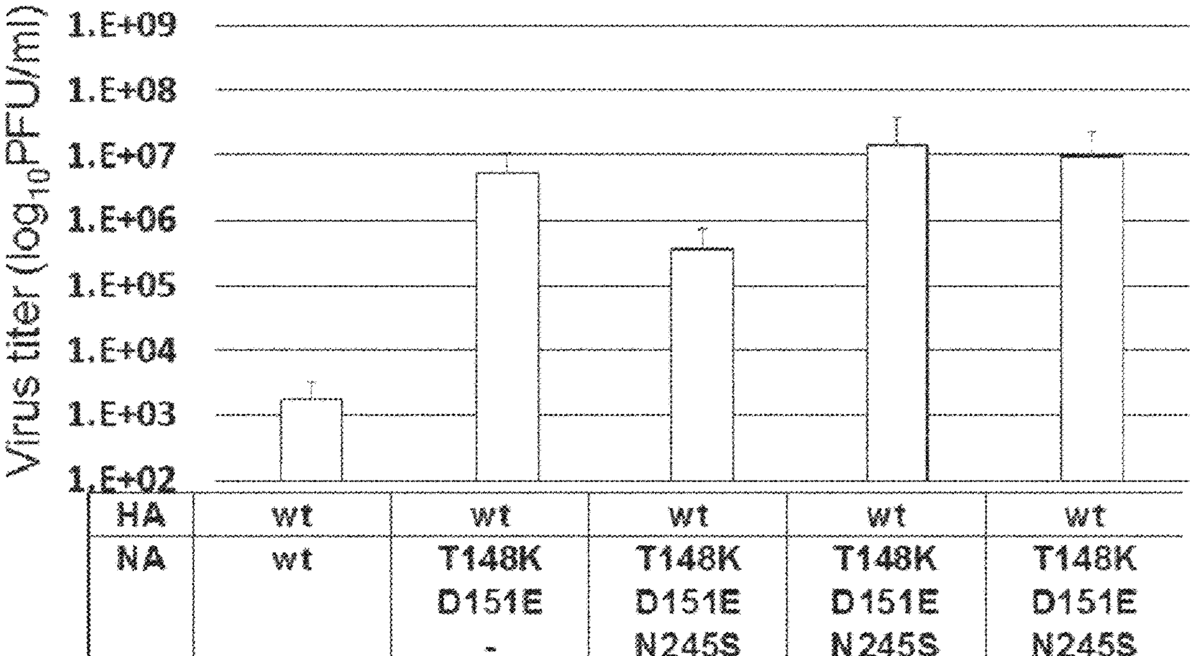
FIG. 28. Introduction of NA mutations into the NA of H3N2 viruses from the 2017/18 season enhanced HY-PR8 backbone virus growth without HA mutations.
Figure 30:
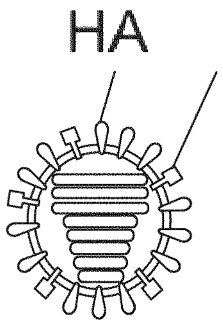
FIG. 30. The HY-PR8 backbone virus possessing A/Yokohama/48/2018HA and A/Yokohama/48/2018NA (T148K, D151E, N245S, H347G, and T369K) acquired the same NA-K148I mutation, and no HA mutations were detected (SEQ ID NO:54).
Figure 31:
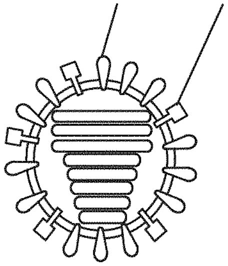
FIG. 31. A HY-PR8 backbone virus possessing A/Yokohama/48/2018HA and A/Yokohama/48/2018NA (T148I, D151E, N245S, H347G, and T369K) only acquired the HA-435L mutation in the stem region.

NA pHH21 plasmids were constructed: Alaska NA-T148K/D151E/N245S (found in E4); Alaska NA-G346V; and Alaska NA-T148K/D151E/N245S/G346V (found in E6). Mutant NAs were combined with WT Alaska HA or HY-PR8 backbone. Eggs were inoculated with the same dosage of WT/mutant Alaska viruses and harvested viruses titrated (FIG. 23). NA-T148K/D151E/N245S/G346V mutant virus grew to a higher titer than WT virus but the single mutation G346V did not increase virus growth compared to WT. These results suggested that a combination of G346V and one (or two to three) other mutations, e.g., 3 mutations such as T148K, D151E and N245S, may be important for virus Alaska virus to grow efficiently in eggs. Harvested virus samples with high titer (>5 Log 10 PFU/mL) were sequenced however none had additional mutations in HA and NA.

The invention will be described by the following non-limiting examples.

Example I

As shown in FIGS. 25-28, certain substitutions in N2 stabilized HA (e.g., did not allow for substitutions in HA) for up to about 8 passages in eggs in various H3N2 isolates from different influenza seasons. However, HA substitutions were found in some but not all isolates passaged in eggs for 10 passages (FIG. 29). Unexpectedly another change in NA (148I) was correlated with stabilizing HA even after more than 8 passages. The presence of that additional change in some cases resulted in a HA change but that change, in the stem region of HA (FIG. 32), is unlikely to alter antigenicity.

Figure 33:
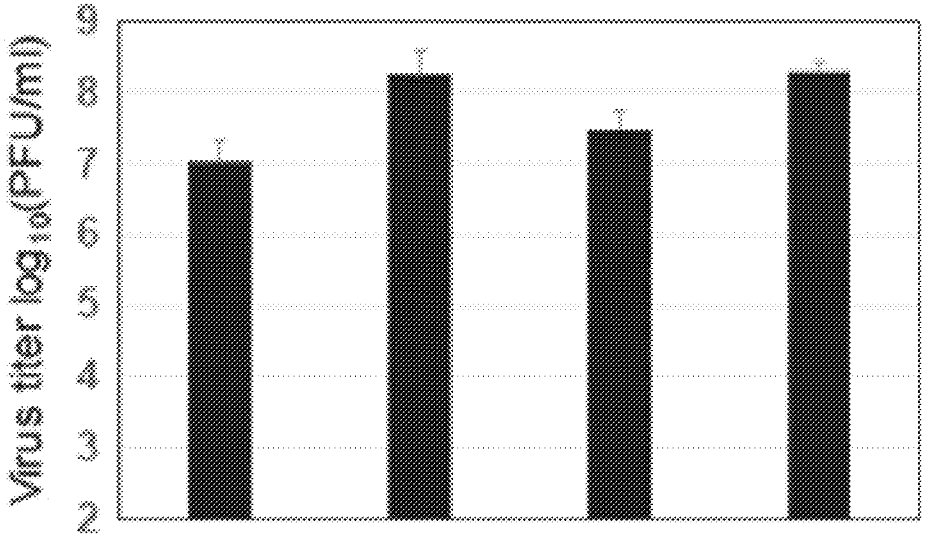
FIG. 33. Effect of introducing NA-T148I, D151E, N245S, H347G, and T369K into the NA of H3N2 viruses from the 2017/18 season.
Figure 34:
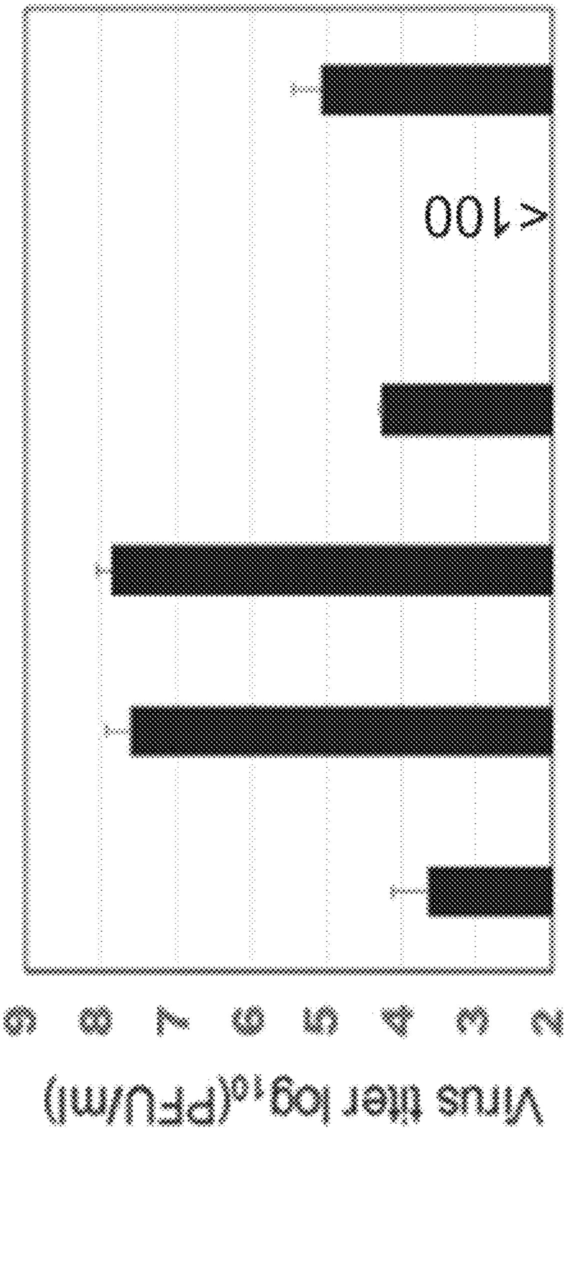
FIG. 34. Effect of introducing NA-T148I, D151E, N245S, H347G, and T369K into the NA of H3N2 viruses from the 2018/19 season (SEQ ID Nos. 55-56).
Figure 36:
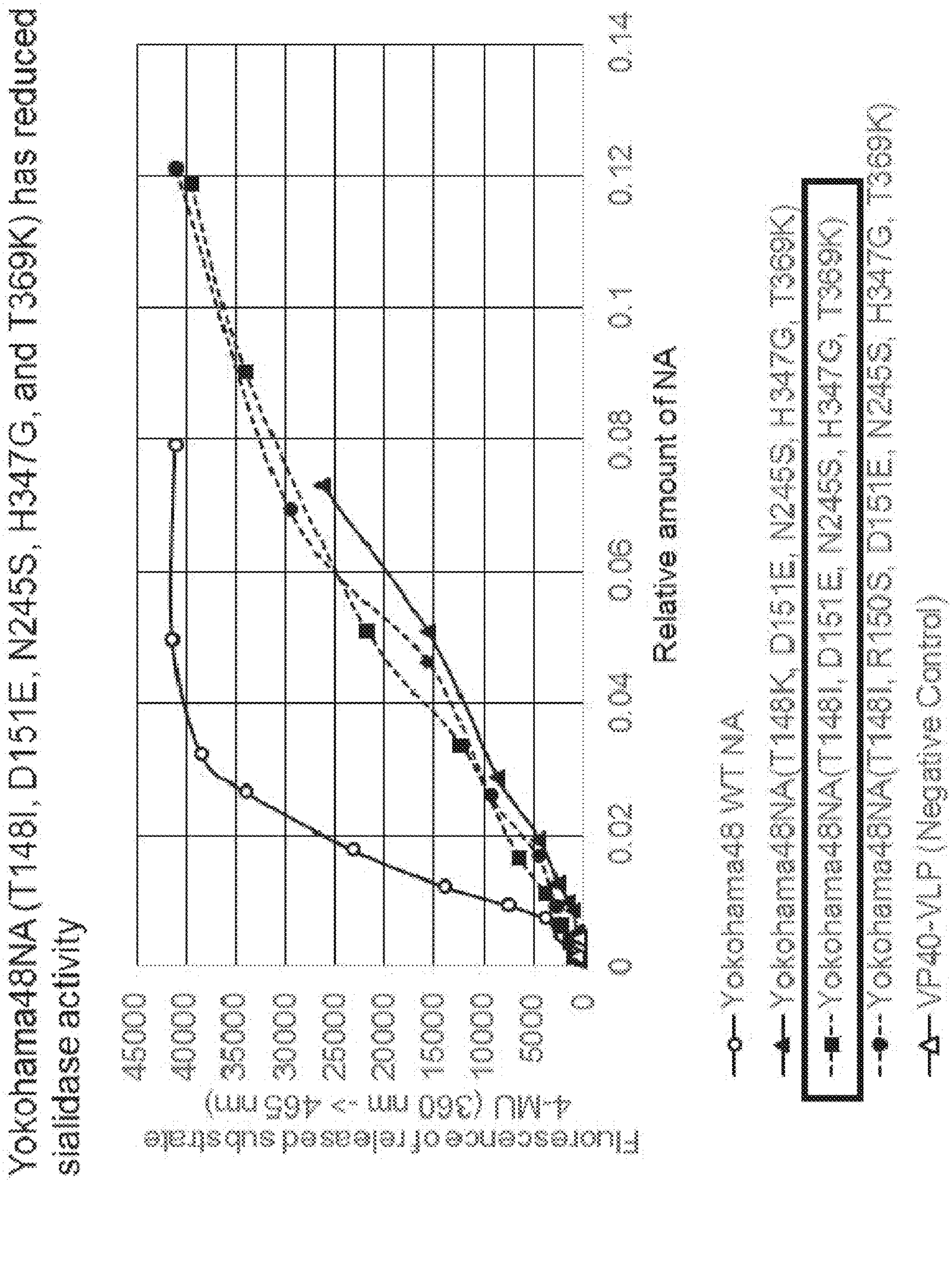
FIG. 36. Yokohama48NA (T148I, D151E, N245S, H347G, and T369K) has reduced sialidase activity.
Figure 37:
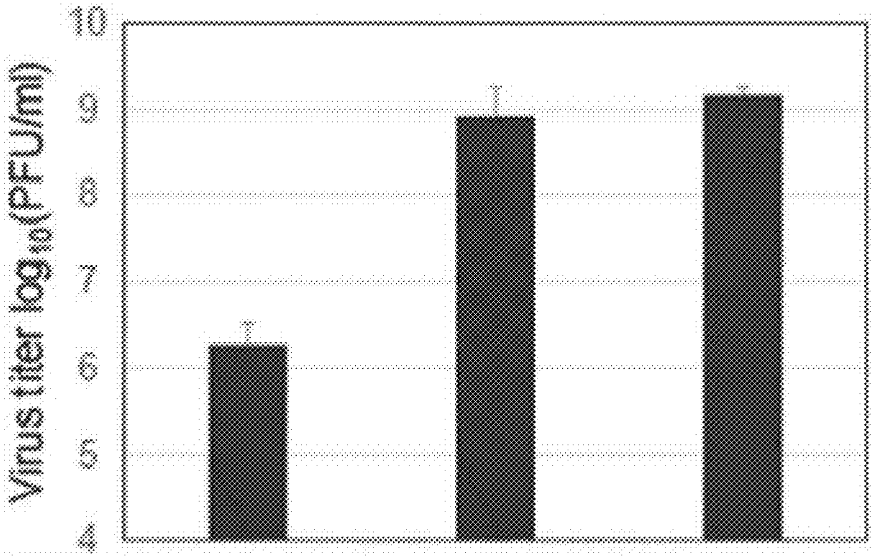
FIG. 37. The growth of Kansas/14/2017 (SEQ ID NO:59) was enhanced by introducing the NA mutations T148I, D151E, N245S, H347G, and T369K or by possessing Yokohama48NA (T148I, D151E, N245S, H347G, and T369K).

148I or 148K was introduced into the NA along with other substitutions that were identified (FIGS. 33-35). The addition of 148I did not substantially alter virus titer in eggs while 148K in some cases impacted titer. Interestingly, viruses having a NA with 148I in combination with other changes had reduced sialidase activity (FIG. 36). For example, viruses having a NA with 148I, 151E, 245S, 347G, and 369K and 148I, 150S, 151E, 245S, 347G and 369K, as well as viruses having a NA with 148K, 151E, 245S, 347G and 369K, had reduced sialidase activity.

Example II

Mutations in the influenza surface glycoprotein neuraminidase (NA) confer efficient replication to recent human H3N2 viruses in eggs without the acquisition of mutations at the antigenic sites of the other surface glycoprotein, (hemagglutinin) HA. With NA mutations, the mutant NAs recognize sialic acid linked to galactose via alpha 2-3 linkages (Siaa2-3 Gal) prevalent on epithelial cells in the chorioallantoic membrane in chicken eggs. The NA mutations allow the viruses to attach and enter cells even under conditions where the interaction between HA and its receptor is inhibited (FIG. 38), suggesting that the mutant NA serves as a receptor-binding protein in place of HA.

By possessing an HA protein with disrupted or no receptor-binding activity, the disclosed mutant NA may confer to influenza viruses such as H3N2 viruses efficient growth in embryonated chicken eggs without the acquisition of any egg-adaptive HA mutations at antigenic sites. Because HA does not encounter selective pressure to recognize the Siaa2-3 Gal receptor in the presence of the mutant NA, the amino acid residues around the HA receptor-binding pocket remain unchanged during passages in embryonated chicken eggs.

Figure 39A:
FIG. 39A. Position of sialic acid relative to residues in NA.
Figure 39B:
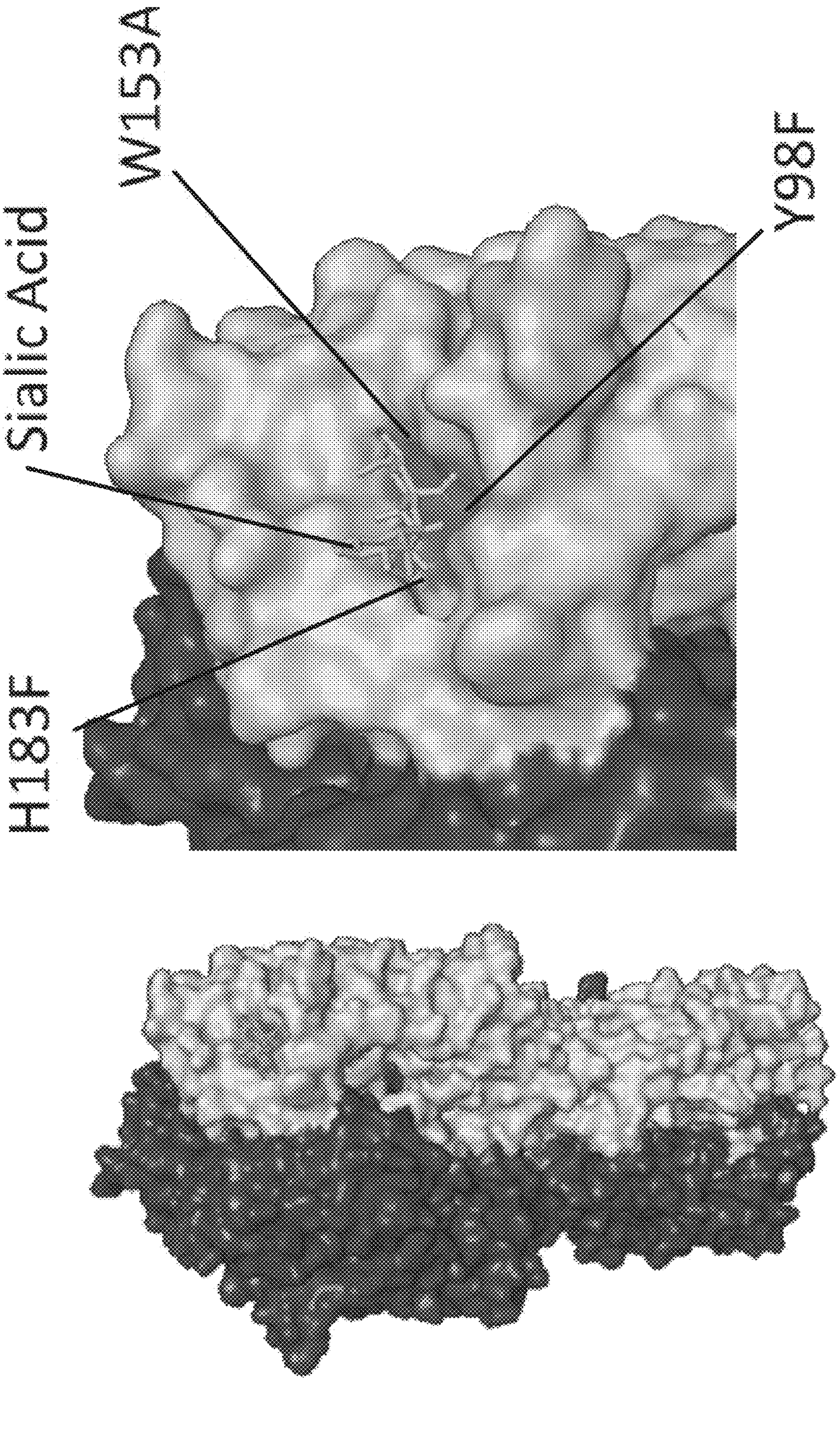
FIG. 39B. Enlarged view of FIG. 38A.
Figure 42:
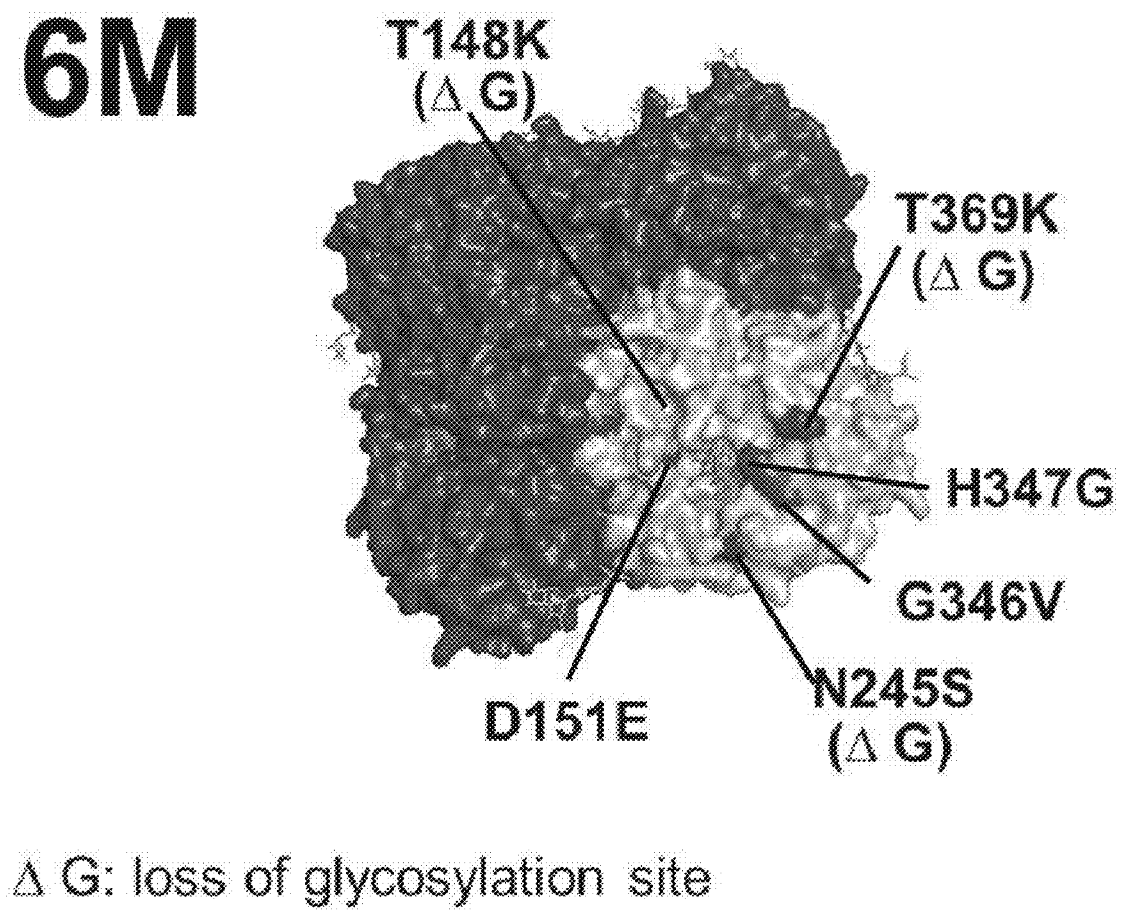
FIG. 42. Exemplary NA residues in 6M virus which were found in egg-grown A/Hong Kong/4801/2014 and A/Alaska/232/2015.

To this end, HA proteins are constructed that lacked or possessed limited receptor-binding activity but retained their antigenicity by introducing three mutations, e.g., Y98F, W153A, and H183F, at sites located inside the receptor-binding pocket that would not affect the antigenicity of the HA (FIGS. 39A-B).

Example III

Figure 43:
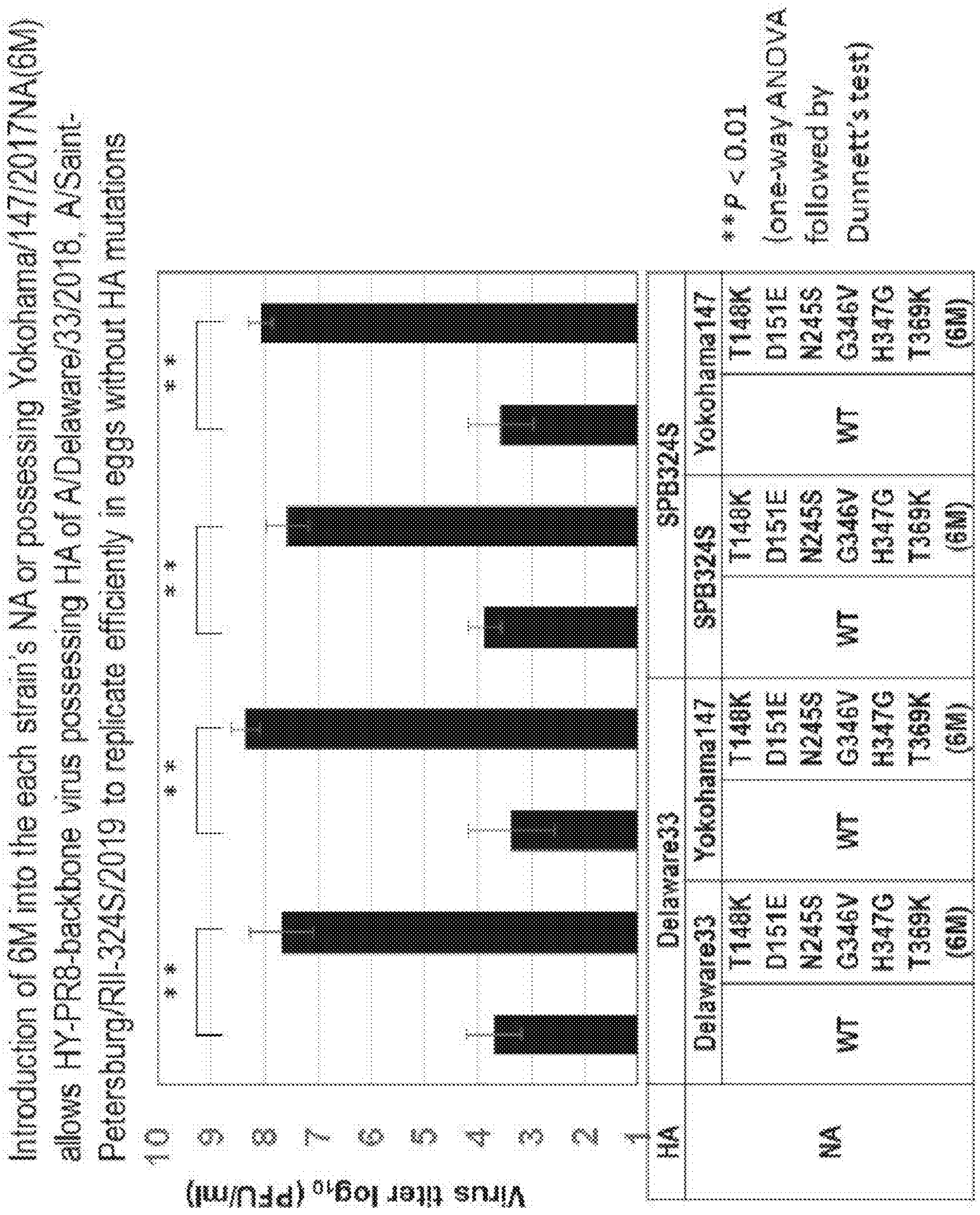
FIG. 43. Viruses in which 6M residues were introduced into the NA of A/Delaware/33/2018 and A/Saint-Petersburg/RII-324S/2019 and viruses possessing Yokohama/147/2017NA(6M) NA enhanced the virus growth of HY-PR8-backbone virus possessing wild type HA of A/Delaware/33/2018 or A/Saint-Petersburg/RII-324S/2019. Harvested viruses possessing each strain's NA(6M) or Yokohama/147/2017NA(6M) were sequenced however none had additional mutations in HA and NA.
Figure 44:
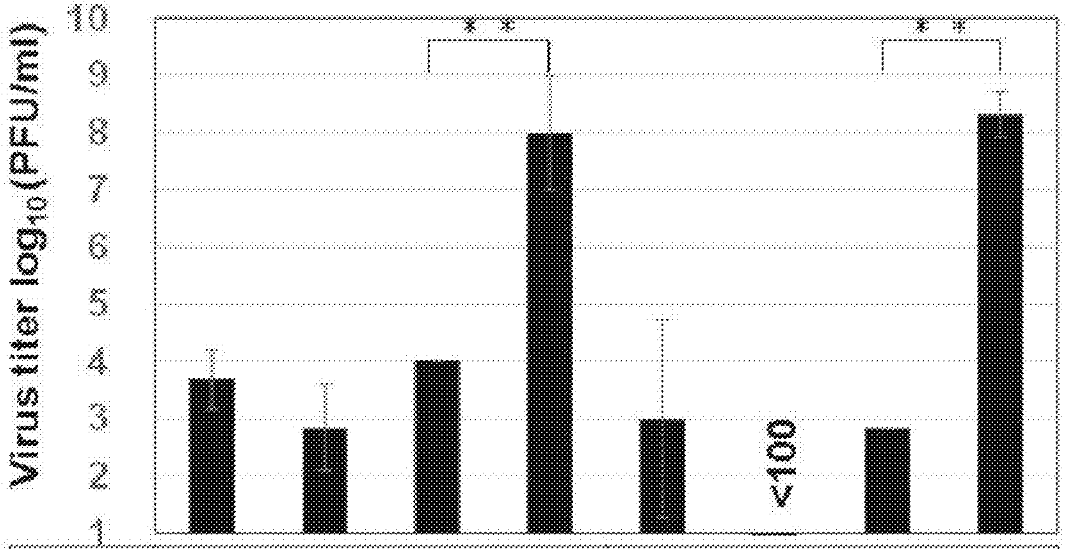
FIG. 44. Viruses in which 6M was introduced into the NA of A/Tokyo/UT-GR85/2019 and A/Kanagawa/IC1820/2019 did not enhance HY-PR8-backbone virus growth. However, viruses possessing Yokohama/147/2017NA(6M) showed enhanced the virus growth of HY-PR8-backbone virus possessing wild type HA of A/Tokyo/UT-GR85/2019 or A/Kanagawa/IC1820/2019 without HA mutations. Harvested viruses possessing Yokohama/147/2017NA(6M) were sequenced however none had additional mutations in HA and NA.
Figure 46:
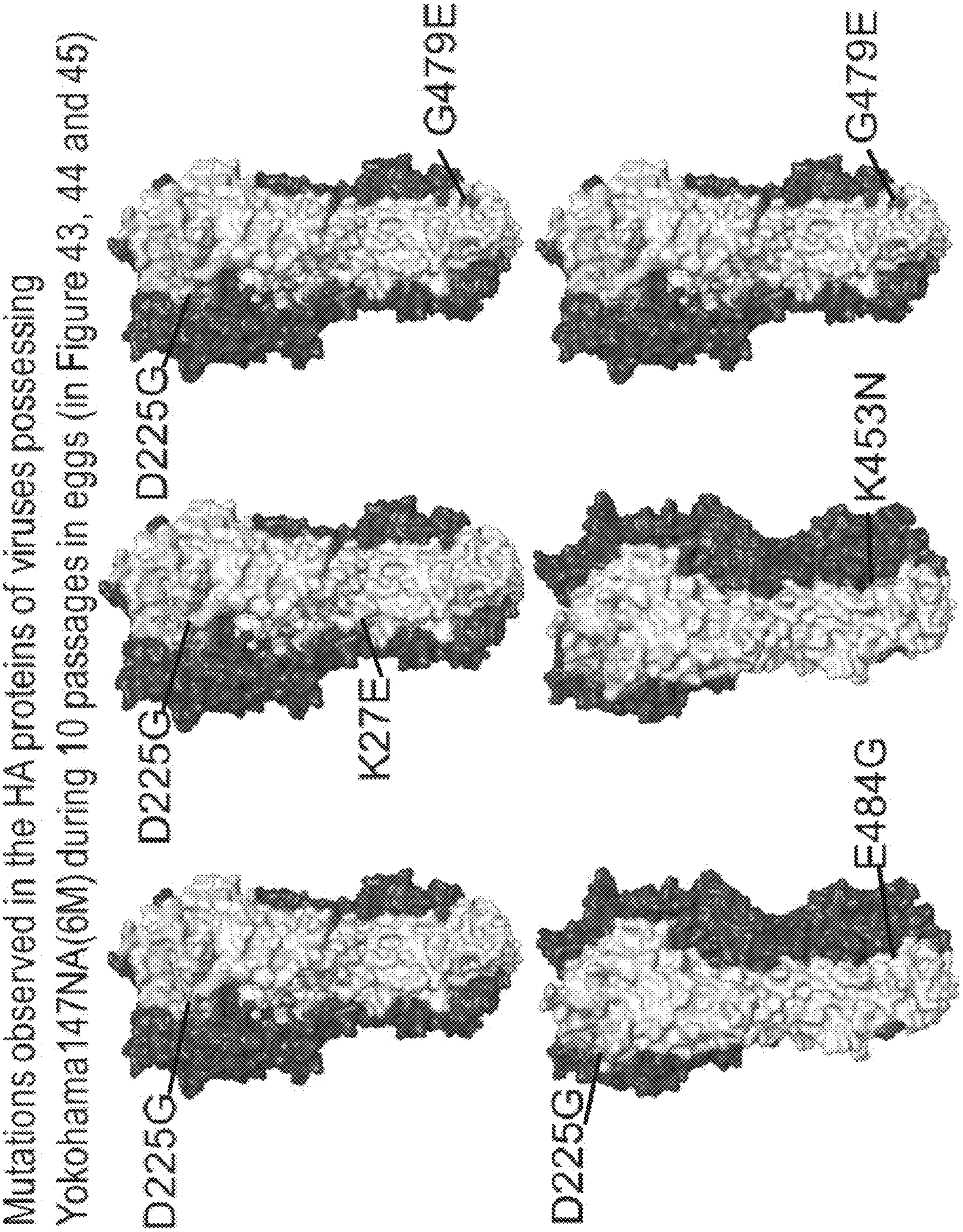
FIG. 46. Location of HA mutations occurred during egg passages (shown in FIG. 43) on the 3D structure of HA protein.
Figure 47:
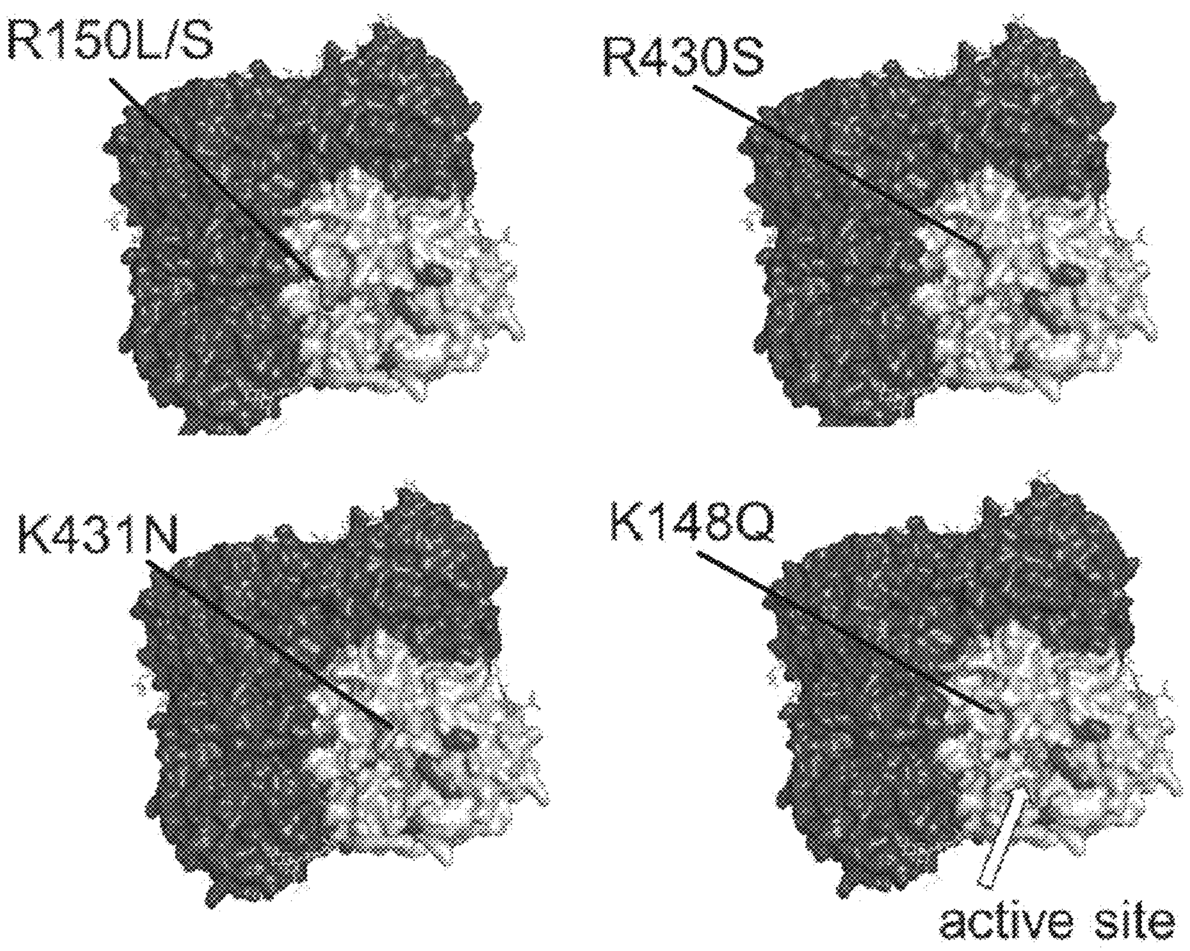
FIG. 47. Location of NA mutations occurred during egg passages (shown in FIG. 43) on the 3D structure of NA protein.

Exemplary NA residues were found in egg-grown A/Hong Kong/4801/2014 and A/Alaska/232/2015 ("6M"). Introducing 6M mutations into the NA of A/Yokohama/48/2018 and A/Yokohama/147/2017 enhanced HY-PR8-backbone virus growth. Therefore, the effect of introducing 6M mutations into other strains and the effect of possessing Yokohama147NA(6M) on the growth of viruses possessing HA from other strains was examined (FIGS. 43-44). Harvested viruses possessing each strain's NA(6M) or Yokohama/147/2017NA(6M) were sequenced. None had additional mutations in HA and NA were observed.

Viruses possessing A/Yokohama/147/2017 NA(6M) acquired HA-D225G and K27E after passage 10. HA-K27E is located in the stem region of HA protein, suggesting that K27E was unlikely to alter HA antigenicity. HA-D225G is located near receptor binding site. However, the reactivity of an H3N2 virus possessing HA-D225N with ferret antiserum differed from that of the wild-type virus by only two-fold, suggesting that HA-D225G alone was unlikely to alter HA antigenicity substantially (Chambers et al., Cell Rep. 2015).

It was analyzed whether the viruses possessing Yokohama147NA(6M) and HA from other strains can also replicate without acquiring HA mutations at major antigenic sites during egg passages. During egg passages, many of the tested viruses acquired HA-D225G but none of them acquired HA mutations at major antigenic sites. G479E, K453N, E484G (located in the stem region) and R545K (located in the cytoplasmic tail) were unlikely to alter HA antigenicity (FIG. 45).

Figure 48:
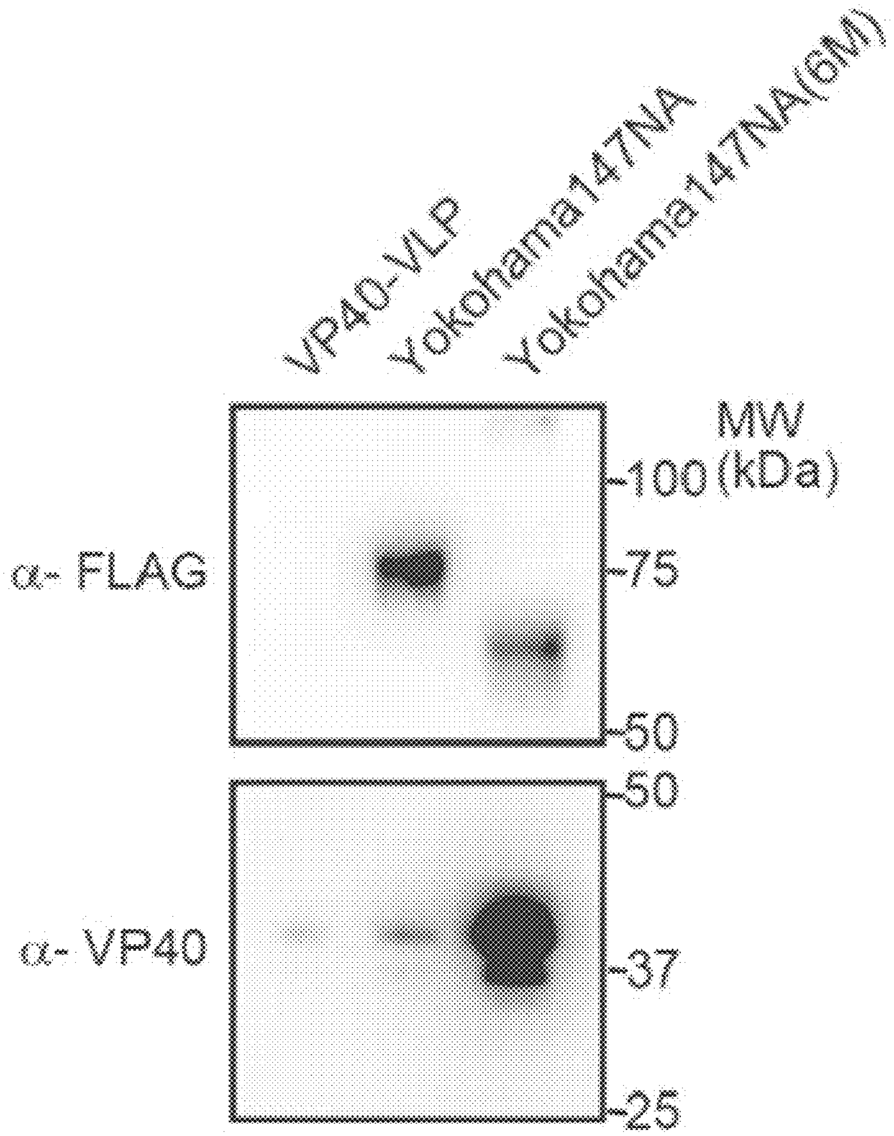
FIG. 48. Reduced molecular weight of Yokohama147NA (6M). VP40-induced VLPs bearing FLAG-tagged Yokohama147NA or Yokohama147NA(6M) were analyzed by immunoblotting with anti-FLAG and anti-VP40 antibodies.
Figure 49:
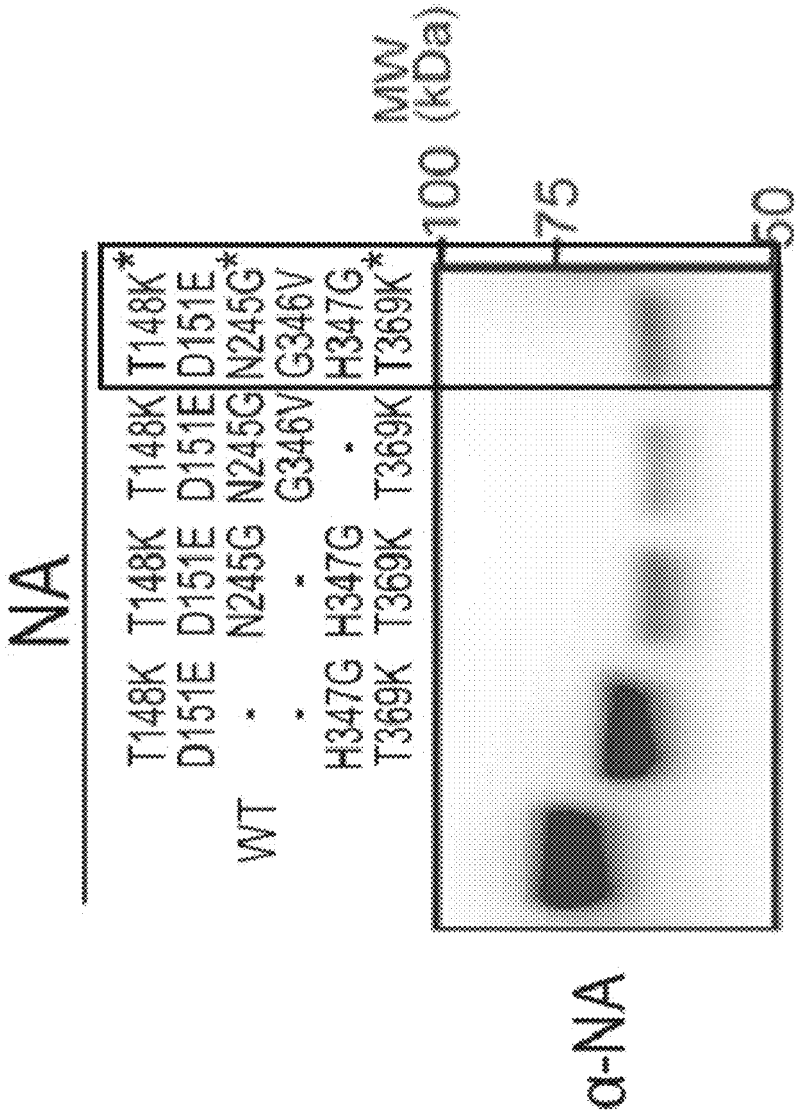
FIG. 49. Loss of glycosylation sites of NA protein due to mutations.

The mechanism of how the NA(6M) mutant viruses can replicate efficiently in eggs was investigated. VP40-induced VLPs bearing FLAG-tagged Yokohama147NA or Yokohama147NA(6M) were prepared. Immunoblotting analysis with anti-FLAG and anti-VP40 antibodies showed reduced molecular weight of Yokohama147NA(6M) protein compared to that of wild-type Yokohama147NA protein (FIG. 48). FIG. 49 shows another western blotting analysis suggesting the loss of glycosylation site of mutant NA protein due to the introduction of 6M mutations.

Figure 50:
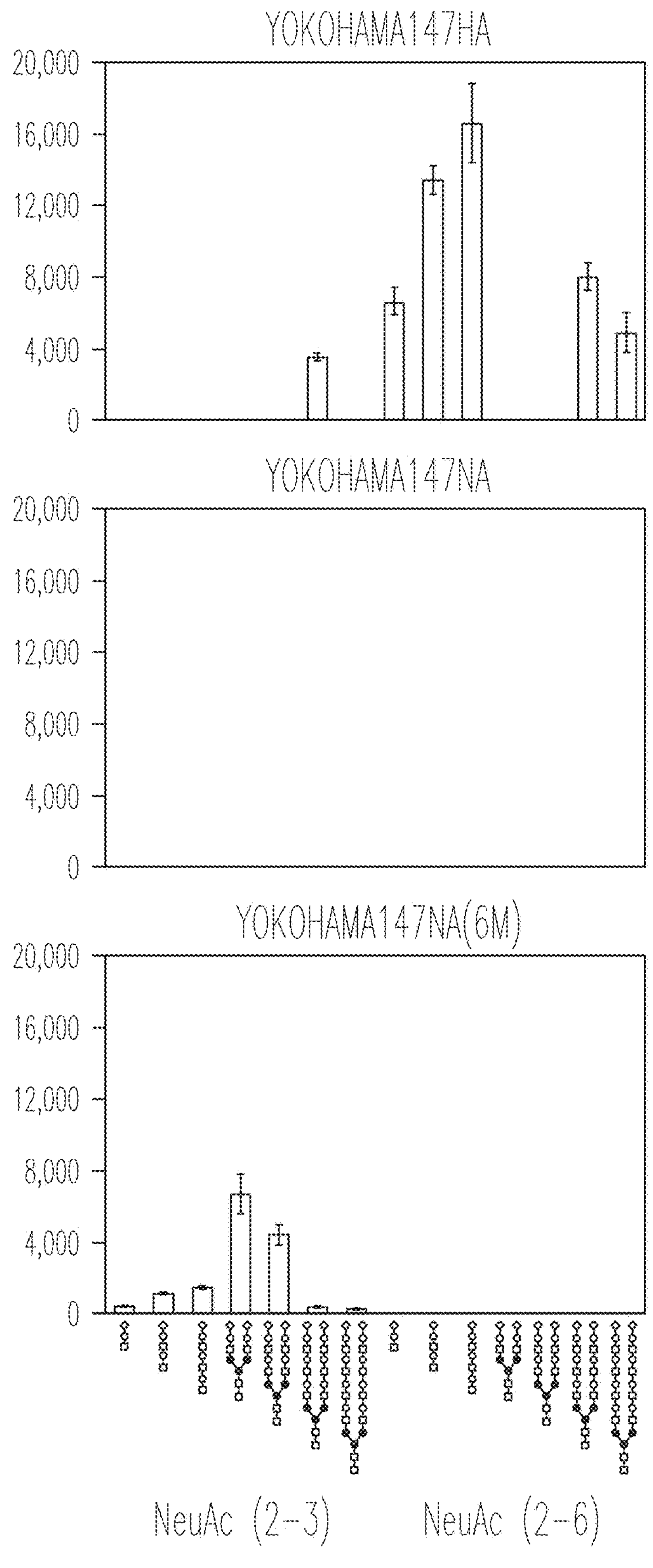
FIG. 50. Receptor-binding specificities of Yokohama147HA, Yokohama147NA, and Yokohama147NA(6M).

Next the receptor-binding specificities of Yokohama147HA, Yokohama147NA, and Yokohama147NA(6M) were analyzed using in a glycan microarray containing a library of a2-3 and a2-6 sialosides, including N-linked glycans representative of those found on chorioallantoic membranes of eggs. The analysis showed Yokohama147NA(6M) bound to a2-3 sialosides found on chorioallantoic membranes of eggs (FIG. 50).

Figure 51:
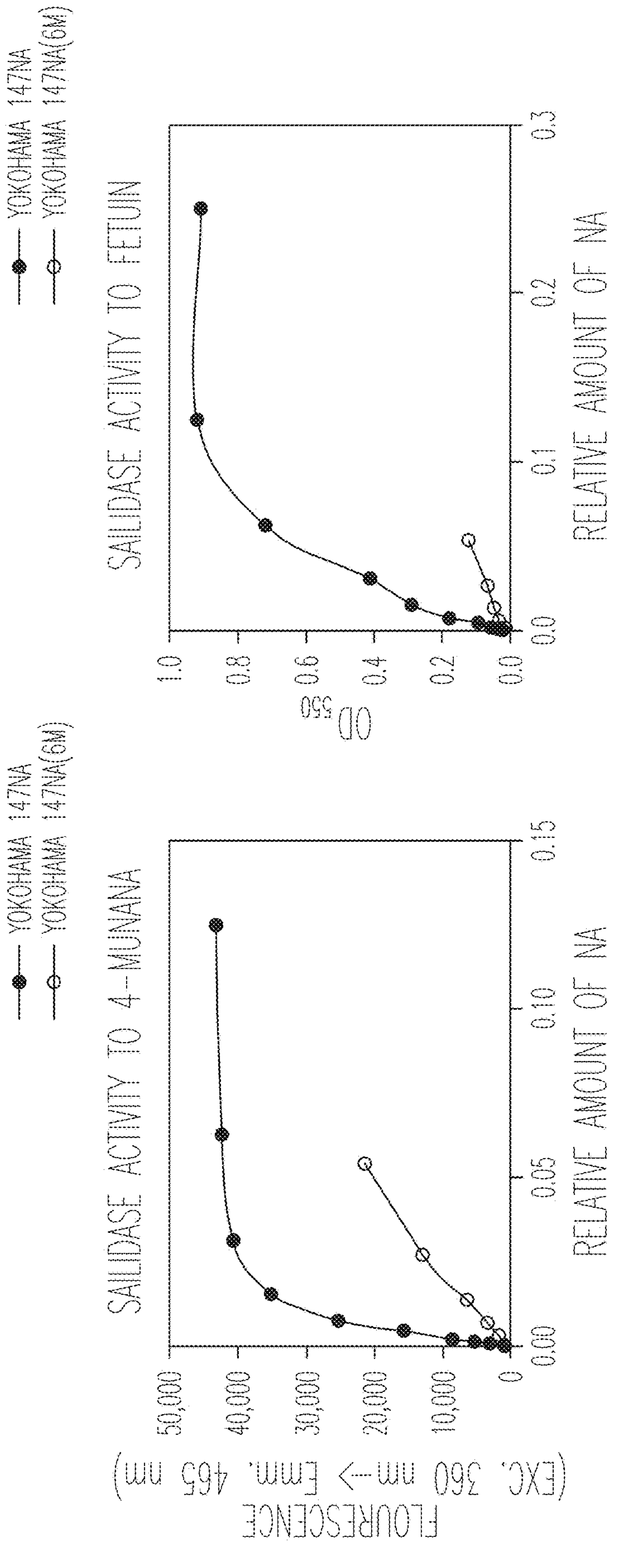
FIG. 51. Introduction of 6M into Yokohama147NA decreased sialidase activity.

It was determined whether 6M mutations alter the NA sialidase activity (FIG. 51). Ebola VP40-based VLPs bearing Yokohama147NA or NA(6M) were serially diluted, incubated with the sialidase substrate 4-MUNANA, and the released 4-MU was quantified to assess sialidase activity. The analysis revealed that introduction of 6M into Yokohama147NA decreased its sialidase activity.

Figure 52:
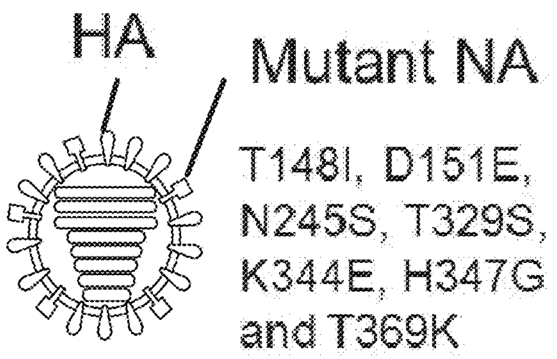
FIG. 52. HY-PR8 backbone virus possessing wild type HA and mutant NA(T148I, D151E, N245S, T329S, K344E, H347G and T369K) (=6M+T148I+T329S+K344E) from A/Kansas/14/2017NA acquired none of HA and NA mutations during egg passages.
Figure 53:
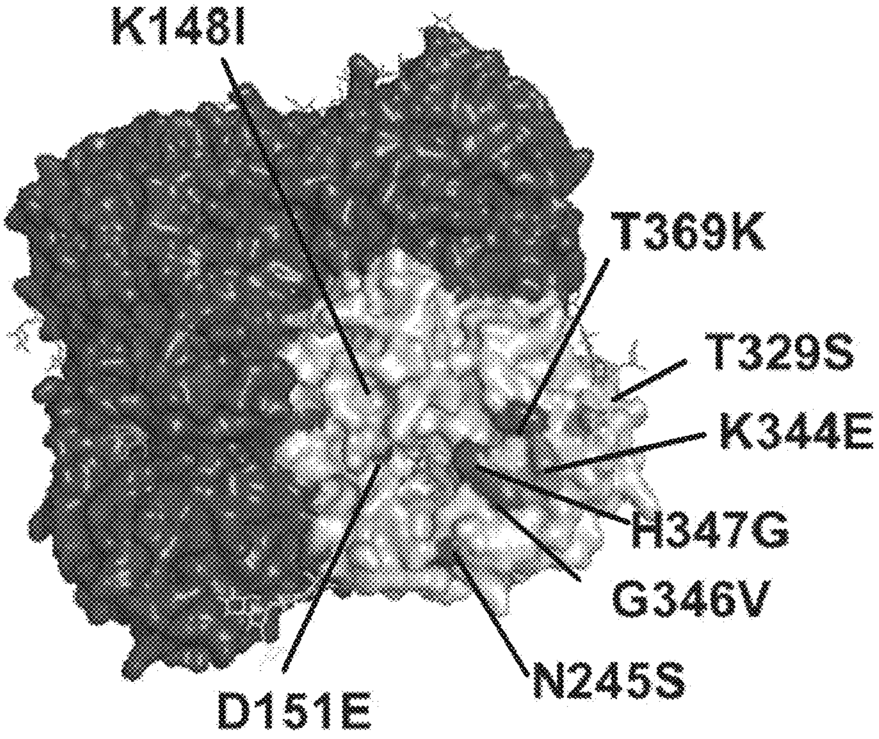
FIG. 53. Location of NA mutations; T148I, D151E, N245S, T329S, K344E, G346V, H347G and T369K on the 3D structure of NA protein. 6M shown in purple and T148I, T329S, K344E shown in green.

To identify further NA mutations that can allow viruses replicate efficiently in eggs without depending on HA receptor binding activity, HY-PR8 backbone viruses were generated that possess HA(del RBS) and A/Kansas/14/2017NA (6M) and then were passaged in eggs. During the passages, a mutant NA was obtained (T148I, D151E, N245S, T329S, K344E, G346V, H347G and T369K) (=6M+T148I+T329S+K344E). HY-PR8 backbone viruses possessing wild type HA and NA(6M+T148I+T329S+K344E) from A/Kansas/14/2017 were prepared and then analyzed to determine if the virus acquired the HA mutations during passages in eggs. The virus possessing NA(6M+T148I+T329S+K344E) did not acquire any of HA and NA mutations during 10 egg passages (FIG. 52).

Example IV

In one embodiment, an isolated recombinant influenza virus is provided comprising a selected NA viral segment encoding a plurality of selected residues or a deletion of residues in NA, wherein the selected NA viral segment does not encode a NA having a threonine (T) or lysine (K) at residue 148, and does not encode a threonine at residue 32, an aspartic acid (D) at position 151, an asparagine (N) at position 245, an asparagine at residue 329, a glycine (G) at position 346, a histidine at residue 347, or includes a NA having a deletion of one or more of residues 46 to 50, or any combination thereof, wherein the numbering is based on N2, wherein the recombinant influenza virus has enhanced replication in avian eggs or has a reduction in HA mutations when grown in avian eggs relative to a corresponding influenza virus that has a NA that encodes a threonine or lysine at residue 148 and has one or more of a threonine at residue 32, does not have a deletion of residues 46 to 50, an aspartic acid at position 147, an aspartic acid at residue 151, an asparagine at residue 245, an asparagine at residue 329, a glycine at residue 346, a histidine at residue 347, or any combination thereof. In one embodiment, the selected NA viral segment does not encode a NA having a threonine at residue 148, and does not encode a NA having an aspartic acid at position 151, an asparagine at position 245, a histidine at residue 347, or a threonine at residue 369, or any combination thereof, wherein the numbering is based on N2, wherein the recombinant influenza virus has enhanced replication in avian eggs or has a reduction in HA mutations when grown in avian eggs relative to a corresponding influenza virus that has a NA that encodes a threonine at residue 148, an aspartic acid at residue 151, an asparagine at residue 245, a histidine at residue 347, and a threonine at residue 369, or any combination thereof. In one embodiment, the selected NA viral segment does not encode a NA having a threonine or lysine at residue 148, and does not encode a NA having an aspartic acid at position 151, an asparagine at position 245, a histidine at residue 347, or a threonine at residue 369, or any combination thereof, wherein the numbering is based on N2, wherein the recombinant influenza virus has enhanced replication in avian eggs or has a reduction in HA mutations when grown in avian eggs relative to a corresponding influenza virus that has a NA that encodes a threonine or lysine at residue 148, an aspartic acid at residue 151, an asparagine at residue 245, a histidine at residue 347, and a threonine at residue 369, or any combination thereof. In one embodiment, the selected NA viral segment encodes a NA having an isoleucine (I), leucine (L), glycine or alanine (A) at residue 148. In one embodiment, the isolated recombinant influenza virus is a reassortant. In one embodiment, the NA viral segment encodes a NA that has at least 90% amino acid sequence identity to SEQ ID NO:1, SEQ ID NO:3, SEQ ID NO:48, SEQ ID NO:49, or SEQ ID NO:50. In one embodiment, the NA viral segment encodes a NA that has at least 90% amino acid sequence identity to SEQ ID NO:2. In one embodiment, the NA viral segment encodes a N2, N3, N7, or N9. In one embodiment, the NA viral segment encodes a N1, N4, N5, N6, N8, N10 or N11. In one embodiment, the residue at position 32 is A, I, G, or L, wherein the deletion is a deletion of residues 46 to 50, wherein the residue at position 147 is N or glutamine (Q), wherein the residue at position 329 is D or glutamic acid E, or wherein the residue at position 346 is serine (S), T, proline (P), tyrosine (Y), tryptophan (W), A, N, I, or L. In one embodiment, the residues at position 346 is V, S, I or L. In one embodiment, the residue at position 148 is I. In one embodiment, the residue at position 151 is E, N or Q. In one embodiment, the residue at position 245 is S, T, I, L, A, N, W, Y, P, V, or G. In one embodiment, the residue at position 347 is G, Q, S, T, Y, C or W. In one embodiment, the residue at position 369 is K, H, R, E, P, or D. In one embodiment, the residue at position 147 is N or Q, the residue at position 329 is D or E, the residue at position 347 is G, Q, S, T, Y, C or W, or any combination thereof. In one embodiment, the residue at position 147 is N or Q, the residue at position 329 is D or E, the residue at position 347 is G or Q, or any combination thereof. In one embodiment, the residue at position 148 is K, R or H, the residue at position 151 is E, N or Q, the residue at position 245 is S, T, I, L, A, W, Y, P, V, or G, or any combination thereof. In one embodiment, the residue at position 148 is K, R or H, the residue at position 151 is E, N or Q, the residue at position 245 is S, T, I, L, A, or V, and/or the residue at position 346 is S, T, P, Y, W, A, N, I, L, or V, or any combination thereof. In one embodiment, the selected NA viral segment does not encode a NA having a threonine at position 148, does not encode a NA having an aspartic acid at position 151, does not encode a NA having an asparagine at position 245, does not encode a NA having a histidine, arginine or an asparagine at residue 347, or any combination thereof. In one embodiment, the selected NA viral segment does not encode a NA having an aspartic acid at position 147, does not encode a NA having an asparagine at residue 329, does not encode a NA having a histidine, arginine or asparagine at residue 347, or any combination thereof. In one embodiment, the selected NA viral segment does not encode a NA having a threonine at position 148, does not encode a NA having an aspartic acid at position 151, does not encode a NA having an asparagine at position 245, does not encode a NA having a glycine at position 346, or any combination thereof. In one embodiment, the HA is H1, H3, H5, H7, or H9. In one embodiment, the virus is an influenza A virus. In one embodiment, the PA, PB1, PB2, NP, M, and NS viral segments have at least 85% nucleic acid sequence identity to SEQ ID Nos. 24 to 29 or 39 to 44 or encode a polypeptide having at least 80% amino acid sequence identity to a polypeptide encoded by SEQ ID Nos. 24 to 29 or 39 to 44. In one embodiment, the PB2 has I, A, L, or G at residue 147.

Also provided, in one embodiment, is an isolated recombinant nucleic acid comprising a nucleic acid sequence for an influenza virus NA viral segment that encodes a NA having a plurality of selected residues or a deletion of residues, wherein the selected NA viral segment does not encode a NA having a threonine or lysine at residue 148, and does not encode a threonine at residue 32, an aspartic acid at position 151, an asparagine at position 245, an asparagine at residue 329, a glycine at position 346, a histidine at residue 347, or include a NA having a deletion of one or more of residues 46 to 50, or any combination thereof, wherein the numbering is based on N2. In one embodiment, the selected NA viral segment does not encode a NA having a threonine at residue 148, and does not encode a NA having an aspartic acid at position 151, an asparagine at position 245, a histidine at residue 347, or a threonine at residue 369, or any combination thereof, wherein the numbering is based on N2, wherein the recombinant influenza virus has enhanced replication in avian eggs or has a reduction in HA mutations when grown in avian eggs relative to a corresponding influenza virus that has a NA that encodes a threonine at residue 148, an aspartic acid at residue 151, an asparagine at residue 245, a histidine at residue 347, and a threonine at residue 369, or any combination thereof. In one embodiment, the selected NA viral segment does not encode a NA having a threonine or lysine at residue 148, and does not encode a NA having an aspartic acid at position 151, an asparagine at position 245, a histidine at residue 347, or a threonine at residue 369, or any combination thereof, wherein the numbering is based on N2, wherein the recombinant influenza virus has enhanced replication in avian eggs or has a reduction in HA mutations when grown in avian eggs relative to a corresponding influenza virus that has a NA that encodes a threonine or lysine at residue 148, an aspartic acid at residue 151, an asparagine at residue 245, a histidine at residue 347, and a threonine at residue 369, or any combination thereof. In one embodiment, the selected NA viral segment encodes a NA having an isoleucine (I), leucine (L), glycine (G) or alanine (A) at residue 148. In one embodiment, the NA has at least 90% amino acid sequence identity to SEQ ID NO:1, SEQ ID NO:2 or SEQ ID NO:3. In one embodiment, the NA is a N2, N3, N7, or N9. In one embodiment, the NA is a N1, N4, N5, N6, N8, N10 or N11. In one embodiment, the HA is H1, H2, H3, H5, H7, or H9. In one embodiment, the residue at position 32 is A, I, G, or L, the residue at position 147 is N or Q, the residue at position 329 is D or E, the residue at position 151 is E, N or Q, the residue at position 148 is I, L, V, A, or G, the residue at position 245 is S, T, I, L, A, W, Y, P, V, or G, the residue at position 347 is G, Q, S, or T, the residue at position 346 is S, T, P, Y, W, A, N, I, L, or V, the residue at position 369 is K, H, R, E, P, or D, or any combination thereof. In one embodiment, the residue at position 151 is E, N or Q, the residue at position 148 is I, L, V, A, or G, the residue at position 245 is S, T, I, L, A, W, Y, P, V, or G, the residue at position 329 is S, I, L, A, W, Y, P, V, or G, the residue at position 347 is G, Q, S, or T, the residue at position 346 is S, T, P, Y, W, A, N, I, L, or V, the residue at position 369 is K, H, R, E, P, or D, or any combination thereof. In one embodiment, the NA has at least 90% amino acid sequence identity to SEQ ID NO:1, SEQ ID NO:2, SEQ ID NO:3, SEQ ID NO:48, or SEQ ID NO:49, or at least 90% amino acid sequence identity to a NA encoded by one of SEQ ID Nos. 51-59 or 69-70.

In one embodiment, a method to prepare influenza virus is provide comprising: contacting a cell with: a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS DNA linked to a transcription termination sequence, wherein the PB1, PB2, PA, NP, NS, and M DNAs in the vectors for vRNA production are from one or more influenza vaccine virus isolates, wherein the NA DNA in the vector for vRNA production encodes a NA having a plurality of selected residues or a deletion of residues, wherein the selected NA viral segment does not encode one or more of: a threonine or lysine at residue 148, a threonine at residue 32, an aspartic acid at position 151, an asparagine at position 245, an asparagine or threonine at residue 329, a lysine at residue 344 a glycine at position 346, a histidine at residue 347, or include a NA having a deletion of one or more of residues 46 to 50, or any combination thereof, wherein the numbering is based on N2; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2; in an amount effective to yield infectious influenza virus. In one embodiment, the NA has at least 90% amino acid sequence identity to SEQ ID NO:1, SEQ ID NO:2, SEQ ID NO:3, SEQ ID NO:48 or SEQ ID NO:49. In one embodiment, the NA is N2, N3, N7, or N9. In one embodiment, the HA is H1, H3, H7, or H9. In one embodiment, the HA is H2, H4, H5, H6, H8, or any of H10-H18. In one embodiment, the residue at position 147 is N or Q, the residue at position 329 is D or E, the residue at position 347 is G, Q, N, S, T, Y, C or W, or the residue at position 346 is S, T, P, Y, W, A, N, I, L, or V. In one embodiment, the residue at position 151 is E, N or Q, the residue at position 148 is I, L, V, A, or G, the residue at position 245 is S, T, I, L, A, W, Y, P, V, or G, the residue at position 347 is G, Q, S, or T, the residue at position 346 is S, T, P, Y, W, A, N, I, L, or V, the residue at position 369 is K, H, D, E, or R, or any combination thereof. In one embodiment, the PA, PB1, PB2, NP, M, and NS viral segments have at least 85% nucleic acid sequence identity to SEQ ID Nos. 24 to 29 or 39 to 44 or encode a polypeptide having at least 80% amino acid sequence identity to a polypeptide encoded by SEQ ID Nos. 24 to 29 or 39 to 44.

Further provided is a method of immunizing an avian or a mammal, comprising: administering to the avian or the mammal a composition having an effective amount of the virus described herein. In one embodiment, the composition comprises at least one other different influenza virus. In one embodiment, the mammal is a human. In one embodiment, the composition is administered intranasally or via injection.

Viruses described herein may be passaged in eggs or other cells.

Exemplary backbone viral segments include but are not limited to: PB2, M202L, F323L; PB1, Q247H; PA, K142N; NP, R74K; M, V97A, Y100H; and NS, K55E, or PB2, 1504V; PB1, M40L/G180W: PA, R401K; NP, I116L and NS1, A30P/R118K.

Example V

In one embodiment, a method to decrease influenza HA binding to cells is provided that includes altering one or more residues in the HA binding pocket of HA that binds to sialic acid on allantoic membranes. In one embodiment, nucleic acid encoding the HA is altered. In one embodiment, the HA is H1, H3, H7, or H9. In one embodiment, the HA is H2, H4, H5, H6, H8, or any of H10-H18. In one embodiment, the residue at position 98, 153 or 183 of HA is altered based on the numbering of H3 HA. In one embodiment, the residue at position 98 is not Y. In one embodiment, the residue at position 153 is not W. In one embodiment, the residue at position 183 is not H. In one embodiment, the residue at position 98 is F, G, I, V, T, H, W, or L. In one embodiment, the residue at position 153 is A, G, I, V, T, or L. In one embodiment, the residue at position 183 is F, A, G, I, L, V, Y, W, P, or T.

In one embodiment, a method to prepare an influenza virus that binds to cells via influenza neuraminidase is provided that includes providing a vector comprising a recombinant nucleic acid molecule comprising sequences for an influenza virus HA segment from a first influenza virus isolate, which segment encodes an HA with an amino acid other than tyrosine at position 98 in HA1, other than tryptophan at position 153 in HA1, other than histidine at position 183 in HA1, or any combination thereof, wherein the numbering for HA1 residues is that for H3; modifying the HA segment to encode F, G, I, V, T, H, W, or L at position 98, encode A, G, I, V, T, or L at position 153, encode F, A, G, I, L, V, Y, W, P, or T at position 183, or any combination thereof, thereby yielding a modified HA segment; and contacting a cell with a vector comprising promoter that yields full length, genomic influenza virus RNA or its complement operably linked to an influenza virus PA segment DNA linked to a transcription termination sequence, a vector comprising a promoter that yields full length, genomic influenza virus RNA or its complement operably linked to an influenza virus PB1 segment DNA linked to a transcription termination sequence, a vector comprising a promoter that yields full length, genomic influenza virus RNA or its complement operably linked to an influenza virus PB2 segment DNA linked to a transcription termination sequence, a vector comprising a promoter that yields full length, genomic influenza virus RNA or its complement operably linked to the modified HA segment linked to a transcription termination sequence, a vector comprising a promoter that yields full length, genomic influenza virus RNA or its complement operably linked to an influenza virus NP segment DNA linked to a transcription termination sequence, a vector comprising a promoter that yields full length, genomic influenza virus RNA or its complement operably linked to an influenza virus NA segment DNA linked to a transcription termination sequence, a vector comprising a promoter that yields full length, genomic influenza virus RNA or its complement operably linked to an influenza virus M segment DNA linked to a transcription termination sequence, and a vector comprising a promoter that yields full length, genomic influenza virus RNA or its complement operably linked to an influenza virus NS segment DNA linked to a transcription termination sequence; and a vector comprising a promoter that yields mRNA operably linked to a DNA segment encoding influenza virus PA, a vector comprising a promoter that yields mRNA operably linked to a DNA segment encoding influenza virus PB1, a vector comprising a promoter that yields mRNA operably linked to a DNA segment encoding influenza virus PB2, and a vector comprising a promoter that yields mRNA operably linked to a DNA segment encoding influenza virus NP, and optionally a vector comprising a promoter that yields mRNA operably linked to a DNA segment encoding influenza virus HA, a vector comprising a promoter that yields mRNA operably linked to a DNA segment encoding influenza virus NA, a vector comprising a promoter that yields mRNA operably linked to a DNA segment encoding influenza virus M1, a vector comprising a promoter that yields mRNA operably linked to a DNA segment encoding influenza virus M2, or a vector comprising a promoter that yields mRNA operably linked to a DNA segment encoding influenza virus NS1 or a vector comprising a promoter that yields mRNA operably linked to a DNA segment encoding influenza virus NS2; in an amount effective to yield infectious influenza virus that binds to cells via the NA.

Example VI

In one embodiment, an isolated recombinant influenza virus comprising a selected NA viral segment encoding a plurality of selected residues, a HA viral segment, and one or more of a PB1 viral segment, a PB2 viral segment, a PA viral segment, a NP viral segment, a M viral segment and a NS viral segment. In one embodiment, the selected NA viral segment does not encode a NA having a threonine or lysine at residue 148, does not encode an aspartic acid (D) at position 151, does not encode an asparagine at position 245, does not encode a threonine at position 329, does not encode a lysine at position 344, does not encode a glycine at position 346, does not encode a histidine at residue 347, and/or does not encode a threonine at position 369, wherein the numbering is based on N2, wherein the recombinant influenza virus has enhanced replication in avian eggs, has reduced sialidase activity, has increased binding to certain sialic acid residues and/or has a reduction in HA mutations when grown in avian eggs relative to a corresponding influenza virus that has a NA that encodes a threonine or lysine at residue 148, encodes an aspartic acid at residue 151, encodes an asparagine at residue 245, encodes a threonine at residue 329, encodes a lysine at residue 344, encodes a glycine at residue 346, encodes a histidine at residue 347, or encodes a threonine at position 369, or any combination thereof. In one embodiment, the NA segment of the recombinant virus has at position 329 a serine (S), valine (V), alanine (A), G, cysteine (C), methionine (M), isoleucine (I) or leucine (L) or at position 346 a V, S, T, proline (P), tyrosine (Y), tryptophan (W), A, N, I, or L. In one embodiment, the NA segment of the recombinant virus has at position 148 an I. In one embodiment, the NA segment of the recombinant virus has at position 151 an E, N or Q. In one embodiment, the NA segment of the recombinant virus has at position 245 a S, T, I, L, A, W, Y, P, V, or G. In one embodiment, the NA segment of the recombinant virus has at position 329 a S, I, L, A, W, Y, P, V, or G. In one embodiment, the NA segment of the recombinant virus has at position 344 an E, H, D, N or Q. In one embodiment, the NA segment of the recombinant virus has at position 346 a V, S, T, I, L, A, W, Y, or P. In one embodiment, the NA segment of the recombinant virus has at position 347 a G, Q, S, T, Y, C or W. In one embodiment, the NA segment of the recombinant virus has at position 369 a K, H, R, E, P, or D. In one embodiment, the recombinant virus is a reassortant. In one embodiment, the NA viral segment encodes a NA that has at least 90% amino acid sequence identity to SEQ ID NO:1, SEQ ID NO:3, SEQ ID NO:48, or SEQ ID NO:49, or has at least 90% amino acid sequence identity to a NA encoded by any one of SEQ ID Nos. 51-59. In one embodiment, the NA viral segment encodes a NA that has at least 90% amino acid sequence identity to SEQ ID NO:2. In one embodiment, the NA viral segment encodes a N2, N3, N7, or N9. In one embodiment, the NA viral segment encodes a N1, N4, N5, N6, N8, N10 or N11. In one embodiment, the HA is H2 or H3. In one embodiment, the virus is an influenza A virus. In one embodiment, the PA, PB1, PB2, NP, M, and NS viral segments have at least 85% nucleic acid sequence identity to SEQ ID Nos. 24 to 29 or 39 to 44 or encode a polypeptide having at least 80% amino acid sequence identity to a polypeptide encoded by SEQ ID Nos. 24 to 29 or 39 to 44. In one embodiment, PB2 has I, A, L, or G at residue 147.

Further provided is an isolated recombinant nucleic acid comprising a nucleic acid sequence for an influenza virus NA viral segment that encodes a NA having a plurality of selected residues, wherein the selected NA viral segment, does not encode a NA having a threonine or lysine at residue 148, does not encode an aspartic acid at position 151, does not encode an asparagine at position 245, does not encode a threonine at position 329, does not encode a lysine at position 344, does not encode a glycine at position 346, does not encode a histidine at residue 347, and/or does not encode a threonine at position 369, wherein the numbering is based on N2. In one embodiment, the NA has at least 90% amino acid sequence identity to SEQ ID NO:1, SEQ ID NO:2, SEQ ID NO:3, SEQ ID NO:48, or SEQ ID NO:49, or at least 90% amino acid sequence identity to a NA encoded by one of SEQ ID Nos. 51-59. In one embodiment, the NA is a N2, N3, N7, or N9. In one embodiment, the NA is a N1, N4, N5, N6, N8, N10 or N11. In one embodiment, the residue at position 148 is I, the residue at position 329 is S, the residue at position 151 is E, N or Q, the residue at position 245 is S, T, I, L, A, V, or G, the residue at position 347 is G, Q, S, or T, the residue at position 346 is S, T, P, Y, W, A, N, I, L, or V, the residue at position 369 is K, H, R, E, P, or D, or any combination thereof. In one embodiment, the residue at position 151 is E, N or Q, the residue at position 148 is I or K, the residue at position 245 is S, T, I, L, A, W, Y, P, V, or G, the residue at position 347 is G, Q, S, or T, the residue at position 346 is S, T, P, Y, W, A, N, I, L, or V, the residue at position 369 is K, H, R, E, P, or D, or any combination thereof.

In one embodiment, a method to prepare influenza virus is provided. The method includes contacting a cell with a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS DNA linked to a transcription termination sequence, wherein the PB1, PB2, PA, NP, NS, and M DNAs in the vectors for vRNA production are from one or more influenza vaccine virus isolates, wherein the NA DNA in the vector for vRNA production encodes a NA having a plurality of selected residues, wherein the selected NA viral segment does not encode a NA having a threonine or lysine at residue 148, does not encode an aspartic acid at position 151, does not encode an asparagine at position 245, does not encode a threonine at position 329, does not encode a lysine at position 344, does not encode a glycine at position 346, does not encode a histidine at residue 347, and/or does not encode a threonine at position 369, wherein the numbering is based on N2; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2; in an amount effective to yield infectious influenza virus. In one embodiment, the NA has at least 90% amino acid sequence identity to SEQ ID NO:1, SEQ ID NO:2, SEQ ID NO:3, SEQ ID NO:48 or SEQ ID NO:49 or at least 90% amino acid sequence identity to a NA encoded by one of SEQ D Nos. 51-59. In one embodiment, the NA is N2, N3, N7, or N9. In one embodiment, the HA is H1, H2, H3, H7, or H9. In one embodiment, HA is H2, H4, H5, H6, H8, or any of H10-H18. In one embodiment, the residue at position 329 is S, A, I, L or G, the residue at position 347 is G, Q, N, S, T, Y, C or W, or the residue at position 346 is S, T, P, Y, W, A, N, I, L, or V. In one embodiment, the residue at position 151 is E, N or Q, the residue at position 148 is K, H, D or E, the residue at position 245 is S, T, I, L, A, W, Y, P, V, or G, the residue at position 347 is G, Q, S, or T, the residue at position 346 is V, S, T, P, Y, W, A, N, I, or L, the residue at position 369 is K, H, D, E, or R, or any combination thereof. In one embodiment, PA, PB1, PB2, NP, M, and NS viral segments have at least 85% nucleic acid sequence identity to SEQ ID Nos. 24 to 29 or 39 to 44 or encode a polypeptide having at least 80% amino acid sequence identity to a polypeptide encoded by SEQ ID Nos. 24 to 29 or 39 to 44. Also provided is isolated virus prepared by the method.

The recombinant virus may be employed in a method of immunizing an avian or a mammal, which includes administering to the avian or the mammal a composition having an effective amount of the virus. In one embodiment, the composition comprises at least one other different influenza virus. In one embodiment, the mammal is a human. In one embodiment, the composition is administered intranasally or via injection.

Example VII

In one embodiment, an isolated recombinant influenza virus comprising a selected NA viral segment encoding a plurality of selected residues or a deletion of residues in NA is provided. The virus includes the selected NA viral segment encoding the plurality of selected residues, a HA viral segment, and one or more of a PB1 viral segment, a PB2 viral segment, a PA viral segment, a NP viral segment, a M viral segment and a NS viral segment. In one embodiment, the selected NA viral segment does not encode a NA having a threonine or lysine at residue 148, does not encode an aspartic acid at position 151, does not encode an asparagine at position 245, does not encode a threonine at position 329, does not encode a lysine at position 344, does not encode a glycine at position 346, does not encode a histidine at residue 347, and does not encode a threonine at position 369, wherein the numbering is based on N2, wherein the recombinant influenza virus has enhanced replication in avian eggs, has reduced sialidase activity, enhanced binding to a2-3 sialosides, or has a reduction in HA mutations when grown in avian eggs relative to a corresponding influenza virus that has a NA that encodes a threonine or lysine at residue 148, encodes an aspartic acid at residue 151, encodes an asparagine at residue 245, encodes a threonine at residue 329, encodes a lysine at residue 344, encodes a glycine at residue 346, encodes a histidine at residue 347, and encodes a threonine at position 369. In one embodiment, the selected NA viral segment does not encode a NA having a threonine or lysine at residue 148, does not encode a threonine at residue 32, does not encode an aspartic acid at position 151, does not encode an asparagine at position 245, does not encode an asparagine or a threonine at residue 329, does not encode a lysine at position 344, does not encode a glycine at position 346, does not encode a histidine at residue 347, and/or does not encode a threonine at residue 369, or includes a NA having a deletion of one or more of residues 46 to 50, or any combination thereof, wherein the numbering is based on N2, wherein the recombinant influenza virus has enhanced replication in avian eggs, has reduced sialidase activity, enhanced binding to a2-3 sialosides, or has a reduction in HA mutations when grown in avian eggs relative to a corresponding influenza virus that has a NA that encodes a threonine or lysine at residue 148 and a threonine at residue 32, does not have a deletion of residues 46 to 50, has an aspartic acid at position 147, has an aspartic acid at residue 151, has an asparagine at residue 245, has an asparagine or threonine at residue 329, has a glycine at residue 346, has a histidine at residue 347, has a threonine at residue 369, or any combination thereof. In one embodiment, the selected NA segment encodes two or more of positions 148, 151, 245, 329, 344, 347, or 369 having lysine or isoleucine at residue 148, glutamic acid at residue 151, serine, threonine, glycine, alanine, leucine or isoleucine at residue 245 or serine, glycine, alanine, leucine or isoleucine residue 329, glutamic acid, aspartic acid, glutamine, asparagine or histidine at residue 344, valine, leucine, isoleucine, threonine or serine at reside 346, glycine, alanine, valine, leucine, isoleucine or threonine at residue 347, or lysine, histidine, aspartic acid or glutamic acid at residue 369. In one embodiment, wherein the selected NA segment encodes two or more of positions 148, 151, 245, 329, 344, 347, or 369 having isoleucine (I) at residue 148, glutamic acid at residue 151, serine, threonine, leucine or isoleucine at residue 245 or serine, leucine or isoleucine at residue 329, glutamic acid, aspartic acid or histidine at residue 344, valine, leucine, or isoleucine at reside 346, glycine, alanine, valine, leucine, or isoleucine at residue 347, or lysine, aspartic acid or glutamic acid at residue 369. In one embodiment, the selected NA segment does not encode threonine at residue 148, does not encode asparagine at residue 245, does not encode threonine at residue 369, does not encode aspartic acid at residue 151, does not encode a lysine at residue 344, does not encode glycine at reside 346, does not encode histidine at residue 347, and does not encode threonine at residue 369. In one embodiment, the selected NA segment encodes lysine or isoleucine (I) at residue 148, encodes glutamic acid (E) at residue 151, encodes serine (S), threonine, glycine, alanine (A), leucine (L) or isoleucine at residue 245, encodes serine, glycine, alanine, leucine or isoleucine at residue 329, encodes glutamic acid, arginine (R), aspartic acid (D) or histidine at residue 344, encodes valine, leucine, isoleucine, threonine or serine at reside 346, encodes glycine, alanine, valine, leucine, isoleucine or threonine at residue 347, or encodes lysine, histidine, aspartic acid or glutamic acid at residue 369. In one embodiment, the selected NA viral segment does not encode a NA having a threonine at residue 148, and does not encode a NA having an aspartic acid at position 151, an asparagine at position 245, a valine, serine, isoleucine or leucine at residue 346, a histidine at residue 347, or a threonine at residue 369, or any combination thereof, wherein the numbering is based on N2, wherein the recombinant influenza virus has enhanced replication in avian eggs or has a reduction in HA mutations when grown in avian eggs relative to a corresponding influenza virus that has a NA that encodes a threonine at residue 148, an aspartic acid at residue 151, an asparagine at residue 245, a histidine at residue 347, and a threonine at residue 369, or any combination thereof; or wherein the selected NA viral segment does not encode a NA having a threonine or lysine at residue 148, and does not encode a NA having an aspartic acid at position 151, an asparagine at position 245, a valine, serine, isoleucine or leucine at residue 346, a histidine at residue 347, or a threonine at residue 369, or any combination thereof, wherein the numbering is based on N2, wherein the recombinant influenza virus has enhanced replication in avian eggs or has a reduction in HA mutations when grown in avian eggs relative to a corresponding influenza virus that has a NA that encodes a threonine or lysine at residue 148, an aspartic acid at residue 151, an asparagine at residue 245, a glycine at residue 346, a histidine at residue 347, and a threonine at residue 369, or any combination thereof. In one embodiment, the selected NA viral segment encodes a NA having an isoleucine, leucine, glycine or alanine at residue 148. In one embodiment, the residue at position 32 is A, I, G, or L, the deletion is a deletion of residues 46 to 50, wherein the residue at position 147 is N or glutamine (Q), wherein the residue at position 329 is D or glutamic acid, or wherein the residue at position 346 is serine, T, proline (P), tyrosine (Y), tryptophan (W), A, N, I, or L. In one embodiment, the residue at position 148 is I, the residue at position 151 is E, N or Q, the residue at position 245 is S, T, I, L, A, N, W, Y, P, V, or G, the residue at position 347 is G, Q, S, T, Y, C or W, the residue at position 369 is K, H, R, E, P, or D, or any combination thereof. In one embodiment, the residue at position 329 is serine, valine, alanine, G, cysteine (C), methionine (M), isoleucine or leucine or wherein the residue at position 346 is V, S, T, proline (P), tyrosine (Y), tryptophan (W), A, N, I, or L. In one embodiment, the residue at position 148 is I, the residue at position 151 is E, N or Q, the residue at position 245 is S, T, I, L, A, W, Y, P, V, or G, the residue at position 329 is S, I, L, A, W, Y, P, V, or G, the residue at position 344 is E, H, D, N or Q, the residue at position 346 is V, S, T, I, L, A, W, Y, or P, the residue at position 347 is G, Q, S, T, Y, C or W, or the residue at position 369 is K, H, R, E, P, or D. In one embodiment, the isolated recombinant influenza virus is a reassortant. In one embodiment, the NA viral segment encodes a NA that has at least 90% amino acid sequence identity to SEQ ID NO:1, SEQ ID NO:2, SEQ ID NO:3, SEQ ID NO:48, or SEQ ID NO:49, or has at least 90% amino acid sequence identity to a NA encoded by any one of SEQ ID Nos. 51-59. In one embodiment, the NA viral segment encodes a N2, N3, N7, or N9 NA. In one embodiment, the NA viral segment encodes a N1, N4, N5, N6, N8, N10 or N11 NA. In one embodiment, the recombinant virus has a H1, H2, H3, H5, H7, or H9 HA. In one embodiment, the isolated recombinant influenza virus is an influenza A virus. In one embodiment, the PA, PB1, PB2, NP, M, and NS viral segments have at least 85% nucleic acid sequence identity to SEQ ID Nos. 24 to 29 or 39 to 44 or encode a polypeptide having at least 80% amino acid sequence identity to a polypeptide encoded by SEQ ID Nos. 24 to 29 or 39 to 44. In one embodiment, the PB2 has I, A, L, or G. In one embodiment, the virus has one or more of PB2-I504V, PB1-M40L/G180W, PA-R401K, NP-I116L, or NS1-A30P/R118K. In one embodiment, the virus has PB2-I504V, PB1-M40L/G180W, PA-R401K, NP-I116L, and NS1-A30P/R118K.

In one embodiment, an isolated recombinant nucleic acid is provided comprising a nucleic acid sequence for an influenza virus NA viral segment that encodes a NA having a plurality of selected residues or a deletion of residues, wherein the selected NA viral segment does not encode a NA having a threonine or lysine at residue 148, and does not encode a threonine at residue 32, an aspartic acid at position 151, an asparagine at position 245, an asparagine or threonine at residue 329, a glycine at position 346, a histidine at residue 347, or include a NA having a deletion of one or more of residues 46 to 50, or any combination thereof, or wherein the selected NA viral segment does not encode a NA having a threonine or lysine at residue 148, does not encode an aspartic acid at position 151, does not encode an asparagine at position 245, does not encode a threonine at position 329, does not encode a lysine at position 344, does not encode a glycine at position 346, does not encode a histidine at residue 347, and does not encode a threonine at position 369, wherein the numbering is based on N2. In one embodiment, the selected NA viral segment does not encode a NA having a threonine or lysine at residue 148, does not encode a NA having an aspartic acid at position 151, does not encode a NA having an asparagine at position 245, does not encode a NA having a glycine at residue 346, does not encode a NA having a histidine at residue 347, or does not encode a NA having a threonine at residue 369, or any combination thereof. In one embodiment, wherein the residue at position 151 is E, N or Q. In one embodiment, the residue at position 148 is I, L, V, A, or G. In one embodiment, the residue at position 245 is S, T, I, L, A, W, Y, P, V, or G or at position 329 is S, I, L, A, W, Y, P, V, or G. In one embodiment, the residue at position 347 is G, Q, S, or T. In one embodiment, the residue at position 346 is S, T, P, Y, W, A, N, I, L, or V. In one embodiment, the residue at position 369 is K, H, R, E, P, or D. In one embodiment, the residue at position 32 is A, I, G, or L, the residue at position 147 is N or Q, the residue at position 329 is D or E, the residue at position 151 is E, N or Q, the residue at position 148 is I, L, V, A, or G, the residue at position 245 is S, T, I, L, A, W, Y, P, V, or G, the residue at position 347 is G, Q, S, or T, the residue at position 346 is S, T, P, Y, W, A, N, I, L, or V, the residue at position 369 is K, H, R, E, P, or D, or any combination thereof. In one embodiment, the residue at position 151 is E, N or Q, the residue at position 148 is I, L, V, A, or G, the residue at position 245 is S, T, I, L, A, W, Y, P, V, or G, the residue at position 347 is G, Q, S, or T, the residue at position 346 is S, T, P, Y, W, A, N, I, L, or V, the residue at position 369 is K, H, R, E, P, or D, or any combination thereof. In one embodiment, the NA has at least 90% amino acid sequence identity to SEQ ID NO:1, SEQ ID NO:2, SEQ ID NO:3, SEQ ID NO:48, or SEQ ID NO:49, or at least 90% amino acid sequence identity to a NA encoded by one of SEQ ID Nos. 51-59. In one embodiment, the NA is a N2, N3, N7, or N9. In one embodiment, the NA is a N1, N4, N5, N6, N8, N10 or N11.

In one embodiment, a method to prepare influenza virus is provided. The method includes contacting a cell with a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS DNA linked to a transcription termination sequence, wherein the PB1, PB2, PA, NP, NS, and M DNAs in the vectors for vRNA production are from one or more influenza vaccine virus isolates, wherein the NA DNA in the vector for vRNA production encodes a NA having a plurality of selected residues or a deletion of residues, wherein the selected NA viral segment does not encode a NA having a threonine or lysine at residue 148, does not encode an aspartic acid at position 151, does not encode an asparagine at position 245, does not encode an asparagine or threonine at residue 329, does not encode a lysine at position 344, does not encode a glycine at position 346, does not encode a histidine at residue 347, and does not encode a threonine at residue 369, or any combination thereof, wherein the numbering is based on N2; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2; in an amount effective to yield infectious influenza virus. In one embodiment, the NA has at least 90% amino acid sequence identity to SEQ ID NO:1, SEQ ID NO:2, SEQ ID NO:3, SEQ ID NO:48 or SEQ ID NO:49 or at least 90% amino acid sequence identity to a NA encoded by one of SEQ D Nos. 51-59. In one embodiment, the NA is N2, N3, N7, or N9. In one embodiment, the HA is H2 or H3. In one embodiment, the residue at position 329 is S, the residue at position 347 is G, and the residue at position 346 is V. In one embodiment, the residue at position 151 is E, N or Q, the residue at position 148 is I, L, V, A, or G, the residue at position 245 is S, T, I, L, A, V or G, the residue at position 344 is E, D, N, H or Q, the residue at position 347 is G, L, I, V, A, S, or T, the residue at position 346 is V, S, T, A, N, I, L, or V, the residue at position 369 is K, H, D, E, or R, or any combination thereof. In one embodiment, the PA, PB1, PB2, NP, M, and NS viral segments have at least 85% nucleic acid sequence identity to SEQ ID Nos. 24 to 29 or 39 to 44 or encode a polypeptide having at least 80% amino acid sequence identity to a polypeptide encoded by SEQ ID Nos. 24 to 29 or 39 to 44. Also provided is isolated virus prepared by the method.

In one embodiment, a method of immunizing an avian or a mammal is provided, comprising: administering to the avian or the mammal a composition having an effective amount of the virus. In one embodiment, the composition comprises at least one other different influenza virus. In one embodiment, the mammal is a human. In one embodiment, the composition is administered intranasally or via injection.

Further provided is a method comprising passaging the virus in eggs.

REFERENCES

*Avery's Drug Treatment: Principles and Practice of Clinical Pharmacology and Therapeutics,* 3rd edition, ADIS Press, Ltd., Williams and Wilkins, Baltimore, Md. (1987).
Aymard-Henry et al., *Virology: A Practical Approach,* Oxford IRL Press, Oxford, 119-150 (1985).
Bachmeyer, *Intervirology,* 5:260 (1975).
Berkow et al., eds., *The Merck Manual,* 16th edition, Merck & Co., Rahway, N.J. (1992).
Hatta et al., *Science,* 293:1840 (2001).
Horimoto et al., *J. Virol.,* 68:3120 (1994).
Horimoto et al., *Vaccine,* 24:3669 (2006).
Keitel et al., in Textbook of Influenza, eds. Nickolson, K. G., Webster, R. G., and Hay, A. (Blackwell, Oxford), pp. 373-390 (1998).
Kuwahara et al., *Jpn. J. Infect. Dis.,* 71:234 (2018).
Laver & Webster, *Virology,* 69:511 (1976).
Neumann et al., *Adv. Virus Res.,* 53:265 (1999).
Neumann et al., *J. Gen. Virol.,* 83:2635 (2002).
Neumann et al., *J. Viral.,* 71:9690 (1997).
Neumann et al., *Proc. Natl. Acad. Sci. USA,* 96:9345 (1999).
Neumann et al., *Virology,* 287:243 (2001).
Osol (ed.), *Remington's Pharmaceutical Sciences*, Mack Publishing Co., Easton, Pa. 1324-1341 (1980).
Sugawara et al., *Biologicals,* 30:303 (2002).
Webby & Webster et al., *Science* 302:1519 (2003).
Wood & Robertson, *Nat. Rev. Microbiol.,* 2:842 (2004).
World Health Organization TSR No. 673 (1982).
World Health Organization. Confirmed human cases of avian influenza A (H5N1). http://www.whointicsr/disease/avian_influenza/country/en/index.html All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated recombinant influenza virus comprising a selected neuraminidase (NA) viral segment encoding a plurality of selected residues in NA, wherein the selected NA viral segment encodes a NA having an isoleucine (I) at residue 148, and wherein the plurality of selected residues in the NA includes when the NA does not encode an aspartic acid (D) at position 151, does not encode an asparagine (N) at position 245, does not encode a threonine (T) at position 329, does not encode a lysine (K) at position 344, does not encode a glycine (G) at position 346, does not encode a histidine (H) at residue 347, or does not encode a threonine at position 369, or any combination thereof, wherein the numbering is based on N2, wherein the recombinant influenza virus has enhanced replication in avian eggs, has reduced sialidase activity, enhanced binding to a2-3 sialosides, or has a reduction in hemagglutinin (HA) mutations when grown in avian eggs relative to a corresponding influenza virus that has a NA that encodes a threonine or lysine at residue 148, encodes an aspartic acid at residue 151, encodes an asparagine at residue 245, encodes a threonine at residue 329, encodes a lysine at residue 344, encodes a glycine at residue 346, encodes a histidine at residue 347, and encodes a threonine at position 369, wherein the numbering is based on N2 of SEQ ID NO:53.

2. The isolated recombinant influenza virus of claim 1 wherein the selected NA segment encodes glutamic acid (E)

at residue 151, serine (S), threonine, glycine, alanine (A), leucine or isoleucine at residue 245, serine, glycine, alanine, leucine or isoleucine residue 329, glutamic acid, aspartic acid or histidine at residue 344, valine, leucine, isoleucine, threonine or serine at reside 346, glycine, alanine, valine, leucine, isoleucine or threonine at residue 347, or lysine, histidine, aspartic acid or glutamic acid at residue 369.

3. The isolated recombinant influenza virus of claim 1 wherein the residue at position 151 is E, N or Q or position 344 is E, D or H.

4. The isolated recombinant influenza virus of claim 1 wherein the residue at position 245 is S, T, I, L, A, V, or G.

5. The isolated recombinant influenza virus of claim 1 wherein the residue at position 347 is G, Q, S, T, Y, C or W.

6. The isolated recombinant influenza virus of claim 1 wherein the residue at position 369 is K, H, R, E, P, or D.

7. The isolated recombinant influenza virus of claim 1 wherein the residue at position 329 is serine, valine, alanine, glycine, isoleucine or leucine.

8. The isolated recombinant influenza virus of claim 1 wherein the residue at position 346 is V, S, T, A, I, or L.

9. The isolated recombinant influenza virus of claim 1 wherein the residue at position 151 is E, N or Q, the residue at position 245 is S, T, I, L, A, W, Y, P, V, or G, the residue at position 329 is S, I, L, A, W, Y, P, V, or G, the residue at position 344 is E, H, D, N or Q, the residue at position 346 is V, S, T, I, L, A, W, Y, or P, the residue at position 347 is G, Q, S, T, Y, C or W, or the residue at position 369 is K, H, R, E, P, or D.

10. The isolated recombinant influenza virus of claim 1 which is a reassortant.

11. The isolated recombinant influenza virus of claim 1 wherein the NA viral segment encodes a NA that has at least 90% amino acid sequence identity to SEQ ID NO:1, SEQ ID NO:2, SEQ ID NO:3, SEQ ID NO:48, SEQ ID NO:49, SEQ ID NO:71, SEQ ID NO:72, SEQ ID NO:73, or SEQ ID NO:74, or has at least 90% amino acid sequence identity to a NA encoded by any one of SEQ ID Nos. 55-59.

12. The isolated recombinant influenza virus of claim 1 wherein the NA viral segment encodes a N2, N3, N7, or N9 or wherein HA is H1, H2, H3, H5, H7, or H9.

13. The isolated recombinant influenza virus of claim 1 wherein polymerase A (PA), polymerase B1 (PB1), polymerase B2 (PB2), nucleoprotein (NP), matrix (M), and non-structural (NS) viral segments have at least 85% nucleic acid sequence identity to SEQ ID Nos. 24 to 29 or 39 to 44 or encode a polypeptide having at least 80% amino acid sequence identity to a polypeptide encoded by SEQ ID Nos. 24 to 29 or 39 to 44.

14. The isolated recombinant influenza virus of claim 1 wherein PB2 has I, A, L, or G at residue 147 based on the numbering of a corresponding polypeptide encoded by SEQ ID NO:26.

15. The isolated recombinant influenza virus of claim 1 which has one or more of PB2-I504V, PB1-M40L/G180W, PA-R401K, NP-I116L, and NS1-A30P/R118K based on the numbering of a corresponding polypeptide encoded by one of SEQ ID Nos. 24-27 or 29.

16. A method of immunizing an avian or a mammal, comprising: administering to the avian or the mammal a composition having an effective amount of the virus of claim 1.

17. The isolated recombinant influenza virus of claim 1 wherein the residue at position 245 is S, the residue at position 346 is V, the residues at position 347 is G, or the residue at position 369 is K.

* * * * *

```
                         SEQUENCE LISTING

<160> NUMBER OF SEQ ID NOS: 77

<210> SEQ ID NO 1
<211> LENGTH: 464
<212> TYPE: PRT
<213> ORGANISM: Influenza virus

<400> SEQUENCE: 1

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Ala
            20                  25                  30

Val Thr Leu His Phe Lys Gln Tyr Glu Phe Asn Ser Pro Met Leu Cys
        35                  40                  45

Glu Pro Thr Ile Ile Glu Arg Asn Ile Thr Glu Ile Val Tyr Leu Thr
    50                  55                  60

Asn Thr Thr Ile Glu Lys Glu Ile Cys Pro Lys Leu Ala Glu Tyr Arg
65                  70                  75                  80

Asn Trp Ser Lys Pro Gln Cys Asn Ile Thr Gly Phe Ala Pro Phe Ser
                85                  90                  95

Lys Asp Asn Ser Ile Arg Leu Ser Ala Gly Gly Asp Ile Trp Val Thr
            100                 105                 110

Arg Glu Pro Tyr Val Ser Cys Asp Pro Asp Lys Cys Tyr Gln Phe Ala
        115                 120                 125

Leu Gly Gln Gly Thr Thr Leu Asn Asn Val His Ser Asn Asn Ile Val
    130                 135                 140

His Asp Arg Thr Pro Tyr Arg Thr Leu Leu Met Asn Glu Leu Gly Val
145                 150                 155                 160

Pro Phe His Leu Gly Thr Lys Gln Val Cys Ile Ala Trp Ser Ser Ser
                165                 170                 175

Ser Cys His Asp Gly Lys Ala Trp Leu His Val Cys Val Thr Gly Asp
            180                 185                 190

Asp Glu Asn Ala Thr Ala Ser Phe Ile Tyr Asn Gly Arg Leu Ala Asp
        195                 200                 205
```

-continued

Ser Ile Val Ser Trp Ser Lys Lys Ile Leu Arg Thr Gln Glu Ser Glu
210 215 220

Cys Val Cys Ile Asn Gly Thr Cys Thr Val Val Met Thr Asp Gly Ser
225 230 235 240

Ala Ser Gly Lys Ala Asp Thr Lys Ile Leu Phe Ile Glu Glu Gly Lys
245 250 255

Ile Val His Thr Ser Thr Leu Ser Gly Ser Ala Gln His Val Glu Glu
260 265 270

Cys Ser Cys Tyr Pro Arg Tyr Pro Gly Val Arg Cys Val Cys Arg Asp
275 280 285

Asn Trp Lys Gly Ser Asn Arg Pro Ile Val Asp Ile Asn Ile Lys Asp
290 295 300

Tyr Ser Ile Val Ser Ser Tyr Val Cys Ser Gly Leu Val Gly Asp Thr
305 310 315 320

Pro Arg Lys Asp Asp Ser Ser Ser Ser Ser His Cys Leu Asp Pro Asn
325 330 335

Asn Glu Glu Gly Gly Gln Gly Val Lys Gly Trp Ala Phe Asp Asp Gly
340 345 350

Asn Asp Val Trp Met Gly Arg Thr Ile Ser Glu Lys Leu Arg Ser Gly
355 360 365

Tyr Glu Thr Phe Lys Val Ile Glu Gly Trp Ser Asn Pro Asn Ser Lys
370 375 380

Leu Gln Ile Asn Arg Gln Val Ile Val Asp Arg Gly Asn Arg Ser Gly
385 390 395 400

Tyr Ser Gly Ile Phe Ser Val Glu Gly Lys Ser Cys Ile Asn Arg Cys
405 410 415

Phe Tyr Val Glu Leu Ile Arg Gly Arg Lys Gln Glu Thr Glu Val Leu
420 425 430

Trp Thr Ser Asn Ser Ile Val Val Phe Cys Gly Thr Ser Gly Thr Tyr
435 440 445

Gly Thr Gly Ser Trp Pro Asp Gly Ala Asp Ile Asn Leu Met Pro Ile
450 455 460

<210> SEQ ID NO 2
<211> LENGTH: 469
<212> TYPE: PRT
<213> ORGANISM: Influenza virus

<400> SEQUENCE: 2

Met Asn Pro Asn Gln Lys Ile Ile Thr Ile Gly Ser Val Ser Leu Thr
1 5 10 15

Ile Ser Thr Ile Cys Phe Phe Met Gln Ile Ala Ile Leu Ile Thr Thr
20 25 30

Val Thr Leu His Phe Lys Gln Tyr Glu Phe Asn Ser Pro Pro Asn Asn
35 40 45

Gln Val Met Leu Cys Glu Pro Thr Ile Ile Glu Arg Asn Val Thr Glu
50 55 60

Ile Val Tyr Leu Thr Asn Thr Thr Ile Glu Lys Glu Ile Cys Pro Lys
65 70 75 80

Pro Ala Glu Tyr Arg Asn Trp Ser Lys Pro Gln Cys Gly Ile Thr Gly
85 90 95

Phe Ala Pro Phe Ser Lys Asp Asn Ser Ile Arg Leu Ser Ala Gly Gly
100 105 110

Asp Ile Trp Val Thr Arg Glu Pro Tyr Val Ser Cys Asp Pro Asp Lys

-continued

```
        115                 120                 125

Cys Tyr Gln Phe Ala Leu Gly Gln Gly Thr Thr Leu Asn Asn Val His
    130                 135                 140

Ser Asn Asn Thr Val Arg Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asn
        195                 200                 205

Gly Arg Leu Val Asp Ser Val Val Ser Trp Ser Lys Asp Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Lys Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Ile Lys Asp His Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Asn Glu
        355                 360                 365

Thr Ser Arg Leu Gly Tyr Glu Thr Phe Lys Val Val Glu Gly Trp Ser
    370                 375                 380

Asn Pro Lys Ser Lys Leu Gln Ile Asn Arg Gln Val Ile Val Asp Arg
385                 390                 395                 400

Gly Asp Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Leu
    450                 455                 460

Asn Leu Met Pro Ile
465


<210> SEQ ID NO 3
<211> LENGTH: 469
<212> TYPE: PRT
<213> ORGANISM: Influenza virus

<400> SEQUENCE: 3

Met Asn Pro Asn Gln Lys Ile Ile Thr Ile Gly Ser Val Ser Leu Thr
1               5                   10                  15
```

-continued

```
Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asp Ile Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly Asp Asp Glu Asn Ala Thr Ala Ser Phe Ile Tyr Asn
        195                 200                 205

Gly Arg Leu Ala Asp Ser Ile Val Ser Trp Ser Lys Lys Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365

Lys Leu Arg Ser Gly Tyr Glu Thr Phe Lys Val Ile Glu Gly Trp Ser
    370                 375                 380

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
            420                 425                 430

Glu Thr Glu Val Leu Trp Thr Ser Asn Ser Ile Val Val Phe Cys Gly
```

-continued

```
        435                 440                 445

Thr Ser Gly Thr Tyr Gly Thr Gly Ser Trp Pro Asp Gly Ala Asp Ile
    450                 455                 460

Asn Leu Met Pro Ile
465


<210> SEQ ID NO 4
<211> LENGTH: 2341
<212> TYPE: DNA
<213> ORGANISM: Influenza virus

<400> SEQUENCE: 4

agcaaaagca ggtcaattat attcagtatg gaaagaataa aagaactacg gaacctgatg     60

tcgcagtctc gcactcgcga gatactgaca aaaaccacag tggaccatat ggccataatt    120

aagaagtaca catcggggag acaggaaaag aacccgtcac ttaggatgaa atggatgatg    180

gcaatgaaat acccaatcac tgctgacaaa aggataacag aaatggttcc ggagagaaat    240

gaacaaggac aaactctatg gagtaaaatg agtgatgctg gatcagatcg agtgatggta    300

tcacctttgg ctgtgacatg gtggaataga aatggacccg tgacaagtac ggtccattac    360

ccaaaagtat acaagactta ttttgacaaa gtcgaaaggt taaaacatgg aacctttggc    420

cctgttcatt ttagaaatca agtcaagata cgccgaagag tagacacaaa ccctggtcat    480

gcggacctca gtgccaagga ggcacaagat gtaattatgg aagttgtttt tcccaatgaa    540

gtgggagcca ggatactaac atcagaatcg caattaacaa taactaaaga gaaaaaagaa    600

gaactccgag attgcaaaat ttctcccttg atggttgcat acatgttaga gagagaactt    660

gtccgaaaaa caagatttct cccagttgct ggcggaacaa gcagtatata cattgaagtt    720

ttacatttga ctcaagggac gtgttgggaa caaatgtaca ctccaggtgg agaagtgagg    780

aatgacgatg ttgaccaaag cctaattatt gcagccagga acatagtaag aagagccgca    840

gtatcagcag atccactagc atctttattg gagatgtgcc acagcacaca aattggcggg    900

acaaggatgg tggacattct tagacagaac ccgactgaag aacaagctgt ggatatatgc    960

aaggctgcaa tgggattgag aatcagctca tccttcagct ttggtgggtt tacatttaaa   1020

agaacaagcg ggtcatcagt caaaaaagag gaagaagtgc ttacaggcaa tctccaaaca   1080

ttgaagataa gagtacatga ggggtatgag gagttcacaa tggtggggaa aagagcaaca   1140

gctatactca gaaaagcaac cagaagattg gttcagctca tagtgagtgg aagagacgaa   1200

cagtcaatag ccgaagcaat aattgtggcc atggtgtttt cacaagagga ttgcatgata   1260

aaagcagtta gaggtgacct gaatttcgtc aacagagcaa atcagcggtt gaaccccatg   1320

catcagcttt taaggcattt tcagaaagat gcgaaagtgc tttttcagaa ttggggaatt   1380

gaacacatcg acagtgtaat gggaatggtt ggagtattac cagatatgac tccaagcaca   1440

gagatgtcaa tgagaggaat aagagtcagc aaaatgggtg tggatgaata ctccagtaca   1500

gagagggtgg tggttagcat tgatcggttt ttgagagttc gagaccaacg cgggaatgta   1560

ttattatctc ctgaagaggt tagtgaaaca cagggaactg agagactgac aataacttat   1620

tcatcgtcga tgatgtggga gattaacggt cctgagtcgg ttttggtcaa tacttatcaa   1680

tggatcatca gaaattggga agctgtcaaa attcaatggt ctcagaatcc tgcaatgttg   1740

tacaacaaaa tggaatttga accatttcaa tctttagtcc ccaaggccat tagaagccaa   1800

tacagtgggt ttgtcagaac tctattccaa caaatgagag acgtacttgg gacatttgac   1860

accacccaga taataaagct tctccctttt gcagccgctc caccaaagca aagcagaatg   1920
```

```
cagttctctt cactgactgt aaatgtgagg ggatcaggga tgagaatact tgtaaggggc   1980

aattctcctg tattcaacta caacaagacc actaaaagac taacaattct cggaaaagat   2040

gccggcactt taattgaaga cccagatgaa agcacatccg gagtggagtc cgctgtattg   2100

agagggtttc tcattatagg taaggaagac agaagatacg ggccagcatt aagcatcaat   2160

gaactgagta accttgcaaa aggggaaaag gctaatgtgc taatcgggca aggagacgtg   2220

gtgttggtaa tgaaacgaaa acgggactct agcatactta ctgacagcca gacagcgacc   2280

aaaagaattc ggatggccat caattaatgt tgaatagttt aaaaacgacc ttgtttctac   2340

t                                                                   2341
```

<210> SEQ ID NO 5
<211> LENGTH: 2341
<212> TYPE: DNA
<213> ORGANISM: Influenza virus

<400> SEQUENCE: 5

```
agcaaaagca ggcaaaccat ttgaatggat gtcaatccga ctctactgtt cctaaaggtt     60

ccagcgcaaa atgccataag caccacattc ccttatactg gagatcctcc atacagccat    120

ggaacaggaa cagggtacac catggacaca gtcaacagaa cacaccaata ttcagataag    180

gggaagtgga cgacaaatac agaaactggg gcaccccaac tcaacccaat tgatggacca    240

ctacctgagg ataatgagcc aagtggatat gcacaaacag actgtgtcct ggaggctatg    300

gccttccttg aagaatccca cccaggtatc tttgagaact catgccttga aacaatggaa    360

gtcgttcaac aaacaagggt ggacaaacta acccaaggtc gccagactta tgattggaca    420

ttaaacagaa atcaaccggc agcaactgca ttagccaaca ccatagaagt ttttagatcg    480

aatggactaa cagctaatga atcaggaagg ctaatagatt tcctcaagga tgtgatggaa    540

tcaatggata aagaggaaat ggagataaca acacactttc aaagaaaaag gagagtaaga    600

gacaacatga ccaagaaaat ggtcacacaa agaacaatag ggaagaaaaa acaaagagtg    660

aataagagag gctatctaat aagagctttg acattgaaca cgatgaccaa agatgcagag    720

agaggtaaat taaaaagaag ggctattgca acacccggga tgcaaattag agggttcgtg    780

tacttcgttg aaactttagc tagaagcatt tgcgaaaagc ttgaacagtc tggacttccg    840

gttgggggta atgaaaagaa ggccaaactg gcaaatgttg tgagaaaaat gatgactaat    900

tcacaagaca cagagctttc tttcacaatc actggggaca acactaagtg gaatgaaaat    960

caaaaccctc gaatgttttt ggcgatgatt acatatatca caaaaaatca acctgagtgg   1020

ttcagaaaca tcctgagcat cgcaccaata atgttctcaa acaaaatggc aagactggga   1080

aaaggataca tgttcgagag taagagaatg aaactccgaa cacaaatacc cgcagaaatg   1140

ctagcaaaca ttgacctgaa gtatttcaat gaatcaacaa ggaagaaaat tgagaaaata   1200

aggcctcttc taatagatgg cacagcatca ttgagccctg ggatgatgat gggcatgttc   1260

aacatgctaa gtacggtttt aggagtctcg atactgaatc ttgggcaaaa gaaatacacc   1320

aagacaacat actggtggga tgggctccaa tcctccgacg attttgccct catagtgaat   1380

gcaccaaatc atgagggaat acaagcagga gtggatagat tttacaggac ctgcaagtta   1440

gtgggaatca acatgagcaa aaagaagtcc tatataaata aaacagggac atttgaattc   1500

acaagctttt tttatcgata tggatttgtg gctaatttta gcatggagct gcccagtttt   1560

ggagtgtctg gaataaacga gtcagctgat atgagcattg gagtaacagt gataaagaac   1620
```

-continued aacatgataa acaatgacct tggaccagca acagcccaga tggctctcca attgttcatc 1680
aaagactaca gatatacata taggtgccat agaggagaca cacaaattca gacgagaaga 1740
tcattcgagc taaagaagct gtgggatcaa acccaatcaa gggcaggact attggtatca 1800
gatgggggac caaacttata caatatccgg aatcttcaca tccctgaagt ctgcttaaag 1860
tgggagctaa tggatgagaa ttatcgggga agactttgta atcccctgaa tccctttgtc 1920
agccataaag aaattgagtc tgtaaacaat gctgtagtga tgccagccca tggtccggcc 1980
aaaagtatgg aatatgatgc cgttgcaact acacactcct ggattcccaa gaggaaccgc 2040
tctattctca acacaagcca aaggggaatt cttgaggatg aacagatgta ccagaagtgc 2100
tgcaacttgt tcgagaaatt tttccctagt agttcatata ggagaccgat tggaatttct 2160
agcatggtgg aggccatggt gtctagggcc cggattgatg ccagaattga cttcgagtct 2220
ggacggatta agaaggaaga gttctctgag atcatgaaga tctgttccac cattgaagaa 2280
ctcagacggc aaaaataatg aatttagctt gtccttcatg aaaaaatgcc ttgtttctac 2340
t 2341

<210> SEQ ID NO 6
<211> LENGTH: 2233
<212> TYPE: DNA
<213> ORGANISM: Influenza virus

<400> SEQUENCE: 6
agcaaaagca ggtactgatt cgaaatggaa gattttgtgc gacaatgctt caacccgatg 60
attgtcgaac ttgcagaaaa agcaatgaaa gagtatgggg aggatctgaa aattgaaaca 120
aacaaatttg cagcaatatg cactcacttg gaggtatgtt tcatgtattc agattttcat 180
ttcatcaatg aacaaggcga atcaatagtg gtagaacttg atgatccaaa tgcactgtta 240
aagcacagat ttgaaataat cgaggggaga gacagaacaa tggcctggac agtagtaaac 300
agtatctgca acactactgg agctgaaaaa ccgaagtttc taccagattt gtatgattac 360
aaggagaaca gattcatcga aattggagtg acaaggagag aagtccacat atattacctt 420
gaaaaggcca ataagattaa atctgagaac acacacattc acattttctc attcactggg 480
gaggaaatgg ccacaaaggc agactacact ctcgacgagg aaagcagggc taggattaag 540
accaggctat ttaccataag acaagaaatg gccaacagag gcctctggga ttcctttcgt 600
cagtccgaaa gaggcgaaga aacaattgaa gaaaaatttg aaatctcagg aactatgcgt 660
aggcttgccg accaaagtct cccaccgaac ttctcctgcc ttgagaattt tagagcctat 720
gtggatggat tcgaaccgaa cggctgcatt gagggcaagc tttctcaaat gtccaaagaa 780
gtgaatgccc aaattgaacc ttttctgaag acaacaccaa gaccaatcaa acttccgaat 840
ggacctcctt gttatcagcg gtccaagttc ctcctgatgg atgctttaaa attgagcatt 900
gaagacccaa gtcacgaagg agaagggatc ccattatatg atgcgatcaa gtgcataaaa 960
acattctttg gatggaaaga accttatata gtcaaaccac acgaaaaggg aataaattca 1020
aattacctgc tgtcatggaa gcaagtattg tcagaattgc aggacattga aaatgaggag 1080
aagattccaa ggactaaaaa catgaagaaa acgagtcaac taaagtgggc tcttggtgag 1140
aacatggcac cagagaaagt agactttgaa aactgcagag acataagcga tttgaagcaa 1200
tatgatagtg acgaacctga attaaggtca ctttcaagct ggatacagaa tgagttcaac 1260
aaggcctgcg agctaactga ttcaatctgg atagagctcg atgaaattgg agaggacgta 1320
gccccaattg aatacattgc aagcatgagg aggaattatt tcacagcaga ggtgtcccat 1380

-continued

```
tgtagagcca ctgagtacat aatgaagggg gtatacatta atactgccct gctcaatgca   1440

tcctgtgcag caatggacga ttttcaacta attcccatga taagcaagtg cagaactaaa   1500

gagggaaggc gaaaaaccaa tttatatgga ttcatcataa agggaagatc tcatttaagg   1560

aatgacacag atgtggtaaa ctttgtgagc atggagtttt ctctcactga cccgagactt   1620

gagccacata aatgggagaa atactgtgtc cttgagatag gagatatgtt actaagaagt   1680

gccataggcc aaatttcaag gcctatgttc ttgtatgtga ggacaaacgg aacatcaaag   1740

gtcaaaatga aatggggaat ggagatgaga cgttgcctcc ttcagtcact ccagcagatc   1800

gagagcatga ttgaagccga gtcctcggtt aaagagaaag acatgaccaa agagtttttt   1860

gagaataaat cagaagcatg gcccattggg gagtccccca agggagtgga agaaggttcc   1920

attgggaaag tctgtaggac tctattggct aagtcagtgt tcaatagcct gtatgcatca   1980

ccacaattgg aaggattttc agcggagtca agaaaactgc tccttgttgt tcaggctctt   2040

agggacaacc tcgaacctgg gacctttgat cttggggggc tatatgaagc aattgaggag   2100

tgcctgatta atgatccctg ggttttgctc aatgcgtctt ggttcaactc cttcctgaca   2160

catgcattaa aatagttatg gcagtgctac tatttgttat ccgtactgtc caaaaaagta   2220

ccttgtttct act                                                      2233
```

<210> SEQ ID NO 7
<211> LENGTH: 1762
<212> TYPE: DNA
<213> ORGANISM: Influenza virus

<400> SEQUENCE: 7

```
agcaaaagca ggggataatt ctattaacca tgaagactat cattgctttg agctacattc     60

tatgtctggt tttcgctcaa aagcttcccg gaaatgacaa cagcacggca acgctgtgcc    120

ttgggcacca tgcagtacca aacggaacga tagtgaaaac aatcacgaat gaccaaattg    180

aagttactaa tgctactgag ctggttcaga gttcctcaac aggtggaata tgcgacagtc    240

ctcatcagat ccttgatgga gaaaactgca cactaataga tgctctattg ggagaccctc    300

agtgtgatgg cttccaaaat aagaaatggg acctttttgt tgaacgcagc aaagcctaca    360

gcaactgtta cccttatgat gtgccggatt atgcctccct taggtcacta gttgcctcat    420

ccggcacact ggagtttaac aatgaaagct tcaattggac tggagtcact cagaatggaa    480

caagctctgc ttgcaaaagg agatctaata aaagtttctt tagtagattg aattggttga    540

cccacttaaa atacaaatac ccagcattga acgtgactat gccaaacaat gaaaaatttg    600

acaaattgta catttggggg gttcaccacc cgggtacgga cagtgatcaa atcagcctat    660

atgctcaagc atcaggaaga atcacagtct ctaccaaaag aagccaacaa actgtaatcc    720

cgaatatcgg atctagaccc agggtaaggg atgtctccag cagaataagc atctattgga    780

caatagtaaa accgggagac atacttttga ttaacagcac agggaatcta attgctcctc    840

ggggttactt caaaatacga agtgggaaaa gctcaataat gagatcagat gcacccattg    900

gcaaatgcaa ttctgaatgc atcactccaa atggaagcat tcccaatgac aaaccatttc    960

aaaatgtaaa caggatcaca tatggggcct gtcccagata tgttaagcaa aacactctga   1020

aattggcaac agggatgcga aatgtaccag agaaacaaac tagaggcata tttggcgcaa   1080

tcgcgggttt catagaaaat ggttgggagg gaatggtgga cggttggtac ggtttcaggc   1140

atcaaaattc tgagggcaca ggacaagcag cagatctcaa aagcactcaa gcagcaatca   1200
```

-continued accaaatcaa tgggaaactg aataggttaa tcgggaaaac aaacgagaaa ttccatcaga 1260
ttgaaaaaga attctcagaa gtagaaggga gaattcagga cctcgagaaa tatgttgagg 1320
acactaaaat agatctctgg tcatacaacg cggagcttct tgttgccctg gagaaccaac 1380
atacaattga tctaactgac tcagaaatga acaaactgtt tgaaagaaca aagaagcaac 1440
tgagggaaaa tgctgaggat atgggcaatg gttgtttcaa aatataccac aaatgtgaca 1500
atgcctgcat agagtcaatc agaaatggaa cttatgacca tgatgtatac agagatgaag 1560
cattaaacaa ccggttccag atcaaaggtg ttgagctgaa gtcaggatac aaagattgga 1620
tcctatggat ttcctttgcc atatcatgtt ttttgctctg tgttgctttg ttggggttca 1680
tcatgtgggc ctgccaaaaa ggcaacatta ggtgcaacat ttgcatttga gtgcattaat 1740
taaaaacacc cttgtttcta ct 1762

<210> SEQ ID NO 8
<211> LENGTH: 1565
<212> TYPE: DNA
<213> ORGANISM: Influenza virus

<400> SEQUENCE: 8
agcaaaagca gggttaataa tcactcactg agtgacatca aaatcatggc gtcccaaggc 60
accaaacggt cttatgaaca gatggaaact gatggggatc gccagaatgc aactgagatt 120
agggcatccg tcgggaagat gattgatgga attgggagat tctacatcca aatgtgcact 180
gaacttaaac tcagtgatta tgaagggcgg ttgatccaga acagcttgac aatagagaaa 240
atggtgctct ctgcttttga tgaaagaagg aataaatatc tggaagaaca ccccagcgcg 300
gggaaagatc ctaagaaaac tgggggggcc atatacagga gagtagatgg aaaatggatg 360
agggaactcg tcctttatga caaagaagaa ataaggcgaa tctggcgcca agccaacaat 420
ggtgaggatg cgacagctgg tctaactcac ataatgatct ggcattccaa tttgaatgat 480
gcaacatacc agaggacaag agctcttgtt cgaaccggaa tggatcccag aatgtgctct 540
ctgatgcagg gctcgactct ccctagaagg tccggagctg caggtgctgc agtcaaagga 600
atcgggacaa tggtgatgga gctgatcaga atggtcaaac gggggatcaa cgatcgaaat 660
ttctggagag gtgagaatgg gcggaaaaca agaagtgctt atgagagaat gtgcaacatt 720
cttaaaggaa aatttcaaac agctgcacaa agagcaatgg tggatcaagt gagagaaagt 780
cggaacccag gaaatgctga gatcgaagat ctcatatttt tggcaagatc tgcattgata 840
ttgagaggat cagttgctca caaatcttgc ctacctgcct gtgtgtatgg acctgcagta 900
tccagtgggt acgacttcga aaaagaggga tattccttgg tgggaataga ccctttcaaa 960
ctacttcaaa atagccaagt atacagccta atcagaccta acgagaatcc agcacacaag 1020
agtcagctgg tatggatggc atgccattct gctgcatttg aagatttaag attgttaagc 1080
ttcatcagag ggacaaaagt atctccacga gggaaacttt caactagagg agtacaaatt 1140
gcttcaaatg agaacatgga taatatggga tcgagcactc ttgaactgag aagcgggtac 1200
tgggccataa ggaccaggag tggaggaaac actaatcaac agagggcctc cgcaggccaa 1260
accagtgtgc aacctacgtt ttctgtacaa agaaacctcc catttgaaaa gtcaaccatc 1320
atggcagcat tcactggaaa tacggaggga agaacttcag acatgagggc agaaatcata 1380
agaatgatgg aaggtgcaaa accagaagaa gtgtcgttcc gggggagggg agttttcgag 1440
ctctcagacg agaaggcaac gaacccgatc gtgccctctt ttgatatgag taatgaagga 1500
tcttatttct tcggagacaa tgcagaagag tacgacaatt aaggaaaaat acccttgttt 1560
ctact 1565

<210> SEQ ID NO 9
<211> LENGTH: 1467
<212> TYPE: DNA
<213> ORGANISM: Influenza virus

<400> SEQUENCE: 9
agcaaaagca ggagtaaaga tgaatccaaa tcaaaagata ataacgattg gctctgtttc 60
cctcaccatt tccacaatat gcttcttcat gcaaattgcc atcctgataa ctactgtaac 120
attgcatttc aagcaatatg aattcaactc ccccccaaac aaccaagtga tgctgtgtga 180
accaacaata atagaaagaa acataacaga gatagtgtat ctgaccaaca ccaccataga 240
gaaggaaata tgccccaaac tagcagaata cagaaattgg tcaaagccgc aatgtaacat 300
tacaggattt gcaccttttt ctaaggacaa ttcgattcgg ctttccgctg gtggggacat 360
ctgggtgaca agagaacctt atgtgtcatg cgatcctgac aagtgttatc aatttgccct 420
tggacaggga acaacactaa acaacgtgca ttcaaatgac atagtacatg ataggacccc 480
ttatcggacc ctattgatga atgagttggg tgttccattt catctgggga ccaagcaagt 540
gtgcatagca tggtccagct caagttgtca cgatggaaaa gcatggctgc atgtttgtgt 600
aacgggggat gatgaaaatg caactgctag cttcatttac aatgggaggc ttgcagatag 660
tattgtttca tggtccaaaa aaatcctcag gacccaggag tcagaatgcg tttgtatcaa 720
tggaacttgt acagtagtaa tgactgatgg gagtgcttca ggaaaagctg atactaaaat 780
actattcatt gaggagggga aaattgttca tactagcaca ttatcaggaa gtgctcagca 840
tgtcgaggag tgctcctgtt atcctcgata tcctggtgtc agatgtgtct gcagagacaa 900
ctggaaaggc tccaataggc ccatcgtaga tataaacata aaggattata gcattgtttc 960
cagttatgtg tgctcaggac ttgttggaga cacacccaga aaaaacgaca gctccagcag 1020
tagccattgc ttggatccaa acaatgagga aggtggtcat ggagtgaaag gctgggcctt 1080
tgatgatgga aatgacgtgt ggatgggaag aacgatcagc gagaagttac gctcaggata 1140
tgaaaccttc aaagtcattg aaggctggtc caaccctaac tccaaattgc agataaatag 1200
gcaagtcata gttgacagag gtaacaggtc cggttattct ggtattttct ctgttgaagg 1260
caaaagctgc atcaatcggt gcttttatgt ggagttgata aggggaagaa aacaggaaac 1320
tgaagtcttg tggacctcaa acagtattgt tgtgttttgt ggcacctcag gtacatatgg 1380
aacaggctca tggcctgatg gggcggacat caatctcatg cctatataag ctttcgcaat 1440
tttagaaaaa aactccttgt ttctact 1467

<210> SEQ ID NO 10
<211> LENGTH: 1027
<212> TYPE: DNA
<213> ORGANISM: Influenza virus

<400> SEQUENCE: 10
agcaaaagca ggtagatatt gaaagatgag ccttctaacc gaggtcgaaa cgtatgttct 60
ctctatcgtt ccatcaggcc ccctcaaagc cgagatcgcg cagagacttg aagatgtctt 120
tgctgggaaa aacacagatc ttgaggctct catggaatgg ctaaagacaa gaccaattct 180
gtcacctctg actaagggga ttctggggtt tgtgttcacg ctcaccgtgc ccagtgagcg 240
aggactgcag cgtagacgct ttgtccaaaa tgccctcaat gggaatggag atccaaataa 300

-continued

```
catggacaaa gcagttaaac tgtataggaa acttaagagg gagataacgt tccatggggc    360

caaagaaata gctctcagtt attctgctgg tgcacttgcc agttgcatgg gcctcatata    420

caataggatg ggggctgtaa ccactgaagt ggcatttggc ctggtatgtg caacatgtga    480

gcagattgct gactcccagc acaggtctca taggcaaatg gtggcaacaa ccaatccatt    540

aataaggcat gagaacagaa tggttttggc cagcactaca gctaaggcta tggagcaaat    600

ggctggatca agtgagcagg cagcggaggc catggagatt gctagtcagg ccaggcaaat    660

ggtgcaggca atgagagcca ttgggactca tcctagctcc agtactggtc taagagatga    720

tcttcttgaa aatttgcaga cctatcagaa acgaatgggg gtgcagatgc aacgattcaa    780

gtgacccact tgttgttgcc gcgagtatca ttgggatctt gcacttgata ttgtggattc    840

ttgatcgtct ttttttcaaa tgcgtctatc gactcttcaa acacggcctt aaaagaggcc    900

cttctacgga aggagtacct gagtctatga gggaagagta tcgaaaggaa cagcagaatg    960

ctgtggatgc tgacgacagt cattttgtca gcatagagtt ggagtaaaaa actaccttgt   1020

ttctact                                                             1027
```

<210> SEQ ID NO 11
<211> LENGTH: 890
<212> TYPE: DNA
<213> ORGANISM: Influenza virus

<400> SEQUENCE: 11

```
agcaaaagca gggtgacaaa gacataatgg attccaacac tgtgtcaagt ttccaggtag     60

attgctttct ttggcatatc cggaaacaag ttgtagacca agaactgagt gatgccccat    120

tccttgatcg gcttcgccga gatcagaggt ccctaagggg aagaggcaat actctcggtc    180

tagacatcaa agcagccacc catgttggaa agcaaattgt agaaaagatt ctgaaagaag    240

aatctgatga ggcacttaaa atgaccatgg tctccacacc tgcttcgcga tacataactg    300

acatgactat tgaggaattg tcaagaaact ggttcatgct aatgcccaag cagaaagtgg    360

aaggacctct ttgcatcaga atggaccagg caatcatgga gaaaaacatc atgttgaaag    420

cgaatttcag tgtgattttt gaccgactag agaccatagt attactaagg gctttcaccg    480

aagagggagc aattgttggc gaaatctcac cattgccttc ttttccagga catactattg    540

aggatgtcaa aaatgcaatt ggggtcctca tcggaggact tgaatggaat gataacacag    600

ttcgagtctc taaaaatcta cagagattcg cttggagaag cagtaatgag aatgggggac    660

ctccacttac tccaaaacag aaacggaaaa tggcgagaac agctaggtca aaagtttgaa    720

gagataagat ggctgattga agaagtgaga cacagactaa aaacaactga aaatagcttt    780

gaacaaataa cattcatgca agcattacaa ctgctgtttg aagtggaaca ggagataaga    840

actttctcat ttcagcttat ttaatgataa aaaacaccct tgtttctact               890
```

<210> SEQ ID NO 12
<211> LENGTH: 1433
<212> TYPE: DNA
<213> ORGANISM: Influenza virus

<400> SEQUENCE: 12

```
atgaatccaa atcaaaagat aataacgatt ggctctgttt ccctcaccat ttccacaata     60

tgcttcttca tgcaaattgc catcctgata actgctgtaa cattgcattt caagcaatat    120

gaattcaact cccccatgct gtgtgaacca acaataatag aaagaaacat aacagagata    180

gtgtatctga ccaacaccac catagagaag gaaatatgcc ccaaactagc agaatacaga    240
```

aattggtcaa agccgcaatg taacattaca ggatttgcac ctttttctaa ggacaattcg 300
attcggcttt ccgctggtgg ggacatctgg gtgacaagag aaccttatgt gtcatgcgat 360
cctgacaagt gttatcaatt tgcccttgga cagggaacaa cactaaacaa cgtgcattca 420
aataacatag tacatgatag gaccccttat cggaccctat tgatgaatga gttgggtgtt 480
ccatttcatc tggggaccaa gcaagtgtgc atagcatggt ccagctcaag ttgtcacgat 540
ggaaaagcat ggctgcatgt ttgtgtaacg gggggatgatg aaaatgcaac tgctagcttc 600
atttacaatg ggaggcttgc agatagtatt gtttcatggt ccaaaaaaat cctcaggacc 660
caggagtcag aatgcgtttg tatcaatgga acttgtacag tagtaatgac tgatgggagt 720
gcttcaggaa aagctgatac taaaatacta ttcattgagg aggggaaaat tgttcatact 780
agcacattat caggaagtgc tcagcatgtc gaggagtgct cctgttatcc tcgatatcct 840
ggtgtcagat gtgtctgcag agacaactgg aaaggctcca ataggcccat cgtagatata 900
aacataaagg attatagcat tgtttccagt tatgtgtgct caggacttgt tggagacaca 960
cccagaaaag acgacagctc cagcagtagc cattgcttgg atccaaacaa tgaggaaggt 1020
ggtcaaggag tgaaaggctg ggcctttgat gatggaaatg acgtgtggat gggaagaacg 1080
atcagcgaga agttacgctc aggatatgaa accttcaaag tcattgaagg ctggtccaac 1140
cctaactcca aattgcagat aaataggcaa gtcatagttg acagaggtaa caggtccggt 1200
tattctggta ttttctctgt tgaaggcaaa agctgcatca atcggtgctt ttatgtggag 1260
ttgataaggg gaagaaaaca ggaaactgaa gtcttgtgga cctcaaacag tattgttgtg 1320
ttttgtggca cctcaggtac atatggaaca ggctcatggc ctgatggggc ggacatcaat 1380
ctcatgccta tataagcttt cgcaatttta gaaaaaaact ccttgtttct act 1433

<210> SEQ ID NO 13
<211> LENGTH: 1733
<212> TYPE: DNA
<213> ORGANISM: Influenza virus

<400> SEQUENCE: 13
atgaagacta tcattgcttt gagctacatt ctatgtctgg ttttcgctca aaagcttccc 60
ggaaatgaca acagcacggc aacgctgtgc cttgggcacc atgcagtacc aaacggaacg 120
atagtgaaaa caatcacgaa tgaccaaatt gaagttacta atgctactga gctggttcag 180
agttcctcaa caggtggaat atgcgacagt cctcatcaga tccttgatgg agaaaactgc 240
acactaatag atgctctatt gggagaccct cagtgtgatg gcttccaaaa taagaaatgg 300
gacctttttg ttgaacgcag caaagcctac agcaactgtt acccttatga tgtgccggat 360
tatgcctccc ttaggtcact agttgcctca tccggcacac tggagtttaa caatgaaagc 420
ttcaattgga ctggagtcac tcagaatgga acaagctctg cttgcaaaag gagatctaat 480
aaaagtttct ttagtagatt gaattggttg acccacttaa aatacaaata cccagcattg 540
aacgtgacta tgccaaacaa tgaaaaattt gacaaattgt acatttgggg ggttcaccac 600
ccgggtacgg acagtgatca aatcagccta tatgctcaag catcaggaag aatcacagtc 660
tctaccaaaa gaagccaaca aactgtaatc ccgaatatcg gatctagacc cagggtaagg 720
gatgtctcca gcagaataag catctattgg acaatagtaa aaccgggaga catacttttg 780
attaacagca cagggaatct aattgctcct cggggttact tcaaaatacg aagtgggaaa 840
agctcaataa tgagatcaga tgcacccatt ggcaaatgca attctgaatg catcactcca 900

```
aatggaagca ttcccaatga caaaccattt caaaatgtaa acaggatcac atatggggcc    960

tgtcccagat atgttaagca aaacactctg aaattggcaa cagggatgcg aaatgtacca   1020

gagaaacaaa ctagaggcat atttggcgca atcgcgggtt tcatagaaaa tggttgggag   1080

ggaatggtgg acggttggta cggtttcagg catcaaaatt ctgagggcac aggacaagca   1140

gcagatctca aaagcactca agcagcaatc aaccaaatca atgggaaact gaataggtta   1200

atcgggaaaa caaacgagaa attccatcag attgaaaaag aattctcaga agtagaaggg   1260

agaattcagg acctcgagaa atatgttgag gacactaaaa tagatctctg gtcatacaac   1320

gcggagcttc ttgttgccct ggagaaccaa catacaattg atctaactga ctcagaaatg   1380

aacaaactgt ttgaaagaac aaagaagcaa ctgagggaaa atgctgagga tatgggcaat   1440

ggttgtttca aaatatacca caaatgtgac aatgcctgca tagagtcaat cagaaatgga   1500

acttatgacc atgatgtata cagagatgaa gcattaaaca accggttcca gatcaaaggt   1560

gttgagctga agtcaggata caaagattgg atcctatgga tttcctttgc catatcatgt   1620

tttttgctct gtgttgcttt gttggggttc atcatgtggg cctgccaaaa aggcaacatt   1680

aggtgcaaca tttgcatttg agtgcattaa ttaaaaacac ccttgtttct act          1733
```

<210> SEQ ID NO 14
<211> LENGTH: 1002
<212> TYPE: DNA
<213> ORGANISM: Influenza virus

<400> SEQUENCE: 14

```
atgagccttc taaccgaggt cgaaacgtat gttctctcta tcgttccatc aggccccctc     60

aaagcccaga tcgcgcagag acttgaagat gtctttgctg ggaaaaacac agatcttgag    120

gctctcatgg aatggctaaa gacaagacca attctgtcac ctctgactaa ggggattctg    180

gggtttgtgt tcacgctcac cgtgcccagt gagcgaggac tgcagcgtag acgctttgtc    240

caaaatgccc tcaatgggaa tggagatcca aataacatgg acaaagcagt taaactgtat    300

aggaaactta agagggagat aacgttccat ggggccaaag aaatagctct cagttattct    360

gctggtgcac ttgccagttg catgggcctc atatacaata ggatgggggc tgtaaccact    420

gaagtggcat ttggcctggt atgtgcaaca tgtgagcaga ttgctgactc ccagcacagg    480

tctcataggc aaatggtggc aacaaccaat ccattaataa ggcatgagaa cagaatggtt    540

ttggccagca ctacagctaa ggctatggag caaatggctg gatcaagtga gcaggcagcg    600

gaggccatgg agattgctag tcaggccagg caaatggtgc aggcaatgag agccattggg    660

actcatccta gctccagtac tggtctaaga gatgatcttc ttgaaaattt gcagacctat    720

cagaaacgaa tgggggtgca gatgcaacga ttcaagtgac ccacttgttg ttgccgcgag    780

tatcattggg atcttgcact tgatattgtg gattcttgat cgtctttttt tcaaatgcgt    840

ctatcgactc ttcaaacacg gccttaaaag aggcccttct acggaaggag tacctgagtc    900

tatgagggaa gagtatcgaa aggaacagca gaatgctgtg gatgctgacg acagtcattt    960

tgtcagcata gagttggagt aaaaaactac cttgtttcta ct                      1002
```

<210> SEQ ID NO 15
<211> LENGTH: 1520
<212> TYPE: DNA
<213> ORGANISM: Influenza virus

<400> SEQUENCE: 15

```
atggcgtccc aaggcaccaa acggtcttat gaacagatgg aaactgatgg ggatcgccag     60
```

aatgcaactg agattagggc atccgtcggg aagatgattg atggaattgg gagattctac 120
atccaaatgt gcactgaact taaactcagt gattatgaag ggcggttgat ccagaacagc 180
ttgacaatag agaaaatggt gctctctgct tttgatgaaa gaaggaataa atatctggaa 240
gaacacccca gcgcggggaa agatcctaag aaaactgggg ggcccatata caggagagta 300
aatggaaaat ggatgaggga actcgtcctt tatgacaaag aagaaataag gcgaatctgg 360
cgccaagcca acaatggtga ggatgcgaca gctggtctaa ctcacataat gatctggcat 420
tccaatttga atgatgcaac ataccagagg acaagagctc ttgttcgaac cggaatggat 480
cccagaatgt gctctctgat gcagggctcg actctcccta gaaggtccgg agctgcaggt 540
gctgcagtca aaggaatcgg gacaatggtg atggagctga tcagaatggt caaacggggg 600
atcaacgatc gaaatttctg gagaggtgag aatgggcgga aaacaagaag tgcttatgag 660
agaatgtgca acattcttaa aggaaaattt caaacagctg cacaaagagc aatggtggat 720
caagtgagag aaagtcggaa cccaggaaat gctgagatcg aagatctcat atttttggca 780
agatctgcat tgatattgag aggatcagtt gctcacaaat cttgcctacc tgcctgtgtg 840
tatggacctg cagtatccag tggtacgac ttcgaaaaag agggatattc cttggtggga 900
atagaccctt tcaaactact tcaaaatagc caagtataca gcctaatcag acctaacgag 960
aatccagcac acaagagtca gctggtatgg atggcatgcc attctgctgc atttgaagat 1020
ttaagattgt taagcttcat cagagggaca aaagtatctc cacgagggaa actttcaact 1080
agaggagtac aaattgcttc aaatgagaac atggataata tgggatcgag cactcttgaa 1140
ctgagaagcg ggtactgggc cataaggacc aggagtggag gaaacactaa tcaacagagg 1200
gcctccgcag gccaaaccag tgtgcaacct acgttttctg tacaaagaaa cctcccattt 1260
gaaaagtcaa ccatcatggc agcattcact ggaaatacgg agggaagaac ttcagacatg 1320
agggcagaaa tcataagaat gatggaaggt gcaaaaccag aagaagtgtc gttccggggg 1380
aggggagttt tcgagctctc agacgagaag gcaacgaacc cgatcgtgcc ctcttttgat 1440
atgagtaatg aaggatctta tttcttcgga gacaatgcag aagagtacga caattaagga 1500
aaaataccct tgtttctact 1520

<210> SEQ ID NO 16
<211> LENGTH: 864
<212> TYPE: DNA
<213> ORGANISM: Influenza virus

<400> SEQUENCE: 16
atggattcca acactgtgtc aagtttccag gtagattgct ttctttggca tatccggaaa 60
caagttgtag accaagaact gagtgatgcc ccattccttg atcggcttcg ccgagatcag 120
aggtccctaa ggggaagagg caatactctc ggtctagaca tcaaagcagc cacccatgtt 180
ggaaagcaaa ttgtagaaaa gattctgaaa gaagaatctg atgaggcact taaaatgacc 240
atggtctcca cacctgcttc gcgatacata actgacatga ctattgagga attgtcaaga 300
aactggttca tgctaatgcc caagcagaaa gtggaaggac ctctttgcat cagaatggac 360
caggcaatca tggagaaaaa catcatgttg aaagcgaatt tcagtgtgat ttttgaccga 420
ctagagacca tagtattact aagggctttc accgaagagg gagcaattgt tggcgaaatc 480
tcaccattgc cttcttttcc aggacatact attgaggatg tcaaaaatgc aattggggtc 540
ctcatcggag gacttgaatg gaatgataac acagttcgag tctctaaaaa tctacagaga 600

```
ttcgcttgga gaagcagtaa tgagaatggg ggacctccac ttactccaaa acagaaacgg    660

aaaatggcga gaacagctag gtcaaaagtt tgaagagata agatggctga ttgaagaagt    720

gagacacaga ctaaaaacaa ctgaaaatag ctttgaacaa ataacattca tgcaagcatt    780

acaactgctg tttgaagtgg aacaggagat aagaactttc tcatttcagc ttatttaatg    840

ataaaaaaca cccttgtttc tact                                           864
```

<210> SEQ ID NO 17
<211> LENGTH: 2317
<212> TYPE: DNA
<213> ORGANISM: Influenza virus

<400> SEQUENCE: 17

```
atggatgtca atccgactct actgttccta aaggttccag cgcaaaatgc cataagcacc     60

acattccctt atactggaga tcctccatac agccatggaa caggaacagg gtacaccatg    120

gacacagtca acagaacaca ccaatattca gataagggga agtggacgac aaatacagaa    180

actggggcac cccaactcaa cccaattgat ggaccactac ctgaggataa tgagccaagt    240

ggatatgcac aaacagactg tgtcctggag gctatggcct tccttgaaga atcccaccca    300

ggtatctttg agaactcatg ccttgaaaca atggaagtcg ttcaacaaac aagggtggac    360

aaactaaccc aaggtcgcca gacttatgat tggacattaa acagaaatca accggcagca    420

actgcattag ccaacaccat agaagttttt agatcgaatg gactaacagc taatgaatca    480

ggaaggctaa tagatttcct caaggatgtg atggaatcaa tggataaaga ggaaatggag    540

ataacaacac actttcaaag aaaaaggaga gtaagagaca acatgaccaa gaaaatggtc    600

acacaaagaa caatagggaa gaaaaaacaa agagtaaata agagaggcta tctaataaga    660

gctttgacat tgaacacgat gaccaaagat gcagagagag gtaaattaaa aagaagggct    720

attgcaacac ccgggatgca aattagaggg ttcgtgtact tcgttgaaac tttagctaga    780

agcatttgcg aaaagcttga acagtctgga cttccggttg gggtaatga aaagaaggcc     840

aaactggcaa atgttgtgag aaaaatgatg actaattcac aagacacaga gctttctttc    900

acaatcactg gggacaacac taagtggaat gaaaatcaaa accctcgaat gtttttggcg    960

atgattacat atatcacaaa aaatcaacct gagtggttca gaaacatcct gagcatcgca   1020

ccaataatgt tctcaaacaa aatggcaaga ctgggaaaag gatacatgtt cgagagtaag   1080

agaatgaaac tccgaacaca aatacccgca gaaatgctag caaacattga cctgaagtat   1140

ttcaatgaat caacaaggaa gaaaattgag aaaataaggc ctcttctaat agatggcaca   1200

gcatcattga gccctgggat gatgatgggc atgttcaaca tgctaagtac ggttttagga   1260

gtctcgatac tgaatcttgg gcaaaagaaa tacaccaaga caacatactg gtgggatggg   1320

ctccaatcct ccgacgattt tgccctcata gtgaatgcac caaatcatga gggaatacaa   1380

gcaggagtgg atagatttta caggacctgc aagttagtgg gaatcaacat gagcaaaaag   1440

aagtcctata taaataaaac agggacattt gaattcacaa gcttttttta tcgatatgga   1500

tttgtggcta attttagcat ggagctgccc agttttggag tgtctggaat aaacgagtca   1560

gctgatatga gcattggagt aacagtgata aagaacaaca tgataaacaa tgaccttgga   1620

ccagcaacag cccagatggc tctccaattg ttcatcaaag actacagata tacatatagg   1680

tgccatagag gagacacaca aattcagacg agaagatcat tcgagctaaa gaagctgtgg   1740

gatcaaaccc aatcaagggc aggactattg gtatcagatg gggaccaaa cttatacaat    1800

atccggaatc ttcacatccc tgaagtctgc ttaaagtggg agctaatgga tgagaattat   1860
```

```
cggggaagac tttgtaatcc cctgaatccc tttgtcagcc ataaagaaat tgagtctgta   1920

aacaatgctg tagtgatgcc agcccatggt ccggccaaaa gtatggaata tgatgccgtt   1980

gcaactacac actcctggat tcccaagagg aaccgctcta ttctcaacac aagccaaagg   2040

ggaattcttg aggatgaaca gatgtaccag aagtgctgca acttgttcga gaaatttttc   2100

cctagtagtt catataggag accgattgga atttctagca tggtggaggc catggtgtct   2160

agggcccgga ttgatgccag aattgacttc gagtctggac ggattaagaa ggaagagttc   2220

tctgagatca tgaagatctg ttccaccatt gaagaactca gacggcaaaa ataatgaatt   2280

tagcttgtcc ttcatgaaaa aatgccttgt ttctact                            2317
```

<210> SEQ ID NO 18
<211> LENGTH: 2209
<212> TYPE: DNA
<213> ORGANISM: Influenza virus

<400> SEQUENCE: 18

```
atggaagatt ttgtgcgaca atgcttcaac ccgatgattg tcgaacttgc agaaaaagca     60

atgaaagagt atggggagga tctgaaaatt gaaacaaaca aatttgcagc aatatgcact    120

cacttggagg tatgtttcat gtattcagat tttcatttca tcaatgaaca aggcgaatca    180

atagtggtag aacttgatga tccaaatgca ctgttaaagc acagatttga aataatcgag    240

gggagagaca gaacaatggc ctggacagta gtaaacagta tctgcaacac tactggagct    300

gaaaaaccga agtttctacc agatttgtat gattacaagg agaacagatt catcgaaatt    360

ggagtgacaa ggagagaagt ccacatatat taccttgaaa aggccaataa gattaaatct    420

gagaacacac acattcacat tttctcattc actggggagg aaatggccac aaaggcagac    480

tacactctcg acgaggaaag cagggctagg attaagacca ggctatttac cataagacaa    540

gaaatggcca acagaggcct ctgggattcc tttcgtcagt ccgaaagagg cgaagaaaca    600

attgaagaaa aatttgaaat ctcaggaact atgcgtaggc ttgccgacca aagtctccca    660

ccgaacttct cctgccttga gaattttaga gcctatgtgg atggattcga accgaacggc    720

tgcattgagg gcaagctttc tcaaatgtcc aaagaagtga atgcccaaat tgaacctttt    780

ctgaagacaa caccaagacc aatcaaactt ccgaatggac ctccttgtta tcagcggtcc    840

aagttcctcc tgatggatgc tttaaaattg agcattgaag acccaagtca cgaaggagaa    900

gggatcccat tatatgatgc gatcaagtgc ataaaaacat tctttggatg gaaagaacct    960

tatatagtca aaccacacga aaagggaata aattcaaatt acctgctgtc atggaagcaa   1020

gtattgtcag aattgcagga cattgaaaat gaggagaaga ttccaaggac taaaaacatg   1080

aagaaaacga gtcaactaaa gtgggctctt ggtgagaaca tggcaccaga gaaagtagac   1140

tttgaaaact gcagagacat aagcgatttg aagcaatatg atagtgacga acctgaatta   1200

aggtcacttt caagctggat acagaatgag ttcaacaagg cctgcgagct aactgattca   1260

atctggatag agctcgatga aattggagag gacgtagccc caattgaata cattgcaagc   1320

atgaggagga attatttcac agcagaggtg tcccattgta gagccactga gtacataatg   1380

aagggggtat acattaatac tgccctgctc aatgcatcct gtgcagcaat ggacgatttt   1440

caactaattc ccatgataag caagtgcaga actaaagagg gaaggcgaaa aaccaattta   1500

tatggattca tcataaaggg aagatctcat ttaaggaatg acacagatgt ggtaaacttt   1560

gtgagcatgg agttttctct cactgacccg agacttgagc cacataaatg ggagaaatac   1620
```

```
tgtgtccttg agataggaga tatgttacta agaagtgcca taggccaaat ttcaaggcct   1680

atgttcttgt atgtgaggac aaacggaaca tcaaaggtca aaatgaaatg ggaatggag    1740

atgagacgtt gcctccttca gtcactccag cagatcgaga gcatgattga agccgagtcc   1800

tcggttaaag agaaagacat gaccaaagag ttttttgaga ataaatcaga agcatggccc   1860

attggggagt cccccaaggg agtggaagaa ggttccattg ggaaagtctg taggactcta   1920

ttggctaagt cagtgttcaa tagcctgtat gcatcaccac aattggaagg attttcagcg   1980

gagtcaagaa aactgctcct tgttgttcag gctcttaggg acaacctcga acctgggacc   2040

tttgatcttg gggggctata tgaagcaatt gaggagtgcc tgattaatga tccctgggtt   2100

ttgctcaatg cgtcttggtt caactccttc ctgacacatg cattaaaata gttatggcag   2160

tgctactatt tgttatccgt actgtccaaa aaagtacctt gtttctact               2209
```

<210> SEQ ID NO 19
<211> LENGTH: 2314
<212> TYPE: DNA
<213> ORGANISM: Influenza virus

<400> SEQUENCE: 19

```
atggaaagaa taaaagaact acggaacctg atgtcgcagt ctcgcactcg cgagatactg     60

acaaaaacca cagtggacca tatggccata attaagaagt acacatcggg gagacaggaa    120

aagaacccgt cacttaggat gaaatggatg atggcaatga aatacccaat cactgctgac    180

aaaaggataa cagaaatggt tccggagaga aatgaacaag gacaaactct atggagtaaa    240

atgagtgatg ctggatcaga tcgagtgatg gtatcacctt tggctgtgac atggtggaat    300

agaaatggac ccgtgacaag tacggtccat tacccaaaag tatacaagac ttattttgac    360

aaagtcgaaa ggttaaaaca tggaaccttt ggccctgttc attttagaaa tcaagtcaag    420

atacgccgaa gagtagacat aaaccctggt catgcggacc tcagtgccaa ggaggcacaa    480

gatgtaatta tggaagttgt tttcccaat gaagtgggag ccaggatact aacatcagaa     540

tcgcaattaa caataactaa agagaaaaaa gaagaactcc gagattgcaa aatttctccc    600

ttgatggttg catacatgtt agagagagaa cttgtccgaa aaacaagatt tctcccagtt    660

gctggcggaa caagcagtat atacattgaa gttttacatt tgactcaagg gacgtgttgg    720

gaacaaatgt acactccagg tggagaagtg aggaatgacg atgttgacca aagcctaatt    780

attgcagcca ggaacatagt aagaagagcc gcagtatcag cagatccact agcatcttta    840

ttggagatgt gccacagcac acaaattggc gggacaagga tggtggacat tcttagacag    900

aacccgactg aagaacaagc tgtggatata tgcaaggctg caatgggatt gagaatcagc    960

tcatccttca gctttggtgg gtttacattt aaaagaacaa gcgggtcatc agtcaaaaaa   1020

gaggaagaag tgcttacagg caatctccaa acattgaaga taagagtaca tgaggggtat   1080

gaggagttca caatggtggg gaaaagagca acagctatac tcagaaaagc aaccagaaga   1140

ttggttcagc tcatagtgag tggaagagac gaacagtcaa tagccgaagc aataattgtg   1200

gccatggtgt tttcacaaga ggattgcatg ataaaagcag ttagaggtga cctgaatttc   1260

gtcaacagag caaatcagcg gttgaacccc atgcatcagc ttttaaggca ttttcagaaa   1320

gatgcgaaag tgctttttca gaattgggga attgagcaca tcgacagtgt aatgggaatg   1380

gttggagtat taccagatat gactccaagc acagagatgt caatgagagg aataagagtc   1440

agcaaaatgg gtgtggatga atactccagt acagagaggg tggtggttag cattgatcgg   1500

tttttgagag ttcgagacca acgcgggaat gtattattat ctcctgaaga ggttagtgaa   1560
```

```
acacagggaa ctgagagact gacaataact tattcatcgt cgatgatgtg ggagattaac   1620
ggtcctgagt cggttttggt caatacttat caatggatca tcagaaattg ggaagctgtc   1680
aaaattcaat ggtctcagaa tcctgcaatg ttgtacaaca aaatggaatt tgaaccattt   1740
caatctttag tccccaaggc cattagaagc caatacagtg ggtttgtcag aactctattc   1800
caacaaatga gagacgtact tgggacattt gacaccaccc agataataaa gcttctccct   1860
tttgcagccg ctccaccaaa gcaaagcaga atgcagttct cttcactgac tgtaaatgtg   1920
aggggatcag ggatgagaat acttgtaagg ggcaattctc ctgtattcaa ctacaacaag   1980
accactaaaa gactaacaat tctcggaaaa gatgccggca ctttaattga agacccagat   2040
gaaagcacat ccggagtgga gtccgctgta ttgagagggt ttctcattat aggtaaggaa   2100
gacagaagat acgggccagc attaagcatc aatgaactga gtaaccttgc aaaaggggaa   2160
aaggctaatg tgctaatcgg gcaaggagac gtggtgttgg taatgaaacg aaaacgggac   2220
tctagcatac ttactgacag ccagacagcg accaaaagaa ttcggatggc catcaattaa   2280
tgttgaatag tttaaaaacg accttgtttc tact                               2314
```

<210> SEQ ID NO 20
<211> LENGTH: 2314
<212> TYPE: DNA
<213> ORGANISM: Influenza virus

<400> SEQUENCE: 20

```
atggaaagaa taaaagaact acggaacctg atgtcgcagt ctcgcactcg cgagatactg     60
acaaaaacca cagtggacca tatggccata attaagaagt acacatcggg gagacaggaa    120
aagaacccgt cacttaggat gaaatggatg atggcaatga aatacccaat cactgctgac    180
aaaaggataa cagaaatggt tccggagaga aatgaacaag gacaaactct atggagtaaa    240
atgagtgatg ctggatcaga tcgagtgatg gtatcacctt tggctgtgac atggtggaat    300
agaaatggac ccgtgacaag tacggtccat tacccaaaag tatacaagac ttattttgac    360
aaagtcgaaa ggttaaaaca tggaaccttt ggccctgttc attttagaaa tcaagtcaag    420
atacgccgaa gagtagacat aaaccctggt catgcggacc tcagtgccaa ggaggcacaa    480
gatgtaatta tggaagttgt ttttcccaat gaagtgggag ccaggatact aacatcagaa    540
tcgcaattaa caataactaa agagaaaaaa gaagaactcc gagattgcaa aatttctccc    600
ttgatggttg catacatgtt agagagagaa cttgtccgaa aaacaagatt cctcccagtt    660
gctggcggaa caagcagtat atacattgaa gttttacatt tgactcaagg gacgtgttgg    720
gaacaaatgt acactccagg tggagaagtg aggaatgacg atgttgacca aagcctaatt    780
attgcagcca ggaacatagt aagaagagcc gcagtatcag cagatccact agcattttta    840
ttggagatgt gccacagcac acaaattggc gggacaagga tggtggacat tcttagacag    900
aacccgactg aagaacaagc tgtggatata tgcaaggctg caatgggatt gagaatcagc    960
tcatccttca gctttggtgg gtttacattt aaaagaacaa gcgggtcatc agtcaaaaaa   1020
gaggaagaac tgcttacagg caatctccaa acattgaaga taagagtaca tgaggggtat   1080
gaggagttca caatggtggg gaaaagagca acagctatac tcagaaaagc aaccagaaga   1140
ttggttcagc tcatagtgag tggaagagac gaacagtcaa tagccgaagc aataattgtg   1200
gccatggtgt tttcacaaga ggattgcatg ataaaagcag ttagaggtga cctgaatttc   1260
gtcaacagag caaatcagcg gttgaacccc atgcatcagc ttttaaggca ttttcagaaa   1320
```

gatgcgaaag tgctttttca gaattgggga attgagcaca tcgacagtgt aatgggaatg 1380
gttggagtat taccagatat gactccaagc acagagatgt caatgagagg aataagagtc 1440
agcaaaatgg gtgtggatga atactccagt acagagaggg tggtggttag cattgatcgg 1500
tttttgagag ttcgagacca acgcgggaat gtattattat ctcctgaaga ggttagtgaa 1560
acacagggaa ctgagagact gacaataact tattcatcgt cgatgatgtg ggagattaac 1620
ggtcctgagt cggttttggt caatacttat caatggatca tcagaaattg ggaagctgtc 1680
aaaattcaat ggtctcagaa tcctgcaatg ttgtacaaca aaatggaatt tgaaccattt 1740
caatctttag tccccaaggc cattagaagc caatacagtg ggtttgtcag aactctattc 1800
caacaaatga gagacgtact tgggacattt gacaccaccc agataataaa gcttctccct 1860
tttgcagccg ctccaccaaa gcaaagcaga atgcagttct cttcactgac tgtaaatgtg 1920
aggggatcag ggatgagaat acttgtaagg ggcaattctc ctgtattcaa ctacaacaag 1980
accactaaaa gactaacaat tctcggaaaa gatgccggca ctttaattga agacccagat 2040
gaaagcacat ccggagtgga gtccgctgta ttgagagggt ttctcattat aggtaaggaa 2100
gacagaagat acgggccagc attaagcatc aatgaactga gtaaccttgc aaaaggggaa 2160
aaggctaatg tgctaatcgg gcaaggagac gtggtgttgg taatgaaacg aaaacgggac 2220
tctagcatac ttactgacag ccagacagcg accaaaagaa ttcggatggc catcaattaa 2280
tgttgaatag tttaaaaacg accttgtttc tact 2314

<210> SEQ ID NO 21
<211> LENGTH: 2314
<212> TYPE: DNA
<213> ORGANISM: Influenza virus

<400> SEQUENCE: 21
atggaaagaa taaaagaact acggaacctg atgtcgcagt ctcgcactcg cgagatactg 60
acaaaaacca cagtggacca tatggccata attaagaagt acacatcggg gagacaggaa 120
aagaacccgt cacttaggat gaaatggatg atggcaatga aatacccaat cactgctgac 180
aaaaggataa cagaaatggt tccggagaga aatgaacaag gacaaactct atggagtaaa 240
atgagtgatg ctggatcaga tcgagtgatg gtatcacctt tggctgtgac atggtggaat 300
agaaatggac ccgtgacaag tacggtccat tacccaaaag tatacaagac ttattttgac 360
aaagtcgaaa ggttaaaaca tggaaccttt ggccctgttc attttagaaa tcaagtcaag 420
atacgccgaa gagtagacat aaaccctggt catgcggacc tcagtgccaa ggaggcacaa 480
gatgtaatta tggaagttgt ttttcccaat gaagtgggag ccaggatact aacatcagaa 540
tcgcaattaa caataactaa agagaaaaaa gaagaactcc gagattgcaa aatttctccc 600
ttgatggttg catacatgtt agagagagaa cttgtccgaa aaacaagatt cctcccagtt 660
gctggcggaa caagcagtat atacattgaa gttttacatt tgactcaagg gacgtgttgg 720
gaacaaatgt acactccagg tggagaagtg aggaatgacg atgttgacca aagcctaatt 780
attgcagcca ggaacatagt aagaagagcc gcagtatcag cagatccact agcatcttta 840
ttggagatgt gccacagcac acaaattggc gggacaagga tggtggacat tcttagacag 900
aacccgactg aagaacaagc tgtggatata tgcaaggctg caatgggatt gagaatcagc 960
tcatccttca gctttggtgg gtttacattt aaaagaacaa gcgggtcatc agtcaaaaaa 1020
gaggaagaac tgcttacagg caatctccaa acattgaaga taagagtaca taaggggtat 1080
gaggagttca caatggtggg gaaaagagca acagctatac tcagaaaagc aaccagaaga 1140

```
ttggttcagc tcatagtgag tggaagagac gaacagtcaa tagccgaagc aataattgtg   1200

gccatggtgt tttcacaaga ggattgcatg ataaaagcag ttagaggtga cctgaatttc   1260

gtcaacagag caaatcagcg gttgaacccc atgcatcagc ttttaaggca ttttcagaaa   1320

gatgcgaaag tgctttttca gaattgggga attgagcaca tcgacagtgt aatgggaatg   1380

gttggagtat taccagatat gactccaagc acagagatgt caatgagagg aataagagtc   1440

agcaaaatgg gtgtggatga atactccagt acagagaggg tggtggttag cattgatcgg   1500

tttttgagag ttcgagacca acgcgggaat gtattattat ctcctgaaga ggttagtgaa   1560

acacagggaa ctgagagact gacaataact tattcatcgt cgatgatgtg ggagattaac   1620

ggtcctgagt cggttttggt caatacttat caatggatca tcagaaattg ggaagctgtc   1680

aaaattcaat ggtctcagaa tcctgcaatg ttgtacaaca aaatggaatt tgaaccattt   1740

caatctttag tccccaaggc cattagaagc caatacagtg ggtttgtcag aactctattc   1800

caacaaatga gagacgtact tgggacattt gacaccaccc agataataaa gcttctccct   1860

tttgcagccg ctccaccaaa gcaaagcaga atgcagttct cttcactgac tgtaaatgtg   1920

aggggatcag ggatgagaat acttgtaagg ggcaattctc ctgtattcaa ctacaacaag   1980

accactaaaa gactaacaat tctcggaaaa gatgccggca ctttaattga agacccagat   2040

gaaagcacat ccggagtgga gtccgctgta ttgagagggt ttctcattat aggtaaggaa   2100

gacagaagat acgggccagc attaagcatc aatgaactga gtaaccttgc aaaaggggaa   2160

aaggctaatg tgctaatcgg gcaaggagac gtggtgttgg taatgaaacg aaaacgggac   2220

tctagcatac ttactgacag ccagacagcg accaaaagaa ttcggatggc catcaattaa   2280

tgttgaatag tttaaaaacg accttgtttc tact                               2314
```

```
<210> SEQ ID NO 22
<211> LENGTH: 1775
<212> TYPE: DNA
<213> ORGANISM: Influenza virus

<400> SEQUENCE: 22

agcaaaagca ggggaaaata aaaacaacca aaatgaaggc aaacctactg gtcctgttat     60

gtgcacttgc agctgcagat gcagacacaa tatgtatagg ctaccatgcg aacaattcaa    120

ccgacactgt tgacacagta ctcgagaaga atgtgacagt gacacactct gttaacctgc    180

tcgaagacag ccacaacgga aaactatgta gattaaaagg aatagcccca ctacaattgg    240

ggaaatgtaa catcgccgga tggctcttgg gaaacccaga atgcgaccca ctgcttccag    300

tgagatcatg gtcctacatt gtagaaacac caaactctga gaatggaata tgttatccag    360

gagatttcat cgactatgag gagctgaggg agcaattgag ctcagtgtca tcattcgaaa    420

gattcgaaat atttcccaaa gaaagctcat ggcccaacca caacacaaac ggagtaacgg    480

cagcatgctc ccatgagggg aaaagcagtt tttacagaaa tttgctatgg ctgacggaga    540

aggagggctc atacccaaag ctgaaaaatt cttatgtgaa caaaaaaggg aaagaagtcc    600

ttgtactgtg ggtattcat cacccgccta acagtaagga acaacagaat ctctatcaga    660

atgaaaatgc ttatgtctct gtagtgactt caaattataa caggagattt accccggaaa    720

tagcagaaag acccaaagta agagatcaag ctgggaggat gaactattac tggaccttgc    780

taaaacccgg agacacaata atatttgagg caaatggaaa tctaatagca ccaatgtatg    840

ctttcgcact gagtagaggc tttgggtccg gcatcatcac ctcaaacgca tcaatgcatg    900
```

agtgtaacac gaagtgtcaa acacccctgg gagctataaa cagcagtctc ccttaccaga 960
atatacaccc agtcacaata ggagagtgcc caaaatacgt caggagtgcc aaattgagga 1020
tggttacagg actaaggaac attccgtcca ttcaatccag aggtctattt ggagccattg 1080
ccggttttat tgaaggggga tggactggaa tgatagatgg atggtatggt tatcatcatc 1140
agaatgaaca gggatcaggc tatgcagcgg atcaaaaaag cacacaaaat gccattaacg 1200
ggattacaaa caaggtgaac actgttatcg agaaaatgaa cattcaattc acagctgtgg 1260
gtaaagaatt caacaaatta gaaaaaagga tggaaaattt aaataaaaaa gttgatgatg 1320
gatttctgga catttggaca tataatgcag aattgttagt tctactggaa aatgaaagga 1380
ctctggattt ccatgactca aatgtgaaga atctgtatga gaaagtaaaa agccaattaa 1440
agaataatgc caaagaaatc ggaaatggat gttttgagtt ctaccacaag tgtgacaatg 1500
aatgcatgga aagtgtaaga aatgggactt atgattatcc caaatattca gaagagtcaa 1560
agttgaacag ggaaaaggta gatggagtga aattggaatc aatggggatc tatcagattc 1620
tggcgatcta ctcaactgtc gccagttcac tggtgctttt ggtctccctg gggcaatca 1680 gtttctggat gtgttctaat ggatctttgc agtgcagaat atgcatctga gattagaatt 1740
tcagagatat gaggaaaaac acccttgttt ctact 1775

<210> SEQ ID NO 23
<211> LENGTH: 1413
<212> TYPE: DNA
<213> ORGANISM: Influenza virus

<400> SEQUENCE: 23
agcaaaagca ggggtttaaa atgaatccaa atcagaaaat aataaccatt ggatcaatct 60
gtctggtagt cggactaatt agcctaatat tgcaaatagg gaatataatc tcaatatgga 120
ttagccattc aattcaaact ggaagtcaaa accatactgg aatatgcaac caaaacatca 180
ttacctataa aaatagcacc tgggtaaagg acacaacttc agtgatatta accggcaatt 240
catctctttg tcccatccgt gggtgggcta tatacagcaa agacaatagc ataagaattg 300
gttccaaagg agacgttttt gtcataagag agccctttat ttcatgttct cacttggaat 360
gcaggacctt ttttctgacc caaggtgcct tactgaatga caagcattca agtgggactg 420
ttaaggacag aagcccttat agggccttaa tgagctgccc tgtcggtgaa gctccgtccc 480
cgtacaattc aagatttgaa tcggttgctt ggtcagcaag tgcatgtcat gatggcatgg 540
gctggctaac aatcggaatt tcaggtccag ataatggagc agtggctgta ttaaaataca 600
acggcataat aactgaaacc ataaaaagtt ggaggaagaa aatattgagg acacaagagt 660
ctgaatgtgc ctgtgtaaat ggttcatgtt ttactataat gactgatggc ccgagtgatg 720
ggctggcctc gtacaaaatt ttcaagatcg aaaaggggaa ggttactaaa tcaatagagt 780
tgaatgcacc taattctcac tatgaggaat gttcctgtta ccctgatacc ggcaaagtga 840
tgtgtgtgtg cagagacaat tggcatggtt cgaaccggcc atgggtgtct ttcgatcaaa 900
acctggatta tcaaatagga tacatctgca gtggggtttt cggtgacaac ccgcgtcccg 960
aagatggaac aggcagctgt ggtccagtgt atgttgatgg agcaaacgga gtaaagggat 1020
tttcatatag gtatggtaat ggtgtttgga taggaaggac caaaagtcac agttccagac 1080
atgggtttga gatgatttgg gatcctaatg gatggacaga gactgatagt aagttctctg 1140
tgaggcaaga tgttgtggca atgactgatt ggtcagggta tagcggaagt ttcgttcaac 1200
atcctgagct gacagggcta gactgtatga ggccgtgctt ctgggttgaa ttaatcaggg 1260
gacgacctaa agaaaaaaca atctggacta gtgcgagcag catttctttt tgtggcgtga 1320
atagtgatac tgtagattgg tcttggccag acggtgctga gttgccattc agcattgaca 1380
agtagtctgt tcaaaaaact ccttgtttct act 1413

<210> SEQ ID NO 24
<211> LENGTH: 2233
<212> TYPE: DNA
<213> ORGANISM: Influenza virus

<400> SEQUENCE: 24
agcgaaagca ggtactgatc caaaatggaa gattttgtgc gacaatgctt caatccgatg 60
attgtcgagc ttgcggaaaa aacaatgaaa gagtatgggg aggacctgaa aatcgaaaca 120
aacaaatttg cagcaatatg cactcacttg gaagtatgct tcatgtattc agattttcac 180
ttcatcaatg agcaaggcga gtcaataatc gtagaacttg gtgatccaaa tgcacttttg 240
aagcacagat ttgaaataat cgagggaaga gatcgcacaa tggcctggac agtagtaaac 300
agtatttgca acactacagg ggctgagaaa ccaaagtttc taccagattt gtatgattac 360
aaggagaata gattcatcga aattggagta acaaggagag aagttcacat atactatctg 420
gaaaaggcca ataaaattaa atctgagaaa acacacatcc acatttctc gttcactggg 480 gaagaaatgg ccacaaaggc agactacact ctcgatgaag aaagcagggc taggatcaaa 540
accagactat tcaccataag acaagaaatg gccagcagag gcctctggga ttcctttcgt 600
cagtccgaga gaggagaaga gacaattgaa gaaaggtttg aaatcacagg aacaatgcgc 660
aagcttgccg accaaagtct cccgccgaac ttctccagcc ttgaaaattt tagagcctat 720
gtggatggat tcgaaccgaa cggctacatt gagggcaagc tgtctcaaat gtccaaagaa 780
gtaaatgcta gaattgaacc tttttgaaa acaacaccac gaccacttag acttccgaat 840
gggcctccct gttctcagcg gtccaaattc ctgctgatgg atgccttaaa attaagcatt 900
gaggacccaa gtcatgaagg agagggaata ccgctatatg atgcaatcaa atgcatgaga 960
acattctttg gatggaagga acccaatgtt gttaaaccac acgaaaaggg aataaatcca 1020
aattatcttc tgtcatggaa gcaagtactg gcagaactgc aggacattga gaatgaggag 1080
aaaattccaa agactaaaaa tatgaagaaa acaagtcagc taaagtgggc acttggtgag 1140
aacatggcac cagaaaaggt agactttgac gactgtaaag atgtaggtga tttgaagcaa 1200
tatgatagtg atgaaccaga attgaggtcg cttgcaagtt ggattcagaa tgagtttaac 1260
aaggcatgcg aactgacaga ttcaagctgg atagagctcg atgagattgg agaagatgtg 1320
gctccaattg aacacattgc aagcatgaga aggaattatt tcacatcaga ggtgtctcac 1380
tgcagagcca cagaatacat aatgaaggga gtgtacatca atactgcctt gcttaatgca 1440
tcttgtgcag caatggatga tttccaatta attccaatga taagcaagtg tagaactaag 1500
gagggaaggc gaaagaccaa cttgtatggt ttcatcataa aaggaagatc ccacttaagg 1560
aatgacaccg acgtggtaaa ctttgtgagc atggagtttt ctctcactga cccaagactt 1620
gaaccacata aatgggagaa gtactgtgtt cttgagatag gagatatgct tataagaagt 1680
gccataggcc aggtttcaag gcccatgttc ttgtatgtga gaacaaatgg aacctcaaaa 1740
attaaaatga aatggggaat ggagatgagg cgttgcctcc tccagtcact tcaacaaatt 1800
gagagtatga ttgaagctga gtcctctgtc aaagagaaag acatgaccaa agagttcttt 1860
gagaacaaat cagaaacatg gcccattgga gagtccccca aaggagtgga ggaaagttcc 1920

```
attgggaagg tctgcaggac tttattagca aagtcggtat tcaacagctt gtatgcatct   1980

ccacaactag aaggattttc agctgaatca agaaaactgc ttcttatcgt tcaggctctt   2040

agggacaacc tggaacctgg gacctttgat cttgggggc tatatgaagc aattgaggag    2100

tgcctgatta atgatccctg ggttttgctt aatgcttctt ggttcaactc cttccttaca   2160

catgcattga gttagttgtg gcagtgctac tatttgctat ccatactgtc caaaaaagta   2220

ccttgtttct act                                                      2233
```

<210> SEQ ID NO 25
<211> LENGTH: 2341
<212> TYPE: DNA
<213> ORGANISM: Influenza virus

<400> SEQUENCE: 25

```
agcgaaagca ggcaaaccat ttgaatggat gtcaatccga ccttactttt cttaaaagtg     60

ccagcacaaa atgctataag cacaactttc ccttatactg gagaccctcc ttacagccat    120

gggacaggaa caggatacac catggatact gtcaacagga cacatcagta ctcagaaaag    180

ggaagatgga caacaaacac cgaaactgga gcaccgcaac tcaacccgat tgatgggcca    240

ctgccagaag acaatgaacc aagtggttat gcccaaacag attgtgtatt ggaggcgatg    300

gctttccttg aggaatccca tcctggtatt tttgaaaact cgtgtattga aacgatggag    360

gttgttcagc aaacacgagt agacaagctg acacaaggcc gacagaccta tgactggact    420

ctaaatagaa accaacctgc tgcaacagca ttggccaaca caatagaagt gttcagatca    480

aatggcctca cggccaatga gtctggaagg ctcatagact tccttaagga tgtaatggag    540

tcaatgaaca aagaagaaat ggggatcaca actcattttc agagaaagag acgggtgaga    600

gacaatatga ctaagaaaat gataacacag agaacaatgg gtaaaaagaa gcagagattg    660

aacaaaagga gttatctaat tagagcattg accctgaaca caatgaccaa agatgctgag    720

agagggaagc taaaacggag agcaattgca accccaggga tgcaaataag gggtttgta     780

tactttgttg agacactggc aaggagtata tgtgagaaac ttgaacaatc agggttgcca    840

gttggaggca atgagaagaa agcaaagttg gcaaatgttg taaggaagat gatgaccaat    900

tctcaggaca ccgaactttc tttcaccatc actggagata acaccaaatg gaacgaaaat    960

cagaatcctc ggatgttttt ggccatgatc acatatatga ccagaaatca gcccgaatgg   1020

ttcagaaatg ttctaagtat tgctccaata atgttctcaa acaaaatggc gagactggga   1080

aaagggtata tgtttgagag caagagtatg aaacttagaa ctcaaatacc tgcagaaatg   1140

ctagcaagca tcgatttgaa atatttcaat gattcaacaa gaaagaagat tgaaaaaatc   1200

cgaccgctct taatagaggg gactgcatca ttgagccctg gaatgatgat gggcatgttc   1260

aatatgttaa gcactgtatt aggcgtctcc atcctgaatc ttggacaaaa gagatacacc   1320

aagactactt actggtggga tggtcttcaa tcctctgacg attttgctct gattgtgaat   1380

gcacccaatc atgaagggat tcaagccgga gtcgacaggt tttatcgaac ctgtaagcta   1440

cttggaatca atatgagcaa gaaaaagtct tacataaaca gaacaggtac atttgaattc   1500

acaagttttt tctatcgtta tgggtttgtt gccaatttca gcatggagct tcccagtttt   1560

ggggtgtctg ggatcaacga gtcagcggac atgagtattg gagttactgt catcaaaaac   1620

aatatgataa acaatgatct tggtccagca acagctcaaa tggcccttca gttgttcatc   1680

aaagattaca ggtacacgta ccgatgccat ataggtgaca cacaaataca aacccgaaga   1740

tcatttgaaa taaagaaact gtgggagcaa acccgttcca aagctggact gctggtctcc   1800
```

```
gacggaggcc caaatttata caacattaga aatctccaca ttcctgaagt ctgcctaaaa   1860
tgggaattga tggatgagga ttaccagggg cgtttatgca acccactgaa cccatttgtc   1920
agccataaag aaattgaatc aatgaacaat gcagtgatga tgccagcaca tggtccagcc   1980
aaaaacatgg agtatgatgc tgttgcaaca acacactcct ggatccccaa aagaaatcga   2040
tccatcttga atacaagtca aagaggagta cttgaggatg aacaaatgta ccaaaggtgc   2100
tgcaatttat ttgaaaaatt cttccccagc agttcataca gaagaccagt cgggatatcc   2160
agtatggtgg aggctatggt ttccagagcc cgaattgatg cacggattga tttcgaatct   2220
ggaaggataa agaaagaaga gttcactgag atcatgaaga tctgttccac cattgaagag   2280
ctcagacggc aaaaatagtg aatttagctt gtccttcatg aaaaaatgcc ttgtttctac   2340
t                                                                   2341
```

<210> SEQ ID NO 26
<211> LENGTH: 2341
<212> TYPE: DNA
<213> ORGANISM: Influenza virus

<400> SEQUENCE: 26

```
agcgaaagca ggtcaattat attcaatatg gaaagaataa aagaactacg aaatctaatg     60
tcgcagtctc gcacccgcga gatactcaca aaaaccaccg tggaccatat ggccataatc    120
aagaagtaca catcaggaag acaggagaag aacccagcac ttaggatgaa atggatgatg    180
gcaatgaaat atccaattac agcagacaag aggataacgg aaatgattcc tgagagaaat    240
gagcaaggac aaactttatg gagtaaaatg aatgatgccg gatcagaccg agtgatggta    300
tcacctctgg ctgtgacatg gtggaatagg aatggaccaa taacaaatac agttcattat    360
ccaaaaatct acaaaactta ttttgaaaga gtcgaaaggc taaagcatgg aacctttggc    420
cctgtccatt ttagaaacca agtcaaaata cgtcggagag ttgacataaa tcctggtcat    480
gcagatctca gtgccaagga ggcacaggat gtaatcatgg aagttgtttt ccctaacgaa    540
gtgggagcca ggatactaac atcggaatcg caactaacga taaccaaaga gaagaaagaa    600
gaactccagg attgcaaaat ttctcctttg atggttgcat acatgttgga gagagaactg    660
gtccgcaaaa cgagattcct cccagtggct ggtggaacaa gcagtgtgta cattgaagtg    720
ttgcatttga ctcaaggaac atgctgggaa cagatgtata ctccaggagg ggaagtgagg    780
aatgatgatg ttgatcaaag cttgattatt gctgctagga acatagtgag aagagctgca    840
gtatcagcag atccactagc atctttattg gagatgtgcc acagcacaca gattggtgga    900
attaggatgg tagacatcct taggcagaac ccaacagaag agcaagccgt ggatatatgc    960
aaggctgcaa tgggactgag aattagctca tccttcagtt ttggtggatt cacatttaag   1020
agaacaagcg gatcatcagt caagagagag gaagaggtgc ttacgggcaa tcttcaaaca   1080
ttgaagataa gagtgcatga gggatatgaa gagttcacaa tggttgggag aagagcaaca   1140
gccatactca gaaaagcaac caggagattg attcagctga tagtgagtgg gagagacgaa   1200
cagtcgattg ccgaagcaat aattgtggcc atggtatttt cacaagagga ttgtatgata   1260
aaagcagtca gaggtgatct gaatttcgtc aatagggcga atcaacgatt gaatcctatg   1320
catcaacttt taagacattt tcagaaggat gcgaaagtgc tttttcaaaa ttggggagtt   1380
gaacctatcg acaatgtgat gggaatgatt gggatattgc ccgacatgac tccaagcatc   1440
gagatgtcaa tgagaggagt gagaatcagc aaaatgggtg tagatgagta ctccagcacg   1500
```

gagagggtag tggtgagcat tgaccgtttt ttgagaatcc gggaccaacg aggaaatgta 1560
ctactgtctc ccgaggaggt cagtgaaaca cagggaacag agaaactgac aataacttac 1620
tcatcgtcaa tgatgtggga gattaatggt cctgaatcag tgttggtcaa tacctatcaa 1680
tggatcatca gaaactggga aactgttaaa attcagtggt cccagaaccc tacaatgcta 1740
tacaataaaa tggaatttga accatttcag tctttagtac ctaaggccat tagaggccaa 1800
tacagtgggt ttgtaagaac tctgttccaa caaatgaggg atgtgcttgg gacatttgat 1860
accgcacaga taataaaact tcttcccttc gcagccgctc caccaaagca aagtagaatg 1920
cagttctcct catttactgt gaatgtgagg ggatcaggaa tgagaatact tgtaaggggc 1980
aattctcctg tattcaacta taacaaggcc acgaagagac tcacagttct cggaaaggat 2040
gctggcactt taactgaaga cccagatgaa ggcacagctg gagtggagtc cgctgttctg 2100
aggggattcc tcattctggg caaagaagac aagagatatg ggccagcact aagcatcaat 2160
gaactgagca accttgcgaa aggagagaag gctaatgtgc taattgggca aggagacgtg 2220
gtgttggtaa tgaaacggaa acgggactct agcatactta ctgacagcca gacagcgacc 2280
aaaagaattc ggatggccat caattagtgt cgaatagttt aaaaacgacc ttgtttctac 2340
t 2341

<210> SEQ ID NO 27
<211> LENGTH: 1565
<212> TYPE: DNA
<213> ORGANISM: Influenza virus

<400> SEQUENCE: 27
agcaaaagca gggtagataa tcactcactg agtgacatca aaatcatggc gtctcaaggc 60
accaaacgat cttacgaaca gatggagact gatggagaac gccagaatgc cactgaaatc 120
agagcatccg tcggaaaaat gattggtgga attggacgat tctacatcca aatgtgcacc 180
gaactcaaac tcagtgatta tgagggacgg ttgatccaaa acagcttaac aatagagaga 240
atggtgctct ctgcttttga cgaaaggaga aataaatacc ttgaagaaca tcccagtgcg 300
gggaaagatc ctaagaaaac tggaggacct atatacagga gagtaaacgg aaagtggatg 360
agagaactca tcctttatga caaagaagaa ataaggcgaa tctggcgcca agctaataat 420
ggtgacgatg caacggctgg tctgactcac atgatgatct ggcattccaa tttgaatgat 480
gcaacttatc agaggacaag agctcttgtt cgcaccggaa tggatcccag gatgtgctct 540
ctgatgcaag gttcaactct ccctaggagg tctggagccg caggtgctgc agtcaaagga 600
gttggaacaa tggtgatgga attggtcaga atgatcaaac gtgggatcaa tgatcggaac 660
ttctggaggg gtgagaatgg acgaaaaaca agaattgctt atgaaagaat gtgcaacatt 720
ctcaaaggga aatttcaaac tgctgcacaa aaagcaatga tggatcaagt gagagagagc 780
cggaacccag ggaatgctga gttcgaagat ctcacttttc tagcacggtc tgcactcata 840
ttgagagggt cggttgctca caagtcctgc ctgcctgcct gtgtgtatgg acctgccgta 900
gccagtgggt acgactttga aagggaggga tactctctag tcggaataga ccctttcaga 960
ctgcttcaaa acagccaagt gtacagccta atcagaccaa atgagaatcc agcacacaag 1020
agtcaactgg tgtggatggc atgccattct gccgcatttg aagatctaag agtattaagc 1080
ttcatcaaag ggacgaaggt gctcccaaga gggaagcttt ccactagagg agttcaaatt 1140
gcttccaatg aaaatatgga gactatggaa tcaagtacac ttgaactgag aagcaggtac 1200
tgggccataa ggaccagaag tggaggaaac accaatcaac agagggcatc tgcgggccaa 1260
atcagcatac aacctacgtt ctcagtacag agaaatctcc cttttgacag aacaaccatt 1320
atggcagcat tcaatgggaa tacagagggg agaacatctg acatgaggac cgaaatcata 1380
aggatgatgg aaagtgcaag accagaagat gtgtctttcc aggggcgggg agtcttcgag 1440
ctctcggacg aaaaggcagc gagcccgatc gtgccttcct ttgacatgag taatgaagga 1500
tcttatttct tcggagacaa tgcagaggag tacgacaatt aaagaaaaat acccttgttt 1560
ctact 1565

<210> SEQ ID NO 28
<211> LENGTH: 1027
<212> TYPE: DNA
<213> ORGANISM: Influenza virus

<400> SEQUENCE: 28
agcaaaagca ggtagatatt gaaagatgag tcttctaacc gaggtcgaaa cgtacgtact 60
ctctatcatc ccgtcaggcc ccctcaaagc cgagatcgca cagagacttg aagatgtctt 120
tgcagggaag aacaccgatc ttgaggttct catggaatgg ctaaagacaa gaccaatcct 180
gtcacctctg actaagggga ttttaggatt tgtgttcacg ctcaccgtgc ccagtgagcg 240
aggactgcag cgtagacgct ttgtccaaaa tgcccttaat gggaacgggg atccaaataa 300
catggacaaa gcagttaaac tgtataggaa gctcaagagg gagataacat tccatggggc 360
caaagaaatc tcactcagtt attctgctgg tgcacttgcc agttgtatgg gcctcatata 420
caacaggatg gggctgtga ccactgaagt ggcatttggc ctggtatgtg caacctgtga 480
acagattgct gactcccagc atcggtctca taggcaaatg gtgacaacaa ccaatccact 540
aatcagacat gagaacagaa tggttttagc cagcactaca gctaaggcta tggagcaaat 600
ggctggatcg agtgagcaag cagcagaggc catggaggtt gctagtcagg ctagacaaat 660
ggtgcaagcg atgagaacca ttgggactca tcctagctcc agtgctggtc tgaaaaatga 720
tcttcttgaa aatttgcagg cctatcagaa acgaatgggg gtgcagatgc aacggttcaa 780
gtgatcctct cactattgcc gcaaatatca ttgggatctt gcacttgaca ttgtggattc 840
ttgatcgtct ttttttcaaa tgcatttacc gtcgctttaa atacggactg aaaggagggc 900
cttctacgga aggagtgcca aagtctatga gggaagaata tcgaaaggaa cagcagagtg 960
ctgtggatgc tgacgatggt cattttgtca gcatagagct ggagtaaaaa actaccttgt 1020
ttctact 1027

<210> SEQ ID NO 29
<211> LENGTH: 890
<212> TYPE: DNA
<213> ORGANISM: Influenza virus

<400> SEQUENCE: 29
agcaaaagca gggtgacaaa aacataatgg atccaaacac tgtgtcaagc tttcaggtag 60
attgctttct ttggcatgtc cgcaaacgag ttgcagacca agaactaggc gatgccccat 120
tccttgatcg gcttcgccga gatcagaaat ccctaagagg aaggggcagt actctcggtc 180
tggacatcaa gacagccaca cgtgctggaa agcagatagt ggagcggatt ctgaaagaag 240
aatccgatga ggcacttaaa atgaccatgg cctctgtacc tgcgtcgcgt tacctaactg 300
acatgactct tgaggaaatg tcaagggact ggtccatgct catacccaag cagaaagtgg 360
caggccctct ttgtatcaga atggaccagg cgatcatgga taagaacatc atactgaaag 420

```
cgaacttcag tgtgattttt gaccggctgg agactctaat attgctaagg gctttcaccg    480

aagagggagc aattgttggc gaaatttcac cattgccttc tcttccagga catactgctg    540

aggatgtcaa aaatgcagtt ggagtcctca tcggaggact tgaatggaat gataacacag    600

ttcgagtctc tgaaactcta cagagattcg cttggagaag cagtaatgag aatgggagac    660

ctccactcac tccaaaacag aaacgagaaa tggcgggaac aattaggtca gaagtttgaa    720

gaaataagat ggttgattga agaagtgaga cacaaactga agataacaga gaatagtttt    780

gagcaaataa catttatgca agccttacat ctattgcttg aagtggagca agagataaga    840

actttctcgt ttcagcttat ttagtactaa aaaacaccct tgtttctact              890


<210> SEQ ID NO 30
<211> LENGTH: 468
<212> TYPE: PRT
<213> ORGANISM: Influenza virus

<400> SEQUENCE: 30

Met Asn Pro Asn Gln Lys Ile Ile Thr Ile Gly Val Val Asn Thr Thr
1               5                   10                  15

Leu Ser Thr Ile Ala Leu Leu Ile Gly Val Gly Asn Leu Ile Phe Asn
            20                  25                  30

Thr Val Ile His Glu Lys Ile Gly Asp His Gln Thr Val Ile His Pro
        35                  40                  45

Thr Thr Thr Thr Pro Ala Ile Pro Asn Cys Ser Asp Thr Ile Ile Thr
    50                  55                  60

Tyr Asn Asn Thr Val Ile Asn Asn Ile Thr Thr Ile Ile Thr Glu Ala
65                  70                  75                  80

Glu Arg Leu Phe Lys Pro Pro Leu Pro Leu Cys Pro Phe Arg Gly Phe
                85                  90                  95

Phe Pro Phe His Lys Asp Asn Ala Ile Arg Leu Gly Glu Asn Lys Asp
            100                 105                 110

Val Ile Val Thr Arg Glu Pro Tyr Val Ser Cys Asp Asn Asp Asn Cys
        115                 120                 125

Trp Ser Phe Ala Leu Ala Gln Gly Ala Leu Leu Gly Thr Lys His Ser
    130                 135                 140

Asn Gly Thr Ile Lys Asp Arg Thr Pro Tyr Arg Ser Leu Ile Gln Phe
145                 150                 155                 160

Pro Ile Gly Thr Ala Pro Val Leu Gly Asn Tyr Lys Glu Ile Cys Ile
                165                 170                 175

Ala Trp Ser Ser Ser Ser Cys Phe Asp Gly Lys Glu Trp Met His Val
            180                 185                 190

Cys Met Thr Gly Asn Asp Asn Asp Ala Ser Ala Gln Ile Ile Tyr Ala
        195                 200                 205

Gly Arg Met Thr Asp Ser Ile Lys Ser Trp Lys Arg Asp Ile Leu Arg
    210                 215                 220

Thr Gln Glu Ser Glu Cys Gln Cys Ile Asp Gly Thr Cys Val Val Ala
225                 230                 235                 240

Val Thr Asp Gly Pro Ala Ala Asn Ser Ala Asp His Arg Val Tyr Trp
                245                 250                 255

Ile Arg Glu Gly Arg Ile Val Lys Tyr Glu Asn Val Pro Lys Thr Lys
            260                 265                 270

Ile Gln His Leu Glu Glu Cys Ser Cys Tyr Val Asp Ile Asp Val Tyr
        275                 280                 285

Cys Ile Cys Arg Asp Asn Trp Lys Gly Ser Asn Arg Pro Trp Met Arg
```

290 295 300

Ile Asn Asn Glu Thr Ile Leu Glu Thr Gly Tyr Val Cys Ser Lys Phe
305 310 315 320

His Ser Asp Thr Pro Arg Pro Ala Asp Pro Ser Thr Val Ser Cys Asp
325 330 335

Ser Pro Ser Asn Val Asn Gly Gly Pro Gly Val Lys Gly Phe Gly Phe
340 345 350

Lys Val Gly Asn Asp Val Trp Leu Gly Arg Thr Met Ser Thr Ser Gly
355 360 365

Arg Ser Gly Phe Glu Ile Ile Lys Val Ala Glu Gly Trp Ile Asn Ser
370 375 380

Pro Asn His Ala Lys Ser Val Thr Gln Thr Leu Val Ser Asn Asn Asp
385 390 395 400

Trp Ser Gly Tyr Ser Gly Ser Phe Ile Val Lys Thr Lys Ala Cys Phe
405 410 415

Gln Pro Cys Phe Tyr Val Glu Leu Ile Arg Gly Arg Pro Asn Lys Asn
420 425 430

Asp Asp Val Ser Trp Thr Ser Asn Ser Ile Val Thr Phe Cys Gly Leu
435 440 445

Asp Asn Glu Pro Gly Ser Gly Asn Trp Pro Asp Gly Ser Asn Ile Gly
450 455 460

Phe Met Pro Lys
465

<210> SEQ ID NO 31
<211> LENGTH: 470
<212> TYPE: PRT
<213> ORGANISM: Influenza virus

<400> SEQUENCE: 31

Met Asn Pro Asn Gln Lys Ile Ile Thr Ile Gly Ser Val Ser Ile Ile
1 5 10 15

Leu Thr Thr Ile Gly Leu Leu Leu Gln Ile Thr Ser Leu Cys Ser Ile
20 25 30

Trp Phe Ser His Tyr Asn Gln Val Thr Gln Thr His Glu Gln Pro Cys
35 40 45

Ser Asn Asn Thr Thr Asn Tyr Tyr Asn Glu Thr Phe Val Asn Val Thr
50 55 60

Asn Val Gln Asn Asn Tyr Thr Thr Val Ile Glu Pro Ser Ala Pro Asp
65 70 75 80

Val Val His Tyr Ser Ser Gly Arg Asp Leu Cys Pro Ile Arg Gly Trp
85 90 95

Ala Pro Leu Ser Lys Asp Asn Gly Ile Arg Ile Gly Ser Arg Gly Glu
100 105 110

Val Phe Val Ile Arg Glu Pro Phe Ile Ser Cys Ser Ile Ser Glu Cys
115 120 125

Arg Thr Phe Phe Leu Thr Gln Gly Ala Leu Leu Asn Asp Lys His Ser
130 135 140

Asn Gly Thr Val Lys Asp Arg Ser Pro Phe Arg Thr Leu Met Ser Cys
145 150 155 160

Pro Ile Gly Val Ala Pro Ser Pro Ser Asn Ser Arg Phe Glu Ser Val
165 170 175

Ala Trp Ser Ala Thr Ala Cys Ser Asp Gly Pro Gly Trp Leu Thr Leu
180 185 190

```
Gly Ile Thr Gly Pro Asp Ala Thr Ala Val Ala Val Leu Lys Tyr Asn
        195                 200                 205

Gly Ile Ile Thr Asp Thr Leu Lys Ser Trp Lys Gly Asn Ile Met Arg
    210                 215                 220

Thr Gln Glu Ser Glu Cys Val Cys Gln Asp Glu Phe Cys Tyr Thr Leu
225                 230                 235                 240

Ile Thr Asp Gly Pro Ser Asp Ala Gln Ala Phe Tyr Lys Ile Leu Lys
                245                 250                 255

Ile Arg Lys Gly Lys Ile Val Ser Met Lys Asp Val Asp Ala Thr Gly
            260                 265                 270

Phe His Phe Glu Glu Cys Ser Cys Tyr Pro Ser Gly Thr Asp Ile Glu
        275                 280                 285

Cys Val Cys Arg Asp Asn Trp Arg Gly Ser Asn Arg Pro Trp Ile Arg
    290                 295                 300

Phe Asn Ser Asp Leu Asp Tyr Gln Ile Gly Tyr Val Cys Ser Gly Ile
305                 310                 315                 320

Phe Gly Asp Asn Pro Arg Pro Val Asp Gly Thr Gly Ser Cys Asn Ser
                325                 330                 335

Pro Val Asn Asn Gly Lys Gly Arg Tyr Gly Val Lys Gly Phe Ser Phe
            340                 345                 350

Arg Tyr Gly Asp Gly Val Trp Ile Gly Arg Thr Lys Ser Leu Glu Ser
        355                 360                 365

Arg Ser Gly Phe Glu Met Val Trp Asp Ala Asn Gly Trp Val Ser Thr
    370                 375                 380

Asp Lys Asp Ser Asn Gly Val Gln Asp Ile Ile Asp Asn Asp Asn Trp
385                 390                 395                 400

Ser Gly Tyr Ser Gly Ser Phe Ser Ile Arg Gly Glu Thr Thr Gly Arg
                405                 410                 415

Asn Cys Thr Val Pro Cys Phe Trp Val Glu Met Ile Arg Gly Gln Pro
            420                 425                 430

Lys Glu Lys Thr Ile Trp Thr Ser Gly Ser Ser Ile Ala Phe Cys Gly
        435                 440                 445

Val Asn Ser Asp Thr Thr Gly Trp Ser Trp Pro Asp Gly Ala Leu Leu
    450                 455                 460

Pro Phe Asp Ile Asp Lys
465                 470
```

<210> SEQ ID NO 32
<211> LENGTH: 470
<212> TYPE: PRT
<213> ORGANISM: Influenza virus

<400> SEQUENCE: 32

```
Met Asn Pro Asn Gln Lys Ile Ile Cys Ile Ser Ala Thr Gly Met Thr
1               5                   10                  15

Leu Ser Val Val Ser Leu Leu Ile Gly Ile Ala Asn Leu Gly Leu Asn
            20                  25                  30

Ile Gly Leu His Tyr Lys Met Gly Asp Thr Pro Asp Val Asn Ile Pro
        35                  40                  45

Asn Met Asn Glu Thr Asn Ser Thr Thr Thr Ile Ile Asn Asn His Thr
    50                  55                  60

Gln Asn Asn Phe Thr Asn Ile Thr Asn Ile Ile Val Asn Lys Asn Glu
65                  70                  75                  80

Glu Gly Thr Phe Leu Asn Leu Thr Lys Pro Leu Cys Glu Val Asn Ser
                85                  90                  95
```

-continued

```
Trp His Ile Leu Ser Lys Asp Asn Ala Ile Arg Ile Gly Glu Asp Ala
            100                 105                 110

His Ile Leu Val Thr Arg Glu Pro Tyr Leu Ser Cys Asp Pro Gln Gly
        115                 120                 125

Cys Arg Met Phe Ala Leu Ser Gln Gly Thr Thr Leu Arg Gly Arg His
    130                 135                 140

Ala Asn Gly Thr Ile His Asp Arg Ser Pro Phe Arg Ala Leu Ile Ser
145                 150                 155                 160

Trp Glu Met Gly Gln Ala Pro Ser Pro Tyr Asn Val Arg Val Glu Cys
                165                 170                 175

Ile Gly Trp Ser Ser Thr Ser Cys His Asp Gly Ile Ser Arg Met Ser
            180                 185                 190

Ile Cys Met Ser Gly Ala Asn Asn Asn Ala Ser Ala Val Val Trp Tyr
        195                 200                 205

Gly Gly Arg Pro Val Thr Glu Ile Pro Ser Trp Ala Gly Asn Ile Leu
    210                 215                 220

Arg Thr Gln Glu Ser Glu Cys Val Cys His Lys Gly Ile Cys Pro Val
225                 230                 235                 240

Val Met Thr Asp Gly Pro Ala Asn Asn Arg Ala Ala Thr Lys Ile Ile
                245                 250                 255

Tyr Phe Lys Glu Gly Lys Ile Gln Lys Ile Glu Glu Leu Ala Gly Asn
            260                 265                 270

Thr Gln His Ile Glu Glu Cys Ser Cys Tyr Gly Ala Val Gly Val Ile
        275                 280                 285

Lys Cys Ile Cys Arg Asp Asn Trp Lys Gly Ala Asn Arg Pro Val Ile
    290                 295                 300

Thr Ile Asp Pro Glu Met Met Thr His Thr Ser Lys Tyr Leu Cys Ser
305                 310                 315                 320

Lys Ile Leu Thr Asp Thr Ser Arg Pro Asn Asp Pro Thr Asn Gly Asn
                325                 330                 335

Cys Asp Ala Pro Ile Thr Gly Gly Ser Pro Asp Pro Gly Val Lys Gly
            340                 345                 350

Phe Ala Phe Leu Asp Arg Glu Asn Ser Trp Leu Gly Arg Thr Ile Ser
        355                 360                 365

Lys Asp Ser Arg Ser Gly Tyr Glu Met Leu Lys Val Pro Asn Ala Glu
    370                 375                 380

Thr Asp Thr Gln Ser Gly Pro Ile Ser His Gln Val Ile Val Asn Asn
385                 390                 395                 400

Gln Asn Trp Ser Gly Tyr Ser Gly Ala Phe Ile Asp Tyr Trp Ala Asn
                405                 410                 415

Lys Glu Cys Phe Asn Pro Cys Phe Tyr Val Glu Leu Ile Arg Gly Arg
            420                 425                 430

Pro Lys Glu Ser Ser Val Leu Trp Thr Ser Asn Ser Ile Val Ala Leu
        435                 440                 445

Cys Gly Ser Lys Glu Arg Leu Gly Ser Trp Ser Trp His Asp Gly Ala
    450                 455                 460

Glu Ile Ile Tyr Phe Lys
465                 470
```

<210> SEQ ID NO 33
<211> LENGTH: 470
<212> TYPE: PRT
<213> ORGANISM: Influenza virus

<400> SEQUENCE: 33

```
Met Asn Pro Asn Gln Lys Leu Phe Ala Leu Ser Gly Val Ala Ile Ala
1               5                   10                  15

Leu Ser Ile Leu Asn Leu Leu Ile Gly Ile Ser Asn Val Gly Leu Asn
            20                  25                  30

Val Ser Leu His Leu Lys Gly Ser Ser Asp Gln Asp Lys Asn Trp Thr
        35                  40                  45

Cys Thr Ser Val Thr Gln Asn Asn Thr Thr Leu Ile Glu Asn Thr Tyr
    50                  55                  60

Val Asn Asn Thr Thr Val Ile Asp Lys Glu Thr Gly Thr Ala Lys Pro
65                  70                  75                  80

Asn Tyr Leu Met Leu Asn Lys Ser Leu Cys Lys Val Glu Gly Trp Val
                85                  90                  95

Val Val Ala Lys Asp Asn Ala Ile Arg Phe Gly Glu Ser Glu Gln Ile
            100                 105                 110

Ile Val Thr Arg Glu Pro Tyr Val Ser Cys Asp Pro Leu Gly Cys Lys
        115                 120                 125

Met Tyr Ala Leu His Gln Gly Thr Thr Ile Arg Asn Lys His Ser Asn
    130                 135                 140

Gly Thr Ile His Asp Arg Thr Ala Phe Arg Gly Leu Ile Ser Thr Pro
145                 150                 155                 160

Leu Gly Ser Pro Pro Val Val Ser Asn Ser Asp Phe Leu Cys Val Gly
                165                 170                 175

Trp Ser Ser Thr Ser Cys His Asp Gly Ile Gly Arg Met Thr Ile Cys
            180                 185                 190

Val Gln Gly Asn Asn Asp Asn Ala Thr Ala Thr Val Tyr Tyr Asp Arg
        195                 200                 205

Arg Leu Thr Thr Thr Ile Lys Thr Trp Ala Gly Asn Ile Leu Arg Thr
    210                 215                 220

Gln Glu Ser Glu Cys Val Cys His Asn Gly Thr Cys Val Val Ile Met
225                 230                 235                 240

Thr Asp Gly Ser Ala Ser Ser Gln Ala Tyr Thr Lys Val Leu Tyr Phe
                245                 250                 255

His Lys Gly Leu Val Ile Lys Glu Glu Ala Leu Lys Gly Ser Ala Arg
            260                 265                 270

His Ile Glu Glu Cys Ser Cys Tyr Gly His Asn Ser Lys Val Thr Cys
        275                 280                 285

Val Cys Arg Asp Asn Trp Gln Gly Ala Asn Arg Pro Val Ile Glu Ile
    290                 295                 300

Asp Met Asn Ala Met Glu His Thr Ser Gln Tyr Leu Cys Thr Gly Val
305                 310                 315                 320

Leu Thr Asp Thr Ser Arg Pro Ser Asp Lys Ser Met Gly Asp Cys Asn
                325                 330                 335

Asn Pro Ile Thr Gly Ser Pro Gly Ala Pro Gly Val Lys Gly Phe Gly
            340                 345                 350

Phe Leu Asp Ser Ser Asn Thr Trp Leu Gly Arg Thr Ile Ser Pro Arg
        355                 360                 365

Ser Arg Ser Gly Phe Glu Met Leu Lys Ile Pro Asn Ala Glu Thr Asp
    370                 375                 380

Pro Asn Ser Lys Ile Thr Glu Arg Gln Glu Ile Val Asp Asn Asn Asn
385                 390                 395                 400

Trp Ser Gly Tyr Ser Gly Ser Phe Ile Asp Tyr Trp Asp Glu Ser Ser
                405                 410                 415
```

Glu Cys Tyr Asn Pro Cys Phe Tyr Val Glu Leu Ile Arg Gly Arg Pro
420 425 430

Glu Glu Ala Lys Tyr Val Gly Trp Thr Ser Asn Ser Leu Ile Ala Leu
435 440 445

Cys Gly Ser Pro Ile Ser Val Gly Ser Gly Ser Phe Pro Asp Gly Ala
450 455 460

Gln Ile Gln Tyr Phe Ser
465 470

<210> SEQ ID NO 34
<211> LENGTH: 470
<212> TYPE: PRT
<213> ORGANISM: Influenza virus

<400> SEQUENCE: 34

Met Asn Pro Asn Gln Lys Ile Ile Thr Val Gly Ser Val Ser Leu Gly
1 5 10 15

Leu Val Val Leu Asn Ile Leu Leu His Ile Val Ser Ile Thr Val Thr
20 25 30

Val Leu Val Leu Pro Gly Asn Gly Asn Asn Lys Asn Cys Asn Glu Thr
35 40 45

Val Ile Arg Glu Tyr Asn Glu Thr Val Arg Ile Glu Lys Val Thr Gln
50 55 60

Trp His Asn Thr Asn Val Ile Glu Tyr Ile Glu Lys Pro Glu Ser Gly
65 70 75 80

His Phe Met Asn Asn Thr Glu Ala Leu Cys Asp Ala Lys Gly Phe Ala
85 90 95

Pro Phe Ser Lys Asp Asn Gly Ile Arg Ile Gly Ser Arg Gly His Val
100 105 110

Phe Val Ile Arg Glu Pro Phe Val Ser Cys Ser Pro Thr Glu Cys Arg
115 120 125

Thr Phe Phe Leu Thr Gln Gly Ser Leu Leu Asn Asp Lys His Ser Asn
130 135 140

Gly Thr Val Lys Asp Arg Ser Pro Tyr Arg Thr Leu Met Ser Val Glu
145 150 155 160

Ile Gly Gln Ser Pro Asn Val Tyr Gln Ala Arg Phe Glu Ala Val Ala
165 170 175

Trp Ser Ala Thr Ala Cys His Asp Gly Lys Lys Trp Met Thr Ile Gly
180 185 190

Val Thr Gly Pro Asp Ala Lys Ala Val Ala Val Val His Tyr Gly Gly
195 200 205

Ile Pro Thr Asp Val Ile Asn Ser Trp Ala Gly Asp Ile Leu Arg Thr
210 215 220

Gln Glu Ser Ser Cys Thr Cys Ile Gln Gly Glu Cys Tyr Trp Val Met
225 230 235 240

Thr Asp Gly Pro Ala Asn Arg Gln Ala Gln Tyr Arg Ala Phe Lys Ala
245 250 255

Lys Gln Gly Lys Ile Val Gly Gln Thr Glu Ile Ser Phe Asn Gly Ser
260 265 270

His Ile Glu Glu Cys Ser Cys Tyr Pro Asn Glu Gly Lys Val Glu Cys
275 280 285

Val Cys Arg Asp Asn Trp Thr Gly Thr Asn Arg Pro Val Leu Val Ile
290 295 300

Ser Pro Asp Leu Ser Tyr Arg Ala Gly Tyr Leu Cys Ala Gly Leu Pro

```
305                 310                 315                 320

Ser Asp Thr Pro Arg Gly Glu Asp Ser Gln Phe Thr Gly Ser Cys Thr
                325                 330                 335

Ser Pro Val Gly Asn Gln Gly Tyr Gly Val Lys Gly Phe Gly Phe Arg
            340                 345                 350

Gln Gly Asn Asp Val Trp Met Gly Arg Thr Ile Ser Arg Thr Ser Arg
        355                 360                 365

Ser Gly Phe Glu Ile Leu Lys Val Arg Asn Gly Trp Val Gln Asn Ser
    370                 375                 380

Lys Glu Gln Ile Lys Arg Gln Val Val Val Asp Asn Leu Lys Trp Ser
385                 390                 395                 400

Gly Tyr Ser Gly Ser Phe Thr Leu Pro Val Glu Leu Thr Lys Arg Asn
                405                 410                 415

Cys Leu Val Pro Cys Phe Trp Val Glu Met Ile Arg Gly Lys Pro Glu
            420                 425                 430

Glu Lys Thr Ile Trp Thr Ser Ser Ser Ser Ile Val Met Cys Gly Val
        435                 440                 445

Asp His Glu Ile Ala Asp Trp Ser Trp His Asp Gly Ala Ile Leu Pro
    450                 455                 460

Phe Asp Ile Asp Lys Met
465                 470
```

<210> SEQ ID NO 35
<211> LENGTH: 465
<212> TYPE: PRT
<213> ORGANISM: Influenza virus

<400> SEQUENCE: 35

```
Met Asn Pro Asn Gln Lys Ile Leu Cys Thr Ser Ala Thr Ala Ile Ile
1               5                   10                  15

Ile Gly Ala Ile Ala Val Leu Ile Gly Ile Ala Asn Leu Gly Leu Asn
            20                  25                  30

Ile Gly Leu His Leu Lys Pro Gly Cys Asn Cys Ser His Ser Gln Pro
        35                  40                  45

Glu Thr Thr Asn Thr Ser Gln Thr Ile Ile Asn Asn Tyr Tyr Asn Glu
    50                  55                  60

Thr Asn Ile Thr Asn Ile Gln Met Glu Glu Arg Thr Ser Arg Asn Phe
65                  70                  75                  80

Asn Asn Leu Thr Lys Gly Leu Cys Thr Ile Asn Ser Trp His Ile Tyr
                85                  90                  95

Gly Lys Asp Asn Ala Val Arg Ile Gly Glu Ser Ser Asp Val Leu Val
            100                 105                 110

Thr Arg Glu Pro Tyr Val Ser Cys Asp Pro Asp Glu Cys Arg Phe Tyr
        115                 120                 125

Ala Leu Ser Gln Gly Thr Thr Ile Arg Gly Lys His Ser Asn Gly Thr
    130                 135                 140

Ile His Asp Arg Ser Gln Tyr Arg Ala Leu Ile Ser Trp Pro Leu Ser
145                 150                 155                 160

Ser Pro Pro Thr Val Tyr Asn Ser Arg Val Glu Cys Ile Gly Trp Ser
                165                 170                 175

Ser Thr Ser Cys His Asp Gly Lys Ser Arg Met Ser Ile Cys Ile Ser
            180                 185                 190

Gly Pro Asn Asn Asn Ala Ser Ala Val Val Trp Tyr Asn Arg Arg Pro
        195                 200                 205
```

-continued

```
Val Thr Glu Ile Asn Thr Trp Ala Arg Asn Ile Leu Arg Thr Gln Glu
    210                 215                 220

Ser Glu Cys Val Cys His Asn Gly Val Cys Pro Val Val Phe Thr Asp
225                 230                 235                 240

Gly Ser Ala Thr Gly Pro Ala Asp Thr Arg Ile Tyr Tyr Phe Lys Glu
                245                 250                 255

Gly Lys Ile Leu Lys Trp Glu Ser Leu Thr Gly Thr Ala Lys His Ile
            260                 265                 270

Glu Glu Cys Ser Cys Tyr Gly Glu Arg Thr Gly Ile Thr Cys Thr Cys
        275                 280                 285

Arg Asp Asn Trp Gln Gly Ser Asn Arg Pro Val Ile Gln Ile Asp Pro
    290                 295                 300

Val Ala Met Thr His Thr Ser Gln Tyr Ile Cys Ser Pro Val Leu Thr
305                 310                 315                 320

Asp Asn Pro Arg Pro Asn Asp Pro Asn Ile Gly Lys Cys Asn Asp Pro
                325                 330                 335

Tyr Pro Gly Asn Asn Asn Asn Gly Val Lys Gly Phe Ser Tyr Leu Asp
            340                 345                 350

Gly Ala Asn Thr Trp Leu Gly Arg Thr Ile Ser Thr Ala Ser Arg Ser
        355                 360                 365

Gly Tyr Glu Met Leu Lys Val Pro Asn Ala Leu Thr Asp Asp Arg Ser
    370                 375                 380

Lys Pro Ile Gln Gly Gln Thr Ile Val Leu Asn Ala Asp Trp Ser Gly
385                 390                 395                 400

Tyr Ser Gly Ser Phe Met Asp Tyr Trp Ala Glu Gly Asp Cys Tyr Arg
                405                 410                 415

Ala Cys Phe Tyr Val Glu Leu Ile Arg Gly Arg Pro Lys Glu Asp Lys
            420                 425                 430

Val Trp Trp Thr Ser Asn Ser Ile Val Ser Met Cys Ser Ser Thr Glu
        435                 440                 445

Phe Leu Gly Gln Trp Asn Trp Pro Asp Gly Ala Lys Ile Glu Tyr Phe
    450                 455                 460

Leu
465
```

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39
<211> LENGTH: 2341
<212> TYPE: DNA
<213> ORGANISM: Influenza virus

<400> SEQUENCE: 39

```
agcgaaagca ggtcaattat attcaatatg gaaagaataa aagaactaag aaatctaatg     60
tcgcagtctc gcacccgcga gatactcaca aaaaccaccg tggaccatat ggccataatc    120
aagaagtaca catcaggaag acaggagaag aacccagcac ttaggatgaa atggatgatg    180
gcaatgaaat atccaattac agcagacaag aggataacgg aaatgattcc tgagagaaat    240
gagcaaggac aaactttatg gagtaaaatg aatgatgccg gatcagaccg agtgatggta    300
tcacctctgg ctgtgacatg gtggaatagg aatggaccaa tgacaaatac agttcattat    360
ccaaaaatct acaaaactta ttttgaaaga gtcgaaaggc taaagcatgg aacctttggc    420
cctgtccatt ttagaaacca agtcaaaata cgtcggagag ttgacataaa tcctggtcat    480
gcagatctca gtgccaagga ggcacaggat gtaatcatgg aagttgtttt ccctaacgaa    540
gtgggagcca ggatactaac atcggaatcg caactaacga taaccaaaga gaagaaagaa    600
gaactccagg attgcaaaat ttctcctttg atggttgcat acatgttgga gagagaactg    660
gtccgcaaaa cgagattcct cccagtggct ggtggaacaa gcagtgtgta cattgaagtg    720
ttgcatttga ctcaaggaac atgctgggaa cagatgtata ctccaggagg ggaagtgaag    780
aatgatgatg ttgatcaaag cttgattatt gctgctagga acatagtgag aagagctgca    840
gtatcagcag acccactagc atctttattg gagatgtgcc acagcacaca gattggtgga    900
attaggatgg tagacatcct taagcagaac ccaacagaag agcaagccgt ggatatatgc    960
aaggctgcaa tgggactgag aattagctca tccttcagtt ttggtggatt cacatttaag   1020
agaacaagcg gatcatcagt caagagagag gaagaggtgc ttacgggcaa tcttcaaaca   1080
ttgaagataa gagtgcatga gggatctgaa gagttcacaa tggttgggag aagagcaaca   1140
gccatactca gaaaagcaac caggagattg attcagctga tagtgagtgg gagagacgaa   1200
cagtcgattg ccgaagcaat aattgtggcc atggtatttt cacaagagga ttgtatgata   1260
aaagcagtta gaggtgatct gaatttcgtc aatagggcga atcagcgact gaatcctatg   1320
catcaacttt taagacattt tcagaaggat gcgaaagtgc tttttcaaaa ttggggagtt   1380
gaacctatcg acaatgtgat gggaatgatt gggatattgc ccgacatgac tccaagcatc   1440
gagatgtcaa tgagaggagt gagaatcagc aaaatgggtg tagatgagta ctccagcacg   1500
gagagggtag tggtgagcat tgaccggttc ttgagagtca gggaccaacg aggaaatgta   1560
ctactgtctc ccgaggaggt cagtgaaaca cagggaacag agaaactgac aataacttac   1620
tcatcgtcaa tgatgtggga gattaatggt cctgaatcag tgttggtcaa tacctatcaa   1680
tggatcatca gaaactggga aactgttaaa attcagtggt cccagaaccc tacaatgcta   1740
tacaataaaa tggaatttga accatttcag tctttagtac ctaaggccat tagaggccaa   1800
tacagtgggt ttgtaagaac tctgttccaa caaatgaggg atgtgcttgg gacatttgat   1860
accgcacaga taataaaact tcttcccttc gcagccgctc caccaaagca aagtagaatg   1920
cagttctcct catttactgt gaatgtgagg ggatcaggaa tgagaatact tgtaaggggc   1980
aattctcctg tattcaacta caacaaggcc acgaagagac tcacagttct cggaaaggat   2040
gctggcactt taaccgaaga cccagatgaa ggcacagctg gagtggagtc cgctgttctg   2100
aggggattcc tcattctggg caaagaagac aggagatatg ggccagcatt aagcatcaat   2160
gaactgagca accttgcgaa aggagagaag gctaatgtgc taattgggca aggagacgtg   2220
gtgttggtaa tgaaacgaaa acgggactct agcatactta ctgacagcca gacagcgacc   2280
aaaagaattc ggatggccat caattagtgt cgaatagttt aaaaacgacc ttgtttctac   2340
```

t 2341

<210> SEQ ID NO 40
<211> LENGTH: 2341
<212> TYPE: DNA
<213> ORGANISM: Influenza virus

<400> SEQUENCE: 40
agcgaaagca ggcaaaccat ttgaatggat gtcaatccga ccttactttt cttaaaagtg 60
ccagcacaaa atgctataag cacaactttc ccttataccg gagaccctcc ttacagccat 120
gggacaggaa caggatacac catggatact gtcaacagga cacatcagta ctcagaaaag 180
ggaagatgga caacaaacac cgaaactgga gcaccgcaac tcaacccgat tgatgggcca 240
ctgccagaag acaatgaacc aagtggttat gcccaaacag attgtgtatt ggaagcaatg 300
gctttccttg aggaatccca tcctggtatt tttgaaaact cgtgtattga aacgatggag 360
gttgttcagc aaacacgagt agacaagctg acacaaggcc gacagaccta tgactggact 420
ttaaatagaa accagcctgc tgcaacagca ttggccaaca caatagaagt gttcagatca 480
aatggcctca cggccaatga gtcaggaagg ctcatagact tccttaagga tgtaatggag 540
tcaatgaaaa aagaagaaat ggggatcaca actcattttc agagaaagag acgggtgaga 600
gacaatatga ctaagaaaat gataacacag agaacaatag gtaaaaggaa acagagattg 660
aacaaaaggg gttatctaat tagagcattg accctgaaca caatgaccaa agatgctgag 720
agagggaagc taaaacggag agcaattgca accccaggga tgcaaataag gggggtttgta 780 tactttgttg agacactggc aaggagtata tgtgagaaac ttgaacaatc agggttgcca 840
gttggaggca atgagaagaa agcaaagttg gcaaatgttg taaggaagat gatgaccaat 900
tctcaggaca ccgaactttc tttcaccatc actggagata acaccaaatg gaacgaaaat 960
cagaatcctc ggatgttttt ggccatgatc acatatatga ccagaaatca gcccgaatgg 1020
ttcagaaatg ttctaagtat tgctccaata atgttctcaa acaaaatggc gagactggga 1080
aaagggtata tgtttgagag caagagtatg aaacttagaa ctcaaatacc tgcagaaatg 1140
ctagcaagca ttgatttgaa atatttcaat gattcaacaa gaaagaagat tgaaaaaatc 1200
cgaccgctct taatagaggg gactgcatca ttgagccctg gaatgatgat gggcatgttc 1260
aatatgttaa gcactgtatt aggcgtctcc atcctgaatc ttggacaaaa gagatacacc 1320
aagactactt actggtggga tggtcttcaa tcctctgacg attttgctct gattgtgaat 1380
gcacccaatc atgaagggat tcaagccgga gtcgacaggt tttatcgaac ctgtaagcta 1440
cttggaatca atatgagcaa gaaaaagtct tacataaaca gaacaggtac atttgaattc 1500
acaagttttt tctatcgtta tgggtttgtt gccaatttca gcatggagct tcccagtttt 1560
ggggtgtctg ggatcaacga gtcagcggac atgagtattg gagttactgt catcaaaaac 1620
aatatgataa acaatgatct tggtccagca acagctcaaa tggcccttca gttgttcatc 1680
aaagattaca ggtacacgta ccgatgccat agaggtgaca cacaaataca aacccgaaga 1740
tcatttgaaa taaagaaact gtgggagcaa acccgttcca aagctggact gctggtctcc 1800
gacggaggcc caaatttata caacattaga aatctccaca ttcctgaagt ctgcctaaaa 1860
tgggaattga tggatgagga ttaccagggg cgtttatgca acccactgaa cccatttgtc 1920
agccataaag aaattgaatc aatgaacaat gcagtgatga tgccagcaca tggtccagcc 1980
aaaaacatgg agtatgatgc tgttgcaaca acacactcct ggatccccaa aagaaatcga 2040
tccatcttga atacaagtca aagaggagta cttgaagatg aacaaatgta ccaaaggtgc 2100
tgcaatttat ttgaaaaatt cttccccagc agttcataca gaagaccagt cgggatatcc 2160
agtatggtgg aggctatggt ttccagagcc cgaattgatg cacggattga tttcgaatct 2220
ggaaggataa agaaagaaga gttcactgag atcatgaaga tctgttccac cattgaagag 2280
ctcagacggc aaaaatagtg aatttagctt gtccttcatg aaaaaatgcc ttgtttctac 2340
t 2341

<210> SEQ ID NO 41
<211> LENGTH: 2233
<212> TYPE: DNA
<213> ORGANISM: Influenza virus

<400> SEQUENCE: 41
agcgaaagca ggtactgatt caaaatggaa gattttgtgc gacaatgctt caatccgatg 60
attgtcgagc ttgcggaaaa aacaatgaaa gagtatgggg aggacctgaa aatcgaaaca 120
aacaaatttg cagcaatatg cactcacttg gaagtatgct tcatgtattc agatttccac 180
ttcatcaatg agcaaggcga gtcaataatc gtagaacttg gtgatcctaa tgcacttttg 240
aagcacagat ttgaaataat cgagggaaga gatcgcacaa tggcctggac agtagtaaac 300
agtatttgca acactacagg ggctgagaaa ccaaagtttc taccagattt gtatgattac 360
aaggaaaata gattcatcga aattggagta acaaggagag aagttcacat atactatctg 420
gaaaaggcca ataaaattaa atctgagaaa acacacatcc acatttctc gttcactggg 480 gaagaaatgg ccacaagggc cgactacact ctcgatgaag aaagcagggc taggatcaaa 540
accaggctat tcaccataag acaagaaatg gccagcagag gcctctggga ttcctttcgt 600
cagtccgaga gaggagaaga gacaattgaa gaaaggtttg aaatcacagg aacaatgcgc 660
aagcttgccg accaaagtct cccgccgaac ttctccagcc ttgaaaattt tagagcctat 720
gtggatggat tcgaaccgaa cggctacatt gagggcaagc tgtctcaaat gtccaaagaa 780
gtaaatgcta gaattgaacc ttttttgaaa acaacaccac gaccacttag acttccgaat 840
gggcctccct gttctcagcg gtccaaattc ctgctgatgg atgccttaaa attaagcatt 900
gaggacccaa gtcatgaagg agagggaata ccgctatatg atgcaatcaa atgcatgaga 960
acattctttg gatggaagga acccaatgtt gttaaaccac acgaaaaggg aataaatcca 1020
aattatcttc tgtcatggaa gcaagtactg gcagaactgc aggacattga gaatgaggag 1080
aaaattccaa agactaaaaa tatgaaaaaa acaagtcagc taaagtgggc acttggtgag 1140
aacatggcac cagaaaaggt agactttgac gactgtaaag atgtaggtga tttgaagcaa 1200
tatgatagtg atgaaccaga attgaggtcg cttgcaagtt ggattcagaa tgagttcaac 1260
aaggcatgcg aactgacaga ttcaagctgg atagagcttg atgagattgg agaagatgtg 1320
gctccaattg aacacattgc aagcatgaga aggaattatt tcacatcaga ggtgtctcac 1380
tgcagagcca cagaatacat aatgaagggg gtgtacatca atactgcctt acttaatgca 1440
tcttgtgcag caatggatga tttccaatta attccaatga taagcaagtg tagaactaag 1500
gagggaaggc gaaagaccaa cttgtatggt ttcatcataa aaggaagatc ccacttaagg 1560
aatgacaccg acgtggtaaa ctttgtgagc atggagtttt ctctcactga cccaagactt 1620
gaaccacaca aatgggagaa gtactgtgtt cttgagatag gagatatgct tctaagaagt 1680
gccataggcc aggtttcaag gcccatgttc ttgtatgtga ggacaaatgg aacctcaaaa 1740
attaaaatga aatggggaat ggagatgagg cgttgtctcc tccagtcact tcaacaaatt 1800

```
gagagtatga ttgaagctga gtcctctgtc aaagagaaag acatgaccaa agagttcttt   1860

gagaacaaat cagaaacatg gcccattgga gagtctccca aaggagtgga ggaaagttcc   1920

attgggaagg tctgcaggac tttattagca aagtcggtat ttaacagctt gtatgcatct   1980

ccacaactag aaggattttc agctgaatca agaaaactgc ttcttatcgt tcaggctctt   2040

agggacaatc tggaacctgg gacctttgat cttgggggc tatatgaagc aattgaggag   2100

tgcctaatta atgatccctg ggttttgctt aatgcttctt ggttcaactc cttccttaca   2160

catgcattga gttagttgtg gcagtgctac tatttgctat ccatactgtc caaaaaagta   2220

ccttgtttct act                                                      2233
```

<210> SEQ ID NO 42
<211> LENGTH: 1565
<212> TYPE: DNA
<213> ORGANISM: Influenza virus

<400> SEQUENCE: 42

```
agcaaaagca gggtagataa tcactcactg agtgacatca aaatcatggc gtcccaaggc     60

accaaacggt cttacgaaca gatggagact gatggagaac gccagaatgc cactgaaatc    120

agagcatccg tcggaaaaat gattggtgga attggacgat tctacatcca aatgtgcaca    180

gaacttaaac tcagtgatta tgagggacgg ttgatccaaa acagcttaac aatagagaga    240

atggtgctct ctgcttttga cgaaaggaga aataaatacc tggaagaaca tcccagtgcg    300

gggaaagatc ctaagaaaac tggaggacct atatacagaa gagtaaacgg aaagtggatg    360

agagaactca tcctttatga caaagaagaa ataaggcgaa tctggcgcca agctaataat    420

ggtgacgatg caacggctgg tctgactcac atgatgatct ggcattccaa tttgaatgat    480

gcaacttatc agaggacaag ggctcttgtt cgcaccggaa tggatcccag gatgtgctct    540

ctgatgcaag gttcaactct ccctaggagg tctggagccg caggtgctgc agtcaaagga    600

gttggaacaa tggtgatgga attggtcagg atgatcaaac gtgggatcaa tgatcggaac    660

ttctggaggg gtgagaatgg acgaaaaaca agaattgctt atgaaagaat gtgcaacatt    720

ctcaaaggga aatttcaaac tgctgcacaa aaagcaatga tggatcaagt gagagagagc    780

cggaacccag ggaatgctga gttcgaagat ctcacttttc tagcacggtc tgcactcata    840

ttgagagggt cggttgctca caagtcctgc ctgcctgcct gtgtgtatgg acctgccgta    900

gccagtgggt acgactttga aagagaggga tactctctag tcggaataga ccctttcaga    960

ctgcttcaaa acagccaagt gtacagccta atcagaccaa atgagaatcc agcacacaag   1020

agtcaactgg tgtggatggc atgccattct gccgcatttg aagatctaag agtattgagc   1080

ttcatcaaag ggacgaaggt ggtcccaaga gggaagcttt ccactagagg agttcaaatt   1140

gcttccaatg aaaatatgga gactatggaa tcaagtacac ttgaactgag aagcaggtac   1200

tgggccataa ggaccagaag tggaggaaac accaatcaac agagggcatc tgcgggccaa   1260

atcagcatac aacctacgtt ctcagtacag agaaatctcc cttttgacag aacaaccgtt   1320

atggcagcat tcactgggaa tacagagggg agaacatctg acatgaggac cgaaatcata   1380

aggatgatgg aaagtgcaag accagaagat gtgtctttcc aggggcgggg agtcttcgag   1440

ctctcggacg aaaaggcagc gagcccgatc gtgccttcct ttgacatgag taatgaagga   1500

tcttatttct tcggagacaa tgcagaggag tacgacaatt aaagaaaaat acccttgttt   1560

ctact                                                               1565
```

<210> SEQ ID NO 43
<211> LENGTH: 1027
<212> TYPE: DNA
<213> ORGANISM: Influenza virus

<400> SEQUENCE: 43
agcaaaagca ggtagatatt gaaagatgag tcttctaacc gaggtcgaaa cgtacgttct 60
ctctatcatc ccgtcaggcc ccctcaaagc cgagatcgca cagagacttg aagatgtctt 120
tgcagggaag aacaccgatc ttgaggttct catggaatgg ctaaagacaa gaccaatcct 180
gtcacctctg actaagggga ttttaggatt tgtgttcacg ctcaccgtgc ccagtgagcg 240
aggactgcag cgtagacgct ttgtccaaaa tgcccttaat gggaacgggg atccaaataa 300
catggacaaa gcagttaaac tgtataggaa gctcaagagg gagataacat tccatggggc 360
caaagaaatc tcactcagtt attctgctgg tgcacttgcc agttgtatgg gcctcatata 420
caacaggatg gggctgtga ccactgaagt ggcatttggc ctggtatgtg caacctgtga 480
acagattgct gactcccagc atcggtctca taggcaaatg gtgacaacaa ccaacccact 540
aatcagacat gagaacagaa tggttttagc cagcactaca gctaaggcta tggagcaaat 600
ggctggatcg agtgagcaag cagcagaggc catggaggtt gctagtcagg ctaggcaaat 660
ggtgcaagcg atgagaacca ttgggactca tcctagctcc agtgctggtc tgaaaaatga 720
tcttcttgaa aatttgcagg cctatcagaa acgaatgggg gtgcagatgc aacggttcaa 780
gtgatcctct cgctattgcc gcaaatatca ttgggatctt gcacttgata ttgtggattc 840
ttgatcgtct ttttttcaaa tgcatttacc gtcgctttaa atacggactg aaaggagggc 900
cttctacgga aggagtgcca aagtctatga gggaagaata tcgaaaggaa cagcagagtg 960
ctgtggatgc tgacgatggt cattttgtca gcatagagct ggagtaaaaa actaccttgt 1020
ttctact 1027

<210> SEQ ID NO 44
<211> LENGTH: 890
<212> TYPE: DNA
<213> ORGANISM: Influenza virus

<400> SEQUENCE: 44
agcaaaagca gggtgacaaa gacataatgg atccaaacac tgtgtcaagc tttcaggtag 60
attgctttct ttggcatgtc cgcaaacgag ttgcagacca agaactaggt gatgccccat 120
tccttgatcg gcttcgccga gatcagaaat ccctaagagg aaggggcagc actcttggtc 180
tggacatcga gacagccaca cgtgctggaa agcagatagt ggagcggatt ctgaaagaag 240
aatccgatga ggcacttaaa atgaccatgg cctctgtacc tgcgtcgcgt tacctaaccg 300
acatgactct tgaggaaatg tcaagggaat ggtccatgct catacccaag cagaaagtgg 360
caggccctct ttgtatcaga atggaccagg cgatcatgga taaaaacatc atactgaaag 420
cgaacttcag tgtgattttt gaccggctgg agactctaat attgctaagg gctttcaccg 480
aagagggagc aattgttggc gaaatttcac cattgccttc tcttccagga catactgctg 540
aggatgtcaa aaatgcagtt ggagtcctca tcggaggact tgaatggaat gataacacag 600
ttcgagtctc tgaaactcta cagagattcg cttggagaag cagtaatgag aatgggagac 660
ctccactcac tccaaaacag aaacgagaaa tggcgggaac aattaggtca gaagtttgaa 720
gaaataagat ggttgattga agaagtgaga cacaaactga aggtaacaga gaatagtttt 780
gagcaaataa catttatgca agccttacat ctattgcttg aagtggagca agagataaga 840

-continued actttctcat ttcagcttat ttaataataa aaaacaccct tgtttctact 890

<210> SEQ ID NO 45

<400> SEQUENCE: 45

000

<210> SEQ ID NO 46
<211> LENGTH: 1701
<212> TYPE: DNA
<213> ORGANISM: Influenza virus

<400> SEQUENCE: 46
atgaagacta tcattgcttt gagctacatt ctatgtctgg ttttcgctca aaaaattcct 60
ggaaatgaca atagcacggc aacgctgtgc cttgggcacc atgcagtacc aaacggaacg 120
atagtgaaaa caatcacaaa tgaccgaatt gaagttacta atgctactga gttggttcag 180
aattcctcaa taggtgaaat atgcgacagt cctcatcaga tccttgatgg agagaactgc 240
acactaatag atgctctatt gggagaccct cagtgtgatg gctttcaaaa taagaaatgg 300
gacctttttg ttgaacgaag caaagcctac agcaactgtt acccttatga tgtgccggat 360
tatgcctccc ttaggtcact agttgcctca tccggcacac tggagtttaa aaatgaaagc 420
ttcaattgga ctggagtcac tcaaaacgga acaagttctg cttgcataag gggatctagt 480
agtagtttct ttagtagatt aaattggttg acccacttaa actacacata tccagcattg 540
aacgtgacta tgccaaacaa ggaacaattt gacaaattgt acatttgggg ggttcaccac 600
ccgggtacgg acaaggacca aatcttcctg tatgctcaat catcaggaag aatcacagta 660
tctaccaaaa gaagccaaca agctgtaatc ccaaatatcg gatctagacc cagaataagg 720
gatatcccta gcagaataag catctattgg acaatagtaa aaccgggaga catacttttg 780
attaacagca cagggaatct aattgctcct aggggttact tcaaaatacg aagtgggaaa 840
agctcaataa tgagatcaga tgcacccatt ggcaaatgca agtctgaatg catcactcca 900
aatggaagca ttcccaatga caaaccattc caaaatgtaa acaggatcac atacggggcc 960
tgtcccagat atgttaagca tagcactctg aaattggcaa caggaatgcg aaatgtacca 1020
gagaaacaaa ctagaggcat atttggcgca atagcgggtt tcatagaaaa tggttgggag 1080
ggaatggtgg atggttggta cggtttcagg catcaaaatt ctgagggaag aggacaagca 1140
gcagatctca aaagcactca agcagcaatc gatcaaatca atgggaagct gaataggttg 1200
atcggaaaaa ccaacgagaa attccatcag attgaaaaag aattctcaga agtagaagga 1260
agagttcaag accttgagaa atatgttgag gacactaaaa tagatctctg gtcatacaac 1320
gcggagcttc ttgttgccct ggagaaccaa catacaattg atctaactga ctcagaaatg 1380
aacaaactgt ttgaaaaaac aaagaagcaa ctgagggaaa atgctgagga tatgggaaat 1440
ggttgtttca aaatatacca caaatgtgac aatgcctgca tagaatcaat aagaaatgaa 1500
acttatgacc acaatgtgta cagggatgaa gcattgaaca accggttcca gatcaaggga 1560
gttgagctga agtcaggata caaagattgg atcctatgga tttcctttgc catatcatgt 1620
tttttgcttt gtgttgcttt gttggggttc atcatgtggg cctgccaaaa gggcaacatt 1680
agatgcaaca tttgcatttg a 1701

<210> SEQ ID NO 47
<211> LENGTH: 1410
<212> TYPE: DNA

<213> ORGANISM: Influenza virus

<400> SEQUENCE: 47

```
atgaatccaa atcaaaagat aataacgatt ggctctgttt ctctcaccat ttccacaata     60
tgcttcttca tgcaaattgc catcctgata actactgtaa cattgcattt caagcaatat    120
gaattcaact cccccccaaa caaccaagtg atgctgtgtg aaccaacaat aatagaaaga    180
aacataacag agatagtgta tttgaccaac accaccatag agaaggaaat atgccccaaa    240
ccagcagaat acagaaattg gtcaaaaccg caatgtggca ttacaggatt tgcacctttc    300
tctaaggaca attcgattag gctttccgct ggtggggaca tctgggtgac aagagaacct    360
tatgtgtcat gcgatcctga caagtgttat caatttgccc ttggacaggg aacaacacta    420
aacaacgtgc attcaaataa cacagtacgt gataggaccc cttatcggac tctattgatg    480
aatgagttgg gtgttccttt ccatctgggg accaagcaag tgtgcatagc atggtccagc    540
tcaagttgtc acgatggaaa agcatggctg catgtttgta taacgggga tgataaaaat    600
gcaactgcta gcttcattta caatgggagg cttatagata gtgttgtttc atggtccaaa    660
gatattctca ggacccagga gtcagaatgc gtttgtatca atggaacttg tacagtagta    720
atgactgatg gaaatgctac aggaaaagct gatactaaaa tactattcat tgaggagggg    780
aaaatcgttc atactagcaa attgtcagga agtgctcagc atgtcgaaga gtgctcttgc    840
tatcctcgat atcctggtgt cagatgtgtc tgcagagaca actggaaagg atccaaccgg    900
cccatcgtag atataaacat aaaggatcat agcattgttt ccagttatgt gtgttcagga    960
cttgttggag acacacccag aaaaaacgac agctccagca gtagccattg tttgaatcct   1020
aacaatgaag aaggtggtca tggagtgaaa ggctgggcct ttgatgatgg aaatgacgtg   1080
tggatgggga gaacaatcaa cgagacgtca cgcttagggt atgaaacctt caaagtcgtt   1140
gaaggctggt ccaaccctaa gtccaaattg cagataaata ggcaagtcat agttgacaga   1200
ggtgataggt ccggttattc tggtattttc tctgttgaag gcaaaagctg catcaatcgg   1260
tgcttttatg tggagttgat taggggaaga aaagaggaaa ctgaagtctt gtggacctca   1320
aacagtattg ttgtgttttg tggcacctca ggtacatatg gaacaggctc atggcctgat   1380
ggggcggacc tcaatctcat gcatatataa                                   1410
```

<210> SEQ ID NO 48
<211> LENGTH: 469
<212> TYPE: PRT
<213> ORGANISM: Influenza virus

<400> SEQUENCE: 48

```
Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Pro Ala Glu Tyr Arg Asn Trp Ser Lys Pro Gln Cys Gly Ile Thr Gly
                85                  90                  95

Phe Ala Pro Phe Ser Lys Asp Asn Ser Ile Arg Leu Ser Ala Gly Gly
```

```
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asn Thr Val Arg Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asn
        195                 200                 205

Gly Arg Leu Ile Asp Ser Val Val Ser Trp Ser Lys Asp Ile Leu Arg
    210                 215                 220

Thr Gln Glu Ser Glu Cys Val Cys Ile Asn Gly Thr Cys Thr Val Val
225                 230                 235                 240

Met Thr Asp Gly Asn Ala Thr Gly Lys Ala Asp Thr Lys Ile Leu Phe
                245                 250                 255

Ile Glu Glu Gly Lys Ile Val His Thr Ser Lys Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Ile Lys Asp His Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asn Pro Asn Asn Glu Glu Gly Gly His Gly Val Lys Gly Trp
            340                 345                 350

Ala Phe Asp Asp Gly Asn Asp Val Trp Met Gly Arg Thr Ile Asn Glu
        355                 360                 365

Thr Ser Arg Leu Gly Tyr Glu Thr Phe Lys Val Val Glu Gly Trp Ser
    370                 375                 380

Asn Pro Lys Ser Lys Leu Gln Ile Asn Arg Gln Val Ile Val Asp Arg
385                 390                 395                 400

Gly Asp Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Leu
    450                 455                 460

Asn Leu Met His Ile
465
```

<210> SEQ ID NO 49
<211> LENGTH: 469
<212> TYPE: PRT
<213> ORGANISM: Influenza virus

<400> SEQUENCE: 49

-continued

```
Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Pro Ala Glu Tyr Arg Asn Trp Ser Lys Pro Gln Cys Gly Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asn Thr Val Arg Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asn
        195                 200                 205

Gly Arg Leu Val Asp Ser Val Val Ser Trp Ser Lys Asp Ile Leu Arg
    210                 215                 220

Thr Gln Glu Ser Glu Cys Val Cys Ile Asn Gly Thr Cys Thr Val Val
225                 230                 235                 240

Met Thr Asp Gly Asn Ala Thr Gly Lys Ala Asp Thr Lys Ile Leu Phe
                245                 250                 255

Ile Glu Glu Gly Lys Ile Val His Thr Ser Lys Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Ile Lys Asp His Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asn Pro Asn Asn Glu Glu Gly Gly His Gly Val Lys Gly Trp
            340                 345                 350

Ala Phe Asp Asp Gly Asn Asp Val Trp Met Gly Arg Thr Ile Asn Glu
        355                 360                 365

Thr Ser Arg Leu Gly Tyr Glu Thr Phe Lys Val Val Glu Gly Trp Ser
    370                 375                 380

Asn Pro Lys Ser Lys Leu Gln Ile Asn Arg Gln Val Ile Val Asp Arg
385                 390                 395                 400

Gly Asp Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
```

```
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Leu
    450                 455                 460

Asn Leu Met His Ile
465
```

<210> SEQ ID NO 50

<400> SEQUENCE: 50

000

<210> SEQ ID NO 51
<211> LENGTH: 1434
<212> TYPE: DNA
<213> ORGANISM: Influenza virus

<400> SEQUENCE: 51

```
atgaatccaa atcaaaagat aataacgatt ggctctgttt ctctcaccat ttccacaata     60

tgctttttca tgcaaattgc cattttgata actactgtaa cattgcattt caagcaatat    120

gaattcaact cccccccaaa caaccaagtg atgctgtgtg aaccaacaat aatagaaaga    180

aacataacag agatagtgta tttaaccaac accaccatag agaaggaaat atgccccaaa    240

ccagcagaat acagaaattg gtcaaaaccg caatgtggca ttacaggatt tgcacctttc    300

tctaaggaca attcgatcag gctttccgct ggtggggaca tctgggtgac aagagaacct    360

tatgtgtcat gcgatcctga caagtgttat caatttgccc ttggacaggg aacaacacta    420

aacaacgtgc attcaaataa caaagtacgt gataggaccc cttatcggac tctattgatg    480

aatgagttgg gtgttccttt ccatctgggg accaagcaag tgtgcatagc atggtccagc    540

tcaagttgtc acgatggaaa agcatggctg catgtttgta taacggggga tgataaaaat    600

gcaactgcta gcttcattta caatgggagg cttgtagata gtgttgtttc atggtccaaa    660

gatattctca ggacccagga gtcagaatgc atttgtatca atggaacttg tacagtagta    720

atgactgatg gaagtgcttc aggaaaagct gatactaaaa tactattcat tgaggagggg    780

aaaatcgttc atactagcac attgtcagga agtgctcagc atgtcgaaga gtgctcttgc    840

tatcctcgat atcctggtgt cagatgtgtc tgcagagaca actggaaggg ctccaatcgg    900

cccatcgtag atataaacat aaaggatcat agcattgttt ccagttatgt gtgttcagga    960

cttgttggag acacacccag aaaaaacgac agctccagca gtagccattg tttggatcct   1020

aacaatgaag aaggtggtca tggagtgaaa ggctgggcct ttgatgatgg aaatgacgtg   1080

tggatgggaa gaacaatcaa cgagacgtca cgcttagggt atgaaacctt caaagtcatt   1140

gaaggctggt ccaaccctaa gtccaaattg cagacaaata ggcaagtcat agttgacaga   1200

ggtgataggt ccggttattc tggtattttc tctgttgaag gcaaaagctg cataaatcgg   1260

tgcttttatg tggagttgat taggggaaga aaagaggaaa ctgaagtctt gtggacctca   1320

aacagtattg ttgtgttttg tggcacctca ggtacatatg gaacaggctc atggcctgat   1380

ggggcggacc tcaatctcat gcctatataa gctttcgcaa ttttagaaaa aact         1434
```

<210> SEQ ID NO 52
<211> LENGTH: 1410
<212> TYPE: DNA
<213> ORGANISM: Influenza virus

<400> SEQUENCE: 52
atgaatccaa atcaaaagat aataacgatt ggctctgttt ctctcaccat ttccacaata 60
tgcttcttca tgcaaattgc catcctgata actactgtaa cattgcattt caagcaatat 120
gaattcaact cccccccaaa caaccaagtg atgctgtgtg aaccaacaat aatagaaaga 180
aacataacag agatagtgta tttgaccaac accaccatag agaaggaaat atgccccaaa 240
ccagcagaat acagaaattg gtcaaaaccg caatgtggca ttacaggatt tgcacctttc 300
tctaaggaca attcgattag gctttccgct ggtggggaca tctgggtgac aagagaacct 360
tatgtgtcat gcgatcctga caagtgttat caatttgccc ttggacaggg aacaacacta 420
aacaacgtgc attcaaataa cacagtacgt gataggaccc cttatcggac tctattgatg 480
aatgagttgg gtgttccttt ccatctgggg accaagcaag tgtgcatagc atggtccagc 540
tcaagttgtc acgatggaaa agcatggctg catgtttgta taacggggga tgataaaaat 600
gcaactgcta gcttcattta caatgggagg cttgtagata gtgttgtttc atggtccaaa 660
gatattctca ggacccagga gtcagaatgc gtttgtatca atggaacttg tacagtagta 720
atgactgatg gaaatgctac aggaaaagct gatactaaaa tactattcat tgaggagggg 780
aaaatcgttc atactagcaa attgtcagga agtgctcagc atgtcgaaga gtgctcttgc 840
tatcctcgat atcctggtgt cagatgtgtc tgcagagaca actggaaagg atccaaccgg 900
cccatcgtag atataaacat aaaggatcat agcattgttt ccagttatgt gtgttcagga 960
cttgttggag acacacccag aaaaaacgac agctccagca gtagccattg tttgaatcct 1020
aacaatgaag aaggtggtca tggagtgaaa ggctgggcct ttgatgatgg aaatgacgtg 1080
tggatgggga gaacaatcaa cgagacgtca cgcttagggt atgaaacctt caaagtcgtt 1140
gaaggctggt ccaaccctaa gtccaaattg cagataaata ggcaagtcat agttgacaga 1200
ggtgataggt ccggttattc tggtattttc tctgttgaag gcaaaagctg catcaatcgg 1260
tgcttttatg tggagttgat taggggaaga aaagaggaaa ctgaagtctt gtggacctca 1320
aacagtattg ttgtgttttg tggcacctca ggtacatatg gaacaggctc atggcctgat 1380
ggggcggacc tcaatctcat gcatatataa 1410

<210> SEQ ID NO 53
<211> LENGTH: 1411
<212> TYPE: DNA
<213> ORGANISM: Influenza virus

<400> SEQUENCE: 53
atgaatccaa atcaaaagat aataacgatt ggctctgttt ctctcacaat ttccacaata 60
tgcttcttca tgcaaattgc catcctgata actactgtaa cattgcattt caagcaatat 120
gaattcaact cccccccaaa taaccaagtg atgctgtgtg aaccaacaat aatagaaaga 180
aacataacag agatagtgta tttgaccaac accaccatag agaaggaaat atgccccaaa 240
ccagcagaat acagaaattg gtcaaaaccg caatgtggca ttacaggatt tgcacctttc 300
tctaaagaca attcgattag gctttccgct ggtggggaca tctgggtgac aagagaacct 360
tatgtgtcat gcgatcttga caagtgttat caatttgccc ttggacaggg aacaacacta 420
aacaacgtgc attcaaataa cacagtacgt gataggaccc cttatcggac tctattgatg 480
aatgagttgg gtgttccttt ccatctgggg accaagcaag tgtgcatagc atggtccagc 540
tcaagttgtc acgatggaaa agcatggctg catgtttgta taacggggga tgataaaaat 600
gcaactgcta gcttcattta cawatgggag gcttgtagat agtgttgttt catggtccaa 660
cgatattctc aggacccagg agtcagaatg cgtttgtatc aatggaactt gtacagtagt 720
aatgactgat ggaaatgcta caggaaaagc tgatactaaa atactattca ttgaggaggg 780
gaaaatcgtt catactagca aattgtcagg aagtgctcag catgtcgaag agtgctcttg 840
ctatcctcga tatcctggtg tcagatgtgt ctgcagagac aactggaaag gatccaaccg 900
gcccatcata gatataaaca taaaggatca tagcattgtt tccagttatg tgtgttcagg 960
acttgttgga gacacaccca gaaaaagcga cagctccagc agtagccatt gtttgaatcc 1020
taacaatgaa gaaggtggtc atggagtgaa aggctgggcc tttgatgatg gaaatgacgt 1080
gtggatgggg agaacaatca acgagacgtc acgcttaggg tatgaaacct tcaaagtcgt 1140
tgaaggctgg tccaacccta agtccaaatt gcagataaat aggcaagtca tagttgacag 1200
aggtgatagg tccggttatt ctggtatttt ctctgttgaa ggcaaaagct gcatcaatcg 1260
gtgcttttat gtggagttga tcaggggaag aaaagaggaa actgaagtct tgtggacctc 1320
aaacagtatt gttgtgtttt gtggcacctc aggtacatat ggaacaggct catggcctga 1380
tggggcggac ctcaatctca tgcatatata a 1411

<210> SEQ ID NO 54
<211> LENGTH: 1410
<212> TYPE: DNA
<213> ORGANISM: Influenza virus

<400> SEQUENCE: 54
atgaatccaa atcaaaagat aataacgatt ggctctgttt ctctcaccat ttccacaata 60
tgcttcttca tgcaaattgc catcctgata actactgtaa cattgcattt caagcaatat 120
gaattcaact cccccccaaa taaccaagtg atgctgtgtg aaccaacaat aatagaaaga 180
aacataacag agatagtgta tttgaccaac accaccatag agaaggaaat atgccccaaa 240
ccagcagaat acagaaattg gtcaaaaccg caatgtggca ttacaggatt tgcacctttc 300
tctaaggaca attcgattag gctttccgct ggtggggaca tctgggtgac aagagaacct 360
tatgtgtcat gcgatcctga caagtgttat caatttgccc ttggacaggg aacaacacta 420
aacaacgtgc attcaaataa cacagtacgt gataggaccc cttatcggac tctattgatg 480
aatgagttgg gtgttccttt ccatctgggg accaagcaag tgtgcatggc atggtccagc 540
tcaagttgtc acgatggaaa agcatggctg catgtttgta taactgggga tgataaaaat 600
gcaactgcta gcttcattta caatgggagg cttgtagata gtgttgtttc atggtccaaa 660
gatattctca ggacccagga gtcagaatgc gtttgcatca atggaacttg tacagtagta 720
atgactgatg gaaatgctac aggaaaagct gatactaaaa tactattcat tgaggagggg 780
aaaatcgttc atactagcaa attgtcagga agtgctcagc atgtcgaaga gtgctcctgc 840
tatcctcgat atcctggtgt cagatgtgtc tgcagagaca actggaaagg atccaaccgg 900
cccattgtag atataaacat aaaggatcat agcattgttt ccagttatgt gtgttcagga 960
cttgttggag acacacccag aaaaagcgac agctccagca gtagccattg tttgaatcct 1020
aacaatgaag aaggtggtca tggagtgaaa ggctgggcct ttgatgatgg aaatgacgtg 1080
tggatgggga gaacaatcaa cgagacgtca cgcttagggt atgaaacctt caaagtcgtt 1140
gaaggctggt ccaactctaa gtccaaattg cagataaata ggcaagtcat agttgacaga 1200
ggtgataggt ccggttattc tggtattttc tctgttgaag gcaaaagctg catcaatcgg 1260
tgcttttatg tggagttgat taggggaaga aaagaggaaa ctgaagtctt gtggacctca 1320
aacagtattg ttgtgttttg tggcacctca ggtacatatg gaacaggctc atggcctgat 1380
ggggcggacc tcaatctcat gcatatataa 1410

<210> SEQ ID NO 55
<211> LENGTH: 1434
<212> TYPE: DNA
<213> ORGANISM: Influenza virus

<400> SEQUENCE: 55
atgaatccaa atcaaaagat aataacgatt ggctctgttt ctctcacaat ttccacaata 60
tgcttcttca tgcaaattgc catcctgata actactgtaa cattgcattt caagcaatat 120
gaattcaact cccccccaaa taaccaagtg atgctgtgtg aaccaacaat aatagaaaga 180
aacataacag agatagtgta tttgaccaac accaccatag agaaggaaat atgccccaaa 240
ccagcagaat acagaaattg gtcaaaaccg caatgtggca ttacaggatt tgcacctttc 300
tctaaggaca attcgattag gctttccgct ggtggggaca tctgggtgac aagagaacct 360
tatgtgtcat gcgatcttga caagtgttat caatttgccc ttggacaggg aacaacacta 420
aacaacgtgc attcaaataa cacagtacgt gataggaccc cttatcggac tctattgatg 480
aatgagttgg gtgttccttt ccatctgggg accaagcaag tgtgcatagc atggtccagc 540
tcaagttgtc acgatggaaa agcatggctg catgtttgta taacggggga tgataaaaat 600
gcaactgcta gcttcattta caatgggagg cttgtagata gtgttgtctc atggtccaat 660
gatattctca ggacccagga atcagaatgc gtttgtatca atggaacttg tacagtagta 720
atgactgatg gaaatgctac aggaaaagct gatactaaaa tactattcat tgaggagggg 780
aaaatcgttc atactagcaa attgtcagga agtgctcagc atgtcgaaga gtgctcttgc 840
tatcctcgat atcctggtgt cagatgtgtc tgcagagaca actggaaagg atccaaccgg 900
cccatcatag atataaacat aaaggatcat agcattgttt ccagttatgt gtgttcagga 960
cttgttggag acacacccag aaaaagcgac agctccagca gtagccattg tttgaatcct 1020
aacaatgaag aaggtggtca tggagtgaaa ggctgggcct ttgatgatgg aaatgacgtg 1080
tggatgggga gaacaatcaa cgagacgtca cgcttagggt atgaaacctt caaagtcgtt 1140
gaaggctggt ccaaccctaa gtccaaattg cagataaata ggcaagtctt agttgacaga 1200
ggtgataggt ccggttattc tggtattttc tctgttgaag gcaaaagctg catcaatcgg 1260
tgcttttatg tggagttgat taggggaaga aaagaggaaa ctgaagtctt gtggacctca 1320
aacagtattg ttgtgttttg tggcacctca ggtacatatg gaacaggctc atggcctgat 1380
ggggcggacc tcaatctcat gcatatataa gctttcgcaa ttttagaaaa aact 1434

<210> SEQ ID NO 56
<211> LENGTH: 1448
<212> TYPE: DNA
<213> ORGANISM: Influenza virus

<400> SEQUENCE: 56
atgaatccaa atcaaaagat aataacgatt ggctctgttt ctctcacaat ttccacaata 60
tgcttcttca tgcaaattgc catcctgata actactgtaa cattgcattt caagcaatat 120
gaattcaact cccccccaaa taaccaagtg atgctgtgtg aaccaacaat aatagaaaga 180
aacataacag agatagtgta tttgaccaac accaccatag agaaggaaat atgccccaaa 240
ccagcagaat acagaaattg gtcaaaaccg caatgtggca ttacaggatt tgcacctttc 300

-continued

```
tctaaggaca attcgattag gctttccgct ggtggggaca tctgggtgac aagagaacct    360
tatgtgtcat gcgatcttga caagtgttat caatttgccc ttggacaggg aacaacacta    420
aacaacgtgc attcaaataa cacagtacgt gataggaccc cttatcggac tctattgatg    480
aatgagttgg gtgttccttt ccatctgggg accaagcaag tgtgcatagc atggtccagc    540
tcaagttgtc acgatggaaa agcatggctg catgtttgta taacgggga tgataaaaat    600
gcaactgcta gcttcattta caatgggagg cttgtagata gtgttgtttc atggtccaac    660
gatattctca ggacccagga gtcagaatgc gtttgtatca atggaacttg tacagtagta    720
atgactgatg gaaatgctac aggaaaggct gacactaaaa tactattcat tgaggagggg    780
aaaatcgtac atactagcaa attgtcagga agtgctcagc atgtcgaaga gtgctcttgc    840
tatcctcgat atcctggtgt cagatgtgtc tgcagagaca actggaaagg atccaaccgg    900
cccatcatag atataaacat aaaggatcat agcattgttt ccaggtatgt gtgttcagga    960
cttgttggag acacacccag aaaaagcgac agctccagca gtagccattg tttgaaccct   1020
aacaatgaaa aaggtggtca tggagtgaaa ggctgggcct ttgatgatgg aaatgacgtg   1080
tggatgggga gaacaatcaa cgagacgtca cgcttagggt atgaaacctt caaagtcgtt   1140
gaaggctggt ccaaccctaa gtccaaattg cagataaata ggcaagtcat agttgacaga   1200
ggtgataggt ccggttattc tggtattttc tctgttgaag gcaaaagctg catcaatcgg   1260
tgcttttatg trgagttgat taggggaaga aaagaggaaa ctgaagtctt gtggacctca   1320
aacagtattg ttgtgttttg tggcacctca ggtacatatg gaacaggctc atggcctgat   1380
ggggcggacc tcaatctcat gcatatataa gctttcgcaa ttttagaaaa aactccttgt   1440
ttctactg                                                            1448
```

<210> SEQ ID NO 57
<211> LENGTH: 1448
<212> TYPE: DNA
<213> ORGANISM: Influenza virus

<400> SEQUENCE: 57

```
atgaatccaa atcaaaagat aataacgatt ggctctgttt ctctcacaat ttccacaata     60
tgcttcttca tgcaaattgc catcctgata actactgtaa cattgcattt caagcaatat    120
gaattcaact cccccccaaa taaccaagtg atgctgtgtg aaccaacaat aatagaaaga    180
aacataacag agatagtgta tttgaccaac accaccatag agaaggaaat atgccccaaa    240
ccagcagaat acagaaattg gtcaaaaccg caatgtggca ttacaggatt tgcacctttc    300
tctaaggaca attcgattag gctttccgct ggtggggaca tctgggtgac aagagaacct    360
tatgtgtcat gcgatcttga caagtgttat caatttgccc ttggacaggg gacaacacta    420
aacaacgtgc attcaaataa cacagtacgt gataggaccc cttaccggac tctattgatg    480
aatgagttgg gtgttccttt ccatctgggg accaagcaag tgtgcatagc atggtccagc    540
tcaagttgtc acgatggaaa agcatggctg catgtttgta taacgggga tgataaaaat    600
gcaactgcta gcttcattta caatgggagg cttgtagata gtgttgtttc atggtccaac    660
gatattctca ggacccagga atcagaatgc gtttgtatca atggaacttg tacagtagta    720
atgactgatg gaaatgctac aggaaaagct gatactaaaa tactattcat cgaggagggg    780
aaaatcattc atactagcaa attgtcagga agtgctcagc atgtcgaaga gtgctcttgc    840
tatcctcgat atcctggtgt cagatgtgtc tgcagagaca actggaaagg atccaaccgg    900
cccatcatag atataaacat aaaggatcat agcattgttt ccagttatgt gtgttcagga    960
```

cttgttggag acacacccag aaaaagcgac agctccagca gtagccattg tttgaatcct 1020
aacaatgaag aaggtggtca tggagtgaaa ggctgggcct ttgatgatgg aaatgacgtg 1080
tggatgggga gaacaatcaa cgagacgtca cgcttagggt atgaaacctt caaagtcgtt 1140
gaaggctggt ccaaccctaa gtccaaattg cagataaata ggcaagtcat agttgacaga 1200
ggtgataggt ccggttattc tggtattttc tctgttgaag gcaaaagctg catcaatcgg 1260
tgcttttatg tggagttgat taggggaaga aaagaggaaa ctgaagtctt gtggacctca 1320
aacagtattg ttgtgttttg tggcacctca ggtacatatg gaacaggctc atggcctgat 1380
ggggcggacc tcaatctcat gcatatataa gctttcgcaa ttttagaaaa aaactccttg 1440
tttctact 1448

<210> SEQ ID NO 58
<211> LENGTH: 1410
<212> TYPE: DNA
<213> ORGANISM: Influenza virus

<400> SEQUENCE: 58
atgaatccaa atcaaaagat aataacgatt ggctctgttt ctctcacaat ttccacaata 60
tgcttcttca tgcaaattgc catcctgata actactgtaa cattgcattt caagcaatat 120
gaattcaact cccccccaaa taaccaagtg atgctgtgtg aaccaacaat aatagaaaga 180
aacataacag agatagtgta tttgaccaac accaccatag agaaggaaat atgccccaaa 240
ccagcagaat acagaaattg gtcaaaaccg caatgtggca ttacaggatt tgcacctttc 300
tctaaggaca attcgattag gctttccgct ggtggggaca tctgggtgac aagagaacct 360
tatgtgtcat gcgatcttga caagtgttat caatttgccc ttggacaggg aacaacacta 420
aacaacgtgc attcaaataa cacagtacgt gatagaaccc cttatcggac tctattgatg 480
aatgagttgg gtgttccttt ccatctgggg accaagcaag tgtgcatagc atggtccagc 540
tcaagctgtc acgatggaaa agcatggctg catgtttgta taacgggga tgataaaaat 600 gcaactgcta gcttcattta caatgggagg cttgtagata gtgttgtttc atggtccaac 660
gatattctca ggacccagga gtcagaatgc gtttgtatca atggaacttg tacagtagta 720
atgactgatg gaaatgctac aggaaaagct gatactaaaa tactattcat tgaggagggg 780
aaaatcgttc atactagcaa attgtcagga agtgctcagc atgtcgaaga gtgctcttgc 840
tatcctcgat atcctggtgt cagatgtgtc tgcagagaca actggaaagg atccaaccgg 900
cccatcatag atataaacat aaaggatcat agcattgttt ccaggtatgt gtgttcagga 960
cttgttggag acacacccag aaaaagcgac agctccagca gtagccattg tttgaaccct 1020
aacaatgaaa aaggtgatca tggagtgaaa ggctgggcct ttgatgatgg aaatgacgtg 1080
tggatgggga gaacaatcaa cgagacgtcg cgcttagggt atgaaacctt caaagtcgtt 1140
gaaggctggt ccaaccctaa gtccaaattg cagataaata ggcaagtcat agttgacaga 1200
ggtgataggt ccggttattc tggtattttc tctgttgaag gcaaaagctg catcaatcgg 1260
tgcttttatg tggagttgat taggggaaga aaagaggaaa ctgaagtctt gtggacctca 1320
aacagtattg ttgtgttttg tggcacctca ggtacatatg gaacaggctc atggcctgat 1380
ggggcggacc tcaatctcat gcatatataa 1410

<210> SEQ ID NO 59
<211> LENGTH: 1434
<212> TYPE: DNA

<213> ORGANISM: Influenza virus

<400> SEQUENCE: 59

```
atgaatccaa atcaaaagat aataacgatt ggctctgttt ctctcaccat ttccacaata      60
tgcttcttca tgcaaattgc catcctgata actactgtaa cattgcattt caagcaatat     120
gaattcaact cccccccaaa caaccaagtg atgctgtgtg aaccaacaat aatagaaaga     180
aacataacag agatagtgta tttgaccaac accaccatag agagggaaat atgccccaaa     240
ccagcagaat acagaaattg gtcaaaaccg caatgtggca ttacaggatt tgcacctttc     300
tctaaggaca attcgattag gctttccgct ggtggggaca tctgggtgac aagagaacct     360
tatgtgtcat gcgatcctga caagtgttat caatttgccc ttggacaggg aacaacaata     420
aacaacgtgc attcaaataa cacagcacgt gataggaccc ctcatcggac tctattgatg     480
aatgagttgg gtgttccttt ccatctgggg accaagcaag tgtgcatagc atggtccagc     540
tcaagttgtc acgatggaaa agcatggctg catgtttgta taacgggga tgataaaaat      600
gcaactgcta gtttcattta caatgggagg cttgtagata gtgttgtttc atggtccaaa     660
gatattctca ggacccagga gtcagaatgc gtttgtatca atggaacttg tacagtagta     720
atgactgatg gaaatgctac aggaaaagct gatactaaaa tattattcat tgaggagggg     780
aaaatcgttc atactagcaa attgtcagga agtgctcagc atgtcgaaga gtgctcttgc     840
tatcctcgat accctggtgt cagatgtgtc tgcagagaca actggaaagg atccaaccgg     900
cccatcgtag atataaacat aaaggatcat agcattgttt ccagttatgt gtgttcagga     960
cttgttggag acacacccag aaaaaccgac agctccagca gcagccattg cttgaatcct    1020
aacaatgaaa aaggtggtca tggagtgaaa ggctgggcct ttgatgatgg aaatgacgtg    1080
tggatgggga gaacaatcaa cgagacgtca cgcttagggt atgaaacctt caaagtcgtt    1140
gaaggctggt ccaaccctaa gtccaaattg cagataaata ggcaagtcat agttgacaga    1200
ggtgataggt ccggttattc tggtattttc tctgttgaag gcaaaagctg catcaatcgg    1260
tgcttttatg tggagttgat taggggaaga aaagaggaaa ctgaagtctt gtggacctca    1320
aacagtattg ttgtgttttg tggcacctca ggtacatatg gaacaggctc atggcctgat    1380
ggggcggacc tcaatctcat gcatatataa gctttcgcaa ttttagaaaa aact          1434
```

<210> SEQ ID NO 60
<211> LENGTH: 1720
<212> TYPE: DNA
<213> ORGANISM: Influenza virus

<400> SEQUENCE: 60

```
atgaagacta tcattgcttt gggctacatt ctatgtctgg ttttcgctca aaaaattcct      60
ggaaatgaca atagcacggc aacgctgtgc cttgggcacc atgcagtacc aaacggaacg     120
atagtgaaaa caatcacaaa tgaccgaatt gaagttacta atgctactga gctggttcag     180
aattcctcaa taggtgaaat atgcgacagt cctcatcaga tccttgatgg agaaaactgc     240
acactaatag atgctctatt gggagaccct cagtgtgatg gctttcaaaa taagaaatgg     300
gacctttttg ttgaacgaag caaagcctac agcaactgtt acccttatga tgtgccggat     360
tatgcctccc ttaggtcact agttgcctca tccggcacac tggagtttaa caatgaaagc     420
ttcaattgga ctggagtcac tcaaaacgga acaagttctg cttgcataag gagatctagt     480
agtagtttct ttagtagatt aaattggttg acccacttaa actacacata cccagcattg     540
aacgtgacta tgccaaacaa tgaacaattt gacaaattgt acatttgggg ggttcaccac     600
```

```
ccgggtacgg acaaggacca aatcttcctg tatgctcaat catcaggaag aatcacagta    660
tctaccaaaa gaagccaaca agctgtaatc ccaaatatcg gatctagacc tagaataagg    720
gatatcccta gcagaataag catctattgg acaatagtaa aaccgggaga catacttttg    780
attaacagca cagggaatct aattgctcct aggggttact tcaaaatacg aagtgggaaa    840
agctcaataa tgagatcaga tgcacccatt ggcaaatgca agtctgaatg catcactcca    900
aatggaagca ttcccaatga caaaccattc caaaatgtaa acaggatcac atacggggcc    960
tgtcccagat atgttaagca tagcactctg aaattggcaa caggaatgcg aaatgtacca   1020
gagaaacaaa ctagaggcat atttggcgca atagcgggtt tcatagaaaa tggttgggag   1080
ggaatggtgg atggttggta cggtttcagg catcaaaatt ctgagggaag aggacaagca   1140
gcagatctca aaagcactca agcagcaatc gatcaaatca atgggaagct gaatcgattg   1200
atcgggaaaa ccaacgagaa attccatcag attgaaaaag aattctcaga agtagaagga   1260
agaattcagg accttgagaa atatgttgag gacactaaaa tagatctctg gtcatacaac   1320
gcggagcttc ttgttgccct ggagaaccaa catacaattg atctaactga ctcagaaatg   1380
aacaaactgt ttgaaaaaac aaagaagcaa ctgagggaaa atgctgagga tatgggaaat   1440
ggttgtttca aaatatacca caaatgtgac aatgcctgca taggatcaat aagaaatgga   1500
acttatgacc acaatgtgta cagggatgaa gcattaaaca accggttcca gatcaaggga   1560
gttgagctga agtcagggta caaagattgg atcctatgga tttcctttgc catatcatgt   1620
tttttgcttt gtgttgcctt gttggggttc atcatgtggg cctgccaaaa gggcaacatt   1680
aggtgcaaca tttgcatttg agtgcattaa ttaaaaacac                         1720
```

```
<210> SEQ ID NO 61
<211> LENGTH: 1701
<212> TYPE: DNA
<213> ORGANISM: Influenza virus

<400> SEQUENCE: 61
```

```
atgaagacta tcattgcttt gagctacatt ctatgtctgg ttttcgctca aaaaattcct     60
ggaaatgaca atagcacggc aacgctgtgc cttgggcacc atgcagtacc aaacggaacg    120
atagtgaaaa caatcacaaa tgaccgaatt gaagttacta atgctactga gttggttcag    180
aattcctcaa taggtgaaat atgcgacagt cctcatcaga tccttgatgg agagaactgc    240
acactaatag atgctctatt gggagaccct cagtgtgatg gctttcaaaa taagaaatgg    300
gaccttttg ttgaacgaag caaagcctac agcaactgtt acccttatga tgtgccggat     360
tatgcctccc ttaggtcact agttgcctca tccggcacac tggagtttaa caatgaaagc    420
ttcaattgga ctggagtcac tcaaaacgga acaagttctg cttgcataag gagatctagt    480
agtagtttct ttagtagatt aaattggttg acccacttaa actacacata tccagcattg    540
aacgtgacta tgccaaacaa ggaacaattt gacaaattgt acatttgggg ggttcaccac    600
ccgggtacgg acaaggacca aatcttcctg tatgctcaat catcaggaag aatcacagta    660
tctaccaaaa gaagccaaca agctgtaatc ccaaatatcg gatctagacc cagaataagg    720
gatatcccta gcagaataag catctattgg acaatagtaa aaccgggaga catacttttg    780
attaacagca cagggaatct aattgctcct aggggttact tcaaaatacg aagtgggaaa    840
agctcaataa tgagatcaga tgcacccatt ggcaaatgca agtctgaatg catcactcca    900
aatggaagca ttcccaatga caaaccattc caaaatgtaa acaggatcac atacggggcc    960
```

tgtcccagat atgttaagca tagcactctg aaattggcaa caggaatgcg aaatgtacca 1020
gagaaacaaa ctagaggcat atttggcgca atagcgggtt tcatagaaaa tggttgggag 1080
ggaatggtgg atggttggta cggtttcagg catcaaaatt ctgagggaag aggacaagca 1140
gcagatctca aaagcactca agcagcaatc gatcaaatca atgggaagct gaatcggttg 1200
atcgggaaaa ccaacgagaa attccatcag attgaaaaag aattctcaga agtagaagga 1260
agagttcaag accttgagaa atatgttgag gacactaaaa tagatctctg gtcatacaac 1320
gcggagcttc ttgttgccct ggagaaccaa catacaattg atctaactga ctcagaaatg 1380
aacaaactgt ttgaaaaaac aaagaagcaa ctgagggaaa atgctgagga tatgggaaat 1440
ggttgtttca aaatatacca caaatgtgac aatgcctgca taggatcaat aagaaatgaa 1500
acttatgacc acaatgtgta cagggatgaa gcattaaaca accggttcca gatcaaggga 1560
gttgagctga agtcagggta caaagattgg atcctatgga tttcctttgc catatcatgt 1620
tttttgcttt gtgttgcttt gttggggttc atcatgtggg cctgccaaaa gggcaacatt 1680
agatgcaaca tttgcatttg a 1701

<210> SEQ ID NO 62
<211> LENGTH: 1733
<212> TYPE: DNA
<213> ORGANISM: Influenza virus

<400> SEQUENCE: 62
atgaagacta tcattgcttt gagctacatt ctatgtctgg ttttcgctca aaaaattcct 60
ggaaatgaca atagcacggc aacgctgtgc cttgggcacc atgcagtacc aaacggaacg 120
atagtgaaaa caatcacaaa tgaccgaatt gaagttacta atgctactga gttggttcag 180
aattcctcaa taggtgaaat atgcgacagt cctcatcaga tccttgatgg agggaactgc 240
acactaatag atgctctatt gggggaccct cagtgtgacg gctttcaaaa taagaaatgg 300 gaccttttg ttgaacgaag cagagcctac agcaactgtt acccttatga tgtgccggat 360
tatgcctccc ttaggtcact agttgcctca tccggcacac tggagtttaa aaatgaaagc 420
tttaattgga ctggagtcac tcaaaacgga aaaagttctg cttgcataag gggatctagt 480
agtagtttct ttagtagatt aaattggttg acccacttaa actacacata tccagcactg 540
aacgtgacta tgccaaacaa ggaacaattt gacaaattgt acatttgggg ggttcaccac 600
ccgggtacgg acaaggacca aatcttcctg tatgctcaat catcaggaag aatcacagta 660
tctaccaaaa gaagccaaca agctgtaatc ccaaatattg gatctagacc cagaataagg 720
gatatcccta gcagaataag catctattgg acaatagtaa aaccgggaga catacttttg 780
attaacagca cagggaatct aattgctcct aggggttact tcaaaatacg aagtgggaaa 840
agctcaataa tgagatcaga tgcacccatt ggcaaatgca agtctgaatg catcactcca 900
aatggaagca ttcccaatga caaaccattc caaaatgtaa acaggatcac atacggggcc 960
tgtcccagat atgttaagca aagcactctg aaattggcaa caggaatgcg aaatgtacca 1020
gagaaacaaa ctagaggcat atttggcgca atagcgggtt tcatagaaaa tggttgggag 1080
ggaatggtgg atggttggta cggtttcagg catcaaaatt ctgagggaag aggacaagca 1140
gcagatctca aaagcactca agcagcaatc gatcaaatca atgggaagct gaatcgattg 1200
atcggaaaaa ccaacgagaa attccatcag attgaaaaag aattctcaga agtagaagga 1260
agagttcaag accttgagaa atatgttgag gacactaaaa tagatctctg gtcatacaac 1320
gcggagcttc ttgttgccct ggagaaccaa catacaattg atctaactga ctcagaaatg 1380

```
aacaaactgt ttgaaaaaac aaaaaagcaa ctgagggaaa atgctgagga tatgggaaat   1440

ggttgtttca aaatatacca caaatgtgac aatgcctgca taggatcaat aagaaatgaa   1500

acttatgacc acaatgtgta cagggatgaa gcattaaaca accggttcca gatcaaggga   1560

gttgagctga agtcagggta caaagattgg atcctatgga tttcctttgc catatcatgt   1620

tttttgcttt gtgttgcttt gttggggttc atcatgtggg cctgccaaaa gggcaacatt   1680

agatgcaaca tttgcatttg agtgcattaa ttaaaaacac ccttgtttct act          1733
```

<210> SEQ ID NO 63
<211> LENGTH: 1730
<212> TYPE: DNA
<213> ORGANISM: Influenza virus

<400> SEQUENCE: 63

```
atgaagacta tcattgcttt gagctacatt ctatgtctgg ttttcgctca aaaaattcct     60

ggaaatgaca atagcacggc aacgctgtgc cttgggcacc atgcagtacc aaacggaacg    120

atagtgaaaa caatcacaaa tgaccgaatt gaagttacta atgctactga gttggttcag    180

aattcctcaa taggtgaaat atgcgacagt cctcatcaga tccttgatgg agaaaactgc    240

acactaatag atgctctatt gggagaccct cagtgtgatg gctttcaaaa taagaaatgg    300

gaccttttg ttgaaagaag caaagcctac agcaactgtt acccttacga tgtgccggat    360

tatgcctccc ttaggtcact agttgcctca tccggcacac tggagtttaa caatgaaagc    420

ttcaattgga ctggagtcaa acaaaacgga acaagttctg cttgtataag gaaatctagt    480

agtagtttct ttagtagatt aaattggttg acccacttaa actacacata tccagcattg    540

aacgtgacta tgccaaacaa tgaacaattt gacaaattgt acatttgggg ggttcaccac    600

ccgggtacgg acaaggacca aatcttcctg tatgctcaat catcaggaag gatcacagta    660

tctaccaaaa gaagccaaca aactgtaatc ccaaatatcg gatccaggcc cagaataagg    720

gatatcccta gcagaataag catctattgg acaatagtaa aaccgggaga catacttttg    780

attaacagca cagggaatct aattgctcct aggggttact tcaaaataca aagtgggaaa    840

agctcaataa tgagatcaga tgcacccatt ggcaaatgca agtctgaatg catcactcca    900

aatggaagca ttcccaatga caaaccattc caaaatgtaa acaggatcac atacggggcc    960

tgtcccagat atgttaagca tagcactctg aaattggcaa caggaatgcg aaatgtacca   1020

gagaaacaaa ctaggggcat atttggcgca atagcgggtt tcatagaaaa tggttgggag   1080

ggaatggtgg atggttggta cggtttcagg catcaaaatt ctgaaggaag aggacaagca   1140

gcagatctca aaagcactca agcagcaatc gatcaaatca atgggaagct gaatcgattg   1200

atcgggaaaa ccaacgagaa attccatcag attgaaaaag aattctcaga agtagaagga   1260

agaattcagg accttgagaa atatgttgag gacactaaaa tagatctctg gtcatacaac   1320

gcggagcttc ttgttgccct ggagaaccaa catacaattg atctaactga ctcagaaatg   1380

aacaaactgt ttgaaaaaac aaagaagcaa ctgagggaaa atgctgagga tatgggaaat   1440

ggttgtttca aaatatacca caaatgtgac aatgcctgca taggttcaat aagaaatgga   1500

acttatgacc acaatgtgta cagggatgaa gcattaaaca accggttcca gatcaaggga   1560

gttgagctga agtcagggta caaagattgg atcctatgga tttcctttgc catatcatgt   1620

tttttgcttt gtgttgcttt gttggggttc atcatgtggg cctgccaaaa gggcaacatt   1680

agatgcaata tttgcatttg agtgcattaa ttaaaaacac ccttgtttct              1730
```

<210> SEQ ID NO 64
<211> LENGTH: 1720
<212> TYPE: DNA
<213> ORGANISM: Influenza virus

<400> SEQUENCE: 64

```
atgaaggcta tcattgcttt gagctacatt ctatgtctgg ttttcgctca aaaaattcct     60

ggaaatgaca atagcacggc aacgctgtgc cttgggcacc atgcagtacc aaacggaacg    120

atagtgaaaa caatcacaaa tgaccgaatt gaagttacta atgctactga gttggttcag    180

aattcctcaa taggtgaaat atgcgacagt cctcatcaga tccttgatgg agggaactgc    240

acactaatag atgctctatt gggggaccct caatgtgacg gctttcaaaa taagaaatgg    300

gaccttttg ttgaacgaag cagagcctac agcaactgtt acccttatga tgtgccggat    360

tatgcctccc ttaggtcact agttgcctca tccggcacac tggagtttaa aaatgaaagc    420

ttcaattggg ctggagtcac tcaaaacgga aaaagttctg cttgcataag gggatctagt    480

agtagtttct ttagtagatt aaattggttg acccacttaa actacacata tccagcactg    540

aacgtgacta tgccaaacaa ggaacaattt gacaaattgt acatttgggg ggttcaccac    600

ccgggtacgg acaaggacca aatcttcctg tatgctcaat catcaggaag aatcacagta    660

tctaccaaaa gaagccaaca agctgtaatc ccaaatatag gatctagacc cagaataagg    720

gatatcccta gcagaataag catctattgg acaatagtaa aaccgggaga catacttttg    780

attaacagca cagggaatct aattgctcct aggggttact tcaaaatacg ragtgggaaa    840

agctcaataa tgagatcaga tgcacccatt ggcaaatgca agtctgaatg catcactcca    900

aatggaagca ttcccaatga caaaccattc caaaatgtaa acaggatcac atacggggcc    960

tgtcccagat atgttaagca aagcactctg aaattggcaa caggaatgcg aaatgtacca   1020

gagaaacaaa ctagaggcat atttggcgca atagcgggtt tcatagaaaa tggttgggag   1080

ggaatggtgg atggttggta cggtttcagg catcaaaatt ctgagggaag aggacaagca   1140

gcagatctca aaagcactca agcagcaatc gatcaaatca atgggaagct gaatcgattg   1200

atcggaaaaa ccaacgagaa attccatcag attgaaaaag aattctcaga agtagaagga   1260

agagttcaag accttgagaa atatgttgag gacactaaaa tagatctctg gtcatacaac   1320

gcggagcttc ttgttgccct ggagaaccaa catacaattg atctaactga ctcagaaatg   1380

aacaaactgt ttgaaaaaac aaagaagcaa ctgagggaaa atgctgagga tatgggaaat   1440

ggttgtttca aaatatacca caaatgtgac aatgcctgca taggatcaat aagaaatgaa   1500

acttatgacc acaatgtgta cagggatgaa gcattaaaca accggttcca gatcaaggga   1560

gttgagctga agtcagggta caaagattgg atcctatgga tttcctttgc catatcatgt   1620

tttttgcttt gtgttgcttt gttggggttc atcatgtggg cctgccaaaa gggcaacatt   1680

agatgcaaca tttgcatttg agtgcattaa ttaaaaacac                         1720
```

<210> SEQ ID NO 65
<211> LENGTH: 1729
<212> TYPE: DNA
<213> ORGANISM: Influenza virus

<400> SEQUENCE: 65

```
atgaagacta tcattgcttt gagctacatt ctatgtctgg ttttcgctca aaaaattcct     60

ggaaatgaca atagcacggc aacgctgtgc cttgggcacc atgcagtacc aaacggaacg    120

atagtgaaaa caatcacaaa tgaccgaatt gaagttacta atgctactga gttggttcag    180
```

aattcctcaa taggtgaaat atgcgacagt cctcatcaga tccttgatgg agggaactgc 240
acactaatag atgctctatt gggggaccct cagtgtgacg gctttcaaaa taagaaatgg 300
gaccttttg ttgaacgaag cagagcctac agcaactgtt acccttatga tgtaccggat 360
tatgcctccc ttaggtcact agttgcctca tccggcacac tggagtttaa aaatgaaagc 420
ttcaattgga ctggagtcaa acaaaacgga acaagttctg cttgcataag gggatctagt 480
agtagtttct ttagtagatt aaattggttg acccacttaa actacacata tccagcactg 540
aacgtgacta tgccaaacaa ggaacaattt gacaaattgt acatttgggg ggttcaccac 600
ccgggtacgg acaaggacca aatcttcctg tatgctcaat catcaggaag aatcacagta 660
tctaccaaaa gaagccaaca agctgtaatc ccaaatatcg gatttagacc cagaataagg 720
gatatcccta gcagaataag catctattgg acaatagtaa aaccgggaga catacttttg 780
attaacagca cagggaatct aattgctcct aggggttact tcaaaatacg aagtgggaaa 840
agctcaataa tgagatcaga tgcacccatt ggcaaatgca agtctgaatg catcactcca 900
aatggaagca ttcccaatga caaaccattc caaaatgtaa acaggatcac atacggggcc 960
tgtcccagat atgttaagca gagcactctg aaattggcaa caggaatgcg aaatgtacca 1020
gagaaacaaa ctagaggcat atttggcgca atagcgggtt tcatagaaaa tggttgggag 1080
ggaatgatgg atggttggta cggtttcagg catcaaaatt ctgagggaag aggacaagca 1140
gcagatctca aaagcactca agcagcaatc gatcaaatca atgggaagct gaatcgattg 1200
atcggaaaaa ccaacgagaa attccatcag attgaaaaag aattctcaga agtagaagga 1260
agagttcaag accttgagaa atatgttgag gacactaaaa tagatctctg gtcatacaac 1320
gcggagcttc ttgttgccct ggagaaccaa catacaattg acctaactga ctcagaaatg 1380
aacaaactgt ttgaaaaaac aaagaagcaa ctgagggaaa atgctgagga tatgggaaat 1440
ggttgtttca aaatatacca caaatgtgac aatgcctgca taggatcaat aagaaatgaa 1500
acttatgacc acaatgtgta cagggatgaa gcattaaaca accggttcca gatcaaggga 1560
gttgagctga agtcagggta caaagattgg atcctatgga tttcctttgc catatcatgt 1620
tttttgcttt gtattgcttt gttggggttc atcatgtggg cctgccaaaa gggcaacatt 1680
agatgcaaca tttgcatttg agtgcattaa ttaaaaacac ccttgtttc 1729

<210> SEQ ID NO 66
<211> LENGTH: 1733
<212> TYPE: DNA
<213> ORGANISM: Influenza virus

<400> SEQUENCE: 66
atgaagacta tcattgcttt gagctacatt ctatgtctgg ttttcgctca aaaaattcct 60
ggaaatgaca atagcacggc aacgctgtgc cttgggcacc atgcagtacc aaacggaacg 120
atagtgaaaa caatcacaaa tgaccgaatt gaagttacta atgctactga gttggttcag 180
aattcctcaa taggtgaaat atgcaacagt cctcatcaga tccttgatgg agggaactgc 240
acactaatag atgctctatt gggggaccct cagtgtgacg gctttcaaaa taagaaatgg 300
gaccttttg ttgaacgaag cagagcctac agcaactgtt acccttatga tgtgccggat 360
tatgcctccc ttaggtcact agttgcctca tccggcacac tggagtttaa aaatgaaagc 420
ttcaattggg ctggagtcac tcaaaacgga aaaagttctg cttgcataag ggttctagt 480
agtagtttct ttagtagatt aaattggttg acccacttaa actacacata tccagcactg 540

```
aacgtgacta tgccaaacaa ggaacaattt gacaaattgt acatttgggg ggttcaccac    600
ccgggtacgg acaaggacca aatcttcctg tatgctcaac catcaggaag aatcacagta    660
tctaccaaaa gaagccaaca agctgtaatc ccaaatatcg gatctagacc cagaataagg    720
gatatcccta gcagaataag catctattgg acaatagtaa aaccgggaga catacttttg    780
attaacagca cagggaatct aattgctcct aggggttact tcaaaatacg aagtgggaaa    840
agctcaataa tgagatcaga tgcacccatt ggcaaatgca agtctgaatg catcactcca    900
aatggaagca ttcccaatga caaaccattc caaaatgtaa acagaatcac atacggggcc    960
tgtcccagat atgttaagca aagcactctg aaattggcaa caggaatgcg aaatgtacca   1020
gagaaacaaa ctagaggcat atttggcgca atagcgggtt tcatagaaaa tggttgggag   1080
ggaatggtgg atggttggta cggtttcagg catcaaaatt ctgagggaag aggacaagca   1140
gcagatctca aaagcactca agcagcaatc gatcaaatca atgggaagct gaatcgattg   1200
atcggaaaaa ccaacgagaa attccatcag attgaaaaag aattctcaga agtagaagga   1260
agggttcaag accttgagaa atatgttgag gacactaaaa tagatctctg gtcatacaac   1320
gcggagcttc ttgttgccct ggagaaccaa catacaattg atctaactga ctcagaaatg   1380
aacaaactgt ttgaaaaaac aaagaagcaa ctgagggaaa atgctgagga tatggggaat   1440
ggttgtttca aaatatacca caaatgtgac aatgcctgca taggatcaat aagaaatgaa   1500
acttatgacc acaatgtgta cagggatgaa gcattaaaca accggttcca gatcaaggga   1560
gttgagctga agtcagggta caaagattgg atcctatgga tttcctttgc catatcatgt   1620
tttttgcttt gtgttgcttt gttggggttc atcatgtggg cctgccaaaa gggcaacatt   1680
agatgcaaca tttgcatttg agtgcattaa ttaaaaacac ccttgtttct act           1733
```

<210> SEQ ID NO 67
<211> LENGTH: 1701
<212> TYPE: DNA
<213> ORGANISM: Influenza virus

<400> SEQUENCE: 67

```
atgaagacta tcattgcttt gagctacatt ctatgtcttg ttttcgctca agaaatccct     60
ggaaatgaca atagcacggc aacgctgtgt cttgggcacc atgcagtacc aaacggaacg    120
atagtgaaaa caatcacaaa tgaccgaatt gaagttacta atgctactga gttggttcag    180
aattcctcaa taggtgaaat atgcgacagt cctcatcaga tccttgatgg agggaactgc    240
acactaatag atgctctatt gggggaccct cagtgtgacg gctttcaaaa taagaaatgg    300
gaccttttg ttgaacgaag cagagcctac agcaactgtt acccttatga tgtgccggat     360
tatgcctccc ttaggtcact agttgcctca tccggcacac tggagtttaa aaatgaaagc    420
ttcaattgga ctggagtcaa acaaaacgga acaagttctg cgtgcataag gggatctagt    480
agtagtttct tcagtagatt aaattggttg acccacttaa actacacata tccagcactg    540
aacgtgacta tgccaaacaa ggaacaattt gacaaattgt acatttgggg ggttcaccac    600
ccgggtacgg acaaggacca aatcttcctg tatgctcaat catcaggaag aatcacagta    660
tctaccaaaa gaagccaaca agctgtaatc ccaaatattg gatctagacc cagaataagg    720
gatatcccta gcagaataag catctattgg acaatagtaa aaccgggaga catacttttg    780
attaacagca cagggaatct aattgctcct aggggttact tcaaaatacg aagtgggaaa    840
agctcaataa tgagatcaga tgcacccatt ggcaaatgca agtctgaatg catcactcca    900
aatggaagca ttcccaatga caaaccgttc caaaatgtaa acaggatcac atacggggcc    960
```

-continued

```
tgtcccagat atgttaagca aagcactctg aaattggcaa caggaatgcg aaatgtacca   1020

gagaaacaaa ccagaggcat atttggcgca atagcgggtt tcatagaaaa tggttgggag   1080

ggaatggtgg atggttggta cggtttcagg catcaaaatt ctgagggaag aggacaagca   1140

gcagatctca aaagcactca agcagcaatc gatcaaatca atgggaagct gaatcgattg   1200

atcggaaaaa ccaacgagaa attccatcag attgaaaaag aattctcaga agtagaagga   1260

agagttcaag accttgagaa atatgttgag gacactaaaa tagatctctg gtcatacaac   1320

gcggagcttc ttgttgccct ggagaaccaa catacaattg acctaactga ctcagaaatg   1380

aacaaactgt ttgaaaaaac aaagaagcaa ctgagggaaa atgctgagga tatgggaaat   1440

ggttgtttca aaatatacca caaatgtgac aatgcctgca taggatcaat aagaaatgaa   1500

acttatgacc acaatgtgta cagggatgaa gcattaaaca accggttcca gatcaaggga   1560

gttgagctga agtcagggta caaagattgg atcctatgga tttcctttgc catatcatgt   1620

tttttgcttt gtattgcttt gttggggttc atcatgtggg cctgccaaaa gggcaacatt   1680

agatgcaaca tttgcatttg a                                              1701
```

<210> SEQ ID NO 68
<211> LENGTH: 1720
<212> TYPE: DNA
<213> ORGANISM: Influenza virus

<400> SEQUENCE: 68

```
atgaagacta tcattgcttt gagctgcatt ctatgtctgg ttttcgctca aaaaattcct     60

ggaaatgaca atagcacggc aacgctgtgc cttgggcacc atgcagtacc aaacggaacg    120

atagtgaaaa caatcacgaa tgaccgaatt gaagttacta atgctactga gctggttcag    180

aactcctcaa taggtgaaat atgcgacagt cctcatcaga tccttgatgg agaaaactgc    240

acactaatag atgctctatt gggagaccct cagtgtgatg gctttcaaaa taagaaatgg    300

gaccttttcg ttgaacgaaa caaagcctac agcaactgtt acccttatga tgtgccggat    360

tatgcatccc ttagatcact agttgcctca tccggcacac tggagtttaa caatgaaagc    420

ttcaattggg ctggagtcac tcaaaacgga acaagttctt cttgcataag gggatctaaa    480

agtagtttct ttagtagatt aaattggttg acccacttaa actccaaata cccagcatta    540

aacgtgacta tgccaaacaa tgaacaattt gacaaattgt acatttgggg tgttcaccac    600

ccgggtacgg acaaggacca aatctccctg tatgcacaat catcaggaag aatcacagta    660

tctaccaaaa gaagccaaca agctgtaatc ccgaatatcg gatctagacc cagaataagg    720

gatatcccta gcagaataag catctattgg acaatagtaa aaccaggaga catacttttg    780

attaacagca cagggaatct aattgctcct aggggttact tcaaaatacg aagtgggaaa    840

agctcaataa tgagatcaga tgcacccatt ggcaagtgca agtctgaatg catcactcca    900

aatggaagca ttccaaatga caaaccattc caaaatgtaa acaggatcac atacggggca    960

tgtcccagat atgttaagca aagcactctg aaattggcaa caggaatgcg aaatgtacca   1020

gagagacaaa ctagaggcat atttggcgca atagcgggtt tcatagaaaa tggttgggag   1080

ggaatggtgg atggttggta cggcttcagg catcaaaatt ctgagggaag aggacaagca   1140

gcagatctta aaagcactca agcagcaatc gatcaaatca atgggaagct gaatcgattg   1200

atcgggaaaa ccaacgagaa attccatcag attgaaaaag agttctcaga agtagaaggg   1260

agaattcagg accttgagaa atatgttgag gacacaaaaa tagatctctg gtcatacaac   1320
```

-continued gcggagcttc ttgttgccct ggagaaccaa catacaattg atctaactga ctcagaaatg 1380
aacaaactgt ttgaaaaaac aaagaagcaa ctgagggaaa atgctgagga tatgggcaat 1440
ggttgtttca aaatatacca caaatgtgac aatgcctgca tggggtcaat cagaaatgga 1500
acttatgacc acaatgtata cagggatgaa gcattaaaca accggttcca gatcaaggga 1560
gttgagctga agtcagggta caaagattgg atcctatgga tttcctttgc catatcatgt 1620
tttttgcttt gtgttgctct gttggggttc atcatgtggg cctgccaaaa gggcaacatt 1680
aggtgcaaca tttgcatttg agtgcattaa ttaaaaacac 1720

<210> SEQ ID NO 69
<211> LENGTH: 1434
<212> TYPE: DNA
<213> ORGANISM: Influenza virus

<400> SEQUENCE: 69
atgaatccaa atcaaaagat aataacgatt ggctctgttt ctctcaccat ttccacaata 60
tgctttttca tgcaaattgc cattttgata actactgtaa cattgcattt caagcaatat 120
gaattcaact ccccccccaaa caaccaagtg atgctgtgtg aaccaacaat aatagaaaga 180
aacataacag agatagtgta tttaaccaac accaccatag agaaggaaat atgccccaaa 240
ccagcagaat acagaaattg gtcaaaaccg caatgtggca ttacaggatt tgcacctttc 300
tctaaggaca attcgatcag gctttccgct ggtggggaca tctgggtgac aagagaacct 360
tatgtgtcat gcgatcctga caagtgttat caatttgccc ttggacaggg aacaacacta 420
aacaacgtgc attcaaataa caaagtacgt gaaaggaccc cttatcggac tctattgatg 480
aatgagttgg gtgttccttt ccatctgggg accaagcaag tgtgcatagc atggtccagc 540
tcaagttgtc acgatggaaa agcatggctg catgtttgta taacgggggga tgataaaaat 600 gcaactgcta gcttcattta caatgggagg cttgtagata gtgttgtttc atggtccaaa 660
gatattctca ggacccagga gtcagaatgc atttgtatca atggaacttg tacagtagta 720
atgactgatg gaagtgcttc aggaaaagct gatactaaaa tactattcat tgaggagggg 780
aaaatcgttc atactagcac attgtcagga agtgctcagc atgtcgaaga gtgctcttgc 840
tatcctcgat atcctggtgt cagatgtgtc tgcagagaca actggaaggg ctccaatcgg 900
cccatcgtag atataaacat aaaggatcat agcattgttt ccagttatgt gtgttcagga 960
cttgttggag acacacccag aaaaaacgac agctccagca gtagccattg tttggatcct 1020
aacaatgaag aaggtggtgg cggagtgaaa ggctgggcct ttgatgatgg aaatgacgtg 1080
tggatgggaa gaacaatcaa cgagaagtca cgcttagggt atgaaacctt caaagtcatt 1140
gaaggctggt ccaaccctaa gtccaaattg cagacaaata ggcaagtcat agttgacaga 1200
ggtgataggt ccggttattc tggtattttc tctgttgaag gcaaaagctg cataaatcgg 1260
tgcttttatg tggagttgat taggggaaga aaagaggaaa ctgaagtctt gtggacctca 1320
aacagtattg ttgtgttttg tggcacctca ggtacatatg gaacaggctc atggcctgat 1380
ggggcggacc tcaatctcat gcctatataa gctttcgcaa ttttagaaaa aact 1434

<210> SEQ ID NO 70
<211> LENGTH: 1410
<212> TYPE: DNA
<213> ORGANISM: Influenza virus

<400> SEQUENCE: 70
atgaatccaa atcaaaagat aataacgatt ggctctgttt ctctcaccat ttccacaata 60

```
tgcttcttca tgcaaattgc catcctgata actactgtaa cattgcattt caagcaatat    120

gaattcaact ccccccaaa caaccaagtg atgctgtgtg aaccaacaat aatagaaaga    180

aacataacag agatagtgta tttgaccaac accaccatag agaaggaaat atgccccaaa    240

ccagcagaat acagaaattg gtcaaaaccg caatgtggca ttacaggatt tgcacctttc    300

tctaaggaca attcgattag gctttccgct ggtggggaca tctgggtgac aagagaacct    360

tatgtgtcat gcgatcctga caagtgttat caatttgccc ttggacaggg aacaacacta    420

aacaacgtgc attcaaataa caaagtacgt gagaggaccc cttatcggac tctattgatg    480

aatgagttgg gtgttccttt ccatctgggg accaagcaag tgtgcatagc atggtccagc    540

tcaagttgtc acgatggaaa agcatggctg catgtttgta taacggggga tgataaaaat    600

gcaactgcta gcttcattta caatgggagg cttgtagata gtgttgtttc atggtccaaa    660

gatattctca ggacccagga gtcagaatgc gtttgtatca atggaacttg tacagtagta    720

atgactgatg gaagtgctac aggaaaagct gatactaaaa tactattcat tgaggagggg    780

aaaatcgttc atactagcaa attgtcagga agtgctcagc atgtcgaaga gtgctcttgc    840

tatcctcgat atcctggtgt cagatgtgtc tgcagagaca actggaaagg atccaaccgg    900

cccatcgtag atataaacat aaaggatcat agcattgttt ccagttatgt gtgttcagga    960

cttgttggag acacacccag aaaaaacgac agctccagca gtagccattg tttgaatcct   1020

aacaatgaag aaggtgttca tggagtgaaa ggctgggcct ttgatgatgg aaatgacgtg   1080

tggatgggga gaacaatcaa cgagaagtca cgcttagggt atgaaacctt caaagtcgtt   1140

gaaggctggt ccaaccctaa gtccaaattg cagataaata ggcaagtcat agttgacaga   1200

ggtgataggt ccggttattc tggtattttc tctgttgaag gcaaaagctg catcaatcgg   1260

tgcttttatg tggagttgat taggggaaga aaagaggaaa ctgaagtctt gtggacctca   1320

aacagtattg ttgtgttttg tggcacctca ggtacatatg gaacaggctc atggcctgat   1380

ggggcggacc tcaatctcat gcatatataa                                    1410
```

```
<210> SEQ ID NO 71
<211> LENGTH: 469
<212> TYPE: PRT
<213> ORGANISM: Influenza virus

<400> SEQUENCE: 71

Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Asn Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125
```

Cys Arg Thr Phe Phe Leu Thr Gln Gly Ala Leu Leu Asn Asp Lys His
130 135 140

Ser Asn Gly Thr Ile Lys Asp Arg Ser Pro Tyr Arg Thr Leu Met Ser
145 150 155 160

Cys Pro Ile Gly Glu Val Pro Ser Pro Tyr Asn Ser Arg Phe Glu Ser
165 170 175

Val Ala Trp Ser Ala Ser Ala Cys His Asp Gly Ile Asn Trp Leu Thr
180 185 190

Ile Gly Ile Ser Gly Pro Asp Asn Gly Ala Val Ala Val Leu Lys Tyr
195 200 205

Asn Gly Ile Ile Thr Asp Thr Ile Lys Ser Trp Arg Asn Asn Ile Leu
210 215 220

Arg Thr Gln Glu Ser Glu Cys Ala Cys Val Asn Gly Ser Cys Phe Thr
225 230 235 240

Val Met Thr Asp Gly Pro Ser Asn Gly Gln Ala Ser Tyr Lys Ile Phe
245 250 255

Arg Ile Glu Lys Gly Lys Ile Val Lys Ser Val Glu Met Asn Ala Pro
260 265 270

Asn Tyr His Tyr Glu Glu Cys Ser Cys Tyr Pro Asp Ser Ser Glu Ile
275 280 285

Thr Cys Val Cys Arg Asp Asn Trp His Gly Ser Asn Arg Pro Trp Val
290 295 300

Ser Phe Asn Gln Asn Leu Glu Tyr Gln Ile Gly Tyr Ile Cys Ser Gly
305 310 315 320

Ile Phe Gly Asp Asn Pro Arg Pro Asn Asp Lys Thr Gly Ser Cys Gly
325 330 335

Pro Val Ser Ser Asn Gly Ala Asn Gly Val Lys Gly Phe Ser Phe Lys
340 345 350

Tyr Gly Asn Gly Val Trp Ile Gly Arg Thr Lys Ser Ile Ser Ser Arg
355 360 365

Asn Gly Phe Glu Met Ile Trp Asp Pro Asn Gly Trp Thr Gly Thr Asp
370 375 380

Asn Asn Phe Ser Ile Lys Gln Asp Ile Val Gly Ile Asn Glu Trp Ser
385 390 395 400

Gly Tyr Ser Gly Ser Phe Val Gln His Pro Glu Leu Thr Gly Leu Asp
405 410 415

Cys Ile Arg Pro Cys Phe Trp Val Glu Leu Ile Arg Gly Arg Pro Lys
420 425 430

Glu Asn Thr Ile Trp Thr Ser Gly Ser Ser Ile Ser Phe Cys Gly Val
435 440 445

Asn Ser Asp Thr Val Gly Trp Ser Trp Pro Asp Gly Ala Glu Leu Pro
450 455 460

Phe Thr Ile Asp Lys
465

<210> SEQ ID NO 72
<211> LENGTH: 470
<212> TYPE: PRT
<213> ORGANISM: Influenza virus

<400> SEQUENCE: 72

Met Asn Pro Asn Gln Lys Leu Phe Ala Leu Ser Gly Val Ala Ile Ala
1 5 10 15

Leu Ser Ile Leu Asn Leu Leu Ile Gly Ile Ser Asn Val Gly Leu Asn
20 25 30

```
Val Ser Leu His Leu Lys Gly Ser Ser Asp Gln Asp Lys Asn Trp Thr
        35                  40                  45

Cys Thr Ser Val Thr Gln Asn Asn Thr Thr Leu Ile Glu Asn Thr Tyr
    50                  55                  60

Val Asn Asn Thr Thr Val Ile Asp Lys Glu Thr Gly Thr Ala Lys Pro
65                  70                  75                  80

Asn Tyr Leu Met Leu Asn Lys Ser Leu Cys Lys Val Glu Gly Trp Val
                85                  90                  95

Val Val Ala Lys Asp Asn Ala Ile Arg Phe Gly Glu Ser Glu Gln Ile
            100                 105                 110

Ile Val Thr Arg Glu Pro Tyr Val Ser Cys Asp Pro Leu Gly Cys Lys
        115                 120                 125

Met Tyr Ala Leu His Gln Gly Thr Thr Ile Arg Asn Lys His Ser Asn
    130                 135                 140

Gly Thr Ile His Asp Arg Thr Ala Phe Arg Gly Leu Ile Ser Thr Pro
145                 150                 155                 160

Leu Gly Ser Pro Pro Val Val Ser Asn Ser Asp Phe Leu Cys Val Gly
                165                 170                 175

Trp Ser Ser Thr Ser Cys His Asp Gly Ile Gly Arg Met Thr Ile Cys
            180                 185                 190

Val Gln Gly Asn Asn Asp Asn Ala Thr Ala Thr Val Tyr Tyr Asp Arg
        195                 200                 205

Arg Leu Thr Thr Thr Ile Lys Thr Trp Ala Gly Asn Ile Leu Arg Thr
    210                 215                 220

Gln Glu Ser Glu Cys Val Cys His Asn Gly Thr Cys Val Val Ile Met
225                 230                 235                 240

Thr Asp Gly Ser Ala Ser Ser Gln Ala Tyr Thr Lys Val Leu Tyr Phe
                245                 250                 255

His Lys Gly Leu Val Ile Lys Glu Glu Ala Leu Lys Gly Ser Ala Arg
            260                 265                 270

His Ile Glu Glu Cys Ser Cys Tyr Gly His Asn Ser Lys Val Thr Cys
        275                 280                 285

Val Cys Arg Asp Asn Trp Gln Gly Ala Asn Arg Pro Val Ile Glu Ile
    290                 295                 300

Asp Met Asn Ala Met Glu His Thr Ser Gln Tyr Leu Cys Thr Gly Val
305                 310                 315                 320

Leu Thr Asp Thr Ser Arg Pro Ser Asp Lys Ser Met Gly Asp Cys Asn
                325                 330                 335

Asn Pro Ile Thr Gly Ser Pro Gly Ala Pro Gly Val Lys Gly Phe Gly
            340                 345                 350

Phe Leu Asp Ser Ser Asn Thr Trp Leu Gly Arg Thr Ile Ser Pro Arg
        355                 360                 365

Ser Arg Ser Gly Phe Glu Met Leu Lys Ile Pro Asn Ala Glu Thr Asp
    370                 375                 380

Pro Asn Ser Lys Ile Thr Glu Arg Gln Glu Ile Val Asp Asn Asn Asn
385                 390                 395                 400

Trp Ser Gly Tyr Ser Gly Ser Phe Ile Asp Tyr Trp Asp Glu Ser Ser
                405                 410                 415

Glu Cys Tyr Asn Pro Cys Phe Tyr Val Glu Leu Ile Arg Gly Arg Pro
            420                 425                 430

Glu Glu Ala Lys Tyr Val Gly Trp Thr Ser Asn Ser Leu Ile Ala Leu
        435                 440                 445
```

Cys Gly Ser Pro Ile Ser Val Gly Ser Gly Ser Phe Pro Asp Gly Ala
450 455 460

Gln Ile Gln Tyr Phe Ser
465 470

<210> SEQ ID NO 73
<211> LENGTH: 465
<212> TYPE: PRT
<213> ORGANISM: Influenza virus

<400> SEQUENCE: 73

Met Asn Pro Asn Gln Lys Ile Leu Cys Thr Ser Ala Thr Ala Ile Ile
1 5 10 15

Ile Gly Ala Ile Ala Val Leu Ile Gly Ile Ala Asn Leu Gly Leu Asn
20 25 30

Ile Gly Leu His Leu Lys Pro Gly Cys Asn Cys Ser His Ser Gln Pro
35 40 45

Glu Thr Thr Asn Thr Ser Gln Thr Ile Ile Asn Asn Tyr Tyr Asn Glu
50 55 60

Thr Asn Ile Thr Asn Ile Gln Met Glu Glu Arg Thr Ser Arg Asn Phe
65 70 75 80

Asn Asn Leu Thr Lys Gly Leu Cys Thr Ile Asn Ser Trp His Ile Tyr
85 90 95

Gly Lys Asp Asn Ala Val Arg Ile Gly Glu Ser Ser Asp Val Leu Val
100 105 110

Thr Arg Glu Pro Tyr Val Ser Cys Asp Pro Asp Glu Cys Arg Phe Tyr
115 120 125

Ala Leu Ser Gln Gly Thr Thr Ile Arg Gly Lys His Ser Asn Gly Thr
130 135 140

Ile His Asp Arg Ser Gln Tyr Arg Ala Leu Ile Ser Trp Pro Leu Ser
145 150 155 160

Ser Pro Pro Thr Val Tyr Asn Ser Arg Val Glu Cys Ile Gly Trp Ser
165 170 175

Ser Thr Ser Cys His Asp Gly Lys Ser Arg Met Ser Ile Cys Ile Ser
180 185 190

Gly Pro Asn Asn Asn Ala Ser Ala Val Val Trp Tyr Asn Arg Arg Pro
195 200 205

Val Ala Glu Ile Asn Thr Trp Ala Arg Asn Ile Leu Arg Thr Gln Glu
210 215 220

Ser Glu Cys Val Cys His Asn Gly Val Cys Pro Val Val Phe Thr Asp
225 230 235 240

Gly Ser Ala Thr Gly Pro Ala Asp Thr Arg Ile Tyr Tyr Phe Lys Glu
245 250 255

Gly Lys Ile Leu Lys Trp Glu Ser Leu Thr Gly Thr Ala Lys His Ile
260 265 270

Glu Glu Cys Ser Cys Tyr Gly Glu Arg Thr Gly Ile Thr Cys Thr Cys
275 280 285

Arg Asp Asn Trp Gln Gly Ser Asn Arg Pro Val Ile Gln Ile Asp Pro
290 295 300

Val Ala Met Thr His Thr Ser Gln Tyr Ile Cys Ser Pro Val Leu Thr
305 310 315 320

Asp Asn Pro Arg Pro Asn Asp Pro Asn Ile Gly Lys Cys Asn Asp Pro
325 330 335

Tyr Pro Gly Asn Asn Asn Asn Gly Val Lys Gly Phe Ser Tyr Leu Asp
340 345 350

```
Gly Ala Asn Thr Trp Leu Gly Arg Thr Ile Ser Thr Ala Ser Arg Ser
        355                 360                 365

Gly Tyr Glu Met Leu Lys Val Pro Asn Ala Leu Thr Asp Asp Arg Ser
    370                 375                 380

Lys Pro Ile Gln Gly Gln Thr Ile Val Leu Asn Ala Asp Trp Ser Gly
385                 390                 395                 400

Tyr Ser Gly Ser Phe Met Asp Tyr Trp Ala Glu Gly Asp Cys Tyr Arg
                405                 410                 415

Ala Cys Phe Tyr Val Glu Leu Ile Arg Gly Arg Pro Lys Glu Asp Lys
            420                 425                 430

Val Trp Trp Thr Ser Asn Ser Ile Val Ser Met Cys Ser Ser Thr Glu
        435                 440                 445

Phe Leu Gly Gln Trp Asn Trp Pro Asp Gly Ala Lys Ile Glu Tyr Phe
    450                 455                 460

Leu
465


<210> SEQ ID NO 74
<211> LENGTH: 469
<212> TYPE: PRT
<213> ORGANISM: Influenza virus

<400> SEQUENCE: 74

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asp Ile Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly Asp Asp Glu Asn Ala Thr Ala Ser Phe Ile Tyr Asn
        195                 200                 205

Gly Arg Leu Ala Asp Ser Ile Val Ser Trp Ser Lys Lys Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
```

```
                245                 250                 255

Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365

Lys Leu Arg Ser Gly Tyr Glu Thr Phe Lys Val Ile Glu Gly Trp Ser
    370                 375                 380

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465


<210> SEQ ID NO 75
<211> LENGTH: 469
<212> TYPE: PRT
<213> ORGANISM: Influenza virus

<400> SEQUENCE: 75

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140
```

```
Ser Asn Asp Ile Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly Asp Asp Glu Asn Ala Thr Ala Ser Phe Ile Tyr Asn
        195                 200                 205

Gly Arg Leu Ala Asp Ser Ile Val Ser Trp Ser Lys Lys Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365

Lys Leu Arg Ser Gly Tyr Glu Thr Phe Lys Val Ile Glu Gly Trp Ser
    370                 375                 380

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465
```

<210> SEQ ID NO 76
<211> LENGTH: 1467
<212> TYPE: DNA
<213> ORGANISM: Influenza virus

<400> SEQUENCE: 76

```
agcaaaagca ggagtaaaga tgaatccaaa tcaaaagata ataacgattg gctctgtttc      60

cctcaccatt tccacaatat gcttcttcat gcaaattgcc atcctgataa ctactgtaac     120

attgcatttc aagcaatatg aattcaactc ccccccaaac aaccaagtga tgctgtgtga     180

accaacaata atagaaagaa acataacaga gatagtgtat ctgaccaaca ccaccataga     240
```

gaaggaaata tgccccaaac tagcagaata cagaaattgg tcaaagccgc aatgtaacat 300
tacaggattt gcaccttttt ctaaggacaa ttcgattcgg ctttccgctg gtggggacat 360
ctgggtgaca agagaacctt atgtgtcatg cgatcctgac aagtgttatc aatttgccct 420
tggacaggga acaacactaa acaacgtgca ttcaaatgac atagtacatg ataggacccc 480
ttatcggacc ctattgatga atgagttggg tgttccattt catctgggga ccaagcaagt 540
gtgcatagca tggtccagct caagttgtca cgatggaaaa gcatggctgc atgtttgtgt 600
aacgggggat gatgaaaatg caactgctag cttcatttac aatgggaggc ttgcagatag 660
tattgtttca tggtccaaaa aaatcctcag gacccaggag tcagaatgcg tttgtatcaa 720
tggaacttgt acagtagtaa tgactgatgg gagtgcttca ggaaaagctg atactaaaat 780
actattcatt gaggagggga aaattgttca tactagcaca ttatcaggaa gtgctcagca 840
tgtcgaggag tgctcctgtt atcctcgata tcctggtgtc agatgtgtct gcagagacaa 900
ctggaaaggc tccaataggc ccatcgtaga tataaacata aaggattata gcattgtttc 960
cagttatgtg tgctcaggac ttgttggaga cacacccaga aaaaacgaca gctccagcag 1020
tagccattgc ttggatccaa acaatgagga aggtggtcat ggagtgaaag gctgggcctt 1080
tgatgatgga aatgacgtgt ggatgggaag aacgatcagc gagaagttac gctcaggata 1140
tgaaaccttc aaagtcattg aaggctggtc caaccctaac tccaaattgc agataaatag 1200
gcaagtcata gttgacagag gtaacaggtc cggttattct ggtattttct ctgttgaagg 1260
caaaagctgc atcaatcggt gcttttatgt ggagttgata aggggaagaa aacaggaaac 1320
tgaagtcttg tggacctcaa acagtattgt tgtgttttgt ggcacctcag gtacatatgg 1380
aacaggctca tggcctgatg gggcggacat caatctcatg cctatataag ctttcgcaat 1440
tttagaaaaa aactccttgt ttctact 1467

<210> SEQ ID NO 77
<211> LENGTH: 469
<212> TYPE: PRT
<213> ORGANISM: Influenza virus

<400> SEQUENCE: 77

Met Asn Pro Asn Gln Lys Ile Ile Thr Ile Gly Ser Val Ser Leu Thr
1 5 10 15

Ile Ala Thr Ile Cys Phe Leu Met Gln Ile Ala Ile Leu Val Thr Thr
20 25 30

Val Thr Leu His Phe Lys Gln Tyr Glu Cys Asn Ser Pro Pro Asn Asn
35 40 45

Gln Val Met Leu Cys Glu Pro Thr Ile Ile Glu Arg Asn Ile Thr Glu
50 55 60

Ile Val Tyr Leu Thr Asn Thr Thr Ile Glu Lys Glu Ile Cys Pro Lys
65 70 75 80

Leu Ala Glu Tyr Arg Asn Trp Ser Lys Pro Gln Cys Asn Ile Thr Gly
85 90 95

Phe Ala Pro Phe Ser Lys Asp Asn Ser Ile Arg Leu Ser Ala Gly Gly
100 105 110

Asp Ile Trp Val Thr Arg Glu Pro Tyr Val Ser Cys Asp Pro Asp Lys
115 120 125

Cys Tyr Gln Phe Ala Leu Gly Gln Gly Thr Thr Leu Asn Asn Gly His
130 135 140

Ser Asn Asp Thr Val His Asp Arg Thr Pro Tyr Arg Thr Leu Leu Met
145 150 155 160

-continued

```
Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly Asp Asp Gly Asn Ala Thr Ala Ser Phe Ile Tyr Asn
        195                 200                 205

Gly Arg Leu Val Asp Ser Ile Gly Ser Trp Ser Lys Lys Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Leu Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Val Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365

Lys Leu Arg Ser Gly Tyr Glu Thr Phe Lys Val Ile Glu Gly Trp Ser
    370                 375                 380

Lys Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Asn Gln
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465
```